United States Patent
Pinto et al.

(10) Patent No.: US 9,738,655 B2
(45) Date of Patent: Aug. 22, 2017

(54) TETRAHYDROISOQUINOLINES CONTAINING SUBSTITUTED AZOLES AS FACTOR XIA INHIBITORS

(71) Applicant: BRISTOL-MYERS SQUIBB COMPANY, Princeton, NJ (US)

(72) Inventors: Donald J. P. Pinto, Pennington, NJ (US); Charles G. Clarke, Cherry Hill, NJ (US); Leon M. Smith, II, Somerset, NJ (US); Michael J. Orwat, New Hope, PA (US); Yoon Jeon, Belle Mead, NJ (US); James R. Corte, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/777,763

(22) PCT Filed: Mar. 25, 2014

(86) PCT No.: PCT/US2014/031651
§ 371 (c)(1),
(2) Date: Sep. 17, 2015

(87) PCT Pub. No.: WO2014/160668
PCT Pub. Date: Oct. 2, 2014

(65) Prior Publication Data
US 2016/0145263 A1    May 26, 2016

Related U.S. Application Data

(60) Provisional application No. 61/804,883, filed on Mar. 25, 2013, provisional application No. 61/840,736, filed on Jun. 28, 2013, provisional application No. 61/894,607, filed on Oct. 23, 2013.

(51) Int. Cl.

| | | |
|---|---|---|
| *A61K 31/00* | (2006.01) | |
| *C07D 491/107* | (2006.01) | |
| *C07D 401/14* | (2006.01) | |
| *C07D 405/14* | (2006.01) | |
| *C07D 413/14* | (2006.01) | |
| *C07D 401/06* | (2006.01) | |
| *C07D 413/04* | (2006.01) | |
| *C07D 413/06* | (2006.01) | |
| *C07D 417/14* | (2006.01) | |
| *C07D 471/10* | (2006.01) | |
| *C07D 487/04* | (2006.01) | |
| *C07D 491/10* | (2006.01) | |

(52) U.S. Cl.
CPC ....... *C07D 491/107* (2013.01); *C07D 401/06* (2013.01); *C07D 401/14* (2013.01); *C07D 405/14* (2013.01); *C07D 413/04* (2013.01); *C07D 413/06* (2013.01); *C07D 413/14* (2013.01); *C07D 417/14* (2013.01); *C07D 471/10* (2013.01); *C07D 487/04* (2013.01); *C07D 491/10* (2013.01)

(58) Field of Classification Search
CPC .................................................. C07D 491/107
USPC .................................................... 514/210.21
See application file for complete search history.

(56) References Cited

U.S. PATENT DOCUMENTS

| | | |
|---|---|---|
| 5,624,936 A | 4/1997 | deSolms |
| 5,869,682 A | 2/1999 | deSolms |
| 7,544,699 B2 | 6/2009 | Mjalli et al. |

FOREIGN PATENT DOCUMENTS

| | | |
|---|---|---|
| DE | 40 34 829 A1 | 5/1992 |
| EP | 0 525 420 B1 | 5/1999 |
| EP | 1 016 663 A1 | 7/2000 |
| EP | 1 125 925 A1 | 8/2001 |
| FR | 1525186 | 5/1968 |
| FR | 7155 M | 2/1970 |
| GB | 2497806 A | 6/2013 |
| JP | 2015-120685 A | 7/2015 |
| KR | 2015-0136294 A | 12/2015 |
| WO | WO 93/20099 A2 | 10/1993 |
| WO | WO 96/34010 A2 | 10/1996 |
| WO | WO 97/36891 A1 | 10/1997 |

(Continued)

OTHER PUBLICATIONS

Venkatesh et al., J. Pharm. Sci. 89, 145-54 (2000).*

(Continued)

*Primary Examiner* — Nizal Chandrakumar
(74) *Attorney, Agent, or Firm* — Hong Liu

(57) ABSTRACT

The present invention provides compounds of Formula (I):

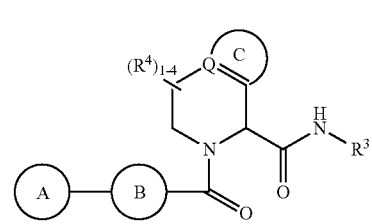

(I)

or stereoisomers, tautomers, or pharmaceutically acceptable salts thereof, wherein all the variables are as defined herein. These compounds are selective factor XIa inhibitors or dual inhibitors of FXIa and plasma kallikrein. This invention also relates to pharmaceutical compositions comprising these compounds and methods of treating thromboembolic and/or inflammatory disorders using the same.

15 Claims, No Drawings

(56) References Cited

FOREIGN PATENT DOCUMENTS

| | | |
|---|---|---|
| WO | WO 99/15530 A1 | 4/1999 |
| WO | WO 99/47545 A2 | 9/1999 |
| WO | WO 99/61444 A2 | 12/1999 |
| WO | WO 00/18733 A1 | 4/2000 |
| WO | WO 00/40571 A1 | 7/2000 |
| WO | WO 00/61608 A2 | 10/2000 |
| WO | WO 01/85695 A1 | 11/2001 |
| WO | WO 02/18369 A2 | 3/2002 |
| WO | WO 03/011222 A2 | 2/2003 |
| WO | WO 03/041641 A2 | 5/2003 |
| WO | WO 2004/080971 A1 | 9/2004 |
| WO | WO 2004/094372 A2 | 11/2004 |
| WO | WO 2005/014533 A2 | 2/2005 |
| WO | WO 2005/099709 A2 | 10/2005 |
| WO | WO 2005/123050 A2 | 12/2005 |
| WO | WO 2005/123680 A1 | 12/2005 |
| WO | WO 2006/017295 A2 | 2/2006 |
| WO | WO 2006/076575 A2 | 7/2006 |
| WO | WO 2006/089005 A2 | 8/2006 |
| WO | WO 2007/054453 A2 | 5/2007 |
| WO | WO 2007/070816 A2 | 6/2007 |
| WO | WO 2007/070818 A1 | 6/2007 |
| WO | WO 2007/070826 A1 | 6/2007 |
| WO | WO 2007/076431 A1 | 7/2007 |
| WO | WO 2008/076805 A2 | 6/2008 |
| WO | WO 2008/079836 A2 | 7/2008 |
| WO | WO 2008/157162 A1 | 12/2008 |
| WO | WO 2009/114677 A1 | 9/2009 |
| WO | WO 2010/151317 A1 | 12/2010 |
| WO | WO 2011/002520 A2 | 1/2011 |
| WO | WO 2011/017296 A1 | 2/2011 |
| WO | WO 2011/100401 A1 | 8/2011 |
| WO | WO 2011/100402 A1 | 8/2011 |
| WO | WO 2013/009527 A2 | 1/2013 |
| WO | WO 2013/022814 A1 | 2/2013 |
| WO | WO 2013/022818 A1 | 2/2013 |
| WO | WO 2013/055984 A1 | 4/2013 |
| WO | WO 2013/056034 A1 | 4/2013 |
| WO | WO 2013/056060 A1 | 4/2013 |
| WO | WO 2013/093484 A1 | 6/2013 |
| WO | WO 2013/111107 A1 | 8/2013 |
| WO | WO 2013/111108 A1 | 8/2013 |
| WO | WO 2013/118805 A1 | 8/2013 |
| WO | WO 2013/167669 A1 | 11/2013 |
| WO | WO 2013/174937 A1 | 11/2013 |
| WO | WO 2014/014050 A1 | 1/2014 |
| WO | WO 2014/022766 A1 | 2/2014 |
| WO | WO 2014/022767 A1 | 2/2014 |
| WO | WO 2014/059202 A1 | 4/2014 |
| WO | WO 2014/059203 A1 | 4/2014 |
| WO | WO 2014/059214 A1 | 4/2014 |
| WO | WO 2014/108679 A1 | 7/2014 |
| WO | WO 2014/108685 A1 | 7/2014 |
| WO | WO 2014/120346 A1 | 8/2014 |
| WO | WO 2014/154794 A1 | 10/2014 |
| WO | WO 2015/011087 A1 | 1/2015 |
| WO | WO 2015/044163 A1 | 4/2015 |
| WO | WO 2015/044165 A1 | 4/2015 |
| WO | WO 2015/044167 A1 | 4/2015 |
| WO | WO 2015/044169 A1 | 4/2015 |
| WO | WO 2015/044170 A1 | 4/2015 |
| WO | WO 2015/044172 A1 | 4/2015 |
| WO | WO 2015/044173 A1 | 4/2015 |
| WO | WO 2015/044174 A1 | 4/2015 |
| WO | WO 2015/047973 A1 | 4/2015 |
| WO | WO 2015/054087 A1 | 4/2015 |
| WO | WO 2015/107724 A1 | 7/2015 |
| WO | WO 2015/116882 A1 | 8/2015 |
| WO | WO 2015/116885 A1 | 8/2015 |
| WO | WO 2015/116886 A1 | 8/2015 |
| WO | WO 2015/120062 A2 | 8/2015 |
| WO | WO 2015/120777 A1 | 8/2015 |
| WO | WO 2015/123090 A1 | 8/2015 |
| WO | WO 2015/123091 A1 | 8/2015 |
| WO | WO 2015/123093 A1 | 8/2015 |
| WO | WO 2015/134998 A1 | 9/2015 |
| WO | WO 2015/160634 A1 | 10/2015 |
| WO | WO 2015/160636 A1 | 10/2015 |
| WO | WO 2015/183709 A1 | 12/2015 |

OTHER PUBLICATIONS

Boger, D.L. et al., "Thermal Atropisomerism of Aglucovancomycin Derivatives: Preparation of (M,M,M)- and (P,M,M)-Aglucovancomycins", J. Am. Chem. Soc., vol. 120, No. 35, pp. 8920-8926 (1998).

Caballero, J. et al., "Quantitative Structure-Activity Relationship Modeling of Growth Hormone Secretagogues Agonist Activity of Some Tetrahydroisoquinoline 1-Carboxamides", Chem. Biol. Drug. Des., vol. 69, pp. 48-55 (2007).

Chan, J.C.Y. et al., "The Characterization of Mice with a Targeted Combined Deficiency of Protein C and Factor XI", American Journal of Pathology, vol. 158, No. 2, pp. 469-479 (2001).

Chen, X. et al., Chapter 32: "The use of bioisosteric groups in lead optimization", Annual Reports in Medicinal Chemistry, vol. 38, pp. 333-346, Elsevier Inc., publ. (2003).

Cho, J.E. et al., "Characterization of Binding Mode for Human Coagulation Factor XI (FXI) Inhibitors", Bull. Korean Chem. Soc., vol. 34, No. 4, pp. 1212-1220 (2013).

Crosby, J.R. et al., "Antithrombotic Effect of Antisense Factor XI Oligonucleotide Treatment in Primates", Arterioscler. Thromb. Vasc. Biol., vol. 33, pp. 1670-1678 (2013), and vol. 33, pp. e127 and e130 (errata) (2013).

Evans, D.A. et al., "Total Syntheses of Vancomycin and Eremomycin Aglycons", Angew. Chem. Int. Ed., vol. 37, No. 19, pp. 2700-2704 (1998).

Gailani, D., "Gene Targeting in Hemostasis, Factor XI", Frontiers in Bioscience, vol. 6, pp. 201-207 (2001).

Gailani, D. et al., "A murine model of factor XI deficiency", Blood Coagulation and Fibrinolysis, vol. 8, pp. 134-144 (1997).

Gruber, A. et al., "Factor XI-dependence of surface- and tissue factor-initiated thrombus propagation in primates", Blood, vol. 102, No. 3, pp. 953-955 (2003).

Hoffman, M., "A cell-based model of coagulation and the role of factor VIIa", Blood Reviews, vol. 17, pp. S1-S5 (2003).

Jiang, G. et al., "Highly Efficient Oxidation of Amines to (mines by Singlet Oxygen and Its Application in Ugi-Type Reactions", Organic Letters, vol. 11, No. 20, pp. 4568-4571 (2009).

Li, J.J. et al., "Tetrahydroisoquinoline 1-carboxamides as growth hormone secretagogues", Bioorganic & Medicinal Chemistry Letters, vol. 15, pp. 1799-1802 (2005).

Matafonov, A. et al., "Evidence for factor IX-independent roles for factor XIa in blood coagulation", Journal of Thrombosis and Haemostasis, vol. 11, pp. 2118-2127 (2013).

MayoClinic.com, "Pulmonary Embolism: Prevention", http://www.mayoclinic.com/health/pulmonary-embolism/DS00429/DSECTION=prevention, accessed May 20, 2013.

Meijers, J.C.M. et al., "High Levels of Coagulation Factor XI as a Risk Factor for Venous Thrombosis", The New England Journal of Medicine, vol. 342, pp. 696-701 (2000).

Meng, D. et al., "Development of a novel tricyclic class of potent and selective FIXa inhibitors", Bioorganic & Medicinal Chemistry Letters (2015), doi: http://dx.doi.org/10.1016/j.bmcl.2015.07.078.

Minnema, M.C. et al., "Activation of Clotting Factors XI and IX in Patients with Acute Myocardial Infarction", Arterioscler. Thromb. Vasc. Biol., vol. 20, pp. 2489-2493 (2000).

Murakami, T. et al., "Evaluation of Factor XIa-$\alpha_1$-Antitrypsin in Plasma, a Contact Phase-Activated Coagulation Factor-Inhibitor Complex, in Patients with Coronary Artery Disease", Arteriosclerosis, Thrombosis, and Vascular Biology, vol. 15, No. 8, pp. 1107-1113 (1995).

Ngouansavanh, T. et al., "IBX-Mediated Oxidative Ugi-Type Multicomponent Reactions: Application to the N and C1 Functionalization of Tetrahydroisoquinoline", Angew. Chem. Int. Ed., vol. 46, pp. 5775-5778 (2007).

(56) References Cited

OTHER PUBLICATIONS

Rosen, E.D. et al., "FXI is Essential for Thrombus Formation Following $FeCl_3$-Induced Injury of the Carotid Artery in the Mouse", Thromb. Haemost., vol. 87, pp. 774-776 (2002).

Schumacher, W.A. et al., "Inhibition of Factor XIa as a New Approach to Anticoagulation", Arterioscler. Thromb. Vasc. Biol., vol. 30, pp. 388-392 (2010).

Schuster, I. et al., "Convenient Synthesis of 1,2,3,4-Tetrahydroisoquinoline-1-Carboxylic Acid Derivatives via Isocyanide-Based Three-Component Reactions", Synthetic Communications, vol. 40, pp. 2488-2498 (2010).

Schuster, I. et al., "Synthesis of 1,2,3,4-Tetrahydroisoquinoline-1-Carboxylic Acid Derivatives Via Ugi Reactions", Letters in Organic Chemistry, vol. 4, No. 2, pp. 102-108 (2007).

Schuster, I. et al., "Synthesis of 1,2,3,4-Tetrahydroisoquinoline-1-carboxylic Acid Derivatives via Ugi Reactions", Magyar Kémiai Folyóirat (Hungarian Journal of Chemistry), vol. 116, No. 3, pp. 126-130 (2010).

Walsh, P.N., "Platelets and Factor XI Bypass the Contact System of Blood Coagulation", Thrombosis and Haemostasis, vol. 82, No. 2, pp. 234-242 (1999).

Wang, X. et al., "Effects of factor IX or factor XI deficiency on ferric chloride-induced carotid artery occlusion in mice", Journal of Thrombosis and Haemostasis, vol. 3, pp. 695-702 (2005).

Wu, Y.-J. et al., "Discovery of (S,E)-3-(2-fluorophenyl)-N-(1-(3-(pyridin-3-yloxy)phenyl)ethyl)-acrylamide as a potent and efficacious KCNQ2 (Kv7.2) opener for the treatment of neuropathic pain", Bioorganic & Medicinal Chemistry Letters, vol. 23, pp. 6188-6191 (2013).

\* cited by examiner

TETRAHYDROISOQUINOLINES CONTAINING SUBSTITUTED AZOLES AS FACTOR XIA INHIBITORS

CROSS REFERENCE TO RELATED APPLICATIONS

This application is entitled to priority pursuant to 35 U.S.C. §119(e) to U.S. provisional patent application Nos. 61/804,883, filed on Mar. 25, 2013, 61/840,736, filed on Jun. 28, 2013, and 61/894,607, filed on Oct. 23, 2013, which are incorporated herein in their entirety.

FIELD OF THE INVENTION

The present invention relates generally to novel substituted tetrahydroisoquinoline compounds, and their analogues thereof, which are inhibitors of factor XIa and/or plasma kallikrein, compositions containing them, and methods of using them, for example, for the treatment or prophylaxis of thromboembolic disorders, or for the treatment of retinal vascular permeability associated with diabetic retinopathy and diabetic macular edema.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007).) The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Therefore, factor XIa plays a key role in propagating this amplification loop and is thus an attractive target for anti-thrombotic therapy.

Plasma prekallikrein is a zymogen of a trypsin-like serine protease and is present in plasma at 35 to 50 μg/mL. The gene structure is similar to that of factor XI. Overall, the amino acid sequence of plasma kallikrein has 58% homology to factor XI. Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastrointestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (Lehmann, A., "Ecallantide (DX-88), a plasma kallikrein inhibitor for the treatment of hereditary angioedema and the prevention of blood loss in on-pump cardiothoracic surgery", *Expert Opin. Biol. Ther.*, 8:1187-1199 (2008)).

The plasma kallikrein-kinin system is abnormally abundant in patients with advanced diabetic macular edema. It has been recently published that plasma kallikrein contributes to retinal vascular dysfunctions in diabetic rats (Clermont, A. et al., "Plasma kallikrein mediates retinal vascular dysfunction and induces retinal thickening in diabetic rats", *Diabetes*, 60:1590-1598 (2011)). Furthermore, administration of the plasma kallikrein inhibitor ASP-440 ameliorated both retinal vascular permeability and retinal blood flow abnormalities in diabetic rats. Therefore, a plasma kallikrein inhibitor should have utility as a treatment to reduce retinal vascular permeability associated with diabetic retinopathy and diabetic macular edema. Other complications of diabetes such as cerebral hemorrhage, nephropathy, cardiomyopathy and neuropathy, all of which have associations with plasma kallikrein may also be considered as targets for a plasma kallikrein inhibitor.

To date, no small molecule synthetic plasma kallikrein inhibitor has been approved for medical use. The large protein plasma kallikrein inhibitors present risks of anaphylactic reactions, as has been reported for Ecallantide. Thus there remains a need for compounds that inhibit plasma kallikrein, that do not induce anaphylaxis and that are orally available. Furthermore, the molecules in the known art feature a highly polar and ionizable guanidine or amidine functionality. It is well known that such functionalities may be limiting to gut permeability and therefore to oral availability.

SUMMARY OF THE INVENTION

The present invention provides novel substituted tetrahydroisoquinoline compounds, their analogues, including stereoisomers, tautomers, pharmaceutically acceptable salts, or solvates thereof, which are useful as selective inhibitors of serine protease enzymes, especially factor XIa and/or plasma kallikrein.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the invention may be used in the treatment of retinal vascular permeability associated with diabetic retinopathy and diabetic macular edema.

The compounds of the present invention may be used in therapy.

The compounds of the present invention may be used for the manufacture of a medicament for the treatment and/or prophylaxis of a thromboembolic disorder.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

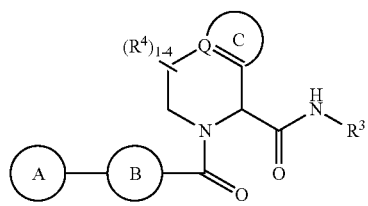

(I)

or stereoisomers, tautomers, pharmaceutically acceptable salts, solvates, or prodrugs thereof, wherein:

ring A is independently selected from the group consisting of: $C_{3-10}$ carbocycle and 5- to 10-membered heterocycle containing carbon atoms and 1-4 heteroatoms selected from the group consisting of N, O, and $S(O)_p$, each optionally substituted with one or more $R^1$ as valence allows;

ring B is 5- to 6-membered heterocycle comprising: carbon atoms and 1-4 heteroatoms selected from N, O and $S(O)_p$, and optionally substituted with one or more $R^2$ as valence allows;

ring C is independently selected from the group consisting of: phenyl and 5- to 6-membered heterocycle containing carbon atoms and 1-4 heteroatoms selected from the group consisting of N, $NR^6$, O, and $S(O)_p$ and optionally substituted with one or more $R^5$ as valence allows;

Q is independently selected from the group consisting of: C, CH, and N;

---- is an optional bond; provided when Q is N, the optional bond is absent;

$R^1$ is independently selected from the group consisting of: H, halo, $NO_2$, OH, CN, $C_{1-6}$ alkyl, $C_{1-4}$ alkoxy, —$CHF_2$, —$CF_3$, —$CH_2NH_2$, —$OCHF_2$, —$CO(C_{1-4}$ alkyl), —$CONH_2$, —COOH, and 5- to 7-membered heterocycle;

$R^2$ is independently selected from the group consisting of: H, =O, OH, $NH_2$, $CF_3$, halo, $C_{1-4}$ alkyl (optionally substituted with OH), $C_{1-3}$alkoxy, and $C(O)C_{1-3}$ alkyl;

$R^3$ is independently selected from the group consisting of: $C_{1-6}$ alkyl substituted with 1-3 $R^{3a}$, $C_{3-10}$ carbocycle substituted with 1-3 $R^{3a}$, and 5-10 membered heterocycle containing carbon atoms and 1-4 heteroatoms selected from N, $NR^7$, O, and $S(O)_p$; wherein said heterocycle is substituted with 1-3 $R^{3a}$;

$R^{3a}$ is independently selected from the group consisting of: H, halogen, $C_{1-4}$ alkyl, —OH, =O, —$CH_2OH$, $C_{1-4}$ alkoxy, —CN, —$NH_2$, —$NH(C_{1-4}$ alkyl), —$N(C_{1-4}$ alkyl)$_2$, —$CO_2H$, —$CH_2CO_2H$, —$CO_2(C_{1-4}$ alkyl), —$CH_2CO_2$ ($C_{1-4}$ alkyl), —$CO_2$—$C_{1-4}$ alkylene-$O(C_{1-4}$ alkyl), —$CO_2$—$C_{1-4}$ alkylene-$N(C_{1-4}$ alkyl)$_2$, —$CO_2$—$C_{1-4}$ alkylene-O—$C_{1-4}$ alkylene-$N(C_{1-4}$ alkyl)$_2$, —$CO_2$—$C_{1-4}$ alkylene-O—$C_{1-4}$ alkylene-$O(C_{1-4}$ alkyl), —$CONH_2$, —$CONH(C_{1-6}$ alkyl), —$CON(C_{1-4}$ alkyl)$_2$, —CONH—$C_{1-4}$ alkylene-$CO_2$ ($C_{1-4}$alkyl), —$CONHCO_2C_{1-4}$ alkyl, —$CONHC_{1-4}$ alkylene-$NHCO(C_{1-4}$ alkyl), —CONH—$C_{1-4}$ alkylene-$CONH_2$, —$NHCOC_{1-4}$ alkyl, —$NHCO_2(C_{1-4}$ alkyl), $R^c$, —$CONHR^c$, and —$CO_2R^c$;

$R^4$ is independently selected from the group consisting of: H, halo, and $C_{1-4}$ alkyl;

$R^5$ is independently selected from the group consisting of: H, halo, $C_{1-4}$ alkyl substituted with 1-2 $R^b$, $C_{2-4}$ alkenyl substituted with 1-2 $R^b$, $C_{2-4}$ alkynyl substituted with 1-2 $R^b$ OH, CN, $NH_2$, —$NH(C_{1-4}$ alkyl), $N(C_{1-4}$ alkyl)$_2$, $C_{1-4}$ alkoxy, —$OCO(C_{1-4}$ alkyl), —O—$C_{1-4}$ alkylene-$O(C_{1-4}$ alkyl), —O—$C_{1-4}$ alkylene-$N(C_{1-4}$ alkyl)$_2$, —$CO_2H$, $CO_2$ ($C_{1-4}$ alkyl), —$CONH_2$, —$(CH_2)_2CONH_2$, —$CONR^9(C_{1-4}$ alkyl), —$CONR^9$—$C_{1-4}$ alkylene $O(C_{1-4}$ alkyl), —CON ($C_{1-4}$ alkyl)$_2$, —$CONR^9$—$C_{1-4}$ alkylene-$N(C_{1-4}$ alkyl)$_2$, —CON($C_{1-4}$ alkyl)-$C_{1-4}$ alkylene-$O(C_{1-4}$ alkyl), —$CONR^9$—$C_{1-4}$ alkylene-$CO_2(C_{1-4}$ alkyl), —$NR^9COC_{1-4}$ alkyl, —$NR^9CO_2C_{1-4}$ alkyl, —$NR^9CONH(C_{1-4}$ alkyl), —$NR^9CONR^9$—$C_{1-4}$ alkylene-$CO_2C_{1-4}$ alkyl, —$NR^9$—$C_{1-4}$ alkylene-OH, —$NR^9$—$C_{1-4}$ alkylene-$N(C_{1-4}$ alkyl)$_2$, $R^8$, —$OR^8$, —O—$C_{1-4}$ alkylene-$R^8$, —$COR^8$, —$CO_2R^8$, —$CONR^9R^8$, —$NR^9COR^8$, —$NR^9R^8$, —$NR^9CO_2R^8$, and —$NR^9CONR^9R^8$;

$R^6$ is independently selected from the group consisting of: H, $C_{1-4}$ alkyl, $C_{1-4}$ alkyl, $COC_{1-4}$ alkyl, $CO_2C_{1-4}$ alkyl, $CO_2Bn$, phenyl, and benzyl;

$R^7$ is independently selected from the group consisting of: H and $C_{1-4}$ alkyl;

$R^8$ is independently selected from the group consisting of: —$(CH_2)_n$—$C_{3-10}$ carbocycle and —$(CH_2)_n$-5- to 10-membered heterocycle containing carbon atoms and 1-4 heteroatoms selected from the group consisting of: N, $NR^a$, O, and $S(O)_p$; wherein said carbocycle or heterocycle is substituted with 1-3 $R^b$;

$R^9$ is independently selected from the group consisting of: H and $C_{1-4}$ alkyl;

$R^a$ is independently selected from the group consisting of: H, $C_{1-4}$ alkyl substituted with 1-2 $R^d$, —$(CH_2)_n OH$, $CO(C_{1-4}$ alkyl), $COCF_3$, $CH_2CF_3$, $CO_2(C_{1-4}$ alkyl), —$CONH_2$, —CONH—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$;

$R^b$ is independently selected from the group consisting of: H, =O, halo, CN, OH, $NO_2$, $C_{1-4}$ alkyl substituted with 1-2 $R^d$, $C_{1-4}$ alkoxy, $OCF_3$, —$(CH_2)_nNH_2$, —$(CH_2)_n$ $N(C_{1-4}$ alkyl)$_2$, $CO(C_{1-4}$ alkyl), $CO(C_{1-4}$ haloalkyl), $CO_2(C_{1-4}$ alkyl), —$(CH_2)_n$—$CONH_2$, —$(CH_2)_n$—$CONH(C_{1-4}$ alkyl), —$(CH_2)_n$—$CON(C_{1-4}$ alkyl)$_2$, —CONH—$C_{1-4}$ alkylene-O ($C_{1-4}$ alkyl), —CONH—$C_{1-4}$ alkylene-$N(C_{1-4}$ alkyl)$_2$, —$NHCO(C_{1-4}$ alkyl), —$NHCO_2(C_{1-4}$ alkyl), —$S(O)_2NH_2$, —$S(O)_2NH(C_{1-4}$alkyl), $S(O)_2N(C_{1-4}$alkyl)$_2$, $R^c$, $COR^c$, $CO_2R^c$, $S(O)_2NH(C_{1-4}$alkyl)$R^c$, $NHCONHR^c$, and $CONHR^c$;

optionally, $R^b$ and $R^b$ together with the carbon atom(s) to which they are both attached form a 5-6 membered heterocyclic ring containing carbon atoms and 1-4 heteroatoms selected from $NR^a$, O, and $S(O)_p$; wherein said heterocycle is optionally substituted with =O;

of $R^a$ and $R^b$ are combined to form a 5-6 membered heterocyclic ring containing carbon atoms and 1-4 heteroatoms selected from N, O, and $S(O)_p$, and optionally substituted with 1-3 $R^e$;

$R^c$ is independently selected from the group consisting of: —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, N($C_{1-4}$ alkyl), O, and $S(O)_p$; wherein each ring moiety is substituted with 1-3 $R^d$;

$R^d$ is independently selected from the group consisting of: H, =O, halo, —OH, $C_{1-4}$ alkyl, $NH_2$, NH($C_{1-4}$ alkyl), N($C_{1-4}$ alkyl)$_2$, $C_{1-8}$ alkoxy optionally substituted with OH, and —NHCO($C_{1-4}$ alkyl), and heterocycle containing carbon atoms and 1-4 heteroatoms selected from the group consisting of: N, NH, N($C_{1-4}$ alkyl), O, and $S(O)_p$;

$R^e$ is independently selected from the group consisting of: H, halo, $C_{1-4}$ alkyl, $C_{1-4}$ alkoxy, $OCF_3$, $NH_2$, $NO_2$, N($C_{1-4}$ alkyl)$_2$, CO($C_{1-4}$ alkyl), CO($C_{1-4}$ haloalkyl), $CO_2$($C_{1-4}$ alkyl), $CONH_2$, —CONH($C_{1-4}$ alkyl), —CON($C_{1-4}$ alkyl)$_2$, —$NHCO_2$($C_{1-4}$ alkyl), —$(CH_2)_n$—$C_{3-6}$ cycloalkyl, —$(CH_2)_n$-phenyl, and —$(CH_2)_n$-5- to 6-membered heterocycle;

n is independently selected from 0, 1, 2, 3, and 4; and p is independently selected from 0, 1, and 2.

In another aspect, the present invention provides compounds of Formula (II):

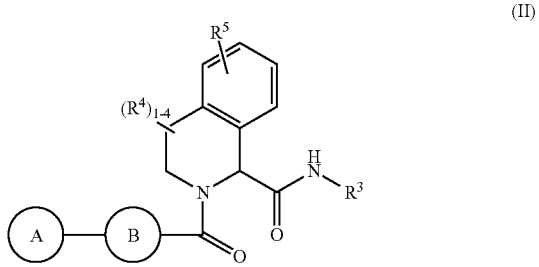

(II)

or stereoisomers, tautomers, pharmaceutically acceptable salts, solvates, or prodrugs thereof, wherein:

ring A is selected from the group consisting of: aryl and 5- to 10-membered heterocycle containing carbon atoms and 1-3 heteroatoms selected from the group consisting of N, NH, $NC_{1-4}$alkyl, O, and $S(O)_p$, each optionally substituted with 1-3 $R^1$;

ring B is 5- to 6-membered heterocycle comprising: carbon atoms and 1-4 heteroatoms selected from N, NH, $S(O)_p$, and O and optionally substituted with 1-3 $R^2$;

$R^5$ is selected from the group consisting of: H, halo, $C_{1-4}$ alkyl substituted with 1-2 $R^b$, $C_{2-4}$ alkenyl substituted with 1-2 $R^b$, OH, CN, $NH_2$, $C_{1-4}$ alkoxy, —O—$C_{1-4}$ alkylene-O ($C_{1-4}$ alkyl), —$NR^9COC_{1-4}$ alkyl, —$NR^9CO_2C_{1-4}$ alkyl, —$NR^9CONH(C_{1-4}$ alkyl), —$NR^9CONR^9$—$C_{1-4}$ alkylene-$CO_2C_{1-4}$ alkyl, —$NR^9$—$C_{1-4}$ alkylene-OH, $R^8$, $NR^9R^8$, —$OR^8$, and —$CONR^9R^8$; and $R^8$ is selected from the group consisting of: —$(CH_2)_n$-aryl, —$(CH_2)_n$—$C_{3-6}$ cycloalkyl and —$(CH_2)_n$-5- to 10-membered heterocycle containing carbon atoms and 1-4 heteroatoms selected from the group consisting of: N, $NR^a$, O, and $S(O)_p$; wherein said carbocycle or heterocycle is substituted with 1-3 $R^b$;

other variables are as defined in Formula (I) above.

In another aspect, the present invention provides compounds of Formula (III):

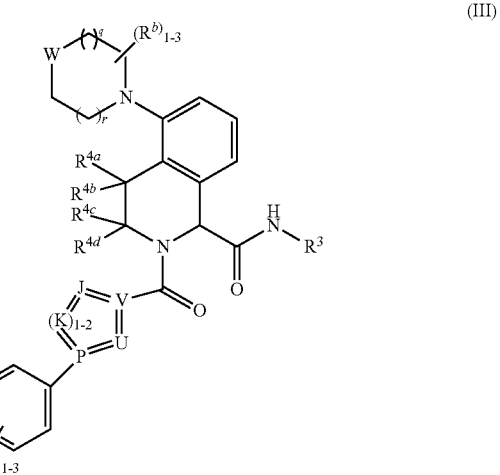

(III)

or stereoisomers, tautomers, pharmaceutically acceptable salts, solvates, or prodrugs thereof, wherein:

---- is an optional bond;

W is selected from the group consisting of $CR^bR^b$, N, $NR^a$, O, and $S(O)_p$;

J, K, P, U, and V are each independently selected from the group consisting of: N, NH, O, $S(O)_p$, $CR^2$, and $CR^2R^2$;

$R^2$ is selected from H, =O, OH, $NH_2$, $CF_3$, halo, and $C_{1-4}$ alkyl;

$R^{4a}$, $R^{4b}$, $R^{4c}$, and $R^{4d}$ are independently selected from the group consisting of: H, F, and $C_{1-4}$ alkyl;

$R^a$ is selected from the group consisting of: H, $C_{1-4}$ alkyl substituted with 1-2 $R^d$, —$(CH_2)_n$OH, $CH_2CF_3$, $CO_2$($C_{1-4}$ alkyl), —$CONH_2$, and $R^c$;

$R^b$ is selected from the group consisting of: H, =O, halo, $C_{1-4}$ alkyl, $C_{1-4}$ alkoxy, $OCF_3$, $NH_2$, $NO_2$, N($C_{1-4}$ alkyl)$_2$, CO($C_{1-4}$ alkyl), CO($C_{1-4}$ haloalkyl), $CO_2$($C_{1-4}$ alkyl), $CONH_2$, —CONH($C_{1-4}$ alkyl), —CON($C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, —$NHCO_2$($C_{1-4}$ alkyl), $R^c$, $COR^c$, $CO_2R^c$, and $CONHR^c$;

optionally, $R^b$ and $R^b$ together with the carbon atom to which they are both attached form a 5-6 membered heterocyclic ring containing carbon atoms and 1-4 heteroatoms selected from $NR^a$, O, and $S(O)_p$, wherein said heterocycle is optionally substituted with =O;

or $R^a$ and $R^b$ together form a 5-6 membered heterocyclic ring containing carbon atoms and 1-4 heteroatoms selected from N, O, and $S(O)_p$, and substituted with 1-3 $R^e$;

$R^c$ is selected from the group consisting of: —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, N($C_{1-4}$ alkyl), O, and $S(O)_p$; wherein each ring moiety is substituted with 1-2 $R^d$;

$R^d$ is selected from the group consisting of: H, =O, halo, —OH, $C_{1-4}$ alkyl, $NH_2$, NH($C_{1-4}$ alkyl), N($C_{1-4}$ alkyl)$_2$, $C_{1-4}$ alkoxy, and —NHCO($C_{1-4}$ alkyl), and heterocycle containing carbon atoms and 1-4 heteroatoms selected from the group consisting of: N, NH, N($C_{1-4}$ alkyl), O, and $S(O)_p$;

$R^e$ is selected from the group consisting of: H, halo, $C_{1-4}$ alkyl, $C_{1-4}$ alkoxy, $OCF_3$, $NH_2$, N($C_{1-4}$ alkyl)$_2$, CO($C_{1-4}$ alkyl), CO($C_{1-4}$ haloalkyl), $CO_2$($C_{1-4}$ alkyl), $CONH_2$, —CONH($C_{1-4}$ alkyl), —CON($C_{1-4}$ alkyl)$_2$, —$NHCO_2$($C_{1-4}$ alkyl), —$(CH_2)_n$—$C_{3-6}$ cycloalkyl, —$(CH_2)_n$-phenyl, and —$(CH_2)_n$-5- to 6-membered heterocycle;

q, is selected from 0, 1, and 2; and r, is selected from 0, 1, and 2;

other variables are as defined in Formula (II) above.

In another aspect, the present invention provides compounds of Formula (IV):

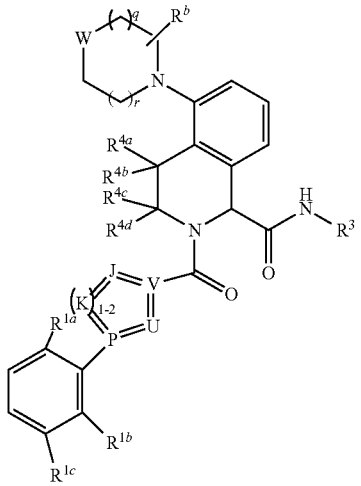

(IV)

or stereoisomers, tautomers, pharmaceutically acceptable salts, solvates, or prodrugs thereof, wherein:

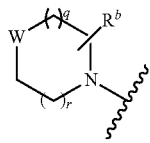

is selected from the group consisting of:

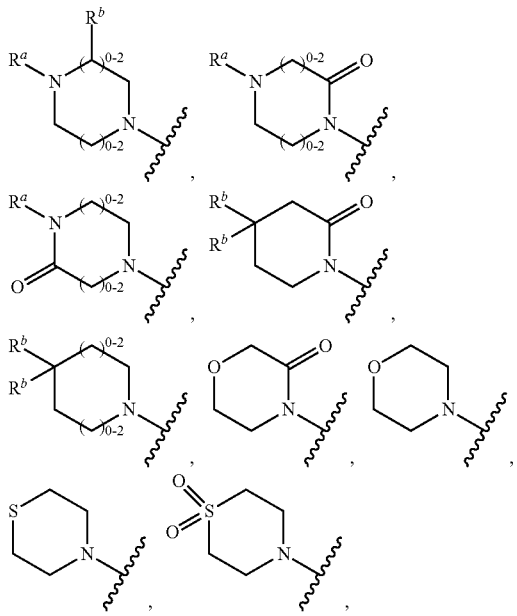

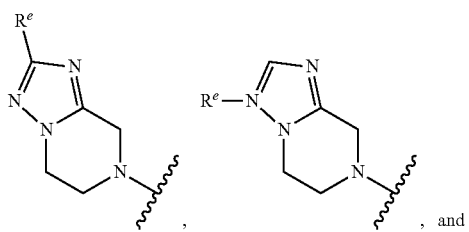

, and

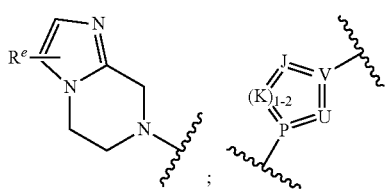

;

is selected from the group consisting of:

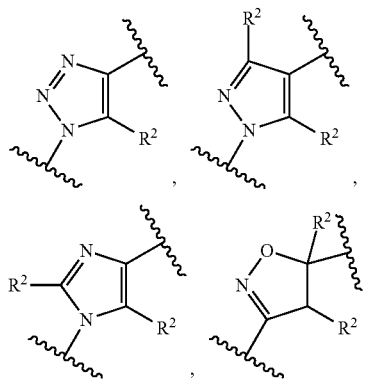

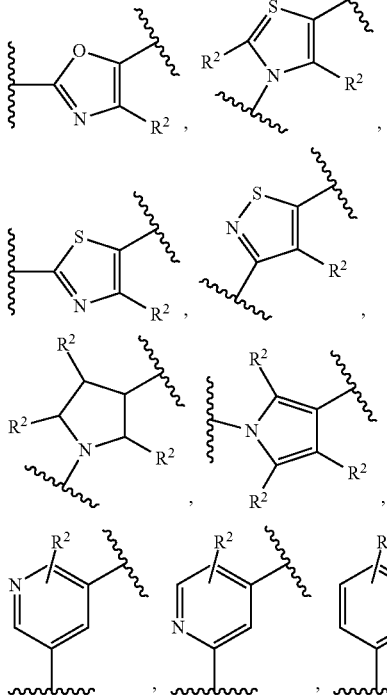

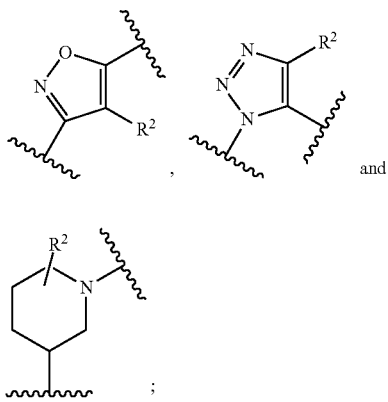

R$^{1a}$ is selected from the group consisting of: H, halo, CN, OH, C$_{1-4}$ alkoxy, —CHF$_2$, —CF$_3$, —CH$_2$NH$_2$, —OCHF$_2$, —CO(C$_{1-4}$ alkyl), —CONH$_2$, and —COOH;

R$^{1b}$ is selected from the group consisting of: H and halo;

R$^{1c}$ is selected from the group consisting of: H, halo, alkyl, and methoxy;

R$^3$ is selected from the group consisting of: phenyl substituted with 1-2 R$^{3a}$, pyridyl substituted with 1-2 R$^{3a}$, quinolinyl substituted with 1-2 R$^{3a}$, tetrahydroquinolinyl substituted with 1-2 R$^{3a}$, isoquinolinyl substituted with 1-2 R$^{3a}$, indolinyl substituted with 1-2 R$^{3a}$, C$_{3-6}$ cycloalkyl substituted with 1-2 R$^{3a}$, and bicycle[2,2,2]octane substituted with 1-2 R$^{3a}$; and R$^{4c}$ and R$^{4d}$ are independently selected from the group consisting of: H and Me;

other variables are as defined in Formula (III) above.

In another aspect, the present invention provides compounds of Formula (IV), or stereoisomers, tautomers, pharmaceutically acceptable salts, solvates, or prodrugs thereof, wherein:

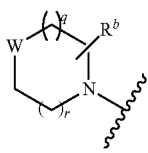

is selected from the group consisting of:

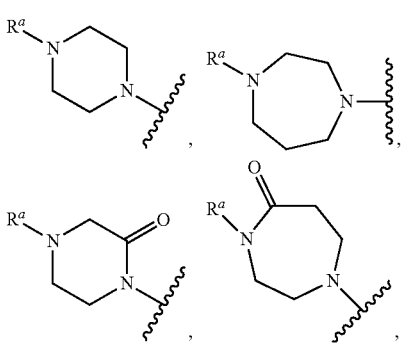

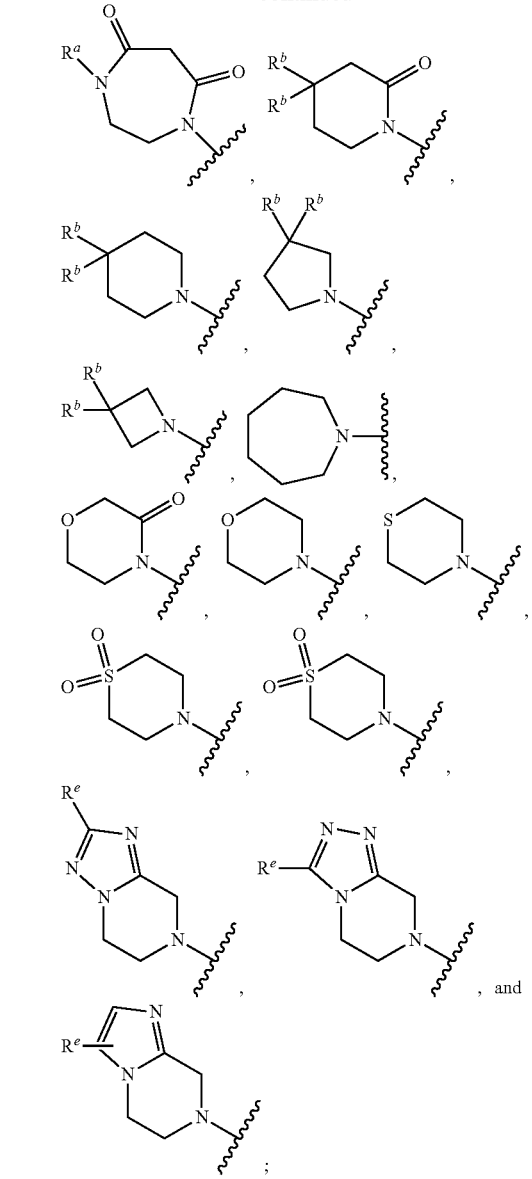

R$^{3a}$ is selected from the group consisting of: H, halo, C$_{1-4}$ alkyl, OH, CH$_2$OH, C$_{1-4}$ alkoxy, CN, NH$_2$, —CO$_2$H, —CH$_2$CO$_2$H, —CO$_2$(C$_{1-4}$ alkyl), —CO$_2$(CH$_2$)$_{1-2}$O(C$_{1-4}$ alkyl), —CO$_2$(CH$_2$)$_{1-2}$CON(C$_{1-4}$ alkyl)$_2$, —CONH$_2$, CONH(C$_{1-4}$ alkyl), —CON(C$_{1-4}$ alkyl)$_2$, —NHCO$_2$(C$_{1-4}$ alkyl), R$^8$, —CONHR$^8$, and —CO$_2$R$^8$;

R$^b$ is selected from the group consisting of: H, C$_{1-4}$ alkyl, OH, CN, NH$_2$, —N(C$_{1-4}$ alkyl)$_2$, C$_{1-4}$ alkoxy, —OCO—C$_{1-4}$ alkyl, —CO$_2$H, —CO$_2$(C$_{1-4}$ alkyl), —CONH$_2$, —CONR$^9$(C$_{1-4}$ alkyl), —CON(C$_{1-4}$ alkyl)$_2$, R$^8$, —OR$^8$, —COR$^8$, and —CO$_2$R$^8$; and optionally, R$^b$ and R$^b$ together with the carbon atom to which they are both attached form a 5-6 membered heterocyclic ring containing carbon atoms and 1-4 heteroatoms selected from NR$^a$, O, and S(O)$_p$; wherein said heterocycle is unsubstituted or substituted with =O; and R$^e$ is selected from the group consisting of: H, halo, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —NHCO$_2$(C$_{1-4}$ alkyl), —(CH$_2$)$_n$—C$_{3-6}$ cycloalkyl, —(CH$_2$)-phenyl, and —(CH$_2$)$_n$-5- to 6-membered heterocycle.

In another aspect, the present invention provides compounds of Formula (IV), or stereoisomers, tautomers, pharmaceutically acceptable salts, solvates, or prodrugs thereof, wherein:

R$^{1b}$ is selected from the group consisting of: H and F; and

R$^{3a}$ is selected from the group consisting of: H, halo, CN, —O, CH$_2$OH, CO$_2$H, —CO$_2$(C$_{1-4}$ alkyl), —CO(CH$_2$)$_{1-2}$CON(C$_{1-4}$ alkyl)$_2$, —CONH$_2$, —CONH(C$_{1-4}$ alkyl), —NHCO$_2$(C$_{1-4}$ alkyl), imidazole, pyrazole, and triazole;

other variables are as defined in Formula (IV) above.

In another aspect, the present invention provides compounds of Formula (IV), or stereoisomers, tautomers, pharmaceutically acceptable salts, solvates, or prodrugs thereof, wherein:

R$^{1a}$ is selected from the group consisting of: H, F, Cl, CN, COMe, OH, OMe, OCHF$_2$, CHF$_2$, and CF$_3$;

R$^{1b}$ is selected from the group consisting of: H and F,

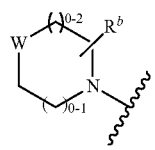

is selected from the group consisting of:

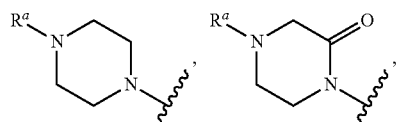

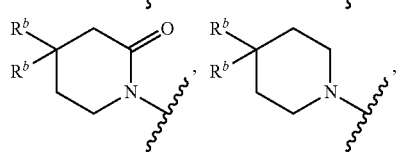

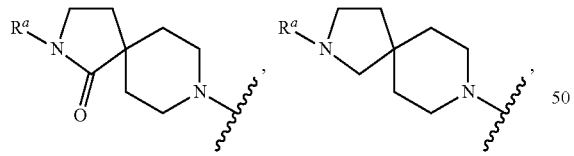

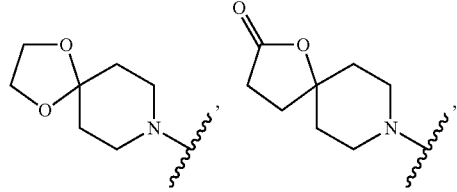

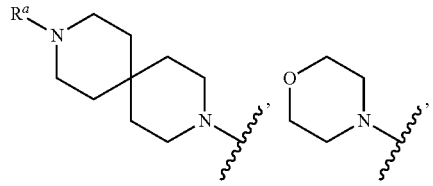

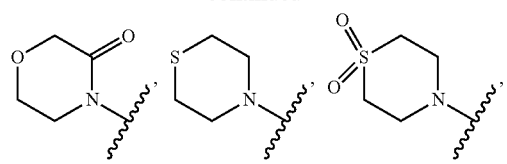

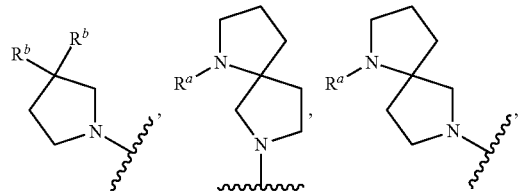

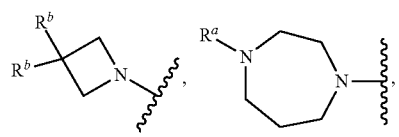

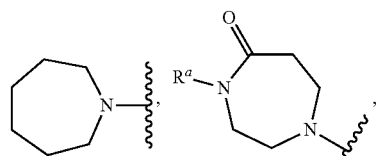

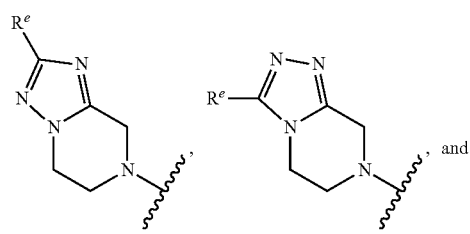

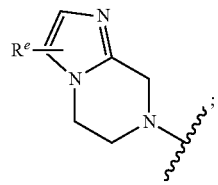

R$^3$ is selected from the group consisting of:

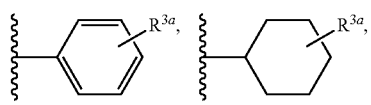

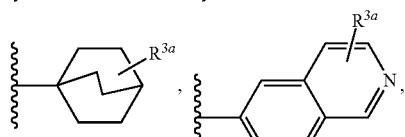

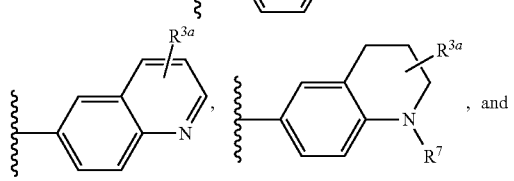

-continued

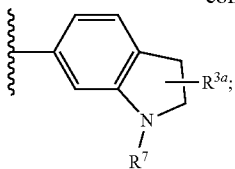

$R^{3a}$ is selected from the group consisting of: H, F, Cl, CN, =O, $CO_2H$, —$CH_2CO_2H$, $CO_2Me$, —$CO_2Et$, —$CO_2(i-Pr)$, —$CO_2(t-Bu)$, —$CO_2(n-Bu)$, —$CO_2(i-Bu)$, —$CO_2(CH_2)_2OMe$, —$CO_2CH_2CON(Me)_2$, —$NHCO_2Me$, —$CO_2(CH_2)_2$-triazole, and —$CO_2(cyclopentyl)$;

$R^b$ is selected from the group consisting of: H, F, Me, Et, i-propyl, CN, OH, —OMe, —$CO_2Me$, —$CO_2Et$, —$CON(Me)_2$, $NH_2$, —$N(Me)_2$, —$O(CH_2)N(Me)_2$, —$O(CH_2)OMe$,

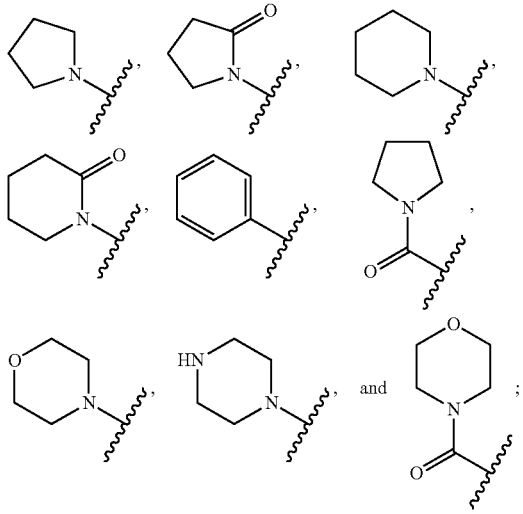

and $R^e$ is selected from the group consisting of: H, halo, $C_{1-4}$ alkyl, $C_{1-4}$ alkoxy, $OCF_3$, $NH_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —$NHCO_2(C_{1-4}$ alkyl), —$(CH_2)_n$—$C_{3-6}$ cycloalkyl, and —$(CH_2)_n$-phenyl;

other variables are as defined in Formula (IV) above.

In another aspect, the present invention provides compounds of Formula (V):

(V)

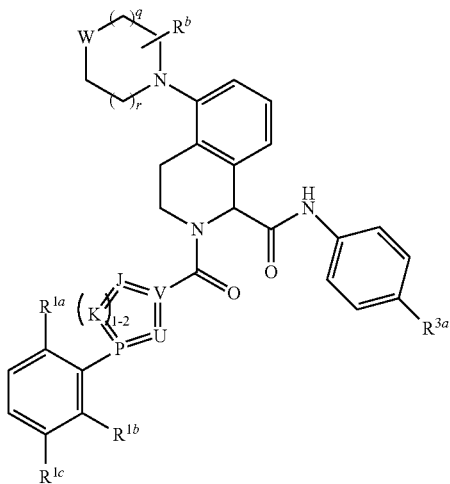

or stereoisomers, tautomers, pharmaceutically acceptable salts, solvates, or prodrugs thereof, wherein:

---- is an optional bond;

$R^{1a}$ is selected from the group consisting of: H, F, Cl, $CHF_2$, and $CF_3$;

$R^{1b}$ is selected from the group consisting of: H, F, and Cl;

$R^{1c}$ is selected from the group consisting of: H and Cl;

$R^{3a}$ is selected from the group consisting of: H, F, Cl, CN, $CO_2H$, —$CH_2CO_2H$, $CO_2Me$, —$CO_2Et$, —$CO_2(i-Pr)$, —$CO_2(t-Bu)$, —$CO_2(n-Bu)$, —$CO_2(i-Bu)$,—and $NHCO_2Me$;

q is 1 or 2; and r is 1 or 2;

other variables are as defined in Formula (III) above.

In another aspect, the present invention provides compounds of Formula (II), or stereoisomers, tautomers, pharmaceutically acceptable salts, solvates, or prodrugs thereof, wherein:

$R^3$ is selected from the group consisting of: phenyl substituted with 1-2 $R^{3a}$, $C_{3-6}$ cycloalkyl substituted with 1-2 $R^{3a}$, and heterocycle substituted with 1-2 $R^{3a}$;

$R^{3a}$ is selected from the group consisting of: H, halo, —OH, —$O(C_{1-4}$ alkyl), —CN, —$CO_2H$, —$CONH_2$, —$CO_2(C_{1-4}$ alkyl), —$CO_2$—$C_{1-4}$ alkylene-$O(C_{1-4}$ alkyl), —$CO_2$—$C_{1-4}$ alkylene-$N(C_{1-4}$ alkyl)$_2$, —$CO_2$—$C_{1-4}$ alkylene-O—$C_{1-4}$ alkylene-$N(C_{1-4}$ alkyl)$_2$, —$CO_2$—$C_{1-4}$ alkylene-O—$C_{1-4}$ alkylene-$O(C_{1-4}$ alkyl), —$NHCO_2(C_{1-4}$ alkyl), $R^c$, and —$CO_2R^c$;

$R^5$ is selected from the group consisting of: H, $R^8$, —$OR^8$, $COR^8$, —$CONHR^8$, and $NHCONHR^8$;

$R^8$ is selected from the group consisting of: —$(CH_2)_n$—$C_{3-6}$ cycloalkyl, —$(CH_2)_n$-phenyl and —$(CH_2)_n$-5- to 10-membered heterocycle containing carbon atoms and 1-4 heteroatoms selected from N, $NR^a$, O, and $S(O)_p$; wherein said cycloalkyl, phenyl and heterocycle are substituted with 1-3 $R^b$;

$R^a$ is selected from the group consisting of: H, $C_{1-4}$ alkyl, —$(CH_2)_nOH$, $CO(C_{1-4}$ alkyl), $COCF_3$, $CH_2CF_3$, $CO_2(C_{1-4}$ alkyl), —$CONH$—$C_{1-4}$ alkylene-$CO_2(C_{1-4}$ alkyl), $C_{1-4}$ alkylene-$CO_2(C_{1-4}$ alkyl), $R^c$, and $CO_2R^c$;

$R^b$ is selected from the group consisting of: H, —O, halo, CN, OH, $NO_2$, $C_{1-4}$ alkyl substituted with 1-2 $R^d$, $C_{1-4}$ alkoxy, $OCF_3$, $(CH_2)_nNH_2$, —$(CH_2)_n$ $N(C_{1-4}$ alkyl)$_2$, $CO(C_{1-4}$ alkyl), $CO(C_{1-4}$ haloalkyl), $CO_2(C_{1-4}$ alkyl), —$(CH_2)_n$—$CONH_2$, —$(CH_2)_n$—$CONH(C_{1-4}$ alkyl), —$(CH_2)_n$—$CON(C_{1-4}$ alkyl)$_2$, —$CONH$—$C_{1-4}$ alkylene-O $(C_{1-4}$ alkyl), —$CONH$—$C_{1-4}$ alkylene-$N(C_{1-4}$ alkyl)$_2$, —$NHCO(C_{1-4}$ alkyl), —$NHCO_2(C_{1-4}$ alkyl), —$S(O)_2NH_2$, —$S(O)_2NH(C_{1-4}$alkyl), $R^c$, $COR^c$, $CO_2R^c$, —$S(O)_2NH(C_{1-4}$alkyl)$R^c$, $NHCONHR^c$, and $CONHR^c$; and $R^c$ is selected from the group consisting of: —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, O, and $S(O)_p$; wherein each ring moiety is substituted with 1-2 $R^d$;

other variables are as defined in Formula (II) above.

In another aspect, the present invention provides compounds of Formula (VI):

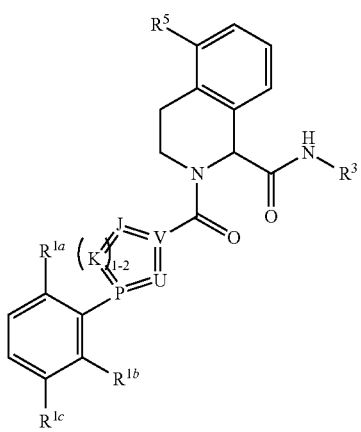

(VI)

or stereoisomers, tautomers, pharmaceutically acceptable salts, solvates, or prodrugs thereof, wherein:

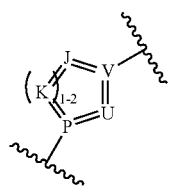

is selected from the group consisting of:

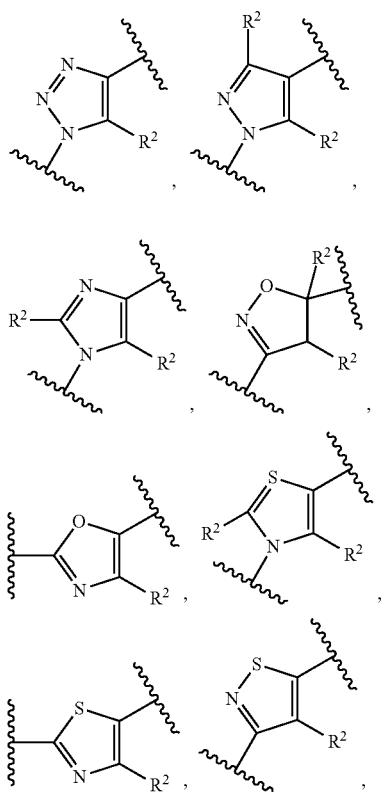

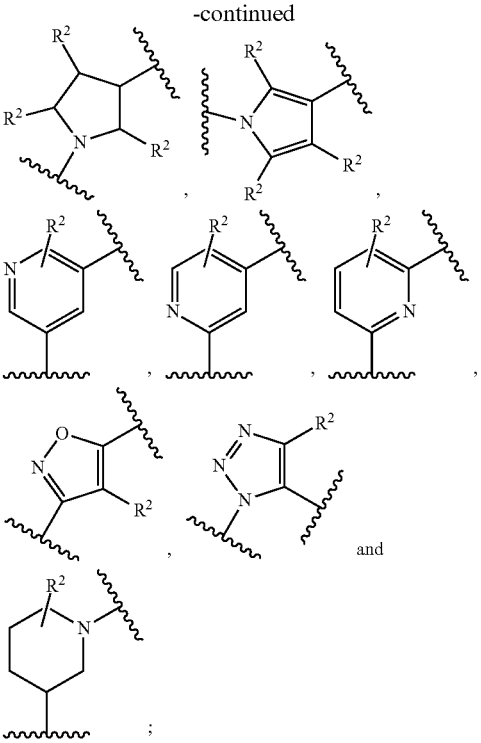

$R^{1a}$ is selected from the group consisting of: H, F, Cl, CN, OH, $C_{1-4}$ alkoxy, —$CHF_2$, —$CF_3$, —$CH_2NH_2$, —$OCHF_2$, —$CO(C_{1-4}$ alkyl), —$CONH_2$, and —COOH;

$R^{1b}$ is selected from the group consisting of: H and halo;

$R^{1c}$ is selected from the group consisting of: H, halo, $C_{1-2}$ alkyl, and methoxy;

$R^2$ is selected from the group consisting of: H, =O, OH, $NH_2$, $CF_3$, halo, and $C_{1-4}$ alkyl;

$R^3$ is selected from the group consisting of: phenyl substituted with 1-2 $R^{3a}$, pyridyl substituted with 1-2 $R^{3a}$, quinolinyl substituted with 1-2 $R^{3a}$, tetrahydroquinolinyl substituted with 1-2 $R^{3a}$, isoquinolinyl substituted with 1-2 $R^{3a}$, indolinyl substituted with 1-2 $R^{3a}$, $C_{3-6}$ cycloalkyl substituted with 1-2 $R^{3a}$, and bicycle[2,2,2]octane substituted with 1-2 $R^{3a}$; and $R^{3a}$ is selected from the group consisting of: H, halo, —OH, =O, —O($C_{1-4}$ alkyl), —CN, —$CO_2H$, —$CONH_2$, —$CO_2(C_{1-4}$ alkyl), —$CO_2$—$(CH_2)_{1-4}$—O($C_{1-4}$ alkyl), —$CO_2$—$(CH_2)_{1-4}$—N($C_{1-4}$ alkyl)$_2$, —$CO_2$—$(CH_2)_{1-4}$—O—$(CH_2)_{1-4}$—N($C_{1-4}$ alkyl)$_2$, —$CO_2$—$(CH_2)_{1-4}$—O—$(CH_2)_{1-4}$—O($C_{1-4}$ alkyl), —$NHCO_2(C_{1-4}$ alkyl), $R^c$, and —$CO_2R^c$;

other variables are as defined in Formula (II) above.

In another aspect, the present invention provides compounds of Formula (VI), or stereoisomers, tautomers, pharmaceutically acceptable salts, solvates, or prodrugs thereof, wherein:

$R^{1a}$ is selected from the group consisting of: H, F, $CF_3$, and $CO(C_{1-4}$ alkyl);

$R^{1b}$ is selected from the group consisting of: H and F;

$R^{1c}$ is Cl;

$R^3$ is selected from the group consisting of:

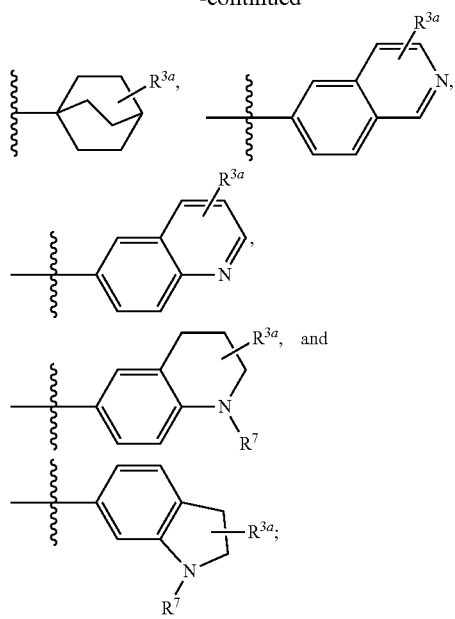
R³ᵃ is selected from the group consisting of: F, —OH, —OMe, —OEt, —CN, —CO₂H, —CONH₂, —CO₂Me, —CO₂Et, —CO₂(t-butyl), —CO₂(CH₂)₂OMe, —CO₂(CH₂)₂N(C₁₋₄ alkyl)₂, —CO₂(CH₂)₂O(CH₂)₂N(C₁₋₄ alkyl)₂, —CO₂(CH₂)₂O(CH₂)₂OMe, —NHCO₂Me, Rᶜ, and —CO₂Rᶜ;
R⁵ is selected from the group consisting of:
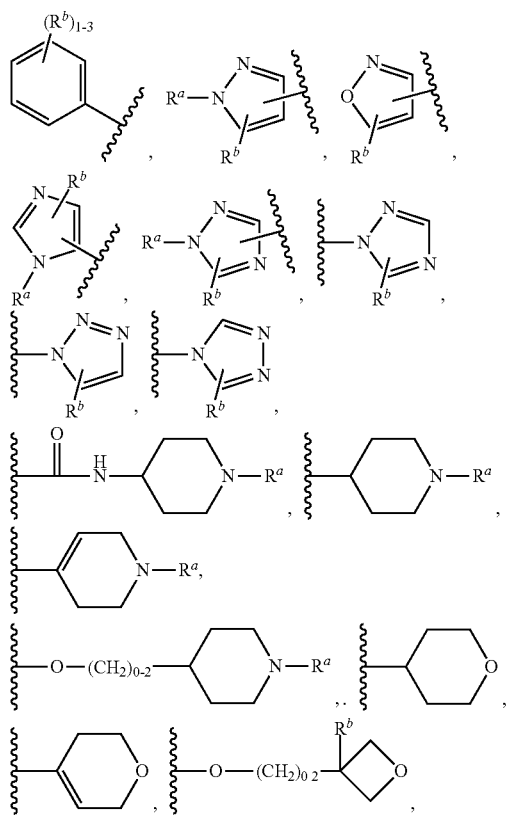
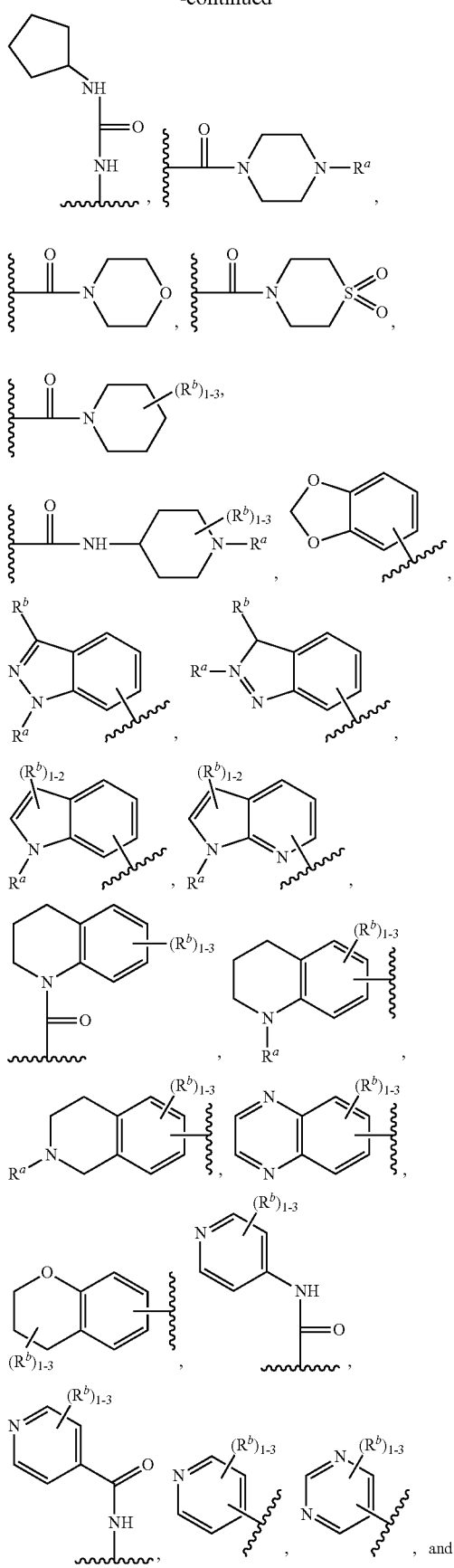

-continued

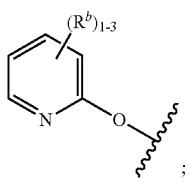

R$^a$ is selected from the group consisting of: H, Me, Et, —(CH$_2$)$_3$OH, COCF$_3$, COMe, CO$_2$Me, CO$_2$Et, CO$_2$(t-butyl), —CONH(CH$_2$)$_2$CO$_2$(C$_{1-4}$ alkyl), R$^c$, and CO$_2$R$^c$;

R$^b$ is selected from the group consisting of: H, Me, Et, Cl, OMe, OCF$_3$, NO$_2$, NH$_2$, N(Me)$_2$, CO$_2$Me, CO$_2$Et, CONH$_2$, —CONH(C$_{1-4}$ alkyl), —CON(C$_{1-4}$ alkyl)$_2$, —CONH(CH$_2$)$_{1-2}$O(C$_{1-4}$ alkyl), —CONH(CH$_2$)$_{1-2}$N(C$_{1-4}$ alkyl)$_2$, —NHCO$_2$(C$_{1-4}$ alkyl), R$^c$, COR$^c$, CONHR$^c$; and R$^c$ is selected from the group consisting of: —(CH$_2$)$_n$—C$_{3-6}$ cycloalkyl, —(CH$_2$)$_n$-phenyl, and —(CH$_2$)$_n$-5- to 6-membered heterocycle, wherein each ring moiety is substituted with 1-2 R$^d$.

In another aspect, the present invention provides compounds of Formula (VI), or stereoisomers, tautomers, pharmaceutically acceptable salts, solvates, or prodrugs thereof, wherein:

R$^{1a}$ is selected from the group consisting of: H, F, CF$_3$, and C(O)Me;

R$^{1b}$ is selected from the group consisting of: H and F;

R$^{1c}$ is Cl;

R$^{3a}$ is selected from the group consisting of: F and —CO$_2$H;

R$^b$ is selected from the group consisting of: Cl, OMe, OCF$_3$, NO$_2$, CONH$_2$, —CONHMe, —CONHEt, —CON(Me)$_2$, —CON(Et)$_2$, —CONH(CH$_2$)$_{1-2}$O(C$_{1-4}$ alkyl), —CONH(CH$_2$)$_{1-2}$N(C$_{1-4}$ alkyl)$_2$, NHCO$_2$Me, NHCO$_2$Et, and COR$^c$; and R$^c$ is selected from the group consisting of: —(CH$_2$)$_n$—C$_{3-6}$ cycloalkyl, —(CH$_2$)$_n$-phenyl, and —(CH$_2$)$_n$-5- to 6-membered heterocycle, wherein each ring moiety is substituted with 1-2 R$^d$;

other variables are as defined in Formula (VT) above.

In another aspect, the present invention provides compounds of Formula (II), or stereoisomers, tautomers, pharmaceutically acceptable salts, solvates, or prodrugs thereof, wherein:

R$^3$ is selected from the group consisting of: phenyl substituted with 1-2 R$^{3a}$ and pyridyl substituted with 1-2 R$^{3a}$;

R$^5$ is selected from the group consisting of: H, halo, C$_{1-4}$ alkyl substituted with 1-2 R$^b$, C$_{2-4}$ alkenyl substituted with 1-2 R$^b$, —OH, CN, —NH$_2$, —N(C$_{1-4}$ alkyl)$_2$, —NH$_2$—C$_{1-4}$ alkylene-OH, —O—C$_{1-4}$ alkylene-O(C$_{1-4}$ alkyl), —O—C$_{1-4}$ alkylene-N(C$_{1-4}$ alkyl)$_2$, —NHCO(C$_{1-4}$ alkyl), —NHSO$_2$(C$_{1-4}$ alkyl);

R$^{3a}$ is selected from the group consisting of: CH$_2$OH and —CO$_2$H;

R$^b$ is selected from the group consisting of: NH$_2$, CONH$_2$, CO$_2$(C$_{1-4}$ alkyl), R$^c$, and COR$^c$; and R$^c$ is selected from the group consisting of: —(CH$_2$)$_n$—C$_{3-6}$ cycloalkyl, —(CH$_2$)$_n$-phenyl, and —(CH$_2$)$_n$-5- to 6-membered heterocycle;

other variables are as defined in Formula (VI) above.

In another aspect, the present invention provides compounds of Formula (II), or stereoisomers, tautomers, pharmaceutically acceptable salts, solvates, or prodrugs thereof, wherein:

R$^5$ is selected from the group consisting of: H, C$_{1-4}$ alkyl substituted with 1-2 R$^b$, C$_{2-4}$ alkenyl substituted with 1-2 R$^b$, —N(Me)$_2$, —O(CH$_2$)$_2$N(Me)$_2$, O(CH$_2$)$_2$OMe, CONH(CH$_2$)$_2$N(Me)$_2$, —NHSO$_2$Me,

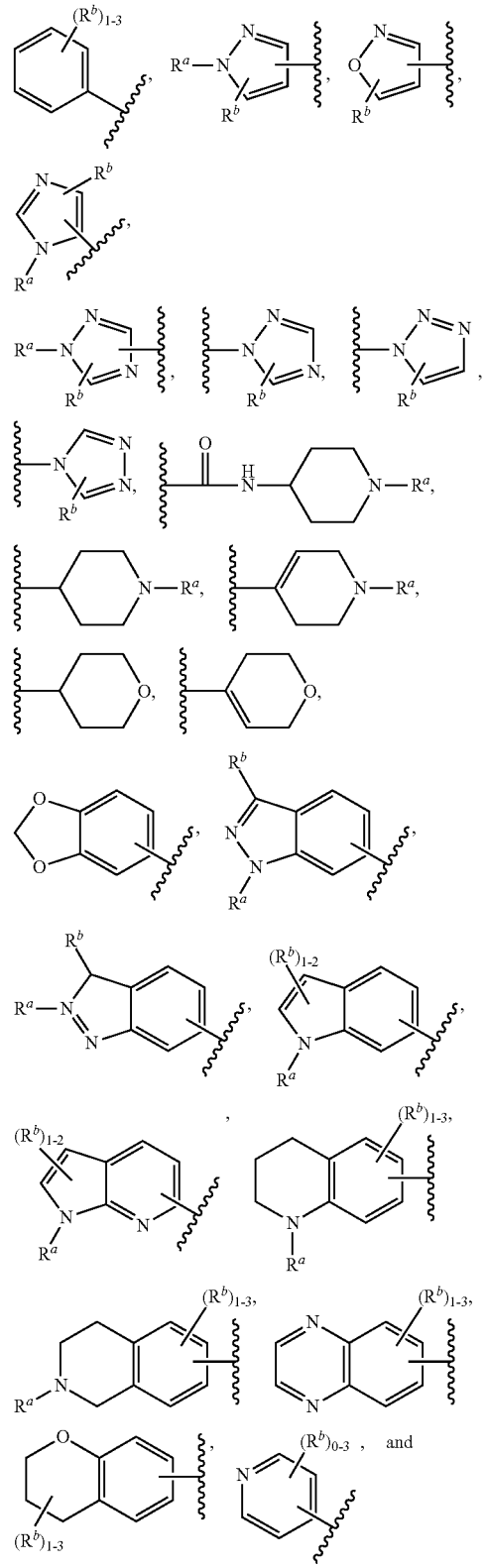

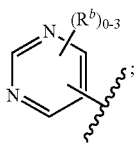

$R^{3a}$ is selected from the group consisting of: F, CN, CH$_2$OH, CO$_2$H, CO$_2$Me, CO$_2$Et, CO$_2$(i-Bu), and NHCO$_2$Me;

$R^a$ is selected from the group consisting of: H, methyl, —(CH$_2$)$_{0-3}$OH, COMe, COCF$_3$, CO$_2$Me, R$^c$, and CO$_2$R$^c$;

$R^b$ is selected from the group consisting of: H, Cl, OMe, OCF$_3$, NO$_2$, NH$_2$, —N(Me)$_2$, —CO$_2$Me, —CO$_2$Et, CONH$_2$, —CONHMe, —CONHEt, —CON(Me)$_2$, —CONH(CH$_2$)$_2$OMe, —CONH(CH$_2$)$_2$N(Me)$_2$, —NHCO$_2$Et, —NHCO$_2$Me, R$^c$, COR$^c$, and CONHR$^c$;

$R^c$ is selected from the group consisting of: —(CH$_2$)$_{0-1}$phenyl, pyrrolidine, pyrazole, imidazole, triazole, —(CH$_2$)$_{0-2}$morpholine, piperidine, methylpiperidine, and methylpiperazine, wherein each ring moiety is substituted with 1-2 R$^d$; and $R^d$ is selected from the group consisting of: H, =O, pyrrolidine, and N(Me)$_2$.

In another aspect, the present invention provides compounds of Formula (VII), (VIII), and (IX):

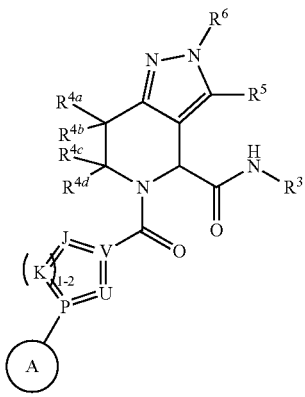

(VII)

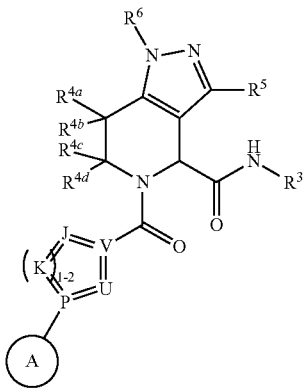

(VIII)

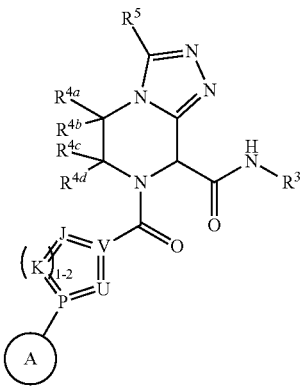

(IX)

or stereoisomers, tautomers, pharmaceutically acceptable salts, solvates, or prodrugs thereof, wherein:

ring A is selected from the group consisting of: C$_{3-10}$ carbocycle and 5- to 10-membered heterocycle containing carbon atoms and 1-3 heteroatoms selected from N, NH, NC$_{1-4}$alkyl, O, and S(O)$_p$, each optionally substituted with one or more R$^1$ as valence allows;

J, K, P, U, and V are each independently selected from the group consisting of: N, NH, O, S(O)$_p$, CR$^2$, and CHR$^2$;

$R^1$ is selected from the group consisting of: H, halo, NO$_2$, C$_{1-6}$ alkyl, OH, OMe, and CN;

$R^2$ is selected from the group consisting of: H, =O, OH, NH$_2$, CF$_3$, halo, C$_{1-4}$ alkyl (optionally substituted with OH), C$_{1-3}$ alkoxy, and C(O)C$_{1-3}$ alkyl;

$R^3$ is selected from the group consisting of: C$_{1-6}$ alkyl substituted with 1-3 R$^{3a}$, C$_{3-10}$ carbocycle substituted with 1-3 R$^{3a}$, and 5-10 membered heterocycle containing carbon atoms and 1-4 heteroatoms selected from the group consisting of N, NR$^7$, O, and S(O)$_p$; wherein said heterocycle is substituted with 1-3 R$^{3a}$;

$R^{3a}$ is selected from the group consisting of: H, halogen, C$_{1-4}$ alkyl, —OH, C$_{1-4}$ alkoxy, —CN, —NH$_2$, —NH(C$_{1-4}$ alkyl), —N(C$_{1-4}$ alkyl)$_2$, —CO$_2$H, —CH$_2$CO$_2$H, —CO$_2$(C$_{1-4}$ alkyl), —CO$_2$—C$_{1-4}$ alkylene-O(C$_{1-4}$ alkyl), —CO$_2$—C$_{1-4}$ alkylene-N(C$_{1-4}$ alkyl)$_2$, —CO$_2$—C$_{1-4}$ alkylene-O—C$_{1-4}$ alkylene-N(C$_{1-4}$ alkyl)$_2$, —CO$_2$—C$_{1-4}$ alkylene-O—C$_{1-4}$ alkylene-O(C$_{1-4}$ alkyl), —CONH$_2$, —CONH(C$_{1-6}$ alkyl), —CON(C$_{1-4}$ alkyl)$_2$, —CONH—C$_{1-4}$ alkylene-CO$_2$(C$_{1-4}$ alkyl), —CONHCO$_2$C$_{1-4}$ alkyl, —CONH—C$_{1-4}$ alkylene-NHCO(C$_{1-4}$ alkyl), —CONH—C$_{1-4}$ alkylene-CONH$_2$, —NHCOC$_{1-4}$ alkyl, —NHCO$_2$(C$_{1-4}$ alkyl), R$^c$, —CONHR$^c$, and —CO$_2$R$^c$;

$R^{4a}$, $R^{4b}$, $R^{4c}$, and $R^{4d}$ are independently selected from the group consisting of: H, F, and C$_{1-4}$ alkyl;

$R^5$ is selected from the group consisting of: H, halo, C$_{1-4}$ alkyl, and —NH$_2$; and $R^6$ is selected from the group consisting of: H and C$_{1-4}$ alkyl.

In another embodiment, the compounds of the present invention have Factor XIa or plasma kallikrein Ki values ≤10 µM.

In another embodiment, the compounds of the present invention have Factor XIa Ki or plasma kallikrein values ≤1 µM.

In another embodiment, the compounds of the present invention have Factor XIa Ki or plasma kallikrein values ≤0.5 µM.

In another embodiment, the compounds of the present invention have Factor XIa Ki or plasma kallikrein values ≤0.1 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof. Preferably, the anti-platelet agent(s) are clopidogrel and/or aspirin, or a combination thereof.

In another embodiment, the present invention provides a method for the treatment and/or prophylaxis of a thromboembolic disorder comprising administering to a patient in need of such treatment and/or prophylaxis a therapeutically effective amount of at least one of the compounds of the present invention or a stereoisomer, a tautomer, a pharmaceutically acceptable salt, or a solvate thereof.

In another embodiment, the present invention provides a compound of the present invention or a stereoisomer, a tautomer, a pharmaceutically acceptable salt, or a solvate thereof, for use in therapy.

In another embodiment, the present invention provides a compound of the present invention or a stereoisomer, a tautomer, a pharmaceutically acceptable salt, or a solvate thereof, for use in therapy for the treatment and/or prophylaxis of a thromboembolic disorder.

In another embodiment, the present invention also provides the use of a compound of the present invention or a stereoisomer, a tautomer, a pharmaceutically acceptable salt, or a solvate thereof, for the manufacture of a medicament for the treatment and/or prophylaxis of a thromboembolic disorder.

In another embodiment, the present invention provides a method for treatment and/or prophylaxis of a thromboembolic disorder, comprising: administering to a patient in need thereof a therapeutically effective amount of a first and second therapeutic agent, wherein the first therapeutic agent is a compound of the present invention or a stereoisomer, a tautomer, a pharmaceutically acceptable salt, or a solvate thereof, and the second therapeutic agent is at least one agent selected from a factor Xa inhibitor such as apixaban, rivaroxaban, betrixaban, edoxaban, an anti-coagulant agent, an anti-platelet agent, a thrombin inhibiting agent such as dabigatran, a thrombolytic agent, and a fibrinolytic agent. Preferably, the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, desulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

The thromboembolic disorder includes arterial cardiovascular thromboembolic disorders, venous cardiovascular thromboembolic disorders, arterial cerebrovascular thromboembolic disorders, and venous cerebrovascular thromboembolic disorders. Examples of the thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for the treatment and/or prophylaxis of an inflammatory disorder comprising: administering to a patient in need of such treatment and/or prophylaxis a therapeutically effective amount of at least one of the compounds of the present invention or a stereoisomer, a tautomer, a pharmaceutically acceptable salt, or a solvate thereof. Examples of the inflammatory disorder include, but are not limited to, sepsis, acute respiratory distress syndrome, and systemic inflammatory response syndrome.

In another embodiment, the present invention provides a method for the prophylaxis of a disease or condition in which plasma kallikrein activity is implicated comprising administering to a patient in need of such treatment and/or prophylaxis a therapeutically effective amount of at least one of the compounds of the present invention or a stereoisomer, a tautomer, a pharmaceutically acceptable salt, or a solvate thereof.

The disease or condition in which plasma kallikrein activity is implicated includes, but not limited to, impaired visual acuity, diabetic retinopathy, diabetic macular edema, hereditary angioedema, diabetes, pancreatitis, nephropathy, cardio myopathy, neuropathy, inflammatory bowel disease, arthritis, inflammation, septic shock, hypotension, cancer, adult respiratory distress syndrome, disseminated intravascular coagulation, and cardiopulmonary bypass surgery.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment and/or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans-(or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-hbutenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The terms "alkylcarbonyl" refer to an alkyl or substituted alkyl bonded to a carbonyl.

The term "carbonyl" refers to C(=O).

The term "hydroxy" or "hydroxyl" refers to OH.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, C(=O)$CH_3$, $SCH_3$, S(=O)$CH_3$, S(=O)$_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, Imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heternaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofiiryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted.

The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology,* 112:309-396, Academic Press (1985);

b) Bundgaard, H., Chapter 5, "Design and Application of Prodrugs", Krosgaard-Larsen, P. et al., eds., *A Textbook of Drug Design and Development,* pp. 113-191, Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$ alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyloxymethyl or ethoxycarbonyloxymethyl, glycyloxymethyl, phenylglycyloxymethyl, (5-methyl-2-oxo-1,3-dioxolen-4-yl)methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice,* The Royal Society of Chemistry, Cambridge, UK (1994); Testa, B. et al., *Hydrolysis in Drug and Prodrug Metabolism. Chemistry, Biochemistry and Enzymology,* VCHA and Wiley-VCH, Zurich, Switzerland (2003); Wermuth, C. G., ed., *The Practice of Medicinal Chemistry,* Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent other wise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "RBF" for round bottom flask, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl Ph phenyl
Bn benzyl
Boc tert-butyloxycarbonyl
Boc$_2$O di-tert-butyl dicarbonate
AcOH or HOAc acetic acid
AlCl$_3$ aluminum chloride
AIBN Azobisisobutyronitrile
BBr$_3$ boron tribromide
BCl$_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz carbobenzyloxy
CH$_2$Cl$_2$ dichloromethane
CH$_3$CN or ACN acetonitrile
CDCl$_3$ deutero-chloroform
CHCl$_3$ chloroform
mCPBA or m-CPBA meta-chloroperbenzoic acid
Cs$_2$CO$_3$ cesium carbonate
Cu(OAc)$_2$ copper (II) acetate
Cy$_2$NMe N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(III)-one
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylpholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
Et$_3$N or TEA triethylamine
EtOAc ethyl acetate
Et$_2$O diethyl ether
EtOH ethanol
GMF glass microfiber filter
Grubbs (II) (1,3-bis(2,4,6-trimethylphenyl)-2-imidazolidinylidene)dichloro (phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex hexane
HOBt or HOBT 1-hydroxybenzotriazole
H$_2$SO$_4$ sulfuric acid
Jones reagent CrO$_3$ in aqueous H$_2$SO$_4$, 2 M
K$_2$CO$_3$ potassium carbonate
K$_2$HPO$_4$ potassium phosphate dibasic
KOAc potassium acetate
K$_3$PO$_4$ potassium phosphate
LAH lithium aluminum hydride
LG leaving group
LiOH lithium hydroxide
MeOH methanol
MgSO$_4$ magnesium sulfate
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NCS N-chlorosuccinimide
NH$_3$ ammonia
NH$_4$Cl ammonium chloride
NH$_4$OH ammonium hydroxide
NH$_4$COOH ammonium formate
OTf triflate or trifluoromethanesulfonate
Pd$_2$(dba)$_3$ tris(dibenzylideneacetone)dipalladium(0)
Pd(OAe)$_2$ palladium(II) acetate
Pd/C palladium on carbon
Pd(dppf)Cl$_2$ [1,1'-bis(diphenylphosphino)ferrocene]dichloropalladium(II)
Ph$_3$PCl$_2$ triphenylphosphine dichloride
PG protecting group
POCl$_3$ phosphorus oxychloride
i-PrOH or IPA isopropanol
PS Polystyrene
SEM-Cl 2-(trimethysilyl)ethoxymethyl chloride
SiO$_2$ silica oxide
SnCl$_2$ tin(II) chloride
TBAI tetra-n-butylammonium iodide
TEA triethylamine
TFA trifluoroacetic acid
THF tetrahydrofuran
TMSCHN$_2$ trimethylsilyldiazomethane
T3P propane phosphonic acid anhydride
TRIS tris (hydroxymethyl) aminomethane
pTsOH p-toluenesulfonic acid The compounds of the present invention can be prepared in a number of ways known to one skilled in the art of organic synthesis.

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, artificial heart valves, and hemodialysis membranes.

Some conditions contribute to the risk of developing thrombosis. For example, alterations of the vessel wall, changes in the flow of blood, and alterations in the composition of the vascular compartment. These risk factors are collectively known as Virchow's triad. (Colman, R. W. et al., eds., *Hemostasis and Thrombosis, Basic Principles and Clinical Practice,* 5th Edition, p. 853, Lippincott Williams & Wilkins (2006)).

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy), are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., *Blood,* 105:453-463 (2005)).

An alternative way of initiation of coagulation is operative when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., *Blood,* 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact Activation Pathway", *Hemostasis and Thrombosis,* pp. 103-122, Lippincott Williams & Wilkins (2001); Schmaier, A. H., "Contact Activation", *Thrombosis and Hemorrhage,* pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., *J. Exp. Med.,* 202:271-281 (2005); Kleinschmitz et al., *J. Exp. Med.,* 203:513-518 (2006)). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D., *Trends Cardiovasc. Med.,* 10:198-204 (2000)).

In addition to the feedback activation mechanisms described above. thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.,* 101:329-354 (2001).) Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al., *Thromb. Haemost.,* 87:774-777 (2002); Wang et al., *J. Thromb. Haemost.,* 3:695-702 (2005)). Also, factor XI deficiency rescues the perinatal lethal phenotype of complete protein C deficiency (Chan et al., *Amer. J. Pathology,* 158:469-479 (2001)). Furthermore, baboon cross-reactive, function blocking antibodies to human factor XI protect against baboon arterial-venous shunt thrombosis (Gruber et al., *Blood,* 102:953-955 (2003)). Evidence for an antithrombotic effect of small molecule inhibitors of factor XIa is also disclosed in published U.S. Patent Publication No. 2004/0180855 A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or post-traumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., *Frontiers in Bioscience*, 6:201-207 (2001); Gailani, D. et al., *Blood Coagulation and Fibrinolysis*, 8:134-144 (1997).) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al., *Arterioscler. Thromb. Vasc. Biol.*, 20:2489-2493 (2000)). A second study establishes a positive correlation between the extent of coronary arteriosclerosis and factor XIa in complex with alpha 1 antitrypsin (Murakami, T. et al., *Arterioscler. Thromb. Vasc. Biol.*, 15:1107-1113 (1995)). In another study, Factor XI levels above the 90th percentile in patients were associated with a 2.2-fold increased risk for venous thrombosis (Meijers, J. C. M. et al., *N. Engl. J. Med.*, 342:696-701 (2000)).

Also, it is preferred to find new compounds with improved activity in in vitro clotting assays, compared with known serine protease inhibitors, such as the activated partial thromboplastin time (aPTT) or prothrombin time (PT) assay (for a description of the aPTT and PT assays see, Goodnight, S. H. et al., "Screening Tests of Hemostasis", *Disorders of Thrombosis and Hemostasis: A Clinical Guide*, 2nd Edition, pp. 41-51, McGraw-Hill, New York (2001)).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

Pre-clinical studies demonstrated significant antithrombotic effects of small molecule factor XIa inhibitors in rabbit and rat model of arterial thrombosis, at doses that preserved hemostasis. (Wong P. C. et al., *American Heart Association Scientific Sessions*, Abstract No. 6118, Nov. 12-15, 2006; Schumacher, W. et al., *Journal of Thrombosis and Haemostasis*, 3(Suppl. 1):P1228 (2005); Schumacher, W. A. et al., *European Journal of Pharmacology*, 167-174 (2007)). Furthermore, it was observed that in vitro prolongation of the aPTT by specific XIa inhibitors is a good predictor of efficacy in our thrombosis models. Thus, the in vitro aPTT test can be used as a surrogate for efficacy in vivo.

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include, but are not limited to, are family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Risk factors for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., *Medicine*(Baltimore), 78(5):285-291 (1999); Levine M. et al., *N. Engl. J. Med.*, 334(11):677-681 (1996); Blom, J. W. et al., *JAMA*, 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and anti-angiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., *British Journal of Surgery*, 88:913-930 (2001).)

A. In Vitro Assays

The effectiveness of compounds of the present invention as inhibitors of the coagulation Factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 25-200 pM (Haematologic Technologies) and the synthetic substrate S-2366 (pyroGlu-Pro-Arg-pNA; CHROMOGENIX® or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 0.5-10 nM, recombinant soluble tissue factor at a concentration of 10-40 nM and the synthetic substrate H-D-Ile-Pro-Arg-pNA (S-2288; CHROMOGENIX® or BMPM-2; AnaSpec) at a concentration of 0.001-0.0075 M.

Factor IXa determinations were made in 0.005 M calcium chloride, 0.1 M sodium chloride, 0.0000001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; CHROMOGENIX®) at a concentration of 0.0002-0.00035 M.

Factor XIIa determinations were made in 0.05 M HEPES buffer at pH 7.4 containing 0.145 M NaCl, 0.005 M KCl, and 0.1% PEG 8000. Determinations were made using purified human Factor XIIa at a final concentration of 4 nM (American Diagnostica) and the synthetic substrate SPECTROZYME® #312 (H-D-CHT-Gly-L-Arg-pNA.2AcOH; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human plasma kallikrein (Enzyme Research Laboratories) at a final assay concentration of 200 pM and the synthetic substrate S-2302 (H-(D)-Pro-Phe-Arg-pNA; CHROMOGENIX®) at a concentration of 0.00008-0.0004 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; CHROMOGENIX® or AnaSpec) at a concentration of 0.0002-0.0004 M.

The Michaelis constant, $K_m$, for substrate hydrolysis by each protease, was determined at 25° C. or 37° C. in the absence of inhibitor. Values of $K_i$ were determined by allowing the protease to react with the substrate in the presence of the inhibitor.

Reactions were allowed to go for periods of 20-180 minutes (depending on the protease) and the velocities (rate of absorbance or fluorescence change versus time) were measured. The following relationships were used to calculate $K_i$ values:

$$(V_{max}*S)/(K_m+S);$$

$$(v_o-v_s)/v_s=I/(K_i(1+S/K_m)) \text{ for a competitive inhibitor with one binding site; or}$$

$$v_s/v_o=A+((B-A)/1+((IC_{50}/(I)_n))); \text{ and}$$

$$K_i=IC_{50}/((1+S/K_m) \text{ for a competitive inhibitor}$$

where:

$v_o$ is the velocity of the control in the absence of inhibitor;
$v_s$ is the velocity in the presence of inhibitor;
$V_{max}$ is the maximum reaction velocity;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme: inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios >20 are considered selective.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5× or IC2×, the inhibitor concentration required to increase the clotting time by 50 or 100 percent, respectively. The IC1.5× or IC2× is found by linear interpolation from relative clotting time versus inhibitor concentration plots using inhibitor concentration that spans the IC1.5× or IC2×.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (SYSMEX®, Dade-Behring, Ill.). Similarly, clotting times can be determined from laboratory animal species or humans dosed with compounds of the invention.

Activated Partial Thromboplastin Time (aPTT) is determined using ALEXIN® (Trinity Biotech, Ireland) or ACTIN® (Dade-Behring, Ill.) following the directions in the package insert. Plasma (0.05 mL) is warmed to 37° C. for 1 minute. ALEXIN® or ACTIN® (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus or INNOVIN®, Dade-Behring, Ill.) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

The exemplified Examples disclosed below were tested in the Factor XIa assay described above and found having Factor XIa inhibitory activity. A range of Factor XIa inhibitory activity (Ki values) of ≤10 μM (10000 nM) was observed. Table A below lists Factor XIa Ki values measured at 25° C. for the following examples.

TABLE A

| Example No. | Factor XIa Ki (nM) |
| --- | --- |
| 1 | 13.48 |
| 2 | 5582.00 |
| 3 | 6.44 |
| 4 | <5.00 |
| 5 | 554.60 |
| 6 | <5.00 |
| 7 | <5.00 |
| 8 | <5.00 |
| 9 | <5.00 |
| 10 | <5.00 |
| 11 | 164.60 |
| 12 | <5.00 |
| 13 | 11.91 |
| 14 | <5.00 |
| 15 | 9.12 |
| 16 | <5.00 |
| 17 | <5.00 |
| 18 | 44.07 |
| 19 | <5.00 |
| 20 | 78.68 |
| 21 | <5.00 |
| 22 | 19.48 |
| 23 | <5.00 |
| 24 | 5.61 |
| 25 | 3550.00 |
| 26 | 7.07 |
| 27 | <5.00 |
| 28 | <5.00 |

TABLE A-continued

| Example No. | Factor XIa Ki (nM) |
| --- | --- |
| 29 | 58.89 |
| 30 | <5.00 |
| 31 | <5.00 |
| 32 | <5.00 |
| 33 | <5.00 |
| 34 | <5.00 |
| 35 | <5.00 |
| 36 | <5.00 |
| 37 | <5.00 |
| 38 | <5.00 |
| 39 | <5.00 |
| 40 | <5.00 |
| 41 | <5.00 |
| 42 | <5.00 |
| 43 | <5.00 |
| 44 | <5.00 |
| 45 | 20.56 |
| 46 | <5.00 |
| 47 | <5.00 |
| 48 | 89.62 |
| 49 | <5.00 |
| 50 | <5.00 |
| 51 | 54.51 |
| 52 | <5.00 |
| 53 | <5.00 |
| 54 | 8.83 |
| 55 | <5.00 |
| 56 | <5.00 |
| 57 | 33.10 |
| 58 | <5.00 |
| 59 | <5.00 |
| 60 | 47.75 |
| 61 | <5.00 |
| 62 | 74.64 |
| 63 | <5.00 |
| 64 | <5.00 |
| 65 | 18.88 |
| 66 | <5.00 |
| 67 | <5.00 |
| 68 | <5.00 |
| 69 | <5.00 |
| 70 | 29.34 |
| 71 | 913.30 |
| 72 | <5.00 |
| 73 | <5.00 |
| 74 | <5.00 |
| 75 | <5.00 |
| 76 | <5.00 |
| 77 | <5.00 |
| 78 | 9.16 |
| 79 | 113.80 |
| 80 | <5.00 |
| 81 | <5.00 |
| 82 | <5.00 |
| 83 | <5.00 |
| 84 | <5.00 |
| 85 | <5.00 |
| 86 | <5.00 |
| 87 | 43.02 |
| 88 | 391.10 |
| 89 | <5.00 |
| 90 | <5.00 |
| 91 | <5.00 |
| 92 | <5.00 |
| 93 | 6.65 |
| 94 | 23.57 |
| 95 | 14.69 |
| 96 | 20.29 |
| 97 | 9.13 |
| 98 | 6.69 |
| 99 | <5.00 |
| 100 | 288.80 |
| 101 | <5.00 |
| 102 | <5.00 |
| 103 | 17.90 |
| 104 | <5.00 |
| 105 | <5.00 |
| 106 | <5.00 |

TABLE A-continued

| Example No. | Factor XIa Ki (nM) |
|---|---|
| 107 | <5.00 |
| 108 | 48.81 |
| 109 | 14.51 |
| 110 | 72.69 |
| 111 | 6.04 |
| 112 | <5.00 |
| 113 | <5.00 |
| 114 | 28.09 |
| 115 | 21.32 |
| 116 | 13.55 |
| 117 | <5.00 |
| 118 | 37.95 |
| 119 | 4444.00 |
| 120 | 3936.00 |
| 121 | 1047.00 |
| 122 | 16.76 |
| 123 | 7.69 |
| 124 | <5.00 |
| 125 | 9.62 |
| 126 | <5.00 |
| 127 | <5.00 |
| 128 | <5.00 |
| 129 | <5.00 |
| 130 | 28.34 |
| 131 | <5.00 |
| 132 | 124.50 |
| 133 | 12.56 |
| 134 | <5.00 |
| 135 | <5.00 |
| 136 | 6.97 |
| 137 | <5.00 |
| 138 | <5.00 |
| 139 | 133.40 |
| 140 | 39.67 |
| 141 | 5.95 |
| 142 | 56.22 |
| 143 | 5.23 |
| 144 | 3029.00 |
| 145 | 7.87 |
| 146 | 1197.00 |
| 147 | 2687.00 |
| 148 | 69.50 |
| 149 | 7159.00 |
| 150 | 2604.00 |
| 151 | — |
| 152 | 465.60 |
| 153 | 5.73 |
| 154 | <5.00 |
| 155 | <5.00 |
| 156 | <5.00 |
| 157 | <5.00 |
| 158 | <5.00 |
| 159 | 13.25 |
| 160 | 30.30 |
| 161 | <5.00 |
| 162 | <5.00 |
| 163 | <5.00 |
| 164 | 9.17 |
| 165 | <5.00 |
| 166 | <5.00 |
| 167 | <5.00 |
| 168 | <5.00 |
| 169 | <5.00 |
| 170 | <5.00 |
| 171 | <5.00 |
| 172 | <5.00 |
| 173 | <5.00 |
| 174 | <5.00 |
| 175 | <5.00 |
| 176 | <5.00 |
| 177 | <5.00 |
| 178 | <5.00 |
| 179 | 5.92 |
| 180 | 5.20 |
| 181 | <5.00 |
| 182 | <5.00 |
| 183 | <5.00 |
| 184 | <5.00 |
| 185 | — |
| 186 | <5.00 |
| 187 | <5.00 |
| 188 | <5.00 |
| 189 | 410.70 |
| 190 | 98.12 |
| 191 | 13.42 |
| 192 | 9.97 |
| 193 | 19.90 |
| 194 | 57.10 |
| 195 | 40.13 |
| 196 | 7.10 |
| 197 | <5.00 |
| 198 | 49.50 |
| 199 | 2305.00 |
| 200 | 41.74 |
| 201 | 9.88 |
| 202 | <5.00 |
| 203 | <5.00 |
| 204 | <5.00 |
| 205 | <5.00 |
| 206 | <5.00 |
| 207 | <5.00 |
| 208 | <5.00 |
| 209 | 915.20 |
| 210 | <5.00 |
| 211 | <5.00 |
| 212 | 20.88 |
| 213 | <5.00 |
| 214 | 713.20 |
| 215 | <5.00 |
| 216 | <5.00 |
| 217 | 15.23 |
| 218 | 720.40 |
| 219 | <5.00 |
| 220 | 768.60 |
| 221 | 178.60 |
| 222 | 29.97 |
| 223 | 2630.00 |
| 224 | <5.00 |
| 225 | <5.00 |
| 226 | <5.00 |
| 227 | <5.00 |
| 228 | <5.00 |
| 229 | <5.00 |
| 230 | <5.00 |
| 231 | 135.80 |
| 232 | 4132.00 |
| 233 | 5.45 |
| 234 | <5.00 |
| 235 | 23.25 |
| 236 | 454.00 |
| 237 | 15.35 |
| 238 | 634.90 |
| 239 | 6.48 |
| 240 | 174.90 |
| 241 | 8.78 |
| 242 | 187.80 |
| 243 | <5.00 |
| 244 | 38.67 |
| 245 | <5.00 |
| 246 | <5.00 |
| 247 | <5.00 |
| 248 | <5.00 |
| 249 | <5.00 |
| 250 | <5.00 |
| 251 | 14.66 |
| 252 | <5.00 |
| 253 | 11.06 |
| 254 | <5.00 |
| 255 | 7.13 |
| 256 | 12.49 |
| 257 | <5.00 |
| 258 | 126.90 |
| 259 | <5.00 |
| 260 | 2463.00 |
| 261 | 947.90 |
| 262 | <5.00 |

TABLE A-continued

| Example No. | Factor XIa Ki (nM) |
| --- | --- |
| 263 | 11.53 |
| 264 | <5.00 |
| 265 | 13.17 |
| 266 | 420.20 |
| 267 | 102.70 |
| 268 | 1428.00 |
| 269 | 33.47 |
| 270 | 20.37 |
| 271 | <5.00 |
| 272 | 975.50 |
| 273 | <5.00 |
| 274 | <5.00 |
| 275 | 10.73 |
| 276 | — |
| 277 | — |
| 278 | <5.00 |
| 279 | <5.00 |
| 280 | 36.51 |
| 281 | 12.75 |
| 282 | <5.00 |
| 283 | 8.27 |
| 284 | <5.00 |
| 285 | <5.00 |
| 286 | 266.20 |
| 287 | <5.00 |
| 288 | 155.40 |
| 289 | <5.00 |
| 290 | 13.42 |
| 291 | <5.00 |
| 292 | 153.60 |
| 293 | <5.00 |
| 294 | 73.92 |
| 295 | <5.00 |
| 296 | 24.92 |
| 297 | 46.29 |
| 298 | 64.84 |
| 299 | 62.71 |
| 300 | <5.00 |
| 301 | <5.00 |
| 302 | 81.70 |
| 303 | 659.10 |
| 304 | 24.23 |
| 305 | <5.00 |
| 306 | — |
| 307 | 164.90 |
| 308 | 6.03 |
| 309 | <5.00 |
| 310 | 82.02 |
| 311 | 18.45 |
| 312 | <5.00 |
| 313 | 4823.00 |
| 314 | <5.00 |
| 315 | <5.00 |
| 316 | 42.88 |
| 317 | <5.00 |
| 318 | <5.00 |
| 319 | <5.00 |
| 320 | 157.80 |
| 321 | 235.60 |
| 322 | 8.21 |
| 323 | 5.28 |
| 324 | 37.15 |
| 325 | 2403.00 |
| 326 | 330.40 |
| 327 | 815.80 |
| 328 | 1966.00 |
| 329 | 26.64 |
| 330 | 3513.00 |
| 331 | 7052.00 |
| 332 | — |
| 333 | 18.19 |
| 334 | 10.61 |
| 335 | <5.00 |
| 336 | <5.00 |
| 337 | 27.92 |
| 338 | — |
| 339 | — |
| 340 | <5.00 |
| 341 | <5.00 |
| 342 | — |
| 343 | — |

The exemplified Examples disclosed below were tested in the Plasma Kallikrein assay described above and found having plasma kallikrein inhibitory activity. A range of plasma kallikrein inhibitory activity (Ki values) of ≤10 μM (10000 nM) was observed. Table B below lists Plasma Kallikrein Ki values measured at 25° C. or 37° C. (*) for the following examples.

TABLE B

| Example No. | Plasma Kallikrein Ki (nM) |
| --- | --- |
| 1 | 20.83 |
| 2 | NT |
| 3 | 13.12 |
| 4 | 6.38 |
| 5 | 1384.00 |
| 6 | 2.40 |
| 7 | 29.95 |
| 8 | 3.37 |
| 9 | 72.90 |
| 10 | 1.08 |
| 11 | 1056.00 |
| 12 | 9.88 |
| 13 | 427.40 |
| 14 | 6.27 |
| 15 | 219.20 |
| 16 | 4.55 |
| 17 | 3.00 |
| 18 | 891.60 |
| 19 | 1.51 |
| 20 | 839.80 |
| 21 | 9.60* |
| 22 | 869.20* |
| 23 | 17.60* |
| 24 | 395.70* |
| 25 | >4340.00* |
| 26 | 62.00* |
| 27 | 46.80* |
| 28 | 55.80* |
| 29 | 1200.00* |
| 30 | 15.73 |
| 31 | 19.85 |
| 32 | 17.50 |
| 33 | 9.54 |
| 34 | 0.46 |
| 35 | 22.95 |
| 36 | 26.68 |
| 37 | 12.90 |
| 38 | 3.51 |
| 39 | 2.63 |
| 40 | 2.81 |
| 41 | 7.68 |
| 42 | 13.12 |
| 43 | 16.22 |
| 44 | 3.28 |
| 45 | 363.80 |
| 46 | 50.15 |
| 47 | 20.04 |
| 48 | 452.50 |
| 49 | 1.39 |
| 50 | 4.94 |
| 51 | 339.80 |
| 52 | 1.79 |
| 53 | 1.21 |
| 54 | 50.37 |
| 55 | 0.92 |
| 56 | 5.60 |
| 57 | 275.60 |
| 58 | 3.24 |

TABLE B-continued

| Example No. | Plasma Kallikrein Ki (nM) |
|---|---|
| 59 | 10.10 |
| 60 | 698.10 |
| 61 | 5.89 |
| 62 | 399.30 |
| 63 | 2.71 |
| 64 | 4.70 |
| 65 | 259.80 |
| 66 | 2.57 |
| 67 | 7.17 |
| 68 | 22.49 |
| 69 | 9.92 |
| 70 | 11.47 |
| 71 | >6000.00* |
| 72 | 13.84 |
| 73 | 4.18 |
| 74 | 27.61 |
| 75 | 25.75 |
| 76 | 15.32 |
| 77 | 7.96 |
| 78 | 36.15 |
| 79 | 719.00 |
| 80 | 6.37 |
| 81 | 20.69 |
| 82 | 23.12 |
| 83 | 12.12 |
| 84 | 15.85 |
| 85 | 5.29 |
| 86 | NT |
| 87 | NT |
| 88 | 2085.00 |
| 89 | 11.40 |
| 90 | 5.37 |
| 91 | 3.84 |
| 92 | 5.60 |
| 93 | 9.65 |
| 94 | 10.54 |
| 95 | 16.86 |
| 96 | 33.99 |
| 97 | 21.71 |
| 98 | 5.20 |
| 99 | 2.74 |
| 100 | 493.80 |
| 101 | 1.75 |
| 102 | 1.39 |
| 103 | 33.98 |
| 104 | 0.96 |
| 105 | 1.69 |
| 106 | 7.58 |
| 107 | 12.50 |
| 108 | 50.04 |
| 109 | 2.29 |
| 110 | 22.99 |
| 111 | 5.60 |
| 112 | 3.16 |
| 113 | 11.94 |
| 114 | 15.20 |
| 115 | 61.30 |
| 116 | 127.90 |
| 117 | 16.29 |
| 118 | 249.80* |
| 119 | 1104.00* |
| 120 | 516.70* |
| 121 | 7896.00* |
| 122 | 99.80* |
| 123 | 21.10* |
| 124 | 36.20* |
| 125 | 54.10* |
| 126 | 94.00* |
| 127 | 195.60* |
| 128 | 65.30* |
| 129 | 34.00* |
| 130 | 125.70* |
| 131 | 60.30* |
| 132 | 1624.00* |
| 133 | 750.30* |
| 134 | 24.40* |
| 135 | 399.40* |
| 136 | 157.30* |
| 137 | 53.40* |
| 138 | 25.90* |
| 139 | >13,020.00* |
| 140 | 2371.00* |
| 141 | 160.60* |
| 142 | 426.50* |
| 143 | 236.70* |
| 144 | 11,650.00* |
| 145 | 251.70* |
| 146 | >2,000.00* |
| 147 | >6,000.00* |
| 148 | 1250.00* |
| 149 | — |
| 150 | >6,000.00* |
| 151 | 815.60 |
| 152 | 2516.00 |
| 153 | 62.22 |
| 154 | 5.26 |
| 155 | 23.91 |
| 156 | 30.10 |
| 157 | 29.50 |
| 158 | 139.60 |
| 159 | 21.88 |
| 160 | 117.30 |
| 161 | 2.46 |
| 162 | 49.92 |
| 163 | — |
| 164 | — |
| 165 | — |
| 166 | — |
| 167 | — |
| 168 | — |
| 169 | — |
| 170 | — |
| 171 | — |
| 172 | — |
| 173 | — |
| 174 | — |
| 175 | — |
| 176 | — |
| 177 | — |
| 178 | — |
| 179 | — |
| 180 | — |
| 181 | — |
| 182 | — |
| 183 | — |
| 184 | — |
| 185 | — |
| 186 | — |
| 187 | — |
| 188 | — |
| 189 | 540.30 |
| 190 | 163.30 |
| 191 | 12.26 |
| 192 | 55.60 |
| 193 | 2.34 |
| 194 | 41.50 |
| 195 | 30.85 |
| 196 | 11.95 |
| 197 | 10.04 |
| 198 | 121.50 |
| 199 | >6,000.00* |
| 200 | 10.70 |
| 201 | 4.21 |
| 202 | 1.11 |
| 203 | 1.29 |
| 204 | 10.98 |
| 205 | 0.64 |
| 206 | 68.07 |
| 207 | 30.86 |
| 208 | 447.20 |
| 209 | 490.90 |
| 210 | 1.34 |
| 211 | 0.52 |
| 212 | 2.89 |

TABLE B-continued

| Example No. | Plasma Kallikrein Ki (nM) |
|---|---|
| 213 | 12.21 |
| 214 | — |
| 215 | 20.24 |
| 216 | 0.36 |
| 217 | 3.12 |
| 218 | — |
| 219 | 1.96 |
| 220 | 178.60 |
| 221 | 9.56 |
| 222 | 10.44 |
| 223 | 3508.00 |
| 224 | 92.01 |
| 225 | 48.80 |
| 226 | 7.65 |
| 227 | — |
| 228 | — |
| 229 | 123.70* |
| 230 | 12.30* |
| 231 | 1286.00* |
| 232 | 29.70* |
| 233 | >13,020.00* |
| 234 | 26.90* |
| 235 | 477.60* |
| 236 | >4,340.00* |
| 237 | 130.20* |
| 238 | >4,340.00* |
| 239 | 84.80* |
| 240 | >4,340.00* |
| 241 | 66.70* |
| 242 | 1230.00* |
| 243 | 37.60* |
| 244 | 635.00* |
| 245 | 68.20* |
| 246 | 29.70* |
| 247 | 9.20* |
| 248 | 83.20* |
| 249 | 20.40* |
| 250 | 6.80* |
| 251 | 600.60* |
| 252 | 42.76 |
| 253 | 156.00 |
| 254 | 26.71 |
| 255 | 218.50 |
| 256 | 197.80 |
| 257 | 24.02 |
| 258 | 1624.00 |
| 259 | 77.89 |
| 260 | 4750.00 |
| 261 | 891.10 |
| 262 | 4.36 |
| 263 | 68.14 |
| 264 | 11.06 |
| 265 | 178.10 |
| 266 | 686.80 |
| 267 | 353.90 |
| 268 | 178.00* |
| 269 | 204.60 |
| 270 | 268.60 |
| 271 | 7.65 |
| 272 | >6,000.00* |
| 273 | 7.65 |
| 274 | 4.87 |
| 275 | 11.83 |
| 276 | — |
| 277 | — |
| 278 | 1.98 |
| 279 | 30.83 |
| 280 | 282.90 |
| 281 | 78.95 |
| 282 | 1.87 |
| 283 | 75.33 |
| 284 | 6.25 |
| 285 | 19.80 |
| 286 | 3286.00 |
| 287 | 1.82 |
| 288 | 824.00 |
| 289 | 2.63 |
| 290 | 100.60 |
| 291 | 15.20 |
| 292 | 758.00 |
| 293 | 3.24 |
| 294 | 111.40 |
| 295 | 2.44 |
| 296 | 185.90 |
| 297 | 1281.00 |
| 298 | 1010.00 |
| 299 | 316.00 |
| 300 | 4.15 |
| 301 | — |
| 302 | — |
| 303 | 1963.00 |
| 304 | 231.50 |
| 305 | 31.70 |
| 306 | |
| 307 | 593.30 |
| 308 | 79.67 |
| 309 | 28.84 |
| 310 | 610.10 |
| 311 | 786.60 |
| 312 | 27.26 |
| 313 | >6,000.00* |
| 314 | 10.29 |
| 315 | 19.63 |
| 316 | 577.90 |
| 317 | 41.13 |
| 318 | 21.15 |
| 319 | 6.41 |
| 320 | 123.50 |
| 321 | 177.10 |
| 322 | 137.80 |
| 323 | 99.25 |
| 324 | 958.20 |
| 325 | >6,000.00* |
| 326 | >2,000.00* |
| 327 | >6,000.00* |
| 328 | >6,000.00* |
| 329 | 229.00 |
| 330 | >6,000.00* |
| 331 | >6,000.00* |
| 332 | — |
| 333 | 61.26 |
| 334 | 6.26 |
| 335 | 96.90* |
| 336 | 1.4* |
| 337 | 68.10* |
| 338 | 251.10* |
| 339 | 84.60* |
| 340 | 13.80* |
| 341 | 46.90* |
| 342 | — |
| 343 | 114.40* |

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arteriovenous Shunt Thrombosis Models.

a. In Vivo Electrically-Induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arteriovenous (AV) Shunt Thrombosis Model

The rabbit AV shunt model, described by Wong et al. (Wong, P. C. et al., *J. Pharmacol. Exp. Ther.* 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, Ill.).

The anti-inflammatory effect of these compounds can be demonstrated in an Evans Blue dye extravasation assay using C1-csterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient. Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels. Solid dispersions are also called solid-state dispersions. In some embodiments, any compound described herein is formulated as a spray dried dispersion (SDD). An SDD is a single phase amorphous molecular dispersion of a drug in a polymer matrix. It is a solid solution prepared by dissolving the drug and a polymer in a solvent (e.g., acetone, methanol or the like) and spray drying the solution. The solvent rapidly evaporates from droplets which rapidly solidifies the polymer and drug mixture trapping the drug in amorphous form as an amorphous molecular dispersion.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions, Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 100 milligrams per dosage unit, and the second anti-coagulant in an amount of about 1 to about 50 milligrams per dosage unit.

Where the compounds of the present invention are administered in combination with an anti-platelet agent, by way of general guidance, typically a daily dosage may be about 0.01 to about 25 milligrams of the compound of the present invention and about 50 to about 150 milligrams of the anti-platelet agent, preferably about 0.1 to about 1 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 1 milligrams of the compound of the present invention, per kilogram of patient body weight and, in the case of the thrombolytic agents, the usual dosage of the thrombolytic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (alliskerin) and vasopepsidase inhibitors, an antiarrythmic agent selected from $I_{Kur}$ inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, $P2Y_1$ receptor antagonists, $P^2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents Other anticoagulant agents (or coagulation inhibitory agents) that may be used in combination with the compounds of this invention include warfarin, heparin (either unfractionated heparin or any commercially available low molecular weight heparin, for example LOVENOX®), synthetic pentasaccharide, direct acting thrombin inhibitors including hirudin and argatroban, as well as other factor VIIa inhibitors, factor IXa inhibitors, factor Xa inhibitors (e.g., ARIXTRA®, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDs) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDs, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as Sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors $P2Y_1$ and $P2Y_{12}$, with $P2Y_{12}$ being even more preferred. Preferred $P2Y_{12}$ receptor antagonists include clopidogrel, ticlopidine, prasugrel, ticagrelor, and cangrelor, and pharmaceutically acceptable salts or prodrugs thereof. Ticlopidine and clopidogrel are also preferred compounds since they are known to be more gentle than aspirin on the gastro-intestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including scrotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohimndin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPARgamma modulators (e.g., rosiglitazone), compounds that have multiple functionality for modulating the activities of various combinations of PPARalpha, PPARganmma and PPARdelta, prubucul or delivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa, XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 μM against the target protease and greater than or equal to 0.1 μM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Example compounds are typically prepared as racemic mixtures. Preparation of homochiral examples may be carried out by techniques known to one skilled in the art.

For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Triazole acids of this invention such as 1c, 1d, 1e and 1f can be easily prepared from readily accessible anilines outlined in Scheme 1. Formation of the arylazide 1b intermediate via diazotization and displacement with sodium azide followed by condensation with appropriate acetylenic compounds and removal of the protecting groups known to those in the art should afford intermediates such as 1c. Condensation of the arylazides with either malonates or ketoesters followed by hydrolysis should afford intermediates of this invention such as 1d, 1e and 1f. In cases wherein the anilines are not available, the corresponding arylcarboxylic acids can be used which are then converted to the anilines via the Curtius rearrangement. Alternatively haloaryl intermediates can be converted to the anilines via amination reaction.

Scheme 1

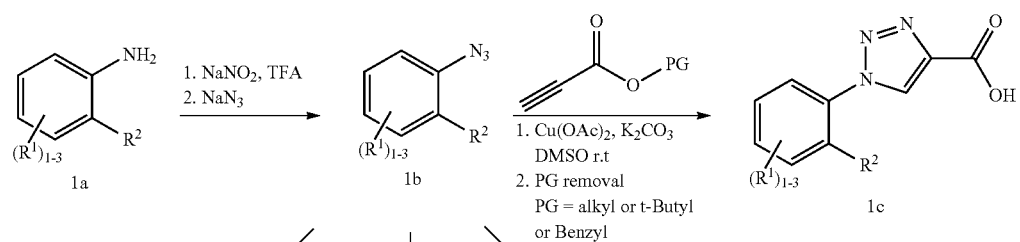

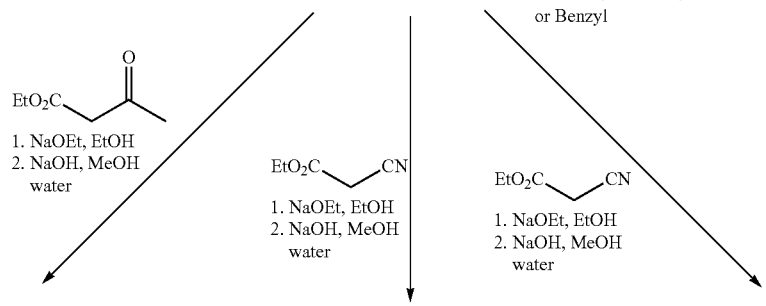

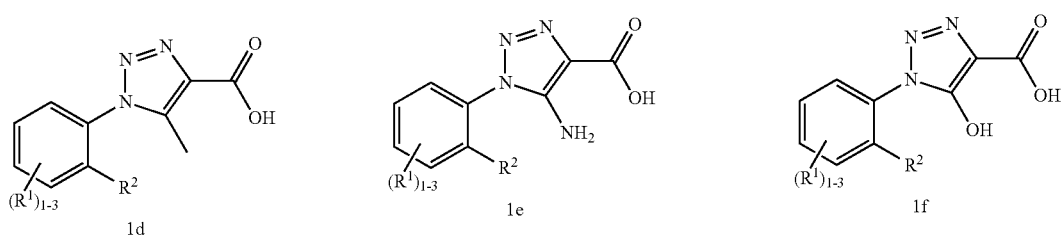

Substituted hydrazine 2a of this invention can be obtained from commercial sources or can be made from the corresponding anilines via diazotization followed by reduction with tin chloride. These can be reacted either directly or after isolation with an appropriate malononitrile to afford aminopyrazolo such as compound 2b. Amino pyrazole intermediates of this invention can be obtained by hydrolysis of the ester 2b. Treatment of 2b with isoamylnitrite in THF under elevated temperatures should provide the requisite pyrazole intermediate which is hydrolyzed to afford pyrazole acid intermediates of this invention such as 2e. Appropriately substituted hydrazines can be condensed with (E)-ethyl 2-((dimethylamino)methylene)-3-oxobutanoate to give, after hydrolysis, the methyl pyrazole derivatives 2d. Furthermore hydroxyl pyrazole intermediates 2g of this invention can be obtained by acylation of 2a followed by condensation with diethyl 2-(ethoxymethylene)malonate. Alternative approaches to pyrazoles can also be obtained via the Chan-Lam coupling (Lam, P. Y. S. et al., Synthesis, 6:829-856 (2011)). The requisite pyrazole 2i and appropriately substituted boronic acids 2h are commercially available. Alternatively these entities could be coupled via the Ullman coupling methodology with CuI, $K_2CO_3$ in DMSO at 130° C. In these cases the boronic acid derivatives would be substituted with the arylbromides or iodides.

Scheme 2

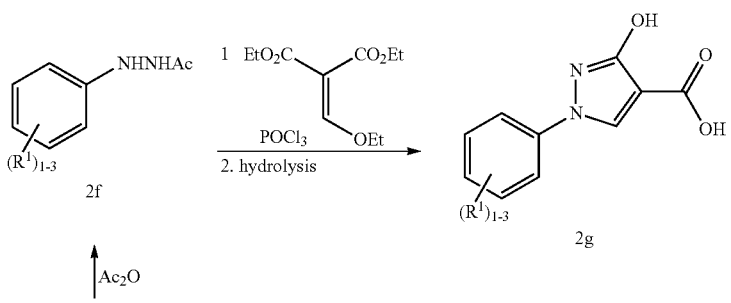

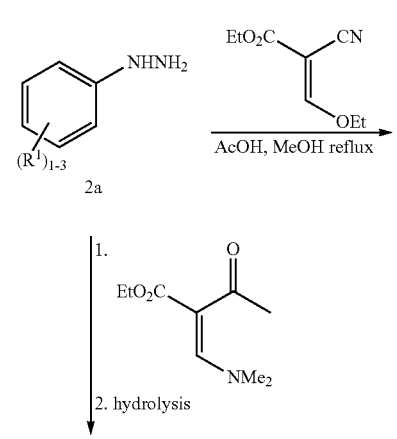
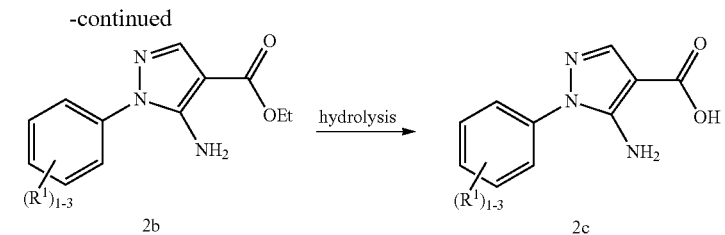
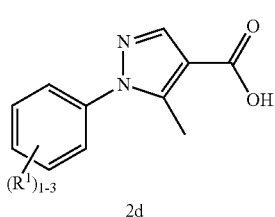
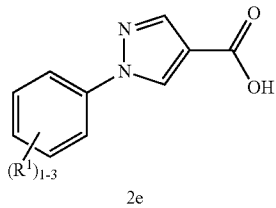
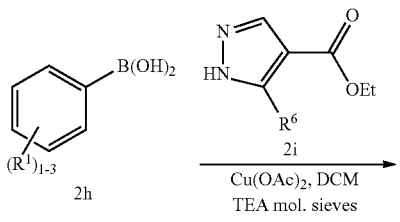
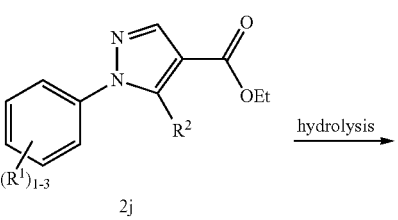

Imidazole acids of this invention such as 3j and 3k can be prepared as outlined in Scheme 3. Ullman coupling between an appropriately substituted imidazole 3g and an appropriately substituted arylhalide 3i can provide the imidazole derivatives 3d and 3e in one step. Hydrolysis of the ester will generate the imidazole acids 3j and 3k. Alternatively, an appropriately substituted imidazole 3g can be coupled to an appropriately substituted arylboronic acid 3i using a modified procedure described by Sreedhar (*Synthesis*, 5:795 (2008)). Alternative approaches to the imidazole derivatives 3j and 3k can be achieved using a modified procedure described by Gomez-Sanchez (*J. Heterocyclic Chem.*, 24:1757 (1987)). Condensation of the ethyl nitroacetate, triethyl orthoformate, and an appropriately substituted aniline 3l can provide ethyl 3-arylamino-2-nitroacrylate 3b. The ethyl 3-arylamino-2-nitrocrotonate derivatives 3c can be prepared by reacting ethyl 3-ethoxy-2-nitrocrotonate 3f with an appropriately substituted aniline 3l. Reacting compounds 3b and 3c with triethyl orthoformate and platinum on carbon under a hydrogen atmosphere at elevated temperature can yield the imidazole derivatives 3d and 3e. Hydrolysis of the ester will generate the imidazole acids 3j and 3k.

Scheme 3

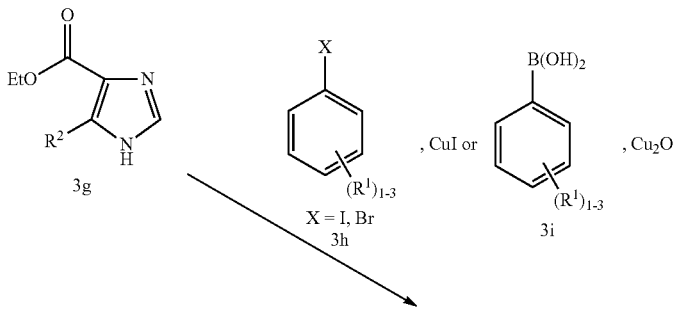

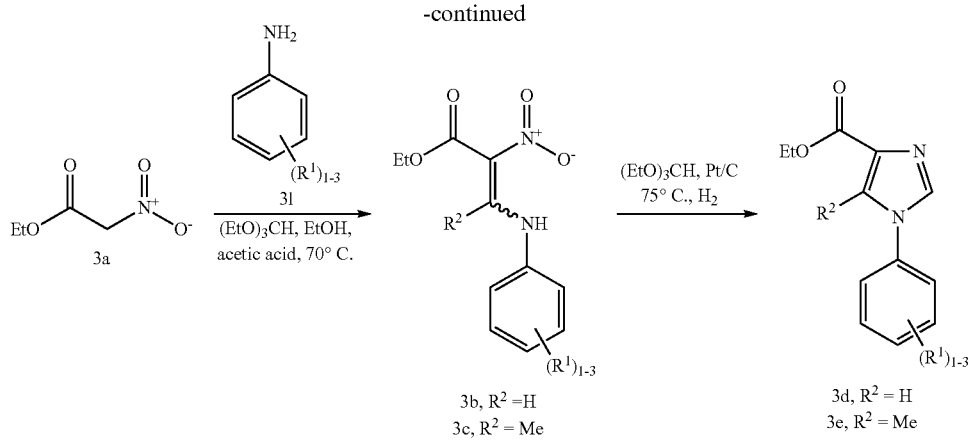

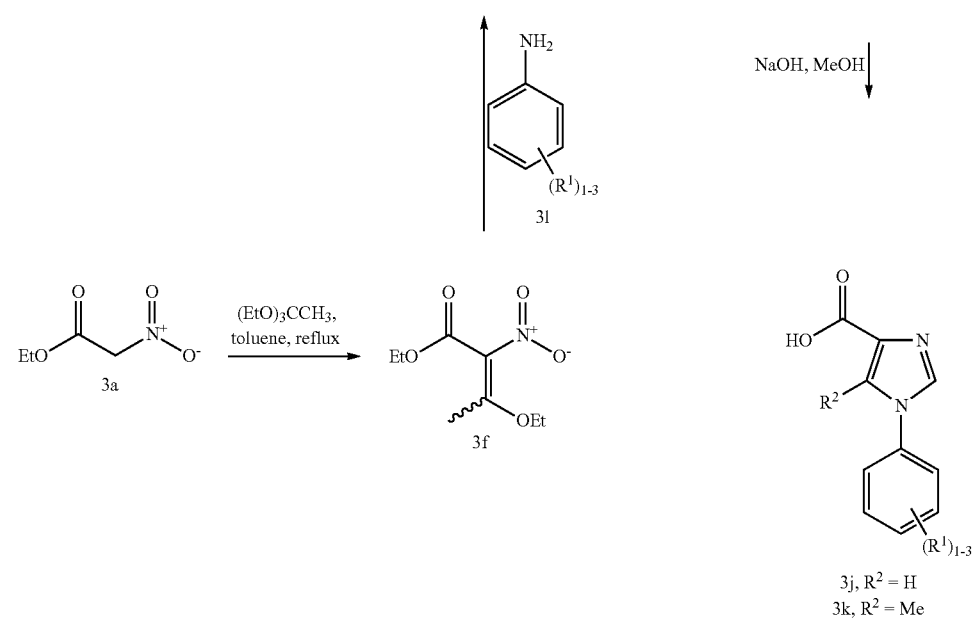

Isoxazoline and isoxazole acids of this invention such as 4f, 4g, 4j and 4k can be prepared as outlined in Scheme 4. Isoxazoline 4d and 4e can be obtained via a [3+2]cycloaddition methodology of oxime 4b which can be derived from benzaldehyde 4a. Chiral separation followed by hydrolysis of 4d and 4e afforded isoxazoline 4f and 4g. Alternatively, cycloaddition of chlorooxime of 4b can be cyclized with methyl propiolate provided ester regioisomer 4h and 4i, which upon hydrolysis afforded isoxazole acids 4j and 4k.

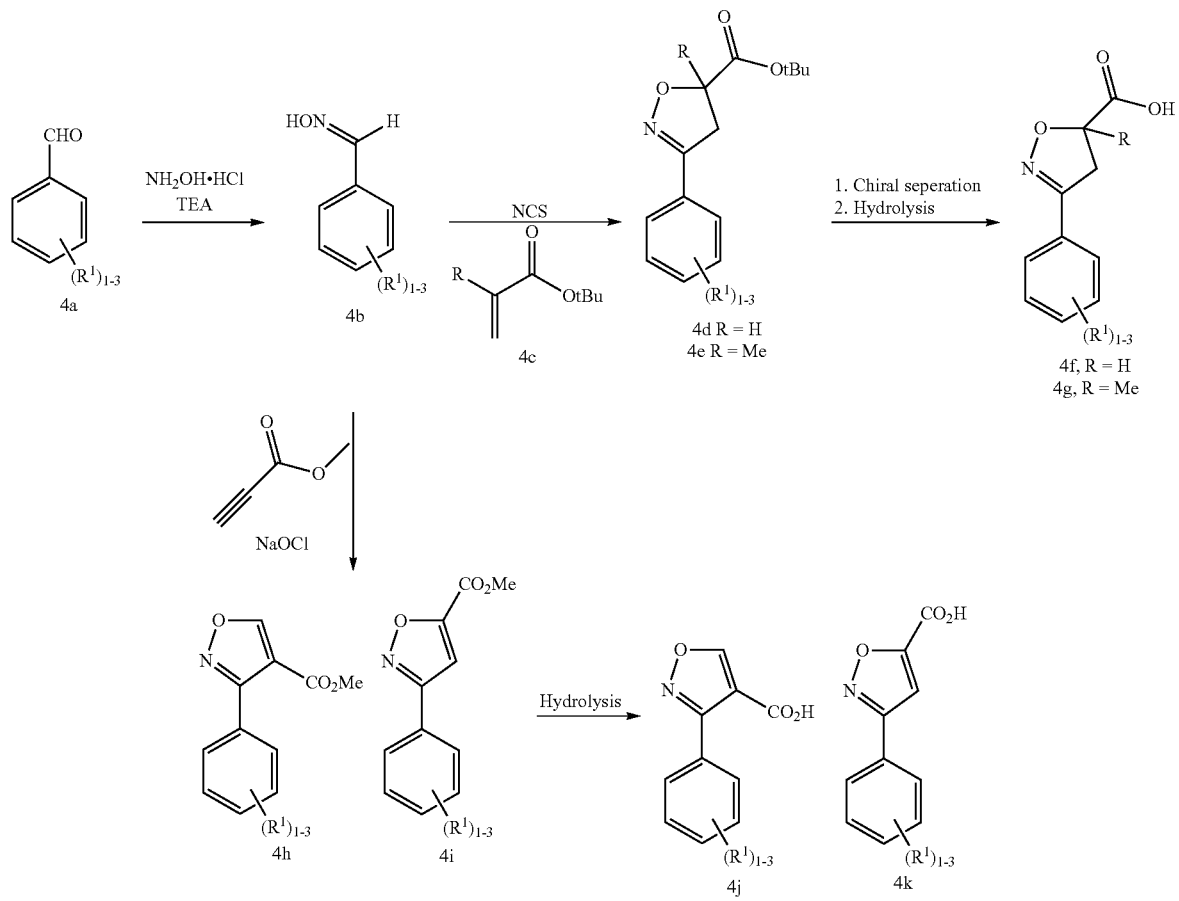

Pyrrolidinone and pyrrolidine acids of this invention such as 5b and 5d can be prepared as outlined in Scheme 5. Pyrrolidinone acids can be obtained one step from condensation of aniline 5b and 2-methylenepentanedioic acid. Esterification of acid 5b followed by reduction of amide gave pyrrolidine 5c. Hydrolysis of the methyl ester afforded pyrrolidine acids 5d.

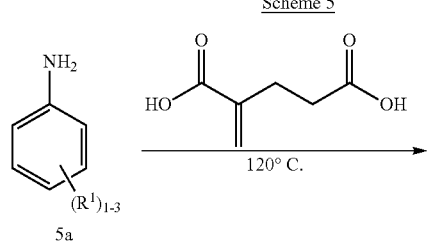

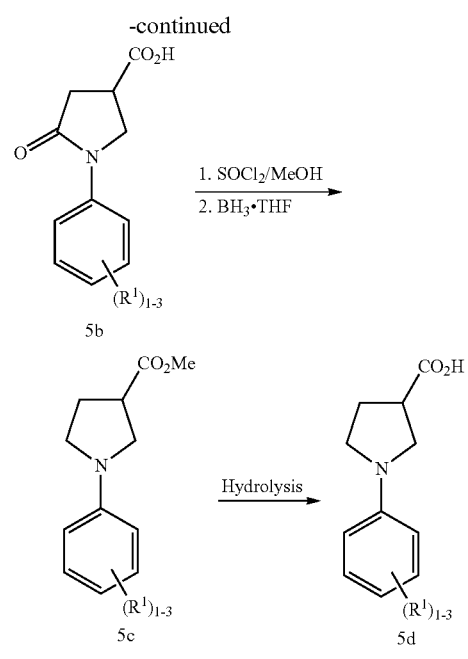

Oxazole acids of this invention such as 6c can be prepared as outlined in Scheme 6. Oxazole 6b can be obtained from condensation of amide 6a and ethyl 3-bromo-2-oxopropanoate. Hydrolysis of the ester 6b afforded oxazole acids 6c.

Scheme 6

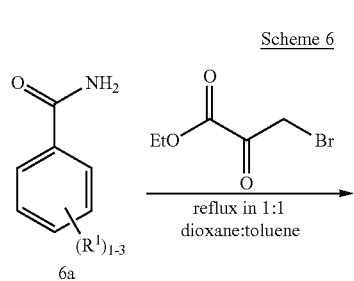

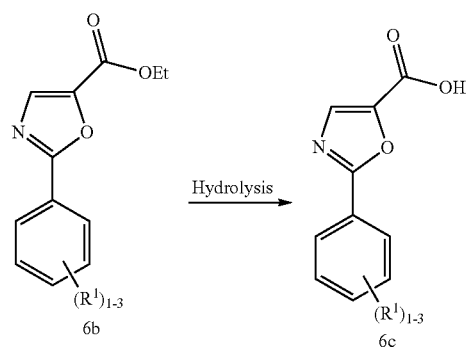

Scheme 7 describes methods for preparing the tetrahydroisoquinoline intermediate 7c and 7e. Method A uses Bischler-Napieralski cyclization to access compounds such as intermediate 7c (Al-Hiari, Y. M. et al., *Journal of Heterocyclic Chemistry*, 42(4):647-659 (2005)) or 7e (Zalan, Z. et al., *Tetrahedron*, 62(12):2883-2891 (2006)). Method B uses the Friedel-Crafts alkylation reaction to access compounds such as intermediate 7c (Topsom, R. D. et al., *Journal of the Chemical Society [Section]D: Chemical Communications*, 15:799 (1971)). Alternatively, as described in Method C, cyclization of intermediate 7h and 3-aminopropanol can afford 7i. Reduction with NaBH$_4$, followed by PCC oxidation gave β-amino aldehyde, which can be converted to 7c under basic conditions (Umetsu, K. et al., *Tetrahedron Letters*, 49(17):2722-2725 (2008)). In Method D, lactam 7k can be synthesized from ketone 7j by the Beckmann rearrangement. Reduction of 7k can afford intermediates such as 7c (Vernier, J. et al., WO 2008/024398 (2008)). In Method E, the dihydroisoquinoline carbaldehyde 7m was converted to 7c under basic conditions (Martin, S. et al., WO 2006/134143 (2006)). In Method F, dihydroisoquinolinethione was converted to 7c treating the thione 7n with bromopropene followed by treatment with perchloric acid and sodium borohydride (Mohinder, B. et al., *Indian Journal of Chemistry, Section B: Organic Chemistry Including Medicinal Chemistry*, 18B(4):312-315 (1979)).

Scheme 7

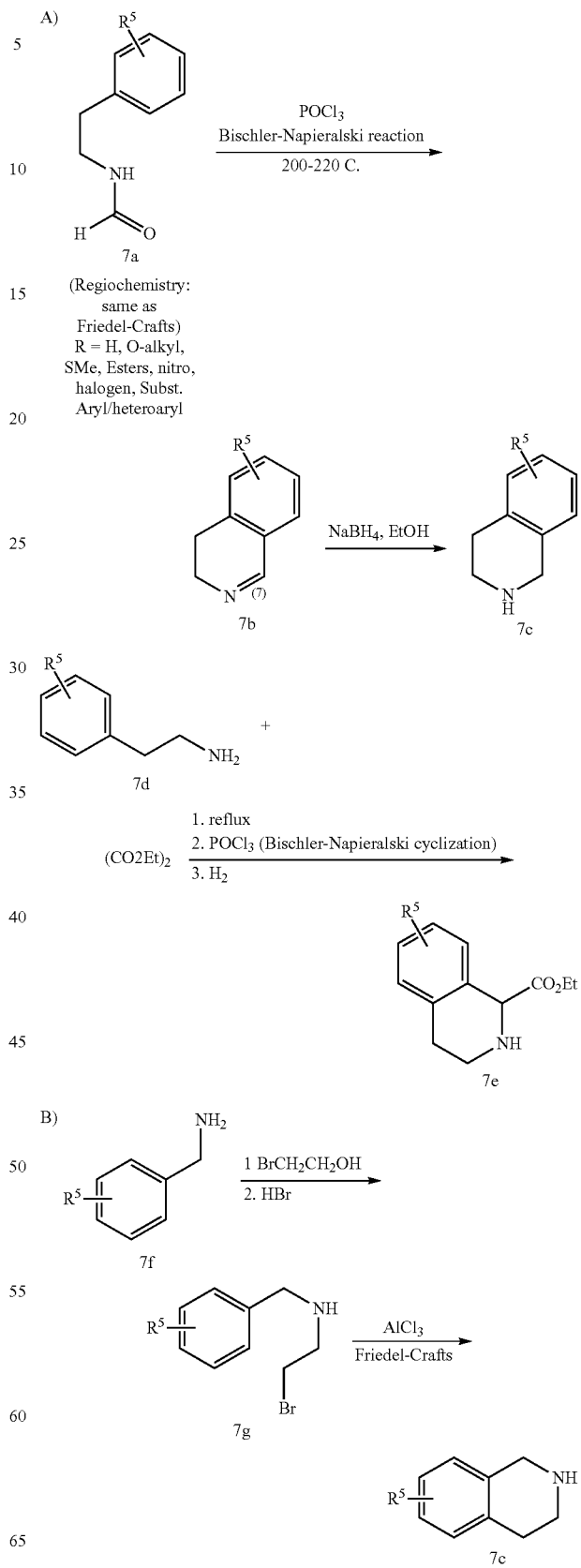

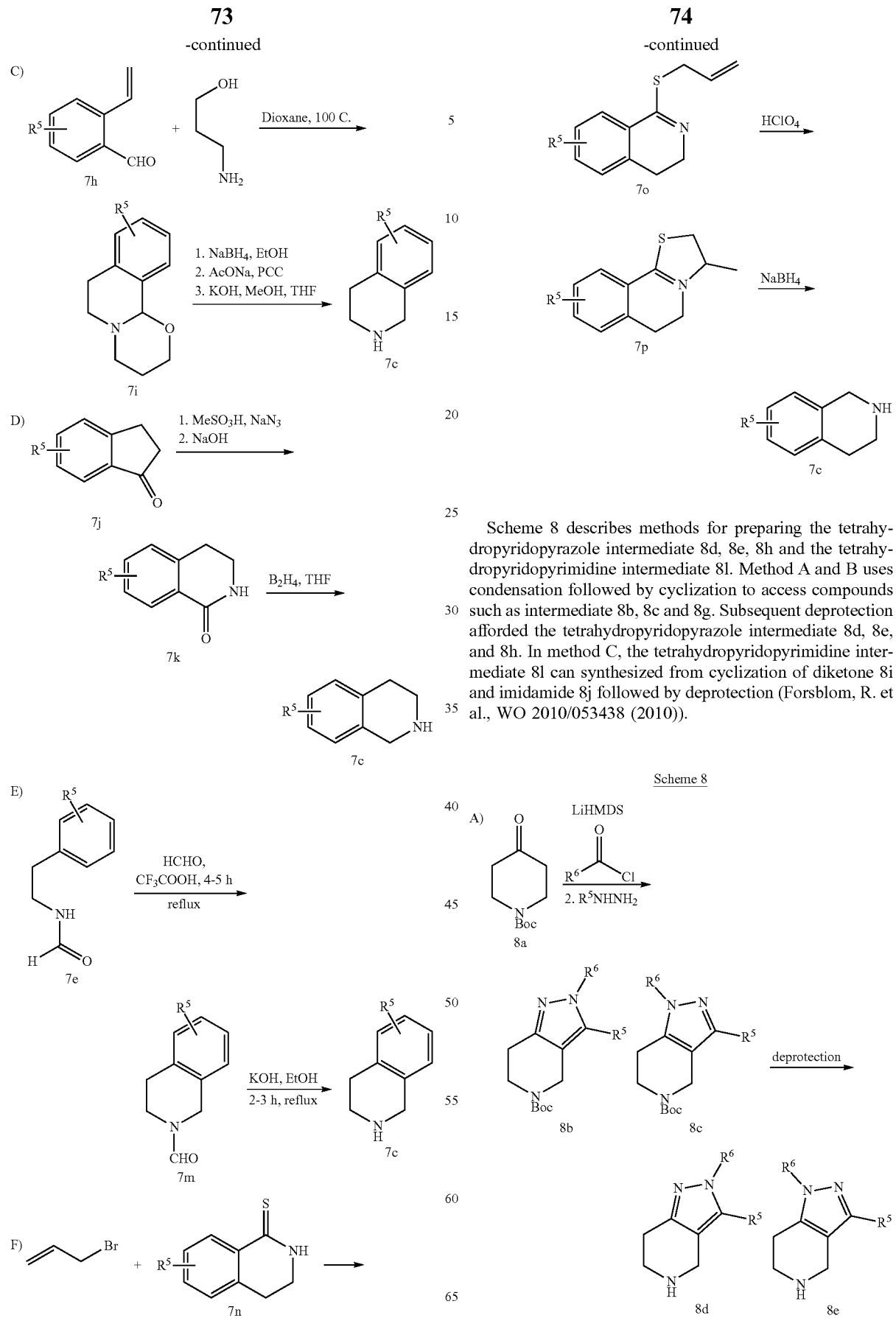

Scheme 8 describes methods for preparing the tetrahydropyridopyrazole intermediate 8d, 8e, 8h and the tetrahydropyridopyrimidine intermediate 8l. Method A and B uses condensation followed by cyclization to access compounds such as intermediate 8b, 8c and 8g. Subsequent deprotection afforded the tetrahydropyridopyrazole intermediate 8d, 8e, and 8h. In method C, the tetrahydropyridopyrimidine intermediate 8l can synthesized from cyclization of diketone 8i and imidamide 8j followed by deprotection (Forsblom, R. et al., WO 2010/053438 (2010)).

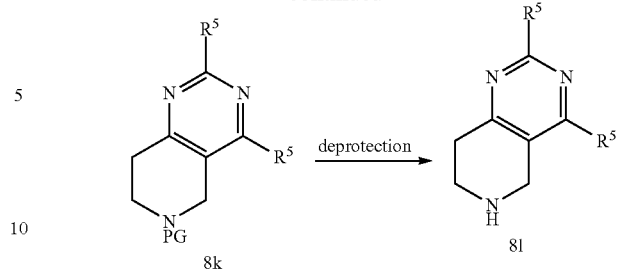

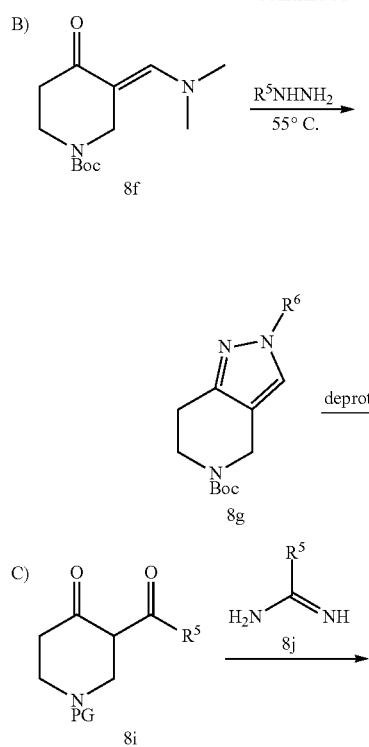

Scheme 9 describes functionalization on 9a and 9d through coupling reactions, such as Suzuki, Buchward, Chan-Lam, Ullman or Mitsunobu reactions or substitution reactions when halogen and hydroxyl groups are present on the aromatic ring. Reduction of isoquinoline 9e using literature conditions, such as $H_2/PtO_2$ (Schlittler, E. et al., *Helv. Chim. Acta.*, 31:914-924 (1948)), $Na/NH_3$ (The Birch reduction of aromatic compounds. Rabideau, P. W. et al., *Organic Reactions*, 42 (1992)) can yield tetrahydroisoquinolines 9f. Esters or amides 9i and be synthesized from commercially available esters 9g or can be obtained via standard reactions involving organometallic reactions of the halogen with $CO_2$. It should be noted that the same sequence of reactions can easily be adopted for other THQ like compounds where the phenyl is replaced with either a 5- or 6-membered heterocyclic ring. In these cases appropriate steps known to those in the art of organic synthesis can be taken to prepare intermediate compounds of this invention.

Scheme 9

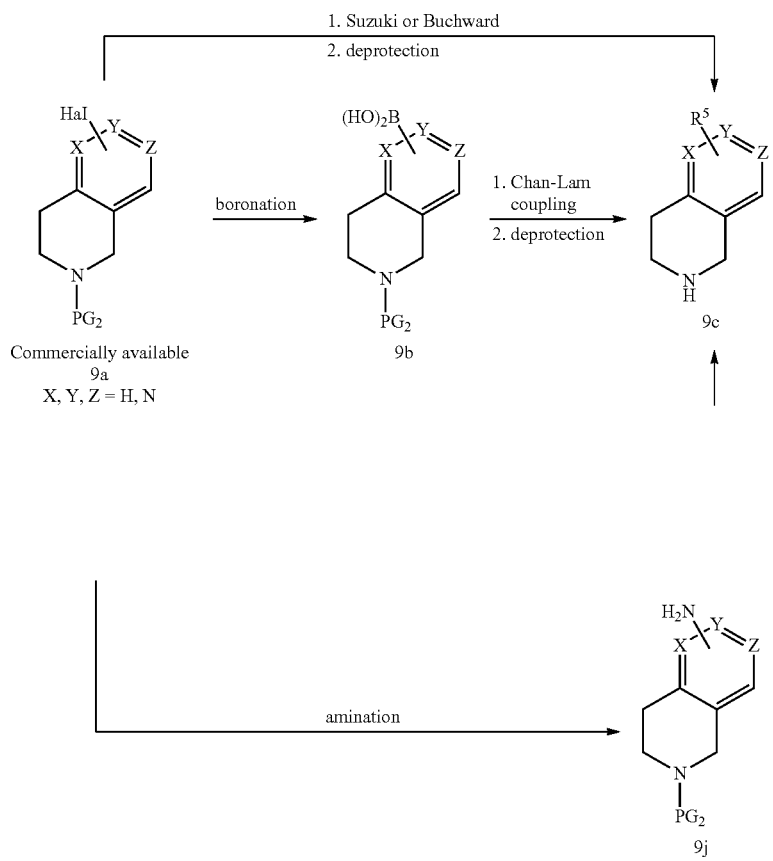

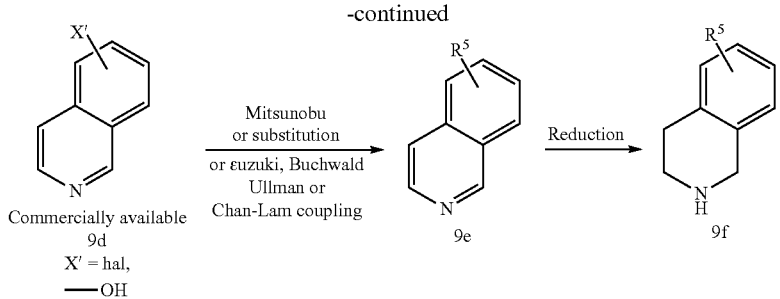

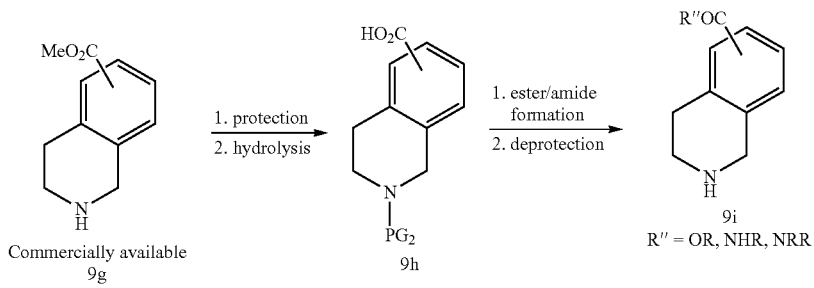

Scheme 10 illustrates a few approaches to the synthesis of compounds of Formula (I). Amide 10c can be prepared by amide coupling of commercially available or readily accessible acid 10a and readily accessible aniline 10b using methods commonly used in the literature, such as T3P/base, HOAt/EDC/base and/or POCl$_3$,pyridine. Deprotection of the protecting group PG$_1$ using appropriate conditions known to those in the art of organic synthesis, followed by coupling with acid 10d can yield compounds of Formula (I). Alternatively, coupling of amine 10e with acid 10d followed by deprotection can give acid 10f. The coupling of acid 10f with amine 10b under standard peptide coupling procedures can yield compounds of Formula (I). Appropriate functionalization of intermediates used in this invention to prepare compounds of Formula (I) can be achieved through the Suzuki, Buchwald, Ullman or Mitsunobu reactions or simple reactions known to those in the art.

Scheme 10

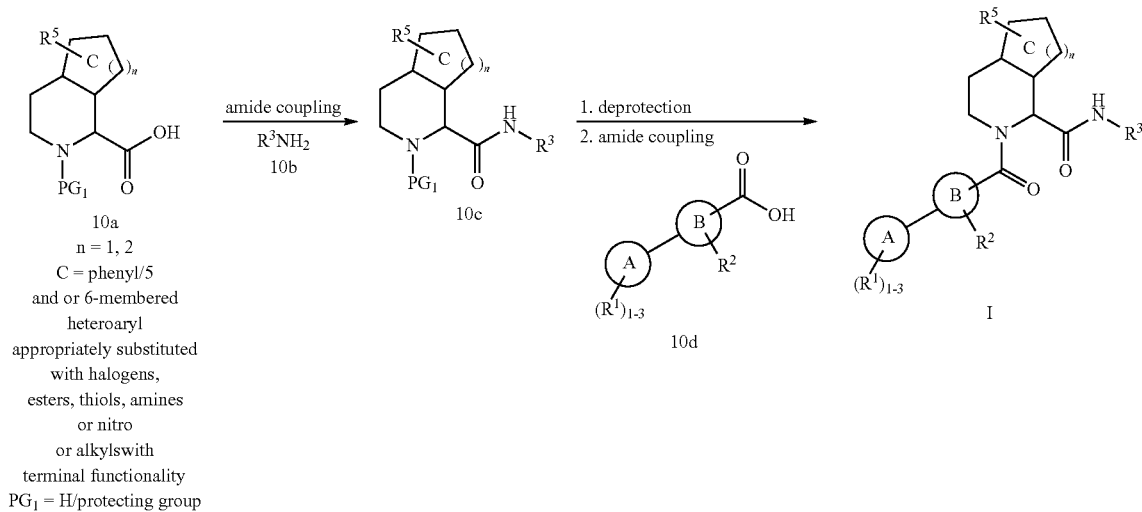

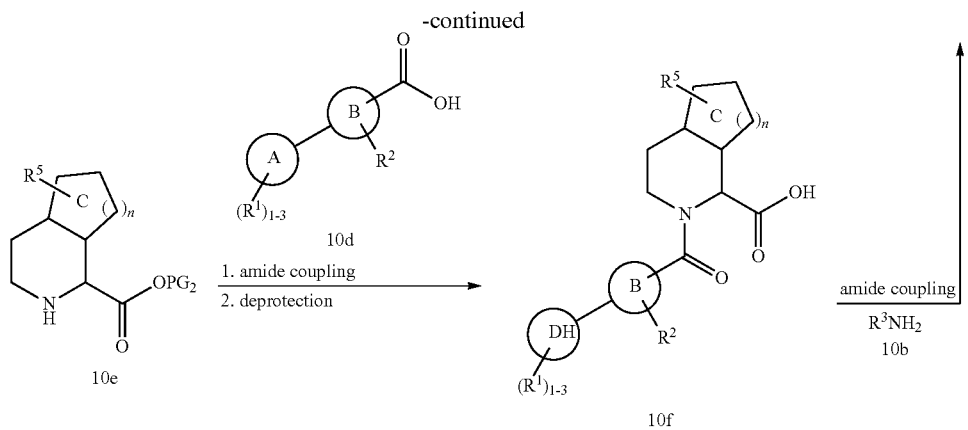

Scheme 11 describes an alternative method to access compounds of formula (I) this invention. Reaction of acid 11a, isocyanide 11b, and imine 11c can give Ugi product I (Schuster, I. et al., *Letters in Organic Chemistry*, 4(2): 102-108 (2007)). Selective oxidation of tetrahydroisoquinoline 11d using known methods such as MnO$_2$ (Aoyama, T. et al., *Synlett*, 1:35-36 (1998)) can yield imine 11c, which can then be used via the three component Ugi coupling procedures described above. Alternatively, TFA can be used as in the Ugi reaction to provide amide 11e. Amine 11f can be obtained from reacting amide 11e with NaBH$_4$. From Amine 11f, formula I can be synthesized by the method described in scheme 10. The Ugi coupling procedures can be used extensively with other imino derived intermediates contained in this invention. Further manipulations of the Ugi derived products can afford compounds of this invention.

Scheme 11

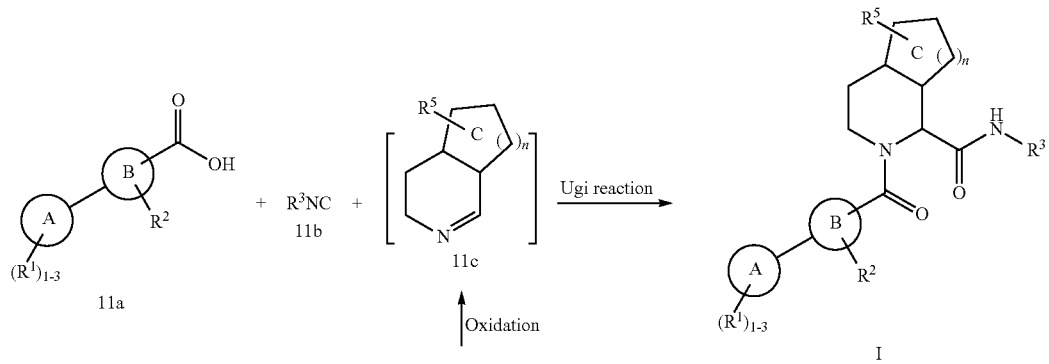

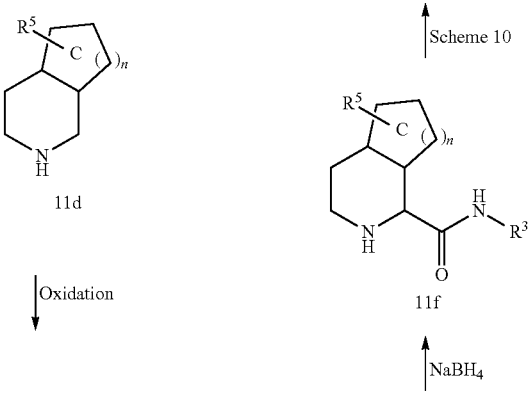

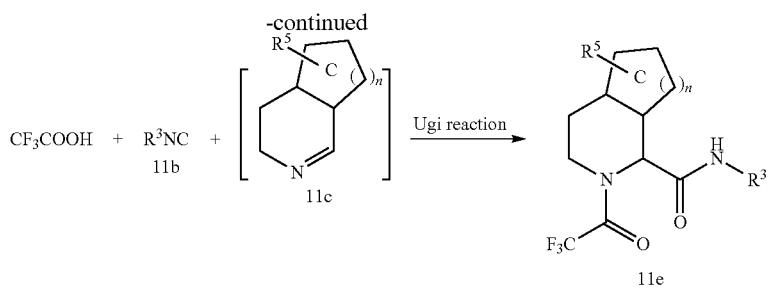

Scheme 12 describes an alternative method to access compounds of formula (I) this invention. Appropriate functionalization of intermediates 12a used in this invention to prepare compounds of Formula (I) can be achieved through the Suzuki, Buchwald, or Ullman reactions or simple reactions known to those in the art

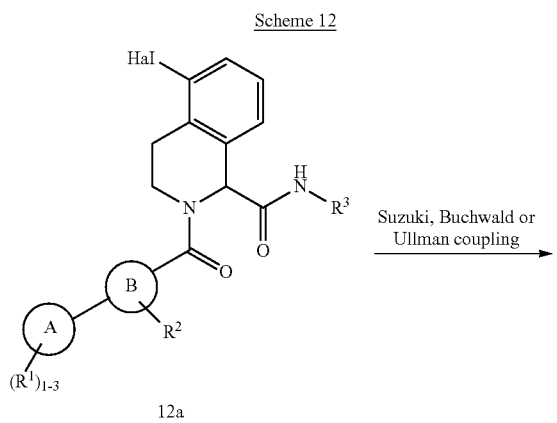

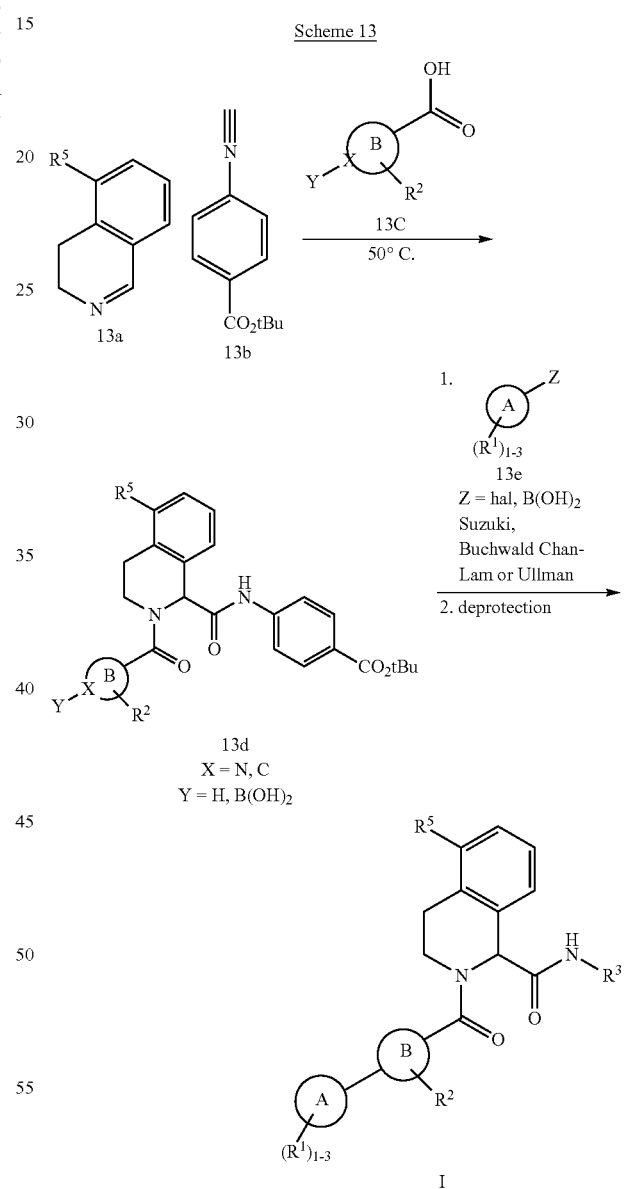

Scheme 13 describes an alternative method to access compounds of formula (I) this invention. Intermediate 13 d can be synthesized from the Ugi reaction of imine 13a, isonitriles 13b and acid 13c. Appropriate functionalization of intermediates 13d used in this invention to prepare compounds of Formula (I) can be achieved through the Suzuki, Buchwald, Chan-Lam or Ullman reactions or simple reactions known to those in the art.

Purification of intermediates and final products was carried out via either normal or reverse phase chromatography. Normal phase chromatography was carried out using prepacked $SiO_2$ cartridges eluting with either gradients of hexanes and EtOAc or DCM and MeOH unless otherwise indicated. Reverse phase preparative HPLC was carried out using C18 columns eluting with gradients of Solvent A (90%

H₂O, 10% MeOH, 0.1% TFA) and Solvent B (10% H₂O, 90% MeOH, 0.1% TFA, UV 220 nm) or with gradients of Solvent A (90% H₂O, 10% ACN, 0.1% TFA) and Solvent B (10% H₂O, 90% ACN, 0.1% TFA, UV 220 nm) or with gradients of Solvent A (98% H₂O, 2% ACN, 0.05% TFA) and Solvent B (98% ACN, 2% H₂O, 0.05% TFA, UV 220 nm) (or) SunFire Prep C18 OBD 5μ 30×100 mm, 25 min gradient from 0-100% B. A=H₂O/ACN/TFA 90:10:0.1. B=ACN/H₂O/TFA 90:10:0.1.

Unless otherwise stated, analysis of final products was carried out by reverse phase analytical HPLC.

Method A: A majority of analytical HPLC runs were: SunFire (4.6×150 mm) (15 min gradient—95:5 H₂O/ACN-to 95:5ACN/H₂O-0.05% TFA).

Method B: A minority of analytical HPLC runs were: ZORBAX® (4.6×75 mm) (8 min gradient–10:90 MeOH/H₂O to 90:10 MeOH/H₂O, 0.2% H₃PO₄).

Method C: A number of analytical HPLC runs were: Waters Acquity UPLC BEH (C18, 2.1×50 mm): 5:95 acetonitrile: water with 10 mM ammonium acetate to 95:5 acetonitrile: water with 10 mM ammonium acetate (3 min gradient).

Method D: A number of analytical HPLC runs were: Waters Acquity UPLC BEH (C18, 2.1×50 mm): 5:95 acetonitrile: water with 10 mM ammonium acetate to 95:5 acetonitrile: water with 10 mM ammonium acetate (4 min gradient).

Method E: A number of analytical HPLC runs were: Waters Acquity UPLC BEH (C18, 2.1×50 mm): 2:98 acetonitrile: water with 0.05% TFA to 98:2 acetonitrile: water with 0.05% TFA (1 min gradient).

A majority of mass spectra runs were run using PHE-NOMENEX® Luna C18 (2×30 mm) (2 min gradient 90% H₂O/10% MeOH/0.1% TFA to 90% MeOH/10% H₂O/0.1% TFA)

INTERMEDIATE 1 tert-Butyl 4-isocyanobenzoate

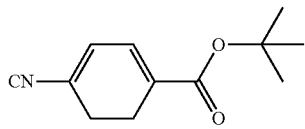

Intermediate 1A. tert-Butyl 4-formamidobenzoate: Combined tert-butyl 4-aminobenzoate (15.3 g, 79 mmol), DMAP (1.935 g, 15.84 mmol), N-methylmorpholine (15.67 mL, 143 mmol) in DCM (120 mL) and, after cooling to 0° C., slowly added formic acid (9.11 mL, 238 mmol). After stirring for 18 h, the reaction was concentrated and then partitioned with 1N HCl (100 mL) and EtOAc (200 mL). The aqueous layer was extracted with EtOAc (100 mL). The combined organic layers were washed with brine (50 mL) and dried (MgSO₄). The desired product was collected as yellow syrup (16 g).

Intermediate 1 To Intermediate 1A in THF (300 mL) was added TEA (33 mL, 238 mmol) and after cooling to 0° C., POCl₃ (7.3 mL, 79 mmol) was slowly added and the reaction was stirred at room temperature. After 24 h, the reaction was partitioned between EtOAc (200 mL) and aqueous NaHCO₃ (100 mL). The aqueous layer was extracted with EtOAc (100 mL). The combined organic layers were washed with brine (50 mL) and dried (MgSO₄). Purification by normal phase chromatography afforded 10.4 g (64.6%) of Intermediate 1 as a green solid. ¹H NMR (400 MHz, CDCl₃) δ 8.02 (d, J 8.59 Hz, 2 H), 7.41 (d, J=8.34 Hz, 2 H), 1.60 (s, 9 H) ppm.

INTERMEDIATE 2

Methyl 4-isocyanobenzoate

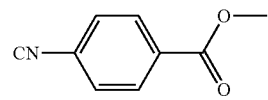

Intermediate 2A. Methyl 4-formamidobenzoate: Methyl 4-aminobenzoate (3.5 g, 23.2 mmol) was dissolved in formic acid (3.55 mL, 93 mmol) with stirring. Afterwards, sodium formate (0.306 g, 4.63 mmol) in portions. After stirring for 14 h, the precipitate was suspended in ice-water, filtered, washed with ice-water, and dried in vacuo to give Intermediate 2A as a white solid. MS (ESI) m/z: 180 (M+H)⁺.

Intermediate 2. Methyl 4-isocyanobenzoate: Intermediate 2A and DIPEA (17.59 mL, 101 mmol) were added to dioxane (11.61 mL) and cooled to 0° C. Phosphorus oxychloride (2.70 mL, 28.9 mmol) in dioxane (23.21 mL) was dropwise. The reaction mixture was allowed to gradually come to room temperature over 5 h. The reaction was quenched with 5% NaHCO₃ (50 mL) and extracted with EtOAc (3×50 mL). The combined organic layers were washed with brine (50 mL), dried (Na₂SO₄), and purified by normal phase chromatography to give methyl 4-isocyanobenzoate (3.63 g, 22.52 mmol, 97% yield) as a dark green solid. MS (ESI) m/z: 162.0 (M+H)⁺. ¹H NMR: (500 MHz, DMSO-d₆) δ 8.02 (d, J=8.5 Hz, 2H), 7.69 (d, J=8.5 Hz, 2H), 3.87 (s, 3H) ppm.

INTERMEDIATE 3

3,4-Dihydroisoquinoline

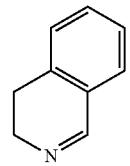

Intermediate 3. To 1,2,3,4-tetrahydroisoquinoline (1.175 mL, 9.39 mmol) in DCM (100 mL) was added manganese dioxide (13.05 g, 150 mmol). After 18 h, the reaction was filtered through CELITE®, and the filter pad was washed with DCM and MeOH. The filtrate was concentrated to afford 0.98 g (80%) of Intermediate 3 as an amber oil. ¹H NMR (400 MHz, chloroform-d) δ 8.34 (1 H, s), 7.22-7.39 (3 H, m), 7.07-7.20 (1 H, m), 3.72-3.84 (2 H, m), 2.67-2.82 (2 H, m) ppm. MS (ESI) m/z: 132.0 (M+H)⁺.

INTERMEDIATE 4

5-(4-Methoxypiperidin-1-yl)-3,4-dihydroisoquinoline

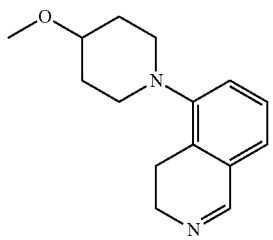 [SMILES: COC1CCN(c2cccc3c2CCN=C3)CC1]

Intermediate 4A. 5-(4-Methoxypiperidin-1-yl)isoquinoline: To 5-bromoisoquinoline (10.40 g, 50 mmol), 4-methoxypiperidine (4.92 mL, 50.0 mmol), $Pd_2(dba)_3$ (0.458 g, 0.500 mmol), BINAP (0.934 g, 1.500 mmol), and t-BuONa (6.73 g, 70.0 mmol) was added degassed toluene (60 mL) and the reaction was heated under $N_2$ to 85° C. for 24 h and then to 105° C. for 3 h. The reaction mixture was cooled to ambient temperature and water was added. The phases were separated and the aqueous layer extracted three times with ethyl acetate. The combined organics were washed with brine, dried ($Na_2SO_4$), filtered and purified by silica gel chromatography to afford 6.34 g (52.4%) of Intermediate 4A as a pale yellow solid. MS (ESI) m/z: 243.2 $(M+H)^+$.

Intermediate 4B. 5-(4-Methoxypiperidin-1-yl)-1,2,3,4-tetrahydroisoquinoline: Intermediate 4A (6.344 g, 26.2 mmol) in EtOH (100 mL) was hydrogenated at 55 psi in the presence of platinum(IV) oxide (0.595 g, 2.62 mmol) for 74 h. The reaction mixture was filtered through CELITE® and the filtrate was evaporated to 6.37 g (94%) of a dark residue for Intermediate 3B. MS (ESI) m/z: 247.2 $(M+H)^+$.

Intermediate 4. Intermediate 4B was oxidized as described for Intermediate 3 to afford 6.32 g (100%) of Intermediate 4 as a yellow viscous oil. MS (ESI) m/z: 245.2 $(M+H)^+$.

The following Intermediates in Table 1 were prepared utilizing Buchwald conditions in a manner similar to Intermediate 4 starting from 5-bromoisoquinoline and the appropriate amine.

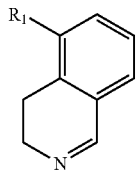

TABLE 1

| Intermediate No. | $R_1$ | Name | M + H |
|---|---|---|---|
| 4C | (piperidine) | 5-(piperidin-1-yl)-3,4-dihydroisoquinoline | 215 |
| 4D | (4-hydroxypiperidine) | 1-(3,4-dihydroisoquinolin-5-yl)piperidin-4-ol | 231 |
| 4E | (4-dimethylaminopiperidine) | 1-(3,4-dihydroisoquinolin-5-yl)-N,N-dimethylpiperidin-4-amine | 258 |
| 4F | (morpholine) | 4-(3,4-dihydroisoquinolin-5-yl)morpholine | 217 |
| 4G | (4-methylpiperazine) | 5-(4-methylpiperazin-1-yl)-3,4-dihydroisoquinoline | 230 |
| 4H | (thiomorpholine 1,1-dioxide) | 4-(3,4-dihydroisoquinolin-5-yl)thio-morpholine 1,1-dioxide | 264 |
| 4I | (3-methoxyazetidine) | 5-(3-methoxyazetidin-1-yl)-3,4-dihydroisoquinoline | 217 |
| 4J | (3-ethoxyazetidine) | 5-(3-ethoxyazetidin-1-yl)-3,4-dihydroisoquinoline | 231 |
| 4K | (3-methoxypyrrolidine) | (R)-5-(3-methoxypyrrolidin-1-yl)-3,4-dihydroisoquinoline | 231 |
| 4L | (4-(2-hydroxypropan-2-yl)piperidine) | 2-(1-(3,4-dihydroisoquinolin-5-yl)piperidin-4-yl)propan-2-ol | 273 |
| 4M | (N,N-dimethylpiperidine-4-carboxamide) | 1-(3,4-dihydroisoquinolin-5-yl)-N,N-dimethylpiperidine-4-carboxamide | 286 |
| 4N | (4-hydroxy-4-methylpiperidine) | 1-(3,4-dihydroisoquinolin-5-yl)-4-methylpiperidin-4-ol | 245 |

TABLE 1-continued

| Intermediate No. | R₁ | Name | M + H |
|---|---|---|---|
| 4O | | 2-((1-(3,4-dihydroisoquinolin-5-yl)-piperidin-4-yl)oxy)-N,N-dimethylethanamine | 302 |
| 4P | | 5-(4-(pyrrolidin-1-yl)piperidin-1-yl)-3,4-dihydroisoquinoline | 283 |
| 4Q | | 1-(1-(3,4-dihydroisoquinolin-5-yl)-piperidin-4-yl)pyrrolidin-2-one | 298 |
| 4R | | 8-(3,4-dihydroisoquinolin-5-yl)-2,8-diazaspiro[4.5]decan-1-one | 284 |
| 4S | | 8-(3,4-dihydroisoquinolin-5-yl)-1-oxa-8-azaspiro[4.5]decan-2-one | 285 |
| 4T | | 5-(3-isopropyl-5,6-dihydro-[1,2,4]triazolo[4,3-a]pyrazin-7(8H)-yl)-3,4-dihydroisoquinoline | 296 |
| 4U | | 5-(4-(oxetan-3-yl)piperidin-1-yl)-3,4-dihydroisoquinoline | 271 |
| 4V | | 4-(3,4-dihydroisoquinolin-5-yl)-1-methylpiperazin-2-one | 244 |

INTERMEDIATE 5

1-(3,4-Dihydroisoquinolin-5-yl)-4-methylpiperazin-2-one

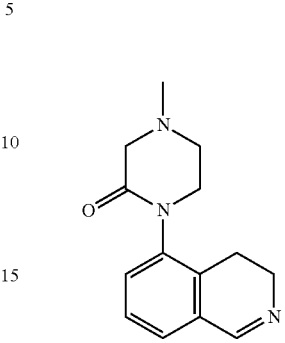

Intermediate 5A. 1-(Isoquinolin-5-yl)-4-methylpiperazin-2-one: To 5-bromoisoquinoline (1.66 g, 7.96 mmol) and 4-methylpiperazin-2-one (1, 8.76 mmol) was added DMSO (7 mL), 1,10-phenanthroline (0.144 g, 0.796 mmol), potassium carbonate (3.30 g, 23.89 mmol) and the mixture was degassed with Ar for 30 min., copper(I)iodide (1.213 g, 6.37 mmol) was added and the reaction was heated in oil bath at 130° C. overnight. The reaction was cooled to room temperature and quenched with NH₄OH (10 mL) and water (20 mL) and diluted with EtOAc. The aqueous layer was extracted EtOAc (2×50 mL) and then, nBuOH (1×30 mL). Combined organic layers were washed with brine and dried (MgSO₄). Purification by silica gel chromatography afforded 1.5 g (78%) yellow solid. MS (ESI) m/z: 242.0 (M+H)⁺

Intermediate 5. 1-(3,4-Dihydroisoquinolin-5-yl)-4-methylpiperazin-2-one: The title compound was prepared from Intermediate 5A (1.5 g, 6.22 mmol) in a similar manner as Intermediate 4 to afford 1.34 g (89%) of a dark oil. MS (ESI) m/z: 244.1 (M+H)⁺.

The following Intermediates in Table 2 were prepared utilizing Ullmann conditions in a manner similar to Intermediate 5 starting from 5-bromoisoquinoline and the appropriate lactam.

TABLE 2

| Intermediate No. | R₂ | Name | M + H |
|---|---|---|---|
| 5B | 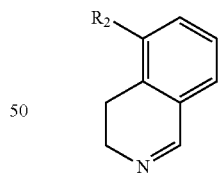 | 4-(3,4-dihydroisoquinolin-5-yl)morpholin-3-one | 231 |

TABLE 2-continued

| Intermediate No. | R2 | Name | M + H |
|---|---|---|---|
| 5C | 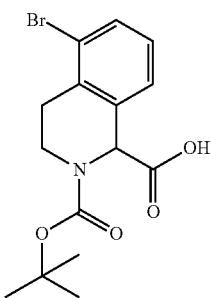 (structure shown) | 4-(3,4-dihydroisoquinolin-5-yl)-1-methyl-1,4-diazepan-5-one | 258 |
| 5D | (structure shown) | (S)-3-((tert-butyldimethylsilyl)oxy)-1-(3,4-dihydroisoquinolin-5-yl)pyrrolidin-2-one | 345 |

INTERMEDIATE 6

5-Bromo-2-(tert-butoxycarbonyl)-1,2,3,4-tetrahydroisoquinoline-1-carboxylic acid

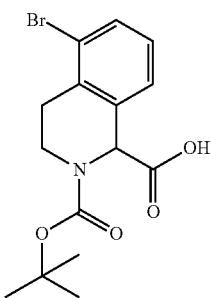 [SMILES: CC(C)(C)OC(=O)N1CCc2c(Br)cccc2C1C(=O)O]

Intermediate 6A. Methyl 5-bromo-1,2,3,4-tetrahydroisoquinoline-1-carboxylate: 5-Bromo-2-(ethoxycarbonyl)-1,2,3,4-tetrahydroisoquinoline-1-carboxylic acid (1 g, 3.05 mmol) (Ortwine et al., J Med. Chem., 35:1345 (1992)), in two batches, was heated in a microwave to 150° C. in 1,4-dioxane (4 mL)/EtOH (2 mL)/2N NaOH (5 mL) for a total of 3 h. The combined reaction mixtures were concentrated, dissolved in MeOH (30 mL) and thionyl chloride (0.222 mL, 3.05 mmol) was slowly added. After 18 h, the solvent was removed and the residue was partitioned with EtOAc (50 mL)/saturated NaHCO₃ (30 mL), phases separated and aqueous layer was extracted with EtOAc (2×25 mL). The combined organic layers were washed with brine (25 mL) and dried (MgSO₄) to afford 0.56 g (80%) of Intermediate 6A as a yellow oil. MS (ESI) m/z: 270/272 (M+H)⁺.

Intermediate 6B. 2-tert-Butyl 1-methyl 5-bromo-3,4-dihydroisoquinoline-1,2(1H)-dicarboxylate: To crude Intermediate 6A (0.65 g, 2.406 mmol) in DCM (10 mL) and NaHCO₃ (0.404 g, 4.81 mmol) was added di-tert-butyl dicarbonate (0.670 mL, 2.89 mmol). After 24 h, the reaction was quenched with water (20 mL) and extracted with DCM (3×30 mL). The combined organic layers were washed with brine (15 mL) and dried (MgSO₄). Purification by silica gel chromatography afforded 0.63 g (70.7%) of Intermediate 6B as a clear oil. MS (ESI) m/z: 391.9 (M+Na)⁺.

Intermediate 6. To a solution of Intermediate 6B (5.0 g, 13.50 mmol) in THF (60 mL)/MeOH (60 mL) was added 1N NaOH (40.5 mL, 40.5 mmol). After 24 h, the reaction mixture was concentrated and the remaining aqueous layer cooled to 0° C. and the pH was adjusted to 5 using 1.0N HCl solution. The solution was extracted with EtOAc (3×75 mL). The combined organic extracts were washed with brine, dried (MgSO₄), filtered, and concentrated to give 4.75 g (99%) of Intermediate 6 as a white solid. ¹H NMR (500 MHz, DMSO-d₆) δ 7.55 (dd, J=17.2, 7.8 Hz, 2H), 7.20 (t, J=7.8 Hz, 1H), 5.49-5.32 (m, 1H), 3.86-3.73 (m, 1H), 3.59-3.48 (m, 1H), 2.92-2.74 (m, 2H), 1.42 (d, J=12.9 Hz, 9H) ppm. MS (ESI) m/z: 255.9 (M+H-tBoc)⁺.

INTERMEDIATE 7 tert-Butyl 5-bromo-1-((4-(tert-butoxycarbonyl)phenyl)carbamoyl)-3,4-dihydroisoquinoline-2(1H)-carboxylate

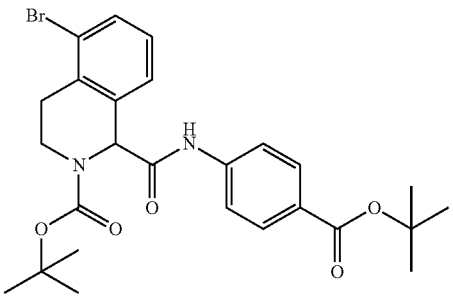 [SMILES: CC(C)(C)OC(=O)c1ccc(NC(=O)C2c3cccc(Br)c3CCN2C(=O)OC(C)(C)C)cc1]

Intermediate 7. tert-Butyl 5-bromo-1-((4-(tert-butoxycarbonyl)phenyl)carbamoyl)-3,4-dihydroisoquinoline-2(1H)-carboxylate: Phosphorus oxychloride (0.861 g, 5.61 mmol) was added to Intermediate 6 (2.0 g, 5.61 mmol) and tert-butyl 4-aminobenzoate (1.085 g, 5.61 mmol) in pyridine (11.35 mL, 140 mmol) at 0° C. After stirring for 4 h, the reaction mixture was quenched with water (50 mL). The solution was extracted with EtOAc (2×75 mL), the combined organic layer was washed several times with 1.0N HCl solution, water, brine, dried over sodium sulfate, filtered, and concentrated to give Intermediate 7 (2.78 g, 5.23 mmol, 93% yield) as a tan solid. This material was sufficiently pure to carry forward to the next reaction with further purification. MS (ESI) m/z: 531.3 (M+H)⁺.

INTERMEDIATE 8

1-(3-Chlorophenyl)-1H-1,2,3-triazole-4-carboxylic acid

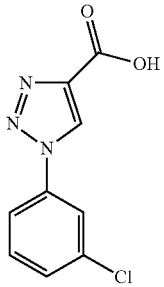

Intermediate 8A. Ethyl 1-(3-chlorophenyl)-1H-1,2,3-triazole-4-carboxylate: Sodium nitrite (1.947 g, 28.2 mmol) dissolved in H$_2$O (5 mL) was added to a cold (<5° C.) TFA (20 mL) solution of 3-chloroaniline (3.6 g, 28.2 mmol). After 0.5 h, sodium azide (1.835 g, 28.2 mmol) dissolved in H$_2$O (1 mL) was added dropwise to the above reaction mixture. The reaction mixture was then stirred cold for 2 h and then quenched with H$_2$O (100 mL) and extracted the organics with EtOAc (2×100 mL). The organic layers were then dried over MgSO$_4$ and concentrated to a brown oil (3.5 g). Approximately 1 g of the azide from the above crude product was taken in a microwave flask. To this was added ethyl propiolate (1.5 mL), DMSO (4 mL), sodium carbonate (0.1 g) and L-proline (0.1 g) and the reaction mixture was heated at 75° C. overnight. The reaction was then quenched with H$_2$O to precipitate out the solids. Filtered the solids and washed with excess H$_2$O followed by drying under vacuum to afford 1.3 g of the desired triazole ester. MS (ESI) m/z: 252.1 (M+H)$^+$.

Intermediate 8. 1-(3-Chlorophenyl)-1H-1,2,3-triazole-4-carboxylic acid: To a solution for Intermediate 8A (0.3 g, 1.192 mmol) in a mixture of THF and H$_2$O (1:1) was added LiOH and stirred at room temperature for 1 h. After 1 h, the reaction mixture was quenched with H$_2$O (50 mL) and extracted the unreacted starting material with EtOAc. The aqueous layer was then acidified and extracted the acid with EtOAc (2×100 mL). The organic layers were then dried over MgSO$_4$ and evaporated to a brown oil which solidified at room temperature. MS (ESI) m/z: 224.0 (M+H)$^+$. $^1$H NMR (400 MHz, MeOD) δ 9.13 (s, 1H), 8.03 (s, 1H), 7.89 (dd, J=2.2 and 8.4 Hz, 2H), 7.61-7.56 (m, 2H) ppm.

INTERMEDIATE 9

1-(3-Chloro-2-fluorophenyl)-1H-1,2,3-triazole-4-carboxylic acid

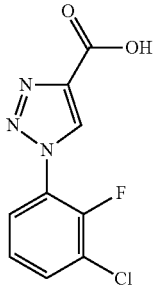 [SMILES: O=C(O)c1cn(-c2cccc(Cl)c2F)nn1]

Intermediate 9. 1-(3-Chloro-2-fluorophenyl)-1H-1,2,3-triazole-4-carboxylic acid: Intermediate 9 was prepared in the same manner as Intermediate 8 replacing 3-chloroaniline with 3-chloro-2-fluoroaniline. MS (ESI) m/z: 242.0 (M+H)$^+$. $^1$H NMR (500 MHz, CDCl$_3$) δ 8.20 (s, 1H), 7.60-7.55 (dt, 1H), 7.42-7.37 (dt, 1H), 7.28-7.23 (dt, 1H) ppm.

INTERMEDIATE 10

1-(3-Chloro-2,6-difluorophenyl)-1H-1,2,3-triazole-4-carboxylic acid

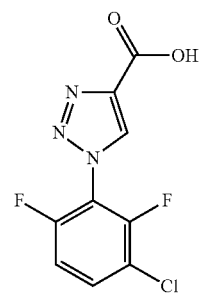 [SMILES: O=C(O)c1cn(-c2c(F)ccc(Cl)c2F)nn1]

Intermediate 10. 1-(3-Chloro-2,6-difluorophenyl)-1H-1,2,3-triazole-4-carboxylic acid: Intermediate 10 was prepared in the same manner as Intermediate 8 replacing 3-chloroaniline with 3-chloro-2,6-difluoroaniline. MS (ESI) m/z: 260.0 (M+H)$^+$. $^1$H NMR (400 MHz, MeOD) δ 8.94 (s, 1H), 7.85 (ddd, J=9.3, 8.1, 5.3 Hz, 1H), 7.40 (td, J=9.2, 2.0 Hz, 1H) ppm.

INTERMEDIATE 11

1-(3-Chloro-2-fluorophenyl)-5-methyl-1H-1,2,3-triazole-4-carboxylic acid

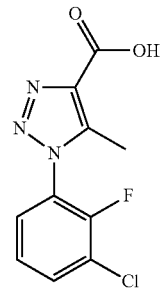 [SMILES: Cc1c(C(=O)O)nnn1-c1cccc(Cl)c1F]

Intermediate 11. 1-(3-Chloro-2-fluorophenyl)-5-methyl-1H-1,2,3-triazole-4-carboxylic acid: To a solution of 3-chloro-2-fluoroaniline (1.7 g, 11.68 mmol) in TFA (10 mL) was added water (2 mL) and the reaction mixture was cooled to 0° C. To the above solution was then added sodium nitrite (0.806 g, 11.68 mmol) over 0.5 h. To the above mixture was then added slowly a solution of sodium azide (1.928 g, 29.7 mmol) in water. The reaction mixture was then stirred at 0° C. for 10 min, and then allowed to warm to room temperature. After 2 h, the reaction mixture was quenched by addition of water (100 mL) and the insoluble solids from the reaction mixture was filtered and dried under suction in the presence of nitrogen. To the azide was then added methyl acetoacetate (1.492 g, 12.85 mmol) in MeOH (12 mL) and methanol, sodium derivative (2.78 g, 12.85 mmol) and the mixture was heated at 65° C. in a sealed tube overnight. The reaction mixture was cooled to room temperature and then to 0° C. followed by addition of THF (50 mL). To the above mixture was then added NaOH (58.4 mL, 58.4 mmol), and the reaction was warmed to 50° C. After 2 h, the organics were concentrated and the remaining aqueous layer was made acidic with 1.0 M HCl solution. The resulting suspension was filtered and the solids were washed with water followed by a small amount of cold MeOH and dried in a oven overnight (50° C.) to give 1-(3-chloro-2-fluorophenyl)-5-methyl-1H-1,2,3-triazole-4-carboxylic acid (1.86 g, 62%) as an off-white solid. MS (ESI) m/z: 256.0 (M+H)$^+$. $^1$H NMR (400 MHz, DMSO-d$_6$) δ 7.99-7.89 (m, 1H), 7.80-7.71 (m, 1H), 7.53 (td, J=8.2, 1.3 Hz, 1H), 2.44 (s, 3H) ppm.

INTERMEDIATE 12

5-Amino-1-(3-chloro-2-fluorophenyl)-1H-1,2,3-triazole-4-carboxylic acid

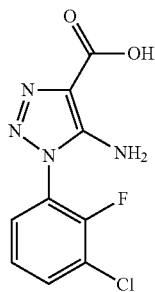 [SMILES: Nc1c(C(=O)O)nnn1-c1cccc(Cl)c1F]

Intermediate 12A. Ethyl 5-amino-1-(3-chloro-2-fluorophenyl)-1H-1,2,3-triazole-4-carboxylate: (PCT International Application No. 2006/047516 (2006)) To a solution of NaOEt (4.99 g, 15.39 mmol) in EtOH (10 mL) at 0° C. was added ethyl 2-cyanoacetate (1.501 mL, 14.11 mmol). The reaction was stirred at 0° C. for 10 min and added 1-azido-3-chloro-2-fluorobenzene (2.2 g, 12.82 mmol). The reaction is allowed to slowly warm up to room temperature and stirred for 14 h. The mixture was treated with water (3 mL) and extracted with EtOAc (3×30 mL). The combined extracts were concentrated and purified by silica gel chromatography to yield the desired product (2.1 g, 58%). MS (ESI) m/z: 285.1 (M+H)$^+$.

Intermediate 12. 5-Amino-1-(3-chloro-2-fluorophenyl)-1H-1,2,3-triazole-4-carboxylic acid: To a solution of Intermediate 5A (100 mg, 0.351 mmol) in THF (15 mL) and MeOH (15.0 mL) was added NaOH (70 mg, 1.756 mmol). The reaction was stirred at 50° C. for 2 h and then concentrated. The mixture was acidified to pH ~5 with 1 N HCl. The resulting solid was filtered and dried to yield the desired product (69 mg, 77%). MS (ESI) m/z: 257.0 (M+H)$^+$.

INTERMEDIATE 13

1-(3-Chloro-2-fluorophenyl)-1H-pyrazole-4-carboxylic acid

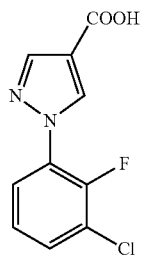 [SMILES: O=C(O)c1cnn(-c2cccc(Cl)c2F)c1]

Intermediate 13A. Ethyl 5-amino-1-(3-chloro-2-fluorophenyl)-1H-pyrazole-4-carboxylate: To a mixture of (3-chloro-2-fluorophenyl)hydrazine hydrochloride (0.67 g, 3.40 mmol), (E)-ethyl 2-cyano-3-ethoxyacrylate (0.633 g, 3.72 mmol) and sodium acetate (0.586 g, 7.12 mmol) at room temperature was added AcOH and H$_2$O to form a slurry. The reaction mixture was continued to stir at room temperature for 0.25 h and then heated at 100° C. overnight. After overnight stirring, the reaction mixture was quenched with H$_2$O (200 mL) and a yellowish brown solid separated. The solids were filtered and washed thoroughly with H$_2$O. Re-dissolved the residue in DCM, dried and evaporated to a brown solid as the desired product (0.76 g, 78%). MS (ESI) m/z: 284.2 (M+H)$^+$. $^1$H NMR (400 MHz, CDCl$_3$) δ 7.76 (s, 1H), 7.51-7.29 (m, 2H), 7.27-7.03 (m, 1H), 5.30-5.06 (m, 2H), 4.24 (q, J=7.2 Hz, 2H), 1.38-1.04 (m, 3H) ppm.

Intermediate 13. 1-(3-Chloro-2-fluorophenyl)-1H-pyrazole-4-carboxylic acid: A mixture of Intermediate 13A (0.317 g, 1.117 mmol), isoamylnitrite (1.304 g, 11.14 mmol) in THF (20 mL) was heated at 100° C. After 2 h, the reaction mixture was concentrated in vacuo to yield the crude product. To the crude product was added NaOH (0.610 g, 10 Eq), MeOH and H$_2$O. The reaction mixture was stirred at room temperature for 2 h. The reaction mixture was then quenched with H$_2$O (100 mL) and extracted the unreacted starting material with EtOAc (2×100 mL). The aqueous layer was then acidified with HCl (1 N) and then extracted the organics with EtOAc (2×100 mL). The combined organic layers were dried over sodium sulfate, filtered, and concentrated to give Intermediate 12 as a brown solid mass. MS (ESI) m/z: 240.9 (M+H)$^+$. $^1$H NMR (400 MHz, CDCl$_3$) δ 8.49 (d, J=2.5 Hz, 1H), 8.12 (s, 1H), 7.77 (ddd, J=8.3, 6.9, 1.8 Hz, 1H), 7.41-7.28 (m, 1H), 7.23-7.10 (m, 1H) ppm.

INTERMEDIATE 14

1-(3-Chlorophenyl)-1H-pyrazole-4 carboxylic acid

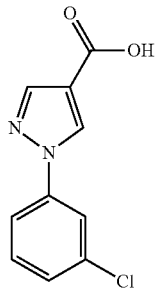 [SMILES: O=C(O)c1cnn(-c2cccc(Cl)c2)c1]

Intermediate 14. 1-(3-Chlorophenyl)-1H-pyrazole-4 carboxylic acid: 1-(1-(3-chlorophenyl)-1H-pyrazol-4-yl)ethanone was dissolved in a solution of MeOH and DMSO (5:1). To this solution was then added a solution of NaOMe (2 N, 10 mL) followed by bleach (20 mL) and stirred at room temperature overnight. After overnight stirring, the reaction mixture was quenched with $H_2O$ (200 mL) and acidified with concentrated HCl. Extracted the organics with EtOAc (2×100 mL) and concentrated to yield a brown solid as the desired product. MS (ESI) m/z: 223.1 (M+H)+. 1H NMR (400 MHz, CD$_3$OD) δ 7.36-7.38 (m, 1 H), 7.47-7.51 (m, 1 H), 7.74-7.77 (m, 1 H), 7.89-7.90 (m, 1 H), 8.04 (s, 1 H), 8.65 (s, 1 H) ppm.

INTERMEDIATE 15

1-(3-Chloro-2-fluorophenyl)-5-methyl-1H-pyrazole-4-carboxylic acid

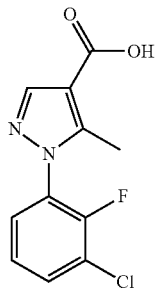 [SMILES: Cc1c(C(=O)O)cnn1-c1cccc(Cl)c1F]

Intermediate 15A. Ethyl 1-(3-chloro-2-fluorophenyl)-5-methyl-1H-pyrazole-4-carboxylate: (Reference: Herold, P. et al., *Tetrahedron*, 56:6497-6499 (2000)) A solution of ethyl 2-((dimethylamino)methylene)-3-oxobutanoate (0.517 g, 2.79 mmol), (3-chloro-2-fluorophenyl)hydrazine hydrochloride (0.500 g, 2.54 mmol) in EtOH (2.54 mL) and TEA (0.707 mL, 5.08 mmol) was stirred at room temperature t. After 10 min, the reaction mixture was concentrated and purified by silica gel chromatography. The desired product, ethyl 1-(3-chloro-2-fluorophenyl)-5-methyl-1H-pyrazole-4-carboxylate (200 mg, 28%), was obtained as an off-white solid. MS (ESI) m/z: 283.1 (M+H)+.

Intermediate 15. 1-(3-Chloro-2-fluorophenyl)-5-methyl-1H-pyrazole-4-carboxylic acid: To a solution of Intermediate 15A (50 mg, 0.177 mmol) in MeOH (0.884 mL) was added 1 N NaOH (aqueous) (1.061 mL, 1.061 mmol) and the reaction was stirred at 50° C. in a sealed vial for 3 h. The reaction mixture was then cooled to room temperature and concentrated. The residue was then partitioned between 1 N HCl (aqueous) and EtOAc. The layers were separated and the aqueous layer was extracted with EtOAc. The organic layers were combined, washed with brine, and concentrated to give Intermediate 15 as an off-white solid (48 mg, 107%). MS (ESI) m/z: 255.0 (M+H)+.

INTERMEDIATE 16

5-Amino-1-(3-chloro-2-fluorophenyl)-1H-pyrazole-4-carboxylic acid

Intermediate 16A. Ethyl 5-amino-1-(3-chloro-2-fluorophenyl)-1H-pyrazole-4-carboxylate: A brown suspension of (3-chloro-2-fluorophenyl)hydrazine hydrochloride (0.500 g, 2.54 mmol) and (E)-ethyl 2-cyano-3-ethoxyacrylate (0.472 g, 2.79 mmol) in EtOH (2.54 mL) and triethylamine (0.707 mL, 5.08 mmol) was warmed to 85° C. After 4.5 h, the reaction was stopped and cooled to room temperature. The reaction was concentrated to give a brown solid. Purification by normal phase chromatography gave Intermediate 16A (0.185 g, 26%) as an off-white solid. MS (ESI) m/z: 284.0 (M+H)+.

Intermediate 16. 5-Amino-1-(3-chloro-2-fluorophenyl)-1H-pyrazole-4-carboxylic acid: Intermediate 16A (0.184 g, 0.649 mmol) in MeOH (3.24 mL) and 1.0 N NaOH (1.946 mL, 1.946 mmol) was stirred at room temperature. After 1 h, the reaction was warmed to 50° C. After 8 h, the reaction was stopped and cooled to room temperature. And concentrated to give a white solid. The white solid was partitioned between EtOAc, water, and 1.0 N NaOH and the layers were separated. The aqueous layer was extracted with EtOAc. The aqueous layer was acidified with 1.0 N HCl and then extracted with EtOAc (2×). The combined organic layers, following acidification, were washed with brine, dried over sodium sulfate, filtered and concentrated to give Intermediate 16 (0.153 g, 92%) as an off-white solid. MS (ESI) m/z: 256.0 (M+H)+ and 258.0 (M+2+H)+. 1H NMR (500 MHz, DMSO-d$_6$) δ 12.02 (br. s., 1H), 7.74 (ddd, J=8.1, 6.7, 1.7 Hz, 1H), 7.69 (s, 1H), 7.50 (td, J=7.4, 1.7 Hz, 1H), 7.37 (td, J=8.0, 1.2 Hz, 1H), 6.43 (s, 2H).

INTERMEDIATE 17

1-(3-Chloro-2-fluorophenyl)-1H-imidazole-4-carboxylic acid, HCl salt

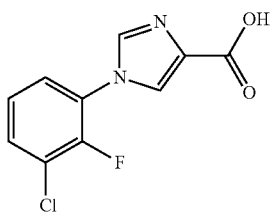 [SMILES: O=C(O)c1cn(-c2cccc(Cl)c2F)cn1]

Intermediate 17A. Ethyl 1-(3-chloro-2-fluorophenyl)-1H-imidazole-4-carboxylate, 1 HCl: A mixture of 1-chloro-2-fluoro-3-iodobenzene (0.549 g, 2.141 mmol), ethyl 1H-imidazole-4-carboxylate (0.3 g, 2.141 mmol), copper(I) iodide (0.082 g, 0.428 mmol), L-proline (0.099 g, 0.856 mmol), and $K_2CO_3$ (0.888 g, 6.42 mmol) in DMSO (4.28 mL) was vacuumed and back-filled with argon for three times, then capped and heated at 110° C. After 20 h, the reaction mixture was cooled to room temperature and diluted with EtOAc. The organic layer was washed with $H_2O$, brine, dried over $Na_2SO_4$, filtered, and concentrated. The crude product was then purified using reverse phase HPLC chromatography to yield the desired product (0.01 g, 1.2%) as a colorless oil. MS (ESI) m/z: 269.0 $(M+H)^+$.

Intermediate 17. 1-(3-Chloro-2-fluorophenyl)-1H-imidazole-4-carboxylic acid: Intermediate 10 was obtained in a similar manner as Intermediate 9 by hydrolysis of Intermediate 17A. MS (ESI) m/z: 241.0 $(M+H)^+$.

INTERMEDIATE 18 tert-Butyl 3-(3-chloro-2-fluorophenyl)-4,5-dihydroisoxazole-5-carboxylate

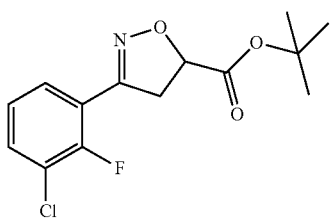 [SMILES: CC(C)(C)OC(=O)C1CC(c2cccc(Cl)c2F)=NO1]

Intermediate 18A. (E)-3-Chloro-2-fluorobenzaldehyde oxime: To a solution of 3-chloro-2-fluorobenzaldehyde (9.61 grams, 60.6 mmol) in THF (50 mL), hydroxylamine hydrochloride (4.21 grams, 60.6 mmol) was added followed by TEA (8.45 mL, 60.6 mmol). After 24 h. the reaction was quenched with water (200 mL), extracted organics with EtOAc (2×100 mL), dried and evaporated. Purified by normal phase chromatography to give 18A (7.5 grams, 71%) as a colorless solid. MS (ESI) m/z: 174.0 $(M+H)^+$.

Intermediate 18. tert-Butyl 3-(3-chloro-2-fluorophenyl)-4,5-dihydroisoxazole-5-carboxylate: NCS (6.92 g, 51.9 mmol) was added to a DMF solution of 18A (7.5 g, 43.2 mmol) and stirred at room temperature. After 3 h, the reaction mixture was quenched with water (200 mL), the organics extracted with EtOAc (2×200 mL), washed with brine (100 mL), dried ($MgSO_4$), filtered, and evaporated to an oil. The material was dissolved in DCM (200 mL), t-butylacrylate (16.61 g, 130 mmol) added, and then cooled to 0° C. Afterwards, TEA (9 mL, 64 mmol) was added and gradually allowed to come to room temperature. The reaction mixture was concentrated, quenched with water (100 mL), extracted organics with EtOAc (2×200 mL), dried ($MgSO_4$), and evaporated to an oil. The crude material was purified by normal phase chromatography to give Intermediate 18 (10.4 grams, 80%) as an oil. MS (ESI) m/z, 321.9 (M+Na), 243.9 (M-tBu). $^1$H NMR (400 MHz, chloroform-d) δ 7.84-7.79 (m, 1H), 7.53-7.46 (m, 1H), 7.18-7.12 (m, 1H), 5.15-5.05 (m, 1H), 3.73-3.65 (m, 2H), 1.53 (s, 9H) ppm. The racemic carboxylic acid was obtained by TFA hydrolysis.

INTERMEDIATE 19

(R)-3-(3-Chloro-2-fluorophenyl)-4,5-dihydroisoxazole-5-carboxylic acid

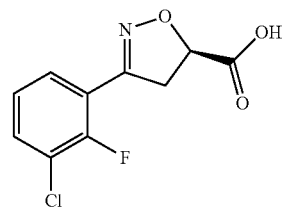 [SMILES: O=C(O)[C@H]1CC(c2cccc(Cl)c2F)=NO1]

Intermediate 19A. (R)-tert-Butyl 3-(3-chloro-2-fluorophenyl)-4,5-dihydroisoxazole-5-carboxylate: Intermediate 18 (2.0 grams, 6.67 mmol) was subjected to chiral SFC purification using CHIRALPAK® IC column (3×25 cm, 5 µM) using a mixture $CO_2$/EtOH:Heptane[1:1 (v/v)](93/7) with a flow rate of 140 mL/min and 100 bar at 40° C. Each separated enantiomer was concentrated separately and the resulting pale yellow oils placed under vacuum overnight. Peak 1 (enantiomer 1) (0.87 g, 43.5%) was set aside. Peak 2 (enantiomer 2) (0.75 g, 37.5%), (R)-tert-butyl 3-(3-chloro-2-fluorophenyl)-4,5-dihydroisoxazole-5-carboxylate, was designated as Intermediate 19A. MS (ESI) m/z: 300.1 $(M+H)^+$, 322.1 (M+Na).

Intermediate 19. (R)-3-(3-Chloro-2-fluorophenyl)-4,5-dihydroisoxazole-5-carboxylic acid: TFA (2 mL) was added to a solution of 19A (0.75 g, 2.50 mmol) in DCM. After 14 h, the reaction mixture was concentrated, and dried under high vacuum to afford Intermediate 19 as a white solid. MS (ESI) m/z: 244.1. $^1$H NMR (400 MHz, chloroform-d) δ 7.82-7.77 (m, 1H), 7.57-7.50 (m, 1H), 7.20-7.16 (m, 1H), 5.30-5.26 (m, 1H), 3.87-3.80 (m, 2H) ppm. The absolute stereochemistry was confirmed by single molecule x-ray crystallography.

INTERMEDIATE 20

1-(3-Chlorophenyl)-5-oxopyrrolidine-3-carboxylic acid

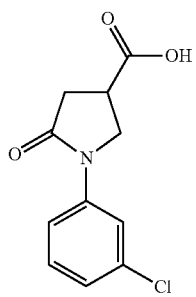 [SMILES: O=C(O)C1CC(=O)N(c2cccc(Cl)c2)C1]

Intermediate 20. 1-(3-Chlorophenyl)-5-oxopyrrolidine-3-carboxylic acid: (Reference: *J. Med. Chem.*, 30:400-405 (1987)) A mixture of 3-chloroaniline (2.55 g, 20 mmol) and 2-methylene succinic acid (2.60 g, 20.00 mmol) was heated at 120° C. (open flask). After 20 min, the reaction was cooled to room temperature. Next, water was added and the reaction mixture was warmed to 110° C. (sealed tube) to give a yellow suspension. After cooling to room temperature, MeOH (20 mL) was added. After 1 h, the mixture was filtered and the solid rinsed with a small amount of MeOH and air-dried to yield a off-white solid as Intermediate 20 (2.5 g, 52%). MS (ESI) m/z: 240.0 (M+H)$^+$. $^1$H NMR (500 MHz, MeOD) δ 7.80 (t, J=2.1 Hz, 1H), 7.49-7.46 (m, 1H), 7.36 (t, J=8.1 Hz, 1H), 7.18 (ddd, J=8.0, 2.1, 1.0 Hz, 1H), 4.16-4.07 (m, 2H), 3.46-3.38 (m, 1H), 2.88 (dd, J=8.3, 1.1 Hz, 2H).

INTERMEDIATE 21

1-(3-Chlorophenyl)pyrrolidine-3-carboxylic acid

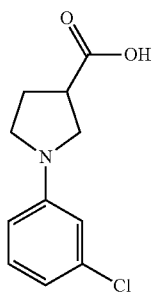 [SMILES: O=C(O)C1CCN(c2cccc(Cl)c2)C1]

Intermediate 21A. Methyl 1-(3-chlorophenyl)-5-oxopyrrolidine-3-carboxylate (Reference: *Tetrahedron*, 62; 4011-4017 (2006)). To a cold solution of MeOH (8.35 mL) (0° C.) was added thionyl chloride (0.335 mL, 4.59 mmol) dropwise. After 30 min, Intermediate 20 (1 g, 4.17 mmol) was added, and the reaction mixture was warmed to room temperature. The reaction mixture was then concentrated and the residue dissolved in EtOAc, washed with saturated NaHCO$_3$, H$_2$O and brine. The organic layers were dried over Na$_2$SO$_4$, filtered and concentrated to yield the desired product (1.04 g, 98%) as yellow oil. MS (ESI) m/z: 254.0 (M+H)$^1$.

Intermediate 21B. Methyl 1-(3-chlorophenyl)pyrrolidine-3-carboxylate: To a solution of 20A (0.27 g, 1.064 mmol) in THF (3 mL) was added BH$_3$-THF complex (1.596 mL, 1.596 mmol) (1M in THF). The reaction mixture was stirred at room temperature. After 17 h, the reaction mixture was quenched by adding 1 mL MeOH, then H$_2$O. The above mixture was then extracted with EtOAc and the organic layers were washed with H$_2$O, brine, dried over Na$_2$SO$_4$, and concentrated. The crude product was then purified using silica gel chromatography to afford a colorless oil as the desired product (0.175 g, 68.6%). MS (ESI) m/z: 240.1 (M+H)$^+$.

Intermediate 21. 1-(3-Chlorophenyl)pyrrolidine-3-carboxylic acid: To a solution of 20B (0.175 g, 0.730 mmol) in MeOH (5 mL) was added 1N NaOH (1.460 mL, 1.460 mmol). The reaction mixture was stirred at room temperature for 2 h. After 2 h, the reaction mixture was then concentrated to remove MeOH. The residue was then neutralized with 1 N HCl (2 mL) and extracted with EtOAc. The organic layer was washed with brine, dried over Na$_2$SO$_4$, filtered, and concentrated. A white solid was obtained as the desired product (0.15 g, 91%). MS (ESI) m/z: 226.1 (M+H)$^+$. $^1$H NMR (500 MHz, CDCl$_3$) δ 10.34 (br. s., 1H), 7.16 (t, J-8.1 Hz, 1H), 6.72-6.68 (m, 1H), 6.57 (t, J=2.2 Hz, 1H), 6.49-6.43 (m, 1H), 3.64-3.52 (m, 2H), 3.48-3.25 (m, 3H), 2.43-2.29 (m, 2H) ppm.

INTERMEDIATE 22

1-(3-Chloro-2-fluorophenyl)-5-oxopyrrolidine-3-carboxylic acid

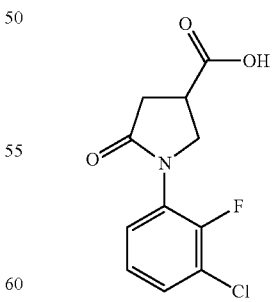

Intermediate 22. 1-(3-Chloro-2-fluorophenyl)-5-oxopyrrolidine-3-carboxylic acid: Intermediate 22 was prepared in a similar manner as Intermediate 20 replacing 3-chloroaniline with 3-chloro-2-fluoroaniline. MS (ESI) m/z: 258.1/260.0 (M+H)$^+$.

INTERMEDIATE 23

1-(3-Chloro-2-fluorophenyl)pyrrolidine-3-carboxylic acid

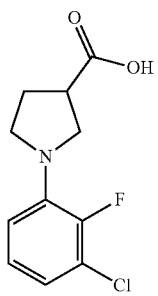 [SMILES: O=C(O)C1CCN(c2cccc(Cl)c2F)C1]

Intermediate 23. 1-(3-Chloro-2-fluorophenyl)pyrrolidine-3-carboxylic acid: Intermediate 23 was prepared in a similar manner as Intermediate 21 replacing Intermediate 20 with Intermediate 22. MS (ESI) m/z: 244.1/245.9 (M+H)+.

INTERMEDIATE 24 tert-Butyl 4-(5-bromo-2-(1-(3-chloro-2-fluorophenyl)-1H-1,2,3-triazole-4-carbonyl)-1,2,3,4-tetrahydroisoquinoline-1-carboxamido)benzoate

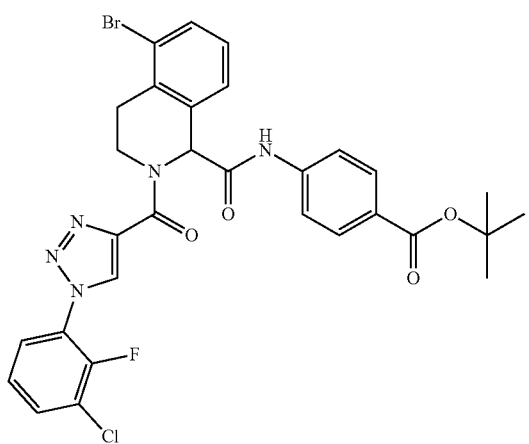 [SMILES: CC(C)(C)OC(=O)c1ccc(NC(=O)C2c3cccc(Br)c3CCN2C(=O)c2cn(-c3cccc(Cl)c3F)nn2)cc1]

Intermediate 24A. 5-Bromo-1,4-dihydroisoquinoline: 5-Bromo-1,2,3,4-tetrahydroisoquinoline (0.500 g, 2.36 mmol) in DCM (25 mL) was treated with manganese dioxide (3.69 g, 42.4 mmol). After 15 h, the reaction mixture was filtered through a plug of CELITE® and filtrate concentrated. The imine was carried forward as is. MS (ESI) m/z: 209.8 (M+H)+.

Intermediate 24. tert-Butyl 4-(5-bromo-2-(1-(3-chloro-2-fluorophenyl)-1H-1,2,3-triazole-4-carbonyl)-1,2,3,4-tetrahydroisoquinoline-1-carboxamido)benzoate: Intermediate 24A (0.100 g, 0.476 mmol), Intermediate 9 (0.115 g, 0.476 mmol), Intermediate 1 (0.097 g, 0.476 mmol) were added to MeOH (0.952 mL) and heated at 50° C. overnight. The solids that precipitated from the reaction were collected by filtration, rinsed with a minimum amount of MeOH followed by Et2O, and dried under vacuum to give Intermediate 24 (130 mg, 42%). MS (ESI) m/z: 654/655.8 (M+H)+. 1H NMR (500 MHz, DMSO-d6) δ 11.01 (s, 1H), 9.19 (d, J=1.4 Hz, 1H), 7.94-7.82 (m, 4H), 7.77-7.68 (m, 3H), 7.64 (d, J=8.0 Hz, 1H), 7.55-7.50 (m, 1H), 7.29 (t, J=7.8 Hz, 1H), 6.02 (s, 1H), 4.55-4.47 (m, 1H), 4.43-4.36 (m, 1H), 3.17-3.07 (m, 2H), 1.54 (s, 9H) ppm.

INTERMEDIATE 25 tert-Butyl 4-(2-(5-bromonicotinoyl)-5-(4-methoxypiperidin-1-yl)-1,2,3,4-tetrahydroisoquinoline-1-carboxamido)benzoate

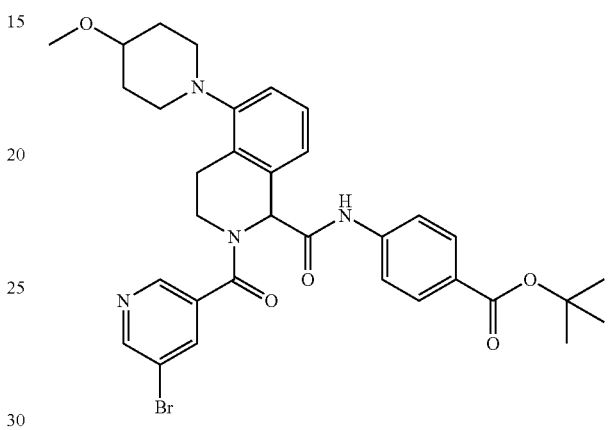

Intermediate 25. tert-Butyl 4-(2-(5-bromonicotinoyl)-5-(4-methoxypiperidin-1-yl)-1,2,3,4-tetrahydroisoquinoline-1-carboxamido)benzoate: To a septa capped pressure vial was charged 5-bromonicotinic acid (497 mg, 2.461 mmol), Intermediate 4 (601.2 mg, 2.461 mmol) and Intermediate 4 (500 mg, 2.461 mmol) were added MeOH (anhydrous) (4.9 mL). The vial was sealed and heated to 50° C. overnight. The reaction mixture was concentrated and the residue purified by normal phase chromatography to give Intermediate 25 (1.19 g, 74.5% yield). MS (ESI) m/z: 650.9 (M+H)+.

INTERMEDIATE 26

2-tert-Butyl 1-methyl 5-bromo-3,4-dihydroisoquinoline-1,2(1H)-dicarboxylate

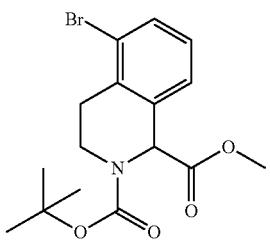 [SMILES: COC(=O)C1c2cccc(Br)c2CCN1C(=O)OC(C)(C)C]

Intermediate 26. 2-tert-Butyl 1-methyl 5-bromo-3,4-dihydroisoquinoline-1,2(1H)-dicarboxylate: To Intermediate 6 (5 g, 14.04 mmol) in MeOH (100 mL) was slowly added excess thionyl chloride (6.15 mL, 84 mmol). After 18 h, additional thionyl chloride (4 eq) was added. After a total of 72 h, the reaction mixture was concentrated to dryness. The residue was combined with dioxane (100 mL), sodium dicarbonate (7.08 g, 84 mmol), BOC$_2$O (3.26 mL, 14.04 mmol), and TEA (5.87 mL, 42.1 mmol). After stirring overnight, the reaction mixture was filtered and filtrate concentrated. The residue was dissolved in EtOAc, washed with saturated NaHCO$_3$ solution. The aqueous layer was washed with additional EtOAc and the combined organic layers were washed with brine (25 mL), dried (MgSO$_4$), filtered, and concentrated. Purification by normal phase chromatography gave Intermediate 26 (4.00 g, 77% yield) as a clear, amber oil which slowly solidified over time. MS (ESI) m/z: 370/372 (M+H)$^+$.

Intermediate 26 (alternative synthesis): 2-tert-Butyl 1-methyl 5-bromo-3,4-dihydroisoquinoline-1,2(1H)-dicarboxylate Intermediate 26. 2-tert-Butyl 1-methyl 5-bromo-3,4-dihydroisoquinoline-1,2(1H)-dicarboxylate: To Intermediate 6 (5 g, 14.04 mmol) in MeOH (100 mL) and acetonitrile (300 mL) was added trimethylsilyldiazomethane 2N in hexane (14.04 mL, 28.08 mmol) dropwise at 0° C. After the completion of the reaction, the solution was concentrated almost to dryness. The wet residue was dissolved in EtOAc, washed with saturated NaHCO$_3$ solution. The aqueous layer was washed with additional EtOAc and the combined organic layers were washed with brine, dried (MgSO$_4$), filtered, and concentrated. Purification by normal phase chromatography gave Intermediate 26B (4.3 g, 83% yield) as a clear oil solidified to white solid upon standing. MS (ESI) m/z: 372.1 (M+H)$^+$.

INTERMEDIATE 27

2-tert-Butyl 1-methyl 5-(4-methoxypiperidin-1-yl)-3,4-dihydroisoquinoline-1,2(1H)-dicarboxylate

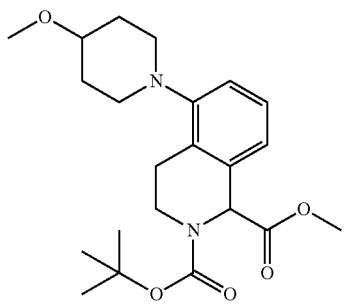

Intermediate 27. 2-tert-Butyl 1-methyl 5-(4-methoxypiperidin-1-yl)-3,4-dihydroisoquinoline-1,2(1H)-dicarboxylate: Intermediate 26 (0.315 g, 0.851 mmol), 4-methoxypiperidine (0.108 g, 0.936 mmol), BINAP (0.016 g, 0.026 mmol), Cs$_2$CO$_3$ (0.554 g, 1.702 mmol) were added dioxane (5 mL) and degassed with argon. After 15 minutes, Pd$_2$(dba)$_3$ (7.79 mg, 8.51 μmol) was added and The mixture heated to 90° C. After 24 h, additional BINAP (0.016 g, 0.026 mmol), Cs$_2$CO$_3$ (0.554 g, 1.702 mmol), and Pd$_2$(dba)$_3$ (7.79 mg, 8.51 μmol) were added and heating continued. After stirring for 5 days, the reaction was diluted with EtOAc (25 mL)/water (10 mL) and filtered. The separated aqueous layer was extracted with EtOAc (2×25 mL). The combined organic layer was washed with brine (15 mL), dried (MgSO$_4$), filtered, and concentrated. Purification by normal phase chromatography gave Intermediate 27 (0.359 g) as a yellow oil. MS (ESI) m/z: 405.0 (M+H)$^+$. $^1$H NMR (400 MHz, chloroform-d) δ 7.23-7.13 (m, 2H), 7.04-6.92 (m, 1H), 5.63-5.31 (m, 1H), 3.95-3.83 (m, 1H), 3.79-3.65 (m, 4H), 3.57-3.46 (m, 1H), 3.44-3.30 (m, 3H), 3.08 (dd, J=9.9, 5.3 Hz, 2H), 3.00-2.88 (m, 2H), 2.81-2.62 (m, 2H), 2.04 (br. s., 1H), 1.76 (br. s., 2H), 1.54-1.44 (m, 10H) ppm.

INTERMEDIATE 28 tert-Butyl 4-(5-(4-methoxypiperidin-1-yl)-1,2,3,4-tetrahydroisoquinoline-1-carboxamido)benzoate

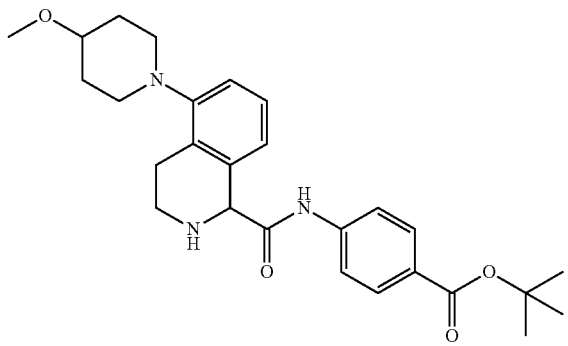 [SMILES: COC1CCN(c2cccc3c2CCNC3C(=O)Nc2ccc(C(=O)OC(C)(C)C)cc2)CC1]

Intermediate 28A. tert-Butyl 4-(5-(4-methoxypiperidin-1-yl)-2-(2,2,2-trifluoroacetyl)-1,2,3,4-tetrahydroisoquinoline-1-carboxamido)benzoate: To a septa capped pressure vial was charged Intermediate 4 (1.985 g, 8.12 mmol), Intermediate 1 (1.651 g, 8.12 mmol) and MeOH (anhydrous) (8.25 mL) were added. A solution of 2,2,2-trifluoroacetic acid (0.622 mL, 8.12 mmol) in MeOH (anhydrous) (8 mL) was added the vial was capped and the contents heated to 50° C. overnight Reaction mixture was evaporated to a gummy residue which was purified by normal phase chromatography to give 28A (2.62 g, 4.67 mmol, 57.4% yield) as a white solid. MS (ESI) m/z: 562.0 (M+H)$^+$.

Intermediate 28. tert-Butyl 4-(5-(4-methoxypiperidin-1-yl)-1,2,3,4-tetrahydroisoquinoline-1-carboxamido)benzoate: To a solution of 28A (2.62 g, 4.67 mmol) in MeOH (anhydrous) (49.1 mL) was added NaBH$_4$ (0.883 g, 23.33 mmol) and the mixture stirred under nitrogen for 1.5 h. Reaction was quenched with saturated aq. NaHCO$_3$ (100 mL) and most of the MeOH was evaporated. The mixture was partitioned between water and ethyl acetate. The aqueous layer was extracted with ethyl acetate (3×) and the combined organics washed with brine, dried (Na$_2$SO$_4$), filtered and evaporated. The residue was purified by normal chromatography to give Intermediate 28 (1.81 g, 3.89 mmol, 83% yield) as a colorless solid. MS (ESI) m/z: 466.0 (M+H)$^+$. $^1$H NMR (500 MHz, methanol-d$_4$) δ 7.94-7.92 (m, 2H), 7.73-7.70 (m, 2H), 7.18-7.14 (m, 1H), 7.12-7.10 (m, 1H), 7.01 (d, J=7.7 Hz, 1H), 4.76 (s, 1H), 3.44-3.39 (m, 4H), 3.38-3.35 (m, 1H), 3.18-3.13 (m, 1H), 3.07-3.00 (m, 1H), 2.97-2.89 (m, 2H), 2.87-2.79 (m, 2H), 2.68-2.60 (m, 1H), 2.12-2.02 (m, 2H), 1.76-1.65 (m, 2H), 1.60 (s, 9H) ppm.

INTERMEDIATE 29

1-(3-Chloro-2,6-difluorophenyl)-5-oxopyrrolidine-3-carboxylic acid

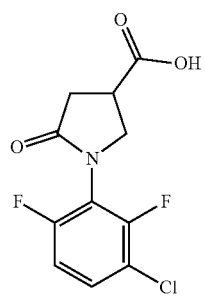 [SMILES: O=C(O)C1CC(=O)N(c2c(F)ccc(Cl)c2F)C1]

Intermediate 29. 1-(3-Chloro-2,6-difluorophenyl)-5-oxopyrrolidine-3-carboxylic acid: Intermediate 29 was prepared in a similar manner as Intermediate 20 replacing 3-chloroanline with 3-chloro-2,6-difluoroaniline. MS (ESI) m/z: 276/278 (M+H)$^+$.

INTERMEDIATE 30

2-tert-Butyl 1-methyl 5-(pyrimidin-5-yl)-3,4-dihydroisoquinoline-1,2(1H)-dicarboxylate

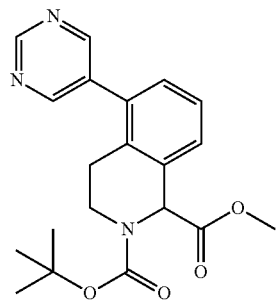 [SMILES: COC(=O)C1c2cccc(-c3cncnc3)c2CCN1C(=O)OC(C)(C)C]

Intermediate 30. 2-tert-Butyl 1-methyl 5-(pyrimidin-5-yl)-3,4-dihydroisoquinoline-1,2(1H)-dicarboxylate: A mixture of Intermediate 26 (0.934 g, 2.52 mmol), pinacol ester pyrimidinyl-5-boronic acid (0.78 g, 3.79 mmol), potassium phosphate, tribasic (1.071 g, 5.05 mmol) and DMSO (16.82 mL) was purged with $N_2$ for several minutes. Then $PdCl_2$(dppf)-$CH_2Cl_2$Adduct (0.206 g, 0.252 mmol) was added and the reaction was heated to 90° C. overnight. The reaction was cooled to room temperature diluted with EtOAc and water. The separated aqueous layer was extracted twice with EtOAc. The combined organic layer was washed with brine, dried (MgSO$_4$), filtered, and concentrated. Purification by normal phase chromatography gave Intermediate 30 (0.94 g, 100% yield). $^1$H NMR (400 MHz, chloroform-d) δ 9.23 (s, 1H), 8.72 (s, 2H), 7.59 (d, J=3.5 Hz, 1H), 7.37 (t, J=7.7 Hz, 1H), 7.22 (d, J=7.5 Hz, 1H), 5.75-5.39 (m, 1H), 3.83-3.70 (m, 4H), 3.67-3.53 (m, 1H), 2.94-2.67 (m, 2H), 1.49 (s, 9H) ppm. MS (ESI) m/z: 370.2 (M+H)$^+$.

INTERMEDIATE 31

2-(tert-Butoxycarbonyl)-5-(pyrimidin-5-yl)-1,2,3,4-tetrahydroisoquinoline-1-carboxylic acid

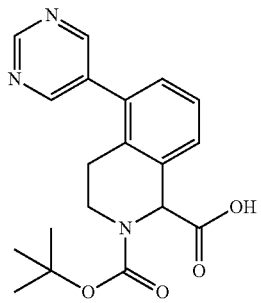 [SMILES: CC(C)(C)OC(=O)N1CCc2c(-c3cncnc3)cccc2C1C(=O)O]

Intermediate 31. 2-(tert-Butoxycarbonyl)-5-(pyrimidin-5-yl)-1,2,3,4-tetrahydroisoquinoline-1-carboxylic acid: A mixture of Intermediate 100 (0.94 g, 2.54 mmol) was treated with LiOH monohydrate (0.320 g, 7.63 mmol) in THF (15 mL), water (15 mL) and MeOH (5 mL) at room temperature overnight. The solvent was evaporated and the remaining aqueous mixture was acidified with 1N HCl to pH 4-5 and extracted twice with EtOAc. The combined organic layer was washed with brine, dried (MgSO$_4$), filtered, and concentrated to give Intermediate 31 (0.81 g, 90% yield) as a beige foam. $^1$H NMR (400 MHz, chloroform-d) δ 9.24 (s, 1H), 8.74 (s, 2H), 7.62 (br. s., 1H), 7.39 (t, J=7.6 Hz, 1H), 7.29-7.16 (m, 3H), 5.73-5.33 (m, 1H), 3.90-3.67 (m, 1H), 3.56 (br. s., 1H), 2.99-2.68 (m, 2H), 1.49 (s, 9H). MS (ESI) m/z: 356.2 (M+H)$^+$.

INTERMEDIATE 32

1-(3-Chloro-2-fluorophenyl)-5-methyl-1H-imidazole-4-carboxylic acid, HCl salt

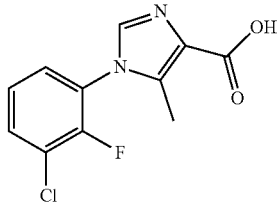 [SMILES: Cc1c(C(=O)O)ncn1-c1cccc(Cl)c1F]

Intermediate 32A. Ethyl 3-((3-chloro-2-fluorophenyl)amino)-2-nitrobut-2-enoate: Using a modified procedure described by Gomez-Sanchez. (Reference: Gomez-Sanchez, A. et al., Anales De Quimica, 81(2): 139 (1985)) A clear, faint yellow solution of ethyl nitroacetate (4.17 mL, 37.6 mmol) and triethylorthoacetate (6.93 mL, 37.6 mmol) in toluene (9.39 mL) was heated to 110° C. A Dean-Stark trap was used to azeotrope the ethanol. Approximately every 30 min, the solvent was removed from the Dean-Stark and additional toluene (6 mL) was added to the reaction flask. Over the course of the reaction the color became a clear, dull yellow color. After 7.5 h, the reaction was stopped and it was cooled to room temperature. Excess solvent and starting materials were removed by distillation (5 mm Hg at 100° C.) leaving ethyl 3-ethoxy-2-nitrobut-2-enoate (5.46 g) as an orange liquid. An orange solution of 3-chloro-2-fluoroaniline (5.86 g, 40.2 mmol) and ethyl 3-ethoxy-2-nitrobut-2-enoate (5.45 g, 26.8 mmol) in ethanol (13.41 mL) was stirred at room temperature. After 7 h, the reaction was stopped and concentrated to give an orange oil. The orange oil was diluted with EtOAc and washed with 1.0 N HCl (2×), saturated NaHCO$_3$, brine, dried over sodium sulfate, filtered and concentrated to give an orange oil. Purification by normal phase chromatography gave Intermediate 32A (2.90 g, 36%) as a viscous orange-yellow oil. $^1$H NMR indicated a 1:1 E:Z mixture. MS (ESI) m/z: 325.0 (M+H)$^+$.

Intermediate 32B. Ethyl 1-(3-chloro-2-fluorophenyl)-5-methyl-1H-imidazole-4-carboxylate: Using a modified procedure described by Gomez-Sanchez. (Reference: Gomez-Sanchez, A. et al., *J. Heterocyclic Chem.*, 24:1757 (1987)) A clear, yellow solution of Intermediate 32A (2.90 g, 9.58 mmol) in triethylorthoformate (96 mL) was degassed with argon for 20 min. Next, platinum on carbon (0.935 g, 0.479 mmol) was added. The flask was equipped with a reflux condenser and the reaction was purged with hydrogen (balloon) for several minutes. The reaction was stirred under a hydrogen atmosphere and the reaction was warmed to 75° C. After a total of 4 h, the reaction was cooled to room temperature. The reaction was placed under vacuum for several minutes and then backfilled with argon (5×). Next, CELITE® was added and the reaction was filtered, washing with ethanol. The filtrate was concentrated to give a clear, yellow-brown oil weighing 3.17 g. Purification by normal phase chromatography provided Intermediate 32B (1.64 g, 61%) as a white solid. MS (ESI) m/z: 283.0 (M+H)$^+$.

Intermediate 32. 1-(3-Chloro-2-fluorophenyl)-5-methyl-1H-imidazole-4-carboxylic acid, 1 HCl: To a clear, colorless solution Intermediate 32B (1.64 g, 5.80 mmol) in methanol (29.0 mL) was added 1.0 M NaOH (17.40 mL, 17.40 mmol). The reaction was stirred at room temperature. After 20 h, the reaction was concentrated under high vacuum with minimal heating to give a white solid. The solid was suspended in water and 1.0 N HCl was added until the mixture was at a pH=1-2. The solid was collected by filtration and rinsed with water, air-dried, and dried under high vacuum to give Intermediate 32 (1.44 g, 81%) as a white solid. $^1$H NMR (500 MHz, DMSO-d$_6$) δ 7.91 (d, J=0.5 Hz, 1H), 7.83 (ddd, J=8.3, 6.9, 1.7 Hz, 1H), 7.63 (td, J=7.5, 1.5 Hz, 1H), 7.46 (td, J=8.1, 1.4 Hz, 1H), 2.32 (s, 3H). MS (ESI) m/z: 255.0 (M+H)$^+$ and 257.0 (M+2+H)$^+$.

INTERMEDIATE 33

Methyl 4-aminobicyclo[2.2.2]octane-1-carboxylate

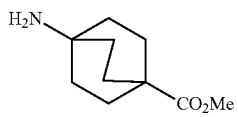

The synthesis was described as Preparation of Bicyclic Amine 2 (BA-2) in U.S. Patent Publication No. US 2010/0267738, published Oct. 21, 2010.

INTERMEDIATE 34 tert-Butyl 4-(5-(4-methylpiperazin-1-yl)-1,2,3,4-tetrahydroisoquinoline-1-carboxamido)benzoate

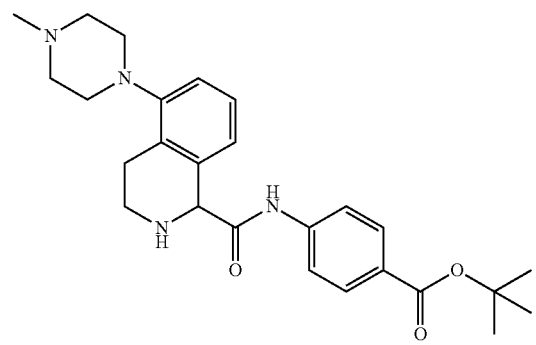 [SMILES: CN1CCN(c2cccc3c2CCNC3C(=O)Nc2ccc(C(=O)OC(C)(C)C)cc2)CC1]

Intermediate 34. The title compound was prepared in a similar manner as Intermediate 28 starting from Intermediate 4G. $^1$H NMR (400 MHz, chloroform-d) δ 9.67 (1 H, s), 7.90-7.94 (2 H, m), 7.59-7.65 (2 H, m), 7.41 (1 H, d, J=7.78 Hz), 7.22 (1H, t, J=7.91 Hz), 7.00 (1 H, d, J=7.78 Hz), 4.75 (1 H, s), 3.23 (1 H, ddd, J=11.67, 5.02, 4.89 Hz), 2.72-3.11 (8 H, m), 2.49-2.67 (4 H, m), 2.36-2.38 (3 H, m), 1.56-1.61 (9 H, m) ppm. MS (EST) m/z: 451.0 (M+H)$^+$.

INTERMEDIATE 35 tert-Butyl 4-(5-(4-(pyrrolidin-1-yl)piperidin-1-yl)-1,2,3,4-tetrahydroisoquinoline-1-carboxamido)benzoate

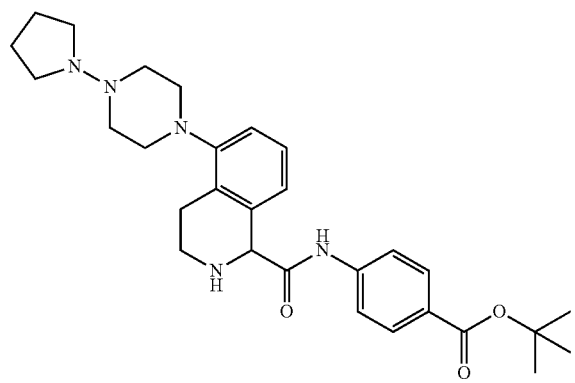 [SMILES: CC(C)(C)OC(=O)c1ccc(NC(=O)C2NCCc3c2cccc3N2CCN(N3CCCC3)CC2)cc1]

Intermediate 35. The title compound was prepared in a similar manner as Intermediate 28 starting from Intermediate 4P. $^1$H NMR (CDCl$_3$) δ 7.85 (d, J=8.4 Hz, 2H), 7.55 (d, J=8.4 hz, 2H), 7.31 (d, 1H), 7.12 (m, 2H), 6.87 (d, 1H), 4.66 (s, 1H), 3.42 (bs, 2H), 3.18-2.49 (m, 10H), 2.00-1.72 (m, 9H), 1.50 (s, 9H) ppm. MS (ESI) m/z: 505.0 (M+H)$^+$.

INTERMEDIATE 36 tert-Butyl 4-(5-(4-(2-oxopyrrolidin-1-yl)piperidin-1-yl)-1,2,3,4-tetrahydroisoquinoline-1-carboxamido)benzoate

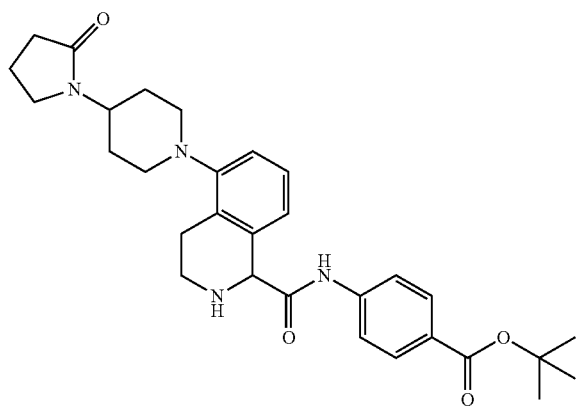 [SMILES: CC(C)(C)OC(=O)c1ccc(NC(=O)C2NCCc3c2cccc3N2CCC(N3CCCC3=O)CC2)cc1]

Intermediate 36. The title compound was prepared in a similar manner as Intermediate 28 starting from Intermediate 4Q. $^1$H NMR (400 MHz, methanol-d$_4$) δ 7.86 (d, J=8.6 Hz, 2H), 7.63 (d, J=8.6 Hz, 2H), 7.30-7.19 (m, 1H), 7.19-7.07 (m, 2H), 5.16 (s, 1H), 3.99-3.85 (m, 1H), 3.76-3.64 (m, 1H), 3.42 (t, J=7.1 Hz, 2H), 3.36-3.29 (m, 1H), 3.16-2.99 (m, 4H), 2.88-2.78 (m, 1H), 2.78-2.60 (m, 1H), 2.41-2.25 (m, 2H), 2.04-1.93 (m, 2H), 1.93-1.78 (m, 2H), 1.68 (br. s., 2H), 1.59-1.42 (m, 9H) ppm. MS (ESI) m/z: 519.0 (M+H)$^+$.

INTERMEDIATE 37 AND INTERMEDIATE 38 tert-Butyl 2,3-dimethyl-6,7-dihydro-2H-pyrazolo[4,3-c]pyridine-5(4H)-carboxylate, and tert-Butyl 1,3-dimethyl-6,7-dihydro-1H-pyrazolo[4,3-c]pyridine-5 (4H)-carboxylate intermediate 37

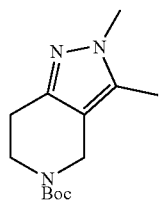

intermediate 38

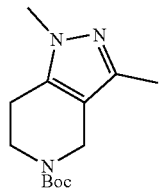

Intermediate 37 and Intermediate 38. tert-Butyl 2,3-dimethyl-6,7-dihydro-2H-pyrazolo[4,3-c]pyridine-5(4H)-carboxylate, and tert-Butyl 1,3-dimethyl-6,7-dihydro-1H-pyrazolo[4,3-c]pyridine-5(4H)-carboxylate: LHMDS (5.52 mL, 5.52 mmol) was added to an ice cold (0° C.) toluene (15 mL) solution of NBoc-4-pyridone (1 g, 5.02 mmol). After stirring at this temperature for 2 min acetyl chloride was syringed in. The reaction mixture became milky yellow. After 5 min at this temperature the reaction mixture was quenched with AcOH (1:1, 10 mL) and stirred at room temperature. for 15 min. To this was then added methylhydrazine (0.213 mL) and the reaction mixture was heated at 50° C.

After 1 h, the crude shows a mixture of regioisomers. Concentrated and purified directly via reverse phase HPLC to afford the desired intermediates.

Intermediate 37: $^1$H NMR (400 MHz, chloroform-d) δ 4.38-4.33 (m, 2H), 3.85 (s, 3H), 3.78-3.72 (m, 2H), 2.72-2.66 (m, 2H), 2.31-2.27 (m, 3H), 1.50 (s, 9H) ppm.

Intermediate 38: $^1$H NMR (400 MHz, chloroform-d) δ 4.38-4.33 (m, 2H), 3.86-3.83 (m, 3H), 3.78-3.72 (m, 2H), 3.39-3.33 (m, 2H), 2.72-2.66 (m, 3H), 2.31-2.27 (m, 2H), 1.50 (s, 9H) ppm.

The respective intermediates were deprotected by heating in methanol/water at 100° C. to afford the respective pyrazolopiperidine analogs.

INTERMEDIATE 39 tert-Butyl 2-methyl-6,7-dihydro-2H-pyrazolo[4,3-c]pyridine-5(4H)-carboxylate

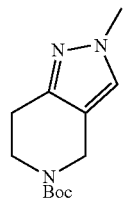 [SMILES: Cn1cc2c(n1)CCN(C(=O)OC(C)(C)C)C2]

Intermediate 39: Methylhydrazine (0.18 g, 3.85 mmol) was added to a AcOH (10 mL) solution of (E)-tert-butyl 3-((dimethylamino)methylene)-4-oxopiperidine-1-carboxylate (0.98 g, 3.85 mmol). The reaction mixture was heated to 55° C. Quenched the reaction with water (100 mL) and extracted organics with EtOAc (2×100 mL), dried and evaporated to an oil (0.9 g). $^1$H NMR (400 MHz, chloroform-d) δ 7.32-7.27 (m, 1H), 4.49-4.41 (m, 2H), 3.75-3.66 (m, 2H), 2.81-2.65 (m, 2H), 2.11 (s, 3H), 1.50 (s, 9H) ppm.

The respective intermediate was deprotected by heating in methanol/water at 100° C. to afford the respective pyrazolopiperidine analog.

The following isonitriles were made in the same manner as Intermediate 1 replacing tert-butyl 4-aminobenzoate with the appropriate commercially available aniline:

INTERMEDIATE 40

Methyl 3-fluoro-4-isocyanobenzoate

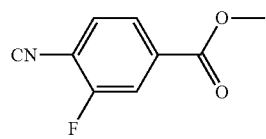

$^1$H NMR (400 MHz, DMSO-d$_6$) δ 7.99-7.95 (m, 1H), 7.92-7.86 (m, 2H), 3.90 (s, 3H) ppm. MS (ESI) m/z: (M+H)$^+$.

INTERMEDIATE 41

1-Fluoro-2-isocyanobenzene

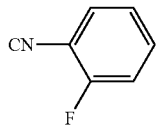

$^1$H NMR (400 MHz, DMSO-$d_6$) δ 7.71 (td, J=7.7, 1.5 Hz, 1H), 7.61-7.54 (m, 1H), 7.52-7.46 (m, 1H), 7.36-7.30 (m, 1H) ppm.

INTERMEDIATE 42

1-Fluoro-3-isocyanobenzene

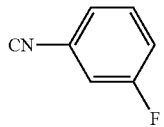

$^1$H NMR (400 MHz, DMSO-$d_6$) δ 7.61-7.52 (m, 2H), 7.46-7.37 (m, 2H) ppm.

INTERMEDIATE 43

3-Isocyanopyridine

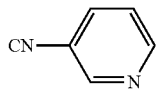

$^1$H NMR (400 MHz, DMSO-$d_6$) δ 8.84 (dd, J=2.4, 0.7 Hz, 1H), 8.69 (dd, J=4.8, 1.3 Hz, 1H), 8.12-8.04 (m, 1H), 7.58 (ddd, J=8.1, 4.8, 0.9 Hz, 1H) ppm.

INTERMEDIATE 44 tert-Butyl 4-(2-(1-(3-chloro-2-fluorophenyl)-1H-1,2,3-triazole-4-carbonyl)-5-(4,4,5,5-tetramethyl-1,3,2-dioxaborolan-2-yl)-1,2,3,4-tetrahydroisoquinoline-1-carboxamido)benzoate

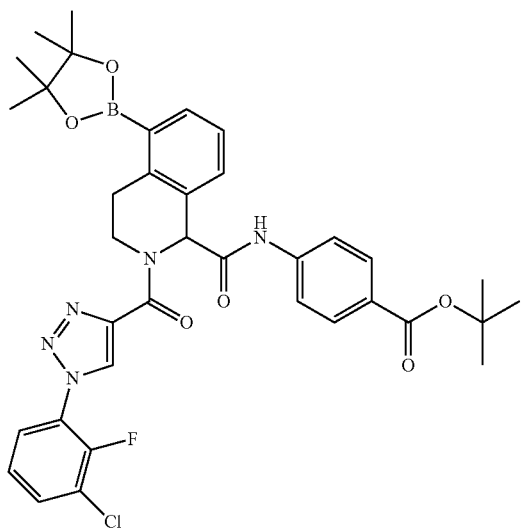 [SMILES: CC(C)(C)OC(=O)c1ccc(NC(=O)C2c3cccc(B4OC(C)(C)C(C)(C)O4)c3CCN2C(=O)c2cn(-c3cccc(Cl)c3F)nn2)cc1]

Intermediate 44. tert-Butyl 4-(2-(1-(3-chloro-2-fluorophenyl)-1H-1,2,3-triazole-4-carbonyl)-5-(4,4,5,5-tetramethyl-1,3,2-dioxaborolan-2-yl)-1,2,3,4-tetrahydroisoquinoline-1-carboxamido)benzoate: Intermediate 24 (0.500 g, 0.763 mmol), 4,4,4',4',5,5,5',5''-octamethyl-2,2'-bi(1,3,2-dioxaborolane) (0.233 g, 0.916 mmol), and potassium acetate (0.150 g, 1.527 mmol) were added to dioxane (1.591 mL) and DMSO (0.318 mL) and degassed for 10 min. Afterwards, 1,1'-bis(diphenylphosphino)ferrocene-palladium(ii) dichloride dichloromethane complex (0.019 g, 0.023 mmol) was added and the mixture was degassed for another 5 min before it was heated at 105° C. for 2 h. The black mixture was cooled and filtered through CELITE®. The CELITE® pad was washed with EtOAc. The filtrates were combined and it was washed with water and brine. The organic layer was separated, dried over Na$_2$SO$_4$, concentrated, and purified by normal phase column chromatography to give the title compound (0.459 g, 0.654 mmol, 86% yield) as a white solid. MS (ESI) m/z: 702 (M+H)$^+$.

INTERMEDIATE 45

1-(3-Chloro-2-fluorophenyl)-3-hydroxy-1H-pyrazole-4-carboxylic acid

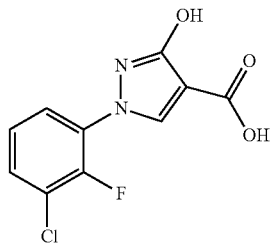 [SMILES: O=C(O)c1cn(-c2cccc(Cl)c2F)nc1O]

Intermediate 45A. N'-(3-Chloro-2-fluorophenyl)acetohydrazide: To a solution of (3-chloro-2-fluorophenyl)hydrazine, HCl (450 mg, 2.284 mmol) in ether (10 mL) and THF (1 mL) at 0° C. was added sodium hydroxide (0.228 mL, 2.284 mmol) and stirred at room temperature for 1 h. The reaction mixture was concentrated, diluted with EtOAc and washed with brine. The crude product was then dried under vacuum and taken to the next step. To a solution of the above obtained oil in ether (10 mL) at 0° C. was added dropwise a solution of acetic anhydride (0.215 mL, 2.284 mmol) in ether (5 mL) and stirred at 0° C. for 30 min. The reaction mixture was concentrated, diluted with ethyl acetate and washed with brine. The organic layer was dried over MgSO$_4$ and concentrated to yield the crude product. The crude product was then taken to the next step without further purification. MS(ESI) m/z: 203.1 (M+H)$^+$.

Intermediate 45B. Ethyl 1-(3-chloro-2-fluorophenyl)-3-hydroxy-1H-pyrazole-4-carboxylate: To Intermediate 45A (261 mg, 1.288 mmol) was added phosphoryl trichloride (973 µL, 10.43 mmol) followed by diethyl 2-(ethoxymethylene)malonate (351 µL, 1.739 mmol) and the resulting solution was heated at 70° C. overnight To the reaction mixture was added water slowly and allowed to stir until the reaction mixture cooled back to room temperature. The crude product was then diluted with ethyl acetate and washed with brine. The organic layer was dried over MgSO$_4$ and concentrated to yield the crude product which was then purified using silica gel chromatography. MS(ESI) m/z: 285.0 (M+H)$^+$.

Intermediate 45C. 1-(3-Chloro-2-fluorophenyl)-3-hydroxy-1H-pyrazole-4-carboxylic acid: To a solution of Intermediate 45B (52 mg, 0.183 mmol) in THF (2 mL) was added LiOH (0.183 mL, 0.183 mmol) and stirred at room temperature overnight. The reaction mixture was acidified using 1 N HCl and then extracted with EtOAc. The organic layer was dried over MgSO$_4$ and concentrated to yield the crude product. The crude product was taken further without any further purification. MS(ESI) m/z: 257.0 (M+H)$^+$.

INTERMEDIATE 46

3-(3-Chloro-2-fluorophenyl)-4,5-dihydroisoxazole-5-carboxylic acid

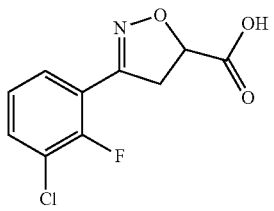 [SMILES: O=C(O)C1CC(c2cccc(Cl)c2F)=NO1]

Intermediate 46. 3-(3-Chloro-2-fluorophenyl)-4,5-dihydroisoxazole-5-carboxylic acid: The title compound was obtained by TFA hydrolysis of racemic Intermediate 18. $^1$H NMR (500 MHz, MeOD) δ 7.72 (ddd, J=8.0, 6.5, 1.7 Hz, 1H), 7.60-7.56 (m, 1H), 7.24 (td, J=8.0, 1.1 Hz, 1H), 5.22 (dd, J=11.8, 6.9 Hz, 1H), 3.84-3.76 (m, 1H), 3.71-3.64 (m, 1H) ppm.

INTERMEDIATE 47

3-(3-Chloro-2,6-difluorophenyl)-4,5-dihydroisoxazole-5-carboxylic acid

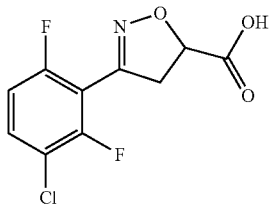 [SMILES: O=C(O)C1CC(c2c(F)ccc(Cl)c2F)=NO1]

Intermediate 47. 3-(3-Chloro-2,6-difluorophenyl)-4,5-dihydroisoxazole-5-carboxylic acid: The t-butyl ester was prepared in the same manner as Intermediate 18 replacing 3-chloro-2-fluorobenzaldehyde with 3-chloro-2,6-difluorobenzaldehyde. This material was dissolved in DCM (10 mL) and treated with TFA (2 mL) and stirred overnight. Concentrated and quenched with water (20 mL) and extracted organics with EtOAc (2×25 mL), dried and evaporated to a film which gradually solidified. $^1$H NMR (CDCl$_3$) δ: 9.35(bs, 1H), 7.35(m, 1H), 6.88(m, 1H), 5.19(m, 1H), 3.80-3.64(m, 2H) ppm.

INTERMEDIATE 48

3-(3-Chloro-2-fluoro-6-(trifluoromethyl)phenyl)-4,5-dihydroisoxazole-5-carboxylic acid

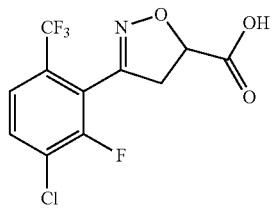 [SMILES: O=C(O)C1CC(c2c(C(F)(F)F)ccc(Cl)c2F)=NO1]

Intermediate 48. 3-(3-Chloro-2-fluoro-6-(trifluoromethyl)phenyl)-4,5-dihydroisoxazole-5-carboxylic acid: The t-butyl ester was prepared in the same manner as Intermediate 18 replacing 3-chloro-2-fluorobenzaldehyde with 3-chloro-2-fluoro-6-(trifluoromethyl)benzaldehyde. This material was dissolved in DCM (10 mL) and treated with TFA (2 mL) and stirred overnight. Concentrated to give a solid which was used directly in subsequent reactions. MS (ESI) m/z: 312 (M+H)$^+$.

INTERMEDIATE 49

3-(3-Chloro-2,6-difluorophenyl)isoxazole-5-carboxylic acid

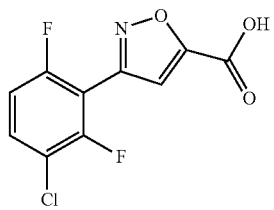 [SMILES: O=C(O)c1cc(-c2c(F)ccc(Cl)c2F)no1]

Intermediate 49A: Methyl 3-(3-chloro-2,6-difluorophenyl)isoxazole-5-carboxylate: To a mixture of 3-chloro-2,6-difluorobenzaldehyde oxime (348.9 mg, 1.821 mmol) and methyl propiolate (0.304 mL, 3.64 mmol) in tetrahydrofuran (3.5 mL) and cooled to 0° C. was added 5.25% sodium hypochlorite solution (7.07 mL, 6.01 mmol) and the mixture allowed to warm to ambient temperature. After stirring at room temperature for 3 days, the reaction was partitioned and aqueous layer extracted with EtOAc (3×).

Combined organics washed with sat'd Na$_2$SO$_3$, brine, dried (Na$_2$SO$_4$), filtered and evaporated to a residue. The title compound was purified by normal phase column chromatography. MS (ESI) m/z: 274 (M+H)$^+$.

Intermediate 49. 3-(3-Chloro-2,6-difluorophenyl)isoxazole-5-carboxylic acid: To a solution of Intermediate 49A (0.547 g, 2 mmol) in MeOH (12 mL) was added lithium hydroxide (1M aq.) (4.00 mL, 4.00 mmol) and the mixture stirred at ambient temperature overnight. Reaction mixture partially evaporated to remove MeOH and then partitioned with EtOAc (5 mL) and added 1N HCl to adjust pH to ~3. Aqueous layer was extracted with EtOAc (3×) and organics washed with brine, dried (Na$_2$SO$_4$), filtered, and evaporated to give a colorless solid. $^1$H NMR (400 MHz, DMSO-d$_6$) δ 12.02 (s, 1H), 8.16 (s, 1H), 7.76-7.66 (m, 1H), 7.27 (td, J=9.4, 1.6 Hz, 1H) ppm.

INTERMEDIATE 50

3-(3-Chloro-2-fluorophenyl)-5-methyl-4,5-dihydroisoxazole-5-carboxylic acid

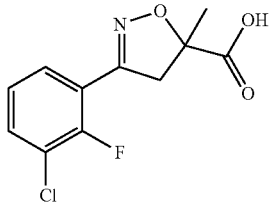 [SMILES: CC1(C(=O)O)CC(c2cccc(Cl)c2F)=NO1]

Intermediate 50A. Methyl 3-(3-chloro-2-fluorophenyl)-5-methyl-4,5-dihydroisoxazole-5-carboxylate: The title compound was prepared in the same manner as Intermediate 18 replacing t-butyl acrylate with methyl methacrylate. MS (ESI) m/z: 272.0/273.9 Cl pattern (M+H)$^+$.

Intermediate 50. 3-(3-Chloro-2-fluorophenyl)-5-methyl-4,5-dihydroisoxazole-5-carboxylic acid: The title compound was hydrolyzed in a similar manner as described in Intermediate 49. MS (ESI) m/z: 256.3 (M+H)$^+$.

INTERMEDIATE 51 tert-Butyl 4-(5-(4-(dimethylcarbamoyl)piperidin-1-yl)-1,2,3,4-tetrahydroisoquinoline-1-carboxamido)benzoate

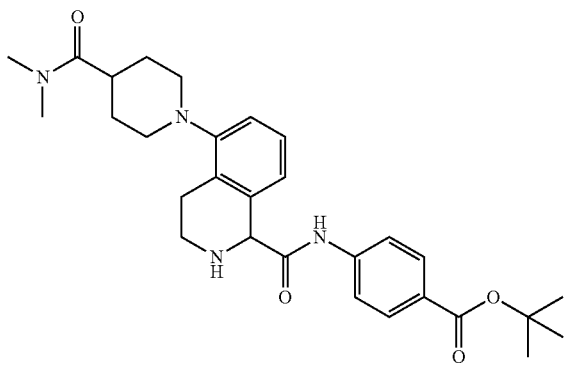 [SMILES: CN(C)C(=O)C1CCN(c2cccc3c2CCNC3C(=O)Nc2ccc(C(=O)OC(C)(C)C)cc2)CC1]

Intermediate 51. tert-Butyl 4-(5-(4-(dimethylcarbamoyl)piperidin-1-yl)-1,2,3,4-tetrahydroisoquinoline-1-carboxamido)benzoate: The title compound was prepared in a similar manner as Intermediate 28 starting from Intermediate 4M. MS (ESI) m/z: 507 (M+H)$^+$.

INTERMEDIATE 52 tert-Butyl 4-(5-(4-methyl-3-oxopiperazin-1-yl)-1,2,3,4-tetrahydroisoquinoline-1-carboxamido)benzoate

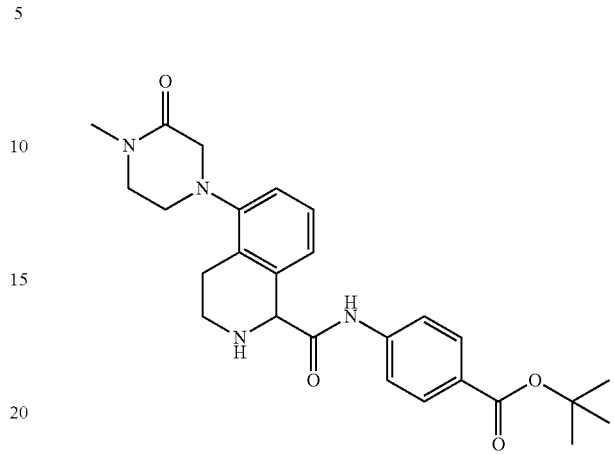

Intermediate 52. tert-Butyl 4-(5-(4-methyl-3-oxopiperazin-1-yl)-1,2,3,4-tetrahydroisoquinoline-1-carboxamido)benzoate: The title compound was prepared in a similar manner as Intermediate 28 starting from Intermediate 4V. MS (ESI) m/z: 465 (M+H)$^+$.

INTERMEDIATE 53 tert-Butyl 4-(5-(4-(2-(dimethylamino)ethoxy)piperidin-1-yl)-1,2,3,4-tetrahydroisoquinoline-1-carboxamido)benzoate

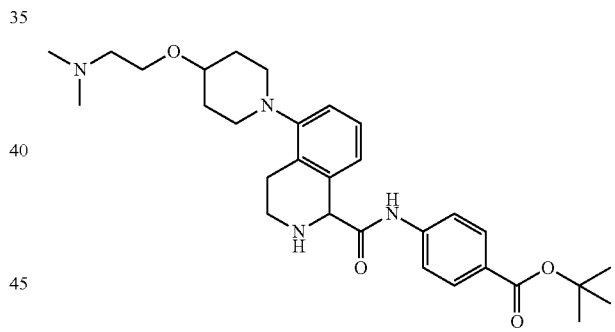

Intermediate 53. tert-Butyl 4-(5-(4-(2-(dimethylamino)ethoxy)piperidin-1-yl)-1,2,3,4-tetrahydroisoquinoline-1-carboxamido)benzoate: The title compound was prepared in a similar manner as Intermediate 28 starting from Intermediate 4O. MS (ESI) m/z: 523 (M+H)$^+$.

INTERMEDIATE 54

5-Methoxy-3,4-dihydroisoquinoline

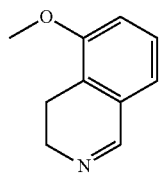

Intermediate 54. 5-Methoxy-3,4-dihydroisoquinoline: The title compound was obtained through PtO$_2$ hydrogenation and MnO$_2$ oxidation of 5-methoxyisoquinoline in a similar manner as described by Intermediate 4. MS (ESI) m/z: 162 (M+H)$^+$.

INTERMEDIATE 55

2-(3-Chloro-2-fluorophenyl)oxazole-4-carboxylic acid

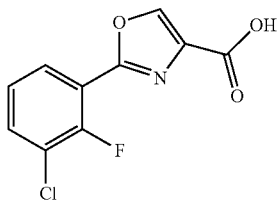 [SMILES: O=C(O)c1coc(-c2cccc(Cl)c2F)n1]

Intermediate 55A. Ethyl 2-(3-chloro-2-fluorophenyl)oxazole-4-carboxylate: A mixture of 3-chloro-2-fluorobenzamide (1 g, 5.76 mmol) and ethyl 3-bromo-2-oxopropanoate (0.723 mL, 5.76 mmol) in dioxane (20 mL) and toluene (20 mL) was stirred at reflux. After stirring for 2 days, the reaction mixture was concentrated and purified by reverse phase prep HPLC to give a white solid (60 mg, 3.9%). MS (ESI) m/z: 279 (M+H)$^+$.

Intermediate 55. A mixture of Intermediate 55A (30 mg, 0.111 mmol) and Lithium hydroxide monohydrate (0.122 mL, 0.122 mmol) in THF (0.12 mL) was stirred vigorously at room temperature for 28 h. Added 0.5 mL 1 N HCl and mixed. Extracted three times with EtOAc. Dried the combined organic layers over MgSO$_4$ and filtered. Solvent was removed in vacuo to give off-white solid (22 mg, 82%). $^1$H NMR-(500 MHz, methanol-d$_4$) δ 8.63 (s, 1H), 8.07 (t, J=6.74 Hz, 1H), 7.71 (t, J=7.01 Hz, 1H), 7.36 (t, J=7.84 Hz, 1H), 5.51 (s, 1H) ppm.

INTERMEDIATE 56

3-(3-Chlorophenyl)-4,5-dihydroisoxazole-5-carboxylic acid

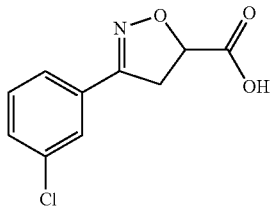 [SMILES: O=C(O)C1CC(c2cccc(Cl)c2)=NO1]

Intermediate 56: 3-(3-Chlorophenyl)-4,5-dihydroisoxazole-5-carboxylic acid: The title compound was prepared in a similar manner as Intermediate 48 starting from 3-chlorobenzaldehyde. $^1$H NMR (CDCl$_3$) δ: 7.71(m, 1H), 7.50(dd, j=1.5 and 8.6 Hz, 1H), 7.36-7.26(m, 2H), 5.20(dd, 1H), 3.61(d, 2H) ppm.

EXAMPLE 1

4-(2-(1-(3-Chloro-2-fluorophenyl)-1H-1,2,3-triazole-4-carbonyl)-1,2,3,4-tetrahydroisoquinoline-1-carboxamido)benzoic acid

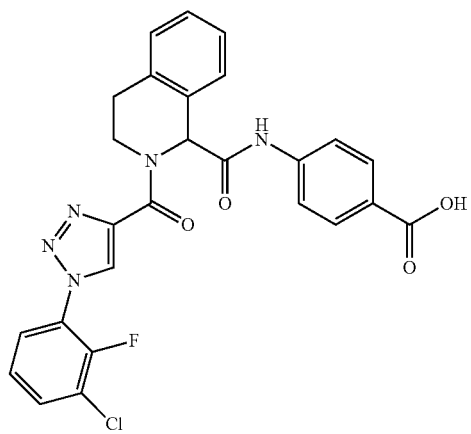 [SMILES: O=C(O)c1ccc(NC(=O)C2c3ccccc3CCN2C(=O)c2cn(-c3cccc(Cl)c3F)nn2)cc1]

1A. tert-Butyl 4-(2-(1-(3-chloro-2-fluorophenyl)-1H-1,2,3-triazole-4-carbonyl)-1,2,3,4-tetrahydroisoquinoline-1-carboxamido)benzoate: 1A was prepared by combining Imine Intermediate 3 (50 mg, 0.38 mmol), carboxylic acid Intermediate 9 (92 mg, 0.38 mmol), and isonitrile Intermediate 1 (77 mg, 0.38 mmol) in pressure vial containing MeOH (0.762 mL, 0.50M). The mixture was heated at 50° C. for 24 h before concentrating to dryness and carried forward to next reaction without further purification. MS (ESI) m/z: 576 (M+H)$^+$.

Example 1. 4-(2-(1-(3-Chloro-2-fluorophenyl)-1H-1,2,3-triazole-4-carbonyl)-1,2,3,4-tetrahydroisoquinoline-1-carboxamido)benzoic acid: 1A was treated with 50% TFA/DCM. After 3 h, the mixture was concentrated and the crude material purified by reverse phase prep HPLC and freeze-dried to give Example 1 (54 mg, 26%) as a white solid. $^1$H NMR (500 MHz, DMSO-d$_6$) δ 12.72 (br. s., 1H), 10.95 (s, 1H), 9.17 (d, J=1.7 Hz, 1H), 7.94-7.86 (m, 4H), 7.78-7.72 (m, 2H), 7.72-7.67 (m, 1H), 7.55-7.48 (m, 1H), 7.34-7.27 (m, 3H), 5.95 (s, 1H), 4.58-4.49 (m, 1H), 4.24 (ddd, J=12.6, 8.3, 4.1 Hz, 1H), 3.27-3.19 (m, 1H), 3.08-2.97 (m, 1H) ppm. MS (ESI) m/z: 520 (M+H)$^+$. Analytical HPLC:room temperature=7.08 min (Method B).

EXAMPLE 2

(R)-4-(2-(1-(3-Chloro-2-fluorophenyl)-1H-1,2,3-triazole-4-carbonyl)-1,2,3,4-tetrahydroisoquinoline-1-carboxamido)benzoic acid

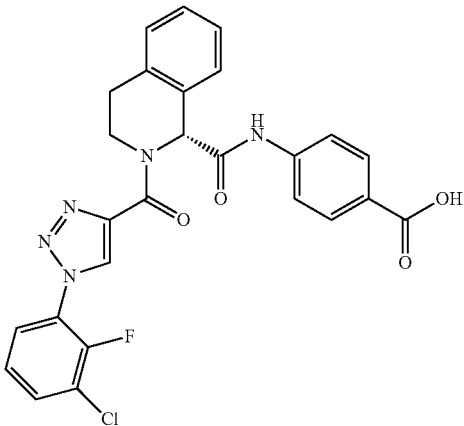 [SMILES: O=C(O)c1ccc(NC(=O)[C@H]2c3ccccc3CCN2C(=O)c2cn(-c3cccc(Cl)c3F)nn2)cc1]

2A. (R)-tert-Butyl 4-(2-(1-(3-chloro-2-fluorophenyl)-1H-1,2,3-triazole-4-carbonyl)-1,2,3,4-tetrahydroisoquinoline-1-carboxamido)benzoate: 2A was the first compound after chiral HPLC separation of 1A (200 mg) using CHIRALPAK® AS-H, 21×250 mm, 5 μ, using 25% IPA/75% $CO_2$ at 45.0 mL/min, 100 bar, and 27° C. Fractions were concentrated and carried forward to next reaction.

Example 2. (R)-4-(2-(1-(3-Chloro-2-fluorophenyl)-1H-1,2,3-triazole-4-carbonyl)-1,2,3,4-tetrahydroisoquinoline-1-carboxamido)benzoic acid: 2A was treated with 50% TFA/DCM. After 2 h, the mixture was concentrated and the crude material purified by reverse phase prep HPLC to give Example 2 (30 mg, 32% over two steps) as a white solid. $^1$H NMR (500 MHz, DMSO-$d_6$) δ 12.72 (br. s., 1H), 10.95 (s, 1H), 9.17 (d, J=1.9 Hz, 1H), 7.93-7.86 (m, 4H), 7.76-7.66 (m, 3H), 7.52 (td, J=8.3, 1.4 Hz, 1H), 7.33-7.25 (m, 3H), 5.94 (s, 1H), 4.56-4.49 (m, 1H), 4.24 (ddd, J=12.5, 8.4, 4.4 Hz, 1H), 3.28-3.19 (m, 1H), 3.04-2.97 (m, 1H) ppm. MS (ESI) m/z: 520 (M+H)$^+$. Analytical HPLC: RT=7.15 min (Method B).

EXAMPLE 3

(S)-4-(2-(1-(3-Chloro-2-fluorophenyl)-1H-1,2,3-triazole-4-carbonyl)-1,2,3,4-tetrahydroisoquinoline-1-carboxamido)benzoic acid

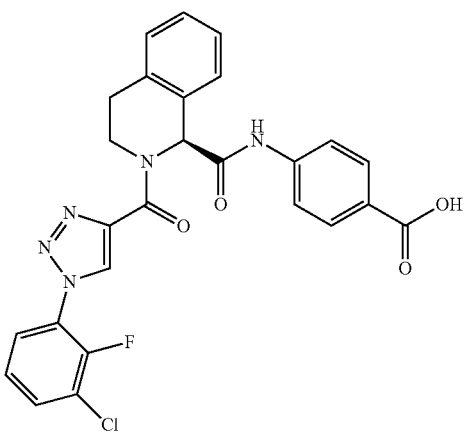 [SMILES: O=C(O)c1ccc(NC(=O)[C@@H]2c3ccccc3CCN2C(=O)c2cn(-c3cccc(Cl)c3F)nn2)cc1]

3A. (S)-tert-Butyl 4-(2-(1-(3-chloro-2-fluorophenyl)-1H-1,2,3-triazole-4-carbonyl)-1,2,3,4-tetrahydroisoquinoline-1-carboxamido)benzoate 3A was the second compound after chiral HPLC separation of 1A (200 mg) using CHIRALPAK® AS-H, 21×250 mm, 5 μ, using 25% IPA/75% $CO_2$ at 45.0 mL/min, 100 bar and 27° C.

Example 3. (S)-4-(2-(1-(3-Chloro-2-fluorophenyl)-1H-1,2,3-triazole-4-carbonyl)-1,2,3,4-tetrahydroisoquinoline-1-carboxamido)benzoic acid 3A was treated with 50% TFA/DCM. After 2 h, the mixture was concentrated and the crude material purified by reverse phase prep HPLC to give Example 3 (36 mg, 38% over two steps) as a white solid. H NMR (500 MHz, DMSO-$d_6$) δ 12.72 (s, 1H), 10.95 (s, 1H), 9.17 (d, J=1.7 Hz, 1H), 7.93-7.85 (m, 4H), 7.77-7.66 (m, 3H), 7.52 (td, J=8.2, 1.2 Hz, 1H), 7.33-7.28 (m, 3H), 5.94 (s, 1H), 4.59-4.47 (m, 1H), 4.24 (ddd, J=12.7, 8.4, 4.3 Hz, 1H), 3.26 3.19 (m, 1H), 3.05-2.97 (m, 1H) ppm. MS (ESI) m/z: 520 (M+H)$^+$. Analytical HPLC: RT—7.12 min (Method B).

EXAMPLE 4

4-((S)-2-((R)-3-(3-Chloro-2-fluorophenyl)-4,5-dihydroisoxazole-5-carbonyl)-1,2,3,4-tetrahydroisoquinoline-1-carboxamido)benzoic acid

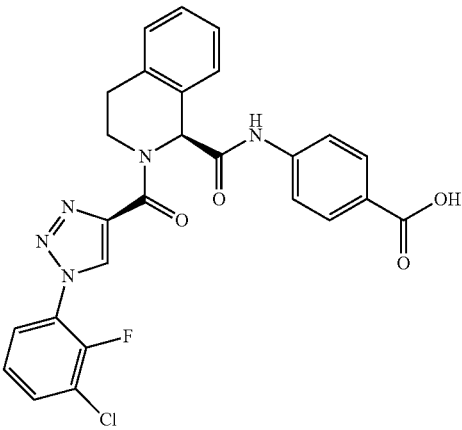

Example 4. 4-((S)-2-((R)-3-(3-Chloro-2-fluorophenyl)-4,5-dihydroisoxazole-5-carbonyl)-1,2,3,4-tetrahydroisoquinoline-1-carboxamido)benzoic acid. Example 4 was prepared in a similar manner as Example 1 replacing Intermediate 9 with Intermediate 19 in the Ugi reaction. The final compound was isolated as the first eluting diastereomer after reverse phase prep. HPLC and freeze-dried as a white solid. $^1$H NMR (500 MHz, $CD_3OD$-$d_4$) δ 7.98-7.94 (m, 2H), 7.77-7.71 (m, 1H), 7.69-7.65 (m, 2H), 7.61-7.57 (m, 1H), 7.53 (d, J=6.1 Hz, 1H), 7.31-7.28 (m, 3H), 7.26-7.21 (m, 1H), 5.84 (s, 1H), 5.77 (dd, J=11.4, 7.6 Hz, 1H), 4.37 (ddd, J=12.2, 6.5, 4.4 Hz, 1H), 3.98-3.91 (m, 1H), 3.88 (ddd, J=12.4, 8.4, 4.3 Hz, 1H), 3.76 (ddd, J=17.3, 11.4, 2.1 Hz, 1H), 3.30-3.21 (m, 1H), 3.05-2.98 (m, 1H) ppm. MS (ESI) m/z: 522 (M+H)$^+$. Analytical HPLC: RT=6.84 min (Method B).

EXAMPLE 5

4-((R)-2-((R)-3-(3-Chloro-2-fluorophenyl)-4,5-dihydroisoxazole-5-carbonyl)-1,2,3,4-tetrahydroisoquinoline-1-carboxamido)benzoic acid

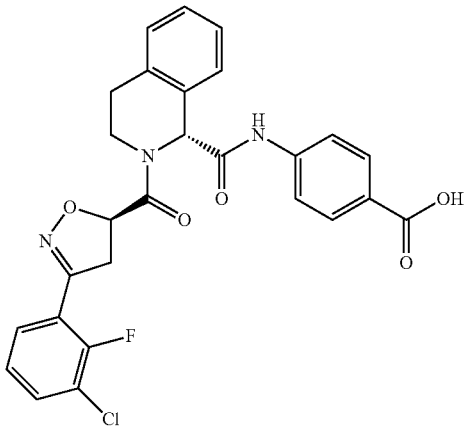 [SMILES: O=C(O)c1ccc(NC(=O)[C@H]2c3ccccc3CCN2C(=O)[C@H]2CC(c3cccc(Cl)c3F)=NO2)cc1]

Example 5. 4-((R)-2-((R)-3-(3-Chloro-2-fluorophenyl)-4,5-dihydroisoxazole-5-carbonyl)-1,2,3,4-tetrahydroisoquinoline-1-carboxamido)benzoic acid: Example 5 was prepared in a similar manner as Example 1 replacing Intermediate 9 with Intermediate 19 in the Ugi reaction. The final compound was isolated as the second eluting diastereomer after reverse phase prep. HPLC and freeze-dried as a white solid. $^1$H NMR (500 MHz, CD$_3$OD-d$_4$) δ 7.99-7.94 (m, 2H), 7.74 (ddd, J=7.9, 6.4, 1.7 Hz, 1H), 7.69-7.65 (m, 2H), 7.63-7.57 (m, 1H), 7.54 (d, J=6.1 Hz, 1H), 7.32-7.23 (m, 4H), 5.87-5.80 (m, 2H), 4.30 (ddd, J=12.4, 6.6, 4.4 Hz, 1H), 4.05 (ddd, J=17.3, 6.9, 1.9 Hz, 1H), 3.93 (ddd, J=12.6, 8.3, 4.1 Hz, 1H), 3.75 (ddd, J=17.5, 11.4, 1.9 Hz, 1H), 3.32-3.26 (m, 1H), 3.10-3.01 (m, 1H) ppm. MS (ESI) m/z: 522 (M+H)$^+$. Analytical HPLC: RT=6.99 min (Method B).

EXAMPLE 6

4-(2-(1-(3-Chloro-2-fluorophenyl)-1H-1,2,3-triazole-4-carbonyl)-5-(4-((2-(dimethylamino)ethyl)carbamoyl)phenyl)-1,2,3,4-tetrahydroisoquinoline-1-carboxamido)benzoic acid

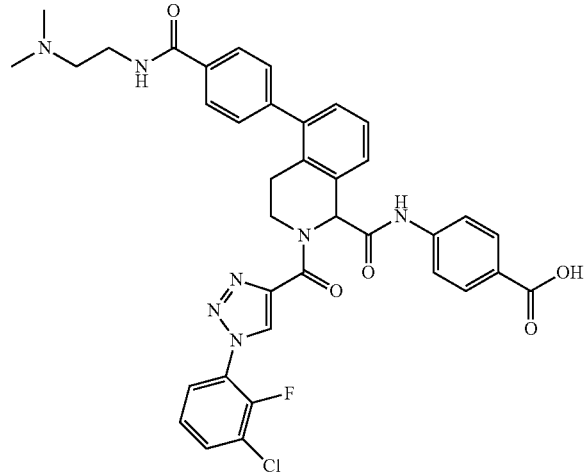 [SMILES: CN(C)CCNC(=O)c1ccc(-c2cccc3c2CCN(C(=O)c2cn(-c4cccc(Cl)c4F)nn2)C3C(=O)Nc2ccc(C(=O)O)cc2)cc1]

6A. tert-Butyl 4-(5-(4-((2-(dimethylamino)ethyl)carbamoyl)phenyl)-1,2,3,4-tetrahydroisoquinoline-1-carboxamido)benzoate, TFA salt: A stirring suspension of Intermediate 7 (0.50 g, 0.94 mmol), N-(2-dimethylaminoethyl)-4-(4,4,5,5-tetramethyl-1,3,2-dioxaborolan-2-yl)benzamide (0.36 g, 1.13 mmol), and Cs$_2$CO$_3$ (0.92 g, 2.82 mmol) in 1,2-dimethoxyethane (12 mL)/water (2.40 mL) was degassed with a stream of argon for 15 minutes. Tetrakis(triphenylphosphine)palladium(0) (0.11 g, 0.094 mmol) was added and the mixture irradiated at 120° C. for 20 minutes. The reaction mixture was filtered through a plug of CELITE®. The filtrate was partitioned between EtOAc and water. The aqueous layer was re-extracted with EtOAc (2×). The combined organic layers were washed with saturated sodium bicarbonate solution, brine, dried over sodium sulfate, filtered and concentrated. The boc-group was selectively removed by dissolving the residue in EtOAc (10 mL)/THF (10 mL) and treatment with HCl (4.0M in dioxane) (1.06 mL, 4.23 mmol) overnight. The reaction mixture was concentrated. The crude residue was purified by reverse phase prep HPLC to give 6A (0.34 g, 0.518 mmol, 55.0% yield) as a white solid. MS (ESI) m/z: 543 (M+H)$^+$.

Example 6. 4-(2-(1-(3-Chloro-2-fluorophenyl)-1H-1,2,3-triazole-4-carbonyl)-5-(4-((2-(dimethylamino)ethyl)carbamoyl)phenyl)-1,2,3,4-tetrahydroisoquinoline-1-carboxamido)benzoic acid: DIPEA (0.036 mL, 0.21 mmol) was added to a solution of 6A (0.04 g, 0.052 mmol), Intermediate 9 (0.019 g, 0.078 mmol), EDC (0.02 g, 0.10 mmol), and HOBt (0.016 g, 0.104 mmol) in DMF (2.0 mL). After 16 h, the reaction mixture was diluted with EtOAc, washed with water, brine, dried over sodium sulfate, filtered, and concentrated. The residue was treated with 50% TFA/DCM. After 2 h, the reaction mixture was concentrated, purified by reverse phase prep HPLC, and lyophilized to give Example 4 (13 mg, 39%) as a white solid. $^1$H NMR (500 MHz, DMSO-d$_6$) δ 11.00 (s, 1H), 9.18 (d, J=1.7 Hz, 1H), 8.75 (t, J=5.6 Hz, 1H), 7.97 (d, J=8.5 Hz, 2H), 7.95-7.85 (m, 4H), 7.80-7.76 (m, 2H), 7.56-7.49 (m, 3H), 7.44 (t, J=7.7 Hz, 1H), 7.30 (d, J=6.6 Hz, 1H), 6.02 (s, 1H), 4.50 (dt, J=12.9, 5.1 Hz, 1H), 4.11 (ddd, J=12.7, 8.8, 3.9 Hz, 1H), 3.64 (q, J=5.8 Hz, 2H), 3.30 (q, J=5.8 Hz, 2H), 3.19-3.11 (m, 1H), 2.96 (dt, J=10.9, 5.3 Hz, 1H). 2.89-2.84 (m, 6H) ppm. MS (ESI) m/z: 710 (M+H)$^+$. Analytical HPLC: RT=5.92 min (Method B).

EXAMPLE 7

4-(2-(1-(3-Chloro-2-fluorophenyl)-5-methyl-1H-1,2,3-triazole-4-carbonyl)-5-(4-((2-(dimethylamino)ethyl)carbamoyl)phenyl)-1,2,3,4-tetrahydroisoquinoline-1-carboxamido)benzoic acid, TFA salt

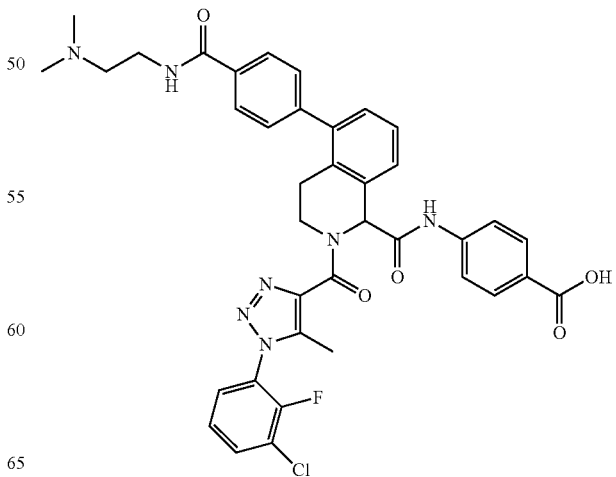

Example 7. 4-(2-(1-(3-Chloro-2-fluorophenyl)-5-methyl-1H-1,2,3-triazole-4-carbonyl)-5-(4-((2-(dimethylamino)ethyl)carbamoyl)phenyl)-1,2,3,4-tetrahydroisoquinoline-1-carboxamido)benzoic acid: Example 7 was made in a similar manner as Example 6 replacing Intermediate 9 with Intermediate 11 in the acid coupling step. $^1$H NMR (500 MHz, methanol-$d_4$) δ 10.64 (s, 1H), 8.05-7.98 (m, 4H), 7.84 (t, J=6.7 Hz, 1H), 7.78-7.69 (m, 3H), 7.60 (t, J=6.7 Hz, 1H), 7.56-7.50 (m, 2H), 7.50-7.41 (m, 2H), 7.34 (d, J=7.4 Hz, 1H), 6.01 (s, 1H), 4.51-4.43 (m, 1H), 4.10 (ddd, J=12.7, 8.8, 3.9 Hz, 1H), 3.82 (t, J=5.8 Hz, 2H), 3.48-3.41 (m, 2H), 3.26-3.20 (m, 1H), 3.08-2.97 (m, 7H), 2.44 (d, J=0.8 Hz, 3H) ppm. MS (ESI) m/z: 724 (M+H)$^+$. Analytical HPLC: RT—5.28 min (Method A).

EXAMPLE 8

4-(2-(1-(3-Chloro-2-fluorophenyl)-1H-pyrazole-4-carbonyl)-5-(4-((2-(dimethylamino)ethyl)carbamoyl)phenyl)-1,2,3,4-tetrahydroisoquinoline-1-carboxamido)benzoic acid, TFA salt

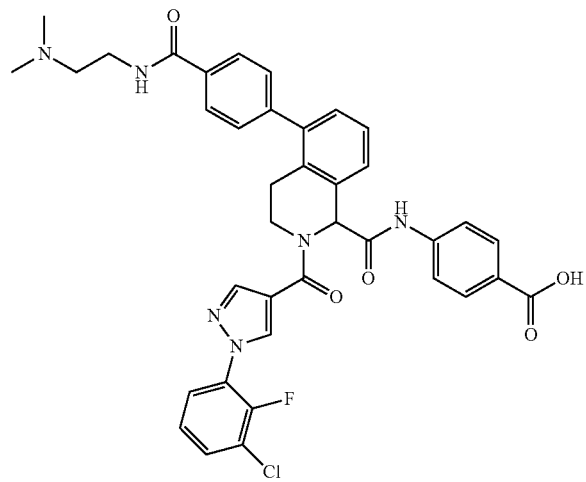 [SMILES: CN(C)CCNC(=O)c1ccc(-c2cccc3c2CCN(C(=O)c2cnn(-c4cccc(Cl)c4F)c2)C3C(=O)Nc2ccc(C(=O)O)cc2)cc1]

Example 8. 4-(2-(1-(3-Chloro-2-fluorophenyl)-1H-pyrazole-4-carbonyl)-5-(4-((2-(dimethylamino)ethyl)carbamoyl)phenyl)-1,2,3,4-tetrahydroisoquinoline-1-carboxamido)benzoic acid: Example 8 was made in a similar manner as Example 6 replacing Intermediate 9 with Intermediate 13 in the acid coupling step. $^1$H NMR (500 MHz, DMSO-$d_6$) δ 10.91 (s, 1H), 8.75 (t, J=5.8 Hz, 1H), 8.71-8.68 (m, 1H), 8.20 (s, 1H), 7.97 (d, J=8.5 Hz, 2H), 7.91 (d, J=8.8 Hz, 2H), 7.82-7.68 (m, 5H), 7.51 (d, J=8.5 Hz, 2H), 7.42 (q, J=7.8 Hz, 2H), 7.30 (d, J=7.2 Hz, 1H), 5.93 (s, 1H), 4.27-4.20 (m, 1H), 3.87-3.77 (m, 1H), 3.64 (q, J=5.8 Hz, 2H), 3.32-3.22 (m, 3H), 2.94-2.85 (m, 7H) ppm. MS (ESI) m/z: 709 (M+H)$^+$.

EXAMPLE 9

4-(2-(1-(3-Chloro-2-fluorophenyl)-5-methyl-1H-1,2,3-triazole-4-carbonyl)-5-(4-(dimethylcarbamoyl)phenyl)-1,2,3,4-tetrahydroisoquinoline-1-carboxamido)benzoic acid

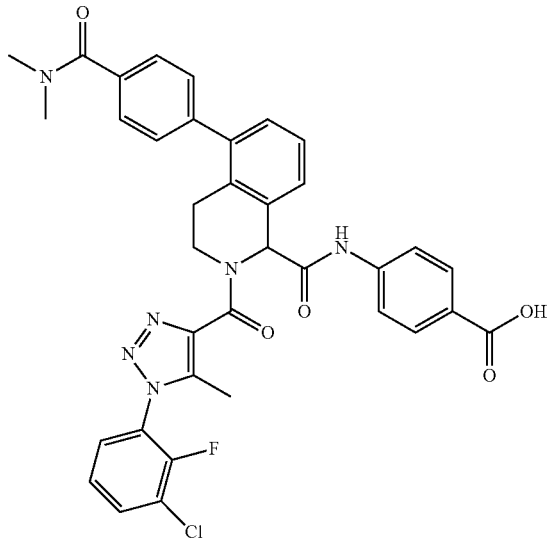 [SMILES: Cc1c(C(=O)N2CCc3c(-c4ccc(C(=O)N(C)C)cc4)cccc3C2C(=O)Nc2ccc(C(=O)O)cc2)nnn1-c1cccc(Cl)c1F]

Example 9. 4-(2-(1-(3-Chloro-2-fluorophenyl)-5-methyl-1H-1,2,3-triazole-4-carbonyl)-5-(4-(dimethylcarbamoyl)phenyl)-1,2,3,4-tetrahydroisoquinoline-1-carboxamido)benzoic acid: Example 9 was made in a similar manner as Example 7 replacing N-(2-dimethylaminoethyl)-4-(4,4,5,5-tetramethyl-1,3,2-dioxaborolan-2-yl)benzamide with N,N-dimethyl-4-(4,4,5,5-tetramethyl-1,3,2-dioxaborolan-2-yl)benzamide in the Suzuki coupling step. $^1$H NMR (500 MHz, methanol-$d_4$) δ 10.62 (s, 1H), 8.01 (d, J=8.5 Hz, 2H), 7.83 (t, J=6.9 Hz, 1H), 7.79-7.67 (m, 3H), 7.65-7.54 (m, 3H), 7.52-7.41 (m, 4H), 7.34 (d, J=7.4 Hz, 1H), 6.00 (s, 1H), 4.47-4.41 (m, 1H), 4.14-4.06 (m, 1H), 3.28-3.23 (m, 1H), 3.16 (br. s., 3H), 3.10 (br. s., 3H), 3.06-3.00 (m, 1H), 2.44 (s, 3H) ppm. MS (ESI) m/z: 688 (M+H)$^+$. Analytical HPLC: RT=9.45 min (Method A).

EXAMPLE 10

(S)-4-(2-(1-(3-Chloro-2-fluorophenyl)-1H-1,2,3-triazole-4-carbonyl)-5-(4-((2-(dimethylamino)ethyl)carbamoyl)phenyl)-1,2,3,4-tetrahydroisoquinoline-1-carboxamido)benzoic acid, TFA salt

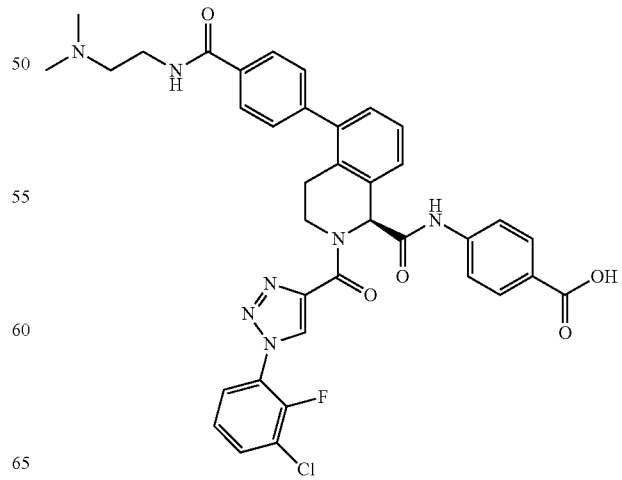

10A. (S)-tert-Butyl 4-(2-(1-(3-chloro-2-fluorophenyl)-1H-1,2,3-triazole-4-carbonyl)-5-(4-((2-(dimethylamino)ethyl)carbamoyl)phenyl)-1,2,3,4-tetrahydroisoquinoline-1-carboxamido)benzoate: 10A was the first compound after chiral HPLC separation of Example 5 (100 mg) using KROMASIL® Cellucoat, 4.6×250 mm ID, 5 μ, using 45% MeOH-DEA/55% $CO_2$ at 45.0 mL/min, 100 bar, and 40° C. to give 10A (34 mg, 78%).

Example 10. (S)-4-(2-(1-(3-Chloro-2-fluorophenyl)-1H-1,2,3-triazole-4-carbonyl) 5 (4((2 (dimethylamino)ethyl)carbamoyl)phenyl)-1,2,3,4-tetrahydroisoquinoline-1-carboxamido)benzoic acid: 10A was treated with 50% TFA/DCM. After 2 h, the mixture was concentrated and the crude material purified by reverse phase prep HPLC to give Example 8 (23 mg, 60%) as a white solid. $^1$H NMR (500 MHz, DMSO-$d_6$) δ 11.00 (s, 1H), 9.21-9.13 (m, 1H), 8.76 (t, J=5.8 Hz, 1H), 7.97 (d, J=8.3 Hz, 2H), 7.95-7.86 (m, 4H), 7.81-7.75 (m, 3H), 7.55-7.49 (m, 3H), 7.44 (t, J=7.7 Hz, 1H), 7.30 (d, J=6.9 Hz, 1H), 6.03 (s, 1H), 4.50 (dt, J=12.7, 5.1 Hz, 1H), 4.11 (ddd, J=12.7, 8.9, 4.0 Hz, 1H), 3.64 (q, J=5.8 Hz, 2H), 3.30 (q, J=5.6 Hz, 2H), 3.20-3.12 (m, 1H), 2.99-2.93 (m, 1H), 2.89-2.86 (m, 6H) ppm. MS (ESI) m/z: 710 (M+H)$^+$. Analytical HPLC: RT=5.88 min (Method A).

EXAMPLE 11

(R)-4-(2-(1-(3-Chloro-2-fluorophenyl)-1H-1,2,3-triazole-4-carbonyl)-5-(4-((2-(dimethylamino)ethyl)carbamoyl)phenyl)-1,2,3,4-tetrahydroisoquinoline-1-carboxamido)benzoic acid TFA salt

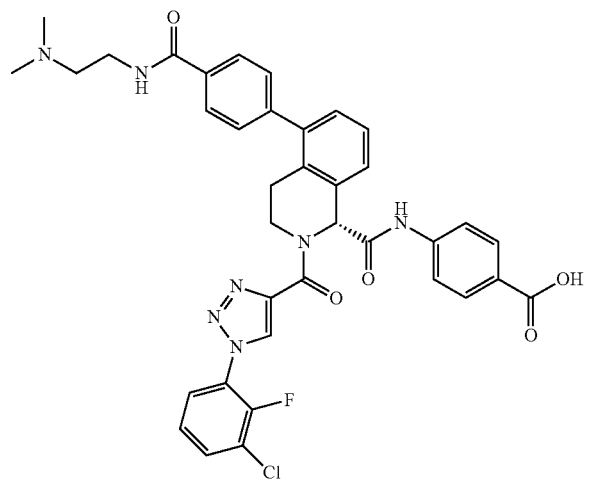 [SMILES: CN(C)CCNC(=O)c1ccc(-c2cccc3c2CCN(C(=O)c2cn(-c4cccc(Cl)c4F)nn2)[C@H]3C(=O)Nc2ccc(C(=O)O)cc2)cc1]

11A. (R)-tert-Butyl 4-(2-(1-(3-chloro-2-fluorophenyl)-1H-1,2,3-triazole-4-carbonyl)-5-(4-((2-(dimethylamino)ethyl)carbamoyl)phenyl)-1,2,3,4-tetrahydroisoquinoline-1-carboxamido)benzoate: 11A (43 mg, 99%) was the second compound after chiral HPLC separation of Example 5 (100 mg) using KROMASIL® Cellucoat, 4.6×250 mm ID, 5 μ, using 45% MeOH-DEA/55% $CO_2$ at 45.0 mL/min, 100 bar, and 40° C.

Example 11. (R)-4-(2-(1-(3-Chloro-2-fluorophenyl)-1H-1,2,3-triazole-4-carbonyl)-5-(4-((2-(dimethylamino)ethyl)carbamoyl)phenyl)-1,2,3,4-tetrahydroisoquinoline-1-carboxamido)benzoic acid: 11A was treated with 50% TFA/DCM. After 2 h, the mixture was concentrated and the crude material purified by reverse phase prep HPLC to give Example 11 (24 mg, 56%) as a white solid. $^1$H NMR (500 MHz, DMSO-$d_6$) δ 11.00 (s, 1H), 9.19-9.13 (m, 1H), 8.76 (t, J=5.6 Hz, 1H), 7.97 (d, J=8.3 Hz, 2H), 7.93-7.85 (m, 4H), 7.80-7.70 (m, 3H), 7.55-7.49 (m, 3H), 7.44 (t, J=7.7 Hz, 1H), 7.32-7.28 (m, 1H), 6.03 (s, 1H), 4.50 (dt, J=12.6, 5.3 Hz, 1H), 4.11 (ddd, J=12.7, 8.8, 3.9 Hz, 1H), 3.64 (q, J=5.8 Hz, 2H), 3.30 (q, J=6.0 Hz, 2H), 3.15 (dt, J=15.7, 4.4 Hz, 1H), 2.99-2.93 (m, 1H), 2.89-2.85 (m, 6H) ppm. MS (ESI) m/z: 710 (M+H)$^+$. Analytical HPLC: RT=5.89 min (Method A).

EXAMPLE 12

4-(2-(1-(3-Chloro-2-fluorophenyl)-1H-1,2,3-triazole-4-carbonyl)-5-(pyrimidin-5-yl)-1,2,3,4-tetrahydroisoquinoline-1-carboxamido)benzoic acid

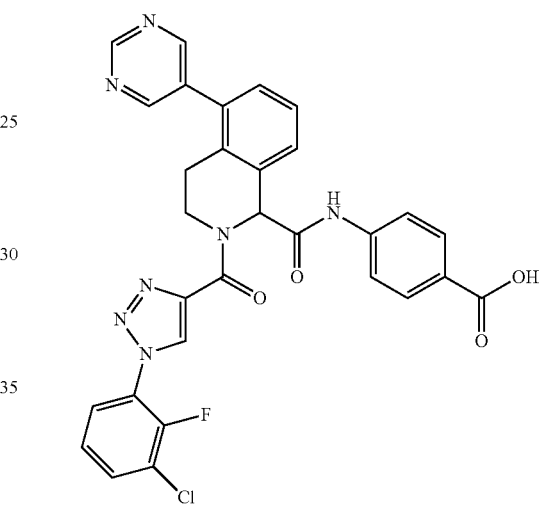

Example 12. 4-(2-(1-(3-Chloro-2-fluorophenyl)-1H-1,2,3-triazole-4-carbonyl)-5-(pyrimidin-5-yl)-1,2,3,4-tetrahydroisoquinoline-1-carboxamido)benzoic acid: Intermediate 24 (0.050 g, 0.076 mmol), pyrimidin-5-ylboronic acid (0.014 g, 0.115 mmol), and cesium carbonate (0.075 g, 0.229 mmol) were added to DME/$H_2O$ (5:1; 3 mL) and degassed for 15 min. Tetrakis(triphenylphosphine)palladium (0) (8.82 mg, 7.63 mmol) was added and the complete mixture irradiated at 120° C. for 15 minutes. The reaction mixture was poured into EtOAc, washed with saturated NaHCO$_3$ solution, brine, dried over sodium sulfate, filtered, and concentrated. The crude material was treated with 50% TFA/DCM for 1 h before concentrating, purifying by reverse phase prep. HPLC, and lyophilization. Example 12 (20 mg, 43%) was isolated as a white solid. $^1$H NMR (500 MHz, DMSO-$d_6$) δ 12.74 (br. s., 1H), 11.02 (s, 1H), 9.25 (s, 1H), 9.17 (d, J=1.9 Hz, 1H), 8.91 (s, 2H), 7.95-7.86 (m, 4H), 7.83 (d, J=7.7 Hz, 1H), 7.79-7.75 (m, 2H), 7.54-7.47 (m, 2H), 7.40 (dd, J=7.6, 1.0 Hz, 1H), 6.06 (s, 1H), 4.47-4.41 (m, 1H), 4.25 (ddd, J=12.7, 8.0, 4.4 Hz, 1H), 3.16-3.07 (m, 1H), 3.05-2.98 (m, 1H) ppm. MS (ESI) m/z: 598 (M+H)$^+$. Analytical HPLC: RT=6.90 min (Method B).

EXAMPLE 13

(R)-4-(2-(1-(3-Chloro-2-fluorophenyl)-1H-1,2,3-triazole-4-carbonyl)-5-(pyrimidin-5-yl)-1,2,3,4-tetrahydroisoquinoline-1-carboxamido)benzoic acid

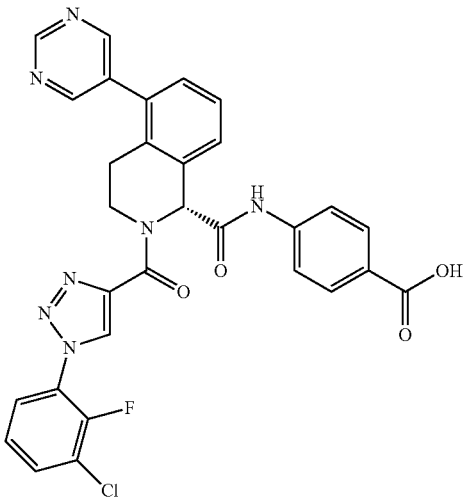 [SMILES: O=C(O)c1ccc(NC(=O)C2c3cccc(-c4cncnc4)c3CCN2C(=O)c2cn(-c3cccc(Cl)c3F)nn2)cc1]

Example 13. (R)-4-(2-(1-(3-Chloro-2-fluorophenyl)-1H-1,2,3-triazole-4-carbonyl)-5-(pyrimidin-5-yl)-1,2,3,4-tetrahydroisoquinoline-1-carboxamido)benzoic acid: Example 13 was the first compound after chiral HPLC separation of Example 12 using OJ-H column, 2×25 cm, using 25% IPA/CO$_2$ at 75.0 mL/min, and 100 bar to give a white solid (15 mg, 21%). $^1$H NMR (400 MHz, DMSO-d$_6$) δ 12.67 (br. s., 1H), 10.94 (s, 1H), 9.17 (s, 1H), 9.09 (d, J=1.8 Hz, 1H), 8.83 (s, 2H), 7.90-7.72 (m, 5H), 7.73-7.62 (m, 2H), 7.48-7.36 (m, 2H), 7.35-7.28 (m, 1H), 5.98 (s, 1H), 4.41-4.30 (m, 1H), 4.17 (ddd, J=12.5, 7.8, 4.3 Hz, 1H), 3.08-2.99 (m, 1H), 2.98-2.88 (m, 1H) ppm. MS (ESI) m/z: 598 (M+H)$^+$. Analytical HPLC: RT=7.28 min (Method A).

EXAMPLE 14

(S)-4-(2-(1-(3-Chloro-2-fluorophenyl)-1H-1,2,3-triazole-4-carbonyl)-5-(pyrimidin-5-yl)-1,2,3,4-tetrahydroisoquinoline-1-carboxamido)benzoic acid

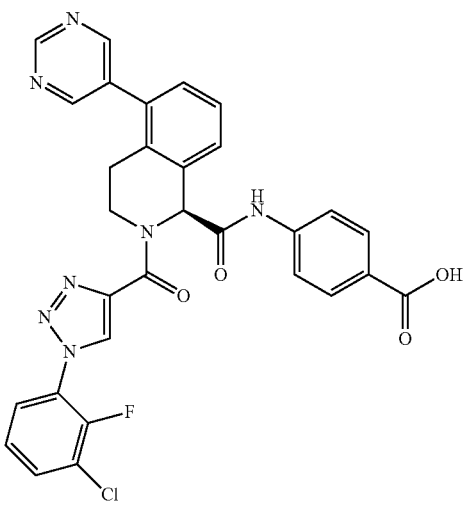

Example 14 was the second compound after chiral separation of Example 12 using OJ-H column, 2×25 cm, using 25% IPA/CO$_2$ at 75.0 mL/min, and 100 bar to give a white solid (12 mg, 17%). $^1$H NMR (400 MHz, DMSO-d$_6$) δ 12.66 (br. s., 1H), 10.94 (s, 1H), 9.17 (s, 1H), 9.09 (d, J=1.8 Hz, 1H), 8.83 (s, 2H), 7.87-7.74 (m, 5H), 7.69 (d, J=8.8 Hz, 2H), 7.48-7.39 (m, 2H), 7.35-7.30 (m, 1H), 5.98 (s, 1H), 4.40-4.32 (m, 1H), 4.17 (ddd, J=12.7, 8.0, 4.6 Hz, 1H), 3.09-3.00 (m, 1H), 2.97-2.87 (m, 1H) ppm. MS (ESI) m/z: 598 (M+H)$^+$. Analytical HPLC: RT—7.27 min (Method A).

EXAMPLE 15

(R)-4-(2-(1-(3-Chloro-2-fluorophenyl)-1H-1,2,3-triazole-4-carbonyl)-5-(6-cyanopyridin-3-yl)-1,2,3,4-tetrahydroisoquinoline-1-carboxamido)benzoic acid, TFA salt

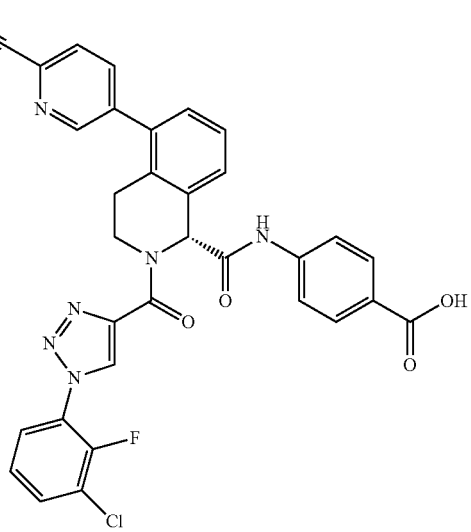

15A. tert-Butyl 4-(2-(1-(3-chloro-2-fluorophenyl)-1H-1,2,3-triazole-4-carbonyl)-5-(6-cyanopyridin-3-yl)-1,2,3,4-tetrahydroisoquinoline-1-carboxamido)benzoate: 15A was prepared in a similar manner as Example 12 replacing pyrimidin-5-ylboronic acid with 5-(4,4,5,5-tetramethyl-1,3,2-dioxaborolan-2-yl)picolinonitrile as a white solid.

Example 15. (R)-4-(2-(1-(3-Chloro-2-fluorophenyl)-1H-1,2,3-triazole-4-carbonyl)-5-(6-cyanopyridin-3-yl)-1,2,3,4-tetrahydroisoquinoline-1-carboxamido)benzoic acid, TFA salt: Example 15 was the early eluting compound after chiral HPLC separation of 15A (126 mg) using OJ-H column, 2×25 cm, using 30% (1:1) MeCN-IPA-0.1% DEA (v/v)/70% CO$_2$ at 65.0 mL/min, 150 bar, and 35° C., followed by t-butyl ester hydrolysis with 50% TFA/DCM, purification by reverse phase prep. HPLC, and freeze-drying to give a white solid (15 mg, 24%). $^1$H NMR (500 MHz, DMSO-d$_6$) δ 12.75 (br. s., 1H), 11.01 (s, 1H), 9.21-9.12 (m, 1H), 8.83 (dd, J=1.8, 1.2 Hz, 1H), 8.21-8.11 (m, 2H), 7.97-7.83 (m, 5H), 7.79-7.70 (m, 2H), 7.54-7.47 (m, 2H), 7.42-7.36 (m, 1H), 6.06 (s, 1H), 4.44 (qd, J=6.4, 4.5 Hz, 1H), 4.22 (ddd, J=12.7, 8.2, 4.1 Hz, 1H), 3.10 (qd, J=7.9, 4.4 Hz, 1H), 3.03-2.92 (m, 1H) ppm. MS (ESI) m/z: 622 (M+H)$^+$. Analytical HPLC: RT=8.35 min (Method A).

EXAMPLE 16

(S)-4-(2-(1-(3-Chloro-2-fluorophenyl)-1H-1,2,3-triazole-4-carbonyl)-5-(6-cyanopyridin-3-yl)-1,2,3,4-tetrahydroisoquinoline-1-carboxamido)benzoic acid, TFA salt

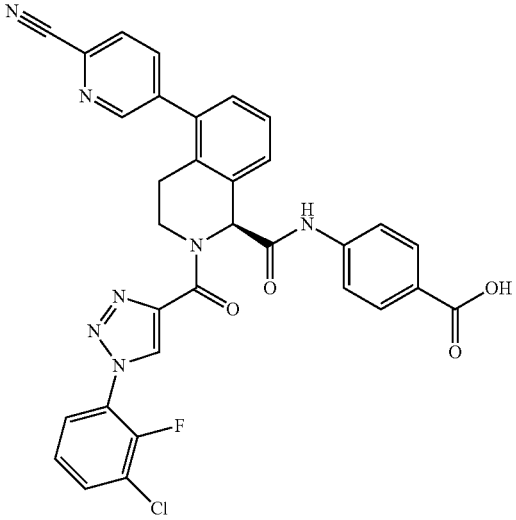 [SMILES: N#Cc1ccc(-c2cccc3c2CCN(C(=O)c2cn(-c4cccc(Cl)c4F)nn2)[C@@H]3C(=O)Nc2ccc(C(=O)O)cc2)cn1]

Example 16. (S)-4-(2-(1-(3-Chloro-2-fluorophenyl)-1H-1,2,3-triazole-4-carbonyl)-5-(6-cyanopyridin-3-yl)-1,2,3,4-tetrahydroisoquinoline-1-carboxamido)benzoic acid, TFA salt: Example 16 was the late eluting compound after chiral HPLC separation of 15A (126 mg) using OJ-H column, 2×25 cm, using 30% (1:1) MeCN-IPA-0.1% DEA (v/v)/70% $CO_2$ at 65.0 mL/min, 150 bar, and 35° C., followed by t-butyl ester hydrolysis with 50% TFA/DCM, purification by reverse phase prep. HPLC, and freeze-drying to give a white solid (16 mg, 26%). $^1$H NMR (500 MHz, DMSO-$d_6$) δ 11.01 (s, 1H), 9.20-9.12 (m, 1H), 8.83 (dd, J=1.9, 1.1 Hz, 1H), 8.22-8.10 (m, 2H), 7.95-7.82 (m, 5H), 7.80-7.74 (m, 2H), 7.54-7.45 (m, 2H), 7.41-7.34 (m, 1H), 6.06 (s, 1H), 4.47-4.39 (m, 1H), 4.22 (ddd, J=12.7, 8.2, 4.1 Hz, 1H), 3.10 (qd, J=8.0, 4.4 Hz, 1H), 3.02-2.95 (m, 1H) ppm. MS (ESI) m/z: 622 (M+H)$^+$. Analytical HPLC: RT=8.37 min (Method A).

EXAMPLE 17

4-((S)-2-((R)-3-(3-Chloro-2-fluorophenyl)-4,5-dihydroisoxazole-5-carbonyl)-5-(pyrimidin-5-yl)-1,2,3,4-tetrahydroisoquinoline-1-carboxamido)benzoic acid

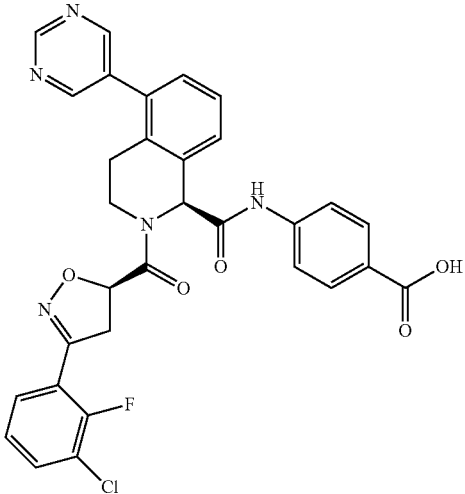 [SMILES: O=C(O)c1ccc(NC(=O)[C@@H]2c3cccc(-c4cncnc4)c3CCN2C(=O)[C@H]2CC(c3cccc(Cl)c3F)=NO2)cc1]

17A. 5-(Pyrimidin-5-yl)-3,4-dihydroisoquinoline: tert-Butyl 5-bromo-3,4-dihydroisoquinoline-2(1H)-carboxylate (0.30 g, 0.96 mmol), pyrimidin-5-ylboronic acid (0.18 g, 1.44 mmol), and $Cs_2CO_3$ (0.94 g, 2.88 mmol) were added to a microwave vial containing DME/$H_2O$ (5:1; 12 mL) and degassed for 15 min. Tetrakis(triphenylphosphine)palladium (0) (0.111 g, 0.096 mmol) was added and the mixture heated at 90° C. overnight before diluting with EtOAc, washed with saturated $NaHCO_3$ solution, brine, dried over sodium sulfate, filtered, and concentrated. The boc group was removed by dissolving in MeOH (2.0 mL) and treatment with HCl (12.01 mL, 48.0 mmol). After 1 h, the reaction mixture was concentrated to dryness. The resulting residue was partitioned between DCM and saturated $NaHCO_3$ solution. The aqueous layer was extracted with EtOAc. The organic layers were washed with brine, dried over sodium sulfate, filtered, and concentrated. The free base was dissolved in DCM (30 mL) and treated with $MnO_2$ (1.504 g, 17.30 mmol). The reaction mixture was filtered through a plug of CELITE® and concentrated to give 17A as a brown oil. MS (ESI) m/z: 210 (M+H)$^+$.

17B. tert-Butyl 4-(2-((S)-3-(3-chloro-2-fluorophenyl)-4,5-dihydroisoxazole-5-carbonyl)-5-(pyrimidin-5-yl)-1,2,3,4-tetrahydroisoquinoline-1-carboxamido)benzoate: Chiral Intermediate 19 (0.058 g, 0.239 mmol), 17A (0.050 g, 0.239 mmol), and Intermediate 1 (0.049 g, 0.239 mmol) were added to a pressure vial containing MeOH (0.478 mL) and heated at 50° C. for 18 h. The reaction mixture was concentrated to dryness. MS (ESI) m/z: 656 (M+H)$^+$.

17C. tert-Butyl 4-((1S)-2-(3-(3-chloro-2-fluorophenyl)-4,5-dihydroisoxazole-5-carbonyl)-5-(pyrimidin-5-yl)-1,2,3,4-tetrahydroisoquinoline-1-carboxamido)benzoate: 17C was isolated as the first eluting diastereomer after reverse phase prep. HPLC of 17B. MS (ESI) m/z: 656 (M+H)$^+$.

Example 17. 4-((S)-2-((R)-3-(3-Chloro-2-fluorophenyl)-4,5-dihydroisoxazole-5-carbonyl)-5-(pyrimidin-5-yl)-1,2,3,4-tetrahydroisoquinoline-1-carboxamido)benzoic acid: 17C was treated with 50% TFA/DCM for 2 h, concentrated, purified by reverse phase prep. HPLC, and lyophilized to give Example 17 (9.2 mg, 12% over three steps) as a white solid. $^1$H NMR (500 MHz, DMSO-$d_6$) δ 12.66 (br. s., 1H), 10.85 (s, 1H), 9.18 (s, 1H), 8.83-8.80 (m, 2H), 7.85-7.80 (m, 2H), 7.68-7.63 (m, 5H), 7.41-7.36 (m, 1H), 7.34-7.29 (m, 1H), 7.25 (td, J=8.0, 0.8 Hz, 1H), 5.86 (s, 1H), 5.66 (dd, J=11.4, 7.6 Hz, 1H), 4.17-4.09 (m, 1H), 3.83-3.70 (m, 2H), 3.65-3.58 (m, 1H), 3.00 (ddd, J=15.8, 7.6, 4.4 Hz, 1H), 2.93-2.84 (m, 1H) ppm. MS (ESI) m/z: 600 (M+H)$^+$. Analytical HPLC: RT—8.24 min (Method A).

EXAMPLE 18

4-((R)-2-((R)-3-(3-Chloro-2-fluorophenyl)-4,5-dihydroisoxazole-5-carbonyl)-5-(pyrimidin-5-yl)-1,2,3,4-tetrahydroisoquinoline-1-carboxamido)benzoic acid

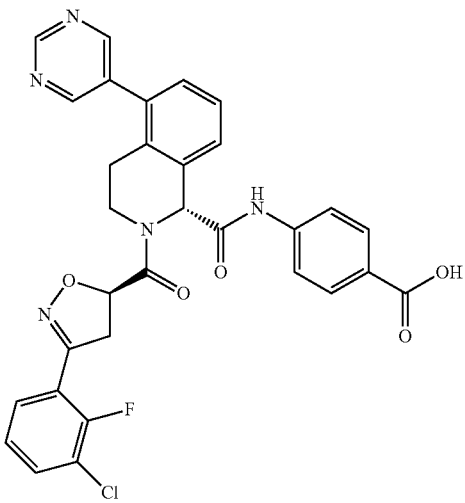 [SMILES: O=C(O)c1ccc(NC(=O)[C@H]2c3cccc(-c4cncnc4)c3CCN2C(=O)[C@H]2CC(c3cccc(Cl)c3F)=NO2)cc1]

18A. tert-Butyl 4-((1R)-2-(3-(3-chloro-2-fluorophenyl)-4,5-dihydroisoxazole-5-carbonyl)-5-(pyrimidin-5-yl)-1,2,3,4-tetrahydroisoquinoline-1-carboxamido)benzoate: 18A was isolated as the second eluting diastereomer after reverse phase prep. HPLC of 17B. MS (ESI) m/z: 656 (M+H)$^+$.

Example 18. 4-((R)-2-((R)-3-(3-Chloro-2-fluorophenyl)-4,5-dihydroisoxazole-5-carbonyl)-5-(pyrimidin-5-yl)-1,2,3,4-tetrahydroisoquinoline-1-carboxamido)benzoic acid: 18A was treated with 50% TFA/DCM for 2 h, concentrated, purified by reverse phase prep. HPLC, and lyophilized to give Example 18 (8.1 mg, 11% over three steps) as a white solid. $^1$H NMR (500 MHz, DMSO-d$_6$) δ 12.74 (br. s., 1H), 10.88 (s, 1H), 9.25 (s, 1H), 8.91 (s, 2H), 7.92-7.88 (m, 2H), 7.78-7.70 (m, 5H), 7.49-7.44 (m, 1H), 7.41-7.31 (m, 2H), 5.90 (s, 1H), 5.86 (dd, J=11.4, 7.0 Hz, 1H), 4.21 (ddd, J=12.5, 6.5, 4.4 Hz, 1H), 3.92-3.85 (m, 1H), 3.80-3.69 (m, 2H), 3.11 (ddd, J=15.7, 8.1, 4.3 Hz, 1H), 2.95-2.88 (m, 1H) ppm. MS (ESI) m/z: 600 (M+H)$^+$. Analytical HPLC: RT=8.43 min (Method A).

Example 19 through Example 29 were prepared in a similar manner as Example 17 replacing pyrimidin-5-ylboronic acid with the appropriate boronic acid or boronate in the Suzuki coupling step and the appropriate isonitrile in the Ugi reaction.

EXAMPLE 19

4-((S)-2-((R)-3-(3-Chloro-2-fluorophenyl)-4,5-dihydroisoxazole-5-carbonyl)-5-(6-(methylcarbamoyl)pyridin-3-yl)-1,2,3,4-tetrahydroisoquinoline-1-carboxamido)benzoic acid, TFA salt

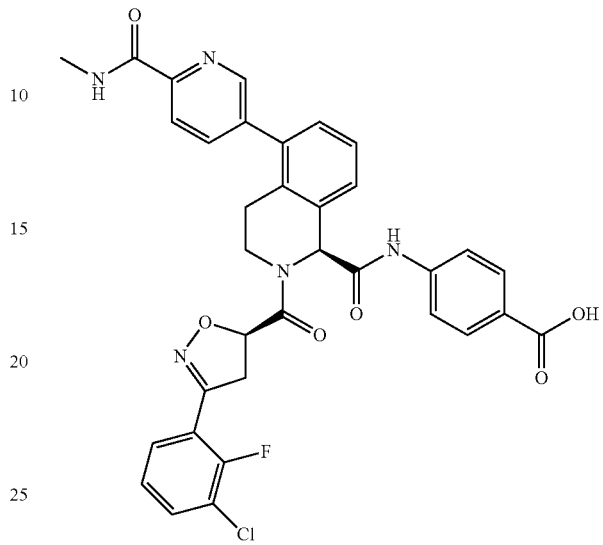

The compound is early eluting diastereomer after reverse phase prep. HPLC. $^1$H NMR (500 MHz, DMSO-d$_6$) δ 10.92 (s, 1H), 8.85 (q, J=4.6 Hz, 1H), 8.65 (d, J=1.7 Hz, 1H), 8.13 (d, J=8.3 Hz, 1H), 8.03 (dd, J=8.3, 2.2 Hz, 1H), 7.91-7.88 (m, 2H), 7.75-7.70 (m, 5H), 7.46-7.42 (m, 1H), 7.37-7.30 (m, 2H), 5.92 (s, 1H), 5.73 (dd, J=11.4, 7.6 Hz, 1H), 4.23-4.17 (m, 1H), 3.90-3.84 (m, 1H), 3.78-3.64 (m, 2H), 3.10 (ddd, J=15.6, 8.2, 4.3 Hz, 1H), 2.97-2.90 (m, 1H), 2.87 (d, J=5.0 Hz, 3H) ppm. MS (ESI) m/z: 656 (M+H)$^+$. Analytical HPLC: RT=8.68 min (Method A).

EXAMPLE 20

4-((R)-2-((R)-3-(3-Chloro-2-fluorophenyl)-4,5-dihydroisoxazole-5-carbonyl)-5-(6-(methylcarbamoyl)pyridin-3-yl)-1,2,3,4-tetrahydroisoquinoline-1-carboxamido)benzoic acid, TFA salt

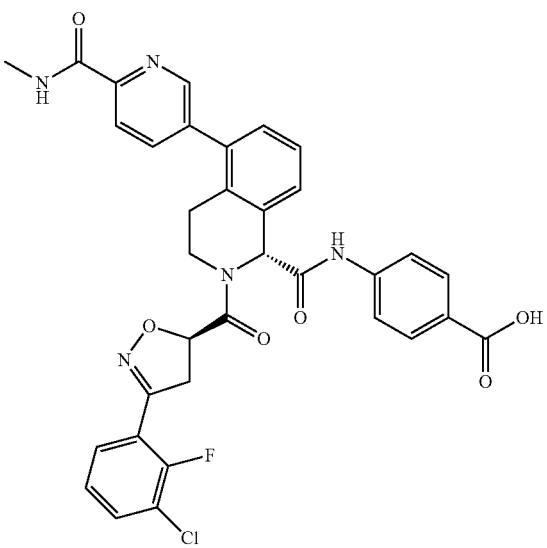 [SMILES: CNC(=O)c1ccc(-c2cccc3c2CCN(C(=O)[C@H]2CC(c4cccc(Cl)c4F)=NO2)[C@H]3C(=O)Nc2ccc(C(=O)O)cc2)cn1]

The compound is late eluting diastereomer ater reverse phase prep. HPLC. ¹H NMR (500 MHz, DMSO-d₆) δ 12.75 (br. s., 1H), 10.88 (s, 1H), 8.85 (q, J=4.7 Hz, 1H), 8.66 (dd, J=2.1, 0.7 Hz, 1H), 8.13 (dd, J=8.0, 0.6 Hz, 1H), 8.04 (dd, J=8.3, 2.2 Hz, 1H), 7.92-7.88 (m, 2H), 7.77-7.70 (m, 5H), 7.48-7.43 (m, 1H), 7.38-7.31 (m, 2H), 5.89 (s, 1H), 5.85 (dd, J=11.3, 7.2 Hz, 1H), 4.24-4.18 (m, 1H), 3.92-3.85 (m, 1H), 3.77-3.69 (m, 2H), 3.10 (ddd, J=15.6, 8.5, 4.3 Hz, 1H), 2.91 (dd, J=10.9, 5.1 Hz, 1H), 2.87 (d, J=4.7 Hz, 3H) ppm. MS (ESI) m/z: 656 (M+H)⁺. Analytical HPLC: RT=8.87 min (Method A).

EXAMPLE 21

4-((S)-2-((R)-3-(3-Chloro-2-fluorophenyl)-4,5-dihydroisoxazole-5-carbonyl)-5-(5-fluoropyridin-3-yl)-1,2,3,4-tetrahydroisoquinoline-1-carboxamido)benzoic acid, TFA salt

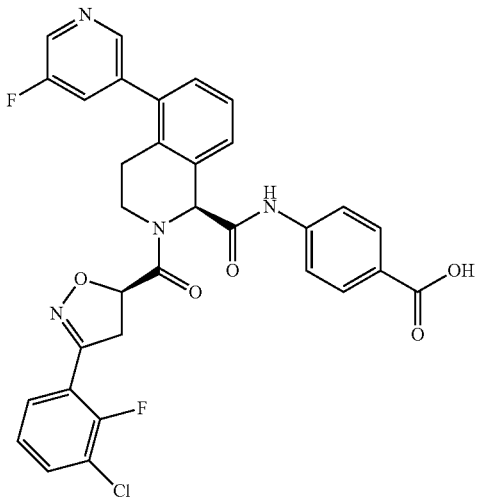 [SMILES: O=C(O)c1ccc(NC(=O)[C@@H]2c3cccc(-c4cncc(F)c4)c3CCN2C(=O)[C@H]2CC(c3cccc(Cl)c3F)=NO2)cc1]

The compound is early eluting diastereomer after reverse phase prep. ¹H NMR (500 MHz, methanol-d₄) δ 8.58 (d, J=2.8 Hz, 1H), 8.50 (s, 1H), 8.05-7.95 (m, 2H), 7.82-7.66 (m, 5H), 7.60 (ddd, J=8.2, 6.9, 1.7 Hz, 1H), 7.46 (t, J=7.7 Hz, 1H), 7.41-7.35 (m, 1H), 7.26 (td, J=8.0, 1.1 Hz, 1H), 5.94 (s, 1H), 5.76 (dd, J=11.4, 7.6 Hz, 1H), 4.37-4.30 (m, 1H), 4.00-3.92 (m, 1H), 3.80-3.72 (m, 2H), 3.33-3.26 (m, 1H), 3.01-2.94 (m, 1H) ppm. MS (ESI) m/z: 617 (M+H)⁺. Analytical HPLC: RT=6.94 min (Method B).

EXAMPLE 22

4-((R)-2-((R)-3-(3-Chloro-2-fluorophenyl)-4,5-dihydroisoxazole-5-carbonyl)-5-(5-fluoropyridin-3-yl)-1,2,3,4-tetrahydroisoquinoline-1-carboxamido)benzoic acid, TFA salt

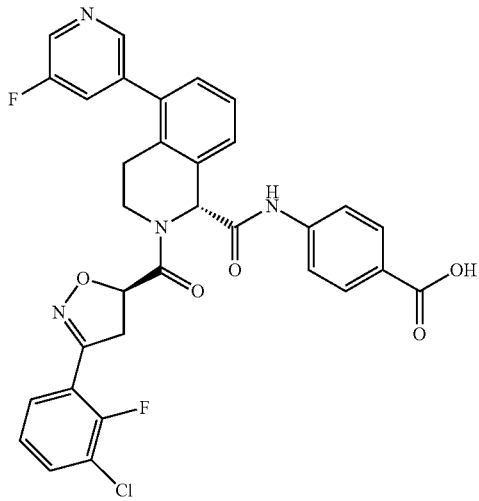 [SMILES: O=C(O)c1ccc(NC(=O)[C@H]2c3cccc(-c4cncc(F)c4)c3CCN2C(=O)[C@H]2CC(c3cccc(Cl)c3F)=NO2)cc1]

The compound is late eluting diastereomer after reverse phase prep. HPLC. ¹H NMR (500 MHz, methanol-d₄) δ 8.58 (d, J=2.8 Hz, 1H), 8.50 (s, 1H), 8.05-7.95 (m, 2H), 7.82-7.66 (m, 5H), 7.60 (ddd, J=8.2, 6.9, 1.7 Hz, 1H), 7.46 (t, J=7.7 Hz, 1H), 7.41-7.35 (m, 1H), 7.26 (td, J=8.0, 1.1 Hz, 1H), 5.94 (s, 1H), 5.76 (dd, J=11.4, 7.6 Hz, 1H), 4.37-4.30 (m, 1H), 4.00-3.92 (m, 1H), 3.80-3.72 (m, 2H), 3.33-3.26 (m, 1H), 3.01-2.94 (m, 1H) ppm. MS (ESI) m/z: 617 (M+H)⁺. Analytical HPLC: RT=7.14 min (Method B).

EXAMPLE 23

4-((S)-2-((R)-3-(3-Chloro-2-fluorophenyl)-4,5-dihydroisoxazole-5-carbonyl)-5-(5-methoxypyridin-3-yl)-1,2,3,4-tetrahydroisoquinoline-1-carboxamido) benzoic acid, TFA salt

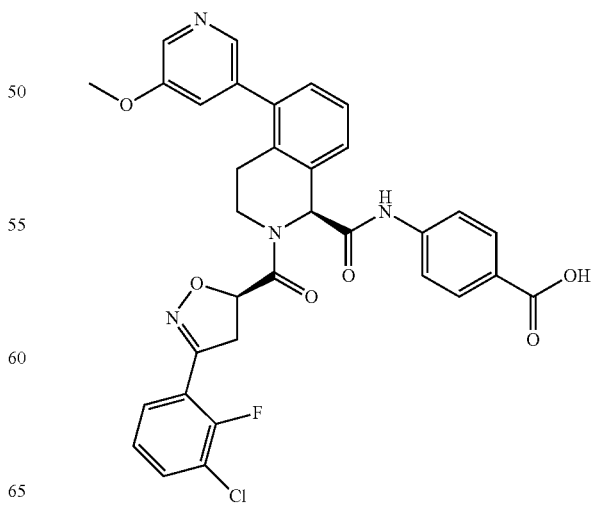

The compound is early eluting diastereomer after reverse phase prep. HPLC. $^1$H NMR (400 MHz, DMSO-$d_6$) δ 10.92 (s, 1H), 7.95-7.88 (m, 2H), 7.79-7.68 (m, 5H), 7.46-7.38 (m, 2H), 7.36-7.28 (m, 2H), 5.92 (s, 1H), 5.73 (dd, J=11.4, 7.5 Hz, 1H), 4.274.15 (m, 1H), 3.93-3.82 (m, 5H), 3.13-3.03 (m, 1H), 3.03-2.88 (m, 1H) ppm. MS (ESI) m/z: 626 (M+H)$^+$. Analytical HPLC: RT=6.23 min (Method B).

EXAMPLE 24

4-((R)-2-((R)-3-(3-Chloro-2-fluorophenyl)-4,5-dihydroisoxazole-5-carbonyl)-5-(5-methoxypyridin-3-yl)-1,2,3,4-tetrahydroisoquinoline-1-carboxamido)benzoic acid, TFA salt

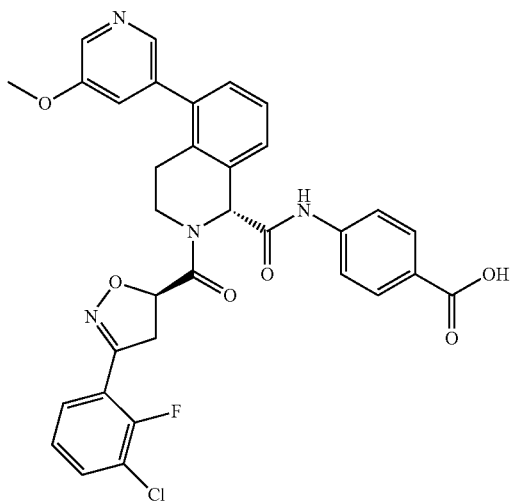 [SMILES: COc1cncc(-c2cccc3c2CCN(C(=O)[C@H]2CC(c4cccc(Cl)c4F)=NO2)[C@H]3C(=O)Nc2ccc(C(=O)O)cc2)c1]

The compound is late eluting diastereomer after reverse phase prep. HPLC. $^1$H NMR (400 MHz, DMSO-$d_6$) δ 10.87 (s, 1H), 7.95-7.87 (m, 2H), 7.77-7.68 (m, 5H), 7.49-7.39 (m, 2H), 7.36-7.30 (m, 2H), 5.91-5.80 (m, 2H), 4.25-4.17 (m, 1H), 3.91 (s, 3H), 3.80-3.68 (m, 2H), 3.15-3.06 (m, 1H), 2.96-2.86 (m, 1H) ppm. MS (ESI) m/z: 626 (M+H)$^+$. Analytical HPLC: RT=6.43 min (Method B).

EXAMPLE 25

(R)-Methyl 4-(2-(1-(3-chloro-2-fluorophenyl)-1H-1,2,3-triazole-4-carbonyl)-5-(pyrimidin-5-yl)-1,2,3,4-tetrahydroisoquinoline-1-carboxamido)benzoate

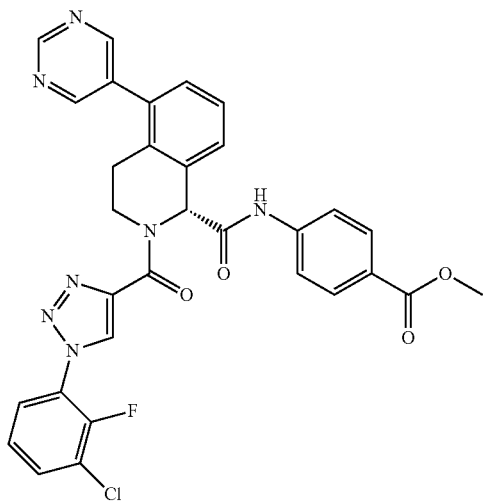 [SMILES: COC(=O)c1ccc(NC(=O)[C@H]2c3cccc(-c4cncnc4)c3CCN2C(=O)c2cn(-c3cccc(Cl)c3F)nn2)cc1]

Example 25 made as described previously for Example 6 replacing N-(2-dimethylaminoethyl)-4-(4,4,5,5-tetramethyl-1,3,2-dioxaborolan-2-yl)benzamide with pyrimidin-5-ylboronic acid in the Suzuki reaction step and Intermediate 1 with Intermediate 2 in Ugi reaction step. The compound was isolated as the early eluting enantiomer after chiral purification using KROMASIL® 5-Cellucoat, 21×250 mm, 5 μ using 35% EtOH/65% CO$_2$ at 75 mL/min, 100 Bar, and 40° C. $^1$H NMR (500 MHz, DMSO-$d_6$) δ 11.06 (s, 1H), 9.24 (s, 1H), 9.20-9.15 (m, 1H), 8.91 (s, 2H), 8.01-7.92 (m, 2H), 7.92-7.85 (m, 2H), 7.85-7.77 (m, 3H), 7.55-7.46 (m, 2H), 7.40 (d, J=7.7 Hz, 1H), 6.05 (s, 1H), 4.49-4.41 (m, 1H), 4.24 (ddd, J=12.7, 8.1, 4.3 Hz, 1H), 3.83 (s, 3H), 3.16-3.08 (m, 1H), 3.04-2.96 (m, 1H) ppm. MS (ESI) m/z: 612 (M+H)$^+$. Analytical HPLC: RT=7.34 min (Method B).

EXAMPLE 26

(S)-Methyl 4-(2-(1-(3-chloro-2-fluorophenyl)-1H-1,2,3-triazole-4-carbonyl)-5-(pyrimidin-5-yl)-1,2,3,4-tetrahydroisoquinoline-1-carboxamido)benzoate

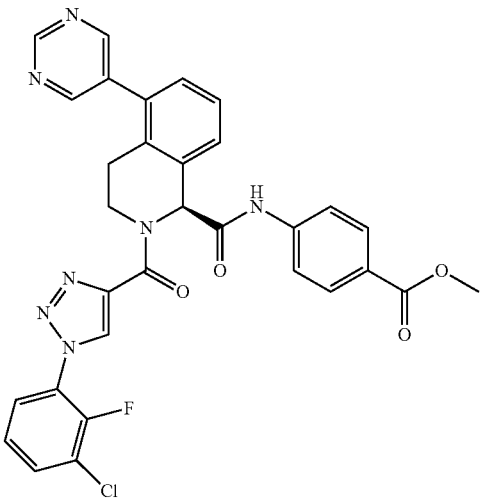 [SMILES: COC(=O)c1ccc(NC(=O)[C@@H]2c3cccc(-c4cncnc4)c3CCN2C(=O)c2cn(-c3cccc(Cl)c3F)nn2)cc1]

Example 26 made as described previously for Example 6 replacing N-(2-dimethylaminoethyl)-4-(4,4,5,5-tetramethyl-1,3,2-dioxaborolan-2-yl)benzamide with pyrimidin-5-ylboronic acid in the Suzuki reaction step and Intermediate 1 with Intermediate 2 in Ugi reaction step. The compound was isolated as the late eluting enantiomer after chiral purification using KROMASIL® 5-Cellucoat, 21×250 mm, 5 μ using 35% EtOH/65% CO$_2$ at 75 mL/min, 100 Bar, and 40° C. 1H NMR (400 MHz, DMSO-$d_6$) δ 11.06 (s, 1H), 9.25 (s, 1H), 9.17 (d, J=1.8 Hz, 1H), 8.91 (s, 2H), 8.02-7.74 (m, 7H), 7.57-7.47 (m, 2H), 7.40 (d, J=6.6 Hz, 1H), 6.05 (s, 1H), 4.49-4.39 (m, 1H), 4.24 (ddd, J=12.7, 8.0, 4.4 Hz, 1H), 3.84 (s, 3H), 3.18-3.08 (m, 1H), 3.07-2.94 (m, 1H) ppm. MS (ESI) m/z: 612 (M+H)$^+$, Analytical HPLC: RT=7.35 min (Method B).

EXAMPLE 27

(S)-Methyl 4-(2-(1-(3-chloro-2-fluorophenyl)-1H-1,2,3-triazole-4-carbonyl)-5-(6-(methylcarbamoyl)pyridin-3-yl)-1,2,3,4-tetrahydroisoquinoline-1-carboxamido)benzoate, TFA salt

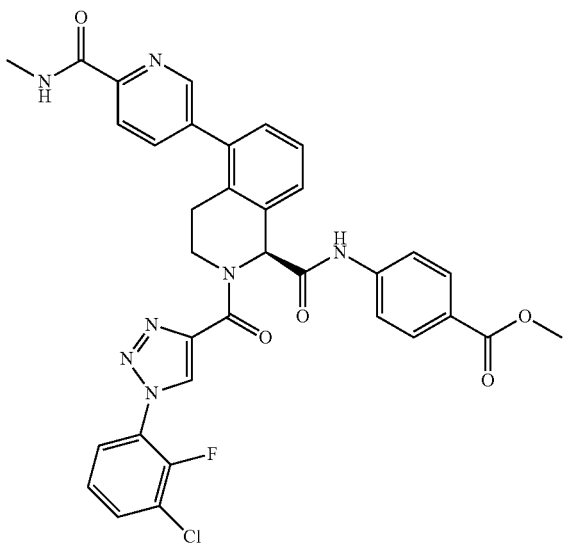

Example 27 was made in a similar manner as Example 26 replacing pyrimidin-5-ylboronic acid with N-methyl-5-(4,4,5,5-tetramethyl-1,3,2-dioxaborolan-2-yl)picolinamide in the Suzuki reaction step. The compound was isolated as the early eluting enantiomer after chiral purification using KROMASIL® 5-Cellucoat, 21×250 mm, 5 µ using 35% EtOH/65% $CO_2$ at 75 mL/min, 100 Bar, and 40° C. $^1$H NMR (500 MHz, DMSO-$d_6$) δ 11.05 (s, 1H), 9.20-9.15 (m, 1H), 8.83 (d, J=5.0 Hz, 1H), 8.66 (s, 1H), 8.15-8.10 (m, 1H), 8.04 (dd, J=8.0, 1.9 Hz, 1H), 7.99-7.93 (m, 2H), 7.91-7.85 (m, 2H), 7.84-7.78 (m, 3H), 7.53-7.45 (m, 2H), 7.38 (d, J=7.7 Hz, 1H), 6.04 (s, 1H), 4.50-4.42 (m, 1H), 4.17 (ddd, J=12.7, 8.4, 4.0 Hz, 1H), 3.83 (s, 3H), 3.17-3.08 (m, 1H), 3.01-2.94 (m, 1H), 2.86 (d, J=4.7 Hz, 3H) ppm. MS (ESI) m/z: 668 (M+H)$^+$. Analytical HPLC: RT=7.40 min (Method B).

EXAMPLE 28

Methyl 4-((S)-2-((R)-3-(3-chloro-2-fluorophenyl)-4,5-dihydroisoxazole-5-carbonyl)-5-(pyrimidin-5-yl)-1,2,3,4-tetrahydroisoquinoline-1-carboxamido)benzoate

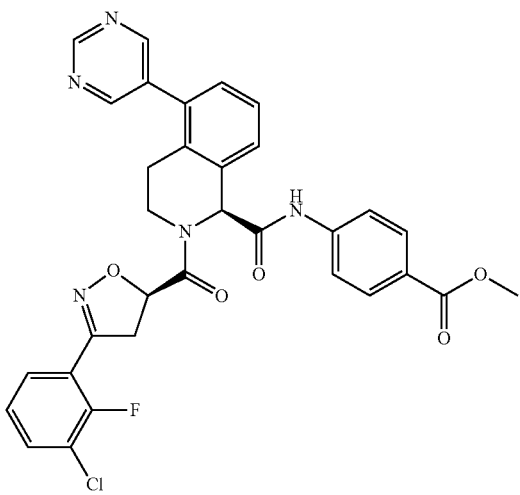 [SMILES: COC(=O)c1ccc(NC(=O)[C@@H]2c3cccc(-c4cncnc4)c3CCN2C(=O)[C@H]2CC(c3cccc(Cl)c3F)=NO2)cc1]

Example 28 was prepared in a similar manner as Example 26 replacing carboxylic acid Intermediate 9 with chiral Intermediate 19 in Ugi reaction step. The compound was isolated as the early eluting diastereomer after purification by reverse phase prep. HPLC. $^1$H NMR (400 MHz, DMSO-$d_6$) δ 10.89 (s, 1H), 9.18 (br. s., 1H), 8.83 (br. s., 1H), 7.87-7.81 (m, 2H), 7.69-7.63 (m, 5H), 7.40-7.35 (m, 1H), 7.33-7.23 (m, 2H), 5.85 (s, 1H), 5.66 (dd, J=11.4, 7.5 Hz, 1H), 4.17-4.08 (m, 1H), 3.83-3.70 (m, 5H), 3.65-3.55 (m, 1H), 3.06-2.98 (m, 1H), 2.94-2.83 (m, 1H) ppm. MS (ESI) m/z: 614 (M+H)$^+$. Analytical HPLC: RT=7.05 min (Method B).

EXAMPLE 29

Methyl 4-((R)-2-((R)-3-(3-chloro-2-fluorophenyl)-4,5-dihydroisoxazole-5-carbonyl)-5-(pyrimidin-5-yl)-1,2,3,4-tetrahydroisoquinoline-1-carboxamido)benzoate

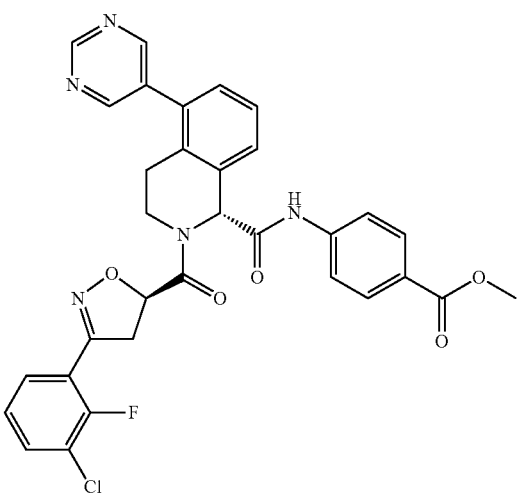 [SMILES: COC(=O)c1ccc(NC(=O)[C@H]2c3cccc(-c4cncnc4)c3CCN2C(=O)[C@H]2CC(c3cccc(Cl)c3F)=NO2)cc1]

Example 29 was prepared in a similar manner as Example 26 replacing carboxylic acid Intermediate 9 with chiral Intermediate 19 in Ugi reaction step. The compound was isolated as the late eluting diastereomer after purification by reverse phase prep. HPLC. $^1$H NMR (400 MHz, DMSO-$d_6$) δ 10.84 (s, 1H), 9.18 (s, 1H), 8.87-8.78 (m, 2H), 7.85 (d, J=8.8 Hz, 2H), 7.70-7.62 (m, 5H), 7.44-7.35 (m, 1H), 7.32-7.20 (m, 2H), 5.84-5.74 (m, 2H), 4.21-4.10 (m, 1H), 3.84-3.60 (m, 6H), 3.08-2.99 (m, 1H), 2.89-2.78 (m, 1H) ppm. MS (EST) m/z: 614 (M+H)$^+$. Analytical HPLC: RT=7.28 min (Method B).

The Examples in Table 3 were made as described previously for Example 12 replacing pyrimidin-5-ylboronic acid with the appropriate boronate/boronic acid in the Suzuki reaction

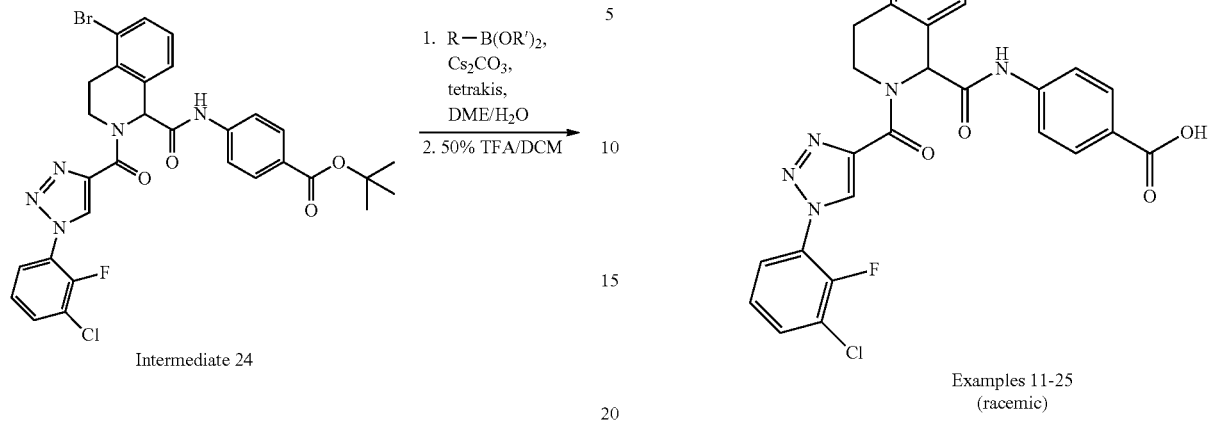

Examples 11-25
(racemic)

TABLE 3

| Example | R | Name | Analytical Data |
|---|---|---|---|
| 30 | pyrimidin-5-yl-NH₂ | 4-(5-(2-aminopyrimidin-5-yl)-2-(1-(3-chloro-2-fluorophenyl)-1H-1,2,3-triazole-4-carbonyl)-1,2,3,4-tetrahydroisoquinoline-1-carboxamido)benzoic acid, TFA salt | $^1$H NMR (500 MHz, DMSO-$d_6$) δ 10.98 (s, 1H), 9.17 (d, J = 1.7 Hz, 1H), 8.30 (s, 2H), 7.95-7.86 (m, 4H), 7.78-7.69 (m, 3H), 7.54-7.49 (m, 1H), 7.40 (t, J = 7.7 Hz, 1H), 7.31-7.27 (m, 1H), 6.00 (s, 1H), 4.52-4.43 (m, 1H), 4.17 (ddd, J = 12.7, 8.5, 4.1 Hz, 1H), 3.19-3.11 (m, 1H), 3.06-2.96 (m, 1H) ppm. MS (ESI) m/z: 613 (M + H)$^+$. Analytical HPLC: RT = 6.34 min (Method B.). |
| 31 | pyrimidin-5-yl-OCH₃ | 4-(2-(1-(3-chloro-2-fluorophenyl)-1H-1,2,3-triazole-4-carbonyl)-5-(2-methoxypyrimidin-5-yl)-1,2,3,4-tetrahydroisoquinoline-1-carboxamido)benzoic acid | $^1$H NMR (500 MHz, CD$_3$OD-$d_4$) δ 8.90 (s, 1H), 8.67-8.62 (m, 2H), 8.00 (d, J = 8.5 Hz, 2H), 7.87 (t, J = 7.0 Hz, 1H), 7.77-7.69 (m, 4H), 7.50-7.43 (m, 2H), 7.37 (d, J = 7.2 Hz, 1H), 6.03 (s, 1H), 4.67-4.57 (m, 1H), 4.26-4.19 (m, 1H), 4.10 (s, 3H), 3.29-3.14 (m, 1H), 3.07-2.99 (m, 1H) ppm. MS (ESI) m/z: 628 (M + H)$^+$. Analytical HPLC: RT = 7.08 min (Method B). |
| 32 | pyrimidin-5-yl-CN | 4-(2-(1-(3-chloro-2-fluorophenyl)-1H-1,2,3-triazole-4-carbonyl)-5-(2-cyanopyrimidin-5-yl)-1,2,3,4-tetrahydroisoquinoline-1-carboxamido)benzoic acid | $^1$H NMR (500 MHz, DMSO-$d_6$) δ 12.74 (br. s., 1H), 11.09-11.00 (m, 1H), 9.22-9.12 (m, 2H), 7.95-7.84 (m, 5H), 7.79-7.72 (m, 2H), 7.58-7.44 (m, 3H), 6.10-6.02 (m, 1H), 4.49-4.42 (m, 1H), 4.27 (ddd, J = 12.6, 8.0, 4.4 Hz, 1H), 3.18-3.11 (m, 1H), 3.09-3.02 (m, 1H) ppm. MS (ESI) m/z: 623 (M + H)$^+$. Analytical HPLC: RT = 6.86 min (Method B). |
| 33 | pyridin-3-yl | 4-(2-(1-(3-chloro-2-fluorophenyl)-1H-1,2,3-triazole-4-carbonyl)-5-(pyridin-3-yl)-1,2,3,4-tetrahydroisoquinoline-1-carboxamido)benzoic acid, TFA salt | $^1$H NMR (400 MHz, DMSO-$d_6$) δ 10.92 (s, 1H), 9.09 (s, 1H), 8.64 (br. s., 2H), 7.95 (d, J = 7 3 Hz, 1H), 7.87-7.77 (m, 4H), 7.75-7.68 (m, 3H), 7.60-7.56 (m, 1H), 7.45-7.36 (m, 2H), 7.28 (d, J = 7.3 Hz, 1H), 5.98 (s, 1H), 4.42-4.33 (m, 1H), 4.17-4.08 (m, 1H), 3.08-2.99 (m, 1H), 2.95-2.87 (m, 1H) ppm. MS (ESI) m/z: 597 (M + H)$^+$. Analytical HPLC: RT = 5.90 min (Method B). |
| 34 | pyrimidin-5-yl-OH | 4-(2-(1-(3-chloro-2-fluorophenyl)-1H-1,2,3-triazole-4-carbonyl)-5-(2-hydroxypyrimidin-5-yl)-1,2,3,4-tetrahydroisoquinoline-1-carboxamido)benzoic acid | $^1$H NMR (400 MHz, DMSO-$d_6$) δ 10.90 (s, 1H), 9.10 (d, J = 1.8 Hz, 1H), 8.28 (br. s., 2H), 7.86-7.77 (m, 4H), 7.71-7.63 (m, 3H), 7.44 (td, J = 8.2, 1.4 Hz, 1H), 7.35-7.30 (m, 1H), 7.25 (d, J = 6.6 Hz, 1H), 5.94 (s, 1H), 4.43-4.32 (m, 1H), 4.18 (ddd, J = 12.6, 7.9, 4.6 Hz, 1H), 3.12-2.90 (m, 2H) ppm. MS (ESI) m/z: 614 (M + H)$^+$. Analytical HPLC: RT = 5.84 min (Method B). |
| 35 | 5-fluoropyridin-3-yl | 4-(2-(1-(3-chloro-2-fluorophenyl)-1H-1,2,3-triazole-4-carbonyl)-5-(5-fluoropyridin-3-yl)-1,2,3,4-tetrahydroisoquinoline-1-carboxamido)benzoic acid, TFA salt | $^1$H NMR (400 MHz, DMSO-$d_6$) δ 10.94 (s, 1H), 9.18-9.07 (m, 1H), 8.56 (d, J = 2.6 Hz, 1H), 8.42 (s, 1H), 7.89-7.77 (m, 5H), 7.77-7.67 (m, 3H), 7.48-7.36 (m, 2H), 7.31-7.26 (m, 1H), 5.98 (s, 1H), 4.42-4.32 (m, 1H), 4.17 (ddd, J = 12.7, 8.0, 4.4 Hz, 1H), 3.06-2.88 (m, 2H), ppm. MS (ESI) m/z: 615 (M + H)$^+$. Analytical HPLC: RT = 7.37 min (Method B). |

TABLE 3-continued

| Example | R | Name | Analytical Data |
|---|---|---|---|
| 36 | (3-methoxypyridin-5-yl) | 4-(2-(1-(3-chloro-2-fluorophenyl)-1H-1,2,3-triazole-4-carbonyl)-5-(5-methoxypyridin-3-yl)-1,2,3,4-tetrahydroisoquinoline-1-carboxamido)benzoic acid, TFA salt | $^1$H NMR (400 MHz, DMSO-$d_6$) δ 11.00 (s, 1H), 9.16 (d, J = 1.8 Hz, 1H), 8.37 (d, J = 2.4 Hz, 1H), 8.22 (s, 1H), 7.94-7.83 (m, 4H), 7.80-7.74 (m, 2H), 7.55-7.42 (m, 3H), 7.34 (d, J = 6.6 Hz, 1H), 6.04 (s, 1H), 4.47-4.40 (m, 1H), 4.20 (ddd, J = 12.7, 8.1, 4.3 Hz, 1H), 3.90 (s, 3H), 3.14-3.04 (m, 1H), 3.04-2.94 (m, 1H) ppm. MS (ESI) m/z: 627 (M + H)$^+$. Analytical HPLC: RT = 6.63 min (Method B). |
| 37 | (5-(methylcarbamoyl)pyridin-3-yl) | 4-(2-(1-(3-chloro-2-fluorophenyl)-1H-1,2,3-triazole-4-carbonyl)-5-(5-(methylcarbamoyl)pyridin-3-yl)-1,2,3,4-tetrahydroisoquinoline-1-carboxamido)benzoic acid, TFA salt | $^1$H NMR (400 MHz, DMSO-$d_6$) δ 10.94 (s, 1H), 9.14-9.07 (m, 1H), 8.96 (s, 1H), 8.74-8.62 (m, 2H), 8.13 (t, J = 2.0 Hz, 1H), 7.87-7.65 (m, 7H), 7.48-7.38 (m, 2H), 7.30 (d, J = 6.8 Hz, 1H), 5.97 (s, 1H), 5.95-5.94 (m, 1H), 4.44-4.34 (m, 1H), 4.08 (ddd, J = 12.7, 8.5, 4.0 Hz, 1H), 3.15-3.03 (m, 1H), 2.96-2.84 (m, 1H), 2.76 (d, J = 4.4 Hz, 3H) ppm. MS (ESI) m/z: 654 (M + H)$^+$. Analytical HPLC: RT = 6.20 min (Method B). |
| 38 | (2-aminopyridin-4-yl) | 4-(5-(2-aminopyridin-4-yl)-2-(1-(3-chloro-2-fluorophenyl)-1H-1,2,3-triazole-4-carbonyl)-1,2,3,4-tetrahydroisoquinoline-1-carboxamido)benzoic acid, bis-TFA salt | $^1$H NMR (400 MHz, DMSO-$d_6$) δ 10.93 (s, 1H), 9.11 (d, J = 1.8 Hz, 1H), 7.95 (d, J = 6.6 Hz, 1H), 7.86-7.79 (m, 6H), 7.68 (d, J = 8.8 Hz, 2H), 7.47-7.40 (m, 2H), 7.29 (d, J = 7.1 Hz, 1H), 6.87-6.82 (m, 2H), 5.96 (s, 1H), 4.48-4.39 (m, 1H), 4.10 (ddd, J = 12.8, 8.7, 4.0 Hz, 1H) 3.17-3.08 (m, 1H), 3.00-2.89 (m, 1H) ppm. MS (ESI) m/z: 612 (M + H)$^+$. Analytical HPLC: RT = 5.61 min (Method B). |
| 39 | (6-aminopyridin-3-yl) | 4-(5-(6-aminopyridin-3-yl)-2-(1-(3-chloro-2-fluorophenyl)-1H-1,2,3-triazole-4-carbonyl)-1,2,3,4-tetrahydroisoquinoline-1-carboxamido)benzoic acid, bis-TFA salt | $^1$H NMR (400 MHz, DMSO-$d_6$) δ 10.91 (s, 1H), 9.10 (d, J = 1.8 Hz, 1H), 7.95-7.90 (m, 2H), 7.86-7.79 (m, 4H), 7.72-7.61 (m, 3H), 7.44 (td, J = 8.2, 1.5 Hz, 1H), 7.36 (t, J = 7.7 Hz, 1H), 7.24 (d, J = 7.1 Hz, 1H), 6.96 (d, J = 9.1 Hz, 1H), 5.95 (s, 1H), 4.45-4.36 (m, 1H), 4.14 (ddd, J = 12.6, 8.1, 4.3 Hz, 1H), 3.12-3.02 (m, 1H), 2.98-2.88 (m, 1H) ppm. MS (ESI) m/z: 612 (M + H)$^+$. Analytical HPLC: RT = 5.62 min (Method B). |
| 40 | (tetrahydroisoquinolin-6-yl) | 4-(2-(1-(3-chloro-2-fluorophenyl)-1H-1,2,3-triazole-4-carbonyl)-1,1',2,2',3,3',4,4'-octahydro-[5,6'-biisoquinoline]-1-carboxamido)benzoic acid, TFA salt | $^1$H NMR (500 MHz, DMSO-$d_6$) δ 10.99 (s, 1H), 9.18 (d, J = 1.7 Hz, 1H), 7.95-7.86 (m, 4H), 7.76 (d, J = 8.5 Hz, 3H), 7.51 (td, J = 8.3, 1.4 Hz, 1H), 7.41 (t, J = 7.7 Hz, 1H), 7.36-7.31 (m, 1H), 7.30-7.24 (m, 3H), 6.02 (s, 1H), 4.50 (dt, J = 12.9, 5.0 Hz, 1H), 4.35 (s, 2H), 4.11 (ddd, J = 12.7, 8.9, 4.0 Hz, 1H), 3.44 (t, J = 6.3 Hz, 2H), 3.20-3.05 (m, 3H), 2.96 (dt, J = 15.9, 4.7 Hz, 1H) ppm. MS (ESI) m/z: 651 (M + H)$^+$. Analytical HPLC: RT = 5.83 min (Method B). |
| 41 | (1H-pyrazol-4-yl) | 4-(2-(1-(3-chloro-2-fluorophenyl)-1H-1,2,3-triazole-4-carbonyl)-5-(1H-pyrazol-4-yl)-1,2,3,4-tetrahydroisoquinoline-1-carboxamido)benzoic acid | $^1$H NMR (500 MHz, DMSO-$d_6$) δ 10.95 (s, 1H), 9.17 (d, J = 1.7 Hz, 1H), 7 92-7.84 (m, 6H), 7.78-7.74 (m, 2H), 7.63-7.60 (m, 1H), 7.52 (td, J = 8.2, 1.5 Hz, 1H), 7.40-7.37 (m, 1H), 7.35-7.30 (m, 1H), 5.97 (s, 1H), 4.55-4.48 (m, 1H), 4.16 (ddd, J = 12.7, 8.2, 4.4 Hz, 1H), 3.27-3.20 (m, 1H), 3.15 (dt, J = 16.2, 5.2 Hz, 1H) ppm. MS (ESI) m/z: 586 (M + H)$^+$. Analytical HPLC: RT = 6.59 min (Method B). |
| 42 | (1-methyl-1H-pyrazol-5-yl) | 4-(2-(1-(3-chloro-2-fluorophenyl)-1H-1,2,3-triazole-4-carbonyl)-5-(1-methyl-1H-pyrazol-5-yl)-1,2,3,4-tetrahydroisoquinoline-1-carboxamido)benzoic acid | $^1$H NMR (500 MHz, DMSO-$d_6$) δ 12.74 (br. s., 1H), 11.01 (s, 1H), 9.17 (d, J = 1.7 Hz, 1H), 7.93-7.86 (m, 4H), 7.83 (d, J = 7.7 Hz, 1H), 7.76 (d, J = 8.8 Hz, 2H), 7.54-7.49 (m, 2H), 7.45 (t, J = 7.7 Hz, 1H), 7.34 (d, J = 7.7 Hz, 1H), 6.35 (d, J = 1.9 Hz, 1H), 6.03 (s, 1H), 4.50-4.43 (m, 1H), 4.17 (dt, J = 8.2, 4.3 Hz, 1H), 3.64 (s, 3H), 3.06-2.99 (m, 1H), 2.80-2.74 (m, 1H) ppm. MS (ESI) m/z: 600 (M + H)$^+$. Analytical HPLC: RT = 7.01 min (Method B). |
| 43 | (1-methyl-1H-pyrazol-3-yl) | 4-(2-(1-(3-chloro-2-fluorophenyl)-1H-1,2,3-triazole-4-carbonyl)-5-(1-methyl-1H-pyrazol-3-yl)-1,2,3,4-tetrahydroisoquinoline-1-carboxamido)benzoic acid | $^1$H NMR (400 MHz, DMSO-$d_6$) δ 10.86 (s, 1H), 9.09 (d, J = 1.8 Hz, 1H), 7.85-7.77 (m, 4H), 7.72-7.65 (m, 3H), 7.61 (d, J = 7.3 Hz, 1H), 7.46-7.42 (m, 2H), 7.27 (t, J = 7.6 Hz, 1H), 6.43 (d, J = 2.0 Hz, 1H), 5.90 (s, 1H), 4.49-4.40 (m, 1H), 4.02 (ddd, J = 12.6, 8.5, 4.2 Hz, 1H) 3.84 (s, 3H), 3.54 (br. s., 1H), 3.31-3.24 (m, 1H). MS (ESI) m/z: 600 (M + H)$^+$. Analytical HPLC: RT = 6.72 min (Method B). |

143

EXAMPLE 44

(S)-4-(2-(1-(3-Chloro-2-fluorophenyl)-1H-1,2,3-triazole-4-carbonyl)-5-(6-(methylcarbamoyl)pyridin-3-yl)-1,2,3,4-tetrahydroisoquinoline-1-carboxamido)benzoic acid, TFA salt

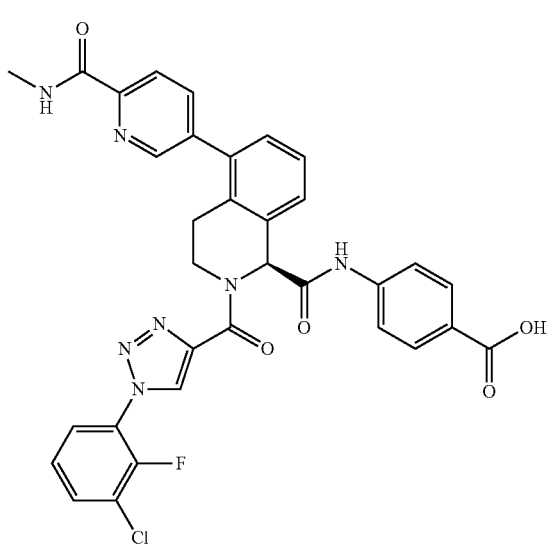 [SMILES: CNC(=O)c1ccc(-c2cccc3c2CCN(C(=O)c2cn(-c4cccc(Cl)c4F)nn2)[C@@H]3C(=O)Nc2ccc(C(=O)O)cc2)cn1]

144

EXAMPLE 45

(R)-4-(2-(1-(3-Chloro-2-fluorophenyl)-1H-1,2,3-triazole-4-carbonyl)-5-(6-(methylcarbamoyl)pyridin-3-yl)-1,2,3,4-tetrahydroisoquinoline-1-carboxamido)benzoic acid, TFA salt

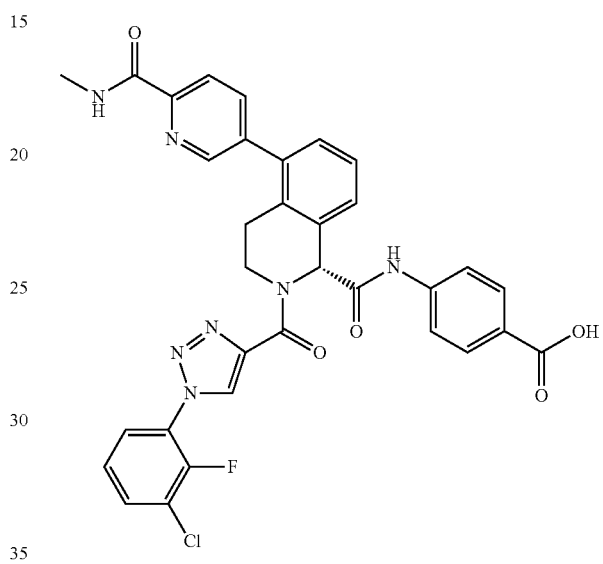

Example 44. (S)-4-(2-(1-(3-Chloro-2-fluorophenyl)-1H-1,2,3-triazole-4-carbonyl)-5-(6-(methylcarbamoyl)pyridin-3-yl)-1,2,3,4-tetrahydroisoquinoline-1-carboxamido)benzoic acid, TFA salt: Example 45 was made in a similar manner as Example 12 utilizing N-methyl-5-(4,4,5,5-tetramethyl-1,3,2-dioxaborolan-2-yl)picolinamide in the Suzuki reaction. The compound was isolated as the first eluting enantiomer after chiral purification using CHIRALCEL® OD-H column, 21×250 mm, using 35% 2:1 EtOH:ACN/65% $CO_2$ at 70.0 mL/min, 100 bar, and 35° C. followed by deprotection, reverse phase prep. HPLC, and lyophilization to give a white solid. $^1$H NMR (400 MHz, DMSO-$d_6$) δ 10.94 (s, 1H), 9.09 (d, J=1.8 Hz, 1H), 8.76 (q, J=4.7 Hz, 1H), 8.58 (dd, J=2.2, 0.7 Hz, 1H), 8.07-8.02 (m, 1H), 7.97 (dd, J=8.1, 2.2 Hz, 1H), 7.87-7.63 (m, 7H), 7.46-7.37 (m, 2H), 7.31 (d, J=6.8 Hz, 1H), 5.97 (s, 1H), 4.46-4.35 (m, 1H), 4.11 (ddd, J=12.5, 8.3, 4.1 Hz, 1H), 3.07-2.99 (m, 1H), 2.96-2.87 (m, 1H), 2.78 (d, J=4.8 Hz, 3H) ppm. MS (ESI) m/z: 654 (M+H)$^+$. Analytical HPLC: RT=7.58 min (Method A).

Example 45. (R)-4-(2-(1-(3-Chloro-2-fluorophenyl)-1H-1,2,3-triazole-4-carbonyl)-5-(6-(methylcarbamoyl)pyridin-3-yl)-1,2,3,4-tetrahydroisoquinoline-1-carboxamido)benzoic acid, TFA salt: The title compound was made in a similar manner as Example 12 utilizing N-methyl-5-(4,4,5,5-tetramethyl-1,3,2-dioxaborolan-2-yl)picolinamide in the Suzuki reaction. The compound was isolated at the second eluting enantiomer after chiral purification using CHIRALCEL® OD-H column, 21×250 mm, using 35% 2:1 EtOH:ACN/65% $CO_2$ at 70.0 mL/min, 100 bar, and 35° C. followed by deprotection, reverse phase prep. HPLC, and lyophilization to give a white solid. $^1$H NMR (400 MHz, DMSO-$d_6$) δ 10.94 (s, 1H), 9.11-9.03 (m, 1H), 8.76 (q, J=4.8 Hz, 1H), 8.58 (d, J=1.5 Hz, 1H), 8.08-8.02 (m, 1H), 7.97 (dd, J=8.0, 2.1 Hz, 1H), 7.87-7.64 (m, 7H), 7.47-7.37 (m, 2H), 7.35-7.27 (m, 1H), 5.97 (s, 1H), 4.43-4.33 (m, 1H), 4.11 (ddd, J=12.7, 8.3, 4.2 Hz, 1H), 3.09-3.00 (m, 1H), 2.96-2.86 (m, 1H), 2.78 (d, J=4.8 Hz, 3H) ppm. MS (ESI) m/z: 654 (M+H)$^+$. Analytical HPLC: RT=7.59 min (Method A).

EXAMPLE 46

4-(2-(5-Amino-1-(3-chloro-2-fluorophenyl)-1H-pyrazole-4-carbonyl)-5-(pyrimidin-5-yl)-1,2,3,4-tetrahydroisoquinoline-1-carboxamido)benzoic acid, TFA salt

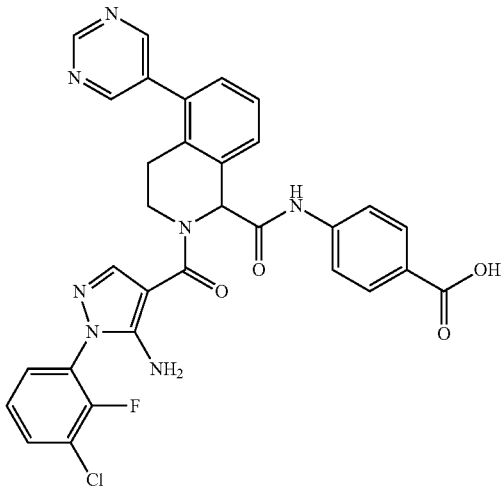 [SMILES: Nc1c(C(=O)N2CCc3c(-c4cncnc4)cccc3C2C(=O)Nc2ccc(C(=O)O)cc2)cnn1-c1cccc(Cl)c1F]

Example 46. 4-(2-(5-Amino-1-(3-chloro-2-fluorophenyl)-1H-pyrazole-4-carbonyl)-5-(pyrimidin-5-yl)-1,2,3,4-tetrahydroisoquinoline-1-carboxamido)benzoic acid, TFA salt: The title compound was made in a similar manner as Example 6 utilizing pyrimidin-5-ylboronic acid in the Suzuki reaction and replacing Intermediate 9 with Intermediate 16 in the amide coupling step. $^1$H NMR (500 MHz, DMSO-d$_6$) δ 10.81 (s, 1H), 9.26 (s, 1H), 8.91 (s, 2H), 7.93-7.85 (m, 4H), 7.78-7.71 (m, 3H), 7.53-7.45 (m, 2H), 7.43-7.36 (m, 2H), 6.60 (br. s., 2H), 5.88 (s, 1H), 4.31-4.22 (m, 1H), 3.90-3.82 (m, 1H), 3.28 (t, J=9.8 Hz, 1H), 2.95 (dt, J=15.3, 4.2 Hz, 1H) ppm. MS (ESI) m/z: 612 (M+H)$^+$. Analytical HPLC: RT=6.13 min (Method B).

EXAMPLE 47

4-(2-(5-Amino-1-(3-chloro-2-fluorophenyl)-1H-pyrazole-4-carbonyl)-5-(6-(methylcarbamoyl)pyridin-3-yl)-1,2,3,4-tetrahydroisoquinoline-1-carboxamido)benzoic acid, TFA salt

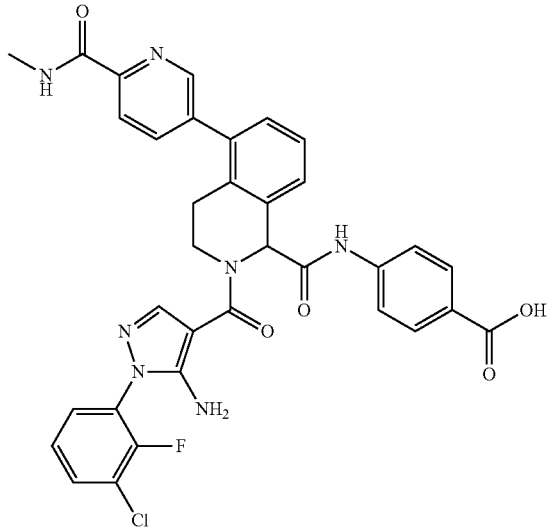 [SMILES: CNC(=O)c1ccc(-c2cccc3c2CCN(C(=O)c2cnn(-c4cccc(Cl)c4F)c2N)C3C(=O)Nc2ccc(C(=O)O)cc2)cn1]

Example 47. 4-(2-(5-Amino-1-(3-chloro-2-fluorophenyl)-1H-pyrazole-4-carbonyl)-5-(6-(methylcarbamoyl)pyridin-3-yl)-1,2,3,4-tetrahydroisoquinoline-1-carboxamido) benzoic acid, TFA salt: title compound was made in a similar manner as Example 6 utilizing N-methyl-5-(4,4,5,5-tetramethyl-1,3,2-dioxaborolan-2-yl)picolinamide in the Suzuki reaction and replacing Intermediate 9 with Intermediate 16 in the coupling step. $^1$H NMR (500 MHz, DMSO-d$_6$) δ 10.80 (s, 1H), 8.84 (q, J=4.7 Hz, 1H), 8.65 (dd, J=2.2, 0.5 Hz, 1H), 8.13 (dd, J=8.0, 0.6 Hz, 1H), 8.03 (dd, J=8.0, 2.2 Hz, 1H), 7.94-7.88 (m, 2H), 7.88-7.84 (m, 2H), 7.78-7.73 (m, 3H), 7.53-7.44 (m, 2H), 7.42-7.37 (m, 2H), 6.61 (br. s., 1H), 5.87 (s, 1H), 4.31-4.23 (m, 1H), 3.85-3.76 (m, 1H), 3.31 (t, J=10.3 Hz, 1H), 2.92 (dt, J=15.5, 4.1 Hz, 1H), 2.87 (d, J=5.0 Hz, 3H) ppm. MS (ESI) m/z: 668 (M+H)$^+$. Analytical HPLC: RT=6.56 min (Method B).

The following Examples in Table 4 were prepared in a similar manner as Example 1 utilizing the multi-component Ugi reaction consisting of the appropriate substituted imines (Intermediates 4, 4C-4T, 5, 5B, or 5C), substituted heterocyclic carboxylic acid (Intermediates 8-17 or 19-23), and isonitriles (Intermediates 1 or 2). Chiral separation was carried out using chiral HPLC on late stage intermediates followed by deprotection and purification where indicated.

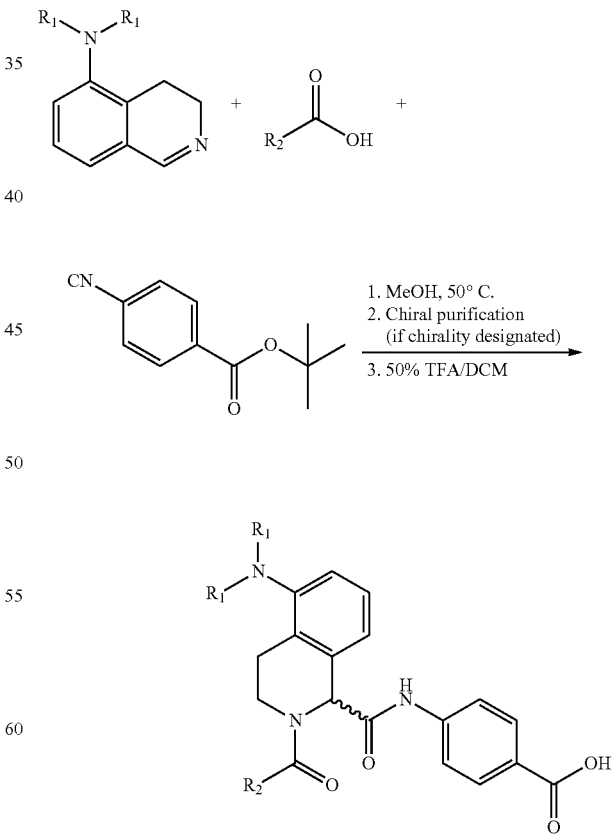

Example 48-87

TABLE 4

| Example | Structure | Name | Analytical Data |
|---|---|---|---|
| 48 | 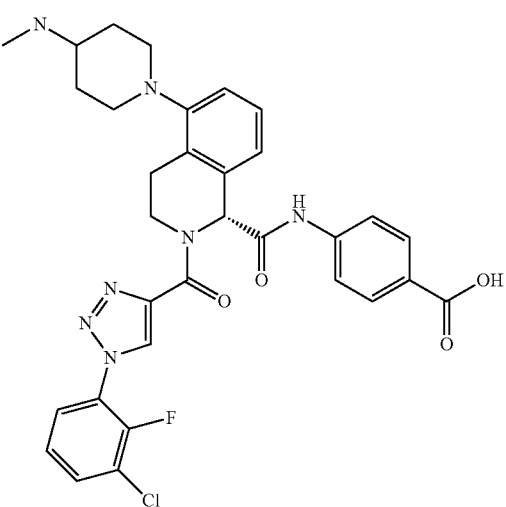<br>R-Enantiomer[a] | (R)-4-(2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamido)benzoic acid, bis-TFA salt | $^1$H NMR (500 MHz, methanol-$d_4$) δ 8.92 (d, J = 2.2 Hz, 1H), 8.02-7.96 (m, 2H), 7.89 (ddd, J = 8.1, 6.6, 1.5 Hz, 1H), 7.78-7.67 (m, 3H), 7.48 (td, J = 8.2, 1.5 Hz, 1H), 7.40-7.36 (m, 1H), 7.32 (t, J = 7.8 Hz, 1H), 7.13 (d, J = 8.0 Hz, 1H), 5.91 (s, 1H), 4.75 (dt, J = 12.7, 4.8 Hz, 1H), 4.13 (ddd, J = 12.8, 8.5, 4.5 Hz, 1H), 3.38-3.36 (m, 1H), 3.30-3.20 (m, 3H), 2.97 (s, 7H), 2.94-2.89 (m, 1H), 2.80-2.73 (m, 1H), 2.27-2.17 (m, 2H), 2.06-1.93 (m, 2H) ppm. MS (ESI) m/z: 646 (M + H)$^+$.<br>Analytical HPLC: RT = 5.40 min (Method B). |
| 49 | 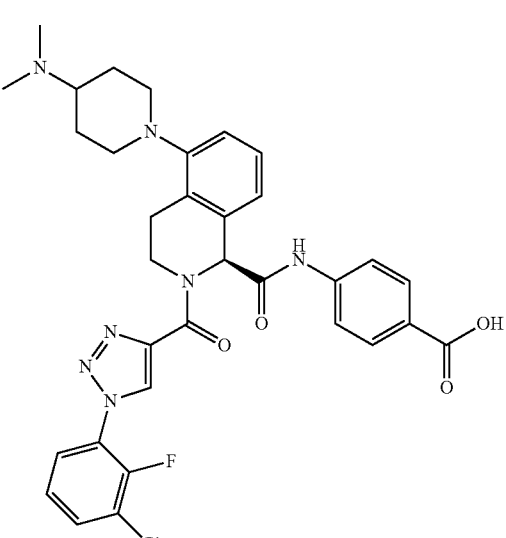<br>S-Enantiomer[a] | (S)-4-(2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamido)benzoic acid, bis-TFA salt | $^1$H NMR (500 MHz, DMSO-$d_6$) δ 10.92 (s, 1H), 9.23-9.10 (m, 1H), 7.94-7.84 (m, 4H), 7.76-7.65 (m, 2H), 7.55-7.48 (m, 1H), 7.42 (d, J = 7.7 Hz, 1H), 7.31-7.25 (m, 1H), 7.04 (d, J = 8.0 Hz, 1H), 5.89 (s, 1H), 4.57 (dt, J = 12.5, 5.0 Hz, 1H), 4.09 (ddd, J = 12.7, 8.7, 4.3 Hz, 1H), 3.35-3.23 (m, 2H), 3.21-3.13 (m, 2H), 3.10-3.04 (m, 1H), 2.85-2.80 (m, 6H), 2.76-2.71 (m, 1H), 2.68-2.62 (m, 1H), 2.12-2.06 (m, 2H), 1.88-1.77 (m, 2H) ppm. MS (ESI) m/z: 646 (M + H)$^+$.<br>Analytical HPLC: RT = 5.39 min (Method B). |

TABLE 4-continued

| Example | Structure | Name | Analytical Data |
|---|---|---|---|
| 50 | 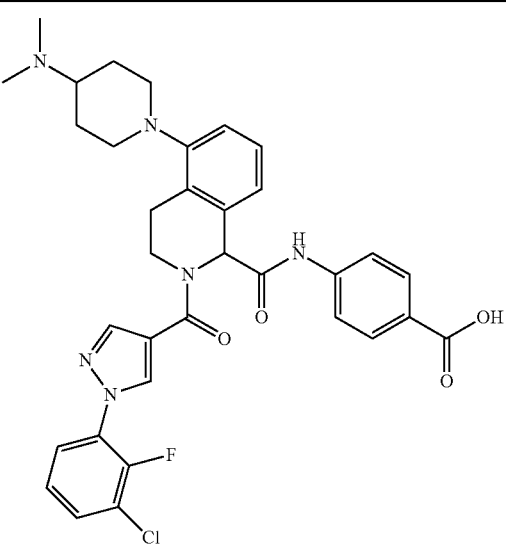 Racemate | 4-(2-(1-(3-chloro-2-fluorophenyl)-1H-pyrazole-4-carbonyl)-5-(4-(dimethylamino)piperidin-1-yl)-1,2,3,4-tetrahydroisoquinoline-1-carboxamido)benzoic acid, bis-TFA salt | $^1$H NMR (500 MHz, DMSO-$d_6$) δ 10.82 (s, 1H), 9.59 (br. s., 1H), 8.73 (d, J = 1.7 Hz, 1H), 8.22 (s, 1H), 7.89 (d, J = 8.5 Hz, 2H), 7.82 (t, J = 6.9 Hz, 1H), 7.74-7.68 (m, 3H), 7.44 (dt, J = 7.5, 3.8 Hz, 2H), 7.27 (t, J = 7.8 Hz, 1H), 7.04 (d, J = 8.3 Hz, 1H), 5.80 (s, 1H), 4.31-4.23 (m, 1H), 3.82-3.75 (m, 1H), 3.35-3.27 (m, 1H), 3.24-3.07 (m, 4H), 2.86-2.77 (m, 7H), 2.68-2.53 (m, 2H), 2.09 (t, J = 14.3 Hz, 2H), 1.84-1.76 (m, 1H) ppm. MS (ESI) m/z: 645 (M + H)$^+$. Analytical HPLC: RT = 5.25 min (Method B). |
| 51 | 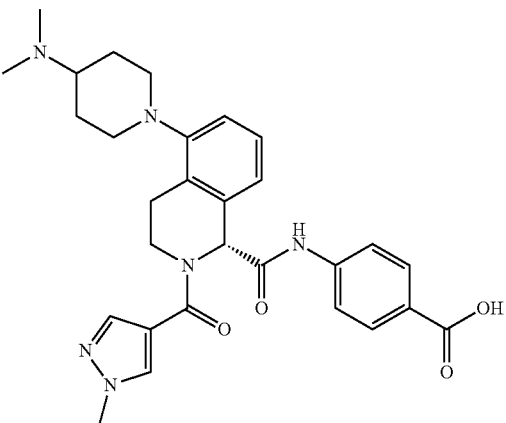 R-Enantiomer[b] | (R)-4-(2-(1-(3-chloro-2-fluorophenyl)-1H-pyrazole-4-carbonyl)-5-(4-(dimethylamino)piperidin-1-yl)-1,2,3,4-tetrahydroisoquinoline-1-carboxamido)benzoic acid, bis-TFA salt | $^1$H NMR (400 MHz, DMSO-$d_6$) δ 10.74 (s, 1H), 8.65 (s, 1H), 8.15 (s, 1H), 7.81 (d, J = 8.8 Hz, 2H), 7.74 (t, J = 6.9 Hz, 1H), 7.64 (d, J = 8.6 Hz, 3H), 7.41-7.33 (m, 2H), 7.19 (t, J = 7.7 Hz, 1H), 6.96 (d, J = 8.1 Hz, 1H), 5.72 (s, 1H), 4.27-4.14 (m, 1H), 3.72 (d, J = 9.6 Hz, 1H), 3.27-3.02 (m, 5H), 2.78-2.70 (m, 7H), 2.54-2.47 (m, 1H), 2.01 (t, J = 12.5 Hz, 2H), 1.81-1.66 (m, 2H) ppm. MS (ESI) m/z: 645 (M + H)$^+$. Analytical HPLC: RT = 5.46 min (Method B). |

| Example | Structure | Name | Analytical Data |
|---|---|---|---|
| 52 | 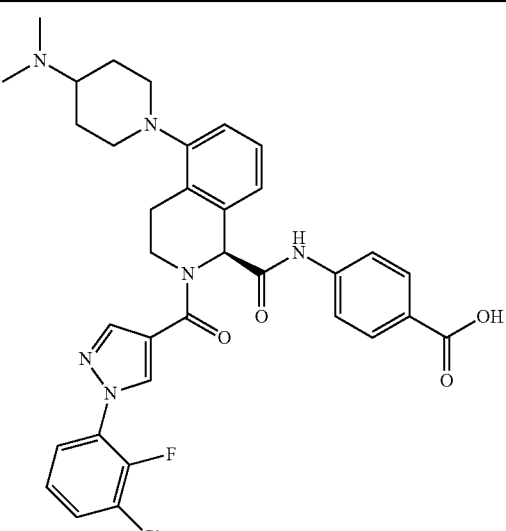<br>S-Enantiomer[b] | (S)-4-(2-(1-(3-chloro-2-fluorophenyl)-1H-pyrazole-4-carbonyl)-5-(4-(dimethylamino)piperidin-1-yl)-1,2,3,4-tetrahydroisoquinoline-1-carboxamido)benzoic acid, bis-TFA salt | $^1$H NMR (500 MHz, DMSO-$d_6$) δ 10.83 (s, 1H), 8.73 (d, J = 1.9 Hz, 1H), 8.23 (s, 1H), 7.89 (d, J = 8.8 Hz, 2H), 7.85-7.79 (m, 1H), 7.72 (d, J = 8.8 Hz, 3H), 7.47-7.41 (m, 2H), 7.27 (t, J = 7.8 Hz, 1H), 7.04 (d, J = 7.7 Hz, 1H), 5.80 (s, 1H), 4.33-4.23 (m, 1H), 3.84-3.74 (m, 1H), 3.37-3.27 (m, 1H), 3.23-3.06 (m, 4H), 2.83-2.79 (m, 7H), 2.63-2.53 (m, 1H), 2.09 (t, J = 14.9 Hz, 2H), 1.89-1.72 (m, 2H) ppm. MS (ESI) m/z: 645 (M + H)$^+$. Analytical HPLC: RT = 5.46 min (Method B). |
| 53 | 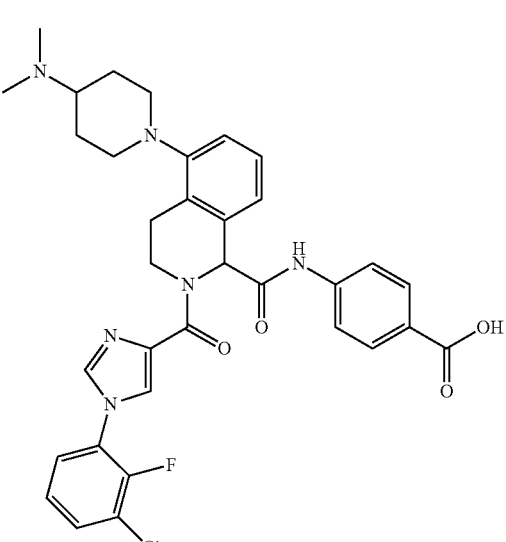<br>Racemate | 4-(2-(1-(3-chloro-2-fluorophenyl)-1H-imidazole-4-carbonyl)-5-(4-(dimethylamino)piperidin-1-yl)-1,2,3,4-tetrahydroisoquinoline-1-carboxamido)benzoic acid, bis-TFA salt | $^1$H NMR (500 MHz, DMSO-$d_6$) δ 10.60 (s, 1H), 9.18 (d, J = 1.7 Hz, 1H), 8.01-7.97 (m, 2H), 7.92-7.88 (m, 2H), 7.63-7.60 (m, 2H), 7.57-7.51 (m, 3H), 7.42 (d, J = 7.7 Hz, 1H), 7.28 (t, J = 7.8 Hz, 1H), 7.04 (d, J = 8.0 Hz, 1H), 5.90 (s, 1H), 4.56-4.51 (m, 1H), 4.17 (ddd, J = 12.4, 8.2, 4.1 Hz, 1H), 3.37-3.28 (m, 1H), 3.25 (d, J = 10.7 Hz, 1H), 3.21-3.14 (m, 2H), 3.10-3.02 (m, 1H), 2.84-2.80 (m, 6H), 2.75-2.64 (m, 2H), 2.09 (d, J = 9.6 Hz, 2H), 1.88-1.76 (m, 2H) ppm. MS (ESI) m/z: 645 (M + H)$^+$. Analytical HPLC: RT = 5.43 min (Method B). |

TABLE 4-continued

| Example | Structure | Name | Analytical Data |
|---|---|---|---|
| 54 | 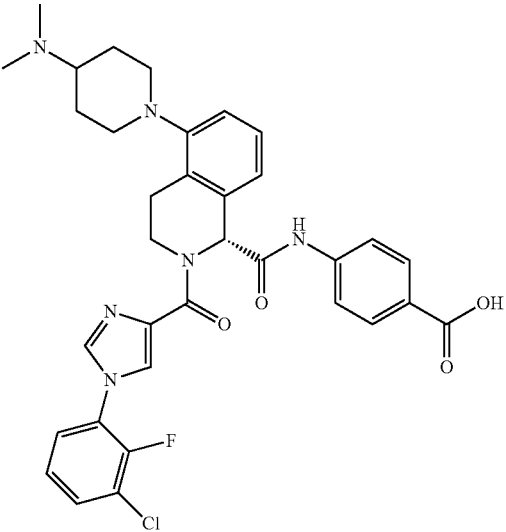 R-Enantiomer[b] | (R)-4-(2-(1-(3-chloro-2-fluorophenyl)-1H-imidazole-4-carbonyl)-5-(4-(dimethylamino)piperidin-1-yl)-1,2,3,4-tetrahydroisoquinoline-1-carboxamido)benzoic acid, bis-TFA salt | $^1$H NMR (400 MHz, DMSO-$d_6$) δ 10.80 (s, 1H), 8.20-8.08 (m, 2H), 7.82 (d, J = 8.8 Hz, 2H), 7.70-7.62 (m, 4H), 7.42-7.28 (m, 2H), 7.17 (t, J = 7.8 Hz, 1H), 6.94 (d, J = 7.8 Hz, 1H), 5.76 (s, 1H), 4.60-4.51 (m, 1H), 4.28-4.13 (m, 1H), 3.27-3.03 (m, 4H), 2.97-2.91 (m, 1H), 2.77-2.71 (m, 6H), 2.65-2.57 (m, 2H), 2.01 (d, J = 9.9 Hz, 2H), 1.80-1.72 (m, 2H) ppm. MS (ESI) m/z: 645 (M + H)$^+$. Analytical HPLC: RT = 5.60 min (Method B). |
| 55 | 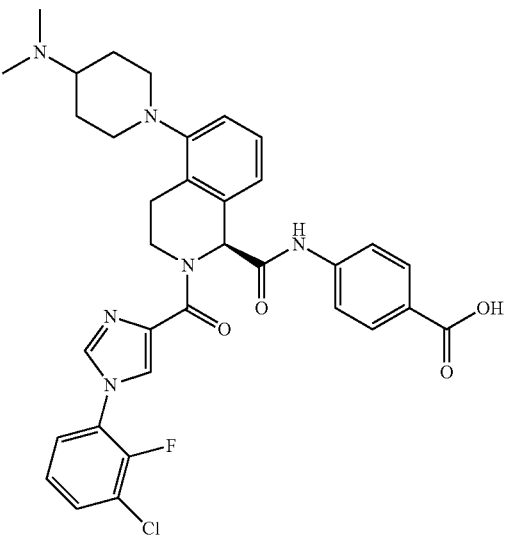 S-Enantiomer[b] | (S)-4-(2-(1-(3-chloro-2-fluorophenyl)-1H-imidazole-4-carbonyl)-5-(4-(dimethylamino)piperidin-1-yl)-1,2,3,4-tetrahydroisoquinoline-1-carboxamido)benzoic acid, bis-TFA salt | $^1$H NMR (400 MHz, DMSO-$d_6$) δ 10.80 (s, 1H), 8.19-8.08 (m, 2H), 7.82 (d, J = 8.6 Hz, 2H), 7.70-7.62 (m, 4H), 7.38-7.29 (m, 2H), 7.16 (d, J = 7.6 Hz, 1H), 6.94 (d, J = 7.8 Hz, 1H), 5.76 (s, 1H), 4.57-4.50 (m, 1H), 4.26-4.16 (m, 1H), 3.27-2.91 (m, 5H), 2.78-2.70 (m, 6H), 2.64-2.57 (m, 2H), 2.05-1.96 (m, 2H), 1.80-1.70 (m, 2H) ppm. MS (ESI) m/z: 645 (M + H)$^+$. Analytical HPLC: RT = 5.58 min (Method B). |

TABLE 4-continued

| Example | Structure | Name | Analytical Data |
|---|---|---|---|
| 56 | 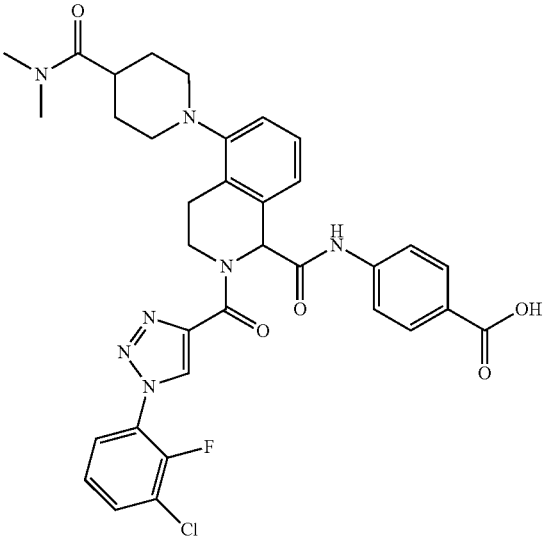 Racemate | 4-(2-(1-(3-chloro-2-fluorophenyl)-1H-1,2,3-triazole-4-carbonyl)-5-(4-(dimethylcarbamoyl)piperidin-1-yl)-1,2,3,4-tetrahydroisoquinoline-1-carboxamido)benzoic acid, TFA salt | $^1$H NMR (400 MHz, DMSO-$d_6$) δ 10.87 (s, 1H), 9.16 (d, J = 1.5 Hz, 1H), 7.93-7.85 (m, 4H), 7.73 (d, J = 8.8 Hz, 2H), 7.52 (t, J = 7.6 Hz, 1H), 7.40 (d, J = 7.8 Hz, 1H), 7.26 (t, J = 7.8 Hz, 1H), 7.02 (d, J = 7.8 Hz, 1H), 5.87 (s, 1H), 4.61-4.51 (m, 1H), 4.00 (t, J = 8.2 Hz, 1H), 3.16-3.01 (m, 8H), 2.87-2.74 (m, 5H), 1.82-1.70 (m, 4H) ppm. MS (ESI) m/z: 674 (M + H)$^+$. Analytical HPLC: RT = 6.73 min (Method B). |
| 57 | 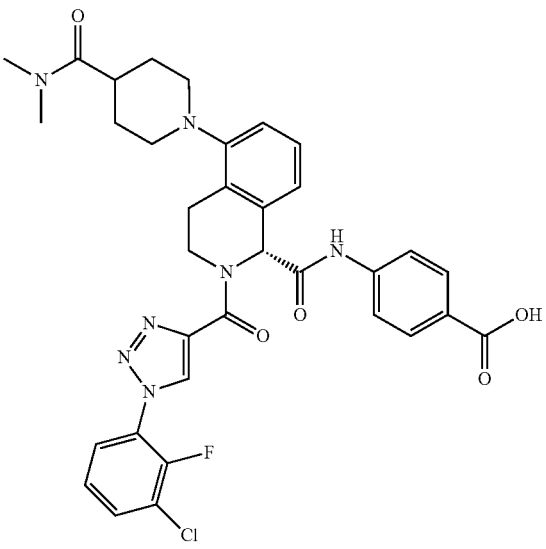 R-Enantiomer$^b$ | (R)-4-(2-(1-(3-chloro-2-fluorophenyl)-1H-1,2,3-triazole-4-carbonyl)-5-(4-(dimethylcarbamoyl)piperidin-1-yl)-1,2,3,4-tetrahydroisoquinoline-1-carboxamido)benzoic acid, TFA salt | $^1$H NMR (500 MHz, DMSO-$d_6$) δ 10.88 (s, 1H), 9.17 (d, J = 1.7 Hz, 1H), 7.93-7.86 (m, 4H), 7.73 (d, J = 8.8 Hz, 2H), 7.52 (td, J = 8.3, 1.4 Hz, 1H), 7.39 (d, J = 7.7 Hz, 1H), 7.26 (t, J = 7.8 Hz, 1H), 7.02 (d, J = 8.0 Hz, 1H), 5.87 (s, 1H), 4.55 (dt, J = 12.4, 4.8 Hz, 1H), 4.00 (ddd, J = 12.7, 8.8, 4.1 Hz, 1H), 3.15-3.05 (m, 7H), 2.84 (s, 3H), 2.80-2.72 (m, 2H), 2.68-2.62 (m, 1H), 1.83-1.70 (m, 4H) ppm. MS (ESI) m/z: 674 (M + H)$^+$. Analytical HPLC: RT = 6.82 min (Method B). |

TABLE 4-continued

| Example | Structure | Name | Analytical Data |
|---|---|---|---|
| 58 | 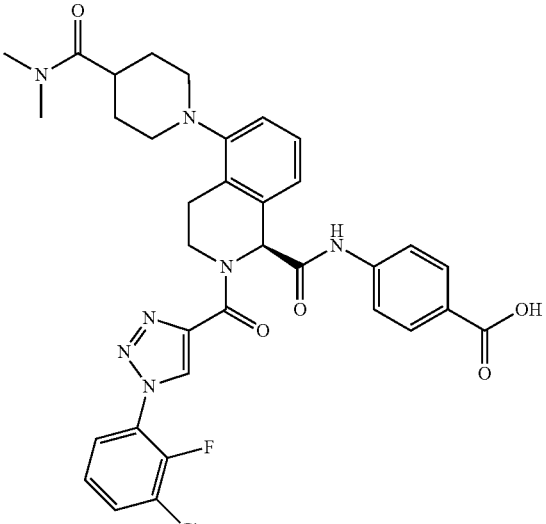 S-Enantiomer[b] | (S)-4-(2-(1-(3-chloro-2-fluorophenyl)-1H-1,2,3-triazole-4-carbonyl)-5-(4-(dimethylcarbamoyl)piperidin-1-yl)-1,2,3,4-tetrahydroisoquinoline-1-carboxamido)benzoic acid, TFA salt | $^1$H NMR (500 MHz, DMSO-$d_6$) δ 10.89 (s, 1H), 9.17 (d, J = 1.7 Hz, 1H), 7.93-7.85 (m, 4H), 7.77-7.71 (m, 2H), 7.52 (td, J = 8.1, 1.4 Hz, 1H), 7.40 (d, J = 7.7 Hz, 1H), 7.26 (t, J = 7.8 Hz, 1H), 7.02 (d, J = 8.0 Hz, 1H), 5.87 (s, 1H), 4.55 (dt, J = 12.6, 4.8 Hz, 1H), 4.00 (ddd, J = 12.6, 8.9, 4.1 Hz, 1H), 3.14-3.03 (m, 7H), 2.84 (s, 3H), 2.80-2.73 (m, 2H), 2.68-2.60 (m, 1H), 1.85-1.70 (m, 4H) ppm. MS (ESI) m/z: 674 (M + H)[+]. Analytical HPLC: RT = 6.87 min (Method B). |
| 59 | 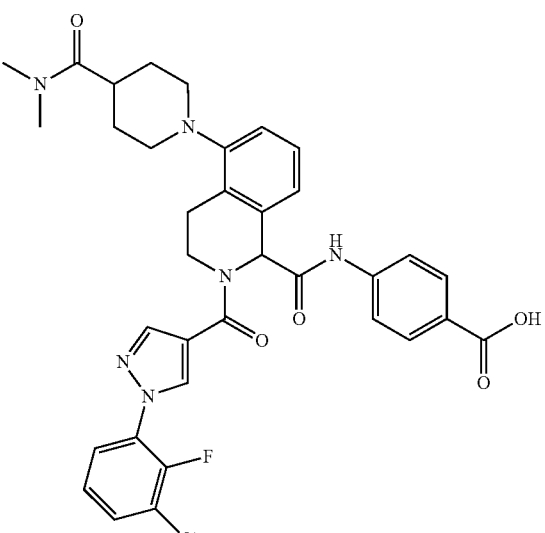 Racemate | 4-(2-(1-(3-chloro-2-fluorophenyl)-1H-pyrazole-4-carbonyl)-5-(4-(dimethylcarbamoyl)piperidin-1-yl)-1,2,3,4-tetrahydroisoquinoline-1-carboxamido)benzoic acid, TFA salt | $^1$H NMR (400 MHz, DMSO-$d_6$) δ 10.70 (s, 1H), 8.65 (s, 1H), 8.14 (s, 1H), 7.81 (d, J = 8.6 Hz, 2H), 7.75-7.71 (m, 1H), 7.64 (d, J = 8.6 Hz, 3H), 7.38-7.31 (m, 2H), 7.17 (t, J = 7.7 Hz, 1H), 6.93 (d, J = 8.1 Hz, 1H), 5.70 (s, 1H), 4.22-4.18 (m, 1H), 3.69 (d, J = 6.1 Hz, 1H), 3.15-2.87 (m, 8H), 2.78-2.66 (m, 5H), 1.75-1.61 (m, 4H). MS (ESI) m/z 673 (M + H)[+]. Analytical HPLC: RT = 6.78 min (Method B). |

TABLE 4-continued

| Example | Structure | Name | Analytical Data |
|---|---|---|---|
| 60 | 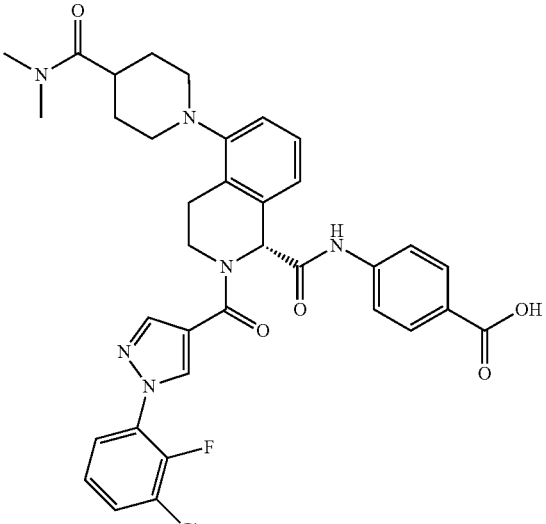<br>R-Enantiomer[b] | (R)-4-(2-(1-(3-chloro-2-fluorophenyl)-1H-pyrazole-4-carbonyl)-5-(4-(dimethylcarbamoyl)piperidin-1-yl)-1,2,3,4-tetrahydroisoquinoline-1-carboxamido)benzoic acid, TFA salt | $^1$H NMR (500 MHz, DMSO-$d_6$) δ 10.79 (s, 1H), 8.72 (d, J = 1.7 Hz, 1H), 8.22 (s, 1H), 7.88 (d, J = 8.8 Hz, 2H), 7.85-7.79 (m, 1H), 7.76-7.69 (m, 3H), 7.46-7.40 (m, 2H), 7.25 (t, J = 7.7 Hz, 1H), 7.01 (d, J = 8.0 Hz, 1H), 5.78 (s, 1H), 4.33-4.24 (m, 1H), 3.80-3.72 (m, 1H), 3.14-3.05 (m, 7H), 2.89-2.82 (m, 4H), 2.80-2.72 (m, 1H), 2.62-2.55 (m, 1H), 1.83-1.69 (m, 4H) ppm. MS (ESI) m/z: 673 (M + H)$^+$. Analytical HPLC: RT = 6.81 min (Method B). |
| 61 | 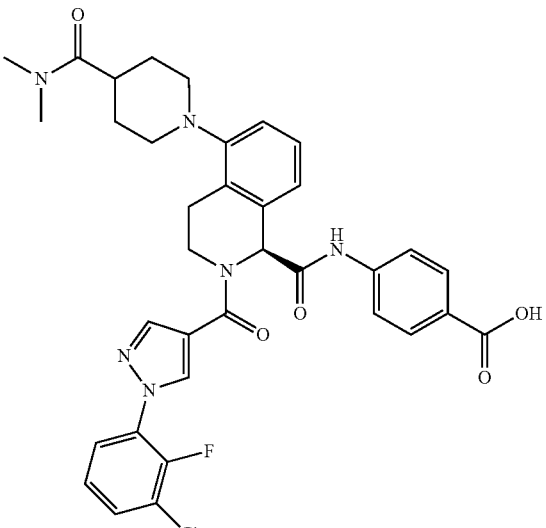<br>S-Enantiomer[b] | (S)-4-(2-(1-(3-chloro-2-fluorophenyl)-1H-pyrazole-4-carbonyl)-5-(4-(dimethylcarbamoyl)piperidin-1-yl)-1,2,3,4-tetrahydroisoquinoline-1-carboxamido)benzoic acid, TFA salt | $^1$H NMR (500 MHz, methanol-$d_4$) δ 8.48 (s, 1H), 8.06 (s, 1H), 7.85 (d, J = 8.8 Hz, 2H), 7.70 (t, J = 7.3 Hz, 1H), 7.57 (d, J = 7.7 Hz, 2H), 7.48 (t, J = 7.0 Hz, 1H), 7.29-7.22 (m, 2H), 7.19 (t, J = 7.8 Hz, 1H), 7.03 (d, J = 8.0 Hz, 1H), 5.69 (s, 1H), 4.32-4.25 (m, 1H), 3.70-3.63 (m, 1H), 3.17-3.12 (m, 4H), 3.06-3.04 (m, 3H), 2.91-2.85 (m, 4H), 2.79-2.74 (m, 1H), 2.67-2.61 (m, 1H), 1.94-1.72 (m, 4H) ppm. MS (ESI) m/z: 673 (M + H)$^+$. Analytical HPLC: RT = 6.76 min (Method B). |

TABLE 4-continued

| Example | Structure | Name | Analytical Data |
|---|---|---|---|
| 62 | 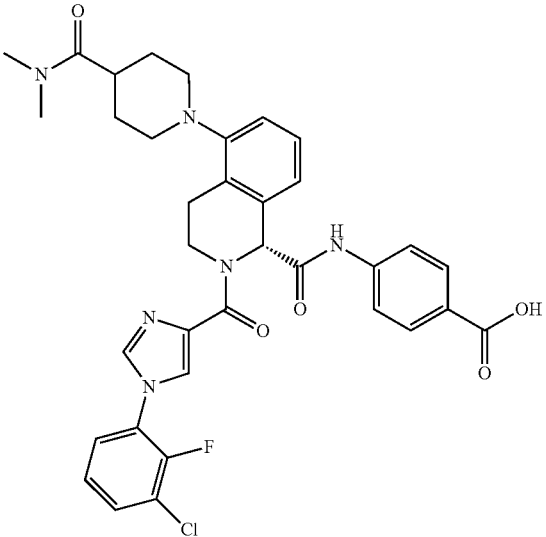<br>R-Enantiomer[b] | (R)-4-(2-(1-(3-chloro-2-fluorophenyl)-1H-imidazole-4-carbonyl)-5-(4-(dimethylcarbamoyl)piperidin-1-yl)-1,2,3,4-tetrahydroisoquinoline-1-carboxamido)benzoic acid, TFA salt | $^1$H NMR (400 MHz, methanol-$d_4$) δ 8.36 (br. s., 1H), 8.19-8.08 (m, 1H), 7.95 (d, J = 7.6 Hz, 2H), 7.75-7.62 (m, 4H), 7.40 (d, J = 7.3 Hz, 3H), 7.20 (d, J = 7.6 Hz, 1H), 5.85 (br. s., 1H), 4.64-4.54 (m, 1H), 4.33-4.23 (m, 1H), 4.09-3.97 (m, 1H), 3.84-3.74 (m, 1H), 3.43-3.33 (m, 2H), 3.27-3.23 (m, 1H), 3.15 (s, 3H), 3.11-3.05 (m, 1H), 2.96 (s, 3H), 2.92-2.84 (m, 1H), 2.06-1.86 (m, 4H), ppm. MS (ESI) m/z: 673 (M + H)$^+$. Analytical HPLC: RT = 6.66 min (Method B). |
| 63 | 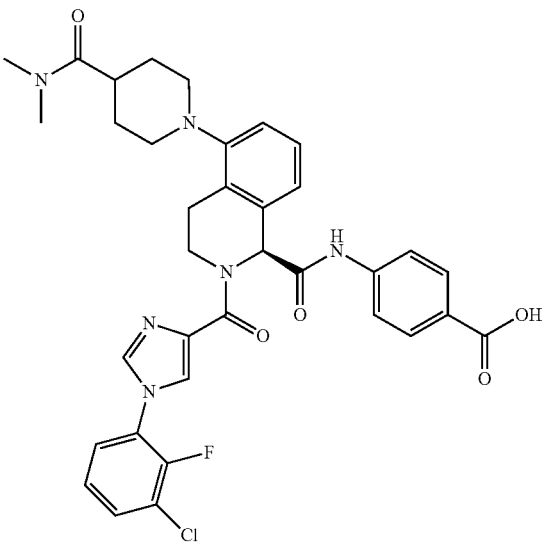<br>S-Enantiomer[b] | (S)-4-(2-(1-(3-chloro-2-fluorophenyl)-1H-imidazole-4-carbonyl)-5-(4-(dimethylcarbamoyl)piperidin-1-yl)-1,2,3,4-tetrahydroisoquinoline-1-carboxamido)benzoic acid, TFA salt | $^1$H NMR (500 MHz, methanol-$d_4$) δ 8.18 (br. s., 1H), 8.03-7.98 (m, 1H), 7.85 (d, J = 17.6 Hz, 2H), 7.64-7.46 (m, 4H), 7.30-7.18 (m, 3H), 7.06 (d, J = 7.7 Hz, 1H), 5.72 (br. s., 1H), 4.56-4.42 (m, 1H), 4.22-4.10 (m, 1H), 3.98-3.85 (m, 1H), 3.76-3.64 (m, 1H), 3.40-3.28 (m, 1H), 3.17-3.10 (m, 1H), 3.08-3.03 (m, 3H), 2.84 (s, 3H), 2.79-2.64 (m, 2H), 1.94-1.73 (m, 4H) ppm. MS (ESI) m/z: 673 (M + H)$^+$. Analytical HPLC: RT = 6.66 min (Method B). |

TABLE 4-continued

| Example | Structure | Name | Analytical Data |
|---|---|---|---|
| 64 | 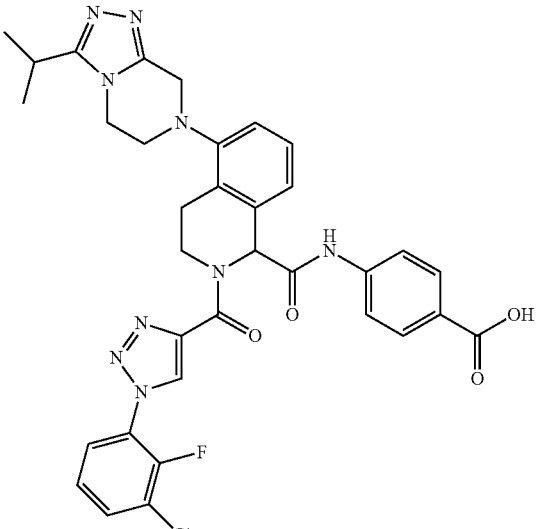 Racemate | 4-(2-(1-(3-chloro-2-fluorophenyl)-1H-1,2,3-triazole-4-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid, TFA salt | $^1$H NMR (400 MHz, DMSO-$d_6$) δ 10.87 (s, 1H), 9.10 (s, 1H), 7.86-7.78 (m, 4H), 7.67 (d, J = 8.6 Hz, 2H), 7.48-7.40 (m, 2H), 7.27 (t, J = 7.8 Hz, 1H), 7.12 (d, J = 8.1 Hz, 1H), 5.87 (s, 1H), 4.52-4.44 (m, 1H), 4.38-4.30 (m, 2H), 4.18-4.12 (m, 3H), 3.21-3.05 (m, 3H), 1.26 (d, J = 6.8 Hz, 6H) ppm. MS (ESI) m/z: 684 (M + H)$^+$. Analytical HPLC: RT = 6.23 min (Method B). |
| 65 | 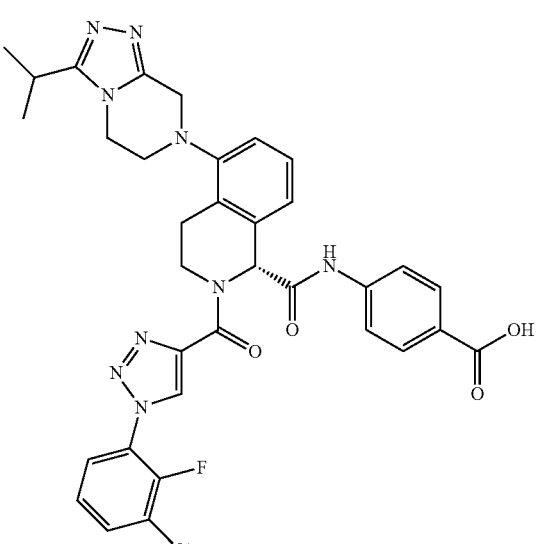 R-Enantiomer$^c$ | (R)-4-(2-(1-(3-chloro-2-fluorophenyl)-1H-1,2,3-triazole-4-carbonyl)-5-(3-isopropyl-5,6-dihydro-[1,2,4]triazolo[4,3-a]pyrazin-7(8H)-yl)-1,2,3,4-tetrahydroisoquinoline-1-carboximido)benzoic acid, TFA salt | $^1$H NMR (500 MHz, methanol-$d_4$) δ 10.63 (s, 1H), 8.91 (d, J = 1.9 Hz, 1H), 8.03-7.97 (m, 2H), 7.91-7.85 (m, 1H), 7.78-7.67 (m, 3H), 7.51-7.43 (m, 2H), 7.39 (t, J = 8.0 Hz, 1H), 7.24 (d, J = 7.7 Hz, 1H), 5.95 (s, 1H), 4.73 (d, J = 12.9 Hz, 1H), 4.54-4.44 (m, 2H), 4.40-4.16 (m, 4H), 3.62-3.50 (m, 2H), 3.31-3.22 (m, 2H), 1.47 (dd, J = 6.9, 3.0 Hz, 6H) ppm. MS (ESI) m/z: 684 (M + H)$^+$. Analytical HPLC: RT = 6.54 min (Method A). |

TABLE 4-continued

| Example | Structure | Name | Analytical Data |
|---|---|---|---|
| 66 | S-Enantiomer | (S)-4-(2-(1-(3-chloro-2-fluorophenyl)-1H-1,2,3-triazole-4-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid, TFA salt | $^1$H NMR (500 MHz, methanol-$d_4$) δ 10.62 (s, 1H), 8.91 (d, J = 2.2 Hz, 1H), 7.99 (d, J = 8.8 Hz, 2H), 7.90-7.85 (m, 1H), 7.78-7.67 (m, 3H), 7.50-7.36 (m, 3H), 7.24 (d, J = 8.0 Hz, 1H), 5.95 (s, 1H), 4.73 (d, J = 13.5 Hz, 1H), 4.53-4.41 (m, 2H), 4.37-4.26 (m, 2H), 4.24-4.14 (m, 1H), 3.63-3.48 (m, 2H), 3.31-3.19 (m, 2H), 1.47 (dd, J = 6.9, 3.3 Hz, 6H) ppm. MS (ESI) m/z: 684 (M + H)$^+$. Analytical HPLC: RT = 6.54 min (Method A). |
| 67 | Racemate | 4-(2-(1-(3-chloro-2-fluorophenyl)-1H-1,2,3-triazole-4-carbonyl)-5-(4-hydroxy-4-methylpiperidin-1-yl)-1,2,3,4-tetrahydroisoquinoline-1-carboxamido)benzoic acid, TFA salt | $^1$H NMR (500 MHz, DMSO-$d_6$) δ 10.89 (s, 1H), 9.17 (d, J = 1.7 Hz, 1H), 7.92-7.84 (m, 4H), 7.73 (d, J = 8.8 Hz, 2H), 7.52 (td, J = 8.2, 1.2 Hz, 1H), 7.38 (d, J = 6.9 Hz, 1H), 7.25 (t, J = 7.8 Hz, 1H), 7.08-7.03 (m, 1H), 5.87 (s, 1H), 4.53 (dt, J = 12.4, 4.8 Hz, 1H), 4.04-3.96 (m, 1H), 3.15-2.94 (m, 4H), 2.84-2.77 (m, 2H), 1.72-1.60 (m, 4H), 1.19 (s, 3H) ppm. MS (ESI) m/z: 633 (M + H)$^+$. Analytical HPLC: RT = 6.44 min (Method B). |

TABLE 4-continued

| Example | Structure | Name | Analytical Data |
|---|---|---|---|
| 68 | 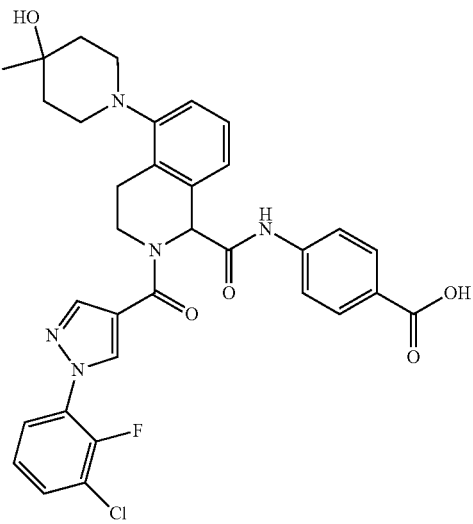<br>Racemate | 4-(2-(1-(3-chloro-2-fluorophenyl)-1H-pyrazole-4-carbonyl)-5-(4-hydroxy-4-methylpiperidin-1-yl)-1,2,3,4-tetrahydroisoquinoline-1-carboxamido)benzoic acid, TFA salt | $^1$H NMR (500 MHz, DMSO-$d_6$) δ 10.79 (s, 1H), 8.72 (d, J = 1.9 Hz, 1H), 8.22 (s, 1H), 7.89 (d, J = 8.8 Hz, 2H), 7.84-7.79 (m, 1H), 7.74-7.69 (m, 3H), 7.48-7.39 (m, 2H), 7.24 (t, J = 7.8 Hz, 1H), 7.10-7.03 (m, 1H), 5.78 (s, 1H), 4.30-4.23 (m, 1H), 3.81-3.72 (m, 1H), 3.14-3.00 (m, 3H), 2.89-2.73 (m, 3H), 1.72-1.58 (m, 4H), 1.19 (s, 3H) ppm. MS (ESI) m/z: 632 (M + H)$^+$. Analytical HPLC: RT = 6.46 min (Method B). |
| 69 | 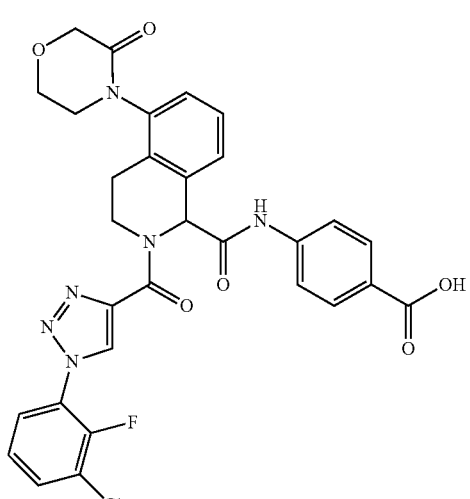<br>Racemate | 4-(2-(1-(3-chloro-2-fluorophenyl)-1H-1,2,3-triazole-4-carbonyl)-5-(3-oxomorpholino)-1,2,3,4-tetrahydroisoquinoline-1-carboxamido)benzoic acid | $^1$H NMR (400 MHz, DMSO-$d_6$) δ 12.65 (br. s., 1H), 11.06-10.85 (m, 1H), 9.10 (dd, J = 4.4, 1.6 Hz, 1H), 7.87-7.79 (m, 4H), 7.72-7.58 (m, 3H), 7.44 (t, J = 8.1 Hz, 1H), 7.36-7.31 (m, 1H), 7.26-7.22 (m, 1H), 6.02-5.90 (m, 1H), 4.47-4.36 (m, 1H), 4.31-4.09 (m, 3H), 3.93 (t, J = 5.1 Hz, 2H), 3.70 (dt, J = 12.9, 6.4 Hz, 1H), 3.52-3.41 (m, 1H), 2.93-2.86 (m, 1H), 2.86-2.74 (m, 1H) ppm. MS (ESI) m/z: 619 (M + H)$^+$. Analytical HPLC: RT = 6.13 min (Method B). |

TABLE 4-continued

| Example | Structure | Name | Analytical Data |
|---|---|---|---|
| 70 | Racemate | 4-(2-(1-(3-chloro-2-fluorophenyl)-1H-pyrazole-4-carbonyl)-5-(4-methyl-7-oxo-1,4-diazepan-1-yl)-1,2,3,4-tetrahydroisoquinoline-1-carboxamido)benzoic acid, TFA salt | $^1$H NMR (400 MHz, DMSO-$d_6$) δ 12.69 (br. s., 1H), 10.93-10.81 (m, 1H), 8.66 (d, J = 14.3 Hz, 1H), 8.13 (d, J = 3.3 Hz, 1H), 7.83 (d, J = 8.8 Hz, 1H), 7.76-7.57 (m, 4H), 7.41-7.15 (m, 3H), 5.84 (br. s, 1H), 4.26-4.10 (m, 2H), 3.92-3.73 (m, 2H), 3.62-3.47 (m, 3H), 3.44-3.32 (m, 2H), 3.22 (d, J = 13.7 Hz, 1H), 3.11-2.97 (m, 1H), 2.84 (br. s., 3H) ppm. MS (ESI) m/z: 645.4 (M + H)$^+$. Analytical HPLC: RT = 5.97 min (Method A). |
| 71 | Racemate | 4-(2-(1-(3-chloro-2,6-difluorophenyl)-5-oxopyrrolidine-3-carbonyl)-5-(4-methoxypiperidin-1-yl)-1,2,3,4-tetrahydroisoquinoline-1-carboxamido)benzoic acid, TFA salt | $^1$H NMR (400 MHz, methanol-$d_4$) δ: 7.96-7.83 (m, 2H), 7.54 (d, J = 8.6 Hz, 2H), 7.49-7.40 (m, 1H), 7.16 (d, J = 12.9 Hz, 2H), 7.08-6.96 (m, 2H), 5.65 (s, 1H), 4.16-3.90 (m, 4H), 3.38 (br. s., 2H), 3.34-3.27 (m, 3H), 3.28-3.25 (m, 1H), 3.15-2.93 (m, 3H), 2.85-2.72 (m, 2H), 2.68-2.57 (m, 2H), 2.08 (br. s., 2H), 1.77-1.56 (m, 2H) ppm. MS (ESI) m/z: 667.1 (M + H)$^+$. Analytical HPLC: RT = 6.55 min (Method A). |
| 72 | Racemate | 4-(2-(1-(3-chloro-2-fluorophenyl)-1H-1,2,3-triazole-4-carbonyl)-5-(4-(2-oxopyrrolidin-1-yl)piperidin-1-yl)-1,2,3,4-tetrahydroisoquinoline-1-carboxamido)benzoic acid, TFA salt | $^1$H NMR (400 MHz, methanol-$d_4$) δ: 8.78 (d, J = 2.3 Hz, 1H), 7.86 (d, J = 8.6 Hz, 2H), 7.81-7.71 (m, 1H), 7.69-7.50 (m, 3H), 7.41-7.29 (m, 1H), 7.30-7.13 (m, 2H), 7.05 (d, J = 7.8 Hz, 1H), 5.78 (s, 1H), 4.84-4.77 (m, 1H), 4.65-4.51 (m, 1H), 4.08-3.88 (m, 2H), 3.43 (t, J = 7.1 Hz, 3H), 3.17-3.07 (m, 2H), 2.96-2.83 (m, 1H), 2.81-2.68 (m, 1H), 2.31 (t, J = 8.1 Hz, 2H), 2.07-1.83 (m, 5H), 1.70 (t, J = 12.1 Hz, 2H) ppm. MS (ESI) m/z: 686.0 (M + H)$^+$. Analytical HPLC: RT = 7.17 min (Method A). |

TABLE 4-continued

| Example | Structure | Name | Analytical Data |
|---|---|---|---|
| 73 | 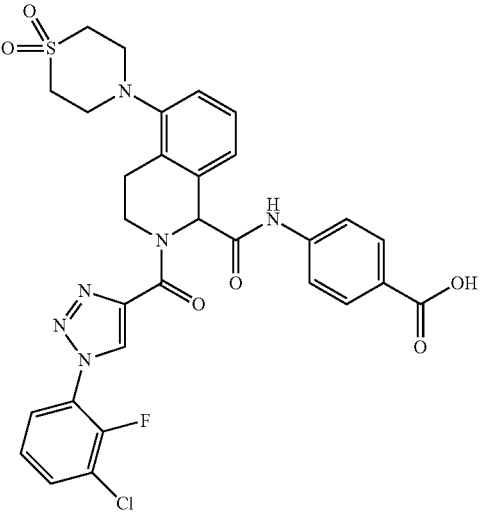 Racemate | 4-(2-(1-(3-chloro-2-fluorophenyl)-1H-1,2,3-triazole-4-carbonyl)-5-(1,1-dioxidothiomorpholino)-1,2,3,4-tetrahydroisoquinoline-1-carboxamido)benzoic acid, TFA salt | $^1$H NMR (400 MHz, methanol-$d_4$) δ 8.90 (br. s., 1H), 8.05-7.93 (m, 2H), 7.93-7.82 (m, 1H), 7.82-7.61 (m, 3H), 7.50-7.36 (m, 2H), 7.36-7.26 (m, 1H), 7.20 (d, J = 8.1 Hz, 1H), 5.92 (s, 1H), 4.75-4.62 (m, 1H), 4.31-4.16 (m, 1H), 3.46 (br. s., 5H), 3.30-3.22 (m, 5H) ppm. MS (ESI) m/z: 652..9 (M + H)$^+$. Analytical HPLC: RT = 7.49 min (Method A). |
| 74 | 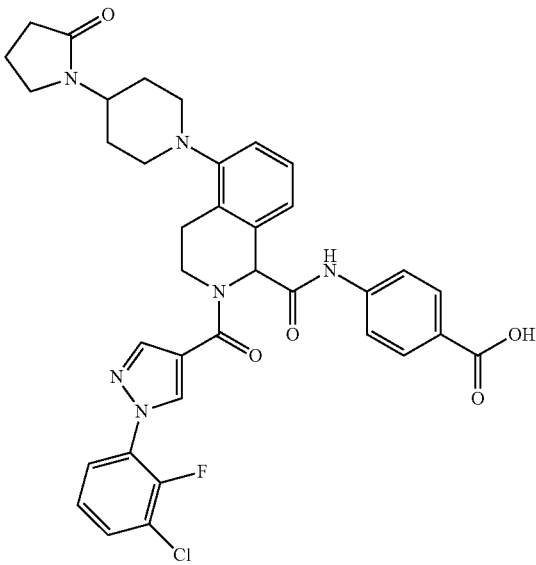 Racemate | 4-(2-(1-(3-chloro-2-fluorophenyl)-1H-pyrazole-4-carbonyl)-5-(4-(2-oxopyrrolidin-1-yl)piperidin-1-yl)-1,2,3,4-tetrahydroisoquinoline-1-carboxamido)benzoic acid, TFA salt | $^1$H NMR (400 MHz, DMSO-$d_6$) δ: 10.58 (s, 1H), 8.52 (s, 1H), 8.01 (s, 1H), 7.68 (d, J = 8.6 Hz, 2H), 7.61 (t, J = 7.1 Hz, 1H), 7.51 (d, J = 8.6 Hz, 3H), 7.30-7.17 (m, 2H), 7.04 (t, J = 7.7 Hz, 1H), 6.84 (d, J = 7.6 Hz, 1H), 5.58 (s, 1H), 4.06 (d, J = 11.1 Hz, 2H), 3.69 (br. s., 1H), 3.57 (br. s., 1H), 3.16 (t, J = 6.9 Hz, 2H), 3.03-2.84 (m, 4H), 2.65 (t, J = 11.6 Hz, 1H), 2.51-2.37 (m, 1H), 2.10-1.96 (m, 2H), 1.80-1.59 (m, 4H), 1.53-1.37 (m, 2H) ppm. MS ESI) m/z: 685.0 (M + H)$^+$. Analytical HPLC: RT = 8.93 min (Method A). |

TABLE 4-continued

| Example | Structure | Name | Analytical Data |
|---|---|---|---|
| 75 | 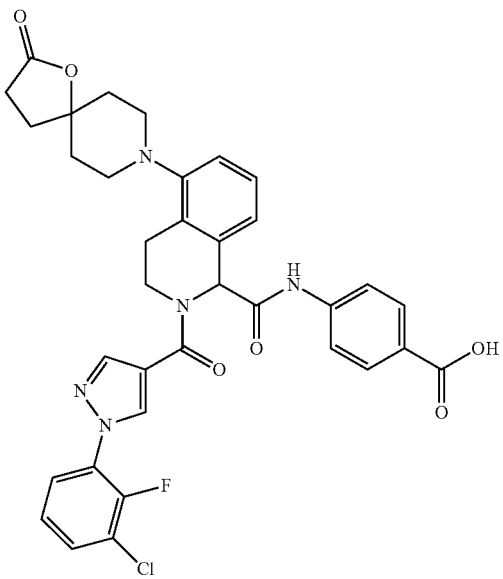<br>Racemate | 4-(2-(1-(3-chloro-2-fluorophenyl)-1H-pyrazole-4-carbonyl)-5-(2-oxo-1-oxa-8-azaspiro[4.5]-decan-8-yl)-1,2,3,4-tetrahydroisoquinoline-1-carboxamido)benzoic acid, TFA salt | $^1$H NMR (400 MHz, methanol-$d_4$) δ: 7.11 (br. s., 1H), 6.69 (s, 1H), 6.49 (d, J = 8.6 Hz, 2H), 6.33 (t, J = 7.5 Hz, 1H), 6.21 (d, J = 8.3 Hz, 2H), 6.11 (t, J = 6.9 Hz, 1H), 5.96-5.77 (m, 3H), 5.67 (d, J = 8.1 Hz, 1H), 4.33 (s, 1H), 2.91 (d, J = 11.6 Hz, 1H), 2.32 (d, J = 5.6 Hz, 1H), 1.80-1.66 (m, 3H), 1.63-1.47 (m, 3H), 1.21 (t, J = 8.2 Hz, 2H), 0.76-0.66 (m, 2H), 0.65-0.50 (m, 4H) ppm. MS (ESI) m/z: 672.0 (M + H)$^+$. Analytical HPLC: RT = 7 78 min (Method A). |
| 76 | 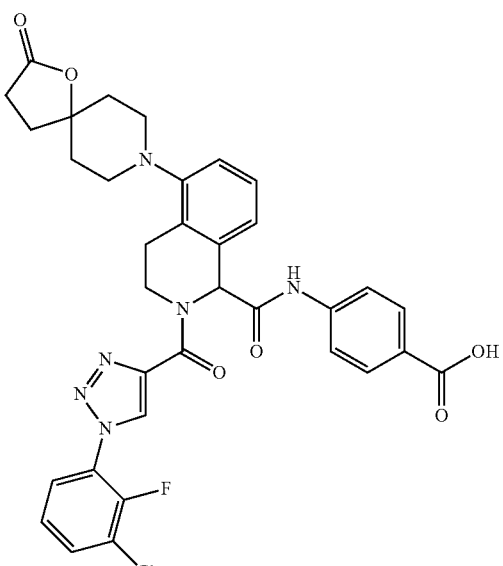<br>Racemate | 4-(2-(1-(3-chloro-2-fluorophenyl)-1H-1,2,3-triazole-4-carbonyl)-5-(2-oxo-1-oxa-8-azaspiro[4.5]decan-8-yl)-1,2,3,4-tetrahydroisoquinoline-1-carboximido)benzoic acid, TFA | $^1$H NMR (400 MHz, methanol-$d_4$) δ 8.89 (br. s., 1H), 7.98 (d, J = 8.6 Hz, 2H), 7.93-7.85 (m, 1H), 7.78-7.65 (m, 3H), 7.50-7.41 (m, 1H), 7.38-7.26 (m, 2H), 7.17 (d, J = 8.1 Hz, 1H), 5.90 (s, 1H), 4.70 (d, J = 12.9 Hz, 1H), 4.13 (br. s., 1H), 3.29-3.11 (m, 3H), 3.08 (br. s., 3H), 2.77-2.66 (m, 2H), 2.21 (t, J = 8.1 Hz, 2H), 2.07 (br. s., 4H) ppm. MS (ESI) m/z: 673.0 (M + H)$^+$. Analytical HPLC: RT = 9.0 min (Method A). |

TABLE 4-continued

| Example | Structure | Name | Analytical Data |
|---|---|---|---|
| 77 | 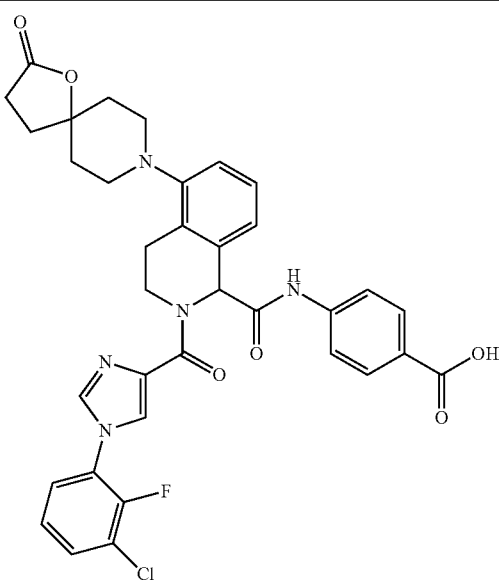<br>Racemate | 4-(2-(1-(3-chloro-2-fluorophenyl)-1H-imidazole-4-carbonyl)-5-(2-oxo-1-oxa-8-azaspiro[4.5]decan-8-yl)-1,2,3,4-tetrahydroisoquinoline-1-carboxamido)benzoic acid, TFA salt | $^1$H NMR (400 MHz, methanol-$d_4$) δ 8.43 (br. s., 1H), 8.16 (br. s., 1H), 7.98 (d, J = 8.3 Hz, 2H), 7.70 (d, J = 8.8 Hz, 3H), 7.42-7.26 (m, 3H), 7.17 (d, J = 7.6 Hz, 2H), 5.85 (br. s., 1H), 4.58 (br. s., 1H), 4.06 (br. s., 1H), 3.28-3.14 (m, 3H), 3.08 (br. s., 3H), 2.77-2.66 (m, 2H), 2.20 (t, J = 8.1 Hz, 2H), 2.07 (br. s., 4H) ppm. MS (ESI) m/z: 671.9 (M + H)$^+$. Analytical HPLC: RT = 8.36 min (Method A). |
| 78 | 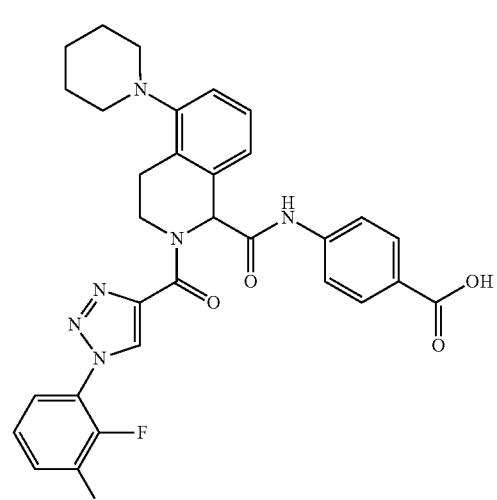<br>Racemate | 4-(2-(1-(3-chloro-2-fluorophenyl)-1H-1,2,3-triazole-4-carbonyl)-5-(piperidin-1-yl)-1,2,3,4-tetrahydroisoquinoline-1-carboxamido)benzoic acid, TFA salt | $^1$H NMR (400 MHz, methanol-$d_4$) δ: 7.61 (d, J = 1.0 Hz, 1H), 6.66 (d, J = 8.6 Hz, 2H), 6.55 (t, J = 7.2 Hz, 1H), 6.47-6.32 (m, 4H), 6.27 (d, J = 8.1 Hz, 1H), 6.23-6.08 (m, 2H), 4.70 (s, 1H), 3.52-3.42 (m, 1H), 2.97 (t, J = 9.2 Hz, 1H), 2.31-2.08 (m, 5H), 0.74 (d, J = 1.0 Hz, 5H), 0.47 (br. s., 2H) ppm. MS (ESI) m/z: 603.0 (M + H)$^+$. Analytical HPLC: RT = 7.40 min (Method A). |

TABLE 4-continued

| Example | Structure | Name | Analytical Data |
|---|---|---|---|
| 79 | R-Enantiomer[e] | (R)-4-(2-(1-(3-chloro-2-fluorophenyl)-1H-1,2,3-triazole-4-carbonyl)-5-(4-methyl-2-oxopiperazin-1-yl)-1,2,3,4-tetrahydroisoquinoline-1-carboxamido)benzoic acid, TFA salt | $^1$H NMR (500 MHz, methanol-$d_4$) δ 8.98-8.81 (m, 1H), 8.06-7.93 (m, 2H), 7.91-7.80 (m, 1H), 7.79-7.63 (m, 4H) 7.52-7.40 (m, 2H), 7.39-7.27 (m, 1H), 6.79-5.93 (m, 1H), 4.64-4.52 (m, 1H), 4.52-4.41 (m, 1H), 4.29-4.11 (m, 2H), 4.11-4.00 (m, 1H), 3.95-3.85 (m, 1H), 3.85-3.75 (m, 2H), 3.22-3.08 (m, 4H), 3.06-2.96 (m, 1H) ppm. MS (ESI) m/z: 632.0 (M + H)$^+$. Analytical HPLC: RT = 7.43 min (Method A). |
| 80 | S-Enantiomer[e] | (S)-4-(2-(1-(3-chloro-2-fluorophenyl)-1H-1,2,3-triazole-4-carbonyl)-5-(4-methyl-2-oxopiprazin-1-yl)-1,2,3,4-tetrahydroisoquinoline-1-carboxamido)benzoic acid, HCl | $^1$H NMR (500 MHz, methanol-$d_4$) δ 8.98-8.87 (m, 1H), 8.08-7.95 (m, 2H), 7.91-7.81 (m, 1H), 7.79-7.62 (m, 4H), 7.53-7.41 (m, 2H), 7.35 (d, J = 7.7 Hz, 1H), 6.15-5.96 (m, 1H), 4.69-4.55 (m, 2H), 4.14 (d, J = 13.8 Hz, 2H), 4.10-3.98 (m, 1H), 3.89 (br. s., 1H), 3.77 (br. s., 2H), 3.20-3.14 (m, 1H), 3.14-3.06 (m, 3H), 3.06-2.96 (m, 1H) ppm. MS (ESI) m/z: 632 (M + H)$^+$. Analytical HPLC: RT = 7.35 min (Method A). |
| 81 | Racemate | 4-(2-(1-(3-chloro-2-fluorophenyl)-1H-1,2,3-triazole-4-carbonyl)-5-(2-oxopiperidin-1-yl)-1,2,3,4-tetrahydroisoquinoline-1-carboxamido)benzoic acid | $^1$H NMR (400 MHz, methanol-$d_4$) δ 7.58 (d, J = 2.5 Hz, 1H), 6.74 (s, 2H), 6.56 (t, J = 6.9 Hz, 1H), 6.48-6.37 (m, 2H), 6.33-6.27 (m, 1H), 6.18-6.06 (m, 2H), 6.00-5.89 (m, 2H), 4.80-4.66 (m, 1H), 3.22 (br. s., 1H), 2.43 (br. s., 1H), 2.24-2.15 (m, 1H), 1.84-1.73 (m, 1H), 1.65 (br. s., 1H), 1.40 (s, 2H), 1.25 (br. s., 2H), 0.79-0.64 (m, 4H) ppm. MS (ESI) m/z: 617.0 (M + H)$^+$. Analytical HPLC: RT = 7.29 min (Method A). |

TABLE 4-continued

| Example | Structure | Name | Analytical Data |
|---|---|---|---|
| 82 | 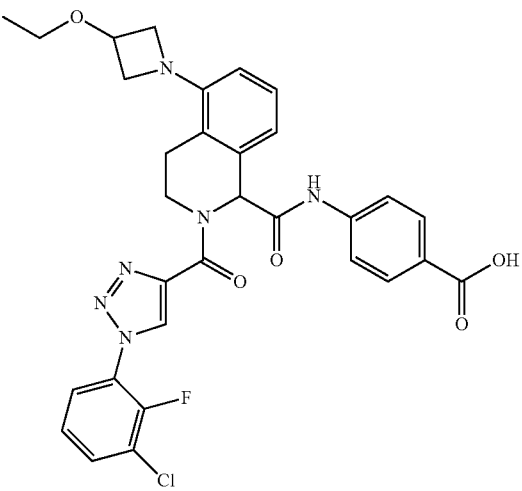 Racemate | 4-(2-(1-(3-chloro-2-fluorophenyl)-1H-1,2,3-triazole-4-carbonyl)-5-(3-ethoxyazetidin-1-yl)-1,2,3,4-tetrahydroisoquinoline-1-carboxamido)benzoic acid, TFA salt | $^1$H NMR (500 MHz, methanol-d$_4$) δ: 8.90 (d, J = 2.2 Hz, 1H), 7.99 (d, J = 8.8 Hz, 2H), 7.91-7.82 (m, 1H), 7.80-7.66 (m, 3H), 7.45 (t, J = 8.3 Hz, 1H), 7.35 (d, J = 4.7 Hz, 2H), 7.09-6.98 (m, 1H), 5.95 (s, 1H), 4.67-4.60 (m, 1H), 4.55-4.43 (m, 3H), 4.40-4.31 (m, 1H), 4.15-4.01 (m, 2H), 3.58 (q, J = 7.2 Hz, 2H), 3.22-3.12 (m, 1H), 3.11-2.98 (m, 1H), 1.25 (t, J = 7.0 Hz, 3H) ppm. MS (ESI) m/z: 618.2 (M + H)$^+$. Analytical HPLC: RT = 10.13 min (Method A). |
| 83 | 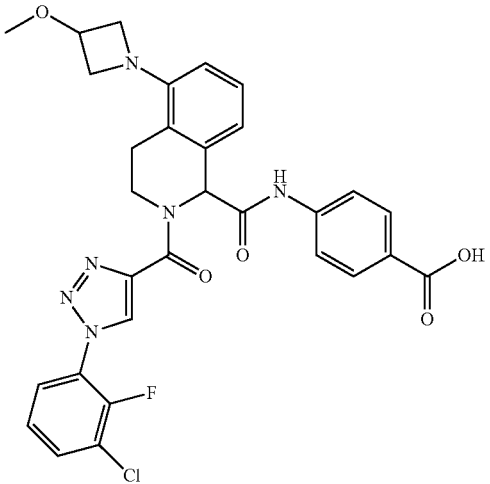 Racemate | 4-(2-(1-(3-chloro-2-fluorophenyl)-1H-1,2,3-triazole-4-carbonyl)-5-(3-methoxyazetidin-1-yl)-1,2,3,4-tetrahydroisoquinoline-1-carboxamido)benzoic acid, TFA salt | $^1$H NMR (500 MHz, methanol-d$_4$) δ 8.89 (d, J = 1.9 Hz, 1H), 7.99 (d, J = 8.8 Hz, 2H), 7.92-7.83 (m, 1H), 7.79-7.65 (m, 3H), 7.49-7.40 (m, 1H), 7.31-7.19 (m, 2H), 6.88-6.77 (m, 1H), 5.91 (s, 1H), 4.68-4.57 (m, 1H), 4.40-4.27 (m, 4H), 3.98-3.84 (m, 2H), 3.42-3.37 (m, 3H), 3.14-3.08 (m, 1H), 3.05-2.96 (m, 1H) ppm. MS (ESI) m/z: 604.9 (M + H)$^+$. Analytical HPLC: RT = 9.56 min (Method A). |

TABLE 4-continued

| Example | Structure | Name | Analytical Data |
|---|---|---|---|
| 84 | 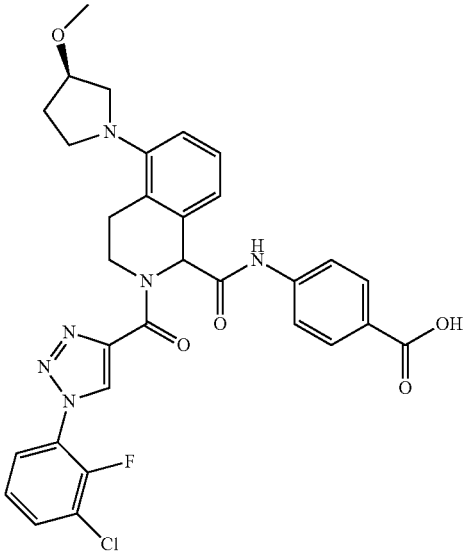 Diastereomeric Mixture | 4-(2-(1-(3-chloro-2-fluorophenyl)-1H-1,2,3-triazole-4-carbonyl)-5-((R)-3-methoxypyrrolidin-1-yl)-1,2,3,4-tetrahydroisoquinoline-1-carboxamido)benzoic acid, TFA salt | $^1$H NMR (500 MHz, methanol-$d_4$) δ 8.92 (t, J = 2.3 Hz, 1H), 7.99 (dd, J = 8.5, 4.4 Hz, 2H), 7.95-7.83 (m, 1H), 7.83-7.64 (m, 3H), 7.54-7.28 (m, 4H), 6.05-5.89 (m, 1H), 4.80-4.75 (m, 1H), 4.75-4.61 (m, 1H), 4.45-4.33 (m, 1H), 4.26 (br. s., 1H), 4.22-4.11 (m, 1H), 3.77 (dd, J = 11.6, 5.0 Hz, 1H), 3.74-3.58 (m, 2H), 3.57-3.49 (m, 1H), 3.49-3.41 (m, 3H), 3.26-3.17 (m, 1H), 2.42-2.23 (m, 2H) ppm. MS (ESI) m/z: 619.0 (M + H)$^+$. Analytical HPLC: RT = 4.80 min (Method A). |
| 85 | 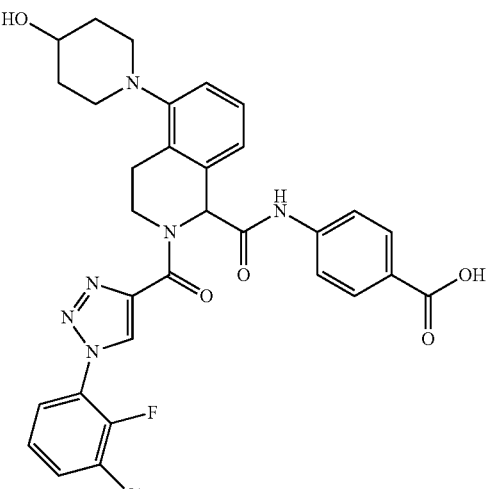 Racemate | 4-(2-(1-(3-chloro-2-fluorophenyl)-1H-1,2,3-triazole-4-carbonyl)-5-(4-hydroxypiperidin-1-yl)-1,2,3,4-tetrahydroisoquinoline-1-carboxamido)benzoic acid, TFA salt | $^1$H NMR (400 MHz, methanol-$d_4$) δ 8.91 (d, J = 2.2 Hz, 1H), 7.98 (d, J = 8.8 Hz, 2H), 7.92-7.82 (m, 1H), 7.82-7.62 (m, 3H), 7.52 (d, J = 7.0 Hz, 1H), 7.51-7.34 (m, 3H), 5.95 (s, 1H), 4.74 (dt, J = 12.7, 4.8 Hz, 1H), 4.30-4.13 (m, 1H), 4.01-3.87 (m, 1H), 3.49 (d, J = 12.5 Hz, 2H), 3.30-3.03 (m, 4H), 2.15 (br. s., 2H), 1.98-1.74 (m, 2H) ppm. MS (ESI) m/z: 619.3 (M + H)$^+$. Analytical HPLC: RT = 9.91 min (Method A). |

TABLE 4-continued

| Example | Structure | Name | Analytical Data |
|---|---|---|---|
| 86 | 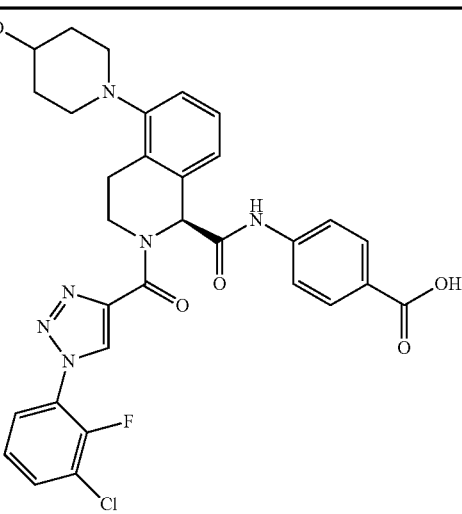<br>S-Enantiomer[d] | (S)-4-(2-(1-(3-chloro-2-fluorophenyl)-1H-1,2,3-triazole-4-carbonyl)-5-(4-hydroxypiperidin-1-yl)-1,2,3,4-tetrahydroisoquinoline-1-carboxamido)benzoic acid, TFA salt | $^1$H NMR (400 MHz, methanol-$d_4$) δ 8.91 (d, J = 2.2 Hz, 1H), 7.97 (d, J = 8.6 Hz, 2H), 7.90-7.80 (m, 1H), 7.79-7.63 (m, 3H), 7.55 (d, J = 5.5 Hz, 1H), 7.48-7.32 (m, 3H), 6.73-5.87 (m, 1H), 4.74 (dt, J = 12.3, 4.7 Hz, 1H), 4.33-4.13 (m, 1H), 3.94 (br. s., 1H), 3.58-3.43 (m, 2H), 3.29-3.07 (m, 4H), 2.17 (br. s., 2H), 1.93 (d, J = 9.9 Hz, 2H) ppm. MS (ESI) m/z: 619.2 (M + H)[+]. Analytical HPLC: RT = 6.78 min (Method A). |
| 87 | 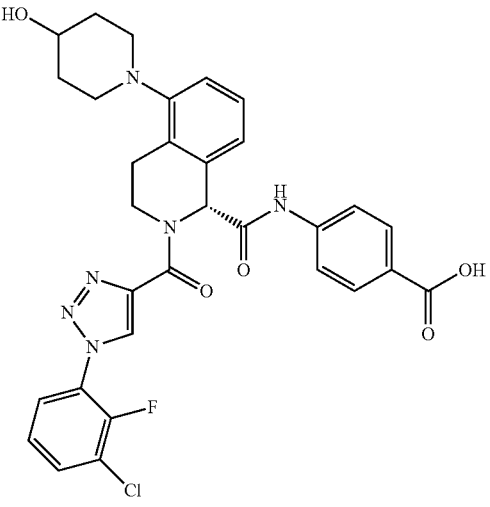<br>R-Enantiomer[d] | (R)-4-(2-(1-(3-chloro-2-fluorophenyl)-1H-1,2,3-triazole-4-carbonyl)-5-(4-hydroxypiperidin-1-yl)-1,2,3,4-tetrahydroisoquinoline-1-carboxamido)benzoic acid, TFA salt | $^1$H NMR (400 MHz, methanol-$d_4$) δ 8.91 (d, J = 2.2 Hz, 1H), 7.97 (d, J = 8.6 Hz, 2H), 7.86 (t, J = 7.3 Hz, 1H), 7.77-7.63 (m, 3H), 7.56 (d, J = 5.1 Hz, 1H), 7.50-7.36 (m, 3H), 6.72-5.90 (m, 1H), 4.80-4.67 (m, 1H), 4.32-4.14 (m, 1H), 3.95 (br. s., 1H), 3.53 (br. s., 2H), 3.27-3.08 (m, 4H), 2.17 (br. s., 2H), 1.93 (d, J = 8.8 Hz, 2H) ppm. MS (ESI) m/z: 619.2 (M + H)[+]. Analytical HPLC: RT = 6.78 min (Method A). |

[a]CHIRALCEL ® OJ-H, 30 x 250 mm ID, 5 μm, using 20% MeOH-DEA/80% $CO_2$ at 35.0 mL/min, 150 bar BP, 35° C.
[b]CHIRALPAK ® AS-H, 30 x 250 mm ID, 5 μm, using 30% MeOH-DEA/70% $CO_2$ at 85.0 mL/min, 100 bar BP, 40° C.
[c]CHIRALCEL ® OJ-H, 30 x 250 mm ID, 5 μm, using 25% MeOH/75% $CO_2$ at 85.0 mL/min, 150 bar BP, 35° C.
[d]CHIRALPAK ® AS-H, 21 x 250 mm ID. 5 μm, using 30% MeOH/70% $CO_2$ at 45.0 mL/min, 100 bar BP, 35° C.
[e]CHIRALCEL ® OD-H, 21 x 200 mm ID, 5 μm, using 30% MeOH/70% $CO_2$ at 70.0 mL/min, 100 bar BP, 40° C.

EXAMPLE 88

(R)-4-(2-(1-(3-Chloro-2-fluorophenyl)-1H-pyrazole-4-carbonyl)-5-morpholino-1,2,3,4-tetrahydroisoquinoline-1-carboxamido)benzoic acid, TFA salt

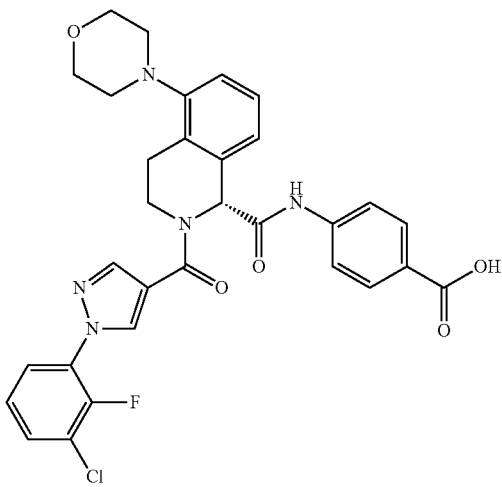 [SMILES: O=C(O)c1ccc(NC(=O)[C@H]2c3cccc(N4CCOCC4)c3CCN2C(=O)c2cnn(-c3cccc(Cl)c3F)c2)cc1]

88A. tert-Butyl 4-(5-morpholino-2-(2,2,2-trifluoroacetyl)-1,2,3,4-tetrahydroisoquinoline-1-carboxamido)benzoate: To Intermediate 4F (0.855 g, 3.95 mmol) and Intermediate 1 (0.803 g, 3.95 mmol) in a vial was added TFA (0.496 g, 4.35 mmol) in DCM (6.59 mL). After stirring overnight, the reaction mixture was concentrated and purified by normal phase chromatography to give a tan solid. MS (ESI) m/z: 534.1 (M+H)$^+$.

88B. tert-Butyl 4-(5-morpholino-1,2,3,4-tetrahydroisoquinoline-1-carboxamido) benzoate: To a suspension of 88A (0.7 g, 1.312 mmol) in MeOH (10 mL) cooled at 0° C., was added NaBH$_4$ (0.298 g, 7.87 mmol). After stirring overnight, the mixture was partitioned between saturated NaHCO$_3$ solution (50 mL) and ethyl acetate (50 mL). The aqueous layer was extracted with ethyl acetate (2×40 mL). The combined organic layers were washed with brine (25 mL), dried (MgSO$_4$), filtered, and concentrated. Product carried forward to next reaction without further purification. MS (ESI) m/z: 438.1 (M+H)$^+$.

88C.(R)-tert-Butyl 4-(5-morpholino-1,2,3,4-tetrahydroisoquinoline-1-carboxamido)benzoate: This intermediate was the early eluting enantiomer after chiral SFC purification using CHIRALCEL® OJ-H, 30×250 mm ID, 5 μm, using 25% MeOH/75% CO$_2$ at 85.0 mL/min, 100 bar BP, 40° C. $^1$H NMR (400 MHz, methanol-d$_4$) δ 7.99-7.88 (m, 2H), 7.77-7.66 (m, 2H), 7.26-7.13 (m, 2H), 7.04 (dd, J=7.7, 0.9 Hz, 1H), 4.90-4.76 (m, 2H), 3.93-3.75 (m, 4H), 3.43-3.35 (m, 1H), 3.04-2.92 (m, 4H), 2.93-2.76 (m, 3H), 1.64-1.55 (m, 9H) ppm. MS (ESI) m/z: 438.1 (M+H)$^+$.

88D. (S)-tert-Butyl 4-(5-morpholino-1,2,3,4-tetrahydroisoquinoline-1-carboxamido)benzoate: This intermediate was the late eluting enantiomer after chiral SFC purification using CHIRALCEL® OJ-H, 30×250 mm ID, 5 μm, using 25% MeOH/75% CO$_2$ at 85.0 mL/min, 100 bar BP, 40° C. $^1$H NMR (400 MHz, methanol-d$_4$) δ 7.81 (d, J=8.6 Hz, 2H), 7.59 (d, J=8.6 Hz, 2H), 7.18-7.00 (m, 2H), 6.92 (d, J=7.3 Hz, 1H), 5.38 (s, 2H), 3.81-3.64 (m, 4H), 3.34-3.24 (m, 1H), 2.98-2.82 (m, 4H), 2.81-2.64 (m, 3H), 1.48 (s, 9H) ppm. MS (ESI) m/z: 438.1 (M+H)$^+$.

Example 88.(R)-4-(2-(1-(3-Chloro-2-fluorophenyl)-1H-pyrazole-4-carbonyl)-5-morpholino-1,2,3,4-tetrahydroisoquinoline-1-carboxamido)benzoic acid, TFA salt: To Intermediate 13 (15.40 mg, 0.064 mmol) and 88C (28 mg, 0.064 mmol) in DMF (0.25 mL) in a vial, cooled at 0° C., was added T3P/50% EtOAc (0.054 mL, 0.192 mmol) and pyridine (0.021 mL, 0.256 mmol). The reaction mixture was allowed to gradually come to rt and stir for 5 h before quenching with saturated aqueous NaHCO$_3$ solution (2 mL) and extracted with ethyl acetate (3×10 mL). The combined organic layers were washed with brine (5 mL), dried (MgSO$_4$), filtered, and concentrated. The t-butyl ester was removed by treatment with 50% TFA/DCM for 2 h. The reaction mixture was concentrated, purified by reverse phase column chromatography, lyophilized to give Example 88 as a white solid (14 mg, 29%). $^1$H NMR (400 MHz, methanol-d$_4$) δ 8.59 (br. s., 1H), 8.17 (br. s., 1H), 7.98 (d, J=8.3 Hz, 2H), 7.82 (br. s., 1H), 7.69 (d, J=6.8 Hz, 2H), 7.60 (br. s., 1H), 7.46-7.24 (m, 3H), 7.11 (d, J=6.8 Hz, 1H), 5.81 (br. s., 1H), 4.38 (br. s., 1H), 3.87 (d, J=18.2 Hz, 6H), 3.27 (br. s., 1H), 3.03 (br. s., 2H), 2.88 (br. s., 2H). MS (ESI) m/z: 604 (M+H)$^+$. Analytical HPLC: RT=8.08 min (Method A).

EXAMPLE 89

(S)-4-(2-(1-(3-Chloro-2-fluorophenyl)-1H-pyrazole-4-carbonyl)-5-morpholino-1,2,3,4-tetrahydroisoquinoline-1-carboxamido)benzoic acid, TFA salt

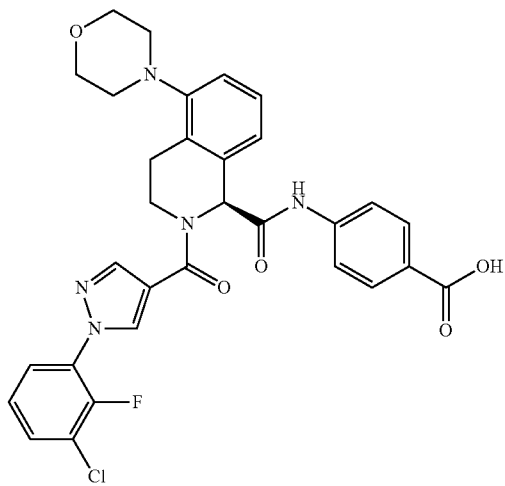 [SMILES: O=C(O)c1ccc(NC(=O)[C@@H]2c3cccc(N4CCOCC4)c3CCN2C(=O)c2cnn(-c3cccc(Cl)c3F)c2)cc1]

Example 89. (S)-4-(2-(1-(3-Chloro-2-fluorophenyl)-1H-pyrazole-4-carbonyl)-5-morpholino-1,2,3,4-tetrahydroisoquinoline-1-carboxamido)benzoic acid, TFA salt: The compound was prepared in the same manner as Example 88 replacing 88C with 88D in the final amide coupling step to give a white solid (29 mg, 48%). $^1$H NMR (400 MHz, methanol-d$_4$) δ: 8.59 (br. s., 1H), 8.17 (s, 1H), 7.97 (d, J=8.6 Hz, 2H), 7.82 (t, J=7.2 Hz, 1H), 7.69 (d, J=8.1 Hz, 2H), 7.60 (t, J=7.3 Hz, 1H), 7.41-7.29 (m, 3H), 7.11 (d, J=7.8 Hz, 1H), 5.80 (s, 1H), 4.39 (d, J-11.4 Hz, 1H), 3.96-3.73 (m, 6H), 3.27 (t, J-4.5 Hz, 2H), 3.08-3.01 (m, 2H), 2.93-2.83 (m, 2H) ppm. MS (ESI) m/z: 604.0 (M+H)$^+$. Analytical HPLC: RT=8.11 min (Method A).

EXAMPLE 90

(S)-4-(2-(1-(3-Chloro-2-fluorophenyl)-1H-1,2,3-triazole-4-carbonyl)-5-morpholino-1,2,3,4-tetrahydroisoquinoline-1-carboxamido)benzoic acid, TFA salt

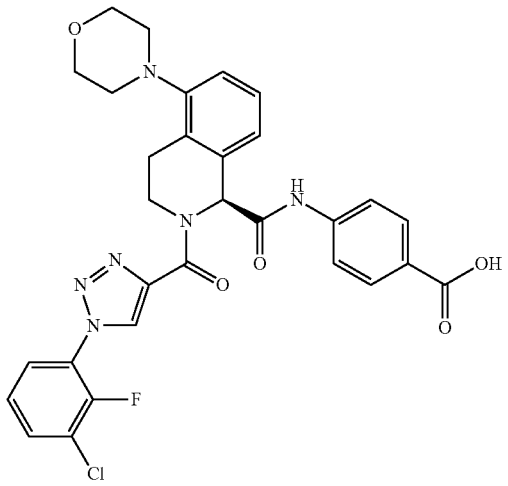 [SMILES: O=C(O)c1ccc(NC(=O)[C@@H]2c3cccc(N4CCOCC4)c3CCN2C(=O)c2cn(-c3cccc(Cl)c3F)nn2)cc1]

Example 90. (S)-4-(2-(1-(3-Chloro-2-fluorophenyl)-1H-1,2,3-triazole-4-carbonyl)-5-morpholino-1,2,3,4-tetrahydroisoquinoline-1-carboxamido)benzoic acid, TFA salt: The title compound was prepared in the same manner as Example 89 replacing Intermediate 13 with Intermediate 9 in the final amide coupling step to give a white solid (13 mg, 38%). $^1$H NMR (400 MHz, methanol-$d_4$) δ: 8.89 (d, J=2.3 Hz, 1H), 7.98 (d, J=8.6 Hz, 2H), 7.88 (t, J=6.6 Hz, 1H), 7.81-7.60 (m, 3H), 7.50-7.40 (m, 1H), 7.40-7.27 (m, 2H), 7.12 (d, J=8.1 Hz, 1H), 5.89 (s, 1H), 4.76-4.62 (m, 1H), 4.16-4.03 (m, 1H), 3.93-3.77 (m, 4H), 3.26 (d, J=5.1 Hz, 2H), 3.02 (br. s., 2H), 2.94 (br. s., 2H) ppm. MS (ESI) m/z: 605.0 (M+H)$^+$. Analytical HPLC: RT=10.63 min (Method A).

EXAMPLE 91

(S)-4-(2-(1-(3-Chloro-2-fluorophenyl)-1H-imidazole-4-carbonyl)-5-morpholino-1,2,3,4-tetrahydroisoquinoline-1-carboxamido)benzoic acid, TFA salt

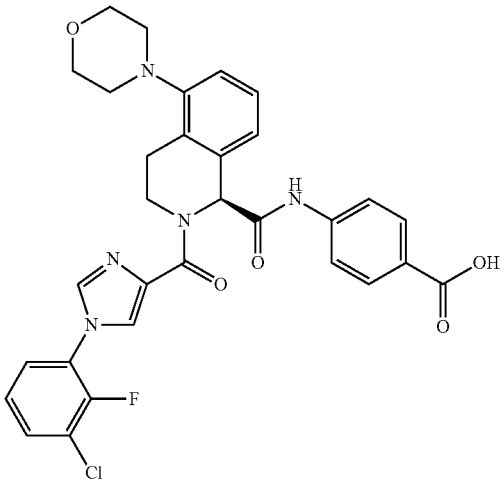 [SMILES: O=C(O)c1ccc(NC(=O)[C@@H]2c3cccc(N4CCOCC4)c3CCN2C(=O)c2cn(-c3cccc(Cl)c3F)cn2)cc1]

Example 91. (S)-4-(2-(1-(3-Chloro-2-fluorophenyl)-1H-imidazole-4-carbonyl)-5-morpholino-1,2,3,4-tetrahydroisoquinoline-1-carboxamido)benzoic acid, TFA salt: The compound was prepared in the same manner as Example 89 replacing Intermediate 13 with Intermediate 17 in the final amide coupling step to give a white solid (12 mg, 59%). $^1$H NMR (400 MHz, methanol-$d_4$) δ: 8.41 (br. s., 1H), 8.15 (br. s., 1H), 7.98 (d, J=8.3 Hz, 2H), 7.79-7.59 (m, 4H), 7.40 (d, J=7.3 Hz, 1H), 7.32 (d, J=14.7 Hz, 2H), 7.11 (d, J=8.6 Hz, 1H), 5.84 (s, 1H), 4.57 (br. s., 1H), 4.16-3.99 (m, 1H), 3.88 (d, J=3.3 Hz, 4H), 3.24 (br. s., 2H), 3.13-2.84 (m, 4H) ppm. MS (ESI) m/z: 604.0 (M+H)$^+$. Analytical HPLC: RT=9.95 min (Method A).

EXAMPLE 92

4-(2-(1-(3-Chloro-2-fluorophenyl)-1H-imidazole-4-carbonyl)-5-(4-(2-oxopyrrolidin-1-yl)piperidin-1-yl)-1,2,3,4-tetrahydroisoquinoline-1-carboxamido)benzoic acid, TFA salt

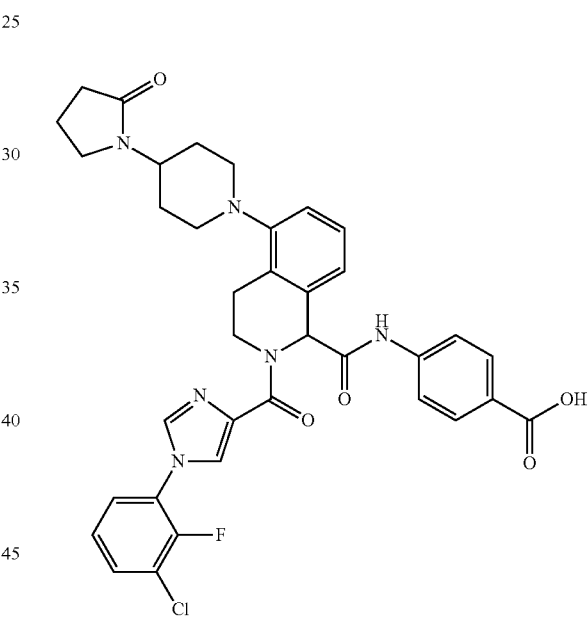

Example 92. 4-(2-(1-(3-Chloro-2-fluorophenyl)-1H-imidazole-4-carbonyl)-5-(4-(2-oxopyrrolidin-1-yl)piperidin-1-yl)-1,2,3,4-tetrahydroisoquinoline-1-carboxamido) benzoic acid, TFA salt: The compound was prepared in a similar manner as Example 88 starting from Intermediate 36 and utilizing Intermediate 17 in the amide coupling step to give a white solid (18 mg, 54%). $^1$H NMR (400 MHz, methanol-$d_4$) δ 8.47 (br. s., 1H), 8.17 (br. s., 1H), 7.98 (d, J=8.3 Hz, 2H), 7.69 (d, J=8.8 Hz, 4H), 7.47-7.35 (m, 2H), 7.31 (t, J=8.0 Hz, 1H), 7.19 (d, J=7.8 Hz, 1H), 5.86 (s, 1H), 4.59 (d, J=11.9 Hz, 1H), 4.07 (br. s., 2H), 4.00 (s, 1H), 3.64-3.48 (m, 2H), 3.25 (br. s., 1H), 3.17-2.98 (m, 2H), 2.98-2.82 (m, 2H), 2.52-2.31 (m, 2H), 2.21-1.95 (m, 4H), 1.84 (d, J=11.9 Hz, 2H) ppm. MS (ESI) m/z: 685.0 (M+H)$^+$. Analytical HPLC: RT=8.16 min (Method A).

EXAMPLE 93

2-(1-(3-Chloro-2-fluorophenyl)-1H-pyrazole-4-carbonyl)-5-(4-(dimethylamino)piperidin-1-yl)-N-(4-(oxazol-2-yl)phenyl)-1,2,3,4-tetrahydroisoquinoline-1-carboxamide, bis-TFA salt

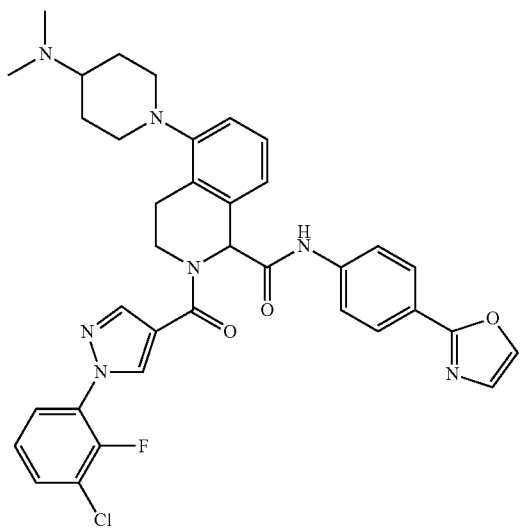 [SMILES: CN(C)C1CCN(c2cccc3c2CCN(C(=O)c2cnn(-c4cccc(Cl)c4F)c2)C3C(=O)Nc2ccc(-c3ncco3)cc2)CC1]

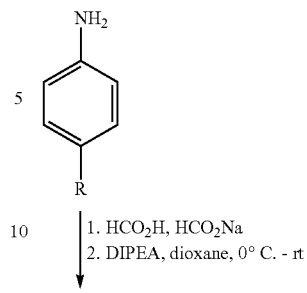

1. HCO₂H, HCO₂Na
2. DIPEA, dioxane, 0° C. - rt

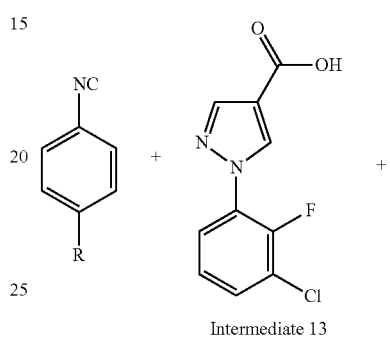

Intermediate 13

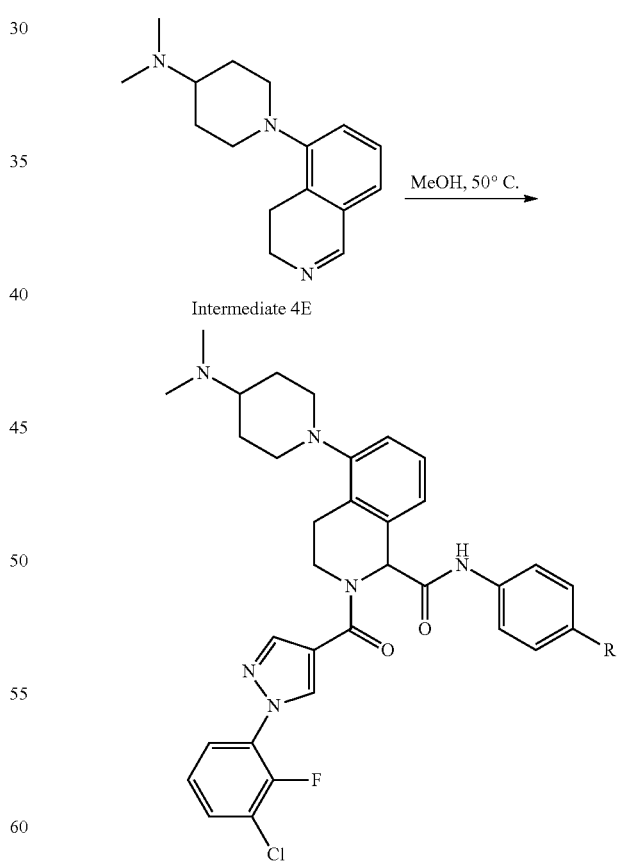

93A. 2-(4-Isocyanophenyl)oxazole: 4-(Oxazol-2-yl)aniline hydrochloride (1.0 g, 5.09 mmol) was dissolved in formic acid (1.343 mL, 35.6 mmol), treated with sodium formate (0.069 g, 1.017 mmol) and stirred for 14 h before quenching with ice-water. The white solid was collected by filtration, rinsed with water, and dried under vacuum at 50° C. for 5 h. Phosphorus oxychloride (0.545 mL, 5.85 mmol) in dioxane (5.10 mL) was added dropwise to the formamide and DIPEA (3.55 mL, 20.34 mmol) in dioxane (2.55 mL) at 0° C. After stirring for 18 h at room temperature, the reaction was quenched with cold dilute NaHCO₃ (50 mL) and stirred for 30 minutes. The solids were collected by filtration, washed with water, and air-dried under vacuum. The isonitrile (638 mg, 74%) was sufficiently pure for subsequent reaction with further purification. MS (ESI) m/z: 171 (M+H)⁺.

Example 93. 2-(1-(3-Chloro-2-fluorophenyl)-1H-pyrazole-4-carbonyl)-5-(4-(dimethylamino)piperidin-1-yl)-N-(4-(oxazol-2-yl)phenyl)-1,2,3,4-tetrahydroisoquinoline-1-carboxamide, TFA salt: To a septa capped pressure vial was charged Intermediate 4E (0.050 g, 0.194 mmol), Intermediate 13 (0.047 g, 0.194 mmol), 93A (0.033 g, 0.194 mmol), and MeOH (0.389 mL) stirred at 50° C. After 20 h, the reaction mixture was concentrated, purified by reverse phase chromatography, and freeze-dried to give Example 93 (35 mg, 20%). ¹H NMR (500 MHz, DMSO-d₆) δ 10.79 (s, 1H), 8.73 (d, J=1.7 Hz, 1H), 8.27-8.16 (m, 2H), 7.93 (d, J=8.8 Hz, 2H), 7.84-7.69 (m, 4H), 7.48-7.42 (m, 2H), 7.34 (d, J=0.8 Hz, 1H), 7.27 (t, J=7.8 Hz, 1H), 7.04 (d, J=7.7 Hz, 1H), 5.81 (s, 1H), 4.31-4.24 (m, 1H), 3.83-3.77 (m, 1H), 3.35-3.28 (m, 1H), 3.25-3.09 (m, 4H), 2.84-2.78 (m, 7H), 2.63-2.54 (m, 1H), 2.13-2.03 (m, 2H), 1.86-1.73 (m, 2H) ppm. MS (ESI) m/z: 668 (M+H)⁺. Analytical HPLC: RT=5.80 min (Method B).

The Examples in Table 5 were made as described previously for Example 93 replacing 4-(oxazol-2-yl)aniline hydrochloride with the appropriate aniline during isonitrile preparation.

TABLE 5

| Example | Structure | Name | Analytical Data |
|---|---|---|---|
| 94 | 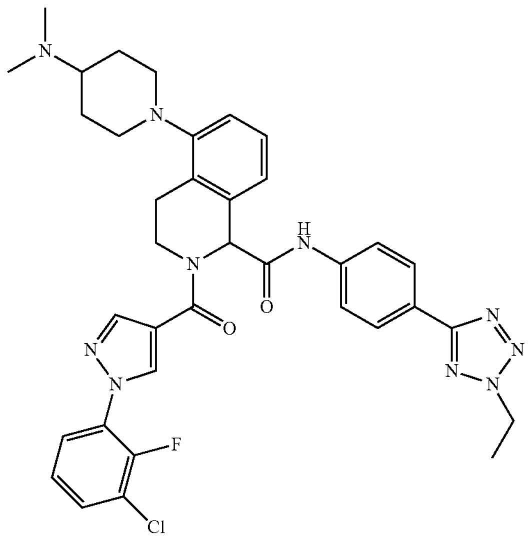 | 2-(1-(3-chloro 2-fluorophenyl)-1H-pyrazole-4-carbonyl)-5-(4-(dimethylamino)piperidin-1-yl)-N-(4-(2-ethyl-2H-tetrazol-5-yl)phenyl)-1,2,3,4-tetrahydroisoquinoline-1-carboxamide, TFA salt | $^1$H NMR (500 MHz, DMSO-d$_6$) δ 10.77 (s, 1H), 8.73 (d, J = 1.7 Hz, 1H), 8.23 (s, 1H), 8.01 (d, J = 8.5 Hz, 2H), 7.83-7.76 (m, 3H), 7.72 (t, J = 6.9 Hz, 1H), 7.48-7.41 (m, 2H), 7.28 (t, J = 7.8 Hz, 1H), 7.04 (d, J = 8.0 Hz, 1H), 5.81 (s, 1H), 4.73 (q, J = 7.4 Hz, 2H), 4.32-4.25 (m, 1H), 3.85-3.76 (m, 1H), 3.35-3.29 (m, 1H), 3.25-3.08 (m, 4H), 2.84-2.77 (m, 7H), 2.61-2.54 (m, 1H), 2.13-2.04 (m, 2H), 1.87-1.72 (m, 2H), 1.57 (t, J = 7.3 Hz, 3H) ppm. MS (ESI) m/z: 668 (M + H)$^+$. Analytical HPLC: RT = 5.93 min (Method B). |
| 95 | 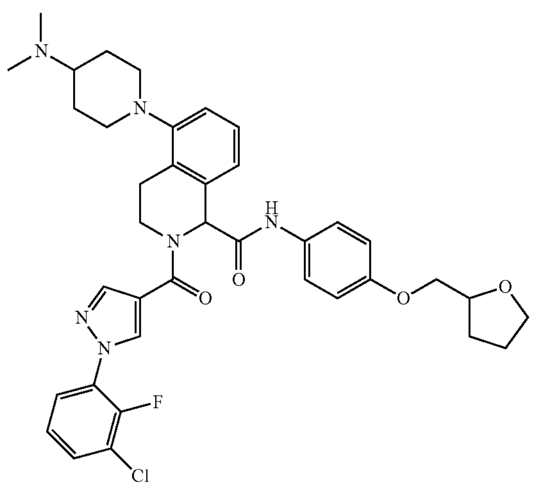 [SMILES: CN(C)C1CCN(c2cccc3c2CCN(C(=O)c2cnn(-c4cccc(Cl)c4F)c2)C3C(=O)Nc2ccc(OCC3CCCO3)cc2)CC1] | 2-(1-(3-chloro-2-fluorophenyl)-1H-pyrazole-4-carbonyl)-5-(4-(dimethylamino)piperidin-1-yl)-N-(4-((tetrahydrofuran-2-yl)methoxy)phenyl)-1,2,3,4-tetrahydroisoquinoline-1-carboxamide, TFA salt | $^1$H NMR (500 MHz, DMSO-d$_6$) δ 10.35 (s, 1H), 9.63 (br.s., 1H), 8.22 (s, 1H), 7.82 (t, J = 7.2 Hz, 1H), 7.72 (t, J = 6.9 Hz, 1H), 7.49 (d, J = 9.1 Hz, 2H), 7.46-7.40 (m, 2H), 7.26 (t, J = 7.7 Hz, 1H), 7.03 (d, J = 7.7 Hz, 1H), 6.87 (d, J = 9.1 Hz, 2H), 5.77 (s, 1H), 4.29-4.21 (m, 1H), 4.12 (qd, J = 6.7, 4.1 Hz, 1H), 3.93-3.84 (m, 2H), 3.82-3.75 (m, 2H), 3.70-3.64 (m, 1H), 3.34-3.27 (m, 1H), 3.25-3.20 (m, 1H), 3.18-3.13 (m, 2H), 3.09-3.04 (m, 1H), 2.84-2.75 (m, 7H), 2.59 (t, J = 11.7 Hz, 1H), 2.09 (t, J = 12.7 Hz, 2H), 2.02-1.95 (m, 1H), 1.91-1.73 (m, 4H), 1.65 (ddt, J = 12.1, 8.6, 6.9 Hz, 1H) ppm. MS (ESI) m/z: 701 (M + H)$^+$. Analytical HPLC: RT = 5.88 min (Method B). |
| 96 | 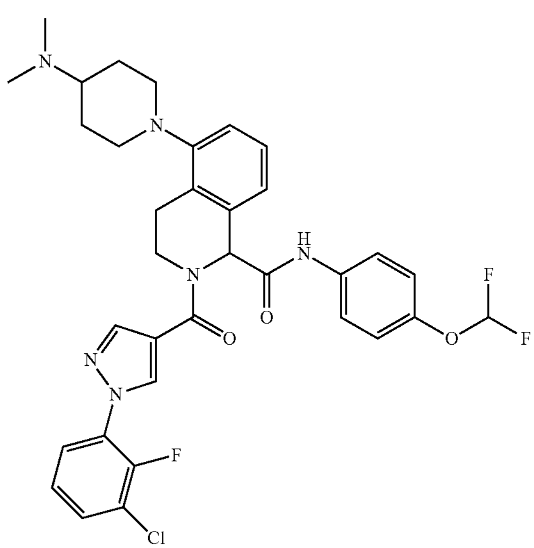 [SMILES: CN(C)C1CCN(c2cccc3c2CCN(C(=O)c2cnn(-c4cccc(Cl)c4F)c2)C3C(=O)Nc2ccc(OC(F)F)cc2)CC1] | 2-(1-(3-chloro-2-fluorophenyl)-1H-pyrazole-4-carbonyl)-N-(4-(difluoromethoxy)phenyl)-5-(4-(dimethylamino)piperidin-1-yl)-1,2,3,4-tetrahydroisoquinoline-1-carboxamide, TFA salt | $^1$H NMR (500 MHz, DMSO-d$_6$) δ 10.59 (s, 1H), 8.72 (d, J = 1.7 Hz, 1H), 8.22 (s, 1H), 7.82 (t, J = 7.0 Hz, 1H), 7.72 (t, J = 6.7 Hz, 1H), 7.63 (d, J = 8.8 Hz, 2H), 7.46-7.40 (m, 2H), 7.29-7.24 (m, 1H), 7.16-7.11 (m, 2H), 7.03 (d, J = 7.7 Hz, 1H), 5.77 (s, 1H), 4.29-4.23 (m, 1H), 3.84-3.77 (m, 1H), 3.34-3.28 (m, 1H), 3.25-3.22 (m, 1H), 3.18-3.07 (m, 3H), 2.85-2.75 (m, 8H), 2.61-2.56 (m, 1H), 2.11-2.06 (m, 2H), 1.85-1.74 (m, 2H) ppm. MS (ESI) m/z: 667 (M + H)$^+$. Analytical HPLC: RT = 5.84 min (Method B). |

TABLE 5-continued

| Example | Structure | Name | Analytical Data |
|---|---|---|---|
| 97 | 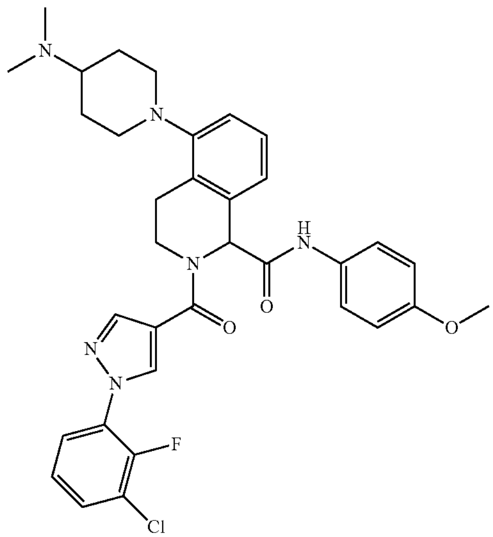 | 2-(1-(3-chloro-2-fluorophenyl)-1H-pyrazole-4-carbonyl)-5-(4-(dimethylamino)piperidin-1-yl)-N-(4-methoxyphenyl)-1,2,3,4-tetrahydroisoquinoline-1-carboxamide, TFA salt | $^1$H NMR (500 MHz, DMSO-$d_6$) δ 10.35 (s, 1H), 8.72 (s, 1H), 8.22 (s, 1H), 7.84-7.80 (m, 1H), 7.72 (t, J = 6.9 Hz, 1H), 7.54-7.49 (m, 2H), 7.46-7.41 (m, 2H), 7.26 (t, J = 7.8 Hz, 1H), 7.03 (d, J = 8.0 Hz, 1H), 6.90-6.84 (m, 2H), 5.77 (s, 1H), 4.27-4.23 (m, 1H), 3.83-3.78 (m, 1H), 3.74-3.71 (m, 4H), 3.34-3.29 (m, 1H), 3.25-3.21 (m, 1H), 3.18-3.14 (m, 1H), 3.10-3.02 (m, 1H), 2.83-2.78 (m, 7H), 2.54-2.57 (m, 1H), 2.11-2.04 (m, 2H), 1.85-1.74 (m, 2H) ppm. MS (ESI) m/z: 631 (M + H)$^+$. Analytical HPLC: RT = 5.60 min (Method B). |

EXAMPLE 98

2-(1-(3-Chloro-2-fluorophenyl)-1H-1,2,3-triazole-4-carbonyl)-5-(4-(dimethylamino) piperidin-1-yl)-N-(4-(5-methyl-1,2,4-oxadiazol-3-yl)phenyl)-1,2,3,4-tetrahydroisoquinoline-1-carboxamide, bis-TFA salt

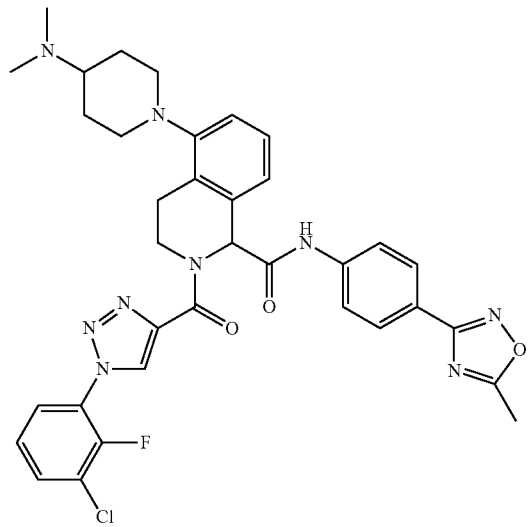 [SMILES: Cc1nc(-c2ccc(NC(=O)C3c4cccc(N5CCC(N(C)C)CC5)c4CCN3C(=O)c3cn(-c4cccc(Cl)c4F)nn3)cc2)no1]

Example 98. 2-(1-(3-Chloro-2-fluorophenyl)-1H-1,2,3-triazole-4-carbonyl)-5-(4-(dimethylamino)piperidin-1-yl)-N-(4-(5-methyl-1,2,4-oxadiazol-3-yl)phenyl)-1,2,3,4-tetrahydroisoquinoline-1-carboxamide, TFA salt: The title compound was made in a similar manner as Example 93 replacing 4-(oxazol-2-yl)aniline hydrochloride with 4-(5-methyl-1,2,4-oxadiazol-3-yl)aniline during isonitrile preparation and using Intermediate 9 in the Ugi reaction. $^1$H NMR (400 MHz, DMSO-$d_6$) δ 10.91 (s, 1H), 9.18 (d, J=1.8 Hz, 1H), 7.95 (d, J=8.8 Hz, 2H), 7.89 (ddd, J=8.3, 6.5, 2.1 Hz, 2H), 7.80 (d, J=8.8 Hz, 2H), 7.56-7.49 (m, 1H), 7.43 (d, J=7.8 Hz, 1H), 7.28 (t, J=7.8 Hz, 1H), 7.04 (d, J=7.8 Hz, 1H), 5.90 (s, 1H), 4.61-4.54 (m, 1H), 4.14-4.06 (m, 1H), 3.34-3.07 (m, 5H), 2.86-2.80 (m, 6H), 2.77-2.68 (m, 2H), 2.65 (s, 3H), 2.12-2.06 (m, 2H), 1.82 (dd, J=11.9, 8.1 Hz, 2H) ppm. MS (ESI) m/z: 684 (M+H)$^+$. Analytical HPLC: RT=6.09 min (Method B).

EXAMPLE 99

N-(4-Carbamoylphenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide, bis-TFA salt

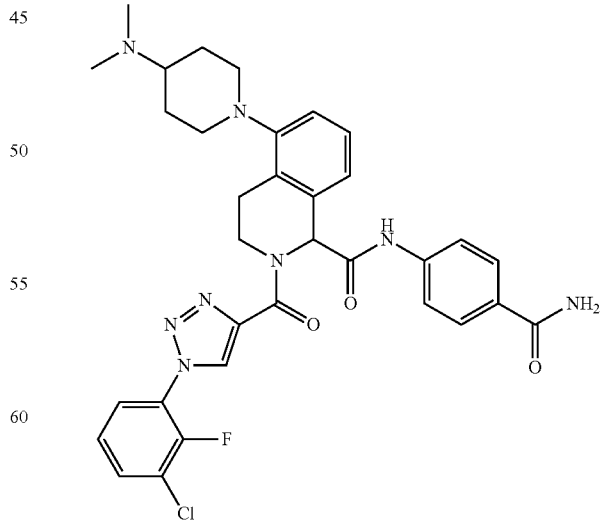

Example 99. N-(4-Carbamoylphenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide, TFA salt: DIPEA (0.168 mL, 0.961 mmol) was added to a stirring solution of the racemate of Example 48 (0.14 g, 0.16 mmol), HOBt (0.032 g, 0.24 mmol), EDC (0.046 g, 0.24 mmol), and NH$_4$Cl (0.051 g, 0.96 mmol) in DMF (1.602 mL). After stirring for 16 h, the reaction was filtered, purified by reverse phase prep. HPLC, and freeze-dried to give Example 99 (101 mg, 71%) as a white solid. $^1$H NMR (500 MHz, DMSO-d$_6$) δ 10.75 (s, 1H), 9.10 (d, J=1.9 Hz, 1H), 7.87-7.74 (m, 5H), 7.60 (d, J=8.8 Hz, 2H), 7.48-7.44 (m, 1H), 7.34 (d, J=7.4 Hz, 1H), 7.20 (t, J=7.8 Hz, 1H), 6.96 (d, J=7.7 Hz, 1H), 5.82 (s, 1H), 4.54-4.47 (m, 1H), 4.07-4.02 (m, 1H), 3.21-3.16 (m, 1H), 3.13-3.06 (m, 1H), 3.03-2.93 (m, 1H), 2.77-2.72 (m, 6H), 2.66-2.57 (m, 2H), 2.03-1.98 (m, 2H), 1.79-1.71 (m, 2H) ppm. MS (ESI) m/z: 645 (M+H)$^+$. Analytical HPLC: RT=5.01 min (Method B).

EXAMPLE 100

(R)-N-(4-Carbamoylphenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide, bis-TFA salt

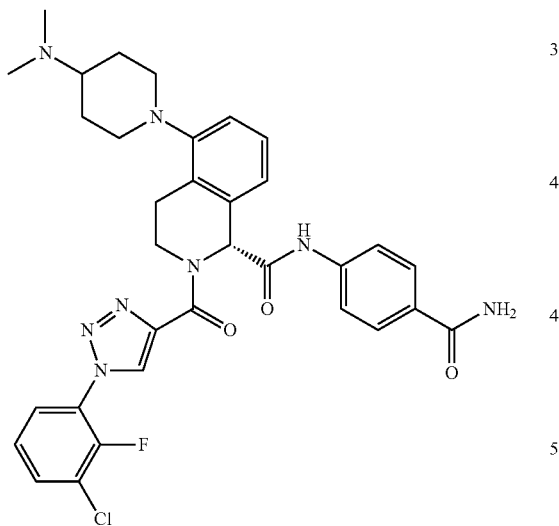

Example 100. ((R)-N-(4-Carbamoylphenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide, bis-TFA salt: The title compound was the early eluting enantiomer after chiral HPLC separation of Example 99 using CHIRALCEL® OD-H, 21×250 mm ID, 5 µ, using 30% MeOH-DEA (0.1%)/70% CO$_2$ at 70.0 mL/min, 100 bar, and 35° C. $^1$H NMR (500 MHz, methanol-d$_4$) δ 10.44 (s, 1H), 8.79 (d, J=2.2 Hz, 1H), 7.78-7.70 (m, 3H), 7.64 (td, J=7.5, 1.5 Hz, 1H), 7.60-7.51 (m, 2H), 7.35 (td, J=8.3, 1.4 Hz, 1H), 7.28-7.23 (m, 1H), 7.19 (t, J=7.8 Hz, 1H), 7.00 (d, J=7.7 Hz, 1H), 5.77 (s, 1H), 4.62 (dt, J=12.4, 4.9 Hz, 1H), 4.06-3.96 (m, 1H), 3.19-3.05 (m, 3H), 2.84 (s, 6H), 2.82-2.75 (m, 1H), 2.67-2.58 (m, 1H), 2.17-2.03 (m, 2H), 1.94-1.77 (m, 2H) ppm. MS (ESI) m/z: 645 (M+H)$^+$. Analytical HPLC: RT=5.17 min (Method B).

EXAMPLE 101

(S)-N-(4-Carbamoylphenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide, bis-TFA salt

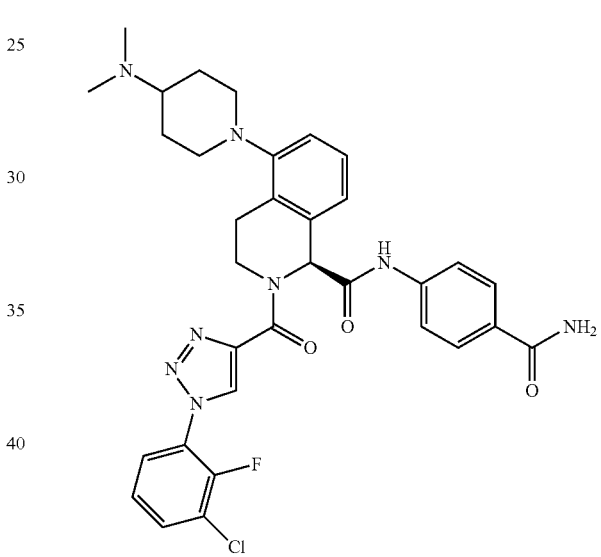

Example 101. ((S)-N-(4-Carbamoylphenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide, bis-TFA salt: The title compound was the late eluting enantiomer after chiral HPLC separation of Example 99 using CHIRALCEL® OD-H, 21×250 mm ID, 5 µ, using 30% MeOH-DEA (0.1%)/70% CO$_2$ at 70.0 mL/min, 100 bar, and 35° C. $^1$H NMR (400 MHz, methanol-d$_4$) δ 10.58 (s, 1H), 8.93 (s, 1H), 7.93-7.85 (m, 3H), 7.80-7.76 (m, 1H), 7.74-7.66 (m, 2H), 7.49 (t, J=8.2 Hz, 1H), 7.42-7.38 (m, 1H), 7.34 (t, J=7.7 Hz, 1H), 7.15 (d, J=7.8 Hz, 1H), 5.93 (s, 1H), 4.80-4.72 (m, 1H), 4.22-4.11 (m, 1H), 3.45-3.39 (m, 2H), 3.31-3.23 (m, 2H), 3.06-2.89 (m, 7H), 2.78 (t, J=11.6 Hz, 1H), 2.24 (t, J=14.0 Hz, 2H), 2.09-1.96 (m, 2H) ppm. MS (ESI) m/z: 645 (M+H)$^+$. Analytical HPLC: RT=5.15 min (Method B).

EXAMPLE 102

N-(4-(1H-Pyrazol-4-yl)phenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide, bis-TFA salt

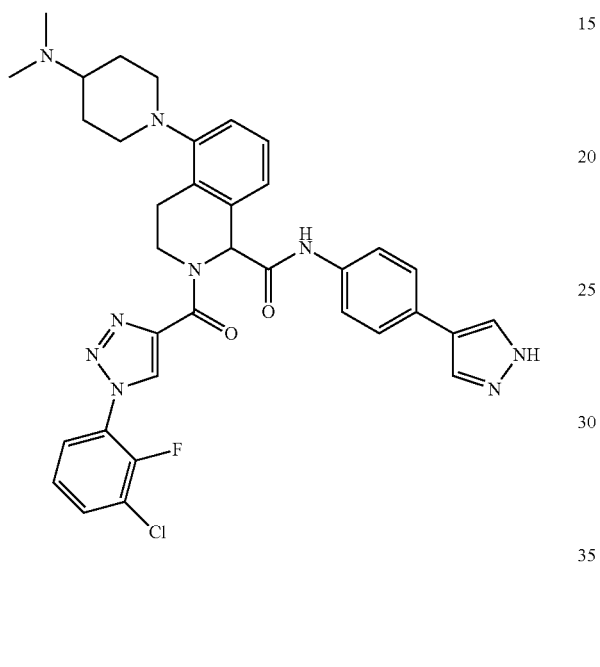

102A. N-(4-Bromophenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide: To a septa capped pressure vial was charged Intermediate 4A (0.250 g, 0.971 mmol), Intermediate 9 (235 mg, 0.971 mmol), commercially available 1-bromo-4-isocyanobenzene (0.177 g, 0.971 mmol) and MeOH (1.94 mL) stirred at 50° C. After 20 h, the reaction was concentrated and purified by normal phase column chromatography to afford 102A (192 mg, 29%) as a solid. MS (ESI) m/z: 680/682 (M+H)$^+$; Br isotope.

Example 102. N-(4-(1H-Pyrazol-4-yl)phenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide, bis-TFA salt: A stirring suspension of 102A (0.040 g, 0.059 mmol), tert-butyl 4-(4,4,5,5-tetramethyl-1,3,2-dioxaborolan-2-yl)-1H-pyrazole-1-carboxylate (0.021 g, 0.07 mmol), and $Cs_2CO_3$ (0.057 g, 0.176 mmol) in DME (2 mL)/Water (0.400 mL) was degassed with argon for 15 min. Tetrakis (triphenylphosphine)palladium(0) (6.79 mg, 5.87 μmol) was added and the mixture irradiated at 120° C. for 20 minutes. The reaction mixture was filtered through a plug of CELITE® and the filtrate partitioned between EtOAc and water. The aqueous layer was re-extracted with EtOAc (2×). The combined organic layers were washed with saturated $NaHCO_3$ solution, brine, dried over sodium sulfate, filtered and concentrated. The boc group was removed by treatment with 50% TFA/DCM for 1 h before concentrating, purifying by reverse phase prep HPLC, and freeze-drying to give a white solid (14 mg, 25%). $^1$H NMR (500 MHz, DMSO-d$_6$) δ 10.60 (s, 1H), 9.18 (d, J=1.7 Hz, 1H), 8.01-7.97 (m, 2H), 7.92-7.88 (m, 2H), 7.63-7.59 (m, 2H), 7.57-7.51 (m, 4H), 7.42 (d, J=7.7 Hz, 1H), 7.28 (t, J=7.8 Hz, 1H), 7.04 (d, J=8.0 Hz, 1H), 5.90 (s, 1H), 4.55-4.51 (m, 1H), 4.21-4.15 (m, 1H), 3.34-3.25 (m, 2H), 3.19-3.14 (m, 2H), 3.09-3.03 (m, 1H), 2.82 (d, J=4.7 Hz, 6H), 2.74-2.66 (m, 2H), 2.11-2.07 (m, 2H), 1.86-1.78 (m, 2H) ppm. MS (ESI) m/z: 668 (M+H)$^+$. Analytical HPLC: RT=5.54 min (Method B).

EXAMPLE 103

(R)-N-(4-(1H-Pyrazol-4-yl)phenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide, bis-TFA salt

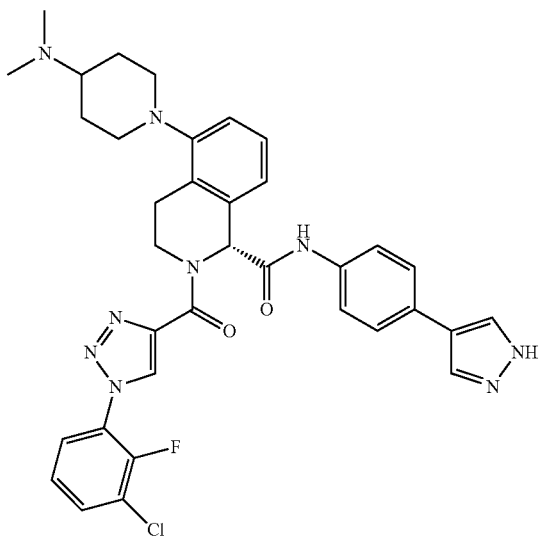 [SMILES: CN(C)C1CCN(c2cccc3c2CCN(C(=O)c2cn(-c4cccc(Cl)c4F)nn2)[C@H]3C(=O)Nc2ccc(-c3cn[nH]c3)cc2)CC1]

Example 103. (R)-N-(4-(1H-Pyrazol-4-yl)phenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide, bis-TFA salt: The title compound was the early eluting enantiomer of after chiral HPLC separation of Example 102 using CHIRALCEL® OD-H, 21×250 mm ID, 5 μ, using 30-50% MeOH-DEA (0.1%)/CO$_2$ at 70.0 mL/min, 100 bar, and 35° C. $^1$H NMR (500 MHz, DMSO-d$_6$) δ 10.60 (s, 1H), 9.18 (d, J=1.4 Hz, 1H), 8.02-7.97 (m, 2H), 7.92-7.87 (m, 2H), 7.63-7.58 (m, 2H), 7.57-7.49 (m, 3H), 7.42 (d, J=7.7 Hz, 1H), 7.28 (t, J=7.8 Hz, 1H), 7.04 (d, J=8.0 Hz, 1H), 5.90 (s, 1H), 4.57-4.49 (m, 1H), 4.17 (ddd, J=12.4, 8.3, 4.1 Hz, 1H), 3.35-3.12 (m, 4H), 3.08-3.02 (m, 1H), 2.85-2.79 (m, 6H), 2.74-2.65 (m, 2H), 2.09 (d, J=10.2 Hz, 2H), 1.89-1.75 (m, 2H) ppm. MS (ESI) m/z: 668 (M+H)$^+$. Analytical HPLC: RT=5.67 min (Method B).

EXAMPLE 104

(S)-N-(4-(1H-Pyrazol-4-yl)phenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide, bis-TFA salt

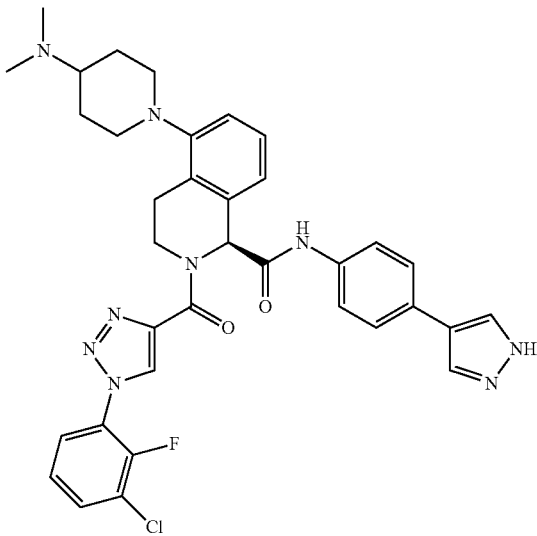 [SMILES: CN(C)C1CCN(c2cccc3c2CCN(C(=O)c2cn(-c4cccc(Cl)c4F)nn2)[C@@H]3C(=O)Nc2ccc(-c3cn[nH]c3)cc2)CC1]

Example 104. (S)-N-(4-(1H-Pyrazol-4-yl)phenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide, bis-TFA salt: the title compound was the late eluting enantiomer after chiral HPLC separation of Example 102 using CHIRALCEL® OD-H, 21×250 mm ID, 5 μ, using 30-50% MeOH-DEA (0.1%)/CO$_2$ at 70.0 mL/min, 100 bar, and 35° C. $^1$H NMR (500 MHz, DMSO-d$_6$) δ 10.52 (s, 1H), 9.10 (d, J=1.7 Hz, 1H), 7.94-7.89 (m, 2H), 7.84-7.79 (m, 2H), 7.55-7.51 (m, 2H), 7.48-7.42 (m, 3H), 7.34 (d, J=7.7 Hz, 1H), 7.23-7.17 (m, 1H), 6.96 (d, J=8.0 Hz, 1H), 5.82 (s, 1H), 4.51-4.42 (m, 1H), 4.09 (ddd, J=12.5, 8.3, 4.3 Hz, 1H), 3.27-3.07 (m, 4H), 3.03-2.94 (m, 1H), 2.78-2.72 (m, 7H), 2.66-2.55 (m, 2H), 2.05-1.97 (m, 2H), 1.81-1.69 (m, 2H) ppm. MS (ESI) m/z: 668 (M+H)$^+$. Analytical HPLC: RT=5.67 min (Method B).

EXAMPLE 105

N-(4-(1H-Tetrazol-5-yl)phenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide, bis-TFA salt

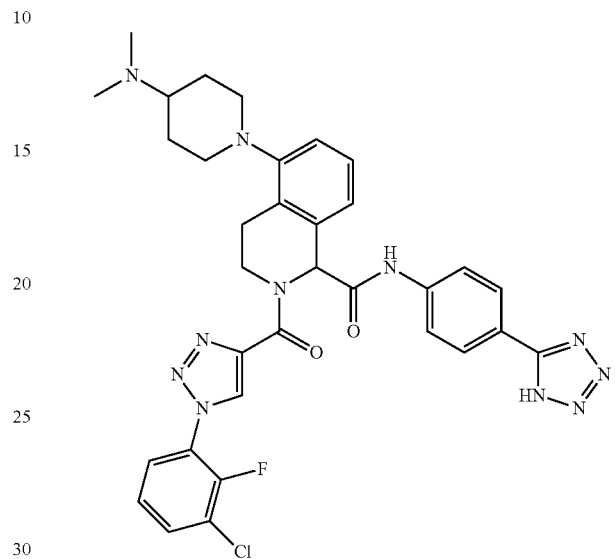

105A. 4-Isocyanobenzonitrile: 105A was prepared in the same manner was Intermediate 1 replacing tert-butyl 4-aminobenzoate with 4-aminobenzonitrile. $^1$H NMR: (400 MHz, DMSO-d$_6$) δ 8.03 (d, J=8.3 Hz, 2H), 7.87-7.77 (m, 2H) ppm.

105B. 2-(1-(3-Chloro-2-fluorophenyl)-1H-1,2,3-triazole-4-carbonyl)-N-(4-cyanophenyl)-5-(4-(dimethylamino)piperidin-1-yl)-1,2,3,4-tetrahydroisoquinoline-1-carboxamide: A septa capped pressure vial was charged Intermediate 4A (0.300 g, 1.17 mmol), Intermediate 9 (282 mg, 1.17 mmol), 105A (0.149 g, 1.17 mmol) and MeOH (2.33 mL) stirred at 60° C. After 20 h, the reaction was concentrated and purified by normal phase column chromatography to give 105B (183 mg, 25%). MS (ESI) m/z: 627 (M+H)$^+$.

Example 105. N-(4-(1H-Tetrazol-5-yl)phenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide, bis-TFA salt: 105B (0.183 g, 0.292 mmol) and trimethyltin azide (0.120 g, 0.584 mmol) were added to toluene (4.86 mL) and heated at 115° C. overnight. The reaction was cooled and treated with MeOH (8 mL). After 1 h, the reaction mixture was concentrated. The crude material was purified by reverse phase prep. HPLC and freeze-dried to give Example 105 as a white solid (23 mg, 8%). $^1$H NMR (500 MHz, DMSO-d$_6$) δ 10.95 (s, 1H), 9.19 (d, J=1.7 Hz, 1H), 8.00 (d, J=8.5 Hz, 2H), 7.92-7.82 (m, 4H), 7.53 (td, J=8.2, 1.5 Hz, 1H), 7.43 (d, J=7.7 Hz, 1H), 7.32-7.26 (m, 1H), 7.05 (d, J=7.7 Hz, 1H), 5.91 (s, 1H), 4.58 (dt, J=12.5, 5.0 Hz, 1H), 4.11 (ddd, J=12.6, 8.6, 3.9 Hz, 1H), 3.36-3.06 (m, 5H), 2.82 (d, J=3.9 Hz, 6H), 2.76-2.63 (m, 2H), 2.12-2.06 (m, 2H), 1.88-1.76 (m, 2H) ppm. MS (ESI) m/z: 670 (M+H)$^+$. Analytical HPLC: RT=5.38 min (Method B).

EXAMPLE 106

4-(2-(1-(3-Chloro-2-fluorophenyl)-1H-1,2,3-triazole-4-carbonyl)-5-(2-methyl-1-oxo-2,8-diazaspiro[4.5]decan-8-yl)-1,2,3,4-tetrahydroisoquinoline-1-carboxamido)benzoic acid, TFA salt

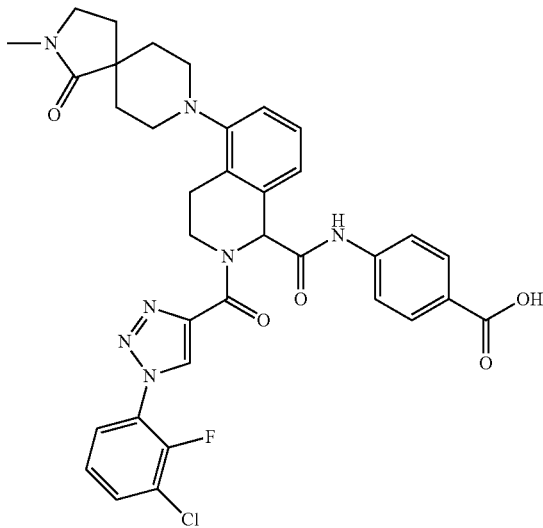 [SMILES: CN1CCC2(CCN(c3cccc4c3CCN(C(=O)c3cn(-c5cccc(Cl)c5F)nn3)C4C(=O)Nc3ccc(C(=O)O)cc3)CC2)C1=O]

106A. tert-Butyl 4-(5-(2-methyl-1-oxo-2,8-diazaspiro[4.5]decan-8-yl)-2-(2,2,2-trifluoroacetyl)-1,2,3,4-tetrahydroisoquinoline-1-carboxamido)benzoate: To a septa capped pressure vial was charged Intermediate 4R (0.652 g, 2.19 mmol) and Intermediate 1 (0.446 g, 2.19 mmol) and DCM (anhydrous) (2.0 mL). A solution of TFA (0.168 mL, 2.19 mmol) in DCM (anhydrous) (2.38 mL) was added, the vial was capped and the contents heated at 50° C. After stirring for 48 h, the reaction mixture was concentrated, purified by reverse phase prep HPLC, and evaporated to give 106A as a solid (218 mg, 16%). MS (ESI) m/z: 615 (M+H)$^+$.

106B. tert-Butyl 4-(5-(2-methyl-1-oxo-2,8-diazaspiro[4.5]decan-8-yl)-1,2,3,4-tetrahydroisoquinoline-1-carboxamido)benzoate (trifluoroacetamide deprotection): NaBH$_4$ (0.134 g, 3.56 mmol) was added to a solution of 106A (0.218 g, 0.355 mmol) in MeOH (11.08 mL) at 0° C. The reaction mixture was stirred at 25° C. for 2 days before quenching with water. The solution was partitioned between EtOAc and aqueous saturated NaHCO$_3$ solution. The organic layer was washed again with aqueous saturated NaHCO$_3$ solution, brine, dried over magnesium sulfate, filtered, and concentrated. The product (0.075 g, 0.145 mmol, 40.8% yield) was sufficiently pure to carry forward next reaction without further purification.

Example 106. 4-(2-(1-(3-Chloro-2-fluorophenyl)-1H-1,2,3-triazole-4-carbonyl)-5-(2-methyl-1-oxo-2,8-diazaspiro[4.5]decan-8-yl)-1,2,3,4-tetrahydroisoquinoline-1-carboxamido)benzoic acid, TFA salt: DIPEA (0.054 mL, 0.308 mmol) was added to a solution of 106B (0.040 g, 0.077 mmol), Intermediate 9 (0.028 g, 0.116 mmol), EDC (0.030 g, 0.154 mmol), and HOBt (0.024 g, 0.154 mmol) in DMF (1.0 mL). After 3 days, the reaction mixture was diluted with EtOAc, washed with water, 1.0 M HCl solution, brine, dried over sodium sulfate, filtered, and concentrated. The residue was treated with 50% TFA/DCM. After 3 h, the reaction mixture was concentrated. The residue was purified by reverse phase prep HPLC and freeze-dried to afford the desired product (10 mg, 16%) as a white solid. $^1$H NMR (500 MHz, DMSO-d$_6$) δ 10.89 (s, 1H), 9.17 (d, J=1.7 Hz, 1H), 7.93-7.84 (m, 4H), 7.73 (d, J=8.8 Hz, 2H), 7.52 (td, J=8.1, 1.4 Hz, 1H), 7.40 (d, J=7.7 Hz, 1H), 7.26 (t, J=7.8 Hz, 1H), 7.05 (d, J=8.0 Hz, 1H), 5.88 (s, 1H), 4.58-4.52 (m, 1H), 4.07-4.00 (m, 1H), 3.31 (t, J=7.0 Hz, 2H), 3.17-3.01 (m, 4H), 2.79-2.73 (m, 4H), 2.72-2.65 (m, 1H), 2.01-1.85 (m, 4H), 1.47 (t, J=12.8 Hz, 2H) ppm. MS (ESI) m/z: 686 (M+H)$^+$. Analytical HPLC: RT=6.78 min (Method B).

EXAMPLE 107

4-(2-(1-(3-Chloro-2-fluorophenyl)-1H-pyrazole-4-carbonyl)-5-(2-methyl-1-oxo-2,8-diazaspiro[4.5]decan-8-yl)-1,2,3,4-tetrahydroisoquinoline-1-carboxamido)benzoic acid, TFA salt

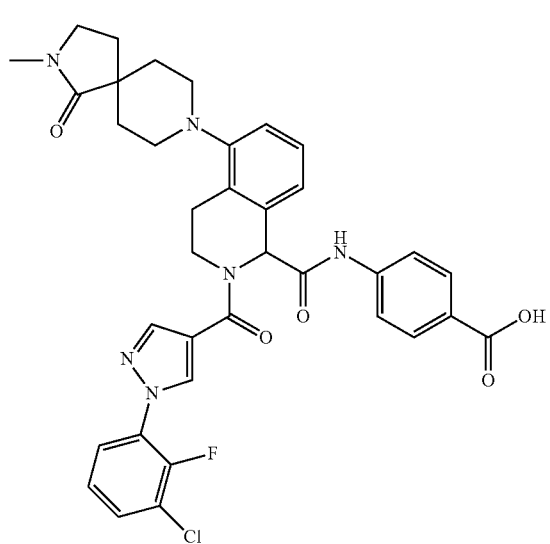 [SMILES: CN1CCC2(CCN(c3cccc4c3CCN(C(=O)c3cnn(-c5cccc(Cl)c5F)c3)C4C(=O)Nc3ccc(C(=O)O)cc3)CC2)C1=O]

Example 107. 4-(2-(1-(3-Chloro-2-fluorophenyl)-1H-pyrazole-4-carbonyl)-5-(2-methyl-1-oxo-2,8-diazaspiro[4.5]decan-8-yl)-1,2,3,4-tetrahydroisoquinoline-1-carboxamido)benzoic acid, TFA salt: The title compound was prepared in a similar manner as Example 106 replacing Intermediate 9 with Intermediate 13 in amide coupling step. $^1$H NMR (500 MHz, DMSO d$_6$) δ 10.79 (s, 1H), 8.72 (d, J=1.7 Hz, 1H), 8.22 (s, 1H), 7.88 (d, J=8.8 Hz, 2H), 7.84-7.80 (m, 1H), 7.71 (d, J=8.8 Hz, 3H), 7.46-7.39 (m, 2H), 7.25 (t, J=7.8 Hz, 1H), 7.03 (d, J=7.7 Hz, 1H), 5.78 (s, 1H), 4.30-4.25 (m, 1H), 3.81-3.75 (m, 1H), 3.30 (t, J=7.0 Hz, 2H), 3.14-3.11 (m, 2H), 3.02 (t, J=12.1 Hz, 2H), 2.85-2.80 (m, 1H), 2.75 (s, 3H), 2.66-2.58 (m, 1H), 1.98-1.85 (m, 4H), 1.54-1.41 (m, 2H) ppm. MS (ESI) m/z: 685 (M+H)$^+$. Analytical HPLC: RT=6.78 min (Method B).

EXAMPLE 108

4-(2-(1-(3-Chloro-2-fluorophenyl)-1H-1,2,3-triazole-4-carbonyl)-5-cyano-1,2,3,4-tetrahydroisoquinoline-1-carboxamido)benzoic acid

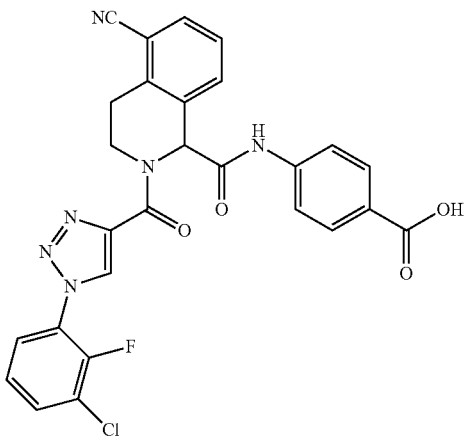 [SMILES: N#Cc1cccc2c1CCN(C(=O)c1cn(-c3cccc(Cl)c3F)nn1)C2C(=O)Nc1ccc(C(=O)O)cc1]

108A. tert-Butyl 4-(2-(1-(3-chloro-2-fluorophenyl)-1H-1,2,3-triazole-4-carbonyl)-5-cyano-1,2,3,4-tetrahydroisoquinoline-1-carboxamido)benzoate: To commercially available 1,2,3,4-tetrahydroisoquinoline-5-carbonitrile (0.30 g, 1.90 mmol) in DCM (anhydrous) (60 mL) was added $MnO_2$ (2.97 g, 34.1 mmol) portionwise and the mixture stirred at ambient temperature overnight. The reaction mixture was filtered through a CELITE® pad with the aid of DCM and evaporated to give as a off-white solid. The imine, Intermediate 9 (0.458 g, 1.90 mmol), and Intermediate 1 (0.385 g, 1.90 mmol) were added to MeOH (3.79 mL) and heated to 50° C. for 18 h. The solids were collected by filtration, washed with cold MeOH, and dried under vacuum to give 108A (0.385 g, 0.641 mmol, 33.8% yield). MS (ESI) m/z: 601 (M+H)$^+$.

Example 108. 4-(2-(1-(3-Chloro-2-fluorophenyl)-1H-1,2,3-triazole-4-carbonyl)-5-cyano-1,2,3,4-tetrahydroisoquinoline-1-carboxamido)benzoic acid: 109A (0.050 g, 0.083 mmol) was treated with 50% TFA/DCM. After 2 h, the reaction mixture was concentrated, purified by reverse phase prep HPLC, and freeze-dried to give Example 109 (22 mg, 46%) as a white solid. $^1$H NMR (400 MHz, DMSO-d$_6$) δ 12.75 (br. s., 1H), 11.02 (s, 1H), 9.19 (d, J=1.5 Hz, 1H), 7.99 (d, J=7.8 Hz, 1H), 7.94-7.82 (m, 5H), 7.73 (d, J=8.8 Hz, 2H), 7.60-7.47 (m, 2H), 6.06 (s, 1H), 4.60-4.42 (m, 2H), 3.28-3.05 (m, 2H) ppm. MS (ESI) m/z: 545 (M+H)$^+$. Analytical HPLC: RT=6.99 min (Method B).

EXAMPLE 109

4-(5-(Aminomethyl)-2-(1-(3-chloro-2-fluorophenyl)-1H-1,2,3-triazole-4-carbonyl)-1,2,3,4-tetrahydroisoquinoline-1-carboxamido)benzoic acid, TFA salt

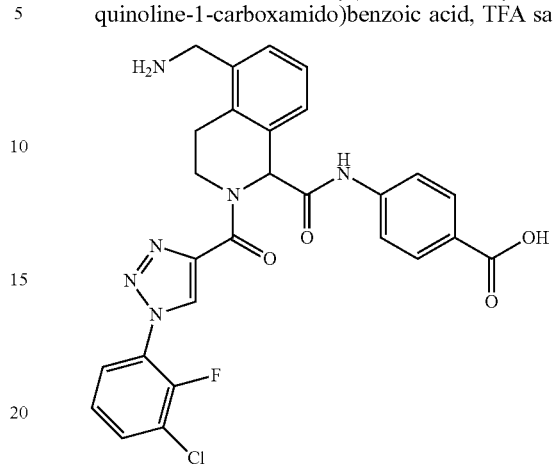

Example 109. 4-(5-(Aminomethyl)-2-(1-(3-chloro-2-fluorophenyl)-1H-1,2,3-triazole-4-carbonyl)-1,2,3,4-tetrahydroisoquinoline-1-carboxamido)benzoic acid, TFA Salt: Raney nickel (slurry in water) (9.77 mg, 0.166 mmol) was added to a solution of 108A (0.100 g, 0.166 mmol) in ammonia MeOH (10 mL) and subjected to a hydrogen atmosphere (55 psi). After 18 h, the reaction mixture was filtered through a CELITE® pad and concentrated. The residue was treated with 50% TFA/DCM for 3 h, concentrated, purified by reverse phase prep, and freeze-dried to give Example 109 (39 mg, 34%) as white solid. $^1$H NMR (400 MHz, DMSO-d$_6$) δ 10.88 (s, 1H), 9.12 (d, J=1.8 Hz, 1H), 7.88-7.77 (m, 4H), 7.66 (d, J=8.8 Hz, 3H), 7.45 (td, J=8.1, 1.4 Hz, 1H), 7.38-7.24 (m, 2H), 5.93 (s, 1H), 4.53-4.43 (m, 1H), 4.35-4.26 (m, 1H), 4.06 (s, 2H), 3.19 3.03 (m, 2H) ppm. MS (ESI) m/z: 549 (M+H)$^+$. Analytical HPLC: RT=5.25 min (Method B).

EXAMPLE 110

4-(5-Bromo-2-(1-(3-chloro-2-fluorophenyl)-1H-1,2,3-triazole-4-carbonyl)-1,2,3,4-tetrahydroisoquinoline-1-carboxamido)benzoic acid

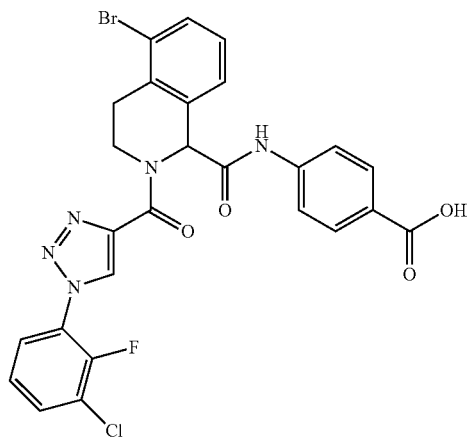 [SMILES: O=C(O)c1ccc(NC(=O)C2c3cccc(Br)c3CCN2C(=O)c2cn(-c3cccc(Cl)c3F)nn2)cc1]

Example 110. 4-(5-Bromo-2-(1-(3-chloro-2-fluorophenyl)-1H-1,2,3-triazole-4-carbonyl)-1,2,3,4-tetrahydroisoquinoline-1-carboxamido)benzoic acid: Intermediate 24 (50 mg, 0.076 mmol) was treated with 50% TFA/DCM for 2 h, concentrated, purified by reverse phase prep, and freeze-dried to give Example 110 (32 mg, 69%) as white solid. $^1$H NMR (400 MHz, DMSO-d$_6$) δ 12.66 (br. s., 1H), 10.92 (s, 1H), 9.11 (d, J=1.5 Hz, 1H), 7.88-7.78 (m, 4H), 7.69-7.61 (m, 3H), 7.56 (d, J=7.8 Hz, 1H), 7.45 (t, J=7.5 Hz, 1H), 7.21 (t, J=7.8 Hz, 1H), 5.94 (s, 1H), 4.47-4.39 (m, 1H), 4.38-4.28 (m, 1H), 3.15-2.99 (m, 2H) ppm. MS (ESI) m/z: 598/600 (M+H)$^+$(Br isotope). Analytical HPLC: RT=7.88 min (Method B).

EXAMPLE 111

4-(2-(1-(3-Chloro-2-fluorophenyl)-1H-1,2,3-triazole-4-carbonyl)-5-((2-hydroxyethyl)amino)-1,2,3,4-tetrahydroisoquinoline-1-carboxamido)benzoic acid, TFA salt

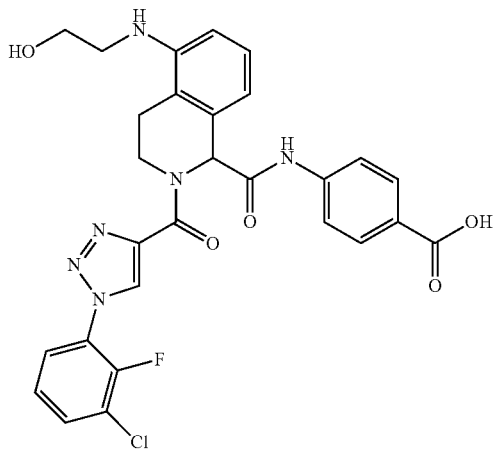 [SMILES: O=C(O)c1ccc(NC(=O)C2c3cccc(NCCO)c3CCN2C(=O)c2cn(-c3cccc(Cl)c3F)nn2)cc1]

Example 111. 4-(2-(1-(3-Chloro-2-fluorophenyl)-1H-1,2,3-triazole-4-carbonyl)-5-((2-hydroxyethyl)amino)-1,2,3,4-tetrahydroisoquinoline-1-carboxamido)benzoic acid, TFA salt: A vial containing K$_2$CO$_3$ (0.106 g, 0.763 mmol), 2-aminoethanol (0.019 g, 0.305 mmol), di-tert-butyl(2',4',6'-triisopropyl-3,6-dimethoxy-[1,1'-biphenyl]-2-yl)phosphine (0.015 g, 0.031 mmol) and tris(dibenzylideneacetone)dipalladium(0) (6.99 mg, 7.63 μmol) was purged with a argon. A separate vial containing Intermediate 24 (0.100 g, 0.153 mmol), t-butanol (1.862 mL), DMF (1.0 mL), and acetic acid (1 drop) was purged with argon through the liquid for 10 min. Then the contents were added to first vial quickly, argon was flushed through and the vial was sealed and heated at 110° C. After 18 h, the reaction mixture was filtered, filtrate concentrated, and the residue purified by reverse phase prep. The t-butyl ester was removed by treatment with 50% TFA/DCM for 3 h, concentrated, the crude material purified by reverse phase prep HPLC, freeze-dried to give a white solid (5 mg, 4%). $^1$H NMR (500 MHz, DMSO-d$_6$) δ 10.91 (s, 1H), 9.16 (d, J=1.7 Hz, 1H), 7.94-7.86 (m, 4H), 7.78-7.73 (m, 2H), 7.52 (td, J=8.1, 1.4 Hz, 1H), 7.10 (t, J=7.8 Hz, 1H), 6.92 (d, J=7.7 Hz, 1H), 6.56 (d, J=8.3 Hz, 1H), 5.89 (s, 1H), 4.50-4.35 (m, 2H), 3.60 (t, J=6.1 Hz, 2H), 3.17 (t, J=6.1 Hz, 2H), 2.88-2.75 (m, 2H) ppm. MS (ESI) m/z: 579 (M+H)$^+$. Analytical HPLC: RT=6.05 min (Method B).

EXAMPLE 112

4-(2-(1-(3-Chloro-2-fluorophenyl)-1H-1,2,3-triazole-4-carbonyl)-5-(piperidin-4-yloxy)-1,2,3,4-tetrahydroisoquinoline-1-carboxamido)benzoic acid, TFA salt

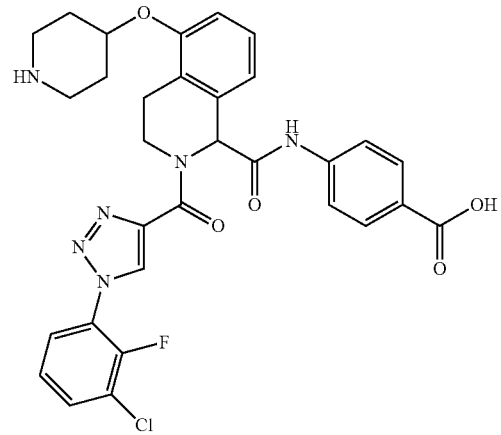 [SMILES: O=C(O)c1ccc(NC(=O)C2c3cccc(OC4CCNCC4)c3CCN2C(=O)c2cn(-c3cccc(Cl)c3F)nn2)cc1]

112A. tert-Butyl 4-((3,4-dihydroisoquinolin-5-yl)oxy)piperidine-1-carboxylate: NaI (0.052 g, 0.344 mmol) was added to a solution of 5-hydroxyisoquinoline (0.500 g, 3.44 mmol), tert-butyl 4-((methylsulfonyl)oxy)piperidine-1-carboxylate (0.962 g, 3.44 mmol), and Cs$_2$CO$_3$ (2.245 g, 6.89 mmol) in DMF (10 mL) and heated at 90° C. overnight. After cooling to room temperature, the reaction mixture was filtered, diluted with DCM (100 mL), washed with water, brine, dried over sodium sulfate, filtered, and concentrated. The residue was purified by normal phase column chromatography to give a brown oil. The heterocyclic ring was reduced by dissolution in EtOH (20 mL), treatment with PtO$_2$ (0.039 g, 0.172 mmol), and stirred under a hydrogen atmosphere (55 psi). After 18 h, the slurry was filtered through a plug of CELITE® and the filtrate concentrated. This material was dissolved in DCM (30 mL), treated with manganese (IV) oxide (5.39 g, 62.0 mmol), and resulting suspension stirred 20 h. The slurry was filtered through a plug of CELITE® and the filtrate concentrated to give a amber oil which was carried forward as is. MS (ESI) m/z: 331 (M+H)$^+$.

Example 112. 4-(2-(1-(3-Chloro-2-fluorophenyl)-1H-1,2,3-triazole-4-carbonyl)-5-(piperidin-4-yloxy)-1,2,3,4-tetrahydroisoquinoline-1-carboxamido)benzoic acid, TFA Salt: The title compound was prepared in a similar manner as Example 1 replacing Intermediate 3 with 112A in Ugi reaction to afford a white solid (89 mg, 19%). $^1$H NMR (500 MHz, DMSO-d$_6$) δ 11.00 (s, 1H), 9.18 (d, J=1.9 Hz, 1H), 7.95-7.85 (m, 4H), 7.80-7.73 (m, 2H), 7.59-7.49 (m, 1H), 7.31-7.21 (m, 2H), 7.09-6.97 (m, 1H), 5.98 (s, 1H), 4.72 (dt, J=6.6, 3.3 Hz, 1H), 4.49-4.38 (m, 2H), 3.19-3.09 (m, 2H), 3.25-3.30 (m, 2H), 3.07-3.00 (m, 2H), 2.16-2.04 (m, 2H), 1.89 (dt, J=6.9, 3.5 Hz, 2H) ppm. MS (ESI) m/z: 619 (M+H)$^+$. Analytical HPLC: RT=5.55 min (Method B).

EXAMPLE 113

4-(2-(1-(3-Chloro-2-fluorophenyl)-1H-1,2,3-triazole-4-carbonyl)-5-(2-methoxyethoxy)-1,2,3,4-tetrahydroisoquinoline-1-carboxamido)benzoic acid

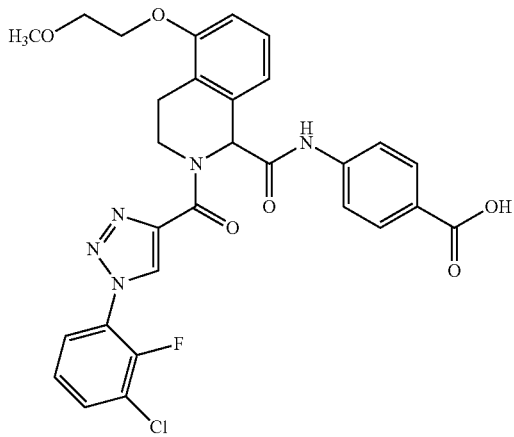 [SMILES: COCCOc1cccc2c1CCN(C(=O)c1cn(-c3cccc(Cl)c3F)nn1)C2C(=O)Nc1ccc(C(=O)O)cc1]

Example 113. 4-(2-(1-(3-Chloro-2-fluorophenyl)-1H-1,2,3-triazole-4-carbonyl)-5-(2-methoxyethoxy)-1,2,3,4-tetrahydroisoquinoline-1-carboxamido)benzoic acid: Example 113 was prepared in a similar manner as Example 112 replacing tert-butyl 4-((methylsulfonyl)oxy)piperidine-1-carboxylate with 2-methoxyethyl methanesulfonate during the alkylation of 5-hydroxyisoquinoline. $^1$H NMR (500 MHz, DMSO-$d_6$) δ 12.73 (br. s., 1H), 10.96 (s, 1H), 9.17 (d, J=1.9 Hz, 1H), 7.93-7.85 (m, 4H), 7.75 (d, J=8.8 Hz, 2H), 7.54-7.49 (m, 1H), 7.28-7.23 (m, 2H), 6.97 (quin, J=4.4 Hz, 1H), 5.95 (s, 1H), 4.47-4.40 (m, 1H), 4.36-4.30 (m, 1H), 4.16-4.11 (m, 2H), 3.70 (t, J=4.5 Hz, 2H), 3.34 (s, 3H), 3.01 (t, J=5.5 Hz, 2H) ppm. MS (ESI) m/z: 594 (M+H)$^+$. Analytical HPLC: RT=7.04 min (Method B).

EXAMPLE 114 AND EXAMPLE 115

4-((S)-2-((R)-3-(3-Chloro-2-fluorophenyl)-4,5-dihydroisoxazole-5-carbonyl)-5-(2-methoxyethoxy)-1,2,3,4-tetrahydroisoquinoline-1-carboxamido)benzoic acid, and 4-((R)-2-((R)-3-(3-Chloro-2-fluorophenyl)-4,5-dihydroisoxazole-5-carbonyl)-5-(2-methoxyethoxy)-1,2,3,4-tetrahydroisoquinoline-1-carboxamido)benzoic acid Example 114

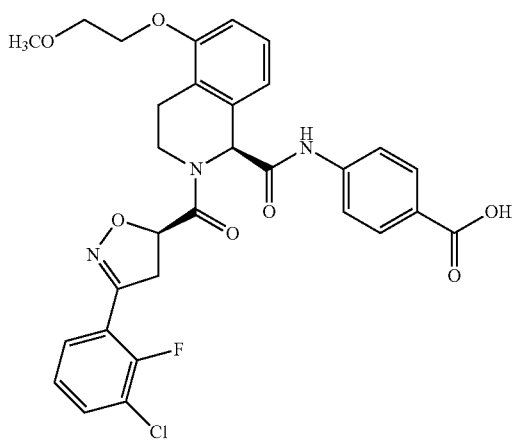

Example 115

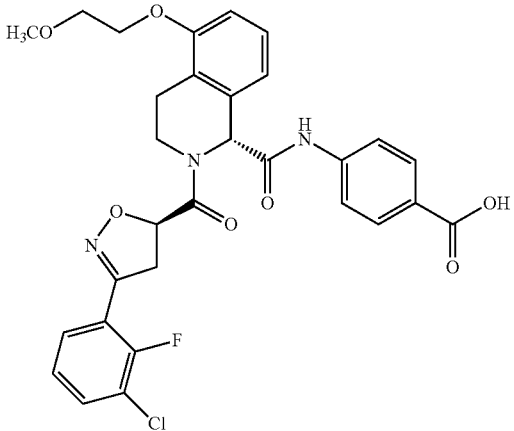

Example 114 and Example 115 were prepared in the same manner as Example 113 replacing Intermediate 9 with chiral Intermediate 19 in Ugi reaction step. Example 114 was obtained as the early eluting diastereomer during reverse phase prep. HPLC while Example 115 was the late eluting diastereomer.

Example 114: 4-((S)-2-((R)-3-(3-Chloro-2-fluorophenyl)-4,5-dihydroisoxazole-5-carbonyl)-5-(2-methoxyethoxy)-1,2,3,4-tetrahydroisoquinoline-1-carboxamido)benzoic Acid: $^1$H NMR (500 MHz, methanol-$d_4$) δ 10.43 (s, 1H), 7.97 (d, J=8.5 Hz, 2H), 7.77-7.71 (m, 1H), 7.67 (d, J=8.5 Hz, 2H), 7.59 (t, J=7.4 Hz, 1H), 7.24 (t, J=8.0 Hz, 2H), 7.12 (d, J=7.7 Hz, 1H), 6.94 (d, J=8.0 Hz, 1H), 5.87 (s, 1H), 5.78 (dd, J=11.4, 7.6 Hz, 1H), 4.29 (ddd, J=12.7, 7.8, 4.5 Hz, 1H), 4.19 (t, J=4.5 Hz, 2H), 3.99-3.91 (m, 2H), 3.83-3.79 (m, 2H), 3.78-3.72 (m, 1H), 3.47 (s, 3H), 3.21-3.12 (m, 1H), 3.11-3.03 (m, 1H) ppm. MS (ESI) m/z: 596 (M+H)$^+$. Analytical HPLC: RT=6.83 min (Method B).

Example 115 4-((R)-2-((R)-3-(3-Chloro-2-fluorophenyl)-4,5-dihydroisoxazole-5-carbonyl)-5-(2-methoxyethoxy)-1,2,3,4-tetrahydroisoquinoline-1-carboxamido)benzoic acid: $^1$H NMR (500 MHz, methanol-$d_4$) δ 10.49 (s, 1H), 7.97 (d, J=8.5 Hz, 2H), 7.74 (t, J=7.0 Hz, 1H), 7.67 (d, J=8.8 Hz, 2H), 7.59 (t, J=7.4 Hz, 1H), 7.25 (t, J=8.1 Hz, 2H), 7.13 (d, J=8.0 Hz, 1H), 6.95 (d, J=8.3 Hz, 1H), 5.86-5.80 (m, 2H), 4.24-4.17 (m, 3H), 4.09-3.95 (m, 2H), 3.85-3.80 (m, 2H), 3.78-3.71 (m, 1H), 3.50-3.47 (m, 3H), 3.15-3.08 (m, 2H) ppm. MS (ESI) m/z: 596 (M+H)$^+$. Analytical HPLC: RT=6.98 min (Method B).

EXAMPLE 116

Ethyl 2-(4-(2-(1-(3-Chloro-2-fluorophenyl)-1H-1,2,3-triazole-4-carbonyl)-5-(6-(methylcarbamoyl)pyridin-3-yl)-1,2,3,4-tetrahydroisoquinoline-1-carboxamido)phenyl)acetate, TFA salt

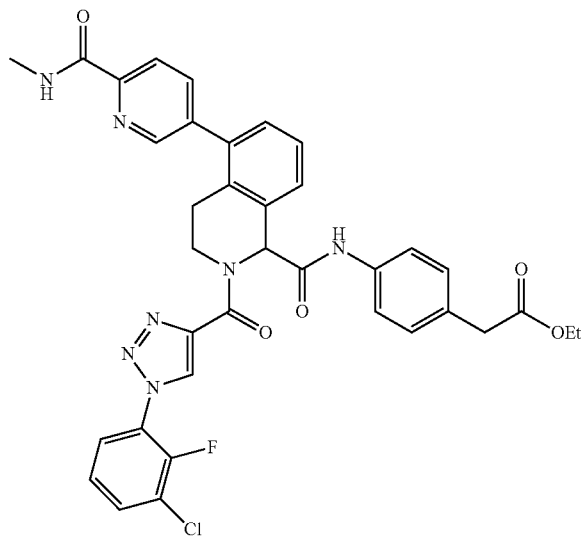 [SMILES: CCOC(=O)Cc1ccc(NC(=O)C2c3cccc(-c4ccc(C(=O)NC)nc4)c3CCN2C(=O)c2cn(-c3cccc(Cl)c3F)nn2)cc1]

116A. Ethyl 2-(4-(5-(6-(methylcarbamoyl)pyridin-3-yl)-1,2,3,4-tetrahydroisoquinoline-1-carboxamido)phenyl)acetate, 2 TFA: $POCl_3$ (0.052 mL, 0.561 mmol) was added dropwise to a mixture of Intermediate 6 (0.200 g, 0.561 mmol) and ethyl 2-(4-aminophenyl)acetate (0.111 g, 0.618 mmol) in pyridine (2.0 mL) at −15° C. for 30 minutes and then gradually allowed to come to room temperature. The, reaction was quenched with water, extracted with EtOAc, washed with 1.0N HCl solution (3×), water, saturated $NaHCO_3$ solution, brine, dried over sodium sulfate, filtered, and concentrated. This material, N-methyl-5-(4,4,5,5-tetramethyl-1,3,2-dioxaborolan-2-yl)picolinamide (0.221 g, 0.842 mmol), and $Cs_2CO_3$ (0.549 g, 1.684 mmol) were added to $DME/H_2O$ (5:1; 12 mL) and degassed for 15 minutes. Tetrakis-(triphenylphosphine)palladium(0) (0.065 g, 0.056 mmol) was added and the complete mixture irradiated at 120° C. for 15 minutes. The reaction mixture was poured into EtOAc, washed with saturated $NaHCO_3$ solution, brine, dried over sodium sulfate, filtered, and concentrated. The crude material was purified by normal phase column chromatography The boc group was removed by treatment with 50% TFA/DCM for 2 h, concentrating, purifying by reverse phase prep HPLC, and concentrating to give 116A (0.090 g, 0.128 mmol, 23% yield) as a tan solid. MS (ESI) m/z: 473 $(M+H)^+$.

Example 116. Ethyl 2-(4-(2-(1-(3-chloro-2-fluorophenyl)-1H-1,2,3-triazole-4-carbonyl)-5-(6-(methylcarbamoyl)pyridin-3-yl)-1,2,3,4-tetrahydroisoquinoline-1-carboxamido)phenyl)acetate, TFA salt. 1-Propanephosphonic acid cyclic anhydride (0.242 g, 0.381 mmol) was added to a solution of 116A (0.090 g, 0.190 mmol), Intermediate 9 (0.046 g, 0.190 mmol), and DIPEA (0.100 mL, 0.571 mmol) in DMF (2.0 mL). After 2 h, the reaction mixture was purified by reverse phase prep. HPLC and freeze-dried. $^1$H NMR (500 MHz, DMSO-$d_6$) δ 10.69 (s, 1H), 9.16 (d, J=1.7 Hz, 1H), 8.84 (q, J=4.6 Hz, 1H), 8.65 (d, J=1.4 Hz, 1H), 8.17-8.08 (m, 1H), 8.04 (dd, J=8.0, 2.2 Hz, 1H), 7.93-7.85 (m, 2H), 7.81 (d, J=7.4 Hz, 1H), 7.60 (d, J=8.5 Hz, 2H), 7.54-7.43 (m, 2H), 7.37 (d, J=7.7 Hz, 1H), 7.24-7.18 (m, 2H), 6.04 (s, 1H), 4.48-4.38 (m, 1H), 4.29-4.20 (m, 1H), 4.07 (q, J=7.2 Hz, 2H), 3.06 (dd, J=7.4, 4.4 Hz, 1H), 3.04-2.95 (m, 1H), 2.86 (d, J=5.0 Hz, 3H), 1.22-1.13 (m, 3H) ppm. MS (ESI) m/z: 696 $(M+H)^+$. Analytical HPLC: RT=7.42 min (Method B).

EXAMPLE 117

2-(4-(2-(1-(3-Chloro-2-fluorophenyl)-1H-1,2,3-triazole-4-carbonyl)-5-(6-(methylcarbamoyl)pyridin-3-yl)-1,2,3,4-tetrahydroisoquinoline-1-carboxamido)phenyl)acetic acid, TFA salt

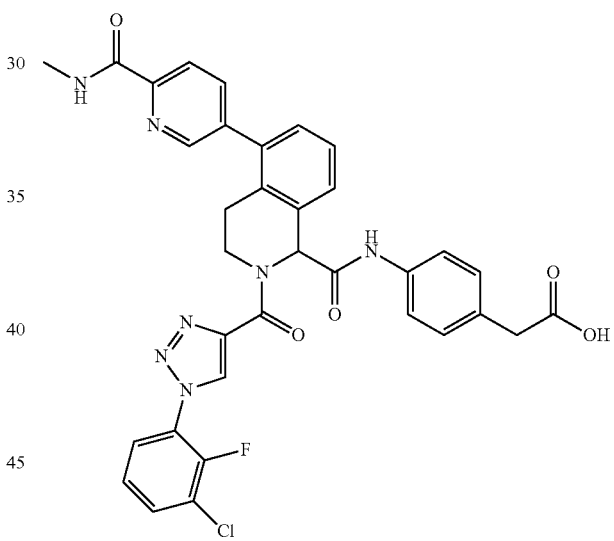

Example 117. 2-(4-(2-(1-(3-Chloro-2-fluorophenyl)-1H-1,2,3-triazole-4-carbonyl)-5-(6-(methylcarbamoyl)pyridin-3-yl)-1,2,3,4-tetrahydroisoquinoline-1-carboxamido)phenyl)acetic acid, TFA salt: The title compound (132 mg, 0.19 mmol) dissolved in THF (4 mL) and $H_2O$ (2 mL) was treated with lithium hydroxide monohydrate (28 mg, 0.67 mmol, 3.5 eq.). After stirring for 18 h, the reaction was concentrated, purified by reverse phase prep. HPLC, and freeze-dried to give a white solid. $^1$H NMR (500 MHz, DMSO-$d_6$) δ 10.68 (s, 1H), 9.16 (d, J=1.7 Hz, 1H), 8.84 (d, J=5.0 Hz, 1H), 8.65 (d, J=1.4 Hz, 1H), 8.15-8.10 (m, 1H), 8.05 (dd, J=8.1, 2.1 Hz, 1H), 7.91-7.84 (m, 2H), 7.81 (d, J=7.4 Hz, 1H), 7.59 (d, J=8.5 Hz, 2H), 7.54-7.45 (m, 2H), 7.37 (d, J=7.2 Hz, 1H), 7.22 (d, J=8.5 Hz, 2H), 6.04 (s, 1H), 4.46-4.37 (m, 1H), 4.30-4.20 (m, 1H), 3.52 (s, 2H), 3.06 (dd, J=7.3, 4.3 Hz, 1H), 3.04-2.96 (m, 1H), 2.86 (d, J=5.0 Hz, 3H) ppm. MS (ESI) m/z: 668 $(M+H)^+$. Analytical HPLC: RT=6.83 min (Method B).

EXAMPLE 118

2-(1-(3-Chloro-2-fluorophenyl)-1H-1,2,3-triazole-4-carbonyl)-5-(4-methoxypiperidin-1-yl)-N-phenyl-1,2,3,4-tetrahydroisoquinoline-1-carboxamide, TFA salt

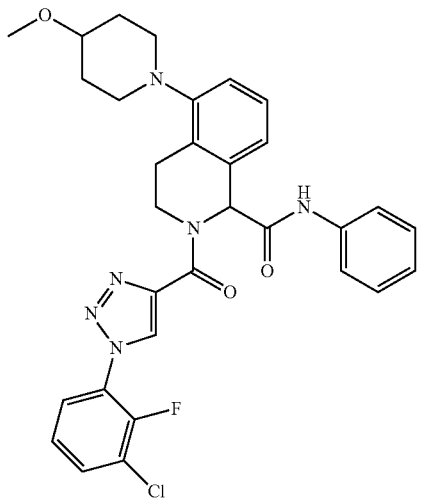 [SMILES: COC1CCN(c2cccc3c2CCN(C(=O)c2cn(-c4cccc(Cl)c4F)nn2)C3C(=O)Nc2ccccc2)CC1]

118A. 2-(tert-Butoxycarbonyl)-5-(4-methoxypiperidin-1-yl)-1,2,3,4-tetrahydroisoquinoline-1-carboxylic acid; Lithium hydroxide monohydrate (0.156 g, 3.71 mmol) was added to a solution of Intermediate 27 (0.500 g, 1.236 mmol) in THF (10 mL)/Water (5.00 mL)/MeOH (0.500 mL) at room temperature. After 18 h, the organics were concentrated and the remaining aqueous layer treated with ice water. The solution was made acidic with 10% citric acid solution, extracted with EtOAc (3×30 mL), washed with brine, dried over sodium sulfate, filtered, and concentrated to give a yellow foam (332 mg, 69%). MS (ESI) m/z: 391.2 $(M+H)^+$.

Example 118. 2-(1-(3-Chloro-2-fluorophenyl)-1H-1,2,3-triazole-4-carbonyl)-5-(4-methoxypiperidin-1-yl)-N-phenyl-1,2,3,4-tetrahydroisoquinoline-1-carboxamide, TFA Salt: DIPEA (0.067 mL, 0.384 mmol) was added to a solution 118A (0.050 g, 0.128 mmol), aniline (0.014 g, 0.154 mmol), and BOP (0.057 g, 0.128 mmol) in DMF (3 mL). After 1 h, the reaction mixture was partitioned between EtOAc and water. The water layer was extracted with additional EtOAc (2×). The combined organic layers were washed with 1.0N HCl solution, brine, dried over sodium sulfate, filtered, and concentrated. The boc group was removed by treatment with 50% TFA/DCM for 1 h before concentrating and placing under vacuum overnight. 1-Propanephosphonic acid cyclic anhydride (0.122 g, 0.192 mmol) was added to the amine TFA salt, Intermediate 9 (0.031 g, 0.128 mmol), and DIPEA (0.067 mL, 0.384 mmol) in DMF (1.0 mL). After 2 h, the reaction was purified directly by reverse phase prep HPLC and freeze-dried to give a white solid (19 mg, 21%). $^1$H NMR (400 MHz, DMSO-$d_6$) δ 10.49 (s, 1H), 9.08 (d, J=1.8 Hz, 1H), 7.86-7.77 (m, 2H), 7.54 (d, J=7.7 Hz, 2H), 7.45 (td, J=8.2, 1.4 Hz, 1H), 7.31 (d, J=7.7 Hz, 1H), 7.26-7.14 (m, 3H), 7.01-6.93 (m, 2H), 5.79 (s, 1H), 4.47-4.38 (m, 1H), 4.00 (ddd, J=12.5, 8.6, 4.2 Hz, 1H), 3.31-3.23 (m, 1H), 3.21 (s, 3H), 3.11-2.90 (m, 4H), 2.70-2.55 (m, 2H), 1.90 (br. s., 2H), 1.62-1.49 (m, 2H) ppm. MS (ESI) m/z: 589 $(M+H)^+$. Analytical HPLC: RT=7.66 min (Method B).

EXAMPLE 119

5-Bromo-2-(1-(3-chloro-2-fluorophenyl)-1H-1,2,3-triazole-4-carbonyl)-N-phenyl-1,2,3,4-tetrahydroisoquinoline-1-carboxamide

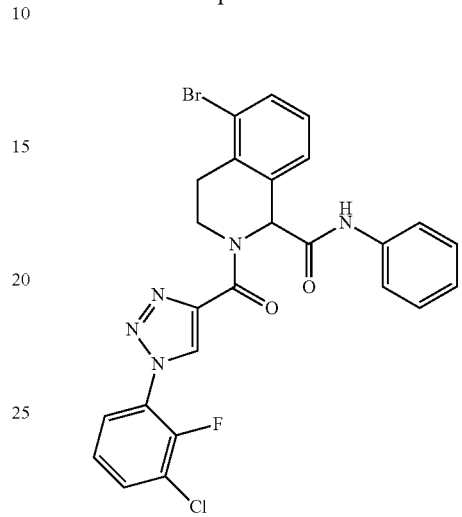

Example 119 was prepared in a similar manner as Example 118 starting from Intermediate 6. The compound was isolated as a white solid after purification by reverse phase prep. HPLC. $^1$H NMR (400 MHz, DMSO-$d_6$) δ 10.61 (s, 1H), 9.10 (d, J=1.5 Hz, 1H), 7.82 (td, J=8.4, 6.8 Hz, 2H), 7.62 (d, J=7.7 Hz, 1H), 7.55 (d, J=7.9 Hz, 3H), 7.44 (t, J=8.3 Hz, 1H), 7.29-7.17 (m, 3H), 7.04-6.97 (m, 1H), 5.94 (s, 1H), 4.46-4.32 (m, 2H), 3.16-2.96 (m, 2H) ppm. MS (ESI) m/z: 554/556 (M+H)+; Br isotope. Analytical HPLC: RT=8.069 min (Method B).

EXAMPLE 120

5-Bromo-2-(1-(3-chloro-2-fluorophenyl)-1H-1,2,3-triazole-4-carbonyl)-N-(4-(hydroxymethyl)phenyl)-1,2,3,4-tetrahydroisoquinoline-1-carboxamide

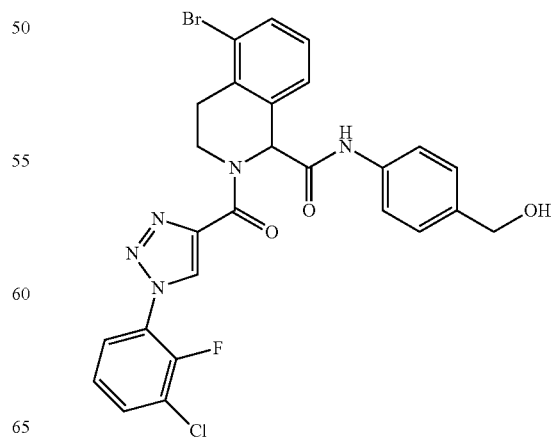

Example 120 was prepared in the same manner as Example 118 replacing aniline with (4-aminophenyl)methanol during the initial amide coupling step. The compound was isolated as a white solid after purification by reverse phase prep. HPLC. $^1$H NMR (400 MHz, DMSO-d$_6$) δ 10.57 (s, 1H), 9.10 (d, J=1.5 Hz, 1H), 7.87-7.77 (m, 2H), 7.64-7.42 (m, 5H), 7.24-7.16 (m, 3H), 5.94 (s, 1H), 5.03 (t, J=5.7 Hz, 1H), 4.43-4.34 (m, 4H), 3.15-2.96 (m, 2H) ppm. MS (ESI) m/z: 584/586 (M+H)+; Br isotope. Analytical HPLC: RT=7.57 min (Method B).

EXAMPLE 121

(R)-2-(1-(3-Chloro-2-fluorophenyl)-1H-1,2,3-triazole-4-carbonyl)-N-(4-(hydroxymethyl)phenyl)-5-(4-methoxypiperidin-1-yl)-1,2,3,4-tetrahydroisoquinoline-1-carboxamide

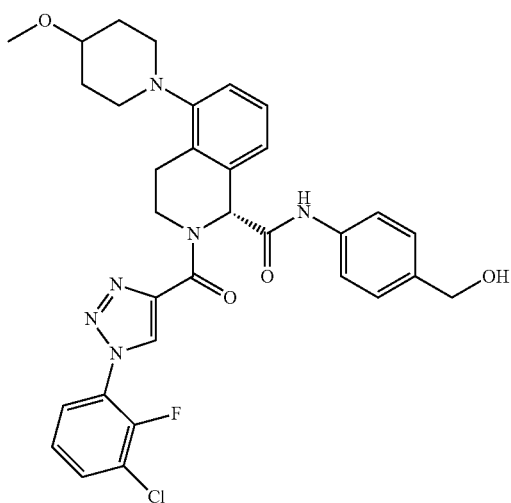 [SMILES: COC1CCN(c2cccc3c2CCN(C(=O)c2cn(-c4cccc(Cl)c4F)nn2)[C@H]3C(=O)Nc2ccc(CO)cc2)CC1]

Example 121 was prepared in a similar manner as Example 120 starting from 118A replacing aniline with (4-aminophenyl)methanol. The title compound was isolated as the early eluting enantiomer after chiral purification using CHIRALCEL® OJ-H, 30×250 mm, 5μ using 35% EtOH/65% CO$_2$ at 85 mL/min, 100 Bar, and 40° C. $^1$H NMR (400 MHz, DMSO-d$_6$) δ 10.45 (s, 1H), 9.08 (d, J=1.5 Hz, 1H), 7.87-7.77 (m, 2H), 7.51-7.44 (m, 3H), 7.30 (d, J=7.7 Hz, 1H), 7.17 (d, J=8.1 Hz, 3H), 6.93 (d, J=7.9 Hz, 1H), 5.79 (s, 1H), 5.02 (t, J=5.6 Hz, 1H), 4.45-4.31 (m, 3H), 4.00 (ddd, J=12.4, 8.3, 4.0 Hz, 1H), 3.21 (s, 3H), 3.04 (dd, J=8.1, 4.2 Hz, 1H), 2.99-2.89 (m, 3H), 2.61 (q, J=9.8 Hz, 2H), 1.95-1.87 (m, 2H), 1.60-1.49 (m, 2H) ppm. MS (ESI) m/z: 619.1 (M+H)$^+$. Analytical HPLC: RT=7.06 min (Method B).

EXAMPLE 122

(S)-2-(1-(3-Chloro-2-fluorophenyl)-1H-1,2,3-triazole-4-carbonyl)-N-(4-(hydroxymethyl)phenyl)-5-(4-methoxypiperidin-1-yl)-1,2,3,4-tetrahydroisoquinoline-1-carboxamide

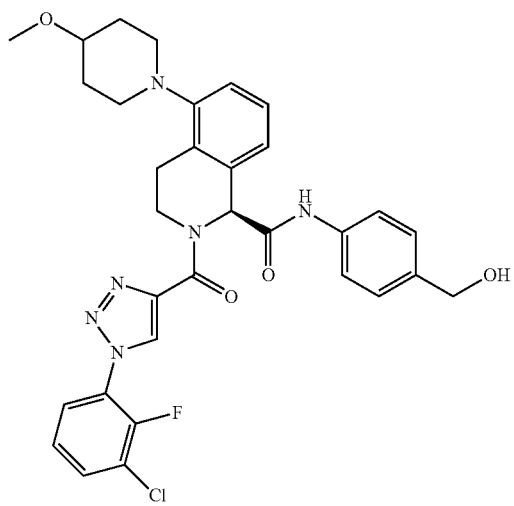 [SMILES: COC1CCN(c2cccc3c2CCN(C(=O)c2cn(-c4cccc(Cl)c4F)nn2)[C@@H]3C(=O)Nc2ccc(CO)cc2)CC1]

Example 122 was prepared in a similar manner as Example 120 starting from 118A. The compound was isolated as the late eluting enantiomer after chiral purification using CHIRALCEL® OJ-H, 30×250 mm, 5μ using 35% EtOH/65% CO$_2$ at 85 mL/min, 100 Bar, and 40° C. $^1$H NMR (400 MHz, DMSO-d$_6$) δ 10.45 (s, 1H), 9.08 (d, J=1.3 Hz, 1H), 7.81 (q, J=7.8 Hz, 2H), 7.52-7.41 (m, 3H), 7.30 (d, J=7.7 Hz, 1H), 7.19-7.13 (m, 3H), 6.93 (d, J=7.9 Hz, 1H), 5.79 (s, 1H), 5.02 (t, J=5.6 Hz, 1H), 4.45-4.32 (m, 3H), 4.00 (dt, J=8.1, 4.3 Hz, 1H), 3.21 (s, 3H), 3.09-3.02 (m, 1H), 2.99-2.88 (m, 3H), 2.61 (q, J=9.8 Hz, 2H), 1.96-1.85 (m, 2H), 1.60-1.47 (m, 2H) ppm. MS (ESI) m/z: 619.1 (M+H)$^+$. Analytical HPLC: RT=7.06 min (Method B).

EXAMPLE 123

4-(2-(1-(3-Chloro-2-fluorophenyl)-1H-1,2,3-triazole-4-carbonyl)-5-(oxetan-3-yloxy)-1,2,3,4-tetrahydroisoquinoline-1-carboxamido)benzoic acid

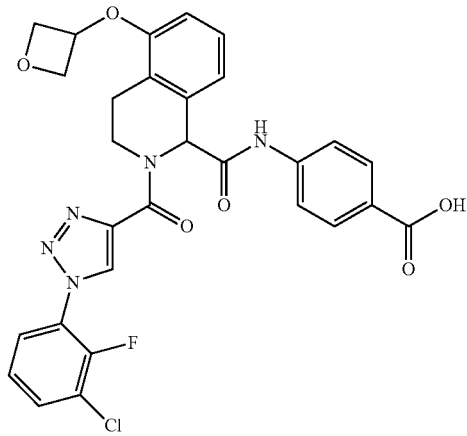 [SMILES: O=C(O)c1ccc(NC(=O)C2c3cccc(OC4COC4)c3CCN2C(=O)c2cn(-c3cccc(Cl)c3F)nn2)cc1]

123A. 5-((3-Methyloxetan-3-yl)methoxy)-3,4-dihydroisoquinoline: To a stirred suspension of isoquinolin-5-ol (0.500 g, 3.44 mmol) and triphenylphosphine resin (3.0 mmol/gram) (1.5 g, 5.17 mmol) in THF (20 mL) were added (3-methyloxetan-3-yl)methanol (0.528 g, 5.17 mmol) and diisopropyl azodicarboxylate (1.045 g, 5.17 mmol) portionwise. After stirring overnight, the reaction was filtered and the filtrate partitioned between water (20 mL) and ethyl acetate (50 mL). The aqueous layer was extracted with ethyl acetate (2×20 mL). The combined organic layers were washed with brine (15 mL), dried (MgSO$_4$), filtered, concentrated and purified by normal phase chromatography to give a solid. The isoquinoline was dissolved in EtOH, treated with PtO$_2$ (0.078 g, 0.344 mmol), and subjected to a hydrogen atmosphere (55 psi). After 18 h, the catalyst was filtered through a plug of CELITE®, filtrate concentrated, purified by normal phase chromatography. The amine was dissolved in DCM (20 mL) and treated with MnO$_2$ (5.39 g, 62.0 mmol). After stirring overnight, the reaction mixture was filtered through a plug of CELITE®, concentrated, and the resultant yellow oil carried forward as is. MS (ESI) m/z: 232 (M+H)$^+$.

Example 123. 4-(2-(1-(3-Chloro-2-fluorophenyl)-1H-1,2,3-triazole-4-carbonyl)-5-(oxetan-3-yloxy)-1,2,3,4-tetrahydroisoquinoline-1-carboxamido)benzoic acid: To a septa capped pressure vial was charged Intermediate 9 (0.095 g, 0.394 mmol), 124A (0.080 g, 0.394 mmol), and Intermediate 1 (0.080 g, 0.394 mmol) MeOH (anhydrous) (0.787 mL) and heated to 50° C. for 48 h. The reaction mixture was concentrated and the residue treated with 50% TFA/DCM. After 2 h, the mixture was concentrated, purified by reverse phase prep. HPLC. and freeze-drying to give a white solid (128 mg, 52%). $^1$H NMR (500 MHz, DMSO-d$_6$) δ 12.74 (br. s., 1H), 10.98 (s, 1H), 9.17 (d, J=1.7 Hz, 1H), 7.98-7.85 (m, 4H), 7.80-7.67 (m, 2H), 7.57-7.47 (m, 1H), 7.41-7.15 (m, 2H), 6.64-6.52 (m, 1H), 5.97 (s, 1H), 5.32 (quin, J=5.5 Hz, 1H), 4.95 (t, J=6.5 Hz, 2H), 4.59 (dd, J=7.3, 5.1 Hz, 2H), 4.50-4.35 (m, 2H), 3.15-2.98 (m, 2H) ppm. MS (ESI) m/z: 592 (M+H)$^+$. Analytical HPLC: RT=6.89 min (Method B).

EXAMPLE 124

4-(2-(1-(3-Chloro-2-fluorophenyl)-1H-1,2,3-triazole-4-carbonyl)-5-((3-methyloxetan-3-yl)methoxy)-1,2,3,4-tetrahydroisoquinoline-1-carboxamido)benzoic acid

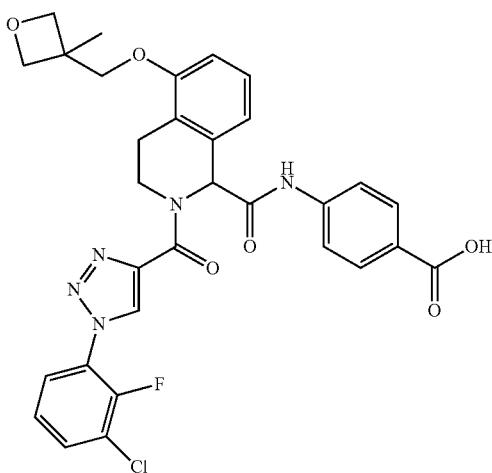 [SMILES: CC1(COc2cccc3c2CCN(C(=O)c2cn(-c4cccc(Cl)c4F)nn2)C3C(=O)Nc2ccc(C(=O)O)cc2)COC1]

Example 124 was made in a similar manner as Example 123 replacing (3-methyloxetan-3-yl)methanol with (3-methyloxetan-3-yl)methanol to give a white solid. $^1$H NMR (500 MHz, DMSO-d$_6$) δ 12.74 (br. s., 1H), 10.99 (s, 1H), 9.17 (d, J=1.7 Hz, 1H), 7.93-7.87 (m, 4H), 7.75 (d, J=8.8 Hz, 2H), 7.52 (td, J=8.3, 1.4 Hz, 1H), 7.29-7.25 (m, 2H), 7.03-6.97 (m, 1H), 5.98 (s, 1H), 4.55 (d, J=5.8 Hz, 2H), 4.41 (t, J=5.9 Hz, 2H), 4.34 (d, J=6.1 Hz, 2H), 4.08 (s, 2H), 3.04-2.99 (m, 2H), 1.40 (s, 3H) ppm. MS (ESI) m/z: 620 (M+H)$^+$. Analytical HPLC: RT=7.18 min (Method B).

EXAMPLE 125

2-(1-(3-Chloro-2-fluorophenyl)-1H-1,2,3-triazole-4-carbonyl)-5-(pyrimidin-5-yl)-N-(quinolin-6-yl)-1,2,3,4-tetrahydroisoquinoline-1-carboxamide, TFA salt

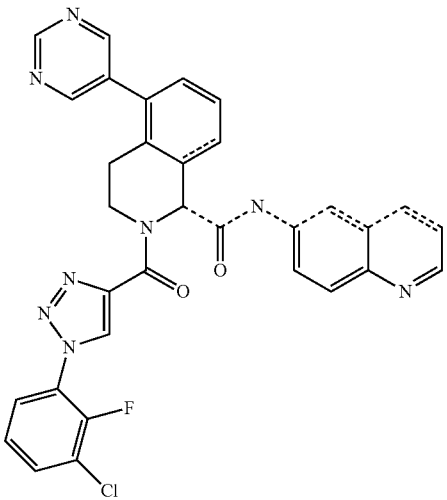

125A. tert-Butyl 5-(pyrimidin-5-yl)-1-(quinolin-6-ylcarbamoyl)-3,4-dihydroisoquinoline-2(1H)-carboxylate: To a solution of Intermediate 31 (50 mg, 0.141 mmol) and 6-aminoquinoline (20.28 mg, 0.141 mmol)) in DCM (3 mL) and pyridine (0.3 mL) at room temperature was added POCl$_3$ (0.020 mL, 0.215 mmol) dropwise. After 3 h, saturated NaHCO$_3$ was added and the mixture was extracted with EtOAc. The insoluble brown solid was filtered and the filtrate was concentrated. Purification by normal phase chromatography gave 125A (16 mg, 23.62% yield). MS (ESI) m/z: 482.3 (M+H)$^+$.

125B. 5-(Pyrimidin-5-yl)-N-(quinolin-6-yl)-1,2,3,4-tetrahydroisoquinoline-1-carboxamide, 2 TFA: 125A (16 mg, 0.033 mmol) was stirred in 1:1 CH$_2$Cl$_2$:TFA (1 mL) for 1 h at room temperature. The mixture was concentrated to dryness and co-evaporated with toluene once to give 126B (19.7 mg, 23% yield). MS(ESI) m/z: 382.3 (M+H)$^+$.

Example 125. 2-(1-(3-Chloro-2-fluorophenyl)-1H-1,2,3-triazole-4-carbonyl)-5-(pyrimidin-5-yl)-N-(quinolin-6-yl)-1,2,3,4-tetrahydroisoquinoline-1-carboxamide, TFA Salt: To a solution of 125B (19 mg, 0.050 mmol), Intermediate 9 (12 mg, 0.050 mmol) and DIPEA (0.043 mL, 0.249 mmol) in DMF (1 mL) was added 1-propanephosphonic acid cyclic anhydride 50% in EtOAc (0.044 mL, 0.075 mmol). The reaction was stirred at room temperature overnight. Purification by reverse phase chromatography gave Example 125 (13 mg, 36% yield) as a white solid. $^1$H NMR (400 MHz, methanol-d$_4$) δ 9.21 (s, 1H), 9.06-8.82 (m, 5H), 8.70 (s, 1H), 8.29-8.14 (m, 2H), 7.95 (dd, J=8.6, 5.3 Hz, 1H), 7.91-7.65 (m, 3H), 7.55-7.34 (m, 3H), 6.07 (s, 1H), 4.71-4.57 (m, 1H), 4.20 (t, J=8.9 Hz, 1H), 3.10-2.94 (m, 1H) ppm. MS (ESI) m/z: 605.3 (M+H)+. Analytical HPLC: RT=5.89 min (Method A).

The following Examples in Table 6 were prepared in a similar manner as Example 126 utilizing the appropriate amine in the initial amide formation step. Esters were converted into corresponding carboxylic acids under lithium hydroxide conditions in final step.

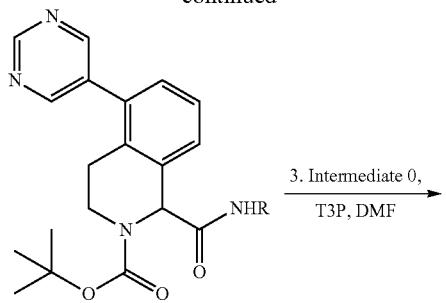

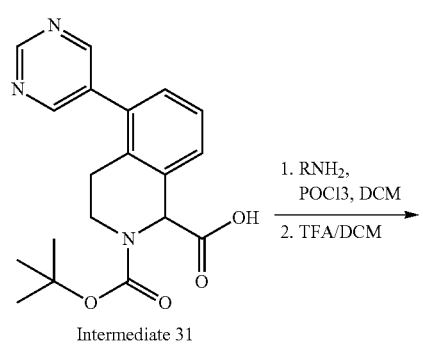

Intermediate 31

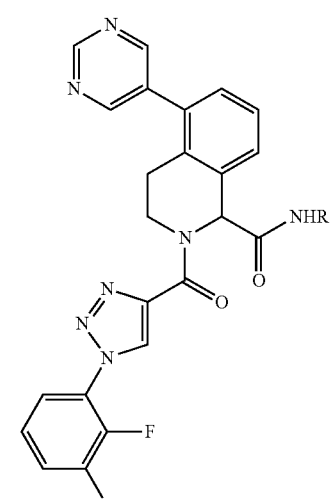

Examples 126-133

TABLE 6

| Example | Structure | Name | Analytical Data |
|---|---|---|---|
| 126 | (structure shown, racemate) | N-(4-(1H-imidazol-2-yl)phenyl)-2-(1-(3-chloro-2-fluorophenyl)-1H-1,2,3-triazole-4-carbonyl)-5-(pyrimidin-5-yl)-1,2,3,4-tetrahy-droisoquinoline-1-carboxamide, TFA salt | $^1$H NMR (400 MHz, DMSO-$d_6$) δ 11.12 (s, 1H), 9.26 (s, 1H), 9.17 (d, J = 1.5 Hz, 1H), 8.92 (br.s., 2H), 8.09-7.81 (m, 8H), 7.74 (br.s., 2H), 7.59-7.35 (m, 3H), 6.06 (s, 1H), 4.55-4.35 (m, 1H), 4.26 (d, J = 8.4 Hz, 1H), 3.19-2.94 (m, 2H) ppm. MS (ESI) m/z: 620.3 (M + H)+. Analytical HPLC: RT = 5.73 min (Method A). |

TABLE 6-continued

| Example | Structure | Name | Analytical Data |
|---|---|---|---|
| 127 | 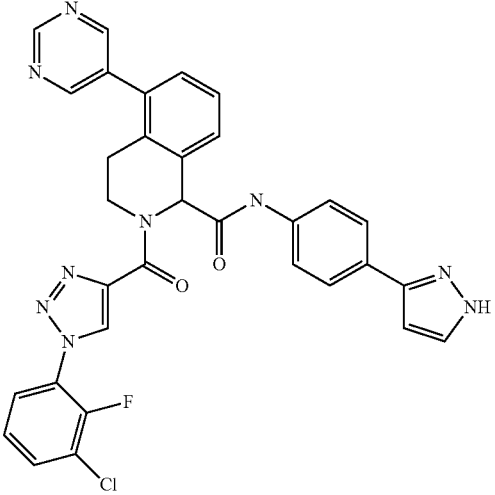 racemate | N-(4-(1H-pyrazol-3-yl)phenyl)-2-(1-(3-chloro-2-fluorophenyl)-1H-1,2,3-triazole-4-carbonyl)-5-(pyrimidin-5-yl)-1,2,3,4-tetrahydroisoquinoline-1-carboxamide, TFA salt | $^1$H NMR (400 MHz, methanol-$d_4$) δ 9.21 (br.s., 1H), 8.95-8.75 (m, 3H), 7.94-7.59 (m, 9H), 7.54-7.26 (m, 5H), 6.89-6.58 (m, 1H), 6.04 (s, 1H), 4.68-4.54 (m, 1H), 4.23 (dt, J = 8.4, 4.5 Hz, 1H), 3.07-2.90 (m, 1H) ppm. MS (ESI) m/z: 620.3 (M + H)$^+$. Analytical HPLC: RT = 8.14 min (Method A). |
| 128 | 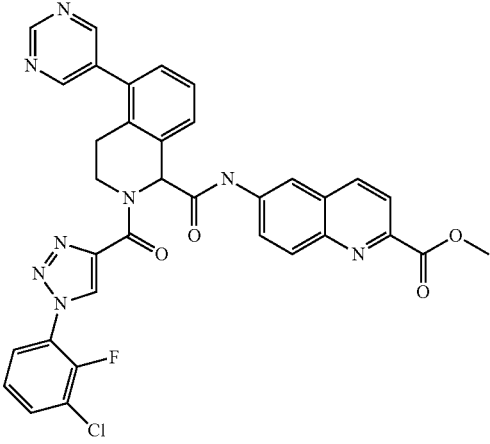 racemate | methyl 6-(2-(1-(3-chloro-2-fluorophenyl)-1H-1,2,3-triazole-4-carbonyl)-5-(pyrimidin-5-yl)-1,2,3,4-tetrahydroisoquinoline-1-carboxamido)quinoline-2-carboxylate, TFA salt | $^1$H NMR (400 MHz, methanol-$d_4$) δ 10.89 (s, 1H), 9.25 (br. s., 1H), 8.91 (s, 3H), 8.58-8.32 (m, 2H), 8.17 (br.s., 2H), 7.96 (d, J = 7.0 Hz, 1H), 7.89-7.62 (m, 4H), 7.59-7.33 (m, 4H), 6.07 (s, 1H), 4.73-4.57 (m, 1H), 4.21 (t, J = 8.9 Ez, 1H), 4.04 (s, 3H), 3.03 (d, J = 16.1 Hz, 1H) ppm. MS (ESI) m/z: 663.4 (M + H)$^+$. Analytical HPLC: RT = 8.89 min (Method A). |
| 129 | 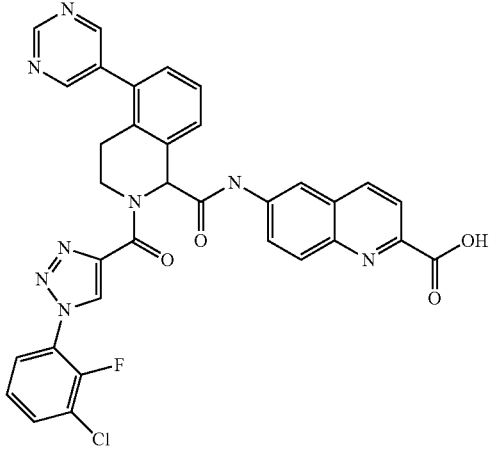 racemate | 6-(2-(1-(3-chloro-2-fluorophenyl)-1H-1,2,3-triazole-4-carbonyl)-5-(pyrimidin-5-yl)-1,2,3,4-tetrahydroisoquinoline-1-carboxamido)quinoline-2-carboxylic acid, TFA salt | $^1$H NMR (400 MHz, methanol-$d_4$) δ 9.21 (s, 1H), 8.99-8.80 (m, 4H), 8.65 (d, J = 8.6 Hz, 1H), 8.58 (s, 1H), 8.35-8.20 (m, 2H), 8.13-8.01 (m, 1H), 7.91-7.66 (m, 4H), 7.55-7.35 (m, 4H), 6.07 (s, 1H), 4.74-4.60 (m, 2H), 4.20 (br.s., 1H), 3.04 (d, J = 16.7 Hz, 1H) ppm. MS (ESI) m/z: 649.3 (M + H)$^+$. Analytical HPLC: RT = 7.50 min (Method A). |

TABLE 6-continued

| Example | Structure | Name | Analytical Data |
|---|---|---|---|
| 130 | 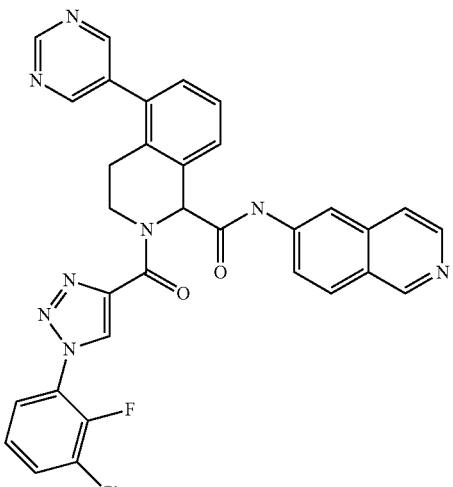 racemate | 2-(1-(3-chloro-2-fluorophenyl)-1H-1,2,3-triazol-4-carbonyl)-N-(isoquinolin-6-yl)-5-(pyrimidin-5-yl)-1,2,3,4-tetrahydroisoquinoline-1-carboxamide, TFA salt | $^1$H NMR (400 MHz, methanol-$d_4$) δ 9.69-9.46 (m, 1H), 9.25 (br.s., 1H), 9.02-8.33 (m, 3H), 8.74 (s, 1H), 8.56-8.37 (m, 2H), 8.29 (br.s., 1H), 8.11 (d, J = 9.0 Hz, (H), 7.94-7.63 (m, 4H), 7.56-7.31 (m, 4H), 6.07 (s, 1H), 4.77-4.64 (m, 1H), 4.27-4.06 (m, 1H), 3.09-2.93 (m, 1H) ppm. MS (ESI) m/z: 605.4 (M + H)$^+$. Analytical HPLC: RT = 5.74 min (Method A). |
| 131 | 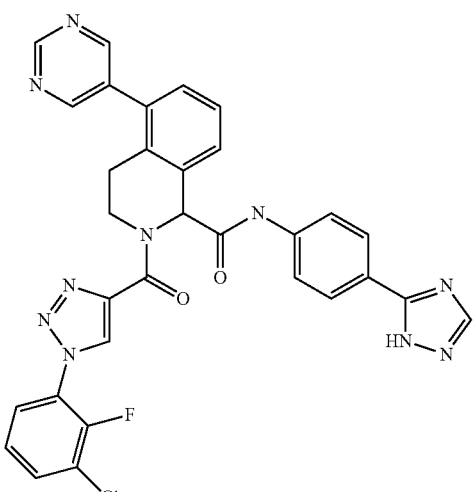 racemate | N-(4-(1H-1,2,4-triazol-5-yl)phenyl)-2-(1-(3-chloro-2-fluorophenyl)-1H-1,2,3-triazole-4-carbonyl)-5-(pyrimidin-5-yl)-1,2,3,4-tetrahydroisoquinoline-1-carboxamide, TFA salt | $^1$H NMR (400 MHz, methanol-$d_4$) δ 10.82-10.58 (m, 1H), 9.39-9.15 (m, 1H), 8.90 (d, J = 2.0 Hz, 3H), 8.78-8.55 (m, 1H), 7.97 (d, J = 8.1 Hz, 2H), 7.91-7.63 (m, 6H), 7.58-7.29 (m, 3H), 6.02 (s, 1H), 4.62 (d, J = 13.6 Hz, 1H), 4.19 (ddd, J = 12.7, 8.9, 3.5 Hz, 1H), 3.07-2.93 (m, 1H) ppm. MS (ESI) m/z: 621.2 (M + H)$^+$. Analytical HPLC: RT = 7.26 min (Method A). |

TABLE 6-continued

| Example | Structure | Name | Analytical Data |
|---|---|---|---|
| 132 | 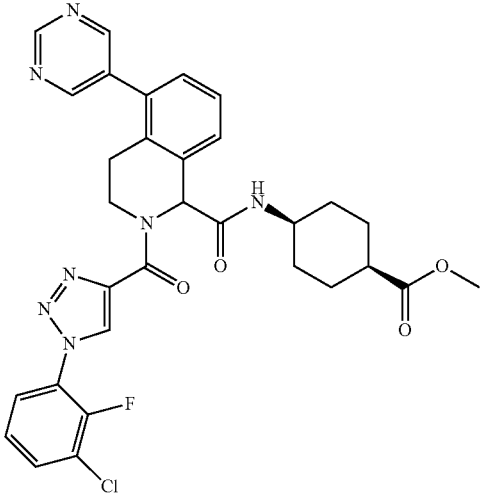<br>distereomeric mixture | (1R,4R)-methyl 4-(2-(1-(3-chloro-2-fluorophenyl)-1H-1,2,3-triazole-4-carbonyl)-5-(pyrimidin-5-yl)-1,2,3,4-tetrahydroisoquinoline-1-carboxamido)cyclohexanecarboxylate | $^1$H NMR (400 MHz, methanol-$d_4$) δ 9.18 (s, 1H), 8.90-8.79 (m, 1H), 8.44-8.35 (m, 1H), 7.98 (s, 1H), 7.92-7.79 (m, 1H), 7.76-7.69 (m, 1H), 7.66-7.60 (m, 1H), 7.50-7.38 (m, 2H), 7.37-7.29 (m, 1H), 5.85 (s, 1H), 4.53-4.37 (m, 1H), 4.34-4.15 (m, 1H), 4.08-3.97 (m, 1H), 3.65 (s, 4H), 3.19-3.07 (m, 1H), 2.99 (m, 1H), 2.41-2.20 (m, 1H), 2.16-1.80 (m, 4H), 1.57-1.25 (m, 4H) ppm. MS (ESI) m/z: 618.15 (M + H)$^+$. Analytical HPLC: RT = 1.77 min (Method C). |
| 133 | 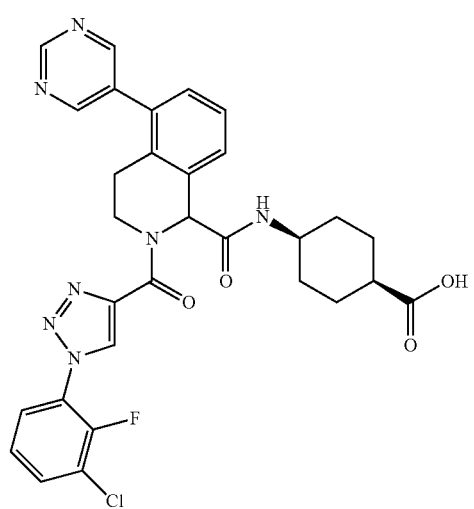<br>distereomeric mixture | (1R,4R)-4-(2-(1-(3-chloro-2-fluorophenyl)-1H-1,2,3-triazole-4-carbonyl)-5-(pyrimidin-5-yl)-1,2,3,4-tetrahydroisoquinoline-1-carboxamido)cyclohexanecarboxylic acid | $^1$H NMR (400 MHz, methanol-$d_4$) δ 9.40-9.19 (m, 1H), 8.89 (s, 2H), 7.85 (s, 1H), 7.72 (s, 1H), 7.64 (d, J = 7.7 Hz, 1H), 7.49-7 38 (m, 2H), 7.37-7.25 (m, 3H), 5.84 (s, 1H), 4.53-4.40 (m, 1H), 4.34-4.18 (m, 1H), 3.62 (t. J = 10.9 Hz, 1H), 3.20-3.08 (m, 1H), 3.05-2.93 (m, 1H), 2.35-2.18 (m, 1H), 2.12-1.81 (m, 4H), 1.58-1.25 (m, 4H) ppm. MS (ESI) m/z: 604.2 (M + H)$^+$. Analytical HPLC: RT = 7.44 min (Method A). |

EXAMPLE 134 AND EXAMPLE 135

(1S)-N-(4-(1H-Imidazol-2-yl)phenyl)-2-(3-(3-chloro-2-fluorophenyl)-4,5-dihydroisoxazole-5-carbonyl)-5-(pyrimidin-5-yl)-1,2,3,4-tetrahydroisoquinoline-1-carboxamide, TFA salt, and (1R)-N-(4-(1H-Imidazol-2-yl)phenyl)-2-(3-(3-chloro-2-fluorophenyl)-4,5-dihydroisoxazole-5-carbonyl)-5-(pyrimidin-5-yl)-1,2,3,4-tetrahydroisoquinoline-1-carboxamide, TFA salt Example 134

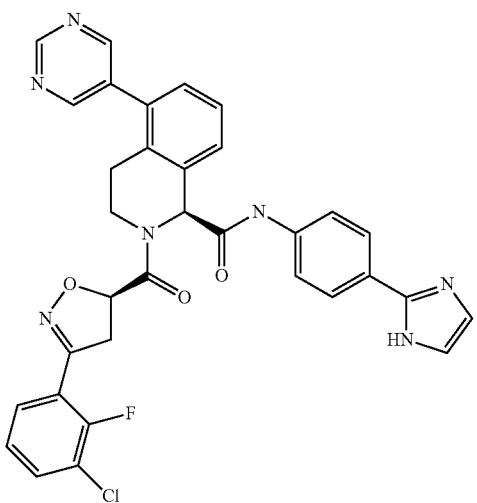

Example 135

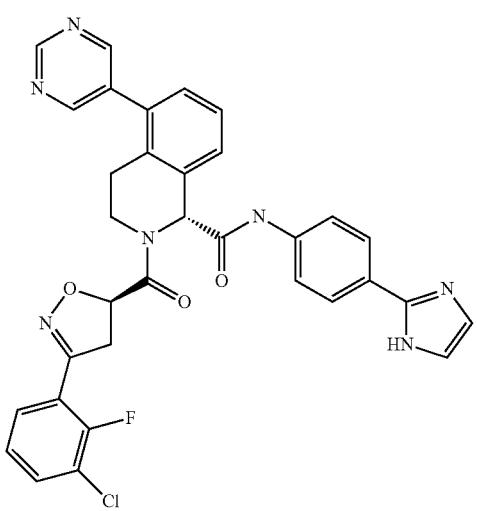

Examples 134 and 135 (S)-N-(4-(1H-Imidazol-2-yl)phenyl)-2-((R)-3-(3-chloro-2-fluorophenyl)-4,5-dihydroisoxazole-5-carbonyl)-5-(pyrimidin-5-yl)-1,2,3,4-tetrahydroisoquinoline-1-carboxamide, TFA salt and (R)-N-(4-(1H-imidazol-2-yl)phenyl)-2-((R)-3-(3-chloro-2-fluorophenyl)-4,5-dihydroisoxazole-5-carbonyl)-5-(pyrimidin-5-yl)-1,2,3,4-tetrahydroisoquinoline-1-carboxamide TFA salt: Example 134 and Example 135 were prepared in the same manner as Example 126 replacing Intermediate 9 with chiral Intermediate 19 and purified by reverse phase prep. HPLC.

Example 134 (early eluting diastereomer): $^1$H NMR (400 MHz, methanol-$d_4$) δ 9.29-9.19 (m, 1H), 8.97-8.84 (m, 2H), 7.86 (d, J=5.7 Hz, 4H), 7.75-7.69 (m, 1H), 7.67 (d, J=7.5 Hz, 1H), 7.60 (s, 3H), 7.46 (s, 1H), 7.42-7.36 (m, 1H), 7.22 (t, J=7.9 Hz, 1H), 5.89 (s, 1H), 5.74 (dd, J=11.4, 7.5 Hz, 1H), 4.41-4.23 (m, 1H), 4.00-3.87 (m, 1H), 3.80-3.65 (m, 2H), 3.02-2.89 (m, 1H) ppm. MS (ESI) m/z: 622.4 (M+H)$^+$. Analytical HPLC: RT=5.72 min (Method A).

Example 135 (late eluting diastereomer): $^1$H NMR (400 MHz, methanol-$d_4$) δ 9.32-9.17 (m, 1H), 8.90 (br. s., 2H), 7.92-7.79 (m, 4H), 7.69 (d, J=7.7 Hz, 2H), 7.63-7.52 (m, 3H), 7.50-7.43 (m, 1H), 7.39 (d, J=7.5 Hz, 1H), 7.27-7.16 (m, 1H), 5.86 (s, 1H), 5.80 (dd, J=11.3, 6.7 Hz, 1H), 4.35-4.21 (m, 1H), 4.04-3.94 (m, 1H), 3.80-3.67 (m, 2H), 2.99 (br. s., 1H) ppm. MS (ESI) m/z: 622.4 (M+H)$^+$. Analytical HPLC: RT=5.79 min (Method A).

EXAMPLE 136

N-(4-(1H-Imidazol-2-yl)phenyl)-2-(1-(3-chloro-2-fluorophenyl)-5-methyl-1H-imidazole-4-carbonyl)-5-(pyrimidin-5-yl)-1,2,3,4-tetrahydroisoquinoline-1-carboxamide, 2 TFA salt

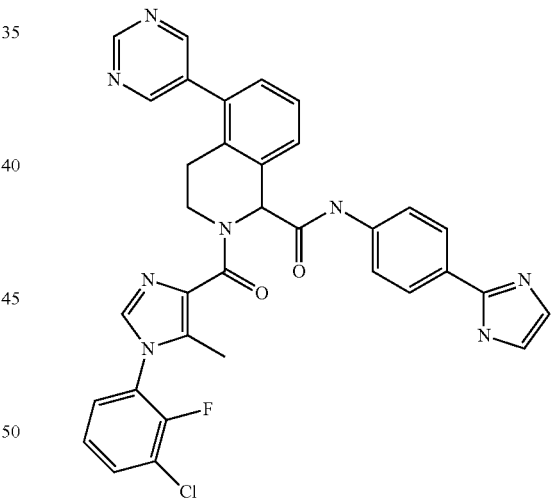

Example 136. N-(4-(1H-Imidazol-2-yl)phenyl)-2-(1-(3-chloro-2-fluorophenyl)-5-methyl-1H-imidazole-4-carbonyl)-5-(pyrimidin-5-yl)-1,2,3,4-tetrahydroisoquinoline-1-carboxamide, 2 TFA: The title compound was prepared in the same manner as Example 125 replacing Intermediate 9 with Intermediate 32. $^1$H NMR (500 MHz, DMSO-$d_6$) δ 11.02 (br. s., 1H), 9.25 (s, 1H), 8.91 (s, 2H), 7.97 (br. s., 3H), 7.92-7.71 (m, 4H), 7.62 (br. s., 3H), 7.51-7.42 (m, 2H), 7.38 (d, J=7.2 Hz, 1H), 6.01 (br. s., 1H), 4.36 (d, J=7.2 Hz, 2H), 3.00 (br. s., 2H), 2.26 (s, 3H) ppm. MS (ESI) m/z: 633.25 (M+H)$^+$. Analytical HPLC: RT=1.59 min (Method C).

EXAMPLE 137

N-(4-(1H-Imidazol-2-yl)phenyl)-2-(1-(3-chloro-2-fluorophenyl)-1H-imidazole-4-carbonyl)-5-(pyrimidin-5-yl)-1,2,3,4-tetrahydroisoquinoline-1-carboxamide, 2 TFA

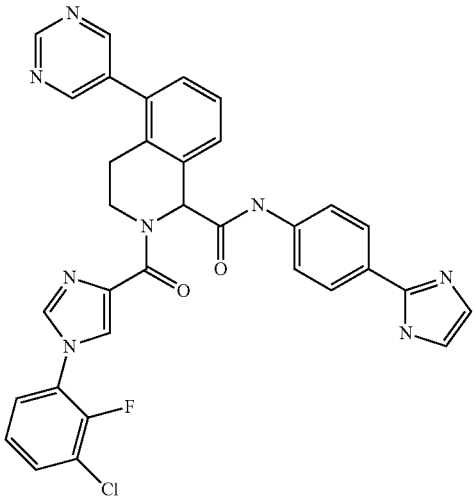 [SMILES: O=C(Nc1ccc(-c2ncc[nH]2)cc1)C1c2cccc(-c3cncnc3)c2CCN1C(=O)c1cn(-c2cccc(Cl)c2F)cn1]

Example 137. N-(4-(1H-Imidazol-2-yl)phenyl)-2-(1-(3-chloro-2-fluorophenyl)-1H-imidazole-4-carbonyl)-5-(pyrimidin-5-yl)-1,2,3,4-tetrahydroisoquinoline-1-carboxamide, 2 TFA: The title compound was prepared in the same manner as Example 125 replacing Intermediate 9 with Intermediate 17. $^1$H NMR (500 MHz, DMSO-$d_6$) δ 14.58 (br. s., 2H), 11.14 (s, 1H), 9.26 (s, 1H), 8.92 (br. s., 2H), 8.31-8.11 (m, 2H), 8.04-7.87 (m, 4H), 7.86-7.65 (m, 5H), 7.59-7.32 (m, 3H), 6.00 (s, 1H), 4.46 (br. s., 2H), 3.03 (br. s., 2H) ppm. MS (ESI) m/z: 619.2 (M+H)$^+$. Analytical HPLC: RT—5.45 min (Method A).

EXAMPLE 138 AND EXAMPLE 139

(S)-N-(4-(H-Imidazol-2-yl)phenyl)-2-(1-(3-chloro-2-fluorophenyl)-1H-1,2,3-triazole-4-carbonyl)-5-(pyrimidin-5-yl)-1,2,3,4-tetrahydroisoquinoline-1-carboxamide, TFA salt, and (R)-N-(4-(1H-Imidazol-2-yl)phenyl)-2-(1-(3-chloro-2-fluorophenyl)-1H-1,2,3-triazole-4-carbonyl)-5-(pyrimidin-5-yl)-1,2,3,4-tetrahydroisoquinoline-1-carboxamide, TFA salt Example 138

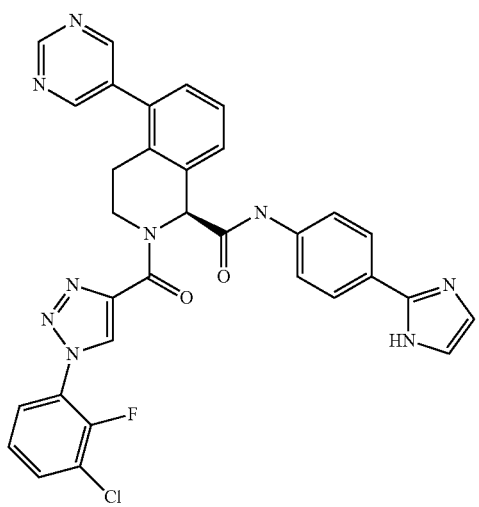

Example 139

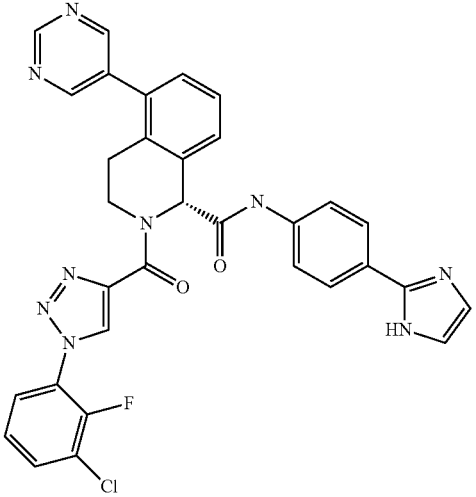

Examples 138 and 139. (S)-N-(4-(1H-Imidazol-2-yl)phenyl)-2-(1-(3-chloro-2-fluorophenyl)-1H-1,2,3-triazole-4-carbonyl)-5-(pyrimidin-5-yl)-1,2,3,4-tetrahydroisoquinoline-1-carboxamide, TFA salt, and (R)-N-(4-(1H-Imidazol-2-yl)phenyl)-2-(1-(3-chloro-2-fluorophenyl)-1H-1,2,3-triazole-4-carbonyl)-5-(pyrimidin-5-yl)-1,2,3,4-tetrahydroisoquinoline-1-carboxamide, TFA salt: The compounds were prepared by chiral separation of Example 126 using CHIRALPAK® AS-H,30×250 mm ID, 5 µm eluting with 23% Methanol-0.1% DEA/77% CO$_2$ at 85 mL/min, 150 Bar, 40° C.

Example 138: $^1$H NMR (400 MHz, methanol-$d_4$) δ 10.87 (s, 1H), 9.41-9.14 (m, 1H), 9.05-8.80 (m, 3H), 8.03-7.82 (m, 5H), 7.81-7.59 (m, 4H), 7.58-7.37 (m, 3H), 6.04 (s, 1H), 4.67 (br. s., 1H), 4.19 (br. s., 1H), 3.11-2.91 (m, 1H) ppm. MS (ESI) m/z: 620.2 (M+H)$^+$. Analytical HPLC: RT=5.73 min (Method A).

Example 139: $^1$H NMR (400 MHz, methanol-$d_4$) δ 10.95-10.83 (m, 1H), 9.34-9.15 (m, 1H), 9.08-8.79 (m, 3H), 7.93 (d, J=11.7 Hz, 5H), 7.76 (d, J=3.7 Hz, 2H), 7.64 (s, 2H), 7.45 (d, J=4.4 Hz, 3H), 6.11-5.99 (m, 1H), 4.77-4.60 (m, 1H), 4.23-4.11 (m, 1H), 3.11-2.90 (m, 2H) ppm. MS (ESI) m/z: 620.2 (M+H)$^+$. Analytical HPLC: RT=5.71 min (Method A).

EXAMPLE 140

N-(4-(1H-Imidazol-2-yl)phenyl)-2-(1-(3-chloro-2-fluorophenyl)-5-methyl-1H-1,2,3-triazole-4-carbonyl)-5-(4-methoxypiperidin-1-yl)-1,2,3,4-tetrahydroisoquinoline-1-carboxamide, 2 TFA salt

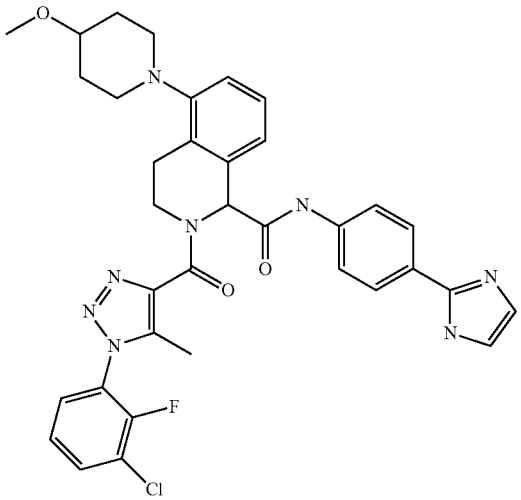 [SMILES: COC1CCN(c2cccc3c2CCN(C(=O)c2nnn(-c4cccc(Cl)c4F)c2C)C3C(=O)Nc2ccc(-c3ncc[nH]3)cc2)CC1]

140A. 2-(tert-Butoxycarbonyl)-5-(4-methoxypiperidin-1-yl)-1,2,3,4-tetrahydroisoquinoline-1-carboxylic acid: Intermediate 27 (172 mg, 0.425 mmol) in MeOH (3 mL) was treated with lithium hydroxide (2M aq.) (425 μl, 0.850 mmol) at 40° C. overnight. The solvent was evaporated and the remaining aqueous mixture was acidified with 0.5N HCl and extracted twice with EtOAc. The combined organic layer was washed with brine, dried (MgSO$_4$), filtered, and concentrated to give 140A (159 mg, 96% yield) as a yellow glass. MS (ESI) m/z: 391.2 (M+H)$^+$.

140B. tert-Butyl 1-((4-(1H-imidazol-2-yl)phenyl)carbamoyl)-5-(4-methoxypiperidin-1-yl)-3,4-dihydroisoquinoline-2(1H)-carboxylate: To a solution of 140A (159 mg, 0.407 mmol) and 4-(1H-imidazol-2yl)-phenylamine (64.4 mg, 0.407 mmol)) in DCM (3 mL) and pyridine (0.3 mL) at room temperature was added POCl$_3$ (0.040 mL, 0.429 mmol) dropwise. After 30 min additional POCl$_3$ (0.020 mL) was added. Once the starting material was consumed, saturated NaHCO$_3$ was added and the mixture was extracted with EtOAc and DCM. The combined organic layer was concentrated to dryness. MS (ESI) m/z: 532.1 (M+H)$^+$. The residue was stirred in 1:1 CH$_2$Cl$_2$:TFA (1 mL) for 1 h at room temperature, concentrated to dryness and purified by reverse phase chromatography to give 140B (55 mg, 20% yield) as a yellow foam. $^1$H NMR (400 MHz, methanol-d$_4$) δ 7.95 (d, J=3.1 Hz, 3H), 7.63 (s, 2H), 7.39-7.10 (m, 3H), 5.34 (s, 1H), 3.79 (d, J=12.3 Hz, 1H), 3.48-3.34 (m, 6H), 3.25-3.01 (m, 4H), 2.94-2.64 (m, 2H), 2.18-1.91 (m, 2H), 1.73 (br. s., 2H) ppm. MS(ESI) m/z: 432.2 (M+H)$^+$.

Example 140. N-(4-(1H-Imidazol-2-yl)phenyl)-2-(1-(3-chloro-2-fluorophenyl)-5-methyl-1H-1,2,3-triazole-4-carbonyl)-5-(4-methoxypiperidin-1-yl)-1,2,3,4-tetrahydroisoquinoline-1-carboxamide, 2 TFA: To a solution of 140B (17 mg, 0.026 mmol), Intermediate 11 (5.93 mg, 0.023 mmol) and DIPEA (0.014 mL, 0.077 mmol) in DMF (1 mL) was added 1-propanephosphonic acid cyclic anhydride 50% in DMF (0.011 mL, 0.039 mmol). The reaction was stirred at room temperature overnight. Purification by reverse phase chromatography gave Example 140 (11 mg, 46% yield) as a white solid. $^1$H NMR (400 MHz, methanol-d$_4$) δ 7.94-7.75 (m, 5H), 7.60 (s, 3H), 7.54-7.40 (m, 2H), 7.32 (s, 4H), 7.28-7.19 (m, 1H), 5.86 (s, 1H), 4.63-4.47 (m, 1H), 4.10-3.94 (m, 1H), 3.40 (s, 4H), 3.24 (br. s., 3H), 3.08-2.79 (m, 2H), 2.42 (s, 3H), 2.13 (br. s., 2H), 1.85 (br. s., 2H) ppm. MS (ESI) m/z: 669.2 (M+H)$^+$. Analytical HPLC: RT=6.13 min (Method A).

EXAMPLE 141

N-(4-(1H-Imidazol-2-yl)phenyl)-2-(1-(3-chloro-2-fluorophenyl)-1H-1,2,3-triazole-4-carbonyl)-5-(4-methoxypiperidin-1-yl)-1,2,3,4-tetrahydroisoquinoline-1-carboxamide, 2 TFA

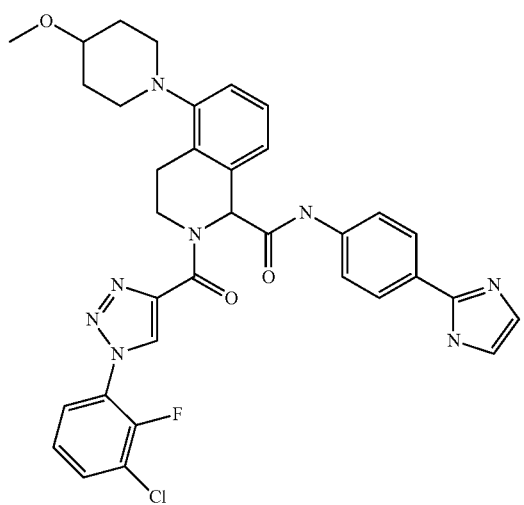 [SMILES: COC1CCN(c2cccc3c2CCN(C(=O)c2cn(-c4cccc(Cl)c4F)nn2)C3C(=O)Nc2ccc(-c3ncc[nH]3)cc2)CC1]

Example 141. N-(4-(1H-Imidazol-2-yl)phenyl)-2-(1-(3-chloro-2-fluorophenyl)-1H-1,2,3-triazole-4-carbonyl)-5-(4-methoxypiperidin-1-yl)-1,2,3,4-tetrahydroisoquinoline-1-carboxamide, 2 TFA: The title compound was prepared in the same manner as Example 140 replacing Intermediate 11 with Intermediate 9. $^1$H NMR (500 MHz, DMSO-d$_6$) δ 12.37 (br. s., 1H), 10.68 (s, 1H), 9.16 (s, 1H), 7.94-7.77 (m, 4H), 7.68 (d, J=8.5 Hz, 2H), 7.52 (t, J=8.1 Hz, 1H), 7.39 (d, J=7.7 Hz, 1H), 7.31-7.12 (m, 2H), 7.07-6.88 (m, 2H), 5.88 (s, 1H), 4.56-4.44 (m, 1H), 4.52 (d, J=12.7 Hz, 1H), 4.12-3.96 (m, 1H), 3.29 (s, 3H), 3.21-2.94 (m, 5H), 2.77-2.60 (m, 3H), 1.99 (br. s., 2H), 1.63 (d, J=10.2 Hz, 2H) ppm. MS (ESI) m/z: 655.1 (M+H)$^+$. Analytical HPLC: RT=1.95 min (Method C).

EXAMPLE 142

Methyl 4-(2-{[1-(3-chloro-2-fluorophenyl)-1H-1,2,3-triazol-4-yl]carbonyl}-5-(pyrimidin-5-yl)-1,2,3,4-tetrahydroisoquinoline-1-amido)bicyclo[2.2.2]octane-1-carboxylate, TFA salt

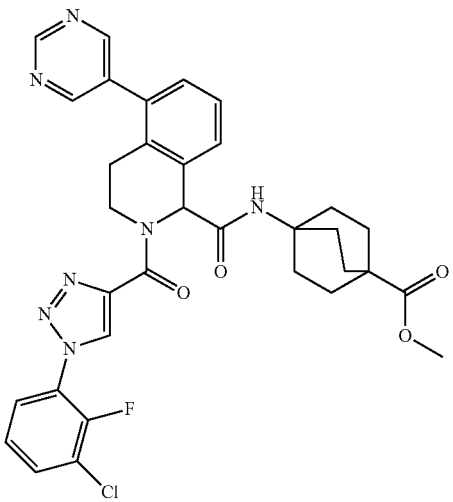 [SMILES: COC(=O)C12CCC(NC(=O)C3c4cccc(-c5cncnc5)c4CCN3C(=O)c3cn(-c4cccc(Cl)c4F)nn3)(CC1)CC2]

142A. tert-Butyl 1-{[4-(methoxycarbonyl)bicyclo[2.2.2]octan-1-yl]carbamoyl}-5-(pyrimidin-5-yl)-1,2,3,4-tetrahydroisoquinoline-2-carboxylate To a cooled (0° C.) suspension of Intermediate 31 (0.030 g, 0.084 mmol), methyl 4-aminobicyclo[2.2.2]octane-1-carboxylate, HCl (0.022 g, 0.101 mmol), and TEA (0.118 mL, 0.844 mmol) in ethyl acetate (0.844 mL) and DMF (0.844 mL) was added a solution of 1-propylphosphonic acid cyclic anhydride (50% wt solution in EtOAc, 0.075 mL, 0.127 mmol). Following the addition, the reaction was allowed to warm to room temperature. After 6 h, additional methyl 4-aminobicyclo[2.2.2]octane-1-carboxylate, HCl (0.022 g, 0.101 mmol), TEA (0.118 mL, 0.844 mmol), and 1-propylphosphonic acid cyclic anhydride (50% wt solution in EA, 0.075 mL, 0.127 mmol) were added. After 16 h, the reaction was stopped. The reaction was partitioned between water and EtOAc and the layers were separated. The aqueous layer was extracted with EtOAc (2×). The organic layers were combined and washed with sat. sodium bicarbonate, brine, dried over sodium sulfate, filtered and concentrated to give 142A (0.024 g, 44% yield), as an off-white solid. This material was used in the next step without further purification. MS (ESI) m/z: 521.2 (M+H)$^+$.

Example 142. 142A was converted to the title compound in two steps. Boc-deprotection with TFA according to the procedure described in 125B followed by coupling with Intermediate acid 9 according to the procedure described in Example 125 gave Example 142 (0.0076 g, 53.0% yield) as a white solid. $^1$H NMR (500 MHz, CD$_3$OD) δ 9.18 (s, 1H), 8.90-8.80 (m, 3H), 7.89-7.81 (m, 1H), 7.78-7.69 (m, 1H), 7.61 (d, J=7.4 Hz, 0.75H), 7.54-7.48 (m, 0.25H), 7.48-7.37 (m, 2H), 7.37-7.28 (m, 1H), 6.45 (bs, 0.25H), 5.83 (s, 0.75H), 4.40-4.28 (m, 1.5H), 4.22-4.13 (m, 0.25H), 3.93-3.84 (m, 0.25H), 3.62 (s, 3H), 3.12-2.89 (m, 2H), 2.02-1.82 (m, 12H). MS (ESI) m/z: 644.2 (M+H)$^+$. Analytical HPLC: RT=9.57 min (Method A).

EXAMPLE 143

4-(2-{[1-(3-Chloro-2-fluorophenyl)-1H-1,2,3-triazol-4-yl]carbonyl}-5-(pyrimidin-5-yl)-1,2,3,4-tetrahydroisoquinoline-1-amido)bicyclo[2.2.2]octane-1-carboxylic acid, 1 TFA

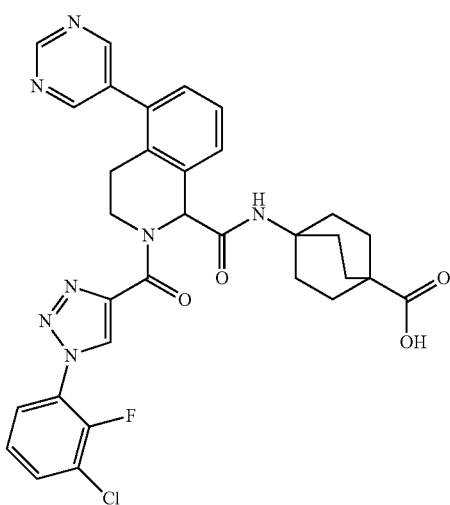 [SMILES: O=C(NC12CCC(C(=O)O)(CC1)CC2)C1c2cccc(-c3cncnc3)c2CCN1C(=O)c1cn(-c2cccc(Cl)c2F)nn1]

To a clear, colorless solution of Example 142 (0.0050 g, 6.60 μmol) in a mixture of methanol (0.275 mL) and water (0.055 mL) was added 1.0 M NaOH (0.013 mL, 0.013 mmol). The clear solution was stirred at room temperature. After 1 h, the reaction was warmed to 50° C. After 1 h, additional 1.0 M NaOH (0.013 mL, 0.013 mmol) was added and the reaction was warmed to 70° C. After 3 h, the reaction was stopped and cooled. The reaction was diluted with 4:1 DMF:MeOH (1 mL) and purified directly by reverse phase chromatography which gave following concentration and lyophilization Example 143 (0.0032 g, 63%), as a white solid. $^1$H NMR (500 MHz, CD$_3$OD) δ 9.20 (s, 1H), 8.91-8.82 (m, 3H), 8.00 (s, 0.5H, NH), 7.92-7.84 (m, 1H), 7.78-7.66 (m, 1H), 7.64 (d, J=7.4 Hz, 0.75H), 7.54 (d, J=6.9 Hz, 0.25H), 7.50-7.40 (m, 2H), 7.39-7.31 (m, 1H), 6.47 (br. s., 0.25H), 5.86 (s, 0.75H), 4.43-4.31 (m, 1.5H), 4.24-4.15 (m, 0.25H), 3.95-3.87 (m, 0.25H), 3.14-2.91 (m, 2H), 2.04-1.86 (m, 12H). MS (ESI) m/z: 630.2 (M+H)$^+$. Analytical HPLC: RT=8.02 min.

EXAMPLE 144 AND EXAMPLE 145

4-(2-{[1-(3-Chloro-2-fluorophenyl)-1H-1,2,3-triazol-4-yl]carbonyl}-5-(pyrimidin-5-yl)-1,2,3,4-tetrahydroisoquinoline-1-amido)bicyclo[2.2.2]octane-1-carboxylic acid, 1 TFA (enantiomer A), and 4-(2-{[1-(3-Chloro-2-fluorophenyl)-1H-1,2,3-triazol-4-yl]carbonyl}-5-(pyrimidin-5-yl)-1,2,3,4-tetrahydroisoquinoline-1-amido)bicyclo[2.2.2]octane-1-carboxylic acid, 1 TFA (enantiomer B)

Example 144

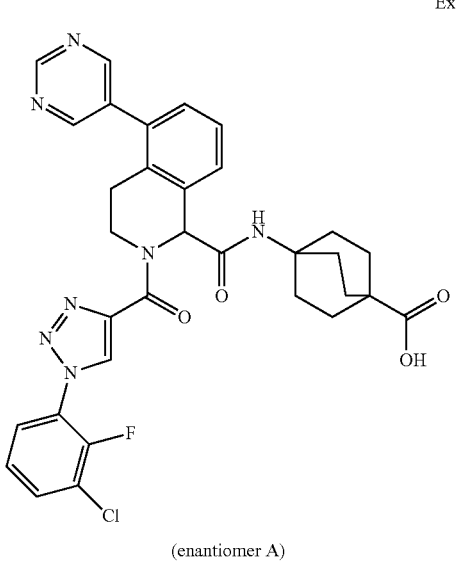

(enantiomer A)

Example 145

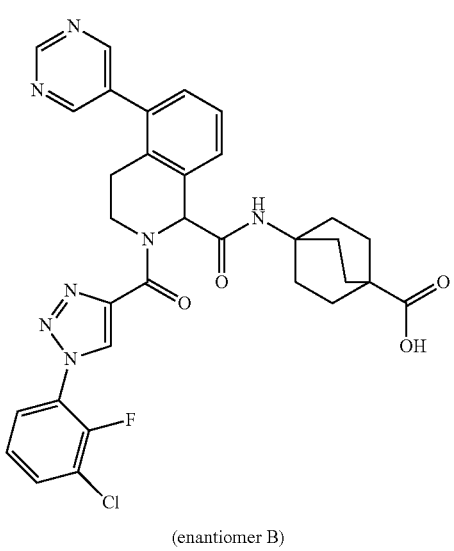

(enantiomer B)

To a clear, colorless solution of 143 (0.0351 g, 0.054 mmol) in a mixture of methanol (2.271 mL) and water (0.454 mL) was added 1.0 M NaOH (0.218 mL, 0.218 mmol). The clear solution was warmed to 70° C. After 4 h, the reaction was stopped, cooled to room temperature, and concentrated to give a white residue. The residue was partitioned between water and EtOAc and the layers were separated. The aqueous layer was extracted with EtOAc (1×). The aqueous layer was acidified with 1.0 M HCl and then extracted with EtOAc (3×). The organic layers, following acidification, were combined and washed with brine, dried over sodium sulfate, filtered and concentrated to give an off-white solid weighing 0.0291 g (85%). The enantiomers were separated by chiral SFC (CHIRALCEL® OD-H, 4.6×250 mm, 5μ, 25% MeOH-ACN(1:1)/75% $CO_2$) The first eluting enantiomer (enantiomer A) was concentrated and punted by reverse phase chromatography to give Example 144 (0.0059 g, 14% yield, >95% ee), as an off-white solid. The second eluting enantiomer (enantiomer B) was concentrated and purified by reverse phase chromatography to give Example 145 (0.0040 g, 10% yield, 80% ee), as an off-white solid.

The following Examples in Table 7 were prepared (library format) in a similar manner as the final amide coupling step of Example 125 starting from Intermediate 28 utilizing the appropriate carboxylic acid and replacing T3P with HATU during amide formation. Final compounds were treated with 50% TFA/DCM and purified by reverse phase chromatography.

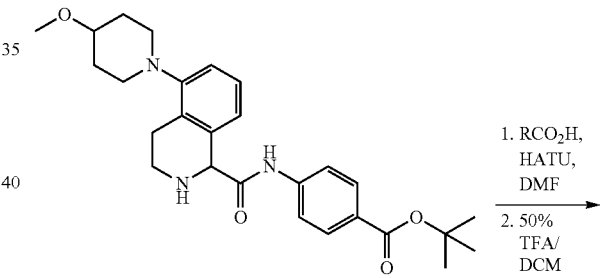

Intermediate 28

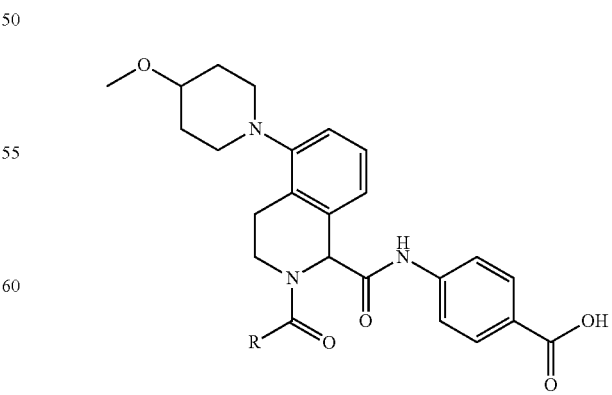

Examples 146-152

TABLE 7

| Example | Structure | Name | LCMS (M + H)+ | HPLC RT (min) |
|---|---|---|---|---|
| 146 | 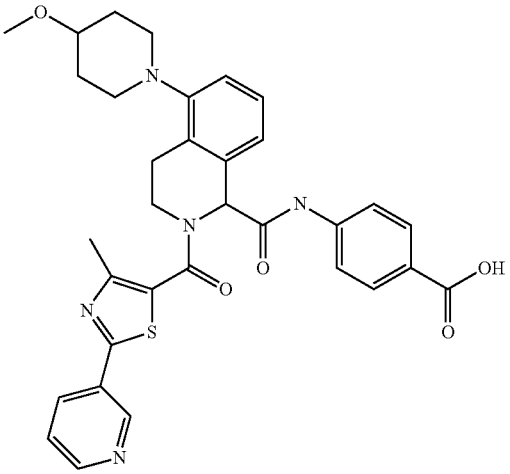 racemate | 4-(5-(4-methoxypiperidin-1-yl)-2-(4-methyl-2-(pyridin-3-yl)thiazole-5-carbonyl)-1,2,3,4-tetrahydroisoquinoline-1-carboxamido)benzoic acid, 2 TFA salt | 612.25 | 2.33 (Method D) |
| 147 | 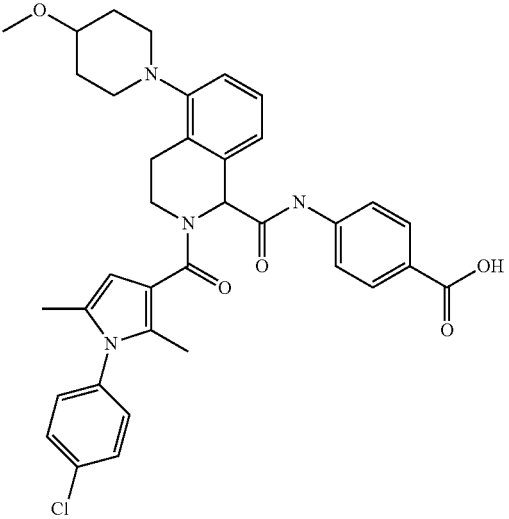 racemate | 4-(2-(1-(4-chlorophenyl)-2,5-dimethyl-1H-pyrrole-3-carbonyl)-5-(4-methoxypiperidin-1-yl)-1,2,3,4-tetrahydroisoquinoline-1-carboxamido)benzoic acid, TFA salt | 641.62 | 2.69 (Method D) |
| 148 | 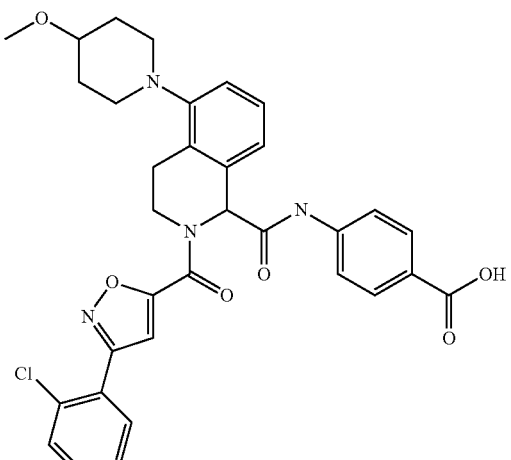 racemate | 4-(2-(3-(2-chlorophenyl)isoxazole-5-carbonyl)-5-(4-methoxypiperidin-1-yl)-1,2,3,4-tetrahydroisoquinoline-1-carboxamido)benzoic acid, TFA salt | 615.46 | 2.38 (Method D) |

TABLE 7-continued

| Example | Structure | Name | LCMS (M + H)+ | HPLC RT (min) |
|---|---|---|---|---|
| 149 | 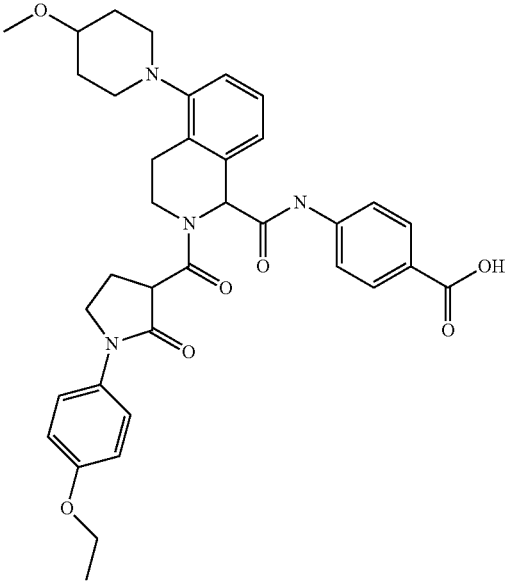 racemate | 4-(2-(1-(4-isopropoxyphenyl)-2-oxopyrrolidine-3-carbonyl)-5-(4-methoxypiperidin-1-yl)-1,2,3,4-tetrahydroisoquinoline-1-carboxamido)benzoic acid, TFA salt | 655.66 | 2.34 (Method D) |
| 150 | 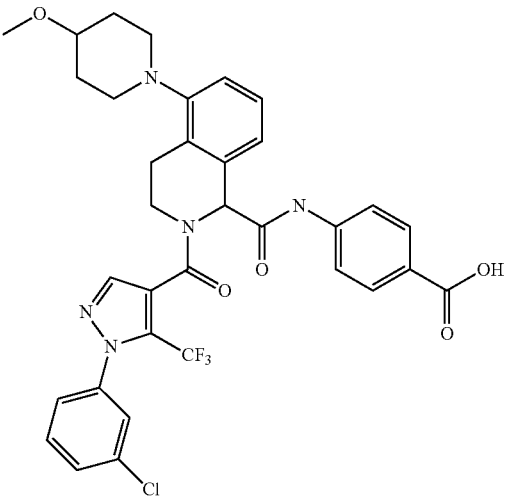 racemate | 4-(2-(1-(3-chlorophenyl)-5-(trifluoromethyl)-1H-pyrazole-4-carbonyl)-5-(4-methoxypiperidin-1-yl)-1,2,3,4-tetrahydroisoquinoline-1-carboxamido)benzoic acid, TFA salt | 682.27 | 2.65 (Method D) |

TABLE 7-continued
| Example | Structure | Name | LCMS (M + H)+ | HPLC RT (min) |
|---|---|---|---|---|
| 151 | 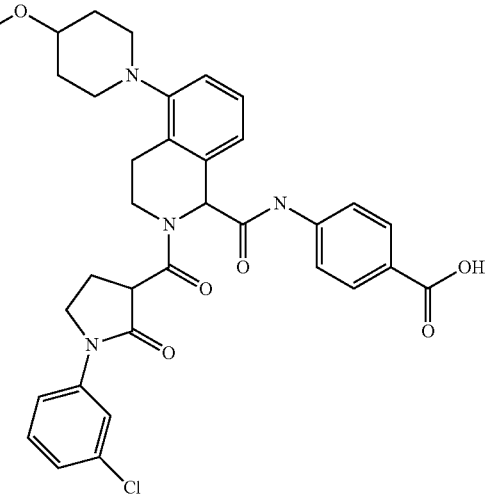 racemate | 4-(2-(1-(3-chlorophenyl)-2-oxopyrrolidine-3-carbonyl)-5-(4-methoxypiperidin-1-yl)-1,2,3,4-tetrahydroisoquinoline-1-carboxamido)benzoic acid, TFA salt | 631.26 | 3.51 |
| 152 | 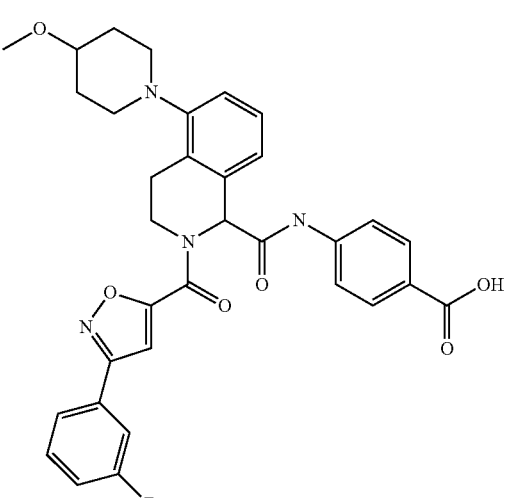 racemate | 4-(2-(3-(3-fluorophenyl) isoxazole-5-carbonyl)-5-(4-methoxypiperidin-1-yl)-1,2,3,4-tetrahydroisoquinoline-1-carboxamido)benzoic acid, TFA salt | 599.26 | 3.96 |

The Examples in Table 8 were made as described previously for Example 12 except in a library format replacing pyrimidin-5-ylboronic acid with the appropriate boronate/boronic acid in the Suzuki reaction.

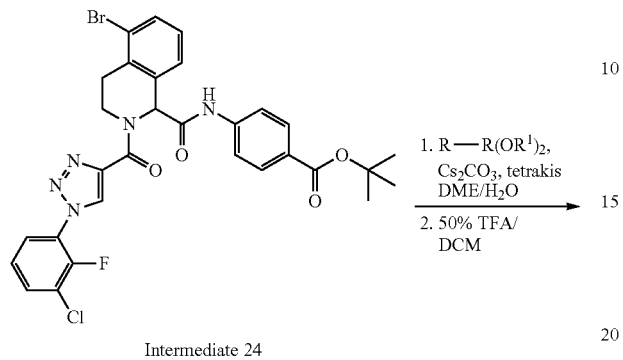

Intermediate 24

1. R—R(OR¹)₂, Cs₂CO₃, tetrakis DME/H₂O
2. 50% TFA/DCM

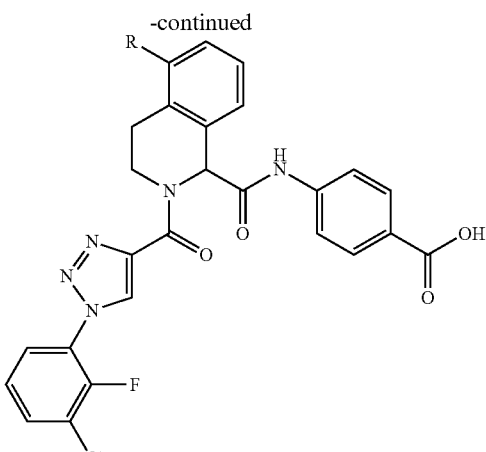

Examples 153-188 (racemic)

TABLE 8

| Example | Structure | Name | LCMS (M + H)⁺ | HPLC RT (min) |
|---|---|---|---|---|
| 153 | 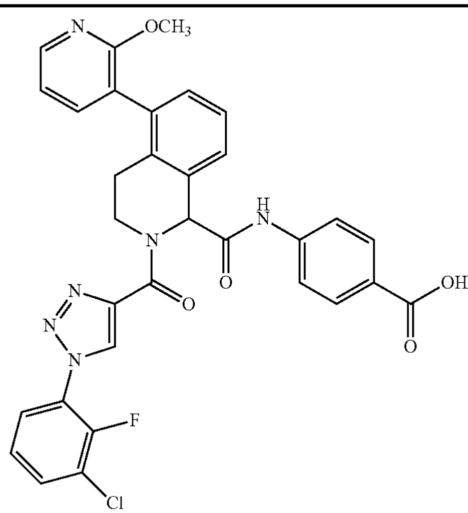 | 4-(2-(1-(3-chloro-2-fluorophenyl)-1H-1,2,3-triazole-4-carbonyl)-5-(2-methoxypyridin-3-yl)-1,2,3,4-tetrahydroisoquinoline-1-carboxamido)benzoic acid, TFA salt | 627.22 | 3.74 (Method D) |
| 154 | 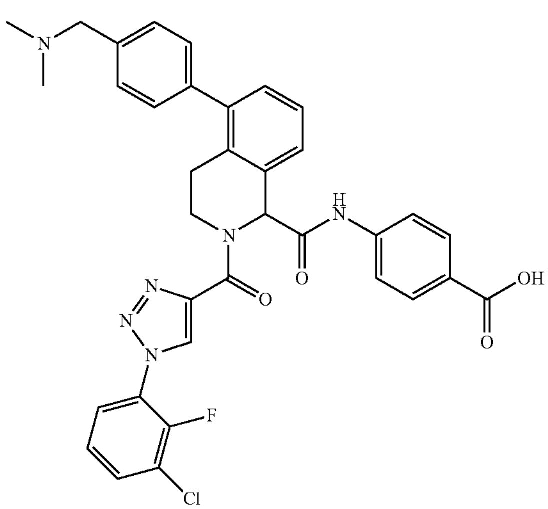 [SMILES: CN(C)Cc1ccc(-c2cccc3c2CCN(C(=O)c2cn(-c4cccc(Cl)c4F)nn2)C3C(=O)Nc2ccc(C(=O)O)cc2)cc1] | 4-(2-(1-(3-chloro-2-fluorophenyl)-1H-1,2,3-triazole-4-carbonyl)-5-(4-((dimethylamino)methyl)phenyl)-1,2,3,4-tetrahydroisoquinoline-1-carboxamido)benzoic acid, TFA salt | 653.26 | 3.49 (Method D) |

TABLE 8-continued

| Example | Structure | Name | LCMS (M + H)+ | HPLC RT (min) |
|---|---|---|---|---|
| 155 | 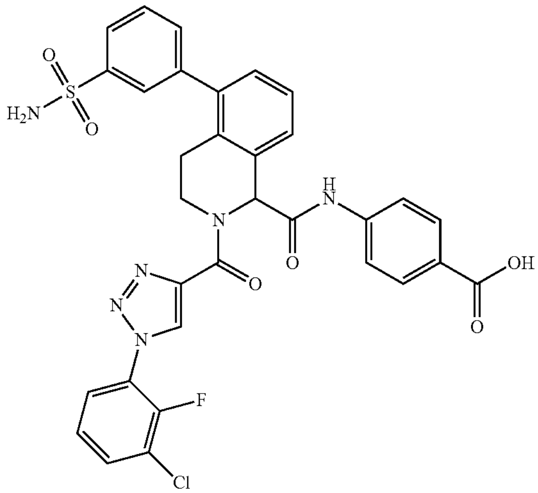 [SMILES: NS(=O)(=O)c1cccc(-c2cccc3c2CCN(C(=O)c2cn(-c4cccc(Cl)c4F)nn2)C3C(=O)Nc2ccc(C(=O)O)cc2)c1] | 4-(2-(1-(3-chloro-2-fluorophenyl)-1H-1,2,3-triazole-4-carbonyl)-5-(3-sulfamoylphenyl)-1,2,3,4-tetrahydroisoquinoline-1-carboxamido)benzoic acid | 675.36 | 2.16 (Method D) |
| 156 | 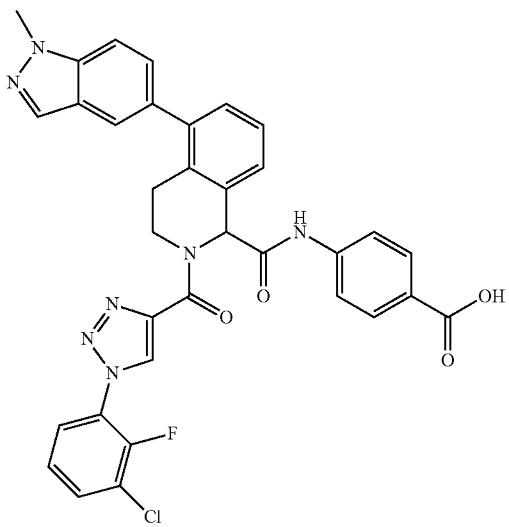 [SMILES: Cn1ncc2cc(-c3cccc4c3CCN(C(=O)c3cn(-c5cccc(Cl)c5F)nn3)C4C(=O)Nc3ccc(C(=O)O)cc3)ccc21] | 4-(2-(1-(3-chloro-2-fluorophenyl)-1H-1,2,3-triazole-4-carbonyl)-5-(1-methyl-1H-indazol-5-yl)-1,2,3,4-tetrahydroisoquinoline-1-carboxamido)benzoic acid | 650.37 | 2.43 (Method D) |
| 157 | 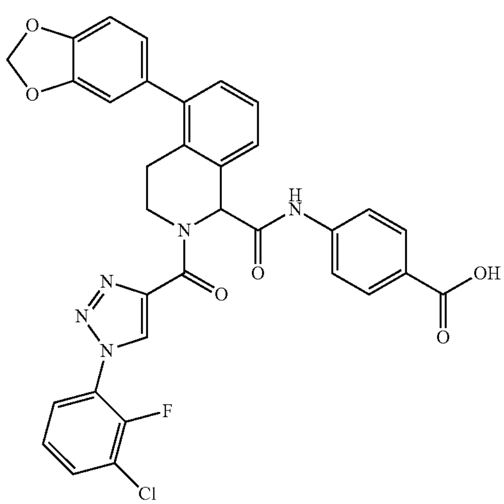 [SMILES: O=C(O)c1ccc(NC(=O)C2c3cccc(-c4ccc5c(c4)OCO5)c3CCN2C(=O)c2cn(-c3cccc(Cl)c3F)nn2)cc1] | 4-(5-(benzo[d][1,3]dioxol-5-yl)-2-(1-(3-chloro-2-fluorophenyl)-1H-1,2,3-triazole-4-carbonyl)-1,2,3,4-tetrahydroisoquinoline-1-carboxamido)benzoic acid | 640.19 | 2.60 (Method D) |

TABLE 8-continued

| Example | Structure | Name | LCMS (M + H)+ | HPLC RT (min) |
|---|---|---|---|---|
| 158 | 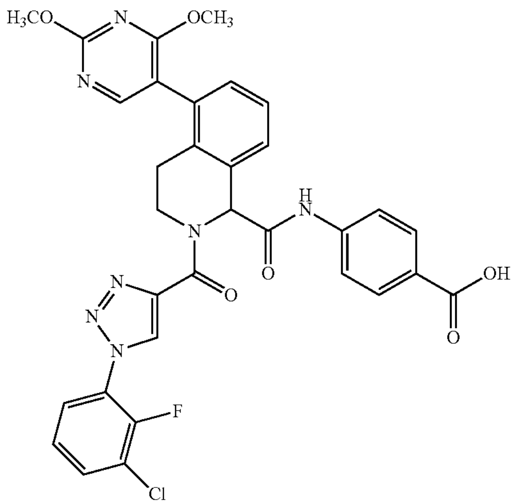 [SMILES: COc1ncc(-c2cccc3c2CCN(C(=O)c2cn(-c4cccc(Cl)c4F)nn2)C3C(=O)Nc2ccc(C(=O)O)cc2)c(OC)n1] | 4-(2-(1-(3-chloro-2-fluorophenyl)-1H-1,2,3-triazole-4-carbonyl)-5-(2,4-dimethoxypyrimidin-5-yl)-1,2,3,4-tetrahydroisoquinoline-1-carboxamido)benzoic acid | 658.21 | 3.65 (Method D) |
| 159 | 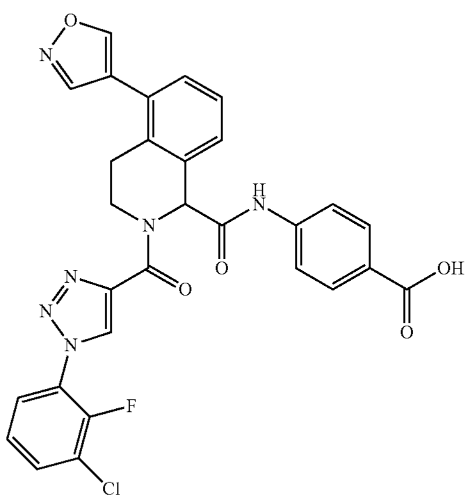 [SMILES: O=C(O)c1ccc(NC(=O)C2c3cccc(-c4cnoc4)c3CCN2C(=O)c2cn(-c3cccc(Cl)c3F)nn2)cc1] | 4-(2-(1-(3-chloro-2-fluorophenyl)-1H-1,2,3-triazole-4-carbonyl)-5-(isoxazol-4-yl)-1,2,3,4-tetrahydroisoquinoline-1-carboxamido)benzoic acid | 587.35 | 3.54 (Method D) |
| 160 | 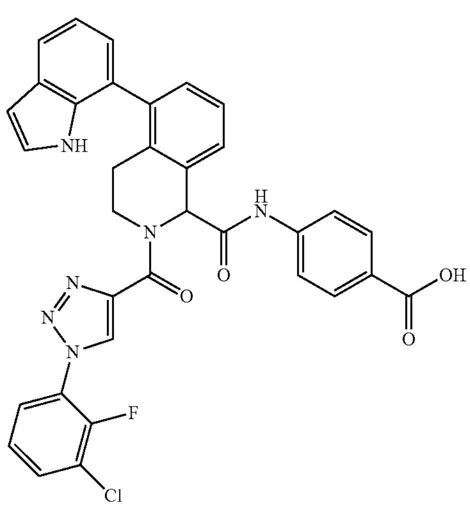 [SMILES: O=C(O)c1ccc(NC(=O)C2c3cccc(-c4cccc5cc[nH]c45)c3CCN2C(=O)c2cn(-c3cccc(Cl)c3F)nn2)cc1] | 4-(2-(1-(3-chloro-2-fluorophenyl)-1H-1,2,3-triazole-4-carbonyl)-5-(1H-indol-7-yl)-1,2,3,4-tetrahydroisoquinoline-1-carboxamido)benzoic acid | 636.17 | 2.31 (Method D) |

TABLE 8-continued

| Example | Structure | Name | LCMS (M + H)+ | HPLC RT (min) |
|---|---|---|---|---|
| 161 | 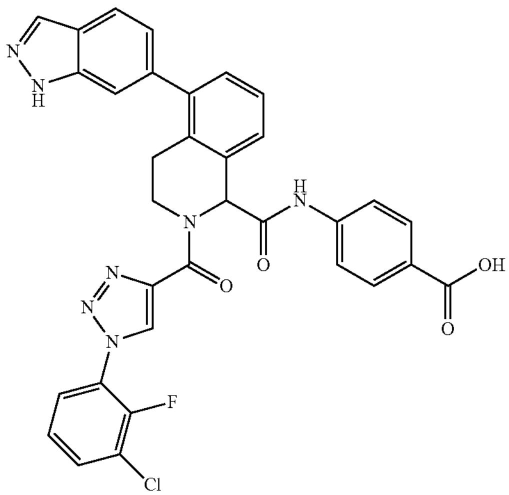 [SMILES: O=C(O)c1ccc(NC(=O)C2c3cccc(-c4ccc5cn[nH]c5c4)c3CCN2C(=O)c2cn(-c3cccc(Cl)c3F)nn2)cc1] | 4-(2-(1-(3-chloro-2-fluorophenyl)-1H-1,2,3-triazole-4-carbonyl)-5-(1H-indazol-6-yl)-1,2,3,4-tetrahydroisoquinoline-1-carboxamido)benzoic acid | 636.17 | 2.31 (Method D) |
| 162 | 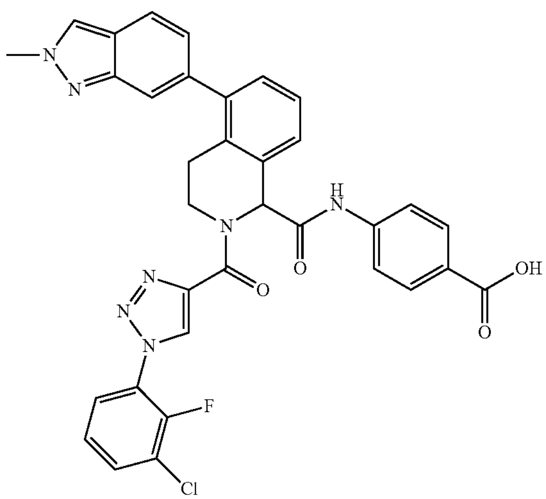 [SMILES: Cn1cc2ccc(-c3cccc4c3CCN(C(=O)c3cn(-c5cccc(Cl)c5F)nn3)C4C(=O)Nc3ccc(C(=O)O)cc3)cc2n1] | 4-(2-(1-(3-chloro-2-fluorophenyl)-1H-1,2,3-triazole-4-carbonyl)-5-(2-methyl-2H-indazol-6-yl)-1,2,3,4-tetrahydroisoquinoline-1-carboxamido)benzoic acid | 650.25 | 2.31 (Method D) |
| 163 | 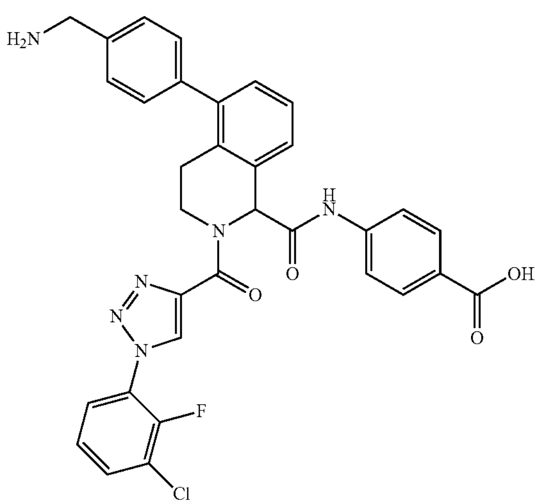 [SMILES: NCc1ccc(-c2cccc3c2CCN(C(=O)c2cn(-c4cccc(Cl)c4F)nn2)C3C(=O)Nc2ccc(C(=O)O)cc2)cc1] | 4-(5-(4-(aminomethyl)phenyl)-2-(1-(3-chloro-2-fluorophenyl)-1H-1,2,3-triazole-4-carbonyl)-1,2,3,4-tetrahydroisoquinoline-1-carboxamido)benzoic acid, TFA salt | 625.19 | 1.90 (Method D) |

TABLE 8-continued

| Example | Structure | Name | LCMS (M + H)+ | HPLC RT (min) |
|---|---|---|---|---|
| 164 | 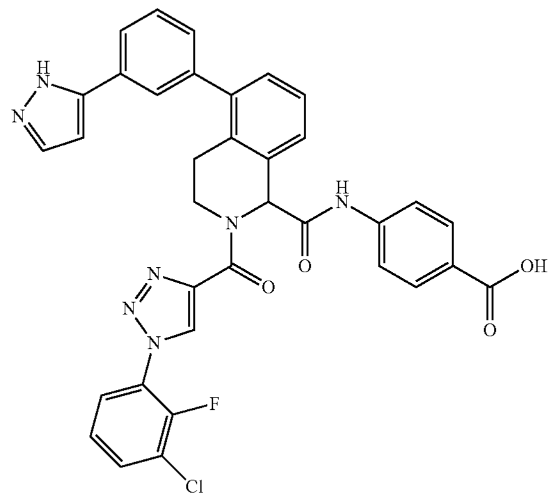 [SMILES: O=C(O)c1ccc(NC(=O)C2c3cccc(-c4cccc(-c5ccn[nH]5)c4)c3CCN2C(=O)c2cn(-c3cccc(Cl)c3F)nn2)cc1] | 4-(5-(3-(1H-pyrazol-5-yl)phenyl)-2-(1-(3-chloro-2-fluorophenyl)-1H-1,2,3-triazole-4-carbonyl)-1,2,3,4-tetrahydroisoquinoline-1-carboxamido)benzoic acid | 662.33 | 3.85 (Method D) |
| 165 | 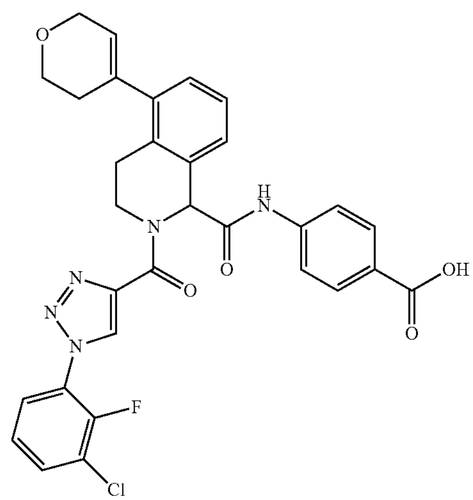 [SMILES: O=C(O)c1ccc(NC(=O)C2c3cccc(C4=CCOCC4)c3CCN2C(=O)c2cn(-c3cccc(Cl)c3F)nn2)cc1] | 4-(2-(1-(3-chloro-2-fluorophenyl)-1H-1,2,3-triazole-4-carbonyl)-5-(3,6-dihydro-2H-pyran-4-yl)-1,2,3,4-tetrahydroisoquinoline-1-carboxamido)benzoic acid | 602.15 | 3.62 (Method D) |
| 166 | 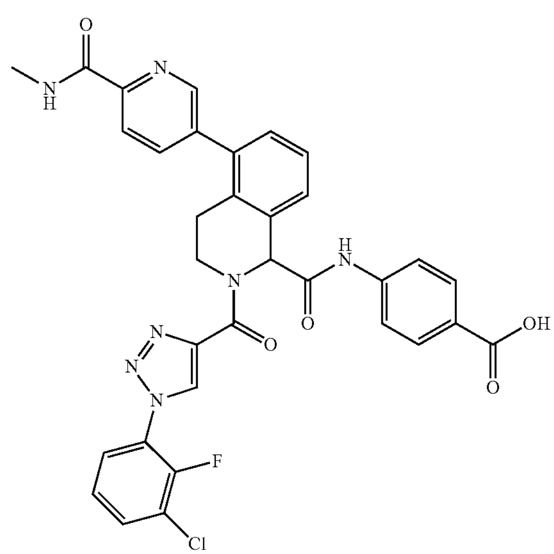 [SMILES: CNC(=O)c1ccc(-c2cccc3c2CCN(C(=O)c2cn(-c4cccc(Cl)c4F)nn2)C3C(=O)Nc2ccc(C(=O)O)cc2)cn1] | 4-(2-(1-(3-chloro-2-fluorophenyl)-1H-1,2,3-triazole-4-carbonyl)-5-(6-(methylcarbamoyl)pyridin-3-yl)-1,2,3,4-tetrahydroisoquinoline-1-carboxamido)benzoic acid, TFA salt | 654.23 | 3.46 (Method D) |

TABLE 8-continued

| Example | Structure | Name | LCMS (M + H)+ | HPLC RT (min) |
|---|---|---|---|---|
| 167 | 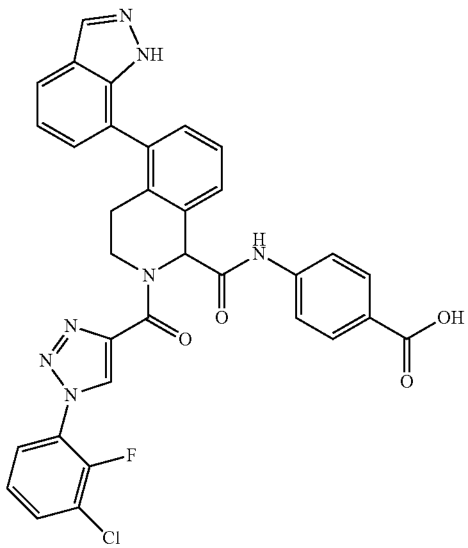 [SMILES: O=C(O)c1ccc(NC(=O)C2c3cccc(-c4cccc5cn[nH]c45)c3CCN2C(=O)c2cn(-c3cccc(Cl)c3F)nn2)cc1] | 4-(2-(1-(3-chloro-2-fluorophenyl)-1H-1,2,3-triazole-4-carbonyl)-5-(1H-indazol-7-yl)-1,2,3,4-tetrahydroisoquinoline-1-carboxamido)benzoic acid | 675.49 | 3.28 (Method D) |
| 168 | 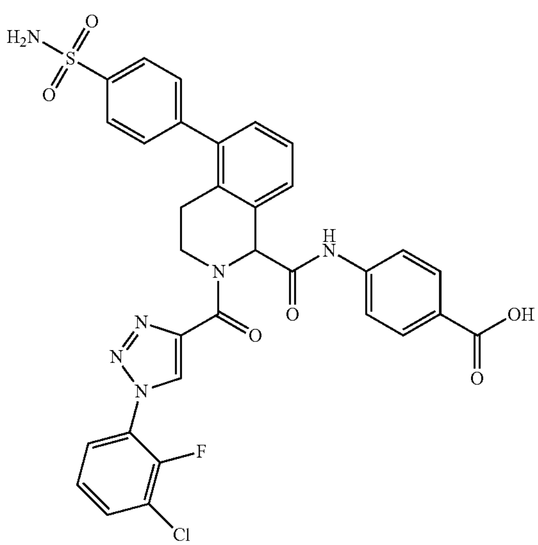 [SMILES: NS(=O)(=O)c1ccc(-c2cccc3c2CCN(C(=O)c2cn(-c4cccc(Cl)c4F)nn2)C3C(=O)Nc2ccc(C(=O)O)cc2)cc1] | 4-(2-(1-(3-chloro-2-fluorophenyl)-1H-1,2,3-triazole-4-carbonyl)-5-(4-sulfamoylphenyl)-1,2,3,4-tetrahydroisoquinoline-1-carboxamido)benzoic acid | 636.19 | 3.91 (Method D) |
| 169 | 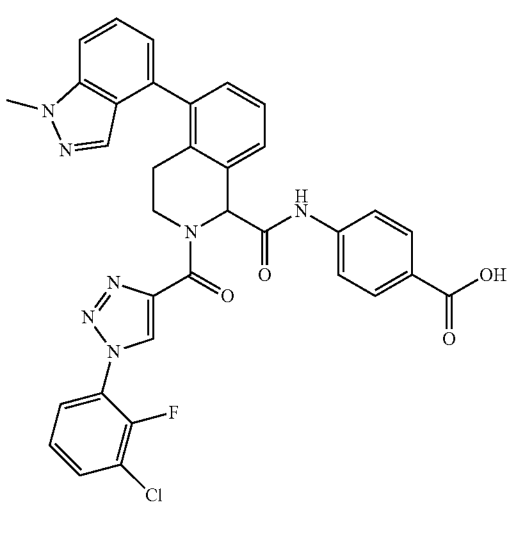 [SMILES: Cn1ncc2c(-c3cccc4c3CCN(C(=O)c3cn(-c5cccc(Cl)c5F)nn3)C4C(=O)Nc3ccc(C(=O)O)cc3)cccc21] | 4-(2-(1-(3-chloro-2-fluorophenyl)-1H-1,2,3-triazole-4-carbonyl)-5-(1-methyl-1H-indazol-4-yl)-1,2,3,4-tetrahydroisoquinoline-1-carboxamido)benzoic acid | 650.19 | 3.88 (Method D) |

TABLE 8-continued

| Example | Structure | Name | LCMS (M + H)+ | HPLC RT (min) |
|---|---|---|---|---|
| 170 | 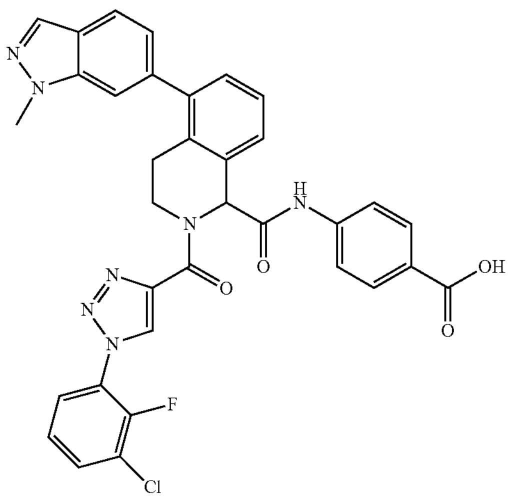 [SMILES: Cn1ncc2ccc(-c3cccc4c3CCN(C(=O)c3cn(-c5cccc(Cl)c5F)nn3)C4C(=O)Nc3ccc(C(=O)O)cc3)cc21] | 4-(2-(1-(3-chloro-2-fluorophenyl)-1H-1,2,3-triazole-4-carbonyl)-5-(1-methyl-1H-indazol-6-yl)-1,2,3,4-tetrahydroisoquinoline-1-carboxamido)benzoic acid | 650.32 | 2.54 (Method D) |
| 171 | 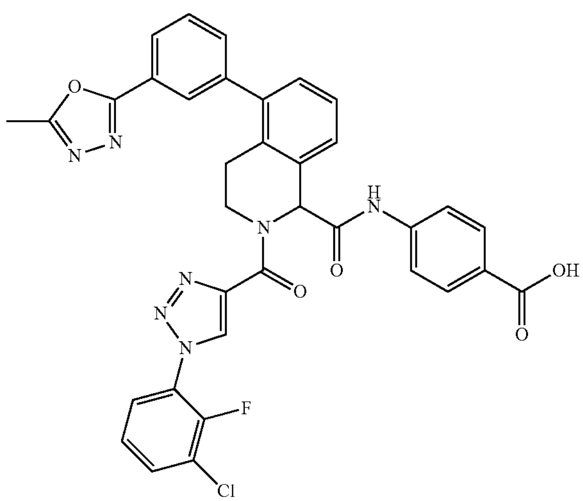 [SMILES: Cc1nnc(-c2cccc(-c3cccc4c3CCN(C(=O)c3cn(-c5cccc(Cl)c5F)nn3)C4C(=O)Nc3ccc(C(=O)O)cc3)c2)o1] | 4-(2-(1-(3-chloro-2-fluorophenyl)-1H-1,2,3-triazole-4-carbonyl)-5-(3-(5-methyl-1,3,4-oxadiazol-2-yl)phenyl)-1,2,3,4-tetrahydroisoquinoline-1-carboxamido)benzoic acid | 678.21 | 3.80 (Method D) |
| 172 | 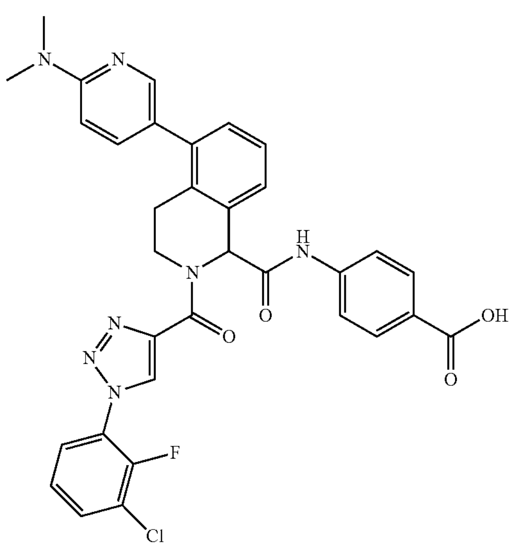 [SMILES: CN(C)c1ccc(-c2cccc3c2CCN(C(=O)c2cn(-c4cccc(Cl)c4F)nn2)C3C(=O)Nc2ccc(C(=O)O)cc2)cn1] | 4-(2-(1-(3-chloro-2-fluorophenyl)-1H-1,2,3-triazole-4-carbonyl)-5-(6-(dimethylamino)pyridin-3-yl)-1,2,3,4-tetrahydroisoquinoline-1-carboxamido)benzoic acid | 640.25 | 3.89 (Method D) |

TABLE 8-continued

| Example | Structure | Name | LCMS (M + H)+ | HPLC RT (min) |
|---|---|---|---|---|
| 173 | 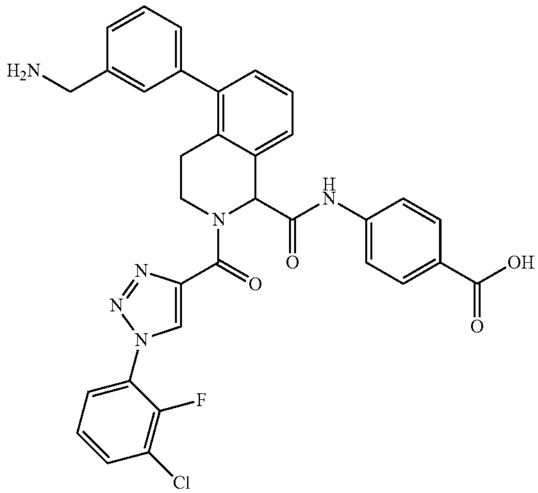 [SMILES: NCc1cccc(-c2cccc3c2CCN(C(=O)c2cn(-c4cccc(Cl)c4F)nn2)C3C(=O)Nc2ccc(C(=O)O)cc2)c1] | 4-(5-(3-(aminomethyl)phenyl)-2-(1-(3-chloro-2-fluorophenyl)-1H-1,2,3-triazole-4-carbonyl)-1,2,3,4-tetrahydroisoquinoline-1-carboxamido)benzoic acid, TFA salt | 623.28 | 2.00 (Method D) |
| 174 | 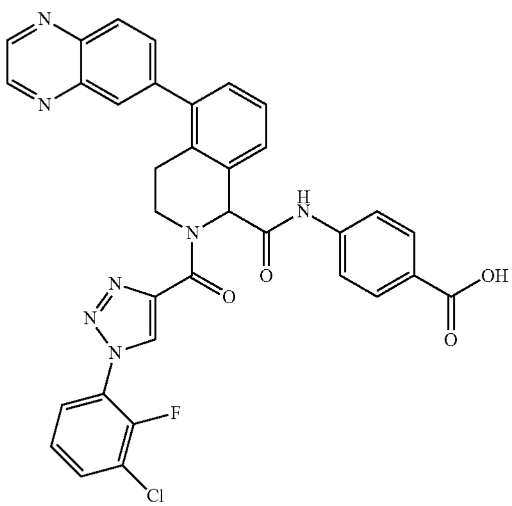 [SMILES: O=C(O)c1ccc(NC(=O)C2c3cccc(-c4ccc5nccnc5c4)c3CCN2C(=O)c2cn(-c3cccc(Cl)c3F)nn2)cc1] | 4-(2-(1-(3-chloro-2-fluorophenyl)-1H-1,2,3-triazole-4-carbonyl)-5-(quinoxalin-6-yl)-1,2,3,4-tetrahydroisoquinoline-1-carboxamido)benzoic acid | 648.21 | 3.71 (Method D) |
| 175 | 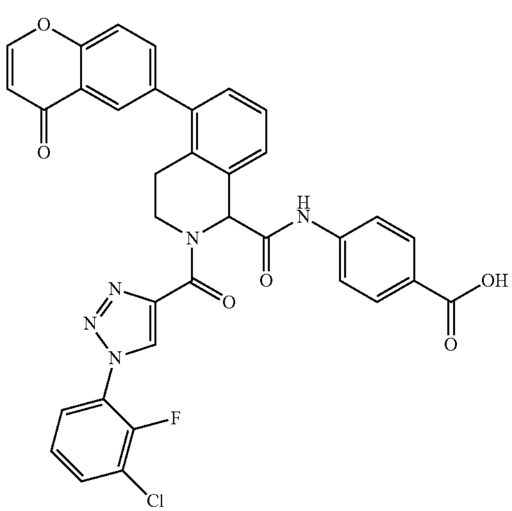 [SMILES: O=C(O)c1ccc(NC(=O)C2c3cccc(-c4ccc5occc(=O)c5c4)c3CCN2C(=O)c2cn(-c3cccc(Cl)c3F)nn2)cc1] | 4-(2-(1-(3-chloro-2-fluorophenyl)-1H-1,2,3-triazole-4-carbonyl)-5-(4-oxo-4H-chromen-6-yl)-1,2,3,4-tetrahydroisoquinoline-1-carboxamido)benzoic acid | 664.14 | 2.37 (Method D) |

TABLE 8-continued

| Example | Structure | Name | LCMS (M + H)+ | HPLC RT (min) |
|---|---|---|---|---|
| 176 | 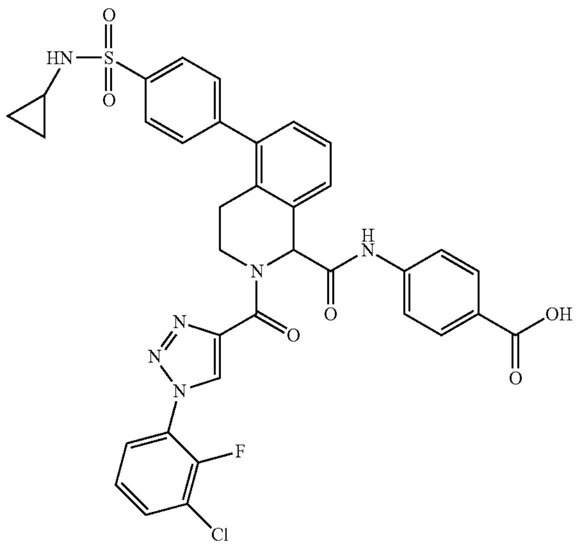 [SMILES: O=C(O)c1ccc(NC(=O)C2c3cccc(-c4ccc(S(=O)(=O)NC5CC5)cc4)c3CCN2C(=O)c2cn(-c3cccc(Cl)c3F)nn2)cc1] | 4-(2-(1-(3-chloro-2-fluorophenyl)-1H-1,2,3-triazole-4-carbonyl)-5-(4-(N-cyclopropylsulfamoyl)phenyl)-1,2,3,4-tetrahydroisoquinoline-1-carboxamido)benzoic acid | 715.12 | 2.47 (Method D) |
| 177 | 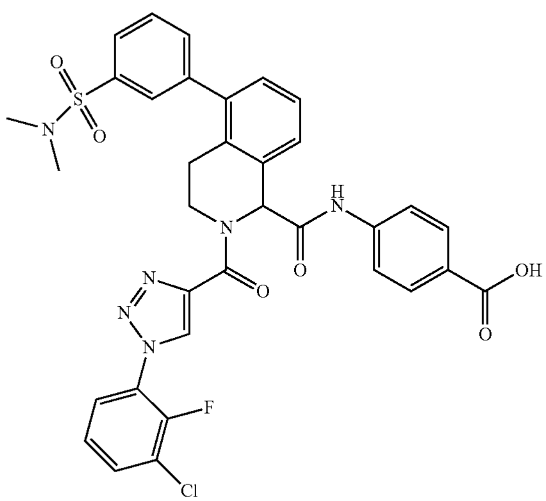 [SMILES: CN(C)S(=O)(=O)c1cccc(-c2cccc3c2CCN(C(=O)c2cn(-c4cccc(Cl)c4F)nn2)C3C(=O)Nc2ccc(C(=O)O)cc2)c1] | 4-(2-(1-(3-chloro-2-fluorophenyl)-1H-1,2,3-triazole-4-carbonyl)-5-(3-(N,N-dimethylsulfamoyl)phenyl)-1,2,3,4-tetrahydroisoquinoline-1-carboxamido)benzoic acid | 703.42 | 2.54 (Method D) |
| 178 | 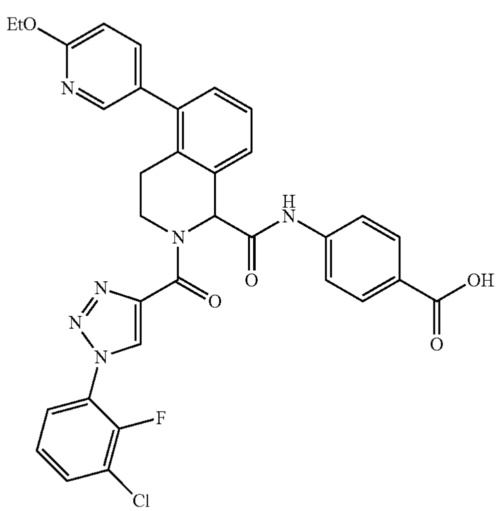 [SMILES: CCOc1ccc(-c2cccc3c2CCN(C(=O)c2cn(-c4cccc(Cl)c4F)nn2)C3C(=O)Nc2ccc(C(=O)O)cc2)cn1] | 4-(2-(1-(3-chloro-2-fluorophenyl)-1H-1,2,3-triazole-4-carbonyl)-5-(6-ethoxypyridin-3-yl)-1,2,3,4-tetrahydroisoquinoline-1-carboxamido)benzoic acid, TFA salt | 641.28 | 2.69 (Method D) |

TABLE 8-continued
| Example | Structure | Name | LCMS (M + H)+ | HPLC RT (min) |
|---|---|---|---|---|
| 179 | 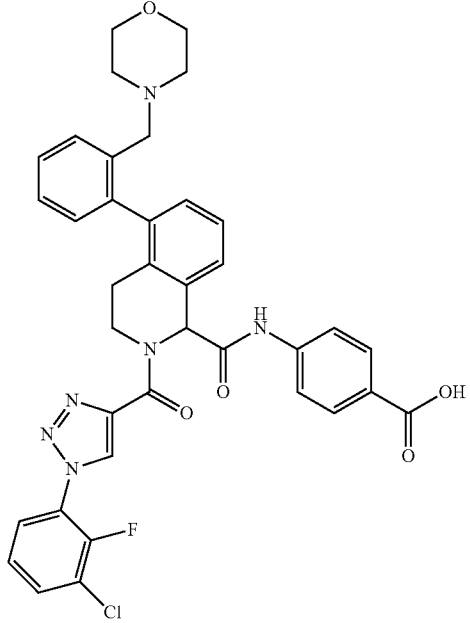 [SMILES: O=C(O)c1ccc(NC(=O)C2c3cccc(-c4ccccc4CN4CCOCC4)c3CCN2C(=O)c2cn(-c3cccc(Cl)c3F)nn2)cc1] | 4-(2-(1-(3-chloro-2-fluorophenyl)-1H-1,2,3-triazole-4-carbonyl)-5-(2-(morpholinomethyl)phenyl)-1,2,3,4-tetrahydroisoquinoline-1-carboxamido)benzoic acid, TFA salt | 695.36 | 4.19 (Method D) |
| 180 | 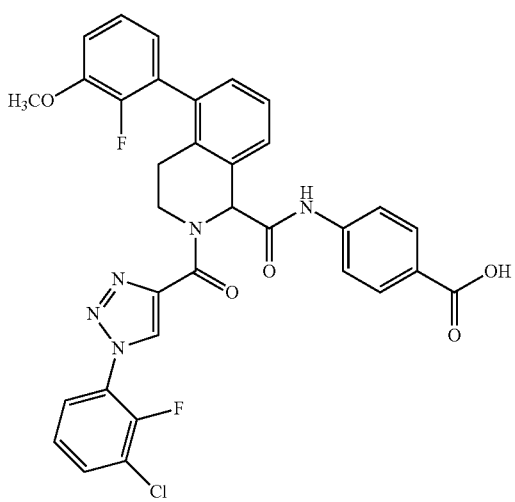 [SMILES: COc1cccc(-c2cccc3c2CCN(C(=O)c2cn(-c4cccc(Cl)c4F)nn2)C3C(=O)Nc2ccc(C(=O)O)cc2)c1F] | 4-(2-(1-(3-chloro-2-fluorophenyl)-1H-1,2,3-triazole-4-carbonyl)-5-(2-fluoro-3-methoxyphenyl)-1,2,3,4-tetrahydroisoquinoline-1-carboxamido)benzoic acid | 644.17 | 2.67 (Method D) |

TABLE 8-continued

| Example | Structure | Name | LCMS (M + H)+ | HPLC RT (min) |
|---|---|---|---|---|
| 181 | 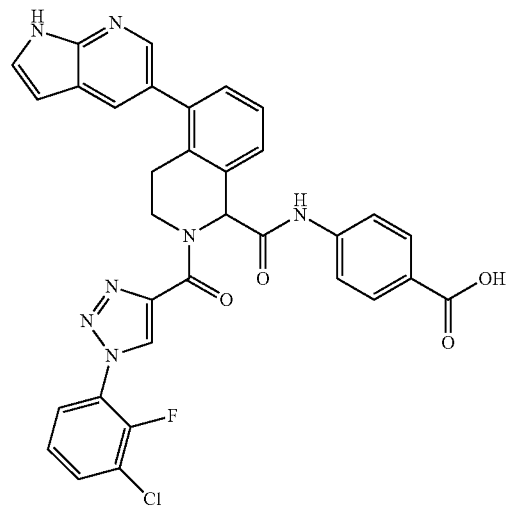 [SMILES: O=C(O)c1ccc(NC(=O)C2c3cccc(-c4cnc5[nH]ccc5c4)c3CCN2C(=O)c2cn(-c3cccc(Cl)c3F)nn2)cc1] | 4-(2-(1-(3-chloro-2-fluorophenyl)-1H-1,2,3-triazole-4-carbonyl)-5-(1H-pyrrolo[2,3-b]pyridin-5-yl)-1,2,3,4-tetrahydroisoquinoline-1-carboxamido)benzoic acid, TFA salt | 636.36 | 2.30 (Method D) |
| 182 | 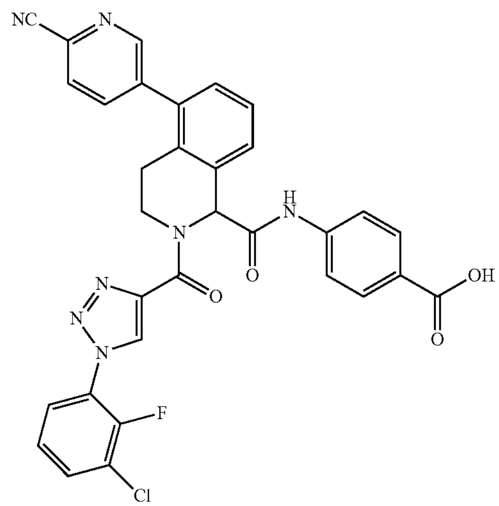 [SMILES: N#Cc1ccc(-c2cccc3c2CCN(C(=O)c2cn(-c4cccc(Cl)c4F)nn2)C3C(=O)Nc2ccc(C(=O)O)cc2)cn1] | 4-(2-(1-(3-chloro-2-fluorophenyl)-1H-1,2,3-triazole-4-carbonyl)-5-(6-cyanopyridin-3-yl)-1,2,3,4-tetrahydroisoquinoline-1-carboxamido)benzoic acid, TFA salt | 622.21 | 3.52 (Method D) |
| 183 | 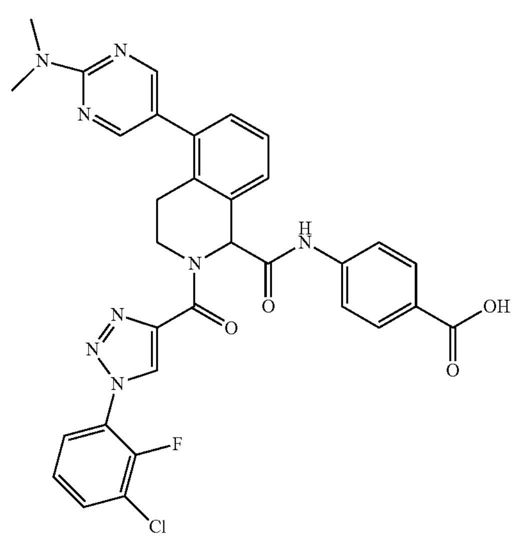 [SMILES: CN(C)c1ncc(-c2cccc3c2CCN(C(=O)c2cn(-c4cccc(Cl)c4F)nn2)C3C(=O)Nc2ccc(C(=O)O)cc2)cn1] | 4-(2-(1-(3-chloro-2-fluorophenyl)-1H-1,2,3-triazole-4-carbonyl)-5-(2-(dimethylamino)pyrimidin-5-yl)-1,2,3,4-tetrahydroisoquinoline-1-carboxamido)benzoic acid | 641.24 | 3.82 (Method D) |

TABLE 8-continued

| Example | Structure | Name | LCMS (M + H)+ | HPLC RT (min) |
|---|---|---|---|---|
| 184 | 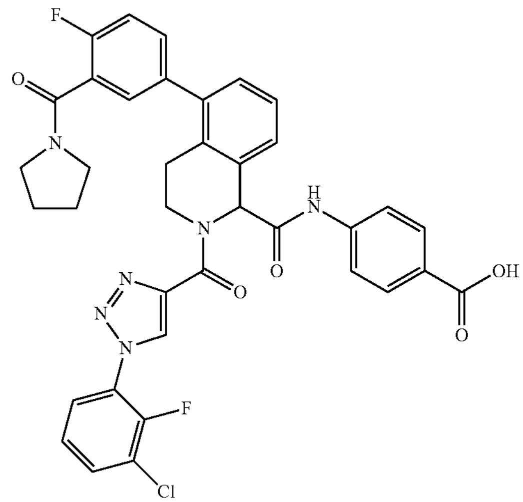 [SMILES: O=C(O)c1ccc(NC(=O)C2c3cccc(-c4ccc(F)c(C(=O)N5CCCC5)c4)c3CCN2C(=O)c2cn(-c3cccc(Cl)c3F)nn2)cc1] | 4-(2-(1-(3-chloro-2-fluorophenyl)-1H-1,2,3-triazole-4-carbonyl)-5-(4-fluoro-3-(pyrrolidine-1-carbonyl)phenyl)-1,2,3,4-tetrahydroisoquinoline-1-carboxamido)benzoic acid | 711.31 | 2.48 (Method D) |
| 185 | 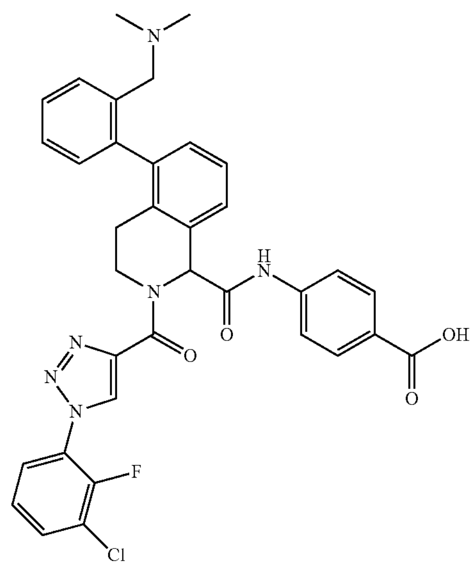 [SMILES: CN(C)Cc1ccccc1-c1cccc2c1CCN(C(=O)c1cn(-c3cccc(Cl)c3F)nn1)C2C(=O)Nc1ccc(C(=O)O)cc1] | 4-(2-(1-(3-chloro-2-fluorophenyl)-1H-1,2,3-triazole-4-carbonyl)-5-(2-((dimethylamino)methyl)phenyl)-1,2,3,4-tetrahydroisoquinoline-1-carboxamido)benzoic acid, TFA salt | 653.26 | 2.28 (Method D) |
| 186 | 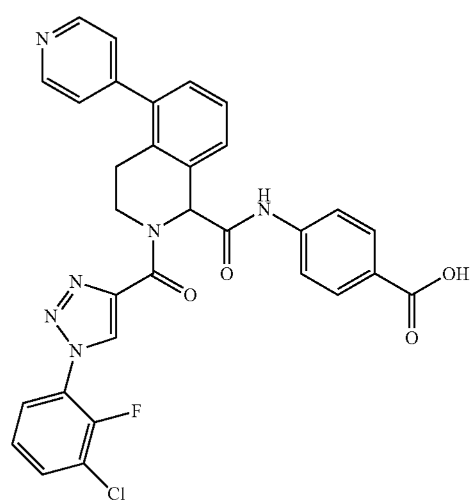 [SMILES: O=C(O)c1ccc(NC(=O)C2c3cccc(-c4ccncc4)c3CCN2C(=O)c2cn(-c3cccc(Cl)c3F)nn2)cc1] | 4-(2-(1-(3-chloro-2-fluorophenyl)-1H-1,2,3-triazole-4-carbonyl)-5-(pyridin-4-yl)-1,2,3,4-tetrahydroisoquinoline-1-carboxamido)benzoic acid, TFA salt | 597.36 | 3.52 (Method D) |

TABLE 8-continued

| Example | Structure | Name | LCMS (M + H)+ | HPLC RT (min) |
|---|---|---|---|---|
| 187 | 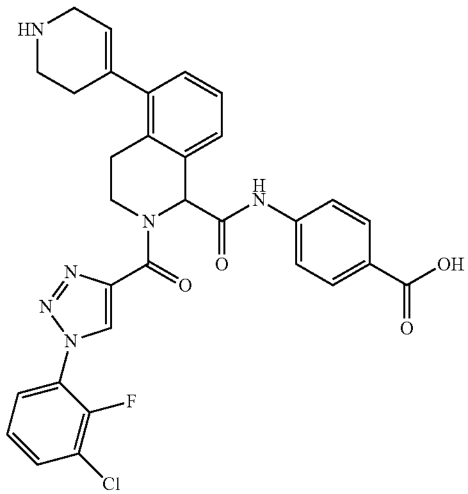 [SMILES: O=C(O)c1ccc(NC(=O)C2c3cccc(C4=CCNCC4)c3CCN2C(=O)c2cn(-c3cccc(Cl)c3F)nn2)cc1] | 4-(2-(1-(3-chloro-2-fluorophenyl)-1H-1,2,3-triazole-4-carbonyl)-5-(1,2,3,6-tetrahydropyridin-4-yl)-1,2,3,4-tetrahydroisoquinoline-1-carboxamido)benzoic acid | 601.17 | 1.79 (Method D) |
| 188 | 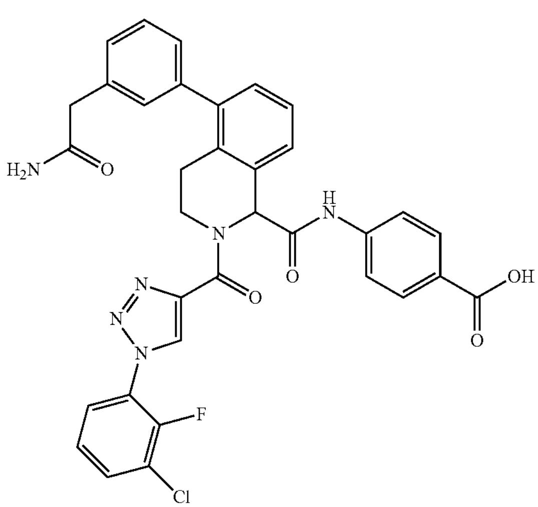 [SMILES: NC(=O)Cc1cccc(-c2cccc3c2CCN(C(=O)c2cn(-c4cccc(Cl)c4F)nn2)C3C(=O)Nc2ccc(C(=O)O)cc2)c1] | 4-(5-(3-(2-amino-2-oxoethyl)phenyl)-2-(1-(3-chloro-2-fluorophenyl)-1H-1,2,3-triazole-4-carbonyl)-1,2,3,4-tetrahydroisoquinoline-1-carboxamido)benzoic acid | 653.07 | 2.27 (Method D) |

EXAMPLE 189

2-(1-(3-Chloro-2-fluorophenyl)-1H-1,2,3-triazole-4-carbonyl)-5-(4-methoxypiperidin-1-yl)-N-(1-methyl-2-oxo-1,2,3,4-tetrahydroquinolin-6-yl)-1,2,3,4-tetrahydroisoquinoline-1-carboxamide, TFA salt

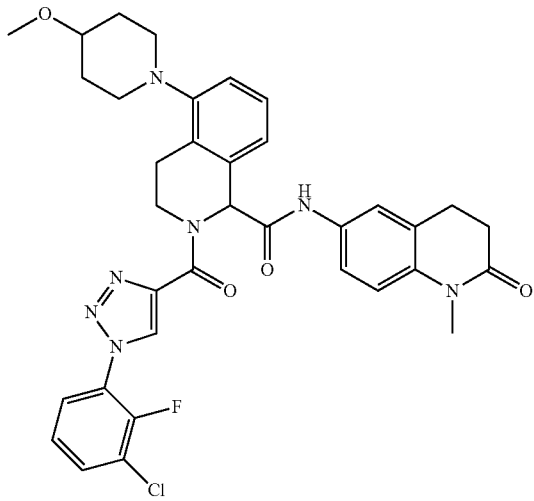 [SMILES: COC1CCN(c2cccc3c2CCN(C(=O)c2cn(-c4cccc(Cl)c4F)nn2)C3C(=O)Nc2ccc3c(c2)CCC(=O)N3C)CC1]

189A. Methyl 2-(1-(3-chloro-2-fluorophenyl)-1H-1,2,3-triazole-4-carbonyl)-5-(4-methoxypiperidin-1-yl)-1,2,3,4-tetrahydroisoquinoline-1-carboxylate: To Intermediate 27 (0.55 g, 1.360 mmol) in dioxane was added HCl (0.340 mL, 1.360 mmol) in dioxane. After stirring overnight, the reaction mixture was concentrated to dryness. To the amine and Intermediate 9 (0.328 g, 1.360 mmol) in DMF(3 mL), T3P/50% EtOAc (0.769 mL, 2.72 mmol) and pyridine (0.660 mL, 8.16 mmol) were added. After stirring overnight, the reaction was quenched with saturated NaHCO₃ solution (15 mL) and extracted with ethyl acetate (3×30 mL). The combined organic layers were washed with brine (15 mL), dried (MgSO₄), filtered, and concentrated. The crude material was purified by normal phase column chromatography to give a brown foam (0.59 g, 82%). $^1$H NMR (400 MHz, methanol-$d_4$) δ 9.99 (d, J=1.5 Hz, 1H), 8.74-8.62 (m, 2H), 8.39-8.30 (m, 1H), 8.13-8.03 (m, 2H), 7.86 (d, J=6.6 Hz, 1H), 6.59 (s, 1H), 5.13-5.05 (m, 1H), 5.00 (dd, J=8.0, 4.4 Hz, 1H), 4.48 (s, 3H), 4.13-4.07 (m, 6H), 3.85-3.76 (m, 3H), 3.50 (dd, J=11.5, 9.5 Hz, 2H), 2.77 (br. s., 2H), 2.43 (d, J=3.8 Hz, 2H) ppm.

189B. 2-(1-(3-Chloro-2-fluorophenyl)-1H-1,2,3-triazole-4-carbonyl)-5-(4-methoxypiperidin-1-yl)-1,2,3,4-tetrahydroisoquinoline-1-carboxylic acid, AcOH salt: To 189A (0.58 g, 1.099 mmol) in THF/water was added LiOH hydrate (0.138 g, 3.30 mmol). After stirring overnight, the reaction was concentrated and partitioned between ethyl acetate (30 mL) and water. The aqueous layer was acidified to pH5 with AcOH and extracted with ethyl acetate (2×20 mL). The combined organic layers were dried (MgSO₄), filtered, and concentrated to give a tan solid (0.59 g, 94%). $^1$H NMR (400 MHz, methanol-$d_4$) δ 8.92-8.82 (m, 1H), 7.94-7.83 (m, 1H), 7.81-7.70 (m, 1H), 7.47 (d, J=8.1 Hz, 1H), 7.37-7.30 (m, 1H), 7.25 (dd, J=14.7, 6.6 Hz, 1H), 7.09 (d, J=7.8 Hz, 1H), 5.78 (s, 1H), 4.52-4.40 (m, 1H), 4.27-4.13 (m, 1H), 3.41 (s, 3H), 3.01 (br. s., 5H), 2.84-2.68 (m, 2H), 2.08 (br. s., 2H), 1.75 (br. s., 2H) ppm.

Example 189. 2-(1-(3-Chloro-2-fluorophenyl)-1H-1,2,3-triazole-4-carbonyl)-5-(4-methoxypiperidin-1-yl)-N-(1-methyl-2-oxo-1,2,3,4-tetrahydroquinolin-6-yl)-1,2,3,4-tetrahydroisoquinoline-1-carboxamide, TFA salt: 194B (51 mg, 0.099 mmol), 6-amino-1-methyl-3,4-dihydroquinolin-2(1H)-one (17.49 mg, 0.099 mmol), and T3P/50% EtOAc (28.1 µl, 0.099 mmol), and pyridine (48.2 µl, 0.595 mmol) were added to DMF (0.25 mL). After stirring overnight, the mixture was quenched with saturated NaHCO₃ solution (5 mL) and extracted with EtOAc (3×10 mL). The combined organic layers were washed with water (10 mL), brine (10 mL), dried (MgSO₄), filtered, concentrated, purified by reverse phase prep. HPLC, and freeze-dried to give Example 189 as a yellow solid (5 mgs, 6%). $^1$H NMR (400 MHz, methanol-$d_4$) δ 8.95-8.86 (m, 1H), 7.92-7.81 (m, 1H), 7.79-7.70 (m, 1H), 7.52-7.30 (m, 6H), 7.07 (d, J=8.6 Hz, 1H), 5.92 (s, 1H), 4.68 (dd, J=12.0, 5.7 Hz, 1H), 4.23 (d, J=8.3 Hz, 1H), 3.60 (br. s., 2H), 3.45-3.41 (s+m, 4H), 3.39-3.36 (m, 2H), 3.28-3.21 (m, 1H), 3.13 (d, J=19.7 Hz, 2H), 2.90-2.87 (m, 1H), 2.61 (t, J=7.3 Hz, 3H), 2.17 (br. s., 3H), 1.90 (br. s., 3H) ppm. MS (ESI) m/z: 672.0 (M+H)⁺. Analytical HPLC: RT=8.68 min (Method A).

EXAMPLE 190

2-(1-(3-Chloro-2-fluorophenyl)-1H-12,3-triazole-4-carbonyl)-5-(4-methoxypiperidin-1-yl)-N-(2-oxoindolin-5-yl)-1,2,3,4-tetrahydroisoquinoline-1-carboxamide, TFA salt

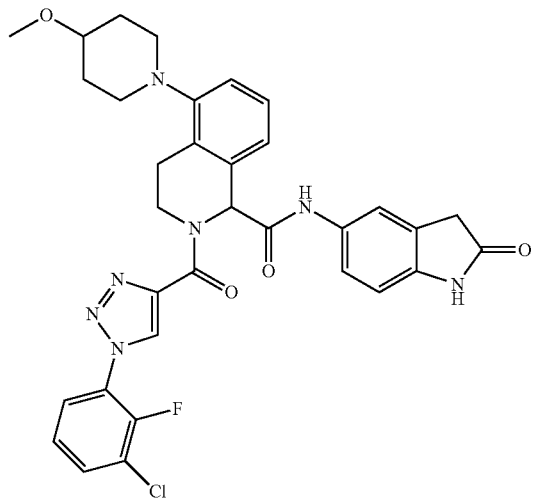 [SMILES: COC1CCN(c2cccc3c2CCN(C(=O)c2cn(-c4cccc(Cl)c4F)nn2)C3C(=O)Nc2ccc3c(c2)CC(=O)N3)CC1]

Example 190: 2-(1-(3-Chloro-2-fluorophenyl)-1H-1,2,3-triazole-4-carbonyl)-5-(4-methoxypiperidin-1-yl)-N-(2-oxoindolin-5-yl)-1,2,3,4-tetrahydroisoquinoline-1-carboxamide, TFA salt: The title compound was prepared in the same manner as Example 189 replacing 6-amino-1-methyl-3,4-dihydroquinolin-2(1H)-one with 5-aminoindolin-2-one. $^1$H NMR (400 MHz, methanol-$d_4$) δ 10.08 (br. s., 1H), 8.78 (br. s., 1H), 7.75 (d, J=7.1 Hz, 1H), 7.62 (d, J=7.3 Hz, 1H), 7.42-7.18 (m, 4H), 7.12 (br. s., 1H), 6.72 (d, J=7.8 Hz, 1H), 5.77 (br. s., 1H), 4.52 (br. s., 1H), 4.07 (br. s., 1H), 3.38 (d, J=11.1 Hz, 3H), 3.30 (s, 3H), 3.16-3.04 (m, 4H), 2.95-2.74 (m, 2H), 2.01 (br. s., 2H), 1.72 (br. s., 2H) ppm. MS (ESI) m/z: 644 (M+H)⁺. Analytical HPLC: RT=7.68 min (Method A).

EXAMPLE 191

4-(5-Acetamido-2-(1-(3-chloro-2-fluorophenyl)-1H-1,2,3-triazole-4-carbonyl)-1,2,3,4-tetrahydroisoquinoline-1-carboxamido)benzoic acid

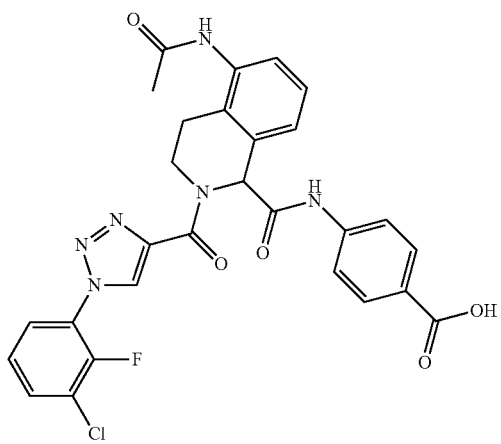 [SMILES: CC(=O)Nc1cccc2c1CCN(C(=O)c1cn(-c3cccc(Cl)c3F)nn1)C2C(=O)Nc1ccc(C(=O)O)cc1]

191A. N-(3,4-Dihydroisoquinolin-5-yl)acetamide: N-(Isoquinolin-5-yl)acetamide (0.28 g, 1.504 mmol) in EtOH(25 mL) was hydrogenated with a catalytic amount of $PtO_2$. After stirring overnight, the slurry was filtered through CELITE® and filtrate concentrated to afford the amine as white solid. This material was treated with $MnO_2$ (1.961 g, 22.56 mmol) in DCM(10 mL). After stirring overnight, the suspension was filtered through CELITE® and filtrate concentrated to give a tan solid. MS (ESI) m/z: 189 $(M+H)^+$.

Example 191. 4-(5-Acetamido-2-(1-(3-chloro-2-fluorophenyl)-1H-1,2,3-triazole-4-carbonyl)-1,2,3,4-tetrahydroisoquinoline-1-carboxamido)benzoic acid Intermediate 9 (0.128 g, 0.531 mmol), 191A (0.1 g, 0.531 mmol), Intermediate 1 (0.108 g, 0.531 mmol) were added to MeOH (0.885 mL) in a small vial and heated to 55° C. After stirring overnight, a small aliquot was deprotected with 50% TFA/DCM, concentrated after 2 h, purified by reverse phase prep. HPLC, and freeze-dried to give the title compound as a white solid. $^1$H NMR (400 MHz, methanol-$d_4$) δ 8.89 (d, J=2.0 Hz, 1H), 7.99 (d, J=8.6 Hz, 2H), 7.88 (t, J=6.7 Hz, 1H), 7.81-7.66 (m, 3H), 7.52 (s, 1H), 7.50-7.44 (m, 1H), 7.35 (dt, J=14.7, 7.3 Hz, 2H), 6.00 (s, 1H), 4.66-4.52 (m, 1H), 4.50-4.38 (m, 1H), 3.24-3.11 (m, 1H), 3.11-2.99 (m, 1H), 2.20 (s, 3H) ppm. MS (ESI) m/z: 577 $(M+H)^+$. Analytical HPLC: RT=6.9 min. (Method A).

EXAMPLE 192

4-(2-(1-(3-Chloro-2-fluorophenyl)-1H-1,2,3-triazole-4-carbonyl)-5-((1-methylpiperidin-4-yl)carbamoyl)-1,2,3,4-tetrahydroisoquinoline-1-carboxamido)benzoic acid, TFA salt.

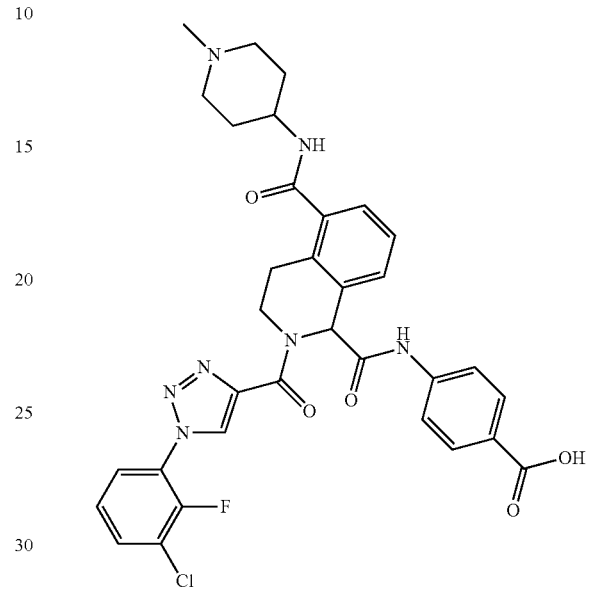

192A. N-(1-Methylpiperidin-4-yl)isoquinoline-5-carboxamide: To isoquinoline-5-carboxylic acid (0.22 g, 1.270 mmol) and 1-methylpiperidin-4-amine (0.145 g, 1.270 mmol) in EtOAc (3 mL)/DMF(1 mL) was added TEA (0.48 mL, 3.464 mmol) and a 50% EtOAc solution of T3P (0.306 mL, 1.082 mmol). After 24 h, the reaction was partitioned with water (15 mL) and ethyl acetate (50 mL). The organic layer was washed with brine (10 mL) and dried ($MgSO_4$). MS (ESI) m/z: 270.1 $(M+H)^+$.

192B. N-(1-Methylpiperidin-4-yl)-3,4-dihydroisoquinoline-5-carboxamide: Crude Intermediate 192A (0.3 g, 1.114 mmol) was hydrogenated and then oxidized as in 191A to afford tan solid (0.13 g, 43%). MS (ESI) m/z: 272.1 $(M+H)^+$.

Example 192. 4-(2-(1-(3-Chloro-2-fluorophenyl)-1H-1,2,3-triazole-4-carbonyl)-5-((1-methylpiperidin-4-yl)carbamoyl)-1,2,3,4-tetrahydroisoquinoline-1-carboxamido)benzoic acid, TFA salt: The title compound was prepared in the same manner as Example 191 starting from 192B. $^1$H NMR (400 MHz, methanol-$d_4$) δ 8.9 (s, 1H), 7.9 (d, J=8.6 Hz, 2H), 7.8 (t, J=7.6 Hz, 1H), 7.7-7.6 (m, 3H), 7.5-7.28 (m, 3H), 6 (s, 1H), 5.6-5.4 (m, 1H), 4.7-4.6 (m, 1H), 4.06 (d, J=5.1 Hz, 1H), 4.1 (t, J=11.7 Hz, 1H), 3.63 (d, J=11.9 Hz, 2H), 3.14 (br. s., 3H), 3 (s, 1H), 2.9-2.8 (m, 3H), 2.05 (d, J=13.1 Hz, 2H), 2.2-2.0 (m, 1H), 1.9-1.8 (m, 1H) ppm. MS (ESI) m/z: 660.0 $(M+H)^+$. Analytical HPLC: RT=4.64 min (Method A).

EXAMPLE 193

4-(2-(1-(3-Chloro-2-fluorophenyl)-1H-1,2,3-triazole-4-carbonyl)-5-(3-cyclopentylureido)-1,2,3,4-tetrahydroisoquinoline-1-carboxamido)benzoic acid

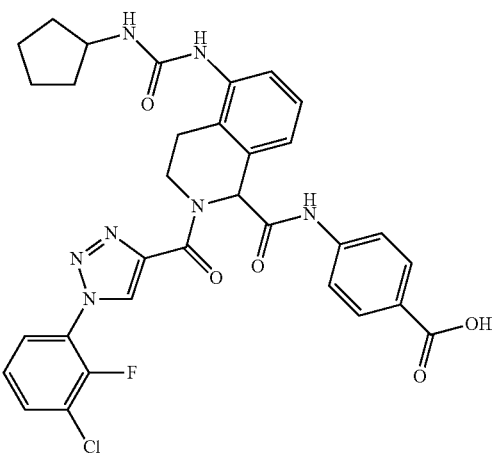 [SMILES: O=C(Nc1cccc2c1CCN(C(=O)c1cn(-c3cccc(Cl)c3F)nn1)C2C(=O)Nc1ccc(C(=O)O)cc1)NC1CCCC1]

193A. 1-Cyclopentyl-3-(3,4-dihydroisoquinolin-5-yl)urea: To isoquinolin-5-amine (0.23 g, 1.595 mmol) in DCM (5 mL) was added Hunig's Base (0.557 mL, 3.19 mmol) and isocyanatocyclopentane (0.180 mL, 1.595 mmol). After stirring overnight, the reaction was quenched with water (15 mL) and extracted with ethyl acetate (3×30 mL). The combined organic layers were washed with brine (10 mL), dried (MgSO$_4$), filtered, and concentrated. The crude yellow solid obtained was hydrogenated and then oxidized as in the 191A to afford a brown solid (0.34 g, 83%). MS (ESI) m/z: 258.1 (M+H)$^+$.

Example 193. 4-(2-(1-(3-Chloro-2-fluorophenyl)-1H-1,2,3-triazole-4-carbonyl)-5-(3-cyclopentylureido)-1,2,3,4-tetrahydroisoquinoline-1-carboxamido)benzoic acid: The title compound was prepared in the same manner as Example 191 starting from 193A. $^1$H NMR (400 MHz, methanol-d$_4$) δ 7.58 (s, 1H), 6.67 (d, J=8.6 Hz, 2H), 6.59-6.54 (m, 1H), 6.47-6.37 (m, 3H), 6.24 (d, J=7.8 Hz, 1H), 6.13 (d, J=9.3 Hz, 1H), 6.06 (d, J=7.8 Hz, 1H), 6.00-5.95 (m, 1H), 4.72-4.63 (m, 1H), 3.26 (br. s., 1H), 3.13 (br. s., 1H), 2.82-2.72 (m, 1H), 1.88-1.70 (m, 3H), 0.71-0.62 (m, 2H), 0.44 (br. s., 2H), 0.33 (br. s., 2H), 0.23-0.14 (m, 2H) ppm. MS (ESI) m/z: 646.0 (M+H)$^+$. Analytical HPLC: RT=8.36 min (Method A).

EXAMPLE 194

4-(5-Chloro-2-(1-(3-chloro-2-fluorophenyl)-1H-1,2,3-triazole-4-carbonyl)-1,2,3,4-tetrahydroisoquinoline-1-carboxamido)benzoic acid

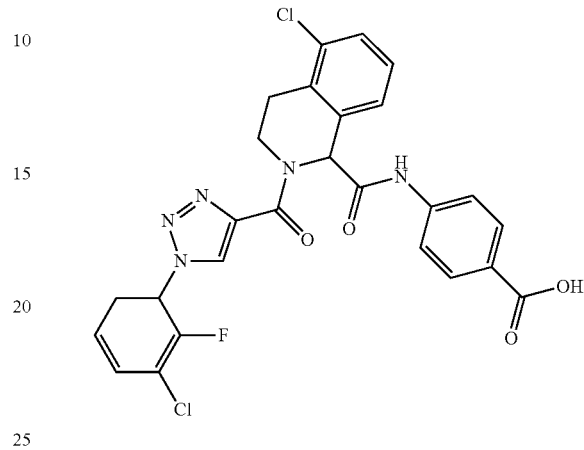

Example 194. 4-(5-Chloro-2-(1-(3-chloro-2-fluorophenyl)-1H-1,2,3-triazole-4-carbonyl)-1,2,3,4-tetrahydroisoquinoline-1-carboxamido)benzoic acid: The title compound was prepared in the same manner as Intermediate 24 replacing 5-bromo-1,2,3,4-tetrahydroisoquinoline with 5-chloro-1,2,3,4-tetrahydroisoquinoline followed by t-butyl ester deprotection with 50% TFA/DCM, purification by reverse phase prep. HPLC, and lyophilization. $^1$H NMR (500 MHz, methanol-d$_4$) δ 8.97-8.86 (m, 1H), 8.03-7.96 (m, 2H), 7.88 (t, J=6.9 Hz, 1H), 7.80-7.67 (m, 3H), 7.53 (d, J=7.7 Hz, 1H), 7.50-7.40 (m, 2H), 7.37-7.26 (m, 1H), 6.69-5.97 (m, 1H), 4.69-4.49 (m, 2H), 3.35-3.29 (m, 2H) ppm. MS (ESI) m/z: 553.9 (M+H)$^+$. Analytical HPLC: RT=13.56 min (Method A).

EXAMPLE 195

4-(2-(1-(3-Chloro-2-fluorophenyl)-1H-1,2,3-triazole-4-carbonyl)-5-fluoro-1,2,3,4-tetrahydroisoquinoline-1-carboxamido)benzoic acid

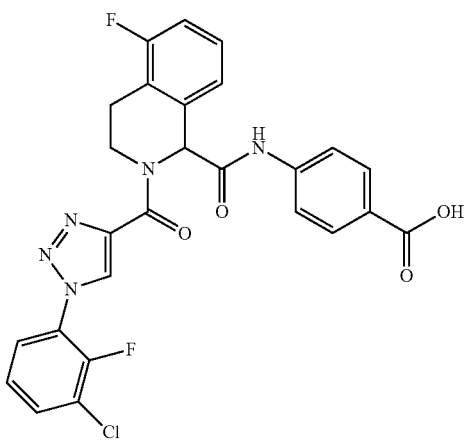 [SMILES: O=C(O)c1ccc(NC(=O)C2c3cccc(F)c3CCN2C(=O)c2cn(-c3cccc(Cl)c3F)nn2)cc1]

Example 195. 4-(2-(1-(3-Chloro-2-fluorophenyl)-1H-1,2,3-triazole-4-carbonyl)-5-fluoro-1,2,3,4-tetrahydroisoquinoline-1-carboxamido)benzoic acid: The title compound was prepared in the same manner as Intermediate 24 replacing 5-bromo-1,2,3,4-tetrahydroisoquinoline with 5-fluoro-1,2,3,4-tetrahydroisoquinoline followed by t-butyl ester deprotection with 50% TFA/DCM, purification by reverse phase prep. HPLC, and lyophilization. 1H NMR (400 MHz, methanol-d$_4$) δ 7.59 (d, J=2.0 Hz, 1H), 6.68 (d, J=8.8 Hz, 2H), 6.56 (t, J=7.2 Hz, 1H), 6.48-6.36 (m, 3H), 6.22-6.06 (m, 2H), 6.05-5.97 (m, 1H), 5.79 (t, J=8.6 Hz, 1H), 4.73 (s, 1H), 3.36-3.23 (m, 1H), 3.23-3.14 (m, 1H), 1.93-1.79 (m, 2H) ppm. MS (ESI) m/z: 537.9 (M+H)$^+$. Analytical HPLC: RT=10.4 min (Method A).

EXAMPLE 196

4-(2-(1-(3-Chloro-2-fluorophenyl)-1H-1,2,3-triazole-4-carbonyl)-5-((S)-3-hydroxy-2-oxopyrrolidin-1-yl)-1,2,3,4-tetrahydroisoquinoline-1-carboxamido)benzoic acid, TFA salt

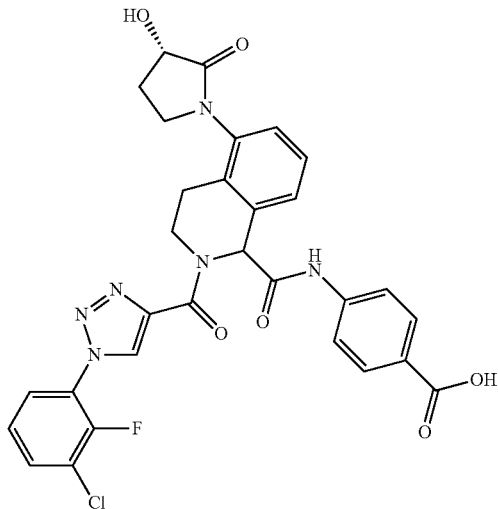 [SMILES: O=C(O)c1ccc(NC(=O)C2c3cccc(N4CC[C@H](O)C4=O)c3CCN2C(=O)c2cn(-c3cccc(Cl)c3F)nn2)cc1]

Example 196. 4-(2-(1-(3-Chloro-2-fluorophenyl)-1H-1,2,3-triazole-4-carbonyl)-5-((S)-3-hydroxy-2-oxopyrrolidin-1-yl)-1,2,3,4-tetrahydroisoquinoline-1-carboxamido) benzoic acid, TFA salt: The title compound was prepared in a similar manner as Example 79 starting from Intermediate 5D followed by removal of silyl group with TBAF. $^1$H NMR (500 MHz, methanol-d$_4$) δ 8.90 (d, J=1.9 Hz, 1H), 8.00 (d, J=8.3 Hz, 2H), 7.93-7.82 (m, 1H), 7.82-7.67 (m, 3H), 7.66-7.57 (m, 1H), 7.50-7.36 (m, 2H), 7.36-7.24 (m, 1H), 6.04 (d, J=3.6 Hz, 1H), 4.63-4.44 (m, 2H), 4.30-4.00 (m, 1H), 3.88-3.68 (m, 2H), 3.19-2.95 (m, 2H), 2.70-2.56 (m, 1H), 2.30-2.08 (m, 1H) ppm. MS (ESI) m/z: 619.0 (M+H)$^+$. Analytical HPLC: RT=9.7 min.

EXAMPLE 197

4-(2-(1-(3-Chloro-2-fluorophenyl)-1H-1,2,3-triazole-4-carbonyl)-5-(2-oxo-4-(2,2,2-trifluoroethyl)piperazin-1-yl)-1,2,3,4-tetrahydroisoquinoline-1-carboxamido)benzoic acid, TFA salt

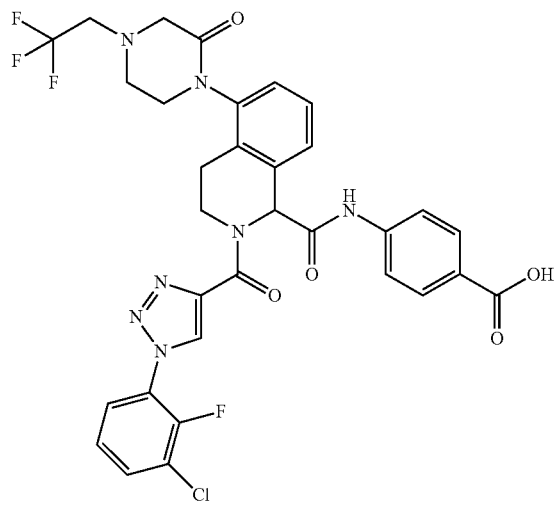 [SMILES: O=C(O)c1ccc(NC(=O)C2c3cccc(N4CCN(CC(F)(F)F)CC4=O)c3CCN2C(=O)c2cn(-c3cccc(Cl)c3F)nn2)cc1]

197A. 1-(Isoquinolin-5-yl)-4-(2,2,2-trifluoroethyl)piperazin-2-one: To a pressure vial was added piperazin-2-one (0.72 g, 7.19 mmol), Cs$_2$CO$_3$ (3.51 g, 10.79 mmol), toluene (7 mL) and 2,2,2-trifluoroethyl trifluoromethanesulfonate (1.6 g, 7.19 mmol), in a pressure vial and stirred 30 min. The reaction was degassed with Ar, then N1,N2-dimethylethane-1,2-diamine (0.634 g, 7.19 mmol), 5-bromoisoquinoline (0.748 g, 3.60 mmol) and copper (I) bromide (0.516 g, 3.60 mmol) were added. The vial was sealed and the reaction was heated to 60° C. After 24 h, additional CuBr and degassed dioxane (5 mL) were added and the heating was resumed. After 24 h, the reaction was quenched with a (1:1) mixture of EtOAc/water (60 mL) and filtered through paper. The aqueous layer was extracted with EtOAc (3×30 mL) and later by nBuOH (2×30 mL). The combined organic layers were washed with brine (15 mL) and dried (MgSO$_4$). The residue was purified by normal phase chromatography to afford product as a orange film (172 mg, 15%). MS (ESI) m/z: 310.2 (M+H)$^+$.

197B. 1-(3,4-Dihydroisoquinolin-5-yl)-4-(2,2,2-trifluoroethyl)piperazin-2-one: 197A was hydrogenated and then oxidized as in 195A to afford 88 mg (50%) of a dark solid. MS (ESI) m/z: 312.1 (M+H)$^+$.

Example 197. 4-(2-(1-(3-Chloro-2-fluorophenyl)-1H-1,2,3-triazole-4-carbonyl)-5-(2-oxo-4-(2,2,2-trifluoroethyl)piperazin-1-yl)-1,2,3,4-tetrahydroisoquinoline-1-carboxamido)benzoic acid, TFA salt: The title compound was prepared in a similar manner as Example 191 starting from 197B. $^1$H NMR (400 MHz, methanol-d$_4$) δ 8.96-8.84 (m, 1H), 8.04-7.94 (m, 2H), 7.92-7.80 (m, 1H), 7.78-7.70 (m, 3H), 7.70-7.60 (m, 1H), 7.49-7.38 (m, 2H), 7.34-7.27 (m, 1H), 6.75-5.86 (m, 1H), 4.63-4.32 (m, 2H), 3.91-3.72 (m, 1H), 3.72-3.47 (m, 3H), 3.30-3.26 (m, 2H), 3.25-3.05 (m, 3H), 3.04-2.88 (m, 1H) ppm. MS (ESI) m/z: 700.3 (M+H)$^+$. Analytical HPLC: RT=9.28 min (Method A).

The following Examples in Table 9 were prepared as lyophilates by the acid chloride or EDC coupling methodology using readily available carboxylic acids with previously described Intermediates 34, 35, or 36. Deprotection of the t-butyl group with TFA followed by reverse phase prep. HPLC using methanol/water/TFA gradient afforded the title compounds.

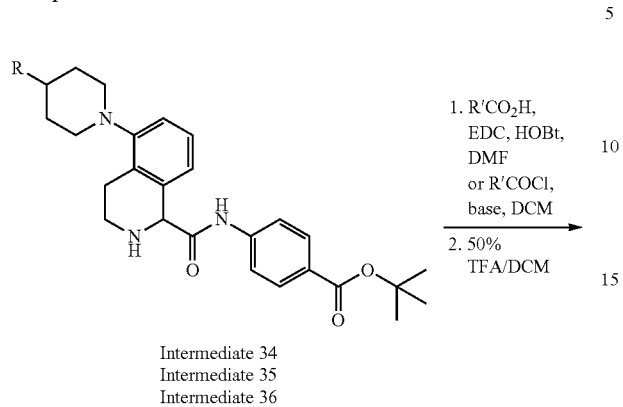

Intermediate 34
Intermediate 35
Intermediate 36

1. R'CO₂H, EDC, HOBt, DMF or R'COCl, base, DCM
2. 50% TFA/DCM

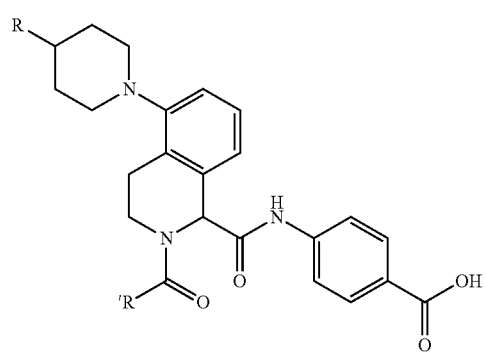

Example 198-217

TABLE 9

| Example | Structure | Name | Analytical Data |
|---|---|---|---|
| 198 | 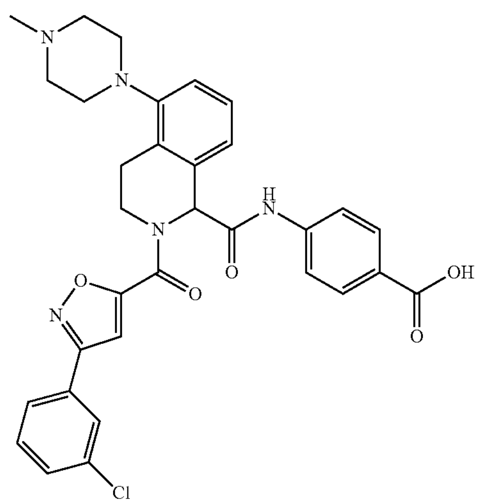 [SMILES: CN1CCN(c2cccc3c2CCN(C(=O)c2cc(-c4cccc(Cl)c4)no2)C3C(=O)Nc2ccc(C(=O)O)cc2)CC1] | 4-(2-(3-(3-chlorophenyl) isoxazole-5-carbonyl)-5-(4-methylpiperazin-1-yl)-1,2,3,4-tetrahydroisoquinoline-1-carboxamido)benzoic acid, 2 TFA salt | $^1$H NMR(400 MHz, MeOD-d$_4$) δ: 7.98-7.95(d, J = 8.6 Hz, 2H), 7.87-7.85(m, 1H), 7.69-7.67(d, J = 8.3 Hz, 2H), 7.55-7.49(m, 2H), 7.46(s, 1H), 7.42-7.31(m, 2H), 7.16-7.14(d, J = 8.2 Hz, 1H), 5.84(s, 1H), 4.39-4.36(m, m, 1H), 3.84-3.78(m, 1H), 3.64-3.57(m, 2H), 3.34-3.34(m, 2H), 3.27-3.16(m, 2H), 2.99(s, 3H) ppm. MS (ESI) m/z: 600.2 (M + H)⁺. Analytical HPLC: RT = 5.66 min (Method B). |
| 199 | 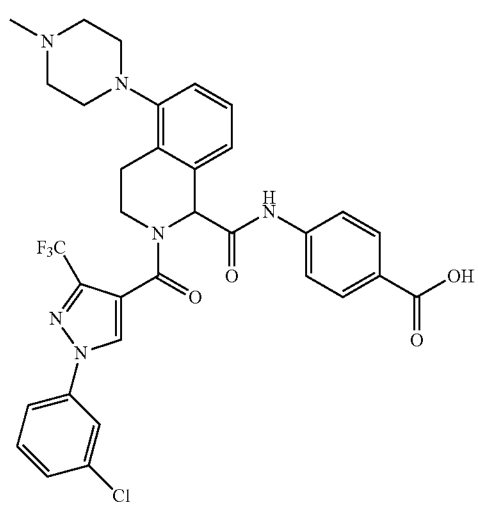 [SMILES: CN1CCN(c2cccc3c2CCN(C(=O)c2cn(-c4cccc(Cl)c4)nc2C(F)(F)F)C3C(=O)Nc2ccc(C(=O)O)cc2)CC1] | 4-(2-(1-(3-chlorophenyl)-3-(trifluoromethyl)-1H-pyrazole-4-carbonyl)-5-(4-methylpiperazin-1-yl)-1,2,3,4-tetrahydroisoquinoline-1-carboxamido)benzoic acid, 2 TFA salt | $^1$H NMR(400 MHz, DMSO-d$_6$) δ: 8.18(s, 1H), 7.90(d, J = 8.6 Hz, 2H), 7.87(m, 1H), 7.72(d, J = 8.2 Hz, 2H), 7.68-7.56(m, 2H), 7.43(d, 1H), 7.37-7.28(m, 1H), 7.06(d, 1H), 5.90(s, 1H), 3.939m, 1H), 3.62-4.49(m, 2H0, 3.30-3.10(m, 4H0, 3.00(m, 1H), 2.86(s, 3H) ppm. MS (ESI) m/z: 667.1 (M + H)⁺. Analytical HPLC: RT = 5.30 min (Method A). |

TABLE 9-continued

| Example | Structure | Name | Analytical Data |
|---|---|---|---|
| 200 | 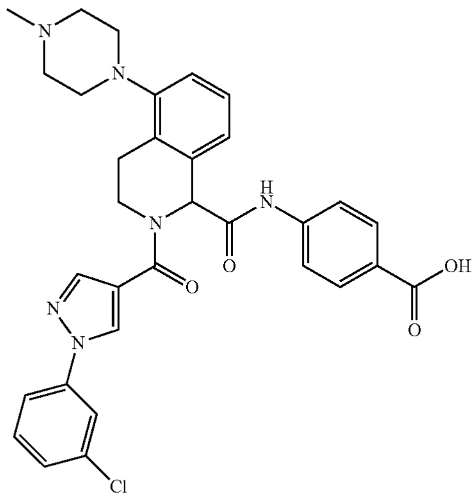 [SMILES: CN1CCN(c2cccc3c2CCN(C(=O)c2cnn(-c4cccc(Cl)c4)c2)C3C(=O)Nc2ccc(C(=O)O)cc2)CC1] | 4-(2-(1-(3-chlorophenyl)-1H-pyrazole-4-carbonyl)-5-(4-methylpiperazin-1-yl)-1,2,3,4-tetrahydroisoquinoline-1-carboxamido)benzoic acid, 2 TFA salt | $^1$H NMR(400 MHz, MeOD-d$_4$) δ: 8.62(bs, 1H), 7.99(bs, 1H), 7.87-7.83(m, 2H), 7.70(bd, 1H), 7.58(bd, 1H), 7.43-7.39(bt, 1H), 7.33-7.21(m, 2H), 7.05-7.03(d, 1H), 5.719bs, 1H), 4.30-4.27(m, 1H), 3.71(bm, 1H), 3.57-3.47(m, 2H), 3.32-3.07(m, 8H) ppm. MS (ESI) m/z: 599.2 (M + H)$^+$. Analytical HPLC: RT = 5.54 min (Method A). |
| 201 | 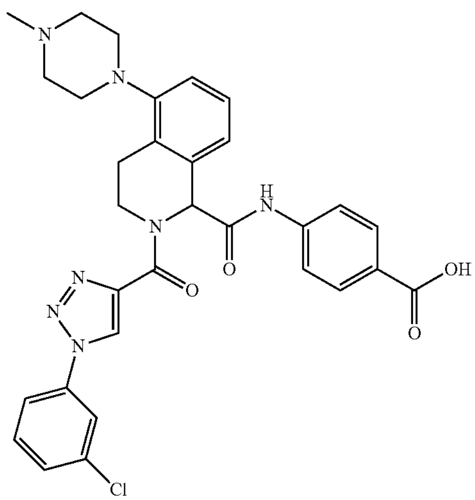 [SMILES: CN1CCN(c2cccc3c2CCN(C(=O)c2cn(-c4cccc(Cl)c4)nn2)C3C(=O)Nc2ccc(C(=O)O)cc2)CC1] | 4-(2-(1-(3-chlorophenyl)-1H-1,2,3-triazole-4-carbonyl)-5-(4-methylpiperazin-1-yl)-1,2,3,4-tetrahydroisoquinoline-1-carboxamido)benzoic acid, 2 TFA salt | $^1$H NMR(400 MHz, MeOD-d$_4$) δ: 9.02(s, 1H), 8.02-7.89(m, 4H), 7.71-7.52(m, 4H), 7.41-7.28(m, 2H), 7.12(d, 1H), 5.87(s, 1H), 4.71(m, 1H), 4.12(m, 1H), 3.60(m, 2H), 3.40-3.12(m, 8H), 2.91(s, 3H) ppm. MS (ESI) m/z: 600.3 (M + H)$^+$. Analytical HPLC: RT = 5.57 min (Method A). |
| 202 | 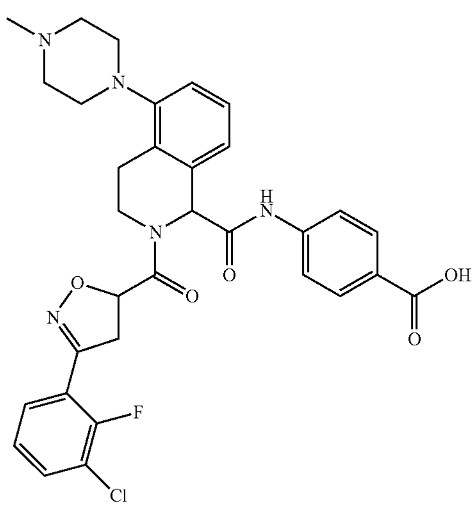 [SMILES: CN1CCN(c2cccc3c2CCN(C(=O)C2CC(c4cccc(Cl)c4F)=NO2)C3C(=O)Nc2ccc(C(=O)O)cc2)CC1] | 4-(2-(3-(3-chloro-2-fluorophenyl)-4,5-dihydroisoxazole-5-carbonyl)-5-(4-methylpiperazin-1-yl)-1,2,3,4-tetrahydroisoquinoline-1-carboxamido)benzoic acid, 2 TFA salt | $^1$H NMR(400 MHz, MeOD-d$_4$) δ: 8.01-7.93(m, 2H), 7.77-7.55(m, 4H), 7.40-7.00(m, 4H), 5.85-5.74(m, 2H), 4.40(m, 1H), 4.30(m, 1H), 4.13-3.93(dd, 1H), 3.80-3.60(m, 4H), 3.48-3.15(m, 6H), 3.00(s, 3H) ppm. MS (ESI) m/z: 620.3 (M + H)$^+$. Analytical HPLC: RT = 5.20 and 5.30 min (diastereomeric mixture; Method B). |

TABLE 9-continued

| Example | Structure | Name | Analytical Data |
|---|---|---|---|
| 203 | 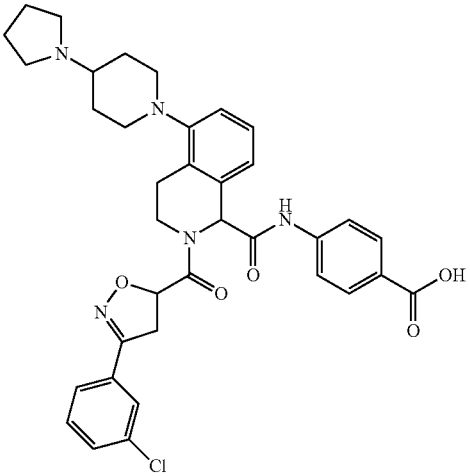 Diastereomer Mixture A | 4-(2-(3-(3-chlorophenyl)-4,5-dihydroisoxazole-5-carbonyl)-5-(4-(pyrrolidin-1-yl)piperidin-1-yl)-1,2,3,4-tetrahydroisoquinoline-1-carboxamido)benzoic acid, 2 TFA salt | $^1$H NMR(400 MHz, MeOD-$d_4$) δ: 7.83(d, J = 8.5 Hz, 2H), 7.63(t 1H), 7.55-7.53(m, 4H), 7.37-7.30(m, 2H), 7.19-7.14(m, 2H), 6.97(dd, 1H), 5.67-5.61(m, 2H), 4.28(m, 1H), 3.80-3.85(m, 1H), 3.75-3.47(m, 6H), 3.20-3.09(m, 6H), 2.83-2.78(m, 1H), 2.59-2.51(m, 1H), 2.20-1.78(m, 8H) ppm. MS (ESI) m/z: 656.3 (M + H)$^+$. Analytical HPLC: RT = 5.87 min (Diastereomer A; Method A). |
| 204 | 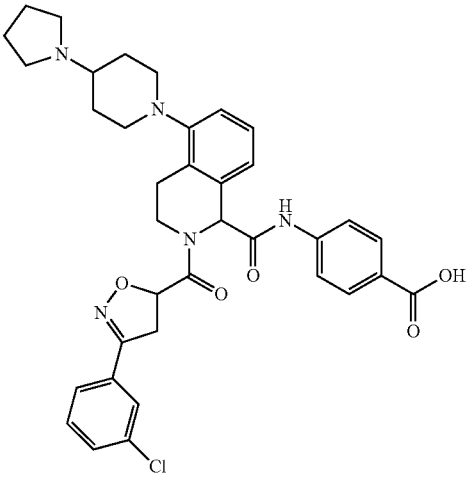 Diastereomer Mixture B | 4-(2-(3-(3-chlorophenyl)-4,5-dihydroisoxazole-5-carbonyl)-5-(4-(pyrrolidin-1-yl)piperidin-1-yl)-1,2,3,4-tetrahydroisoquinoline-1-carboxamido)benzoic acid, 2 TFA salt | $^1$H NMR(400 MHz, MeOD-$d_4$) δ: 8.76(m, 1H), 7.96(m, 1H), 7.85(d, 2H), 7.64(bm, 1H), 7.55(d, 4H), 7.35-7.31(m, 2H), 7.20-7.15(m, 2H), 6.98-6.96(dd, 1H), 5.71(m, 1H), 5.62(s, 1H), 4.19(m, 1H), 3.92-3.86(m, 1H), 3.63-3.51(m, 4H), 3.20-3.05(m, 7H), 2.80-2.85(m, 1H), 2.65-2.59(m, 1H), 2.21-2.05(m, 4H), 2.00-1.78(m, 4H) ppm. MS (ESI) m/z: 656.3 (M + H)$^+$. Analytical HPLC: RT = 6.01 min (Diastereomer B; Method A). |

TABLE 9-continued

| Example | Structure | Name | Analytical Data |
|---|---|---|---|
| 205 | 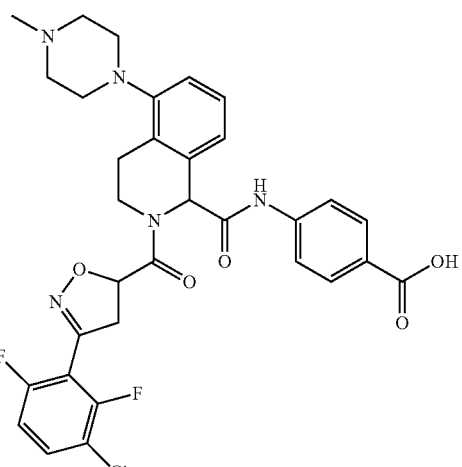<br>Diastereomeric Mixture | 4-(2-(3-(3-chloro-2,6-difluorophenyl)-4,5-dihydroisoxazole-5-carbonyl)-5-(4-methylpiperazin-1-yl)-1,2,3,4-tetrahydroisoquinoline-1-carboxamido)benzoic acid, 2 TFA salt | $^1$H NMR (400 MHz, methanol-$d_4$) δ: 7.89-7.81 (m, 2H), 7.60-7.48 (m, 3H), 7.28-7.18 (m, 2H), 7.08-7.00 (m, 2H), 5.77-5.70 (m, 1H), 5.69-5.60 (m, 1H), 4.33-4.25 (m, 1H), 4.21-4.15 (m, 1H), 4.03-3.99 (m, 1H), 4.04-3.93 (m, 1H), 3.89-3.79 (m, 1H), 3.63-3.44 (m, 4H), 3.37-3.24 (m, 4H), 3.16-3.01 (m, 2H), 2.93-2.88 (bs, 2H) ppm. MS (ESI) m/z: 638.2 (M + H)$^+$. Analytical HPLC: RT = 5.04/5.22 min (diastereomeric mixture; Method B). |
| 206 | 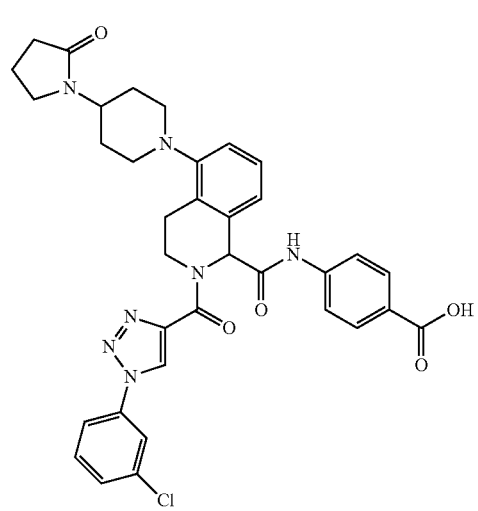 [SMILES: O=C(O)c1ccc(NC(=O)C2c3cccc(N4CCC(N5CCCC5=O)CC4)c3CCN2C(=O)c2cn(-c3cccc(Cl)c3)nn2)cc1] | 4-(2-(1-(3-chlorophenyl)-1H-1,2,3-triazole-4-carbonyl)-5-(4-(2-oxopyrrolidin-1-yl)piperidin-1-yl)-1,2,3,4-tetrahydroisoquinoline-1-carboxamido)benzoic acid, TFA salt | $^1$H NMR(400 MHz, MeOD-$d_4$) δ: 11.30(s, 1H), 9.77(s, 1H), 8.76(s, 1H), 8.68-8.60(m, 3H), 8.42-8.27(m, 4H), 8.06-7.99(m, 2H), 7.99(m, 1H), 6.59(s, 1H), 4.82-4.71(m, 2H), 4.26-4.21(m, 4H), 3.99(m, 7H), 3.70-3 49(m, 4H), 3.13-3.09(m, 2H), 2.80-2.50(m, 6H) ppm. MS (ESI) m/z: 658.2 (M + H)$^+$. Analytical HPLC: RT = 8.04 min (Method A). |
| 207 | 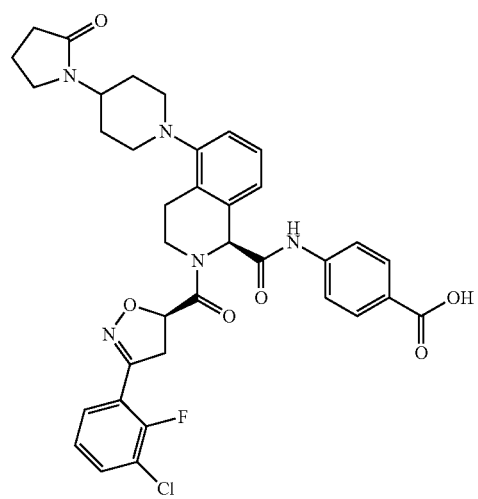<br>Diastereomer A | 4-((S)-2-((R)-3-(3-chloro-2-fluorophenyl)-4,5-dihydroisoxazole-5-carbonyl)-5-(4-(2-oxopyrrolidin-1-yl)piperidin-1-yl)-1,2,3,4-tetrahydroisoquinoline-1-carboxamido)benzoic acid, TFA salt | $^1$H NMR(400 MHz, MeOD-$d_4$) δ: 7.84 (d, J = 8.4 Hz, 2H), 7.64-7.68(m, 1H), 7.56-7.51(dd, J = 2.1 and 8.3 Hz, 2H), 7.49-7.45(m, 1H), 7.19-7.15(m, 3H), 7.01(dd, J = 1.8 and 8.3 Hz, 1H), 5.69-5.70(m, 1H), 5.63(s, 1H), 4.27-4.24(m, 1H), 3.95(m, 1H), 3.85-3.79(m, 1H), 3.68-3.60(m, 1H), 3.57-3.50(m, 1H), 3.43(t, 2H), 3.19-3.10(m, 5H), 2.89(bt, 1H), 2.71(bt, 1H), 2.33(t, 2H), 2.00-1.85(m, 4H), 1.71(m, 2H) ppm. MS (ESI) m/z: 688.3 (M + H)$^+$. Analytical HPLC: RT = 7.91 min (Diastereomer A; Method A). |

TABLE 9-continued

| Example | Structure | Name | Analytical Data |
|---|---|---|---|
| 208 | Diastereomer B | 4-((R)-2-((R)-3-(3-chloro-2-fluorophenyl)-4,5-dihydroisoxazole-5-carbonyl)-5-(4-(2-oxopyrrolidin-1-yl)piperidin-1-yl)-1,2,3,4-tetrahydroisoquinoline-1-carboxamido)benzoic acid, TFA salt | H NMR(400 MHz, MeOD-d$_4$) δ: 7.84-7.82(d, J = 8.3 Hz, 2H) 7.62-7.60(m, 1H), 7.55-7.52(dd, J = 1.8 and 8.1 Hz, 2H), 7.50-7.48(m, 1H), 7.01(dd, J = 1.8 and 8.1 Hz, 1H), 5.72-5.70(m, 1H), 5.62(s, 1H), 4.20-4.16(m, 1H), 3.98-3.91(m, 2H), 3.67-3.59(m, 2H), 3.47-3.41(t, 2H), 3.19-3.10(m, 5H), 2.89(bt, 1H), 2.73(bt, 1H), 2.33-2.29(t, 2H), 2.01-1.91(m, 4H), 1.72(m, 2H) ppm. MS (ESI) m/z: 688.3 (M + H)$^+$. Analytical HPLC: RT = 8.02 min (Diastereomer B; Method A). |
| 209 | 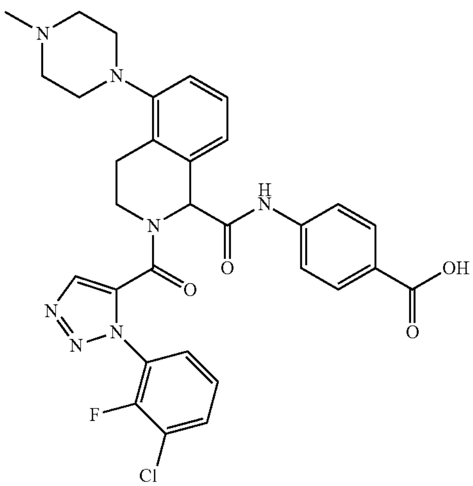 | 4-(2-(1-(3-chloro-2-fluorophenyl)-1H-1,2,3-triazole-5-carbonyl)-5-(4-methylpiperazin-1-yl)-1,2,3,4-tetrahydroisoquinoline-1-carboxamido)benzoic acid | $^1$H NMR(400 MHz, MeOD-d$_4$) δ: 8.83(s, 1H), 8.05 (s, 1H), 7.89(d, J = 8.4 Hz, 2H), 7.59(bt, 1H), 7.49 (bt, 1H), 7.38(d, J = 8.3 Hz, 2H), 7.04(m, 1H), 7.04-6.99(t, 2H), 5.92(s, 1H), 3.92(m, 3H), 3.51(bs, 5H), 3.30-2.90(m, 5H), 2.77(m, 2H), 2.21-2.06(m, 6H) ppm. MS (ESI) m/z: 672.4 (M + H)$^+$. Analytical HPLC: RT = 7.41 min (Method A). |
| 210 | 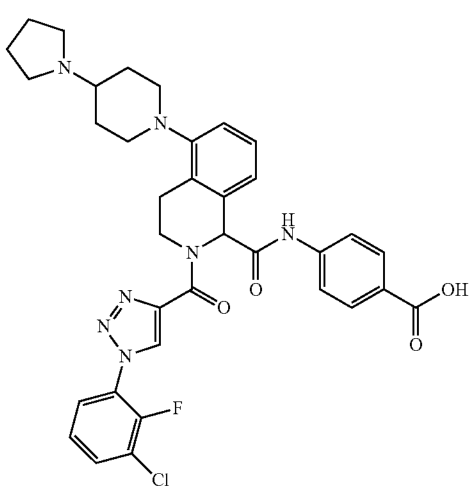 [SMILES: O=C(O)c1ccc(NC(=O)C2c3cccc(N4CCC(N5CCCC5)CC4)c3CCN2C(=O)c2cn(-c3cccc(Cl)c3F)nn2)cc1] | 4-(2-(1-(3-chloro-2-fluorophenyl)-1H-1,2,3-triazole-4-carbonyl)-5-(4-(pyrrolidin-1-yl)piperidin-1-yl)-1,2,3,4-tetrahydroisoquinoline-1-carboxamido)benzoic acid, 2 TFA salt | $^1$H NMR(400 MHz, MeOD-d$_4$) δ: 8.78(d, J = 1.9 Hz, 1H), 7.87(d, J = 8.6 Hz, 2H), 7.75(bt, 1H), 7.68-7.54(m, 3H), 7.36-7.31(dt, 1H), 7.26-7.18(m, 2H), 7.00(bd, 1H), 5.76(s, 1H), 4.00(m, 1H), 3.60(m, 2H), 3.21-3.08(m, 4H), 2.80(bt, 1H), 2.60(bt, 1H), 2.20-1.80(m, 8H) ppm. MS (ESI) m/z: 672.5 (M + H)$^+$. Analytical HPLC: RT = 7.50 min (Method A). |

TABLE 9-continued

| Example | Structure | Name | Analytical Data |
|---|---|---|---|
| 211 | 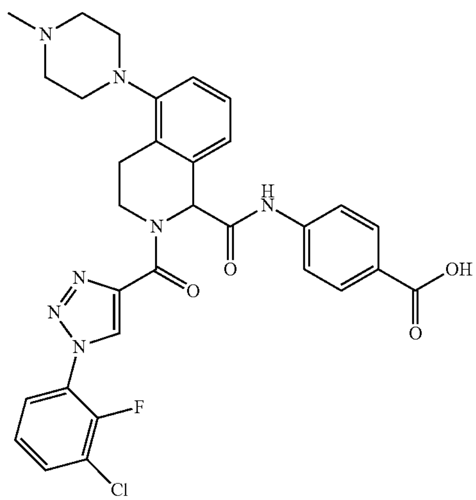 [SMILES: CN1CCN(c2cccc3c2CCN(C(=O)c2cn(-c4cccc(Cl)c4F)nn2)C3C(=O)Nc2ccc(C(=O)O)cc2)CC1] | 4-(2-(1-(3-chloro-2-fluorophenyl)-1H-1,2,3-triazole-4-carbonyl)-5-(4-methylpiperazin-1-yl)-1,2,3,4-tetrahydroisoquinoline-1-carboxamido)benzoic acid, 2 TFA salt | $^1$H NMR(400 MHz, MeOD-d$_4$) δ: 8.78(s, 1H), 7.988(d, J = 8.4 Hz, 2H), 7.77-7.74(m, 1H), 7.66-7.52(m, 3H), 7.36-7.29(m, 2H), 7.27-7.21(t, 1H), 7.06(d, J = 8.2 Hz, 1H), 6.50(bs, 1H), 5.80(s, 1H), 4.62(m, 1H), 4.10(m, 1H), 3.52(bt, 2H), 3.41-3.06(m, 8H), 2.90(s, 3H) ppm. MS (ESI) m/z: 618.3 (M + H)$^+$. Analytical HPLC: RT = 5.04 min (Method B). |
| 212 | 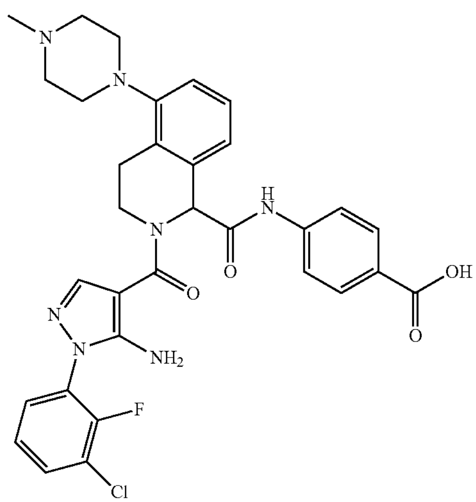 [SMILES: CN1CCN(c2cccc3c2CCN(C(=O)c2cnn(-c4cccc(Cl)c4F)c2N)C3C(=O)Nc2ccc(C(=O)O)cc2)CC1] | 4-(2-(5-amino-1-(3-chloro-2-fluorophenyl)-1H-pyrazole-4-carbonyl)-5-(4-methylpiperazin-1-yl)-1,2,3,4-tetrahydroisoquinoline-1-carboxamido)benzoic acid, 2 TFA salt | $^1$H NMR(400 MHz, MeOD-d$_4$) δ: 7.86(d, J = 8.8 Hz, 2H), 7.76(s, 1H), 7.58(d, J = 8.8 Hz, 2H), 7.55(s, 1H), 7.45-7.42(m, 2H), 7.38(m, 1H), 7.32-7.30(d, 1H), 7.24-7.22(t, 2H), 7.05(d, J = 7.1 Hz, 1H), 5.64(s, 1H), 4.35-4.30(m, 1H), 3.68-3.65(m, 1H), 3.60-3.45(m, 2H), 3.32-5.15(m, 8H), 2.90(s, 3H) ppm. MS (ESI) m/z: 614.2 (M + H)$^+$. Analytical HPLC: RT = 6.55 min (Method A). |
| 213 | 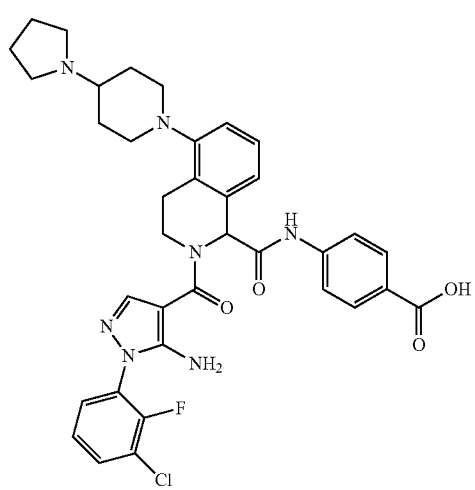 [SMILES: Nc1c(C(=O)N2CCc3c(cccc3N3CCC(N4CCCC4)CC3)C2C(=O)Nc2ccc(C(=O)O)cc2)cnn1-c1cccc(Cl)c1F] | 4-(2-(5-amino-1-(3-chloro-2-fluorophenyl)-1H-pyrazole-4-carbonyl)-5-(4-(pyrrolidin-1-yl)piperidin-1-yl)-1,2,3,4-tetrahydroisoquinoline-1-carboxamido)benzoic acid, 3TFA salt | $^1$H NMR(400 MHz, MeOD-d$_4$) δ: 10.35(s, 1H), 7.86(d, J = 8.8 Hz, 2H), 7.76(s, 1H), 7.60-7.47(m, 3H), 7.43(m, 2H), 7.38(m, 1H), 7.25(d, J = 8.4 Hz, 1H), 7.17(t, 1H), 7.00-6.98(d, J = 7.7 Hz, 1H), 5.61(s, 1H), 4.34-4.31(m, 1H), 3.67-3.60(m, 3H), 3.17-3.11(m, 6H), 2.85(t, 1H), 2.54(t, 1H), 2.21-2.05(m, 4H), 2.00-1.79(m, 5H) ppm. MS (ESI) m/z: 668.2 (M + H)$^+$. Analytical HPLC: RT = 5.26 min (Method B). |

//

TABLE 9-continued

| Example | Structure | Name | Analytical Data |
|---|---|---|---|
| 214 | 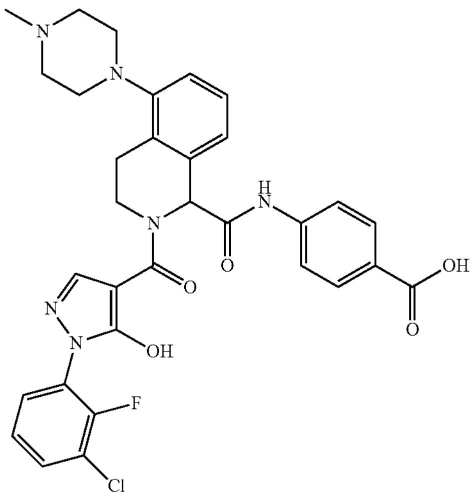 [SMILES: CN1CCN(c2cccc3c2CCN(C(=O)c2cnn(-c4cccc(Cl)c4F)c2O)C3C(=O)Nc2ccc(C(=O)O)cc2)CC1] | 4-(2-(1-(3-chloro-2-fluorophenyl)-5-hydroxy-1H-pyrazole-4-carbonyl)-5-(4-methylpiperazin-1-yl)-1,2,3,4-tetrahydroisoquinoline-1-carboxamido)benzoic acid, 2 TFA salt. | $^1$H NMR(400 MHz, MeOD-d$_4$) δ: 7.87-7.79(m, 4H), 7.71(d, J = 8.8 Hz, 1H), 7.57-7.53(m, 2H), 7.37-7.32(m, 2H), 7.31-7.23(m, 2H), 7.07(d, J = 7.8 Hz, 1H), 5.75(s, 1H), 4.35(m, 1H), 3.65(m, 1H), 3.59-3.49(m, 3H), 3.38-3.16(m (MeOH peak overlap, 7H)), 2.91(s, 3H) ppm. MS (ESI) m/z: 615.1 (M + H)$^+$. Analytical HPLC: RT = 5.96 min (Method B). |
| 215 | 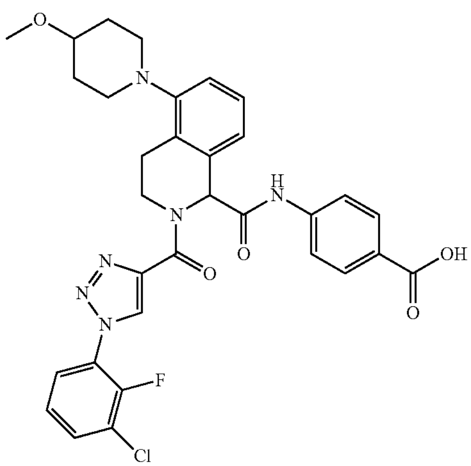 [SMILES: COC1CCN(c2cccc3c2CCN(C(=O)c2cn(-c4cccc(Cl)c4F)nn2)C3C(=O)Nc2ccc(C(=O)O)cc2)CC1] | 4-(2-(1-(3-chloro-2-fluorophenyl)-1H-1,2,3-triazole-4-carbonyl)-5-(4-methoxypiperidin-1-yl)-1,2,3,4-tetrahydroisoquinoline-1-carboxamido)benzoic acid, TFA salt | $^1$H NMR(400 MHz, MeOD-d$_4$) δ: 8.79(s, 1H), 7.87(d, J = 8.4 Hz, 2H)7.75(t, 1H), 7.70-7.52(m, 3H), 7.37-7.05(m, 4H), 4.61 (m, 1H), 4.05(m, 1H), 3.48(bm, 2H), 3.14(cp, 2H), 3.01-2.81(m, 4H), 2.10(bm, 2H), 1.82(bm, 2H) ppm. MS (ESI) m/z: 633.1 (M + H)$^+$. Analytical HPLC: RT = 7.27 min (Method B). |
| 216 | Diastereomer Mixture A | 4-(2-(3-(3-chlorophenyl)-4,5-dihydroisoxazole-5-carbonyl)-5-(4-methylpiperazin-1-yl)-1,2,3,4-tetrahydroisoquinoline-1-carboxamido)benzoic acid, 2 TFA salt | $^1$H NMR(400 MHz, MeOD-d$_4$) δ: 7.84-7.82(d, J = 8.4 Hz, 2H), 7.64(m, 1H), 7.55-7.51(m, 3H), 7.35-7.30(m, 2H), 7.26-7.18(m, 1H), 7.03-7.01(dd, 1H), 5.65(s, 1H), 5.63-5.60(t, 1H), 4.30(m, 1H), 3.82-3.75(dd, 1H), 3.59-3.48(m, 3H), 3.16-3.03(m, 3H), 2.91(s, 3H) ppm. MS (ESI) m/z: 602.2 (M + H)$^+$. Analytical HPLC: RT = 5.12 min (Diastereomer A; Method B). |

TABLE 9-continued

| Example | Structure | Name | Analytical Data |
|---|---|---|---|
| 217 | 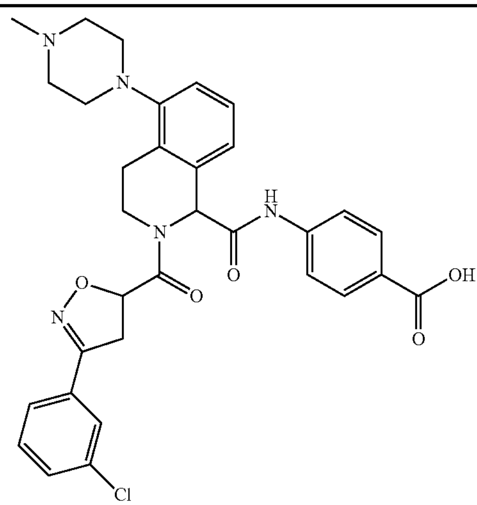 | 4-(2-(3-(3-chlorophenyl)-4,5-dihydroisoxazole-5-carbonyl)-5-(4-methylpiperazin-1-yl)-1,2,3,4-tetrahydroisoquinoline-1-carboxamido)benzoic acid, 2 TFA salt<br><br>Diastereomer Mixture B | $^1$H NMR(400 MHz, MeOD-d$_4$) δ: 7.86-7.84(d, J = 8.5 Hz, 2H), 7.64(sm, 1H), 7.55-7.53(d, J = 8.5 Hz, 3H), 7.36-7.31(m, 2H), 7.26-7.19(m, 2H), 7.04-7.02(dd, 1H), 7.53-7.68(m, 1H), 7.66(s, 1H), 4.20-4.16(m, 1H), 3.94-3.88(dd, J = 6.8 Hz, 1H), 3.71-3.65(m, 1H), 3.58-3.49(m, 2H), 3.14-3.02(m, 2H), 2.91(s, 3H) ppm. MS (ESI) m/z: 602.2 (M + H)$^+$. Analytical HPLC: RT = 5.64 min (Method B). |

EXAMPLE 218

N-(4-Carbamoylphenyl)-2-(1-(3-chloro-2-fluorophenyl)-1H-1,2,3-triazole-4-carbonyl)-5-(4-(2-oxopyrrolidin-1-yl)piperidin-1-yl)-1,2,3,4-tetrahydroisoquinoline-1-carboxamide, TFA salt

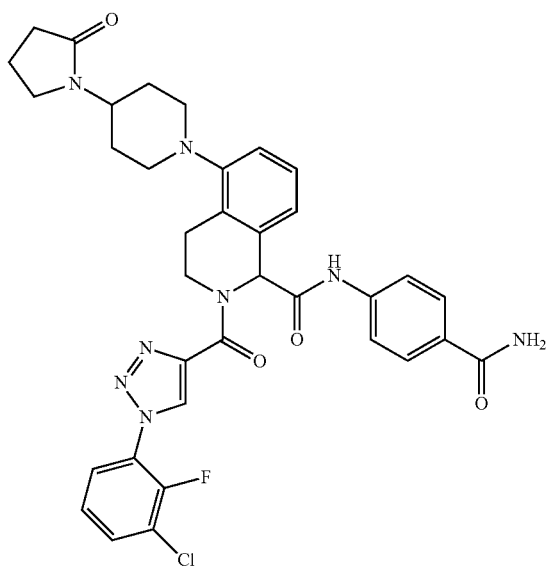 [SMILES: NC(=O)c1ccc(NC(=O)C2c3cccc(N4CCC(N5CCCC5=O)CC4)c3CCN2C(=O)c2cn(-c3cccc(Cl)c3F)nn2)cc1]

Example 218. N-(4-Carbamoylphenyl)-2-(1-(3-chloro-2-fluorophenyl)-1H-1,2,3-triazole-4-carbonyl)-5-(4-(2-oxopyrrolidin-1-yl)piperidin-1-yl)-1,2,3,4-tetrahydroisoquinoline-1-carboxamide, TFA salt: The title compound prepared dissolving Example 72 (9 mg) taken up in THF (1 mL), and to this was added TEA (0.3 mL) and MeCO$_2$Cl (0.1 mL) at 0° C. After 1 h at this temperature ammonium chloride (0.5 g) was added and stirring continued overnight at ambient temperature overnight. Concentrated and dissolved residue in MeOH and purified via prep HPLC and concentrated to a white solid. $^1$H NMR (400 MHz, MeOD-d$_4$) δ: 9.01 (s, 2H), 8.02 (m, 1H), 7.86-7.67 (m, 1H), 7.67 (d, 1H), 7.60 (m, 1H), 7.57 (m, 2H), 7.30 (d, 2H), 5.84 (s, 1H), 4.67 (m, 1H), 4.06 (m, 1H), 3.55-3.52 (m, 1H), 3.50-3.20 (m, 8H), 2.91 (m, 1H), 2.69 (m, 2H), 2.40 (m, 2H), 2.07-2.03 (m, 2H) ppm. MS (ESI) m/z: 667.3 (M+H)$^+$. Analytical HPLC: RT=6.95 min (Method B).

EXAMPLE 219

Ethyl 4-(2-(1-(3-chloro-2-fluorophenyl)-1H-1,2,3-triazole-4-carbonyl)-5-(4-(pyrrolidin-1-yl)piperidin-1-yl)-1,2,3,4-tetrahydroisoquinoline-1-carboxamido)benzoate, 2 TFA salt

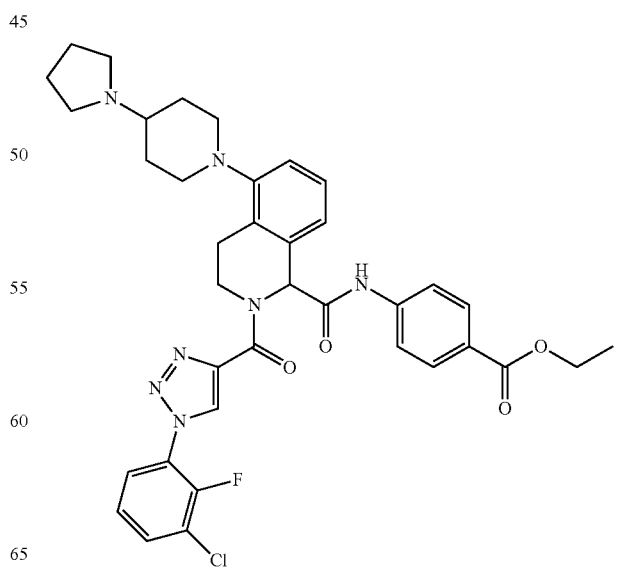

Example 219. Ethyl 4-(2-(1--(3-chloro-2-fluorophenyl)-1H-1,2,3-triazole-4-carbonyl)-5-(4-(pyrrolidin-1-yl)piperidin-1-yl)-1,2,3,4-tetrahydroisoquinoline-1-carboxamido)benzoate, 2 TFA salt: Thionyl chloride (1 mL) was added dropwise to an EtOH (1 mL) solution of Example 72 and stirred at room temperature overnight. A mixture of compounds was observed and the desired product was viable by HPLC/LCMS. Concentrated and purified directly via a reverse phase prep. HPLC. Pure peaks corresponding to the products were collected and concentrated and lyophilized. $^1$H NMR (400 MHz, MeOD-$d_4$) δ: 10.55 (s, 1H), 8.81 (s, 1H), 7.91 (m, 2H), 7.75 (t, 1H), 7.71-7.59 (m, 3H), 7.35 (t, 1H), 7.30-7.18 (m, 2H), 7.03 (d, 1H), 5.80 (s, 1H), 4.69 (m, 1H), 4.25 (q, 2H), 4.06 (m, 1H), 3.75 (bm, 2H), 3.20 (m, 5H), 2.85 (t, 1H), 2.67 (t, 2H), 2.20 (m, 5H), 2.00 (m, 2H), 1.87 (m, 3H) ppm. MS (ESI) m/z: 700.2 (M+H)$^+$. Analytical HPLC: RT=8.59 min (Method A).

EXAMPLE 220

4-(5-(1-(3-Chloro-2-fluorophenyl)-1H-1,2,3-triazole-4-carbonyl)-2-methyl-4,5,6,7-tetrahydro-2H-pyrazolo[4,3-c]pyridine-4-carboxamido)benzoic acid

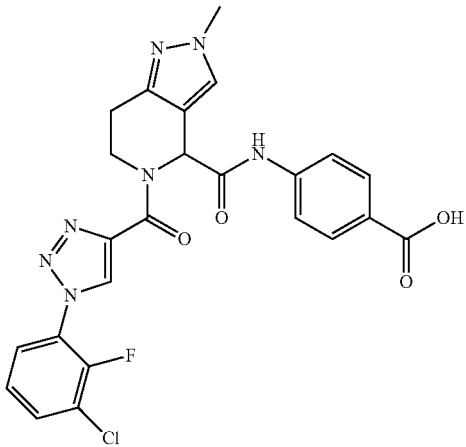 [SMILES: Cn1cc2c(n1)CCN(C(=O)c1cn(-c3cccc(Cl)c3F)nn1)C2C(=O)Nc1ccc(C(=O)O)cc1]

Example 220. 4-(5-(1-(3-Chloro-2-fluorophenyl)-1H-1,2,3-triazole-4-carbonyl)-2-methyl-4,5,6,7-tetrahydro-2H-pyrazolo[4,3-c]pyridine-4-carboxamido)benzoic acid: The title compound was prepared as a white lyophilate following the MnO$_2$ oxidation of deprotected Intermediate 39, subsequent 3-component Ugi reaction, as described previously in Example 1 with Intermediate 1 and Intermediate 9 followed by TFA deprotection of the t-butyl ester. $^1$H NMR (400 MHz, methanol-$d_4$) δ 8.79 (s, 1H), 7.92-7.86 (d, 2H), 7.80-7.69 (m, 1H), 7.66-7.57 (m, 3H), 7.54-7.44 (m, 1H), 7.37-7.26 (m, 1H), 6.53-6.45 (m, 1H), 5.95-5.88 (m, 1H), 3.99-3.84 (m, 1H), 3.80-3.73 (bs, 3H), 3.70 (m, 1H), 2.92-2.69 (m, 2H) ppm. MS (ESI) m/z: 524.0 (M+H)$^+$. Analytical HPLC: RT=6.10 min (Method B).

EXAMPLE 221

4-(5-(1-(3-Chloro-2-fluorophenyl)-1H-1,2,3-triazole-4-carbonyl)-1,3-dimethyl-4,5,6,7-tetrahydro-1H-pyrazolo[4,3-c]pyridine-4-carboxamido)benzoic acid

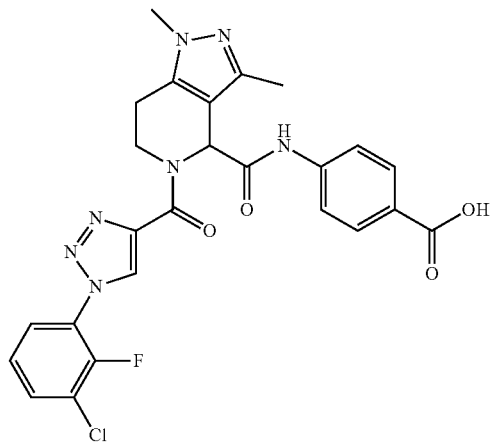 [SMILES: Cc1nn(C)c2c1C(C(=O)Nc1ccc(C(=O)O)cc1)N(C(=O)c1cn(-c3cccc(Cl)c3F)nn1)CC2]

Example 221. 4-(5-(1-(3-Chloro-2-fluorophenyl)-1H-1,2,3-triazole-4-carbonyl)-1,3-dimethyl-4,5,6,7-tetrahydro-1H-pyrazolo[4,3-c]pyridine-4-carboxamido)benzoic acid: Prepared in a manner similar to Example 220 starting from the imine of deprotected Intermediate 38 (0.02 g), Intermediate 1 (0.027 g), and Intermediate 9 (0.032 g) stirred in MeOH (1 mL) at 50° C. overnight. Final deprotection of the t-butyl ester and purification of the reaction mixture via reverse phase prep. HPLC using methanol/water/TFA gradient afforded the title compound (0.01 g). MS (ESI) m/z: 538.0 (M+H)$^+$. Analytical HPLC: RT=6.41 min (Method B).

EXAMPLE 222

4-(5-(1-(3-Chloro-2-fluorophenyl)-1H-1,2,3-triazole-4-carbonyl)-2,3-dimethyl-4,5,6,7-tetrahydro-2H-pyrazolo[4,3-c]pyridine-4-carboxamido)benzoic acid

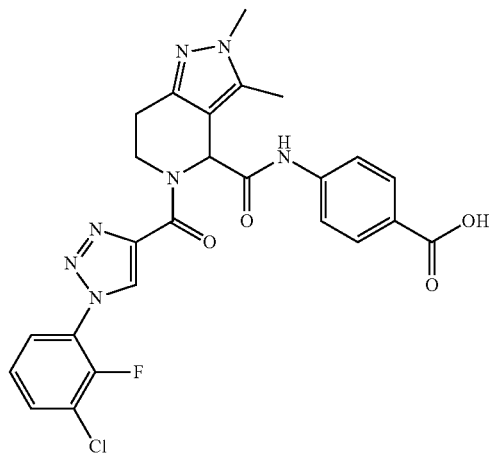 [SMILES: Cc1c2c(nn1C)CCN(C(=O)c1cn(-c3cccc(Cl)c3F)nn1)C2C(=O)Nc1ccc(C(=O)O)cc1]

Example 222. 4-(5-(1-(3-Chloro-2-fluorophenyl)-1H-1,2,3-triazole-4-carbonyl)-2,3-dimethyl-4,5,6,7-tetrahydro-2H-pyrazolo[4,3-c]pyridine-4-carboxamido)benzoic acid: The title compound was prepared in a similar manner as Example 220 starting from Intermediate 37. $^1$H NMR (500 MHz, methanol-d$_4$) Shift 8.86-8.78 (m, 1H), 7.91-7.85 (m, 2H), 7.78-7.71 (m, 1H), 7.66-7.55 (m, 3H), 7.35-7.28 (m, 1H), 6.43-6.35 (m, 1H), 5.99-5.92 (m, 1H), 4.94-4.85 (m, 1H), 3.97-3.88 (m, 1H), 3.69 (s, 3H), 3.04-2.93 (m, 1H), 2.84-2.70 (m, 1H), 2.26-2.19 (bs, 3H) ppm. MS (ESI) m/z: 538.1 (M+H)$^+$. Analytical HPLC: RT=6.21 min (Method A).

EXAMPLE 223

4-(7-(1-(3-Chloro-2-fluorophenyl)-1H-1,2,3-triazole-4-carbonyl)-3-isopropyl-5,6,7,8-tetrahydro-[1,2,4]triazolo[4,3-a]pyrazine-8-carboxamido)benzoic acid

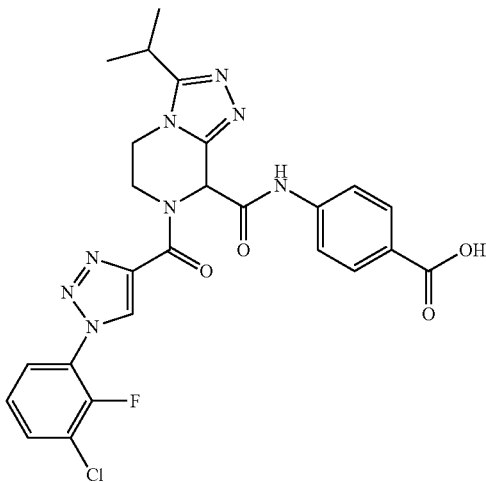 [SMILES: CC(C)c1nnc2n1CCN(C(=O)c1cn(-c3cccc(Cl)c3F)nn1)C2C(=O)Nc1ccc(C(=O)O)cc1]

Example 223. 4-(7-(1-(3-Chloro-2-fluorophenyl)-1H-1,2,3-triazole-4-carbonyl)-3-isopropyl-5,6,7,8-tetrahydro-[1,2,4]triazolo[4,3-a]pyrazine-8-carboxamido)benzoic acid. The title compound was prepared from MnO$_2$ oxidation of commercially available 3-isopropyl-5,6,7,8-tetrahydro-[1,2,4]triazolo[4,3-a]pyrazine, Ugi reaction with Intermediate 1 and Intermediate 9, subsequent TFA deprotection of the t-butyl ester group and purification by reverse phase prep. HPLC. $^1$H NMR (500 MHz, methanol-d$_4$) δ 9.06-8.99 (m, 1H), 8.02 (s, 2H), 7.92-7.84 (m, 1H), 7.82-7.73 (m, 3H), 7.42-7.26 (m, 1H), 5.74-5.62 (m, 1H), 4.62-4.32 (m, 4H), 3.44-3.36 (m, 1H), 1.50 (d, J=6.9 Hz, 6H) ppm. MS (ESI) m/z: 553.1 (M+H)$^+$. Analytical HPLC: RT=6.53 min (Method A).

EXAMPLE 224

4-(2-(1-(3-Chloro-2-fluorophenyl)-1H-pyrazole-4-carbonyl)-5-(4-(2-methoxypropan-2-yl)piperidin-1-yl)-1,2,3,4-tetrahydroisoquinoline-1-carboxamido)benzoic acid, TFA salt

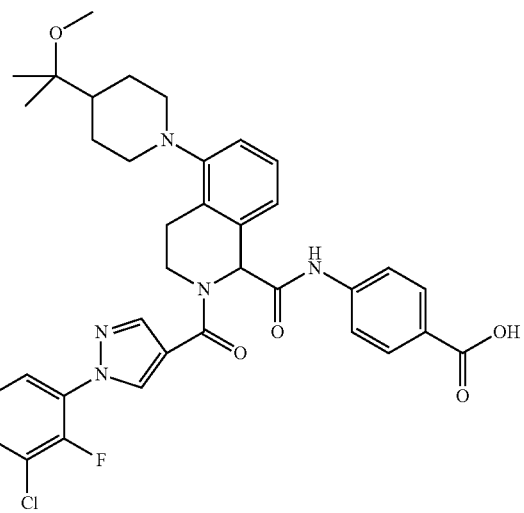

224A. tert-Butyl 5-(4-(2-hydroxypropan-2-yl)piperidin-1-yl)-3,4-dihydroisoquinoline-2(1H)-carboxylate: 2-(Piperidin-4-yl)propan-2-ol (1 g, 6.98 mmol), commercially available tert-butyl 5-bromo-3,4-dihydroisoquinoline-2(1H)-carboxylate (1.982 g, 6.35 mmol), sodium t-butoxide (0.915 g, 9.52 mmol), BINAP (0.119 g, 0.190 mmol) were combined in toluene (12 mL) in a vial and degassed with Ar. After 15 minutes, Pd$_2$(dba)$_3$ (0.058 g, 0.063 mmol) was added, the sealed, and heated to 85° C. overnight. The reaction was diluted with EtOAc(25 mL)/water (10 mL) and filtered through CELITE®. The aqueous layer was extracted with additional EtOAc (2×25 mL). The combined organic layer was washed with brine (15 mL), dried (MgSO$_4$), and purified by normal phase chromatography to give a light yellow foam (2.1 g, 84%). $^1$H NMR (400 MHz, chloroform-d) δ 7.18 (t, J=7.7 Hz, 1H), 6.93 (s, 1H), 6.91-6.82 (m, 1H), 4.58 (s, 2H), 3.60 (br. s., 2H), 3.20 (d, J=11.9 Hz, 2H), 2.85 (t, J=5.7 Hz, 2H), 2.63 (t, J=11.5 Hz, 2H), 1.86 (d, J=11.6 Hz, 2H), 1.61-1.57 (m, 1H), 1.56-1.49 (s, 9H), 1.47-1.37 (m, 1H), 1.30-1.23 (m, 7H) ppm.

224B. tert-Butyl 5-(4-(2-methoxypropan-2-yl)piperidin-1-yl)-3,4-dihydroisoquinoline-2(1H)-carboxylate: To 224A (0.42 g, 1.121 mmol) and excess iodomethane (0.478 g, 3.36 mmol) in DMF (4 mL), cooled in ice bath, was added NaH (0.090 g, 2.243 mmol). After stirring for 48 h, the reaction was partitioned with water (20 mL) and ethyl acetate (50 mL). The aqueous layer was extracted with ethyl acetate (2×2 0 mL). The combined organic layers were washed with brine (15 mL), dried (MgSO$_4$), and purified by normal phase chromatography to give a yellow oil (219 mg, 50%). MS (ESI) m/z: 389 (M+H)$^+$.

224C. 5-(4-(2-Methoxypropan-2-yl)piperidin-1-yl)-3,4-dihydroisoquinoline: 224C (0.219 g, 0.564 mmol) was deprotected with 50% TFA/DCM. After 2 h, the reaction mixture was concentrated and partitioned with dilute NaOH (20 mL) and ethyl acetate (50 mL). The aqueous layer was extracted with ethyl acetate (2×20 mL). The combined organic layers were washed with brine (15 mL), dried (MgSO)$_4$, and concentrated. The amine was oxidized with MnO$_2$ (0.882 g, 10.15 mmol) in DCM. After 24 h, the reaction was filtered, filtrate concentrated, and carried forward to the next reaction.

Example 224. 4-(2-(1-(3-Chloro-2-fluorophenyl)-1H-pyrazole-4-carbonyl)-5-(4-(2 methoxypropan-2-yl)piperidin-1-yl)-1,2,3,4-tetrahydroisoquinoline-1-carboxamido)benzoic acid, TFA salt: The title compound was obtained by Ugi reaction with 224C, Intermediate 1, and Intermediate 13, subsequent TFA deprotection of the t-butyl ester group and purification by reverse phase prep. HPLC. $^1$H NMR (400 MHz, methanol-d$_4$) δ: 8.59 (br. s., 1H), 8.17 (br. s., 1H), 7.98 (d, J=8.8 Hz, 2H), 7.81 (d, J=7.6 Hz, 1H), 7.69 (d, J=8.1 Hz, 2H), 7.59 (d, J=6.6 Hz, 1H), 7.47 (br. s., 1H), 7.41-7.33 (m, 2H), 7.31 (br. s., 1H), 5.85 (br. s., 1H), 4.41 (br. s., 1H), 3.82 (br. s., 2H), 3.50 (br. s., 1H), 3.24 (s, 3H), 3.15-3.05 (m, 1H), 2.92 (br. s., 1H), 2.05-1.83 (m, 3H), 1.74 (br. s., 3H), 1.21 (s, 6H) ppm. MS (ESI) m/z: 674.0 (M+H)$^+$. Analytical HPLC: RT=7.81 min (Method A).

EXAMPLE 225

4-(2-(1-(3-Chloro-2-fluorophenyl)-1H-pyrazole-4-carbonyl)-5-(4-(2-(3-hydroxy-2-(hydroxymethyl)-2-methylpropoxy)propan-2-yl)piperidin-1-yl)-1,2,3,4-tetrahydroisoquinoline-1-carboxamido)benzoic acid, TFA salt

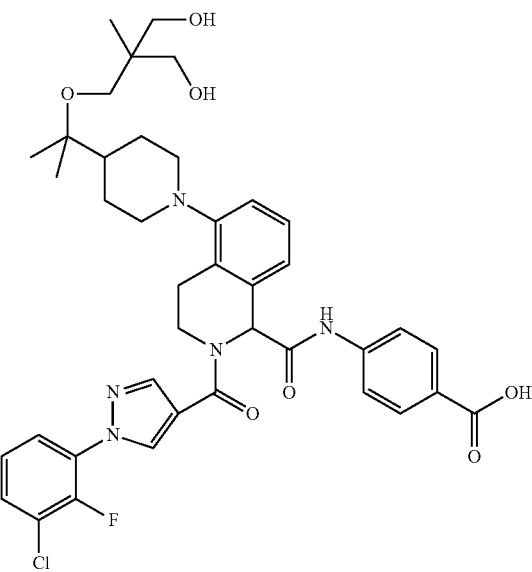 [SMILES: CC(CO)(CO)COC(C)(C)C1CCN(c2cccc3c2CCN(C(=O)c2cnn(-c4cccc(Cl)c4F)c2)C3C(=O)Nc2ccc(C(=O)O)cc2)CC1]

Example 225. 4-(2-(1-(3-Chloro-2-fluorophenyl)-1H-pyrazole-4-carbonyl)-5-(4-(2-(3-hydroxy-2-(hydroxymethyl)-2-methylpropoxy)propan-2-yl)piperidin-1-yl)-1,2,3,4-tetrahydroisoquinoline-1-carboxamido)benzoic acid, TFA salt: The title compound was prepared in a similar manner as Example 224 replacing CH$_3$I with 3-(chloromethyl)-3-methyloxetane. $^1$H NMR (400 MHz, methanol-d$_4$) δ: 8.47 (br. s., 1H), 8.06 (s, 1H), 7.86 (d, J=8.8 Hz, 2H), 7.70 (t, 1=7.6 Hz, 1H), 7.57 (d, J=8.1 Hz, 2H), 7.48 (t, J=7.2 Hz, 1H), 7.34 (d, J=7.1 Hz, 1H), 7.25 (t, J=7.8 Hz, 2H), 7.16 (d, J=7.6 Hz, 1H), 5.72 (s, 1H), 4.78-4.72 (m, 4H), 4.40-4.23 (m, 1H), 3.70 (br. s., 1H), 3.48-3.36 (m, 5H), 3.12-2.93 (m, 1H), 2.76 (s, 1H), 1.95-1.79 (m, 2H), 1.79-1.53 (m, 3H), 1.24 (s, 6H), 0.78 (s, 3H) ppm. MS (ESI) m/z: 762.1 (M+H)$^+$. Analytical HPLC: RT=6.51 min (Method A).

EXAMPLE 226

4-(2-(1-(3-Chloro-2-fluorophenyl)-1H-1,2,3-triazole-4-carbonyl)-5-(4-(oxetan-3-yl)piperazin-1-yl)-1,2,3,4-tetrahydroisoquinoline-1-carboxamido)benzoic acid, TFA salt

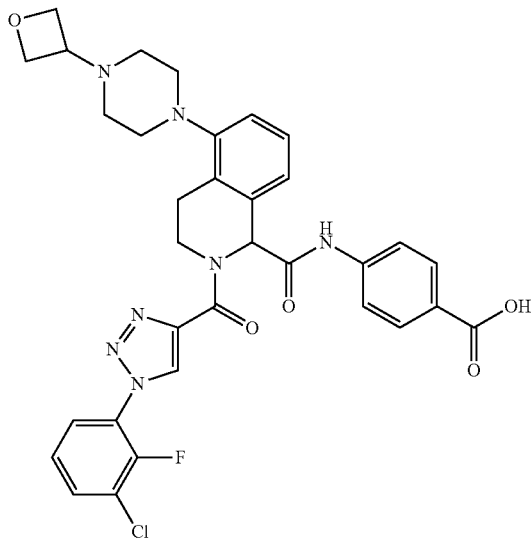 [SMILES: O=C(O)c1ccc(NC(=O)C2c3cccc(N4CCN(C5COC5)CC4)c3CCN2C(=O)c2cn(-c3cccc(Cl)c3F)nn2)cc1]

226A. 5-(4-(Oxetan-3-yl)piperazin-1-yl)isoquinoline: To a vial was added 5-(piperazin-1-yl)isoquinoline, HCl (0.48 g, 1.922 mmol), DCM (3 mL) and MeOH (3 mL) and then, oxetan-3-one (0.416 g, 5.77 mmol). After 24 h, sodium triacetoxyborohydride (0.815 g, 3.84 mmol) was added and stirred for 2 h before concentrating and quenching with saturated NaHCO$_3$ (10 mL) and extracted with ethyl acetate (3×10 mL). The combined organic layers were washed with brine (5 mL), dried (MgSO$_4$), concentrated, and the residue was purified by normal phase column chromatography to afford the title compound (70 mg, 13%) as a yellow oil. MS (ESI) m/z: 270.2 (M+H)$^+$.

226B: 5-(4-(Oxetan-3-yl)piperazin-1-yl)-3,4-dihydroisoquinoline: The intermediate 226A (0.1 g, 0.371 mmol) was hydrogenated and then oxidized as in the example of Intermediate 4 to afford a yellow oil (84 mg, 83%). MS (ESI) m/z: 272.2 (M+H)$^+$.

Example 226. 4-(2-(1-(3-Chloro-2-fluorophenyl)-1H-1,2,3-triazole-4-carbonyl)-5-(4-(oxetan-3-yl)piperazin-1-yl)-1,2,3,4-tetrahydroisoquinoline-1-carboxamido)benzoic acid, TFA salt: The title compound was obtained by Ugi reaction with 226B, Intermediate 1, and Intermediate 9, subsequent TFA deprotection of the t-butyl ester group and purification by reverse phase prep. HPLC. $^1$H NMR (400 MHz, methanol-d$_4$) δ 8.79 (d, J=2.2 Hz, 1H), 7.91-7.82 (m, 2H), 7.79-7.71 (m, 1H), 7.67-7.52 (m, 3H), 7.38-7.30 (m, 2H), 7.25 (t, J=7.9 Hz, 1H), 7.07 (d, J=7.7 Hz, 1H), 5.80 (s, 1H), 4.90-4.81 (m, 2H), 4.71-4.58 (m, 1H), 4.48-4.35 (m, 1H), 4.13-3.99 (m, 1H), 3.5-3 (m, 8H, under MeOD), 3.18-3.02 (m, 4H) ppm. MS (ESI) m/z: 660.2 (M+H)$^+$. Analytical HPLC: RT=5.62 min (Method A).

EXAMPLE 227

4-((S)-2-((R)-3-(3-Chloro-2-fluorophenyl)-4,5-dihydroisoxazole-5-carbonyl)-5-(4-(oxetan-3-yl)piperazin-1-yl)-1,2,3,4-tetrahydroisoquinoline-1-carboxamido)benzoic acid, 2 TFA salt

EXAMPLE 228

4-((R)-2-((R)-3-(3-Chloro-2-fluorophenyl)-4,5-dihydroisoxazole-5-carbonyl)-5-(4-(oxetan-3-yl)piperazin-1-yl)-1,2,3,4-tetrahydroisoquinoline-1-carboxamido)benzoic acid, 2 TFA salt

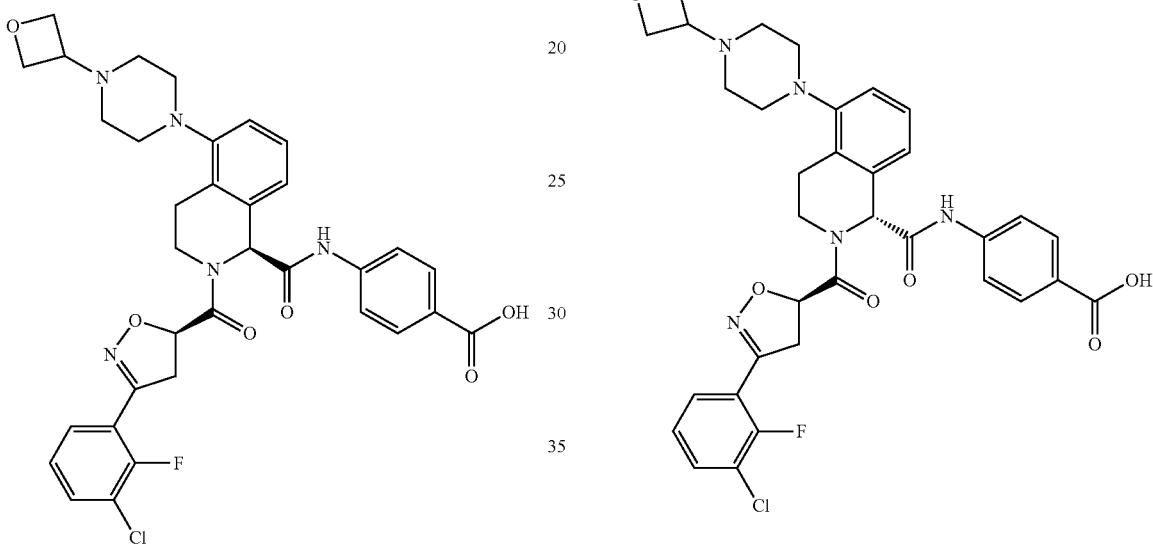

Example 227. 4-((S)-2-((R)-3-(3-Chloro-2-fluorophenyl)-4,5-dihydroisoxazole-5-carbonyl)-5-(4-(oxetan-3-yl)piperazin-1-yl)-1,2,3,4-tetrahydroisoquinoline-1-carboxamido)benzoic acid, 2 TFA salt: The title compound was prepared in a similar manner as Example 226 replacing Intermediate 9 with chiral Intermediate 19. The compound was isolated as the early eluting diastereomer after reverse phase column chromatography. $^1$H NMR (400 MHz, methanol-$d_4$) δ 7.96-7.90 (m, 2H), 7.80-7.68 (m, 1H), 7.67-7.54 (m, 3H), 7.42-7.29 (m, 2H), 7.24 (td, J=8.0, 1.0 Hz, 1H), 7.20-7.07 (m, 1H), 5.85-5.72 (m, 2H), 5.00-4.88 (m, 6H), 4.53 (t, J=6.3 Hz, 1H), 4.42 (dt, J=12.0, 4.6 Hz, 1H), 3.97 (ddd, J=17.4, 7.6, 1.8 Hz, 1H), 3.75 (ddd, J=17.4, 11.4, 2.0 Hz, 1H), 3.70-3.62 (m, 1H), 3.51-3.14 (m, 8H) ppm. MS (ESI) m/z: 662.2 (M+H)$^+$. Analytical HPLC: RT=6.05 min (Method A).

Example 228. 4-((R)-2-((R)-3-(3-Chloro-2-fluorophenyl)-4,5-dihydroisoxazole-5-carbonyl)-5-(4-(oxetan-3-yl)piperazin-1-yl)-1,2,3,4-tetrahydroisoquinoline-1-carboxamido)benzoic acid, 2 TFA salt: The title compound was prepared in a similar manner as Example 226 replacing Intermediate 9 with Intermediate 19. The compound was isolated as the late eluting diastereomer after reverse phase column chromatography. $^1$H NMR (400 MHz, methanol-$d_4$) δ 8.06-7.92 (m, 2H), 7.80-7.70 (m, 1H), 7.67-7.64 (m, 2H), 7.64-7.57 (m, 1H), 7.42-7.31 (m, 2H), 7.29-7.23 (m, 1H), 7.17 (dd, J=7.8, 1.0 Hz, 1H), 5.85-5.80 (m, 1H), 5.80-5.74 (m, 1H), 5.00-4.92 (m, 2H), 4.90-4.80 (m, 4H) 4.62-4.50 (m, 1H), 4.30 (dt, J=12.5, 5.2 Hz, 1H), 4.09 (ddd, J=17.4, 6.8, 1.8 Hz, 1H), 3.67 (br. s., 3H), 3.50-3.09 (m, 8H) ppm. MS (ESI) m/z: 662.2 (M+H)$^+$. Analytical HPLC: RT=6.41 min (Method A).

EXAMPLE 229

4-(2-(1-(3-Chloro-2 fluorophenyl) 1H 1,2,3 triazolo-4-carbonyl) 5 (4(2,2,2 trifluoroethyl)piperazin-1-yl)-1,2,3,4-tetrahydroisoquinoline-1-carboxamido)benzoic acid, TFA salt

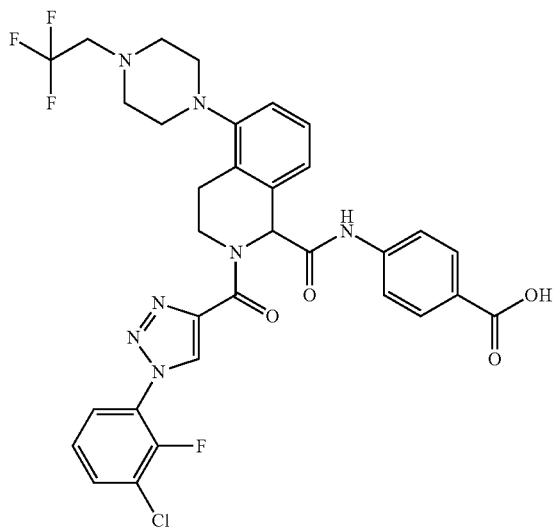 [SMILES: O=C(O)c1ccc(NC(=O)C2c3cccc(N4CCN(CC(F)(F)F)CC4)c3CCN2C(=O)c2cn(-c3cccc(Cl)c3F)nn2)cc1]

229A. 5-(4-(2,2,2-Trifluoroethyl)piperazin-1-yl)isoquinoline: To 5-(piperazin-1-yl)isoquinoline, HCl (0.265 g, 1.061 mmol) in DMF (3 mL), cooled to 0° C., was added 2,2,2-trifluoroethyl trifluoromethanesulfonate (0.246 g, 1.061 mmol) and 60% NaH (0.127 g, 3.18 mmol). After 48 h, the reaction was partitioned with water (10 mL) and ethyl acetate (30 mL). The aqueous layer was extracted with EtOAc (2×10 mL). The combined organic layers were washed with water (10 mL), brine (10 mL) and dried (MgSO$_4$). The residue was purified normal phase chromatography to afford a yellow oil (53 mg, 16.9%). MS (ESI) m/z: 296.1 (M+H)$^+$.

Example 229. 4-(2-(1-(3-Chloro-2-fluorophenyl)-1H-1,2,3-triazole-4-carbonyl)-5-(4-(2,2,2-trifluoroethyl)piperazin-1-yl)-1,2,3,4-tetrahydroisoquinoline-1-carboxamido) benzoic acid, TFA salt: The title compound was prepared in a similar manner as Example 226 starting from 229A. $^1$H NMR (400 MHz, methanol-d$_4$) δ 8.90 (d, J=2.2 Hz, 1H), 8.03-7.93 (m, 2H), 7.92-7.85 (m, 1H), 7.81-7.64 (m, 3H), 7.52-7.41 (m, 1H), 7.39-7.27 (m, 2H), 7.13 (d, J=7.0 Hz, 1H), 6.64-5.84 (m, 1H), 4.76-4.66 (m, 1H), 4.18-4.05 (m, 1H), 3.40 (s, 1H), 3.28-3.19 (m, 2H), 3.19-2.94 (m, 9H) ppm. MS (ESI) m/z: 686.2 (M+H)$^+$. Analytical HPLC: RT=9.28 min (Method A).

EXAMPLE 230

4-((S)-2-((R)-3-(3-Chloro-2-fluorophenyl)-4,5-dihydroisoxazole-5-carbonyl)-5-(4-(2,2,2-trifluoroethyl) piperazin-1-yl)-1,2,3,4-tetrahydroisoquinoline-1-carboxamido)benzoic acid, 2 TFA salt

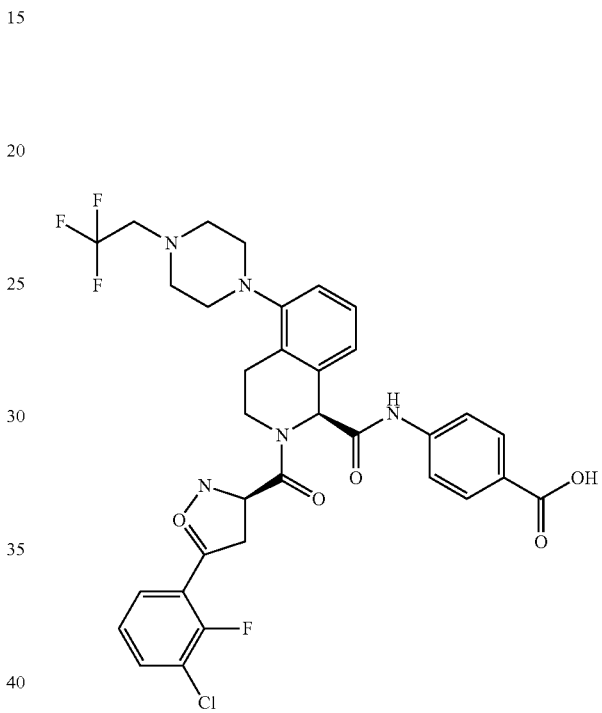

Example 230. 4-((S)-2-((R)-3-(3-Chloro-2-fluorophenyl)-4,5-dihydroisoxazole-5-carbonyl)-5-(4-(2,2,2-trifluoroethyl)piperazin-1-yl)-1,2,3,4-tetrahydroisoquinoline-1-carboxamido)benzoic acid, 2 TFA salt: The title compound was prepared in a similar manner as Example 229 replacing Intermediate 9 with Intermediate 19. The compound was isolated as the early eluting diastereomer after reverse phase column chromatography. $^1$H NMR (500 MHz, methanol-d$_4$) δ 8.02-7.88 (m, 2H), 7.79-7.70 (m, 1H), 7.67-7.61 (m, 2H), 7.61-7.53 (m, 1H), 7.35-7.20 (m, 3H), 7.10 (dd, J=7.4, 1.7 Hz, 1H), 5.81-5.70 (m, 2H), 4.37 (dt, J=12.0, 4.7 Hz, 1H), 3.94 (ddd, J=17.3, 7.7, 1.9 Hz, 1H), 3.76 (ddd, J=17.3, 11.4, 2.1 Hz, 1H), 3.70-3.58 (m, 1H), 3.53-3.41 (m, 2H), 3.31-3.21 (m, 1H), 3.21-2.94 (m, 9H) ppm. MS (ESI) m/z: 688.2 (M+H)$^+$. Analytical HPLC: RT=10.1 min (Method A).

EXAMPLE 231

4-((R)-2-((R)-3-(3-Chloro-2-fluorophenyl)-4,5-dihydroisoxazole-5-carbonyl)-5-(4-(2,2,2-trifluoroethyl)piperazin-1-yl)-1,2,3,4-tetrahydroisoquinoline-1-carboxamido)benzoic acid, 2 TFA salt

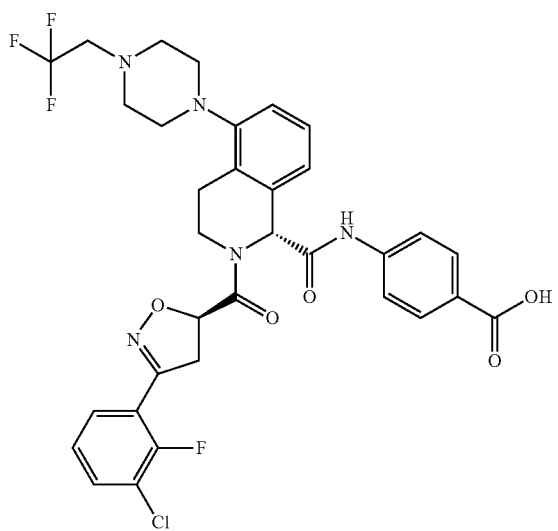 [SMILES: O=C(O)c1ccc(NC(=O)[C@H]2c3cccc(N4CCN(CC(F)(F)F)CC4)c3CCN2C(=O)[C@H]2CC(c3cccc(Cl)c3F)=NO2)cc1]

Example 231. 4-((R)-2-((R)-3-(3-Chloro-2-fluorophenyl)-4,5-dihydroisoxazole-5-carbonyl)-5-(4-(2,2,2-trifluoroethyl)piperazin-1-yl)-1,2,3,4-tetrahydroisoquinoline-1-carboxamido)benzoic acid, 2 TFA salt: The title compound was prepared in a similar manner as Example 229 replacing Intermediate 9 with chiral Intermediate 19. The compound was isolated as the late eluting diastereomer after reverse phase column chromatography. $^1$H NMR (500 MHz, methanol-$d_4$) δ 7.91 (d, J=8.5 Hz, 2H), 7.70 (t, J=6.9 Hz, 1H), 7.62 (d, J=8.5 Hz, 2H), 7.56 (t, J=7.3 Hz, 1H), 7.34-7.29 (m, 1H), 7.29-7.18 (m, 2H), 7.09 (d, J=8.0 Hz, 1H), 5.82 (dd, J=11.4, 6.7 Hz, 1H), 5.76 (s, 1H), 4.32-4.23 (m, 1H), 4.04 (dd, J=17.3, 6.6 Hz, 1H), 3.79-3.68 (m, 2H), 3.62 (q, J=9.4 Hz, 2H), 3.26-3.11 (m, 8H), 3.11-2.97 (m, 2H) ppm. MS (ESI) m/z: 688.2 (M+H)$^+$. Analytical HPLC: RT=10.3 min (Method A).

EXAMPLE 232

Methyl 4-((S)-2-((R)-3-(3-chloro-2-fluorophenyl)-4,5-dihydroisoxazole-5-carbonyl)-5-(4-(oxetan-3-yl)piperazin-1-yl)-1,2,3,4-tetrahydroisoquinoline-1-carboxamido)benzoate, 2 TFA salt

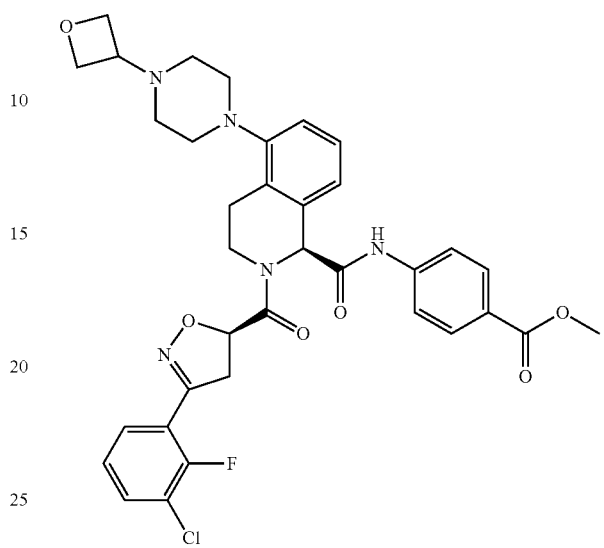

Example 232. Methyl 4-((S)-2-((R)-3-(3-chloro-2-fluorophenyl)-4,5-dihydroisoxazole-5-carbonyl)-5-(4-(oxetan-3-yl)piperazin-1-yl)-1,2,3,4-tetrahydroisoquinoline-1-carboxamido)benzoate, 2 TFA salt: The title compound was prepared in a similar manner as Example 227 replacing Intermediate 1 with Intermediate 2. The compound was isolated as the early eluting diastereomer after reverse phase column chromatography. $^1$H NMR (500 MHz, DMSO-$d_6$) δ 7.97-7.87 (m, 2H), 7.80-7.65 (m, 3H), 7.44-7.08 (m, 5H), 7.08-6.93 (m, 2H), 5.78-5.68 (m, 2H), 4.72 (br. s., 4H), 4.37-4.18 (m, 2H), 4.04-3.78 (m, 4H), 3.73-3.59 (m, 3H), 3.24-2.77 (m, 8H) ppm. MS (ESI) m/z: 676.3 (M+H)$^+$. Analytical HPLC: RT=1.60 min (Method C).

EXAMPLE 233

Methyl 4-((R)-2-((R)-3-(3-chloro-2-fluorophenyl)-4,5-dihydroisoxazole-5-carbonyl)-5-(4-(oxetan-3-yl)piperazin-1-yl)-1,2,3,4-tetrahydroisoquinoline-1-carboxamido)benzoate, 2 TFA salt

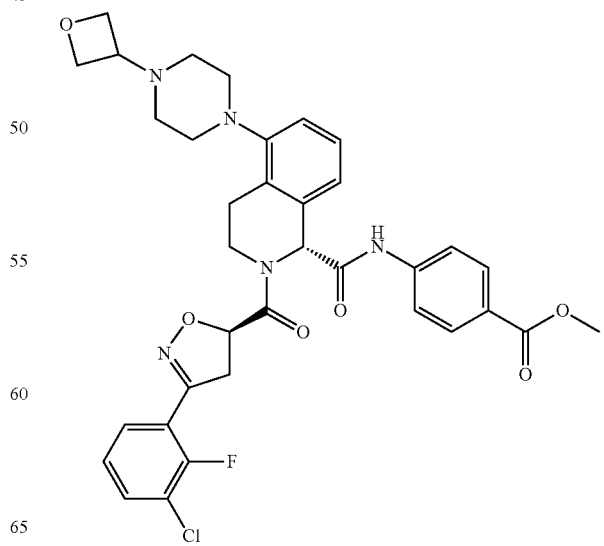

Example 233. Methyl 4-((R)-2-((R)-3-(3-chloro-2-fluorophenyl)-4,5-dihydroisoxazole-5-carbonyl)-5-(4-(oxetan-3-yl)piperazin-1-yl)-1,2,3,4-tetrahydroisoquinoline-1-carboxamido)benzoate, 2 TFA salt: The title compound was prepared in a similar manner as Example 228 replacing Intermediate 1 with Intermediate 2. The compound was isolated as the late eluting diastereomer after reverse phase column chromatography. $^1$H NMR (500 MHz, DMSO-d$_6$) δ 7.90 (d, J=8.5 Hz, 2H), 7.79-7.66 (m, 4H), 7.39-7.30 (m, 2H), 7.30-7.20 (m, 1H), 7.02 (d, J=8.0 Hz, 1H), 5.86 (dd, J=11.4, 7.3 Hz, 1H), 5.70 (s, 1H), 4.58 (t, J=6.5 Hz, 2H), 4.54-4.45 (m, 2H), 4.25 (dt, J=12.2, 4.6 Hz, 1H), 3.93-3.85 (m, 1H), 3.84-3.80 (m, 3H), 3.78-3.72 (m, 1H), 3.64-3.53 (m, 4H), 3.15-3.05 (m, 1H), 3.05-2.98 (m, 1H), 2.98-2.89 (m, 3H), 2.87 (br. s., 2H), 2.47 (br. s., 2H) ppm. MS (ESI) m/z: 676.3 (M+H)$^+$. Analytical HPLC: RT=1.48 min (Method C).

EXAMPLE 234

4-((1S)-2-(3-(3-Chloro-2-fluorophenyl)-4,5-dihydroisoxazole-5-carbonyl)-5-(4-(oxetan-3-yl)piperidin-1-yl)-1,2,3,4-tetrahydroisoquinoline-1-carboxamido)benzoic acid, TFA salt Example 234. 4-((S)-2-((R)-3-(3-Chloro-2-fluorophenyl)-4,5-dihydroisoxazole-5-carbonyl)-5-(4-(oxetan-3-yl) piperidin-1-yl)-1,2,3,4-tetrahydroisoquinoline-1-carboxamido)benzoic acid, TFA salt: The title compound was prepared utilizing the Ugi reaction as in Example 1 replacing Imine Intermediate 3 with Intermediate 4U and Intermediate 9 with chiral Intermediate 19. The compound was isolated as the early eluting enantiomer after reverse phase column chromatography. $^1$H NMR (500 MHz, DMSO-d$_6$) δ 10.75 (d, J=13.2 Hz, 1H), 7.92-7.82 (m, 2H), 7.77-7.61 (111, 4H), 7.40-7.30 (m, 2H), 7.25-7.18 (m, 1H), 7.00 (d, J=8.0 Hz, 1H), 5.90-5.66 (m, 2H), 4.65 (t, J=6.7 Hz, 2H), 4.40 (t, J=5.9 Hz, 2H), 4.25 (dd, J=11.7, 5.4 Hz, 1H), 3.92-3.81 (m, 1H), 3.78-3.65 (m, 1H), 3.67-3.56 (m, 1H), 3.12-2.97 (m, 4H), 2.86-2.78 (m, 1H), 2.73-2.64 (m, 1H), 2.60-2.54 (m, 2H), 1.87-1.60 (m, 3H), 1.34-1.17 (m, 2H) ppm. MS (ESI) m/z: 661.2 (M+H)$^+$. Analytical HPLC: RT=1.65 min (Method C).

The compounds in Table 11 were prepared utilizing the Ugi reaction as in Example 1 replacing Isonitrile Intermediate 1 with isonitrile Intermediates 40, 41, 42, 43, or commercially available isonitriles, Imine Intermediate 3 with Intermediate 4, and Intermediate 9 with Intermediate 19. Final compounds were purified by reverse phase prep. HPLC and freeze-dried.

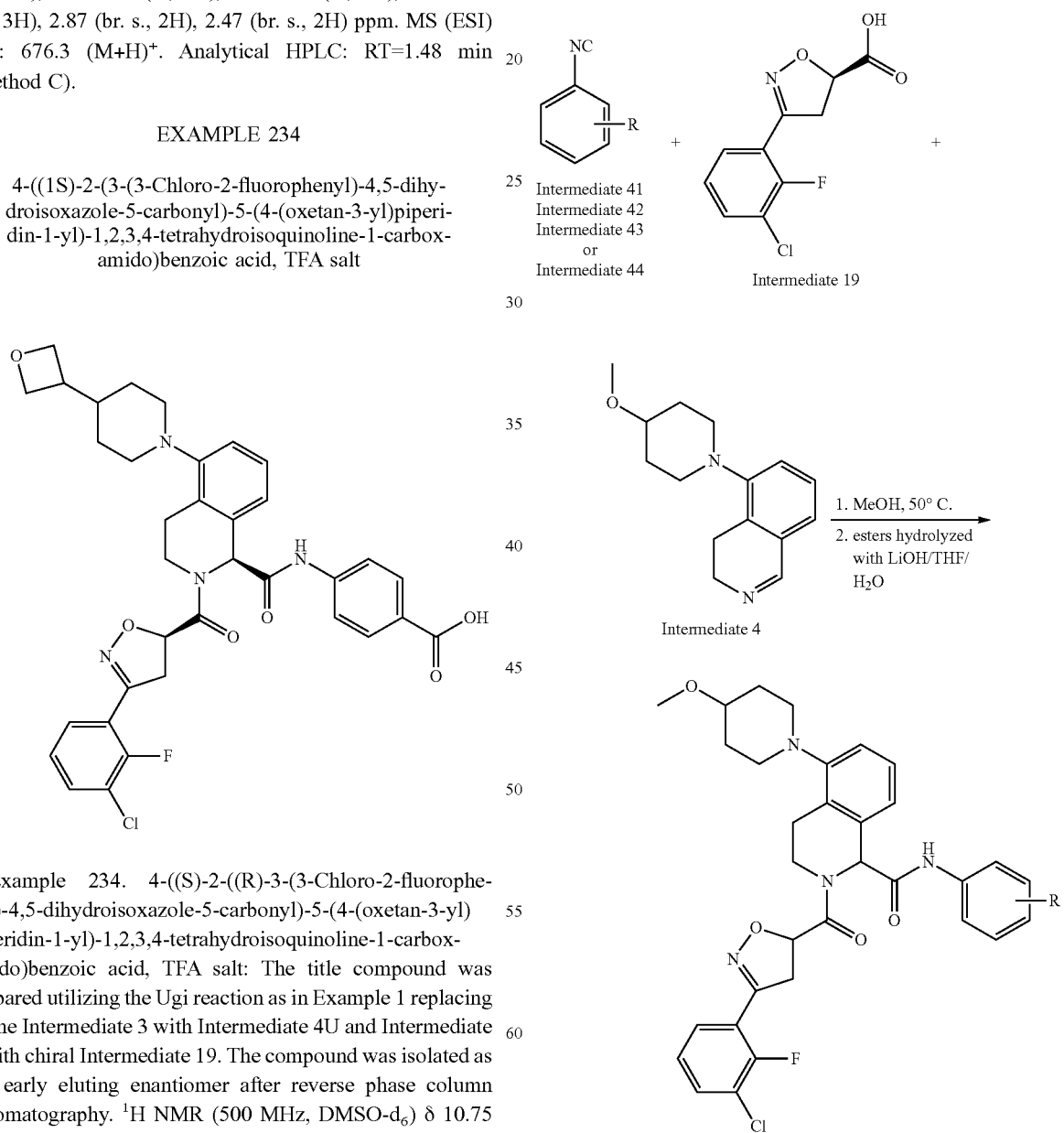

Intermediate 41
Intermediate 42
Intermediate 43
or
Intermediate 44

Intermediate 19

1. MeOH, 50° C.
2. esters hydrolyzed with LiOH/THF/ H$_2$O

Intermediate 4

Example 235-244

TABLE 11

| Example | Structure | Name | Analytical Data |
|---|---|---|---|
| 235 | 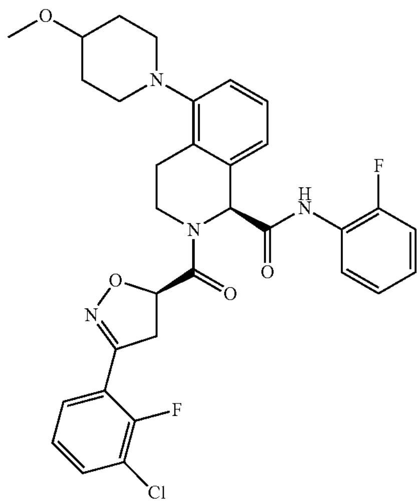 [SMILES: COC1CCN(c2cccc3c2CCN(C(=O)[C@H]2CC(c4cccc(Cl)c4F)=NO2)[C@@H]3C(=O)Nc2ccccc2F)CC1] | (S)-2-((R)-3-(3-chloro-2-fluorophenyl)-4,5-dihydroisoxazole-5-carbonyl)-N-(2-fluorophenyl)-5-(4-methoxypiperidin-1-yl)-1,2,3,4-tetrahydroisoquinoline-1-carboxamide, TFA salt | $^1$H NMR (500 MHz, DMSO-d$_6$) δ 10.19 (s, 1H), 7.81-7.71 (m, 3H), 7.38-7.31 (m, 2H), 7.27-7.20 (m, 2H), 7.16-7.09 (m, 2H), 7.00 (d, J = 8.0 Hz, 1H), 5.94 (s, 1H), 5.75 (dd, J = 11.4, 7.6 Hz, 1H), 4.22-4.15 (m, 1H), 3.90-3.83 (m, 1H), 3.73-3.65 (m, 2H), 3.35 (br.S., 1H), 3.29 (s, 3H), 3.10-2.98 (m, 4H), 2.75-2.64 (m, 2H), 2.05-1.94 (m, 2H), 1.69-1.57 (m, 2H) ppm. MS (ESI) m/z: 609 (M + H)$^+$. Analytical HPLC: RT = 7.55 min (Method B). (early eluting enantiomer) |
| 236 | 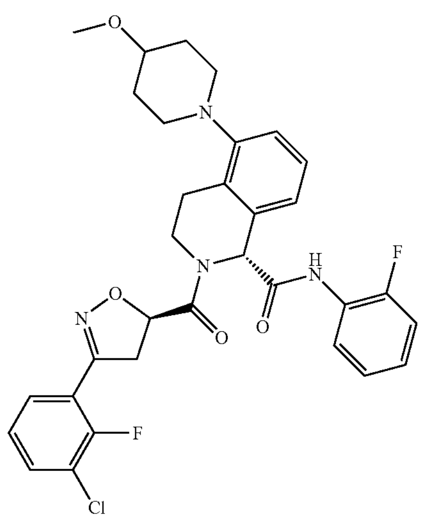 [SMILES: COC1CCN(c2cccc3c2CCN(C(=O)[C@H]2CC(c4cccc(Cl)c4F)=NO2)[C@H]3C(=O)Nc2ccccc2F)CC1] | (R)-2-((R)-3-(3-chloro-2-fluorophenyl)-4,5-dihydroisoxazole-5-carbonyl)-N-(2-fluorophenyl)-5-(4-methoxypiperidin-1-yl)-1,2,3,4-tetrahydroisoquinoline-1-carboxamide, TFA salt | $^1$H NMR (500 MHz, DMSO-d$_6$) δ 10.15 (s, 1H), 7.77-7.72 (m, 3H), 7.36-7.32 (m, 2H), 7 26-7.20 (m, 2H), 7.15-7.09 (m, 2H), 7.01 (d, J = 8.0 Hz, 1H), 5.90 (s, 1H), 5.86 (dd, J = 11.4, 7.0 Hz, 1H), 4.22-4.17 (m, 1H), 3.93-3.87 (m, 1H), 3.78-3.65 (m, 2H), 3.38-3.32 (m, 1H), 3.29 (s, 3H), 3.07-2.97 (m, 4H), 2.75-2.64 (m, 2H), 2.05-1.96 (m, 2H), 1.68-1.58 (m, 2H) ppm. MS (ESI) m/z: 609 (M + H)$^+$. Analytical HPLC: RT = 7.67 min (Method B). (late eluting enantiomer) |
| 237 | 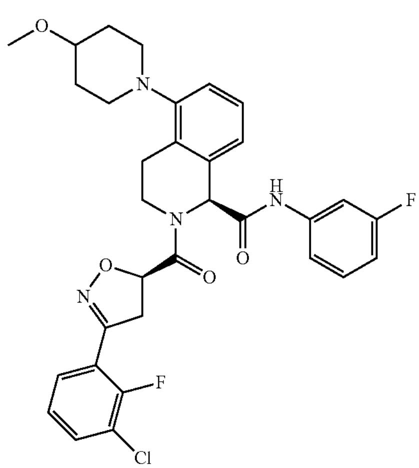 [SMILES: COC1CCN(c2cccc3c2CCN(C(=O)[C@H]2CC(c4cccc(Cl)c4F)=NO2)[C@@H]3C(=O)Nc2cccc(F)c2)CC1] | (S)-2-((R)-3-(3-chloro-2-fluorophenyl)-4,5-dihydroisoxazole-5-carbonyl)-N-(3-fluorophenyl)-5-(4-methoxypiperidin-1-yl)-1,2,3,4-tetrahydroisoquinoline-1-carboxamide, TFA salt | $^1$H NMR (400 MHz, DMSO-d$_6$) δ 10.62 (s, 1H), 7.69-7.62 (m, 2H), 7.47 (dt, J = 11.6, 1.7 Hz, 1H), 7.29-7.19 (m, 4H), 7.14 (t, J = 7.7 Hz, 1H), 6.92 (d, J = 7.5 Hz, 1H), 6.83-6.76 (m, 1H), 5.68 (dd, J = 11.3, 7.6 Hz, 1H), 5.62 (s, 1H), 4.19-4.13 (m, 1H), 3.83-3.75 (m, 1H), 3.65-3.54 (m, 2H), 3.27 (dt, J = 8.1, 4.0 Hz, 1H), 3.21 (s, 3H), 3.06-2.89 (m, 4H), 2.70-2.53 (m, 2H), 1.99-1.86 (m, 2H), 1.62-1.49 tm, 2H) ppm. MS (ESI) m/z: 609 (M + H)$^+$. Analytical HPLC: R7 = 7.53 min (Method B). (early eluting enantiomer) |

TABLE 11-continued

| Example | Structure | Name | Analytical Data |
|---|---|---|---|
| 238 | 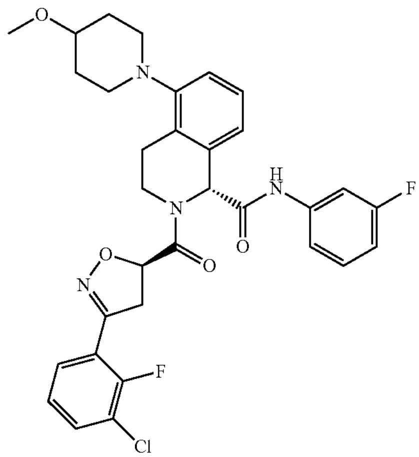 [SMILES: COC1CCN(c2cccc3c2CCN(C(=O)[C@H]2CC(c4cccc(Cl)c4F)=NO2)[C@H]3C(=O)Nc2cccc(F)c2)CC1] | (R)-2-((R)-3-(3-chloro-2-fluorophenyl)-4,5-dihydroisoxazole-5-carbonyl)-N-(3-fluorophenyl)-5-(4-methoxypiperidin-1-yl)-1,2,3,4-tetrahydroisoquinoline-1-carboxamide, TFA salt | $^1$H NMR (400 MHz, DMSO-d$_6$) δ 10.62-10.57 (m, 1H), 7.70-7.62 (m, 2H), 7.49-7.42 (m, 1H), 7.29-7.21 (m, 4H), 7.15 (t, J = 7.8 Hz, 1H), 6.94 (d, J = 7.7 Hz, 1H), 6.84-6.77 (m, 1H), 5.79 (dd, J = 11.2, 7.3 Hz, 1H), 5.60 (s, 1H), 4.17 (dt, J = 12.4, 4.9 Hz, 1H), 3.84-3.77 (m, 1H), 3.72-3.63 (m, 1H), 3.60-3.52 (m, 1H), 3.31-3.25 (m, 1H), 3.22 (s, 3H), 3.06-2.91 (m, 4H), 2.69-2.58 (m, 2H), 1.97-1.86 (m, 2H), 1.61-1.50 (m, 2H) ppm. MS (ESI) m/z: 609 (M + H)$^+$. Analytical HPLC: RT = 7.80 min (Method E). (late eluting enantiomer) |
| 239 | 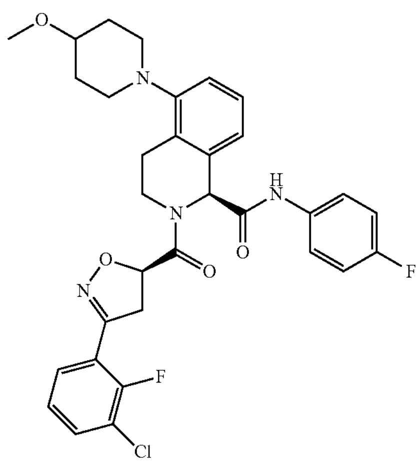 [SMILES: COC1CCN(c2cccc3c2CCN(C(=O)[C@H]2CC(c4cccc(Cl)c4F)=NO2)[C@@H]3C(=O)Nc2ccc(F)cc2)CC1] | (S)-2-((R)-3-(3-chloro-2-fluorophenyl)-4,5-dihydroisoxazole-5-carbonyl)-N-(4-fluorophenyl)-5-(4-methoxypiperidin-1-yl)-1,2,3,4-tetrahydroisoquinoline-1-carboxamide, TFA salt | $^1$H NMR (400 MHz, DMSO-d$_6$) δ 10.45 (s, 1H), 7.70-7.62 (m, 2H), 7.55-7.48 (m, 2H), 7.29-7.19 (m, 2H), 7.13 (t, J = 7.8 Hz, 1H), 7.07-7.01 (m, 2H), 5.92 (d, J = 8.1 Hz, 1H), 5.67 (dd, J = 11.4, 7.5 Hz, 1H), 5.63 (s, 1H), 4.19-4.10 (m, 1H), 3.84-3.74 (m, 1H), 3.65-3.55 (m, 2H), 3.26 (d, J = 3.3 Hz, 1H), 3.22-3.19 (m, 3H), 3.07-2.99 (m, 1H), 2.97-2.89 (m, 3H), 2.67-2.56 (m, 2H), 1.96-1.87 (m, 2H), 1.61-1.49 (m, 2H) ppm. MS (ESI) m/z: 609 (M + H)$^+$. Analytical HPLC: RT = 7.55 min (Method B). (early eluting enantiomer) |
| 240 | 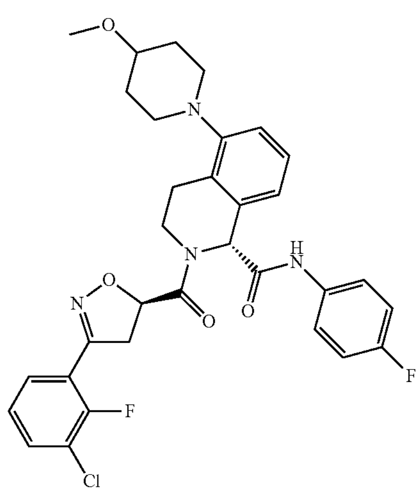 [SMILES: COC1CCN(c2cccc3c2CCN(C(=O)[C@H]2CC(c4cccc(Cl)c4F)=NO2)[C@H]3C(=O)Nc2ccc(F)cc2)CC1] | (R)-2-((R)-3-(3-chloro-2-fluorophenyl)-4,5-dihydroisoxazole-5-carbonyl)-N-(4-fluorophenyl)-5-(4-methoxypiperidin-1-yl)-1,2,3,4-tetrahydroisoquinoline-1-carboxamide, TFA salt | $^1$H NMR (400 MHz, DMSO-d$_6$) δ 10.42 (s, 1H), 7.69-7.63 (m, 2H), 7.51-7.46 (m, 2H), 7.29-7.20 (m, 2H), 7.14 (t, J = 7.8 Hz, 1H), 7.07-7.01 (m, 2H), 6.93 (d, J = 7.7 Hz, 1H), 5.79 (dd, J = 11.3, 7.2 Hz, 1H), 5.60 (s, 1H), 4.19-4.13 (m, 1H), 3.84-3.76 (m, 1H), 3.71-3.54 (m, 2H), 3.31-3.24 (m, 1H), 3.22 (s, 3H), 3.07-2.88 (m, 4H), 2.69-2.56 (m, 2H), 1.97-1.87 (m, 2H), 1.56 (t, J = 9.5 Hz, 2H) ppm. MS (ESI) m/z: 609 (M + H)$^+$. Analytical HPLC: RT = 7.70 min (Method B). (late eluting enantiomer) |

… TABLE 11-continued

| Example | Structure | Name | Analytical Data |
|---|---|---|---|
| 241 | 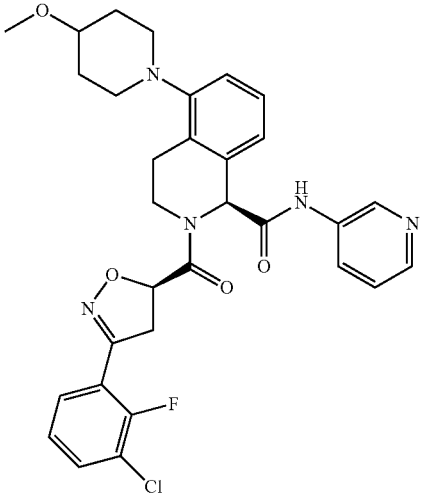 [SMILES: COC1CCN(c2cccc3c2CCN(C(=O)[C@H]2CC(c4cccc(Cl)c4F)=NO2)[C@@H]3C(=O)Nc2cccnc2)CC1] | (S)-2-((R)-3-(3-chloro-2-fluorophenyl)-4,5-dihydroisoxazole-5-carbonyl)-5-(4-methoxypiperidin-1-yl)-N-(pyridin-3-yl)-1,2,3,4-tetrahydroisoquinoline-1-carboxamide, TFA salt | $^1$H NMR (400 MHz, DMSO-d$_6$) δ 10.85 (br. s., 1H), 8.81 (br. s., 1H), 8.29 (br. s., 1H), 8.06 (d, J = 5.5 Hz, 1H), 7.69-7.62 (m, 2H), 7.29-7.12 (m, 3H), 6.93 (d, J = 7.5 Hz, 1H), 5.68 (dd, J = 11.6, 7.6 Hz, 1H), 5.65 (s, 1H), 4.20-4.13 (m, 1H), 3.85-3.75 (m, 1H), 3.66-3.54 (m, 2H), 3.27 (dt, J = 8.0, 4.1 Hz, 1H), 3.22 (s, 3H), 3.05-2.90 (m, 4H), 2.69-2.54 (m, 2H), 1.97-1.86 (m, 2H), 1.54 (d, J = 11.7 Hz, 2H) ppm. MS (ESI) m/z: 592 (M + H)$^+$. Analytical HPLC: RT = 6.32 min (Method B). (early eluting enantiomer) |
| 242 | 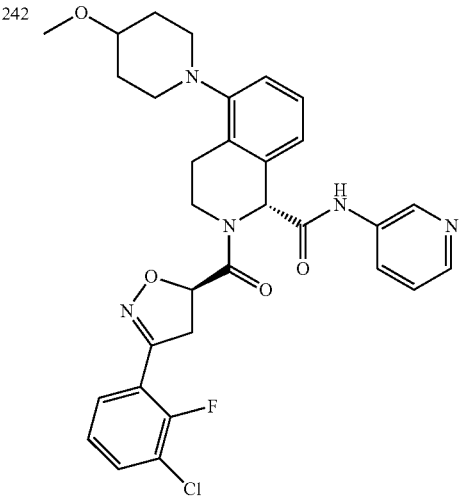 | (R)-2-((R)-3-(3-chloro-2-fluorophenyl)-4,5-dihydroisoxazole-5-carbonyl)-5-(4-methoxypiperidin-1-yl)-N-(pyridin-3-yl)-1,2,3,4-tetrahydroisoquinoline-1-carboxamide, TFA salt | $^1$H NMR (400 MHz, DMSO-d$_6$) δ 10.93 (s, 1H), 8.85 (d, J = 2.0 Hz, 1H), 8.33 (d, J = 4.4 Hz, 1H), 8.14-8.04 (m, 1H), 7.66 (dd, J = 8.0, 6.9 Hz, 2H), 7.57-7.49 (m, 1H), 7.30-7.22 (m, 2H), 7.19-7.13 (m, 1H), 6.95 (d, J = 7.7 Hz, 1H), 5.80 (dd, J = 11.2, 7.3 Hz, 1H), 5.66-5.60 (m, 1H), 4.18 (dt, J = 12.4, 4.8 Hz, 1H), 3.84-3.73 (m, 1H), 3.72-3.64 (m, 1H), 3.54 (td, J = 8.4, 4.2 Hz, 1H), 3.27 (dt, J = 8.1, 4.2 Hz, 1H), 3.22 (s, 3H), 3.06-2.90 (m, 4H), 2.70-2.55 (m, 2H), 2.00-1.85 (m, 2H), 1.65-1.50 (m, 2H) ppm. MS (ESI) m/z: 592 (M + H)$^+$. Analytical HPLC: RT = 6.52 min (Method B). (late eluting enantiomer) |
| 243 | 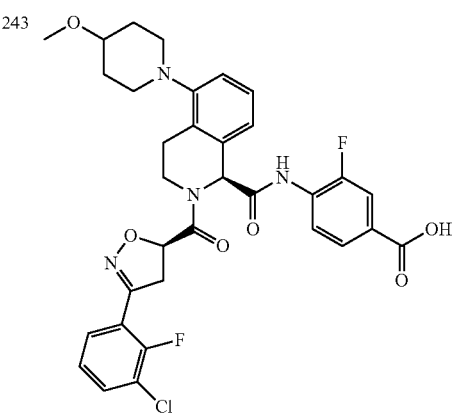 | 4-((S)-2-((R)-3-(3-chloro-2-fluorophenyl)-4,5-dihydroisoxazole-5-carbonyl)-5-(4-methoxypiperidin-1-yl)-1,2,3,4-tetrahydroisoquinoline-1-carboxamide)-3-fluorobenzoic acid, TFA salt | $^1$H NMR (400 MHz, DMSO-d$_6$) δ 10.40 (s, 1H), 7.99 (t, J = 8.3 Hz, 1H), 7.69-7.62 (m, 4H), 7.30-7.14 (m, 3H), 6.92 (d, J = 7.7 Hz, 1H), 5.92 (s, 1H), 5.58 (dd, J = 11.4, 7.7 Hz, 1H), 4.16-4.10 (m, 1H), 3.83-3.77 (m, 1H), 3.65-3.54 (m, 2H), 3.27 (d, J = 4.0 Hz, 1H), 3.22 (s, 3H), 3.00-2.91 (m, 4H), 2.68-2.55 (m, 2H), 1.95-1.87 (m, 2H), 1.61-1.50 (m, 2H) ppm. MS (ESI) m/z: 653 (M + H)$^+$. Analytical HPLC: RT = 7.30 min (Method B). (early eluting enantiomer) |

TABLE 11-continued

| Example | Structure | Name | Analytical Data |
|---|---|---|---|
| 244 | 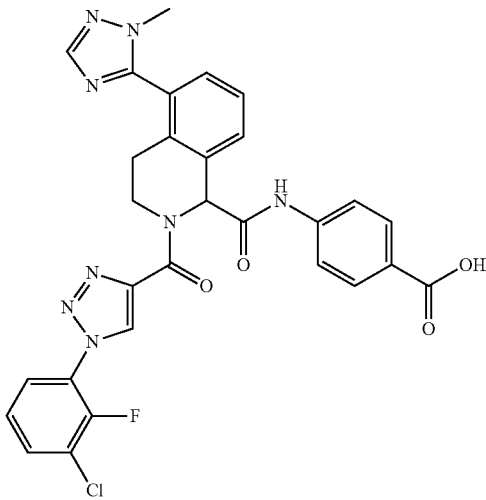 | 4-((R)-2-((R)-3-(3-chloro-2-fluorophenyl)-4,5-dihydroisoxazole-5-carbonyl)-5-(4-methoxypiperidin-1-yl)-1,2,3,4-tetrahydroisoquinoline-1-carboxamido)-3-fluorobenzoic acid, TFA salt | $^1$H NMR (400 MHz, DMSO-$d_6$) δ 13.00 (br. s., 1H), 10.38 (s, 1H), 7.95 (t, J = 8.3 Hz, 1H), 7.70-7.60 (m, 4H), 7.32-7.24 (m, 2H), 7.15 (t, J = 7.8 Hz, 1H), 6.93 (d, J = 7.9 Hz, 1H), 5.88 (s, 1H), 5.79 (dd, J = 11.3, 6.9 Hz, 1H), 4.14 (dt, J = 12.4, 4.9 Hz, 1H), 3.86-3.76 (m, 1H), 3.71-3.51 (m, 2H), 3.32-3.23 (m, 1H), 3.22 (s, 3H), 3.04-2.89 (m, 1H), 2.69-2.54 (m, 2H), 1.99-1.87 (m, 2H), 1.64-1.46 (m, 2H) ppm. MS (ESI) m/z: 653 (M + H)$^+$. Analytical HPLC RT = 7.46 min (Method B). (late eluting enantiomer) |

EXAMPLE 245

4-(2-(1-(3-Chloro-2-fluorophenyl)-1H-1,2,3-triazole-4-carbonyl)-5-(1-methyl-1H-1,2,4-triazol-5-yl)-1,2,3,4-tetrahydroisoquinoline-1-carboxamido)benzoic acid, TFA salt

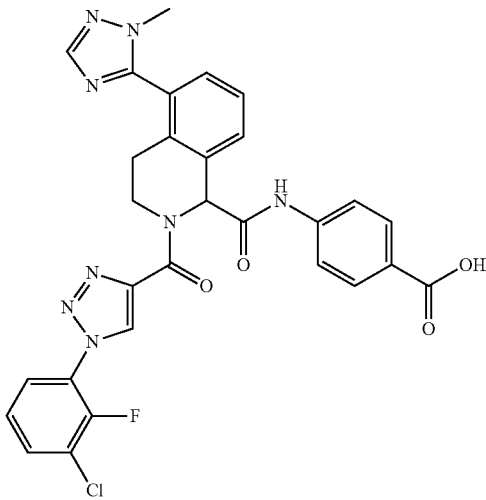 [SMILES: Cn1ncnc1-c1cccc2c1CCN(C(=O)c1cn(-c3cccc(Cl)c3F)nn1)C2C(=O)Nc1ccc(C(=O)O)cc1]

Example 245. 4-(2-(1-(3-Chloro-2-fluorophenyl)-1H-1,2,3-triazole-4-carbonyl)-5-(1-methyl-1H-1,2,4-triazol-5-yl)-1,2,3,4-tetrahydroisoquinoline-1-carboxamido)benzoic acid, TFA salt: Intermediate 44 (0.050 g, 0.071 mmol), 5-bromo-1-methyl-1H-1,2,4-triazole (0.017 g, 0.107 mmol), and Na$_2$CO$_3$ (2.0M aq. solution) (0.178 mL, 0.356 mmol) were added to dioxane (1.0 mL) and degassed for 15 min. Tetrakis (triphenylphosphine)palladium(0) (8.23 mg, 7.12 mol) was added and the mixture was irradiated at 120° C. for 15 min. The reaction mixture was poured into EtOAc, washed with saturated NaHCO$_3$ solution, brine, dried over sodium sulfate, filtered, and concentrated. The t-butyl ester group was removed was treatment with 50% TFA/DCM, concentrated, purified by reverse phase prep. HPLC, and freeze-dried to give the title compound as a white solid (14.3 mg, 27%). $^1$H NMR (400 MHz, DMSO-$d_6$) δ 11.02 (s, 1H), 9.21-9.15 (m, 1H), 8.14-8.05 (m, 1H), 7.93-7.84 (m, 5H), 7.75 (d, J=8.8 Hz, 2H), 7.54-7.45 (m, 3H), 6.05 (s, 1H), 4.51-4.40 (m, 1H), 4.19 (ddd, J=12.7, 8.3, 4.2 Hz, 1H), 3.76 (s, 3H), 3.11-3.02 (m, 1H), 2.91-2.81 (m, 1H) ppm. MS (ESI) m/z: 601 (M+H)$^+$. Analytical HPLC: RT=6.14 min (Method B).

EXAMPLE 246

4-(2-(1-(3-Chloro-2-fluorophenyl)-1H-1,2,3-triazole-4-carbonyl)-5-(1-methyl-1H-imidazol-4-yl)-1,2,3,4-tetrahydroisoquinoline-1-carboxamido)benzoic acid, TFA salt

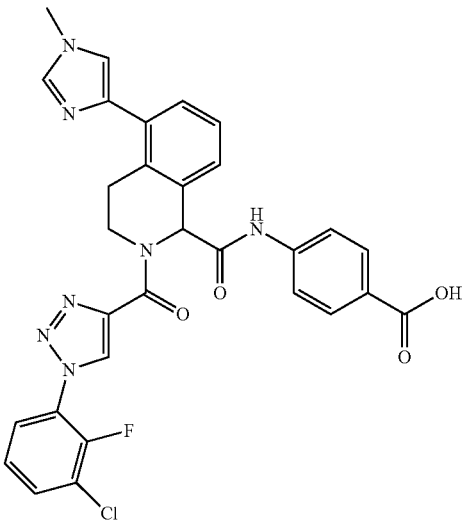 [SMILES: Cn1cnc(-c2cccc3c2CCN(C(=O)c2cn(-c4cccc(Cl)c4F)nn2)C3C(=O)Nc2ccc(C(=O)O)cc2)c1]

Example 246. 4-(2-(1-(3-Chloro-2-fluorophenyl)-1H-1,2,3-triazole-4-carbonyl)-5-(1-methyl-1H-imidazol-4-yl)-1,2,3,4-tetrahydroisoquinoline-1-carboxamido)benzoic acid, TFA salt: The title compound was prepared in the same manner as Example 245 replacing 5-bromo-1-methyl-1H-1,2,4-triazole with 4-bromo-1-methyl-1H-imidazole. $^1$H NMR (400 MHz, DMSO-$d_6$) δ 10.93 (s, 1H), 9.12 (d, J=1.8 Hz, 1H), 7.91-7.76 (m, 5H), 7.76-7.65 (m, 3H), 7.51-7.34

(m, 4H), 5.99-5.91 (m, 1H), 4.51-4.40 (m, 1H), 4.26-4.16 (m, 1H), 3.81 (s, 3H), 3.21-3.09 (m, 2H) ppm. MS (ESI) m/z: 600 (M+H)+. Analytical HPLC: RT=5.14 min (Method B).

EXAMPLE 247

4-((S)-2-((R)-3-(3-Chloro-2-fluorophenyl)-4,5-dihydroisoxazole-5-carbonyl)-5-(4H-1,2,4-triazol-4-yl)-1,2,3,4-tetrahydroisoquinoline-1-carboxamido)benzoic acid, TFA salt

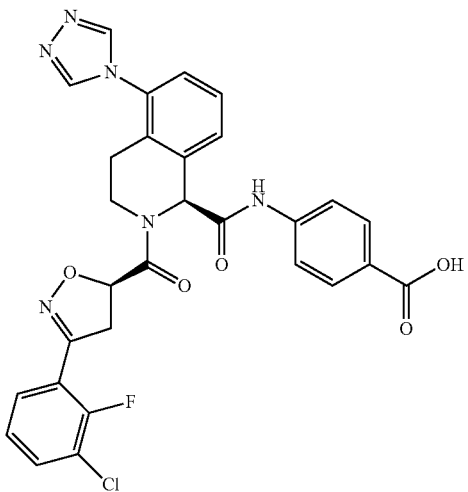 [SMILES: O=C(O)c1ccc(NC(=O)[C@@H]2c3cccc(-n4cnnc4)c3CCN2C(=O)[C@H]2CC(c3cccc(Cl)c3F)=NO2)cc1]

247A.5-(4H-1,2,4-Triazol-4-yl)isoquinoline: Using a modified procedure described by Varano (Varano, F. et al., *J Med. Chem.*, 45(5): 1035-1044 (2002)). To two large microwave vials containing in equal portions a suspension of isoquinolin-5-amine (0.865 g, 6.0 mmol) and N'-formylformohydrazide (0.793 g, 9 mmol) in pyridine (24 mL) was added, TMSI (5.71 mL, 45 mmol) dropwise followed by TEA (2.84 mL, 20.4 mmol). The reaction vessels were sealed and heated at 100° C. for 4 h. The reaction was cooled to room temperature, concentrated, the residue dissolved in EtOAc, washed with 1.5M potassium phosphate, brine, dried over sodium sulfate, filtered, and concentrated. The crude residue was purified by normal phase column chromatography to give a solid (0.467 g, 39.7% yield). $^1$H NMR (400 MHz, DMSO-$d_6$) δ 9.45 (d, J=0.7 Hz, 1H), 8.95 (s, 2H), 8.56 (d, J=6.2 Hz, 1H), 8.35-8.30 (m, 1H), 7.93 (dd, J=7.5, 1.1 Hz, 1H), 7.80 (dd, J=8.1, 7.5 Hz, 1H), 7.29 (d, J=6.2 Hz, 1H). MS (ESI) m/z: 197 (M+H)+.

Example 247. 4-((S)-2-((R)-3-(3-Chloro-2-fluorophenyl)-4,5-dihydroisoxazole-5-carbonyl)-5-(4H-1,2,4-triazol-4-yl)-1,2,3,4-tetrahydroisoquinoline-1-carboxamido)benzoic acid, TFA salt: The title compound was prepared by similar methods described for Example 226 starting from 247A. The compound was isolated as the early eluting diastereomer after reverse phase prep. HPLC. $^1$H NMR (500 MHz, DMSO-$d_6$) δ 12.74 (br. s., 1H), 10.98 (s, 1H), 8.91-8.87 (m, 2H), 7.97-7.90 (m, 2H), 7.81-7.71 (m, 5H), 7.51 (t, J=8.0 Hz, 1H), 7.46-7.42 (m, 1H), 7.37-7.31 (m, 1H), 5.98 (s, 1H), 5.77 (dd, J=11.4, 7.6 Hz, 1H), 4.20 (ddd, J=12.7, 7.9, 4.4 Hz, 1H), 3.94-3.84 (m, 2H), 3.75-3.68 (m, 2H), 2.88-2.83 (m, 1H) ppm. MS (ESI) m/z: 589 (M+H)+. Analytical HPLC: RT=1.16 min (Method C).

EXAMPLE 248

4-((R)-2-((R)-3-(3-Chloro-2-fluorophenyl)-4,5-dihydroisoxazole-5-carbonyl)-5-(4H-1,2,4-triazol-4-yl)-1,2,3,4-tetrahydroisoquinoline-1-carboxamido)benzoic acid, TFA salt

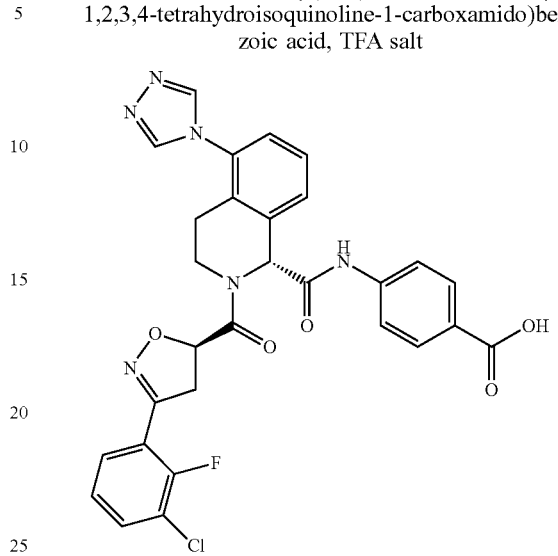

Example 248. 4-((R)-2-((R)-3-(3-Chloro-2-fluorophenyl)-4,5-dihydroisoxazole-5-carbonyl)-5-(4H-1,2,4-triazol-4-yl)-1,2,3,4-tetrahydroisoquinoline-1-carboxamido)benzoic acid, TFA salt: The title compound was isolated as the late eluting diastereomer after reverse phase prep. HPLC of Example 247. $^1$H NMR (500 MHz, DMSO-$d_6$) δ 10.93 (s, 1H), 8.94-8.84 (m, 2H), 7.94-7.89 (m, 2H), 7.84-7.70 (m, 5H), 7.54-7.49 (m, 1H), 7.44 (d, J=8.0 Hz, 1H), 7.34 (t, J=8.0 Hz, 1H), 5.96 (s, 1H), 5.88 (dd, J=11.3, 7.2 Hz, 1H), 4.19 (ddd, J=12.5, 7.7, 4.3 Hz, 1H), 3.93-3.86 (m, 2H), 3.79-3.72 (m, 2H), 2.89-2.84 (m, 1H), 2.77 (d, J=4.7 Hz, 1H) ppm. MS (ESI) m/z: 589 (M+H)+. Analytical HPLC: RT=1.18 min (Method C).

EXAMPLE 249

4-(2-(1-(3-Chloro-2-fluorophenyl)-1H-1,2,3-triazole-4-carbonyl)-5-(4H-1,2,4-triazol-4-yl)-1,2,3,4-tetrahydroisoquinoline-1-carboxamido)benzoic acid, TFA salt

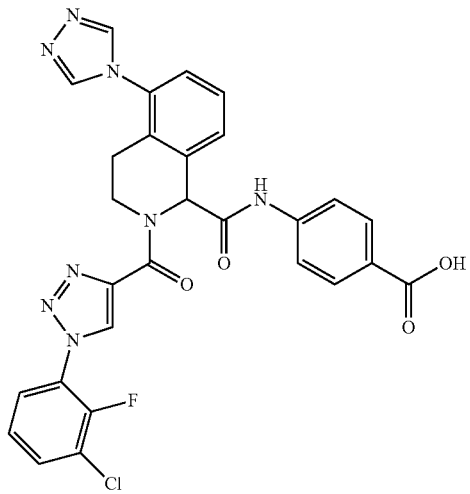 [SMILES: O=C(O)c1ccc(NC(=O)C2c3cccc(-n4cnnc4)c3CCN2C(=O)c2cn(-c3cccc(Cl)c3F)nn2)cc1]

Example 249. 4-(2-(1-(3-Chloro-2-fluorophenyl)-1H-1,2,3-triazole-4-carbonyl)-5-(4H-1,2,4-triazol-4-yl)-1,2,3,4-tetrahydroisoquinoline-1-carboxamido)benzoic acid, TFA salt: The title compound was prepared by similar methods described for Example 247 starting from 247A and replacing Intermediate 19 with Intermediate 9 in the Ugi reaction step. ¹H NMR (400 MHz, DMSO-$d_6$) δ 12.68 (br, s, 1H), 10.98 (s, 1H), 9.10 (d, J=1.8 Hz, 1H), 8.81 (s, 2H), 7.94-7.75 (m, 5H), 7.69 (d, J=8.8 Hz, 2H), 7.51-7.36 (m, 3H), 6.03 (s, 1H), 4.42-4.27 (m, 2H), 2.78 (d, J=3.1 Hz, 2H) ppm. MS (ESI) m/z: 587 (M+H)⁺. Analytical HPLC: RT=5.89 min (Method B).

EXAMPLE 250

4-((S)-2-((R)-3-(3-Chloro-2-fluorophenyl)-4,5-dihydroisoxazole-5-carbonyl)-5-(3-methyl-1H-1,2,4-triazol-1-yl)-1,2,3,4-tetrahydroisoquinoline-1-carboxamido)benzoic acid, TFA salt

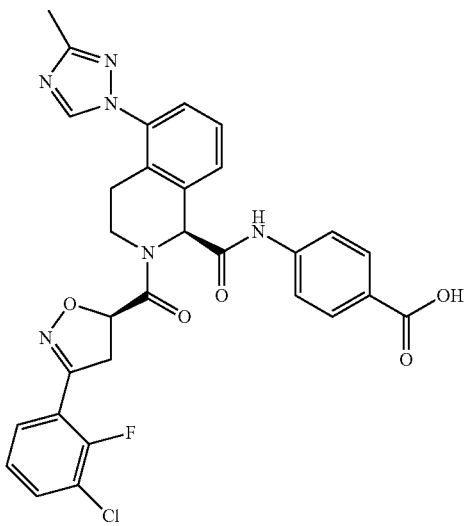 [SMILES: Cc1ncn(-c2cccc3c2CCN(C(=O)[C@H]2CC(c4cccc(Cl)c4F)=NO2)[C@@H]3C(=O)Nc2ccc(C(=O)O)cc2)n1]

250A. 5-(3-Methyl-1H-1,2,4-triazol-1-yl)isoquinoline: A mixture of 5-bromoisoquinoline (0.500 g, 2.403 mmol), 3-methyl-1H-1,2,4-triazole (0.599 g, 7.21 mmol), $K_2CO_3$ (0.996 g, 7.21 mmol), and CuI (0.458 g, 2.403 mmol) in NMP (5.0 mL) was heated at 150° C. overnight. The reaction mixture was cooled to room temperature, filtered through a plug of CELITE®, filter cake washed with 10% MeOH/DCM, filtrate absorbed onto silica gel, purified by reverse phase prep. HPLC, and concentrated to give a white solid (80 mg, 16%). ¹H NMR (400 MHz, methanol-$d_4$) δ 9.43 (d, J=0.7 Hz, 1H), 8.83 (s, 1H), 8.57 (d, J=6.2 Hz, 1H), 8.35 (d, J=8.4 Hz, 1H), 7.99 (dd, J=7.3, 1.1 Hz, 1H), 7.90-7.81 (m, 2H), 2.55 (s, 3H) ppm. MS (ESI) m/z: 211 (M+H)⁺.

Example 250. 4-((S)-2-((R)-3-(3-Chloro-2-fluorophenyl)-4,5-dihydroisoxazole-5-carbonyl)-5-(3-methyl-1H-1,2,4-triazol-1-yl)-1,2,3,4-tetrahydroisoquinoline-1-carboxamido)benzoic acid, TFA salt: The title compound was prepared by similar methods described for Example 226 starting from 250A. The compound was isolated as the early eluting diastereomer after reverse phase prep. HPLC. ¹H NMR (400 MHz, methanol-$d_4$) δ 10.51 (s, 1H), 8.77 (d, J=7.9 Hz, 1H), 8.05-7.95 (m, 2H), 7.79-7.67 (m, 4H), 7.63-7.58 (m, 1H), 7.54-7.45 (m, 2H), 7.25 (td, J=7.9, 2.6 Hz, 1H), 6.00 (s, 1H), 5.79-5.72 (m, 1H), 4.36-4.28 (m, 1H), 4.01-3.85 (m, 2H), 3.76 (dd, J=17.2, 11.4 Hz, 1H), 3.21-3.11 (m, 1H), 2.98-2.89 (m, 1H), 2.50 (s, 3H) ppm. MS (ESI) m/z: 603 (M+H)⁺. Analytical HPLC: RT=6.13 min (Method B).

EXAMPLE 251

4-((R)-2-((R)-3-(3-Chloro-2-fluorophenyl)-4,5-dihydroisoxazole-5-carbonyl)-5-(3-methyl-1H-1,2,4-triazol-1-yl)-1,2,3,4-tetrahydroisoquinoline-1-carboxamido)benzoic acid, TFA salt

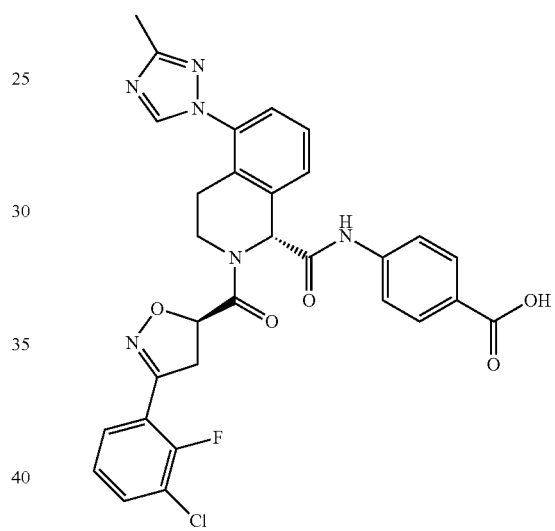

Example 251: 4-((R)-2-((R)-3-(3-Chloro-2-fluorophenyl)-4,5-dihydroisoxazole-5-carbonyl)-5-(3-methyl-1H-1,2,4-triazol-1-yl)-1,2,3,4-tetrahydroisoquinoline-1-carboxamido)benzoic acid, TFA salt the title compound was isolated as the late eluting diastereomer after reverse phase prep. HPLC of Example 250. ¹H NMR (400 MHz, methanol-$d_4$) δ 10.56 (s, 1H), 8.76 (s, 1H), 8.05-7.97 (m, 2H), 7.83-7.67 (m, 4H), 7.61 (t, J=7.5 Hz, 1H), 7.56-7.45 (m, 2H), 7.30-7.23 (m, 1H), 5.98 (s, 1H), 5.83 (dd, J=11.2, 6.8 Hz, 1H), 4.29-4.19 (m, 1H), 4.08 (dd, J=17.4, 6.8 Hz, 1H), 3.98-3.90 (m, 1H), 3.79-3.69 (m, 1H), 3.16-3.08 (m, 1H), 3.04-2.95 (m, 1H), 2.52 (s, 3H) ppm. MS (ESI) m/z: 603 (M+H)⁺. Analytical HPLC: RT=6.41 min (Method B).

The following Examples in Table 12 were synthesized by routine Ugi reaction conditions as demonstrated in Example 226 utilizing of the appropriate substituted imines (Intermediates 4, 4C, 4D, 4F, 4L, 4M, 4V, 5B, 54), substituted heterocyclic carboxylic acid (Intermediates 9, 10, 11, 13, 15, 16, 17, 21, 22, 45, 46, 47, 48, 49, or 50), and isonitriles (Intermediates 1). In most cases, the final compounds were purified by normal phase column chromatography and/or reverse phase prep. HPLC. Chiral separation was carried out using chiral HPLC on late stage intermediates followed by deprotection and purification where indicated.

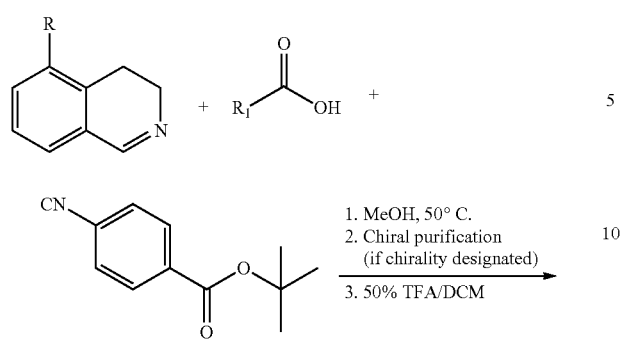
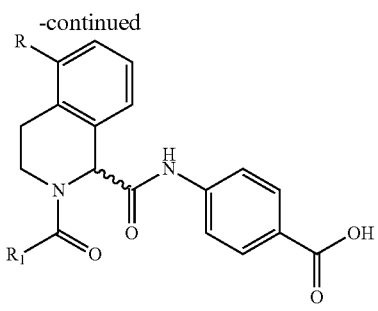

Examples 252-303

TABLE 12

| Example | Structure | Name | Analytical Data |
|---|---|---|---|
| 252 | 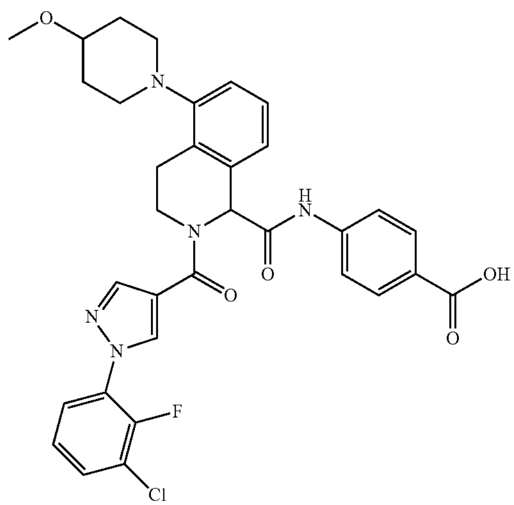 [SMILES: COC1CCN(c2cccc3c2CCN(C(=O)c2cnn(-c4cccc(Cl)c4F)c2)C3C(=O)Nc2ccc(C(=O)O)cc2)CC1] | 4-(2-(1-(3-chloro-2-fluorophenyl)-1H-pyrazole-4-carbonyl)-5-(4-methoxypiperidin-1-yl)-1,2,3,4-tetrahydroisoquinoline-1-carboxamido)benzoic acid, TFA salt | $^1$H NMR (400 MHz, methanol-$d_4$) δ 10.47 (br. s., 1H), 8.57 (s, 1H), 8.15 (s, 1H), 7.95 (d, J = 8.8 Hz, 2H), 7.80 (t, J = 7.3 Hz, 1H), 7.67 (d, J = 7.6 Hz, 2H), 7.57 (t, J = 6.9 Hz, 1H), 7.39-7.30 (m, 2H), 7.30-7.22 (m, 1H), 7.11 (d, J = 7.6 Hz, 1H), 5.78 (s, 1H), 4.37 (d, J = 12.1 Hz, 1H), 3.76 (br. s., 1H), 3.39 (s, 3H), 3.23 (br. s., 1H), 3.13 (m, 2H), 2.91 (t, J = 9.2 Hz, 1H), 2.73 (d, J = 8.6 Hz, 2H), 2.06 (d, J = 13.4 Hz, 2H), 1.75 (d, J = 9.9 Hz, 2H) ppm. MS (ESI) m/z: 632 (M + H)$^+$. Analytical HPLC: RT = 8.82 min (Method A). (racemate) |
| 253 | 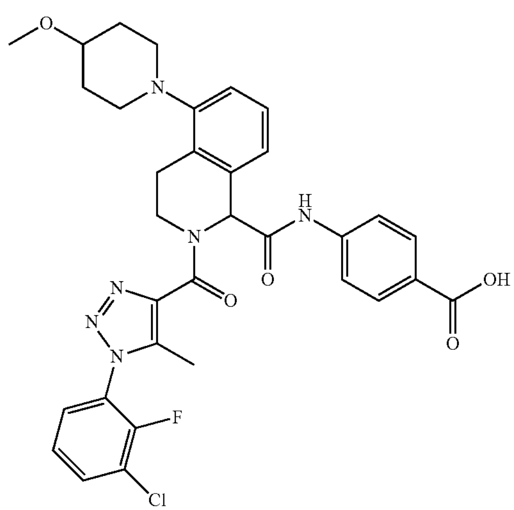 [SMILES: COC1CCN(c2cccc3c2CCN(C(=O)c2nnn(-c4cccc(Cl)c4F)c2C)C3C(=O)Nc2ccc(C(=O)O)cc2)CC1] | 4-(2-(1-(3-chloro-2-fluorophenyl)-5-methyl-1H-1,2,3-triazole-4-cabonyl)-5-(4-methoxypiperidin-1-yl)-1,2,3,4-tetrahydroisoquinoline-1-carboxamido)benzoic acid, TFA salt | $^1$H NMR (400 MHz, methanol-$d_4$) δ 10.52 (s, 1H), 7.97 (d, J = 8.6 Hz, 2H), 7.82 (d, J = 6.6 Hz, 1H), 7.69 (d, J = 8.6 Hz, 1H), 7.65-7.58 (m, 1H), 7.51-7.43 (m, 1H), 7.41-7.24 (m, 3H), 7.15 (s, 1H), 5.85 (s, 1H), 4.5 (d, J = 12.6 Hz, 1H), 4.03 (s, 1H), 3.40 (s, 3H), 3.19 (d, J = 15.2 Hz, 2H), 2.57-2.71 (m, 2H), 2.42 (s, 3H), 2.10 (br. s., 2H), 1.78 (br. s., 2H) ppm. MS (ESI) m/z: 647 (M + H)$^+$. Analytical HPLC: RT = 8.79 min (Method A). (racemate) |

TABLE 12-continued

| Example | Structure | Name | Analytical Data |
|---|---|---|---|
| 254 | 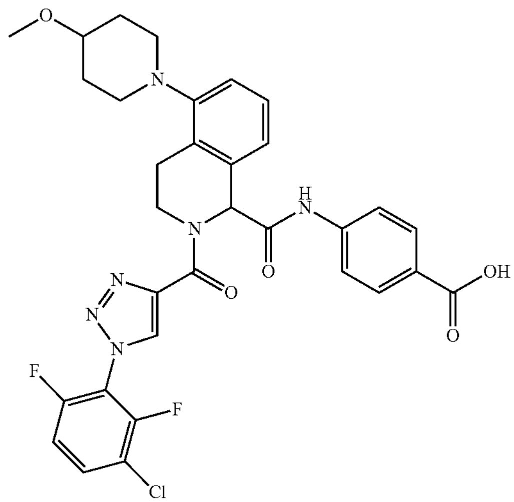 [SMILES: COC1CCN(c2cccc3c2CCN(C(=O)c2cn(-c4c(F)ccc(Cl)c4F)nn2)C3C(=O)Nc2ccc(C(=O)O)cc2)CC1] | 4-(2-(1-(3-chloro-2,6-difluorophenyl)-1H-1,2,3-triazole-4-carbonyl)-5-(4-methoxypiperidin-1-yl)-1,2,3,4-tetrahydroisoquinoline-1-carboxamido)benzoic acid, TFA salt | $^1$H NMR (500 MHz, methanol-$d_4$) δ 10.55-10.52 (m, 1H), 8.87-8.84 (m, 1H), 7.98-7.94 (m, 2H), 7.87-7.80 (m, 1H), 7.71-7.66 (m, 2H), 7.42-7.33 (m, 2H), 7.32-7.26 (m, 1H), 7.19-7.12 (m, 1H), 5.88-5.85 (m, 1H), 4.72-4.65 (m, 1H), 4.12-4.05 (m, 1H), 3.40 (s, 3H), 3.26-3.20 (m, 2H), 2.97-2.88 (m, 1H), 2.86-2.75 (m, 1H), 2.15-2.04 (m, 2H), 1.87-1.72 (m, 2H) ppm. MS (ESI) m/z: 651 (M + H)$^+$. Analytical HPLC: RT = 8.78 min (Method A). (racemate) |
| 255 | 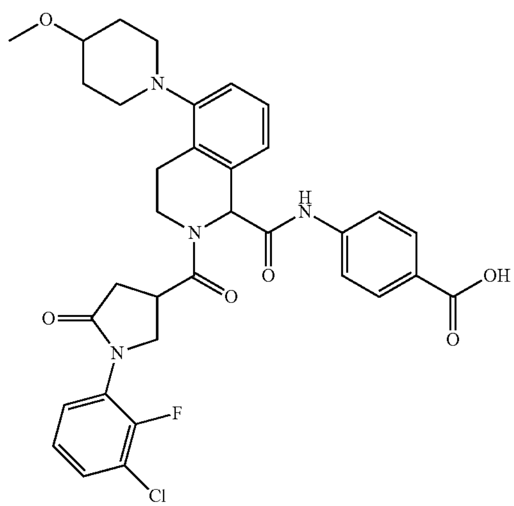 [SMILES: COC1CCN(c2cccc3c2CCN(C(=O)C2CC(=O)N(c4cccc(Cl)c4F)C2)C3C(=O)Nc2ccc(C(=O)O)cc2)CC1] | 4-(2-(1-(3-chloro-2-fluorophenyl)-5-oxopyrrolidine-3-carbonyl)-5-(4-methoxypiperidin-1-yl)-1,2,3,4-tetrahydroisoquinoline-1-carboxamido)benzoic acid, TFA salt | $^1$H NMR (500 MHz, methanol-$d_4$) δ 10.43 (s, 1H), 7.99-7.95 (m, 2H), 7.68-7.67 (m, 1H), 7.66 (d, J = 1.7 Hz, 1H), 7.45 (dddd, J = 19.8, 8.1, 6.7, 1.7 Hz, 2H), 7.35-7.31 (m, 1H), 7.28 (t, J = 7.8 Hz, 1H), 7.23 (td, J = 8.1, 1.4 Hz, 1H), 7.13 (d, J = 7.7 Hz, 1H), 5.76 (s, 1H), 4.26 (dt, J = 11.8, 4.7 Hz, 1H), 4.16-4.03 (m, 3H), 3.54 (td, J = 10.8, 4.0 Hz, 1H), 3.42 (s, 3H), 3.28-3.13 (m, 4H), 3.04-2 91 (m, 3H), 2.84-2.73 (m, 1H), 2.17-2.05 (m, 2H), 1.81 (br. s., 2H) ppm. MS (ESI) m/z: 649 (M + H)$^+$. (diastereomeric mixture) |
| 256 | 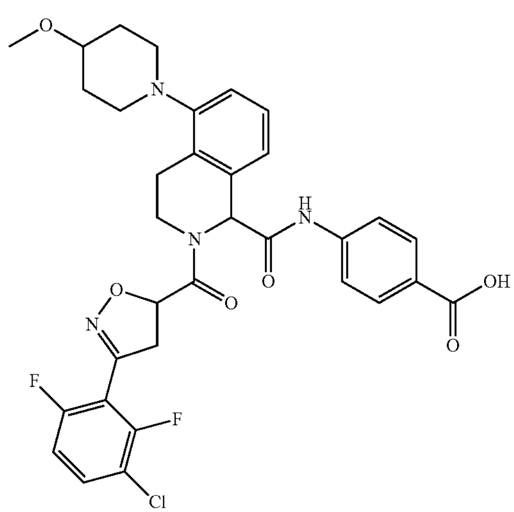 [SMILES: COC1CCN(c2cccc3c2CCN(C(=O)C2CC(c4c(F)ccc(Cl)c4F)=NO2)C3C(=O)Nc2ccc(C(=O)O)cc2)CC1] | 4-(2-(3-(3-chloro-2,6-difluorophenyl)-4,5-dihydroisoxazole-5-carbonyl)-5-(4-methoxypiperidin-1-yl)-1,2,3,4-tetrahydroisoquinoline-1-carboxamido)benzoic acid, TFA salt | $^1$H NMR (400 MHz, methanol-$d_4$) δ 10.45 (s, 1H), 7.97-7.92 (m, 2H), 7.68-7.57 (m, 3H), 7.17-7.26 (m, 2H), 7.20 (d, J = 8.1 Hz, 1H), 7.13. (td, J = 9.5, 1.8 Hz, 1H), 5.83 (dd, J = 11.4, 7.1 Hz, 1H), 5.76 (s, 1H), 4.29 (dt, J = 12.6, 4.7 Hz, 1H), 4.03 (dd, J = 17.4, 7.1 Hz, 1H), 3.80-3.64 (m, 2H), 3.48 (br. s, 1H), 3,42-3.38 (m, 3H), 3.26-3.14 (m, 3H), 2.99 (br. s., 1H), 2.89 (br. s., 1H), 2.76 (br. s., 1H), 2.12 (br. s., 2H), 1.84 (br. s., 2H) ppm. MS (ESI) m/z: 653 (M + H)$^+$. Analytical HPLC: RT = 8.86 min (Method A). (diastereomeric mixture) |

TABLE 12-continued

| Example | Structure | Name | Analytical Data |
|---|---|---|---|
| 257 | 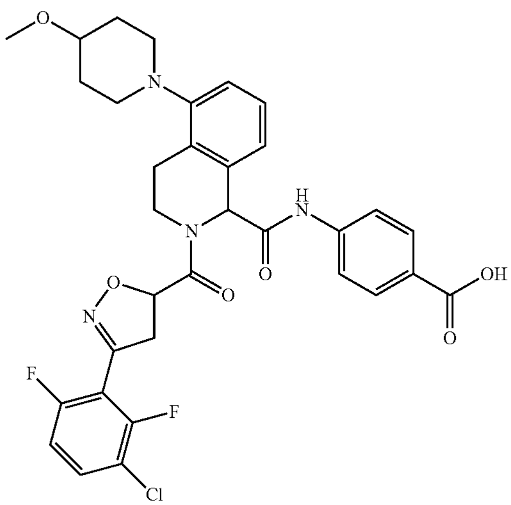 [SMILES: COC1CCN(c2cccc3c2CCN(C(=O)C2CC(c4c(F)ccc(Cl)c4F)=NO2)C3C(=O)Nc2ccc(C(=O)O)cc2)CC1] | 4-(2-(3-(3-chloro-2,6-difluorophenyl)-4,5-dihydroisoxazole-5-carbonyl)-5-(4-methoxypiperidin-1-yl)-1,2,3,4-tetrahydroisoquinoline-1-carboxamido)benzoic acid, TFA salt | $^1$H NMR (400 MHz, methanol-$d_4$) δ 10.38 (s, 1H), 7.97-7.90 (m, 2H), 7.67-7.56 (m, 3H), 7.35-7.24 (m, 2H), 7.20-7.08 (m, 2H), 5.79-5.71 (m, 2H), 4.35 (dt, J = 11.9, 4.8 Hz, 1H), 3.90 (dd, J = 17.4, 8.1 Hz, 1H), 3.75-3.59 (m, 2H), 3.51-3.43 (m, 1H), 3.41-3.38 (m, 3H), 3.28-3.11 (m, 3H), 2.98 (t, J = 9.7 Hz, 1H), 2.84 (br. s., 2H), 2.11 (br. s., 2H), 1.81 (br. s., 2H) ppm. MS (ESI) m/z: 653 (M + H)$^+$. Analytical HPLC: RT = 8.78 min (Method A). (diastereomeric mixture) |
| 258 | 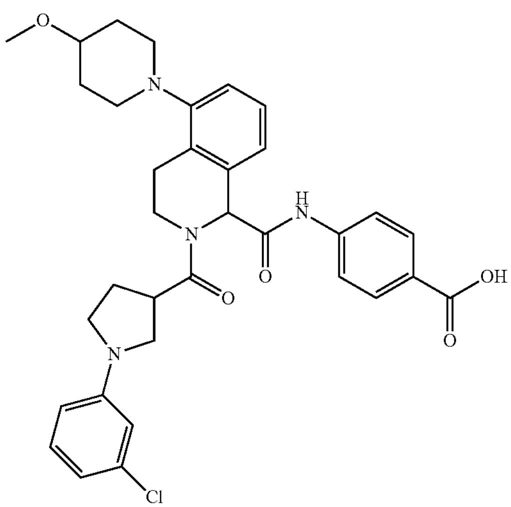 [SMILES: COC1CCN(c2cccc3c2CCN(C(=O)C2CCN(c4cccc(Cl)c4)C2)C3C(=O)Nc2ccc(C(=O)O)cc2)CC1] | 4-(2-(1-(3-chlorophenyl)pyrrolidine-3-carbonyl)-5-(4-methoxypiperidin-1-yl)-1,2,3,4-tetrahydroisoquinoline-1-carboxamido)benzoic acid, TFA salt | $^1$H NMR (400 MHz, methanol-$d_4$) δ 10.37 (s, 1H), 7.96-7.91 (m, 1H), 7.63 (dd, J = 8.8, 1.5 Hz, 2H), 7.34-7.29 (m, 1H), 7.29-7.23 (m, 1H), 7.13 (d, J = 7.6 Hz, 1H), 7.09 (t, J = 8.1 Hz, 1H), 6.60-6.56 (m, 1H), 6.54 (t, J = 2.1 Hz, 1H), 6.49 (dd, J = 8.1, 2.0 Hz, 1H), 5.72 (s, 1H), 4.33-4.25 (m, 1H), 3.75 (quin, J = 7.3 Hz, 1H), 3.63-3.52 (m, 2H), 3.51-3.40 (m, 3H), 3.40 (s, 3H), 3.25-3.15 (m, 2H), 2.95 (br. s., 1H), 2.79 (br. s., 3H), 2.45-2.24 (m, 2H), 2.11 (br. s., 2H), 1.80 (br. s., 2H) ppm. MS (ESI) m/z: 617 (M + H)$^+$. Analytical HPLC: RT = 9.78 min (Method A). (diastereomeric mixture) |
| 259 | 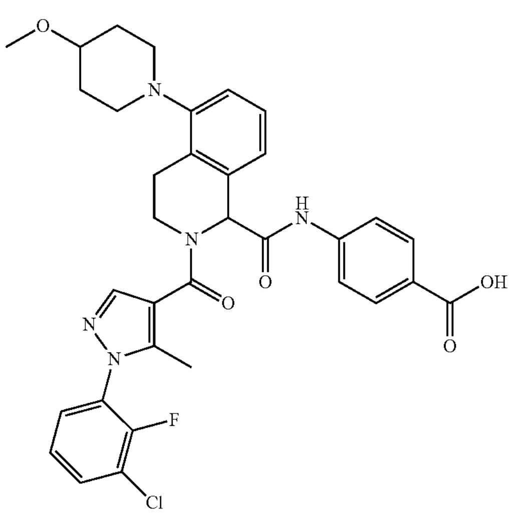 [SMILES: COC1CCN(c2cccc3c2CCN(C(=O)c2cnn(-c4cccc(Cl)c4F)c2C)C3C(=O)Nc2ccc(C(=O)O)cc2)CC1] | 4-(2-(1-(3-chloro-2-fluorophenyl)-5-methyl-1H-pyrazole-4-carbonyl)-5-(4-methoxypiperidin-1-yl)-1,2,3,4-tetrahydroisoquinoline-1-carboxamido)benzoic acid, TFA salt | $^1$H NMR (500 MHz, methanol-$d_4$) δ 10.55 (br. s., 1H), 8.03-7.95 (m, 3H), 7.74 (t, J = 6.9 Hz, 1H), 7.69 (d, J = 8.3 Hz, 2H), 7.54 (br. s., 1H), 7.43 (br. s., 2H), 7.35 (t, J = 7.8 Hz, 1H), 7.24 (d, J = 7.2 Hz, 1H), 5.84 (br. s., 1H), 4.29 (d, J = 11.6 Hz, 1H), 3.80-3.71 (m, 1H), 3.52-3.45 (m, 1H), 3.42 (s, 3H), 3.31-3.24 (m, 2H), 3.22-3.15 (m, 1H), 3.08-2.99 (m, 1H), 2.91 (br. s., 1H), 2.35 (br. s., 3H), 2.20-2.08 (m, 2H), 1.86 (br. s., 2H) ppm. MS (ESI) m/z: 646 (M + H)$^+$. Analytical HPLC: RT = 8.38 min (Method A). (racemate) |

TABLE 12-continued

| Example | Structure | Name | Analytical Data |
|---|---|---|---|
| 260 | 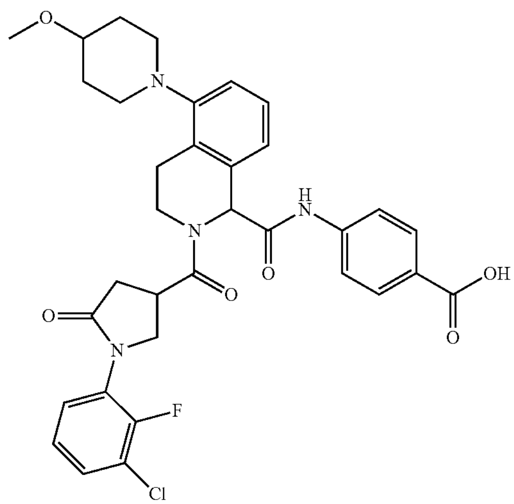 [SMILES: COC1CCN(c2cccc3c2CCN(C(=O)C2CC(=O)N(c4cccc(Cl)c4F)C2)C3C(=O)Nc2ccc(C(=O)O)cc2)CC1] | 4-(2-(1-(3-chloro-2-fluorophenyl)-5-oxopyrrolidine-3-carbonyl)-5-(4-methoxypiperidin-1-yl)-1,2,3,4-tetrahydroisoquinoline-1-carboxamido)benzoic acid, TFA salt | $^1$H NMR (500 MHz, methanol-$d_4$) δ 7.97 (s, 2H), 7.67-7.66 (m, 1H), 7.66-7.64 (m, 1H), 7.47 (ddd, J = 8.1, 6.7, 1.7 Hz, 1H), 7.41 (ddd, J = 8.1, 6.6, 1.5 Hz, 1H), 7.36-7.33 (m, 1H), 7.31-7.27 (m, 1H), 7.22 (td, J = 8.1, 1.4 Hz, 1H), 7.15 (d, J = 8.0 Hz, 1H), 5.77 (s, 1H), 4.24-4.18 (m, 2H), 4.13-4.02 (m, 2H), 3.61-3.54 (m, 1H), 3.49-3.43 (m, 1H), 3.42 (s, 3H), 3.28-3.14 (m, 4H), 2.99-2.93 (m, 1H), 2.93-2.89 (m, 2H), 2.79 (br s, 1H), 2.10 (d, J = 16.2 Hz, 2H), 1.80 (d, J = 11.8 Hz, 2H) ppm. MS (ESI) m/z: 649 (M + H)$^+$. Analytical HPLC: RT = 7.62 min (Method A). (diastereomeric mixture) |
| 261 | 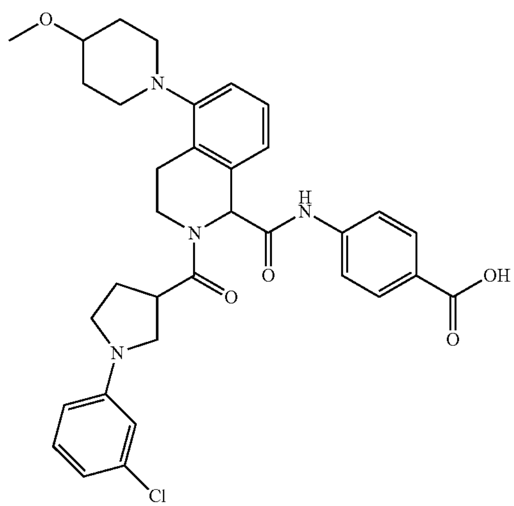 [SMILES: COC1CCN(c2cccc3c2CCN(C(=O)C2CCN(c4cccc(Cl)c4)C2)C3C(=O)Nc2ccc(C(=O)O)cc2)CC1] | 4-(2-(1-(3-chlorophenyl)pyrrolidine-3-carbonyl)-5-(4-methoxypiperidin-1-yl)-1,2,3,4-tetrahydroisoquinoline-1-carboxamido)benzoic acid, TFA salt | $^1$H NMR (500 MHz, methanol-$d_4$) δ 10.40 (s, 1H), 7.97-7.93 (m, 2H), 7.66-7.62 (m, 2H), 7.56 (br. s., 2H), 7.46-7.41 (m, 1H), 7.37-7.28 (m, 4H), 7.18 (d, J = 7.2 Hz, 1H), 7.13 (t, J = 8.1 Hz, 1H), 6.63-6.60 (m, 1H), 6.60-6.58 (m, 1H), 6.53 (dd, J = 8.4, 1.8 Hz, 1H), 5.76 (s, 1H), 4.32 (dt, J = 12.1, 4.7 Hz, 1H), 3.78 (quin, J = 7.5 Hz, 1H), 3.68-3.59 (m, 2H), 3.55 (dd, J = 9.2, 7.0 Hz, 1H), 3.50-3.43 (m, 1H), 3 42 (s, 3H), 3.41-3.37 (m, 1H), 3.22-3.17 (m, 1H), 3.00 (br. s., 1H), 2.85 (br. s., 1H), 2.40-2.24 (m, 2H), 2.13 (br. s., 2H), 1.83 (br. s., 2H) ppm. MS (ESI) m/z: 617.1 (M + H)$^+$. Analytical HPLC: RT = 9.74 min (Method A). (diastereomeric mixture) |
| 262 | 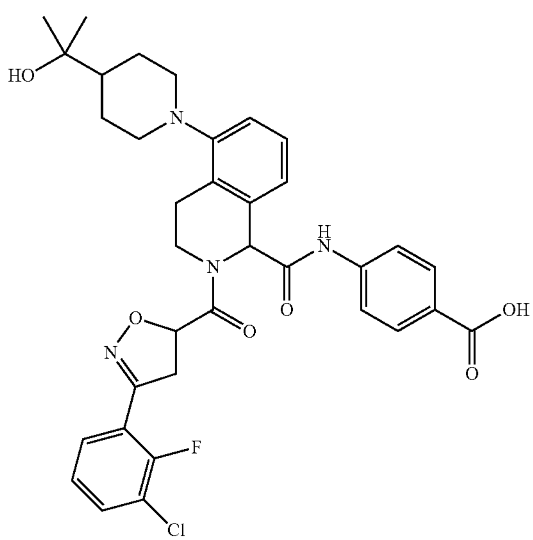 [SMILES: CC(C)(O)C1CCN(c2cccc3c2CCN(C(=O)C2CC(c4cccc(Cl)c4F)=NO2)C3C(=O)Nc2ccc(C(=O)O)cc2)CC1] | 4-(2-(3-(3-chloro-2-fluorophenyl)-4,5-dihydroisoxazole-5-carbonyl)-5-(4-(2-hydroxypropan-2-yl)piperidin-1-yl)-1,2,3,4-tetrahydroisoquinoline-1-carboxamido)benzoic acid, TFA salt | $^1$H NMR (400 MHz, methanol-$d_4$) δ 10.41 (s, 1H), 7.97-7.92 (m, 2H), 7.75 (ddd, J = 8.0, 6.4, 1.5 Hz, 1H), 7.67-7.62 (m, 2H), 7.59 (td, J = 7.5, 1.6 Hz, 1H), 7.40-7.29 (m, 2H), 7.24 (td, J = 8.0, 1.0 Hz, 2H), 5.80-5.73 (m, 2H), 4.44-4.36 (m, 1H), 3.98-3.90 (m, 1H), 3.81-3.62 (m, 2H), 3.38 (br. s., 3H), 3.18 (d, J = 4.0 Hz, 1H), 3.01 (br. s., 1H), 2.86 (br. s., 1H), 2.05-1.91 (m, 2H), 1.80-1.62 (m, 2H), 1.56 (d, J = 11.9 Hz, 1H), 1.24 (s, 6H) ppm. MS (ESI) m/z: 663.0 (M + H)$^+$. Analytical HPLC: RT = 7.61 min (Method A). (diastereomer mixture) |

TABLE 12-continued

| Example | Structure | Name | Analytical Data |
|---|---|---|---|
| 263 | 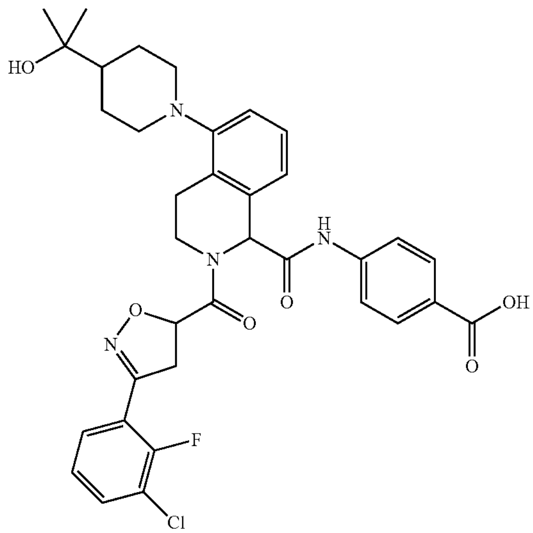 [SMILES: CC(C)(O)C1CCN(c2cccc3c2CCN(C(=O)C2CC(c4cccc(Cl)c4F)=NO2)C3C(=O)Nc2ccc(C(=O)O)cc2)CC1] | 4-(2-(3-(3-chloro-2-fluorophenyl)-4,5-dihydroisoxazole-5-carbonyl)-5-(4-(2-hydroxypropan-2-yl)piperidin-1-yl)-1,2,3,4-tetrahydroisoquinoline-1-carboxamido)benzoic acid, TFA salt | $^1$H NMR (400 MHz, methanol-$d_4$) δ 10.48 (s, 1H), 7.98-7.94 (m, 2H), 7.73 (ddd, J = 8.0 6.4, 1.5 Hz, 1H), 7.68-7.63 (m, 2H), 7.0 (td, J = 7.5, 1.6 Hz, 1H), 7.41-7.31 (m, 2H), 7.29-7.22 (m, 2H), 5.84 (dd, J = 11.4, 6.8 Hz, 1H), 5.78 (s, 1H), 4.32 (dt, J = 12.4, 4.6 Hz, 1H), 4.07 (ddd, J = 17.5, 6.9, 1.9 Hz, 1H), 3.81-3.70 (m, 2H), 3.38 (br. s., 3H), 3.29-3.18 (m, 2H), 3.03 (br. s., 1H), 2.89 (br. s., 1H), 2.06-1.93 (m, 2H), 1.80-1.63 (m, 2H), 1.57 (d, J = 12.1 Hz, 1H), 1.25 (s, 6H) ppm. MS (ESI) m/z: 663.0 (M + H)$^+$. Analytical HPLC: RT = 7.60 min (Method A). (diastereomer mixture) |
| 264 | 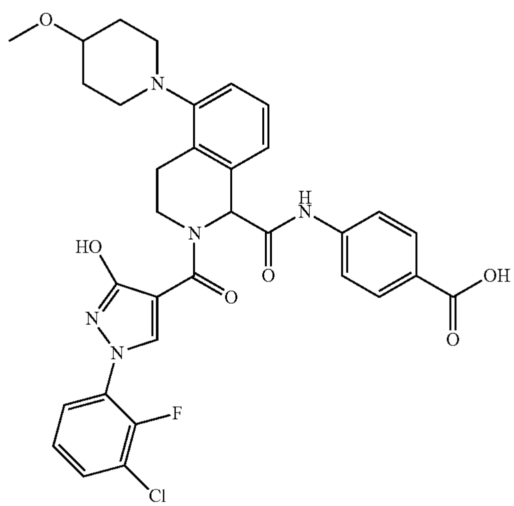 [SMILES: COC1CCN(c2cccc3c2CCN(C(=O)c2cn(-c4cccc(Cl)c4F)nc2O)C3C(=O)Nc2ccc(C(=O)O)cc2)CC1] | 4-(2-(1-(3-chloro-2-fluorophenyl)-3-hydroxy-1H-pyrazole-4-carbonyl)-5-(4-methoxypiperidin-1-yl)-1,2,3,4-tetrahydroisoquinoline-1-carboxamido)benzoic acid, TFA salt | $^1$H NMR (400 MHz, methanol-$d_4$) δ 10.52-10.45 (m, 1H), 8.38 (br. s., 1H), 7.97 (d, J = 8.3 Hz, 2H), 7.75 (t, J = 7.5 Hz, 1H), 7.68 (d, J = 8.1 Hz, 2H), 7.48 (t, J = 6.8 Hz, 1H), 7.41 (d, J = 7.3 Hz, 1H), 7.37-7.26 (m, 2H), 7.23 (d, J = 7.8 Hz, 1H), 5.84 (br. s., 1H), 4.32 (d, J = 11.1 Hz, 1H), 3.79 (br. s., 1H), 3.52-3.44 (m, 1H), 3.41 (s, 3H), 3.30-3.21 (m, 2H), 3.04 (d, J = 8.1 Hz, 1H), 2.88 (br. s., 1H), 2.13 (br. s., 2H), 1.84 (br. s., 2H) ppm. MS (ESI) m/z: 647.9 (M + H)$^+$. Analytical HPLC: RT = 9.19 min (Method A). (racemate) |
| 265 | 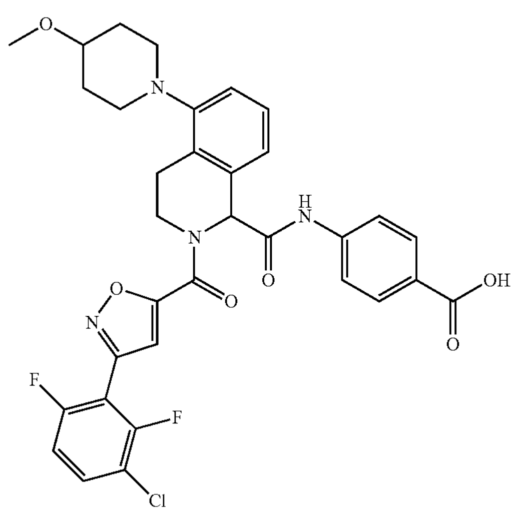 [SMILES: COC1CCN(c2cccc3c2CCN(C(=O)c2cc(-c4c(F)ccc(Cl)c4F)no2)C3C(=O)Nc2ccc(C(=O)O)cc2)CC1] | 4-(2-(3-(3-chloro-2,6-difluorophenyl)isoxazole-5-carbonyl)-5-(4-methoxypiperidin-1-yl)-1,2,3,4-tetrahydroisoquinoline-1-carboxamido)benzoic acid, TFA salt | $^1$H NMR (400 MHz, methanol-$d_4$) δ 10.60-10.55 (m, 1H), 8.02-7.95 (m, 2H), 7.77-7.66 (m, 3H), 7.45-7.16 (m, 5H), 5.87 (s, 1H), 4.46-4.34 (m, 1H), 3.88-3.76 (m, 1H), 3.41 (s, 3H), 3.52-3.18 (m, 6H), 3.06-2.94 (m, 1H), 2.94-2.79 (m, 1H), 2.21-2.04 (m, 2H), 1.93-1.73 (m, 2H) ppm. MS (ESI) m/z: 651.1 (M + H)$^+$. Analytical HPLC: RT = 0.97 min (Method E). (racemate) |

TABLE 12-continued

| Example | Structure | Name | Analytical Data |
|---|---|---|---|
| 266 | 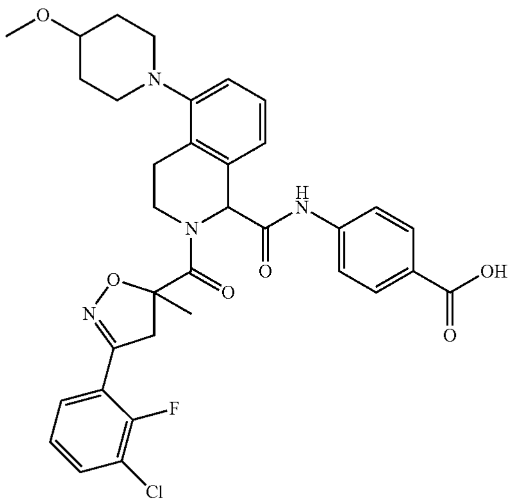 [SMILES: COC1CCN(c2cccc3c2CCN(C(=O)C2(C)CC(c4cccc(Cl)c4F)=NO2)C3C(=O)Nc2ccc(C(=O)O)cc2)CC1] | 4-(2-(3-(3-chloro-2-fluorophenyl)-5-methyl-4,5-dihydroisoxazole-5-carbonyl)-5-(4-methoxypiperidin-1-yl)-1,2,3,4-tetrahydroisoquinoline-1-carboxamido)benzoic acid, TFA salt | $^1$H NMR (400 MHz, methanol-$d_4$) δ 10.44-10.40 (m, 1H), 7.93 (d, J = 8.6 Hz, 2H), 7.78-7.69 (m, 1H), 7.66-7.55 (m, 3H), 7.41-7.17 (m, 4H), 5.74 (s, 1H), 4.59-4.48 (m, 1H), 4.33-4.23 (m, 1H), 3.77-3.67 (m, 1H), 3.52-3.42 (m, 2H), 3.41 (s, 3H), 3.38-3.21 (m, 4H), 3.17-3.07 (m, 1H), 3.06-2.98 (m, 1H), 2.97-2.86 (m, 1H), 2.20-2.07 (m, 2H), 1.93-1.78 (m, 2H), 1.75 (s, 3H) ppm. MS (ESI) m/z: 649.0 (M + H)$^+$. Analytical HPLC: RT = 9.45 min (Method A). (diastereomer mixture) |
| 267 | 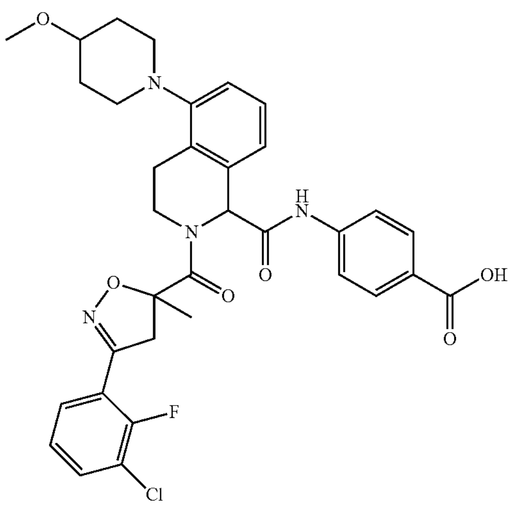 [SMILES: COC1CCN(c2cccc3c2CCN(C(=O)C2(C)CC(c4cccc(Cl)c4F)=NO2)C3C(=O)Nc2ccc(C(=O)O)cc2)CC1] | 4-(2-(3-(3-chloro-2-fluorophenyl)-5-methyl-4,5-dihydroisoxazole-5-carbonyl)-5-(4-methoxypiperidin-1-yl)-1,2,3,4-tetrahydroisoquinoline-1-carboxamido)benzoic acid, TFA salt | $^1$H NMR (400 MHz, methanol-$d_4$) δ 10.50-10.44 (m, 1H), 7.97 (d, J = 8.8 Hz, 2H), 7.74-7.63 (m, 3H), 7.63-7.55 (m, 1H), 7.24 (s, 4H), 5.71 (s, 1H), 4.45-4.32 (m, 2H), 4.06-3.96 (m, 1H), 3.42 (s, 3H), 3.53-3.40 (m, 2H), 3.19-3.08 (m, 2H), 3.08-2.91 (m, 3H), 2.21-2.09 (m, 2H), 1.95-1.86 (m, 2H), 1.95-1.86 (m, 2H), 1.84 (s, 3H) ppm. MS (ESI) m/z: 649.0 (M + H)$^+$. Analytical HPLC: RT = 9.52 min (Method A). (diastereomer mixture) |
| 268 | 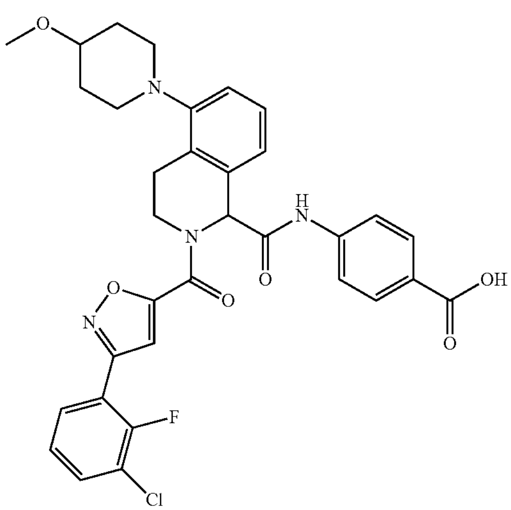 | 4-(2-(3-(3-chloro-2-fluorophenyl)isoxazole-5-carbonyl)-5-(4-methoxypiperidin-1-yl)-1,2,3,4-tetrahydroisoquinoline-1-carboxamido)benzoic acid, TFA salt | $^1$H NMR (500 MHz, methanol-$d_4$) δ 10.49 (s, 1H), 9.24 (s, 1H), 7.95 (d, J = 8.5 Hz, 2H), 7.66 (d, J = 8.5 Hz, 2H), 7.64-7.58 (m, 2H), 7.29 (t, J = 8.0 Hz, 1H), 7.24-7.20 (m, 2H), 7.07-7.02 (m, 1H), 5.78 (s, 1H), 4.10-4.04 (m, 1H), 3.50 (ddd, J = 12.5, 8.7, 4.4 Hz, 1H), 3.41-3.38 (m, 3H), 3.12-2.99 (m, 3H), 2.82-2.73 (m, 2H), 2.68 (t, J = 10.2 Hz, 1H), 2.04 (d, J = 6.1 Hz, 2H), 1.94 (s, 1H), 1.70 (br. s., 2H) ppm. MS (ESI) m/z: 633.0 (M + H)$^+$. Analytical HPLC RT = 8.97 min (Method A). (racemate) |

TABLE 12-continued

| Example | Structure | Name | Analytical Data |
|---|---|---|---|
| 269 | 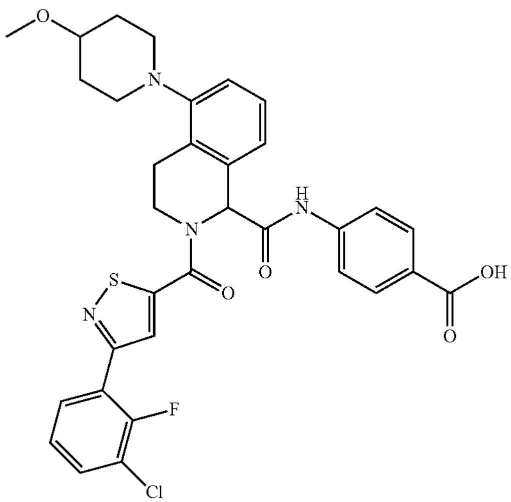 [SMILES: COC1CCN(c2cccc3c2CCN(C(=O)c2cc(-c4cccc(Cl)c4F)ns2)C3C(=O)Nc2ccc(C(=O)O)cc2)CC1] | 4-(2-(3-(3-chloro-2-fluorophenyl)isothiazole-5-carbonyl)-5-(4-methoxypiperidin-1-yl)-1,2,3,4-tetrahydroisoquinoline-1-carboxamido)benzoic acid, TFA salt | $^1$H NMR (400 MHz, methanol-d$_4$) δ 10.60-10.56 (m, 1H), 8.03 (d, J = 2.8 Hz, 1H), 8.05-7.99 (m, 1H), 7.96 (d, J = 8 8 Hz, 2H), 7.68 (d, J = 8.6 Hz, 2H), 7.58 (t, J = 6.8 Hz, 1H), 7.48 (d, J = 7.3 Hz, 1H), 7.40-7.32 (m, 1H), 7.32-7.24 (m, 2H), 5.89 (s, 1H), 4.37-4.29 (m, 1H), 3.78-3.68 (m, 1H), 3.43 (br. s., 1H), 3.40 (s, 3H), 3.25-3.16 (m, 1H), 3.07 (t, J = 8.6 Hz, 1H), 2.96 (br. s., 1H), 2.13 (d, J = 3.0 Hz, 2H), 1.86 (br. s., 2H) ppm. MS (ESI) m/z: 648.9 (M + H)$^+$. Analytical HPLC: RT = 10.53 min (Method A). (racemate) |
| 270 | 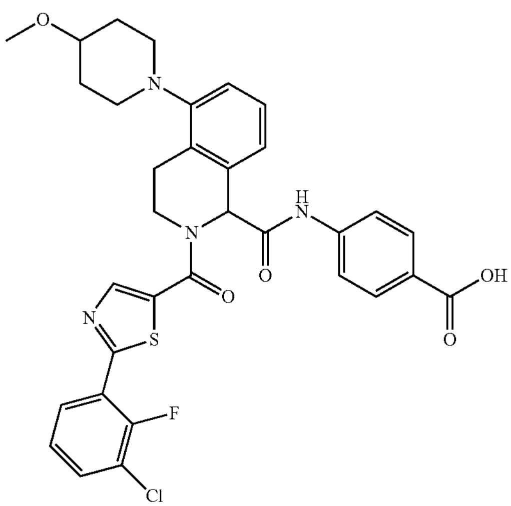 [SMILES: COC1CCN(c2cccc3c2CCN(C(=O)c2cnc(-c4cccc(Cl)c4F)s2)C3C(=O)Nc2ccc(C(=O)O)cc2)CC1] | 4-(2-(2-(3-chloro-2-fluorophenyl)thiazole-5-carbonyl)-5-(4-methoxypiperidin-1-yl)-1,2,3,4-tetrahydroisoquinoline-1-carboxamido)benzoic acid, TFA salt | $^1$H NMR (400 MHz, methanol-d$_4$) δ 10.56-10.50 (m, 1H), 8.38 (br. s., 1H), 8.24 (t, J = 6.6 Hz, 1H), 7.96 (d, J = 8.6 Hz, 2H), 7.71-7.60 (m, 3H), 7.47 (d, J = 7.6 Hz, 1H), 7.39-7.31 (m, 2H), 7.27 (br. s., 1H), 5.84 (s, 1H), 4.47 (d, J = 11.4 Hz, 1H), 3.83 (br. s., 1H), 3.49 (d, J = 3.5 Hz, 1H), 3.41 (s, 3H), 3.28-3.20 (m, 1H), 3.09 (d, J = 8.8 Hz, 1H), 2.95 (br. s., 1H), 2.22-2.06 (m, 2H), 1.88 (br. s., 2H) ppm. MS (ESI) m/z: 648.9 (M + H)$^+$. Analytical HPLC: RT = 10.11 min (Method A). (racemate) |
| 271 | 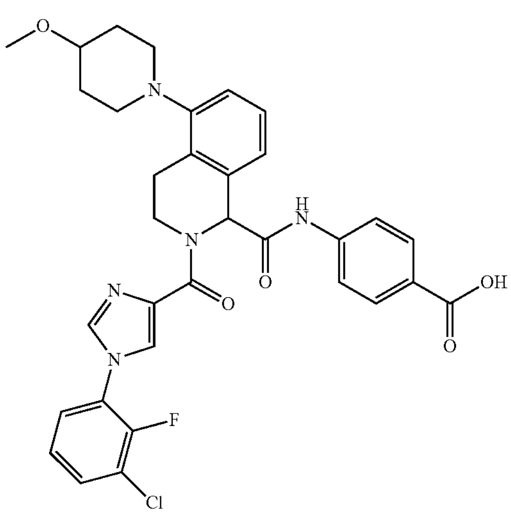 | 4-(2-(1-(3-chloro-2-fluorophenyl)-1H-imidazole-4-carbonyl)-5-(4-methoxypiperidin-1-yl)-1,2,3,4-tetrahydroisoquinoline-1-carboxamido)benzoic acid, TFA salt | $^1$H NMR (400 MHz, methanol-d$_4$) δ 8.33 (s, 1H), 8.14 (br. s., 1H), 7.97 (d, J = 8.1 Hz, 2H), 7.78-7.55 (m, 4H), 7.49 (d, J = 5.6 Hz, 1H), 7.3) (t, J = 7.6 Hz, 3H), 6.76-6.69 (m, 1H), 5.89 (br. s., 1H), 4.62 (d, J = 12.1 Hz, 1H), 4.12 (br. s., 1H), 3.60-3.47 (m, 2H), 3.42 (s, 3H), 3.30-3.02 (m, 3H), 2.19 (br. s., 2H), 2.08-1.83 (m, 2H) ppm. MS (ESI) m/z: 631.9 (M + H)$^+$. Analytical HPLC: RT = 8.18 min (Method A). (racemate) |

TABLE 12-continued

| Example | Structure | Name | Analytical Data |
|---|---|---|---|
| 272 | 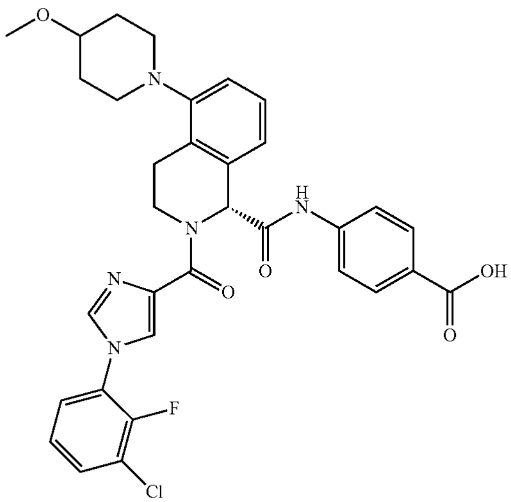 [SMILES: COC1CCN(c2cccc3c2CCN(C(=O)c2cn(-c4cccc(Cl)c4F)cn2)C3C(=O)Nc2ccc(C(=O)O)cc2)CC1] | (R)-4-(2-(1-(3-chloro-2-fluorophenyl)-1H-imidazole-4-carbonyl)-5-(4-methoxypiperidin-1-yl)-1,2,3,4-tetrahydroisoquinoline-1-carboxamido)benzoic acid, TFA salt | $^1$H NMR (400 MHz, methanol-d$_4$) δ 8.31 (t, J = 1.4 Hz, 1H), 8.13 (br. s., 1H), 7.97 (d, J = 8.3 Hz, 2H), 7.77-7.58 (m, 4H), 7.52-7.28 (m, 4H), 5.89 (s, 1H), 4.62 (d, J = 12.1 Hz, 1H), 4.12 (br. s., 1H), 3.58-3.46 (m, 1H), 3.42 (s, 3H), 3.30-2.99 (m, 3H), 2.18 (br. s., 2H), 2.06-1.81 (m, 2H) ppm. MS (ESI) m/z: 631.9 (M + H)$^+$. Analytical HPLC: RT = 7.94 min (Method A). (homochiral$^a$) |
| 273 | 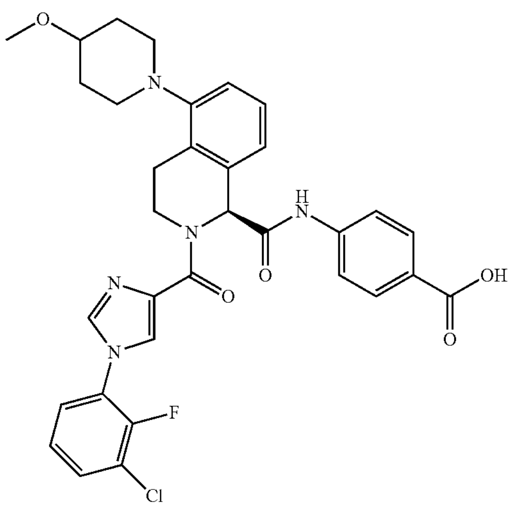 [SMILES: COC1CCN(c2cccc3c2CCN(C(=O)c2cn(-c4cccc(Cl)c4F)cn2)[C@@H]3C(=O)Nc2ccc(C(=O)O)cc2)CC1] | (S)-4-(2-(1-(3-chloro-2-fluorophenyl)-1H-imidazole-4-carbonyl)-5-(4-methoxypiperidin-1-yl)-1,2,3,4-tetrahydroisoquinoline-1-carboxamide)benzoic acid, TFA salt | $^1$H NMR (400 MHz, methanol-d$_4$) δ 8.32 (br. s., 1H), 8.14 (br. s., 1H), 7.97 (d, J = 6.8 Hz, 2H), 7.76-7.57 (m, 4H), 7.53-7.28 (m, 4H), 5.90 (br. s., 1H), 4.66-4.56 (m, 1H), 4.18-4.06 (m, 1H), 3.51 (br. s., 2H), 3.42 (s, 3H), 3.28-2.99 (m, 3H), 2.27-2.10 (m, 2H), 2.06-1.82 (m, 2H) ppm. MS (ESI) m/z: 631.9 (M + H)$^+$. Analytical HPLC: RT = 7.95 min (Method A). (homochiral$^a$) |
| 274 | 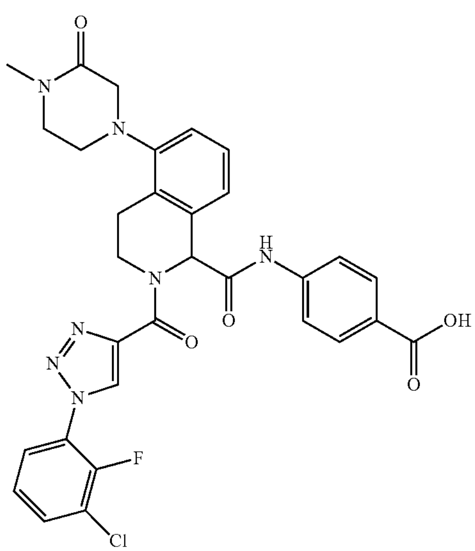 [SMILES: CN1CCN(c2cccc3c2CCN(C(=O)c2cn(-c4cccc(Cl)c4F)nn2)C3C(=O)Nc2ccc(C(=O)O)cc2)CC1=O] | 4-(2-(1-(3-chloro-2-fluorophenyl)-1H-1,2,3-triazole-4-carbonyl)-5-(4-methyl-3-oxopiperazin-1-yl)-1,2,3,4-tetrahydroisoquinoline-1-carboxamido)benzoic acid, TFA salt | $^1$H NMR (400 MHz, methanol-d$_4$) δ 7.98 (d, J = 8.8 Hz, 2H), 7.87 (t, J = 7.3 Hz, 1H), 7.77-7.63 (m, 4H), 7.48-7.28 (m, 3H), 7.10 (d, J = 7.8 Hz, 1H), 5.91 (s, 1H), 4.73-4.64 (m, 1H), 4.14 (ddd, J = 12.5, 8.5, 4.3 Hz, 1H), 3.74-3.45 (m, 5H), 3.29-3.18 (m, 4H), 3.04 (s, 4H) ppm. MS (ESI) m/z: 631.8 (M + H)$^+$. Analytical HPLC: RT = 7.92 min (Method A). (racemate) |

TABLE 12-continued

| Example | Structure | Name | Analytical Data |
|---|---|---|---|
| 275 | | 4-(2-(1-(3-chloro-2-fluoroplienyl)-1H-1,2,3-triazole-4-carbonyl)-5-methoxy-1,2,3,4-tetrahydroisoquinoline-1-carboxamido)benzoic acid, TFA salt | $^1$H NMR (400 MHz, methanol-d$_4$) δ 8.86 (d, J = 2.0 Hz, 1H), 7.97 (d, J = 8.6 Hz, 2H), 7.86 (t, J = 6.8 Hz, 1H), 7.75-7.67 (m, 4H), 7.4-7.37 (m, 1H), 7.30-7.24 (m, 1H), 7.15 (d, J = 7.8 Hz, 1H), 6.94 (d, J = 8.1 Hz, 1H), 5.96 (s, 1H), 4.54-4.41 (m, 2H), 3.87 (s, 4H), 3.12-3.06 (m, 2H) ppm. MS (ESI) m/z: 549.8 (M + H)$^+$. Analytical HPLC: RT = 9.96 min (Method A). (racemate) |
| 276 diastereomer A | | 4-(2-(3-(3-chloro-2-fluoropheny)-4,5-dihydroisoxazole-5-carbonyl)-5-(4-(dimethylcarbamoyl)piperidin-1-yl)-1,2,3,4-tetrahydroisoquinoline-1-carboxamido)benzoic acid, TFA salt | $^1$H NMR (500 MHz, methanol-d$_4$) δ 10.41 (s, 1H), 7.97-7.93 (m, 2H), 7.75 (ddd, J = 8.0, 6.3, 1.7 Hz, 1H), 7.68-7.63 (m, 2H), 7.59 (td, J = 7.6, 1.7 Hz, 1H), 7.33-7.22 (m, 3H), 7.14 (d, J = 7.2 Hz, 1H), 5.82-5.74 (m, 2H), 4.38 (dt, J = 12.0, 4.7 Hz, 1H), 3.95-3.88 (m, 1H), 3.77 (ddd, J = 17.3. 11.4, 2.1 Hz, 1H), 3.68-3.60 (m, 1H), 3.30-3.26 (m, 1H), 3.24-3.21 (m, 1H), 3.18 (s, 3H), 2.99 (s, 3H), 2.93-2.85 (m, 1H), 2.82-2.73 (m, 1H), 2.08-1.84 (m, 5H) ppm. MS (ESI) m/z: 676.0 (M + H). Analytical HPLC: RT = 7.66 min (Method A). (homochiral) |
| 277 diastereomer B | | 4-(2-(3-(3-chloro-2-fluorophenyl)-4,5-dihydroisoxazole-5-carbonyl)-5-(4-(dimethylcarbamoyl)piperidin-1-yl)-1,2,3,4-tetrahydroisoquinoline-1-carboxamido)benzoic acid, TFA salt | $^1$H NMR (500 MHz, methanol-d$_4$) δ 10.48 (s, 1H), 7.98-7.94 (m, 2H), 7.74 (ddd, J = 7.9, 6.4, 1.7 Hz, 1H), 7.66 (dd, J = 9.1, 1.9 Hz, 2H), 7.60 (t, J = 6.7 Hz, 1H), 7.35-7.23 (m, 3H), 7.16 (d, J = 7.4 Hz, 1H), 5.84 (dd, J = 11.4, 7.0 Hz, 1H), 5.75 (s, 1H), 4.31 (dt, J = 12.4, 4.9 Hz, 1H), 4.05 (ddd, J = 17.4, 6.9, 1.8 Hz, 1H), 3.81-3.70 (m, 2H), 3.26-3.21 (m, 2H), 3.18 (s, 3H), 2.99 (s, 3H), 2.94-2.78 (m, 2H), 2.09-1.84 (m, 4H) ppm. MS (ESI) m/z: 676.0 (M + H)$^+$. Analytical HPLC: RT = 7.66 min (Method A). (homochiral) |

TABLE 12-continued

| Example | Structure | Name | Analytical Data |
|---|---|---|---|
| 278 | diastereomer C | 4-(2-(3-(3-chloro-2-fluorophenyl)-4,5-dihydroisoxazole-5-carbonyl)-5-(4-(dimethylcarbamoyl)piperidin-1-yl)-1,2,3,4-tetrahydroisoquinoline-1-carboxamido)benzoic acid, TFA salt | $^1$H NMR (500 MHz, methanol-d$_4$) δ 7.97-7.92 (m, 2H), 7.77-7.73 (m, 1H), 7.67-7.63 (m, 2H), 7.61-7.57 (m, 1H), 7.33-7.22 (m, 3H), 7.15 (d, J = 7.4 Hz, 1H), 5.81-5.75 (m, 2H), 4.42-4.35 (m, 1H), 3.95-3.88 (m, 1H), 3.81-3.73 (m, 1H), 3.68-3.61 (m, 1H), 3.30-3.20 (m, 4H), 3.18 (s, 3H), 2.99 (s, 3H), 2.90 (t, J = 11.4 Hz, 1H), 2.79 (t, J = 11.3 Hz, 1H), 2.08-1.85 (m, 5H) ppm. MS (ESI) m/z: 676.0 (M + H)$^+$. Analytical HPLC: RT = 7.59 min (Method A). (homochiral) |
| 279 | diastereomer D | 4-(2-(3-(3-chloro-2-fluoropheny)-4,5-dihydroisoxazole-5-carbonyl)-5-(4-(dimethylcarbamoyl)piperidin-1-yl)-1,2,3,4-tetrahydroisoquinoline-1-carboxamido)benzoic acid, TFA salt | $^1$H NMR (500 MHz, methanol-d$_4$) δ 7.98-7.94 (m, 2H), 7.74 (ddd, J = 7.9, 6.4, 1.7 Hz, 1H), 7.68-7.64 (m, 2H), 7.62-7.57 (m, 1H), 7.35-7.22 (m, 4H), 7.17 (d, J = 8.0 Hz, 1H), 5.84 (dd, J = 11.6, 6.9 Hz, 1H), 5.75 (s, 1H), 4.34-4.28 (m, 1H), 4.05 (ddd, J = 17.3, 6.9, 1.9 Hz, 1H), 3.81-3.70 (m, 2H), 3.26-3.21 (m, 2H), 3.18 (s, 3H), 2.99 (s, 3H), 2.95-2.78 (m, 2H), 2.09-1.85 (m, 4H) ppm. MS (ESI) m/z: 676.0 (M + H)$^+$. Analytical HPLC: RT = 7.64 min (Method A). (homochiral) |

TABLE 12-continued

| Example | Structure | Name | Analytical Data |
|---|---|---|---|
| 280 | 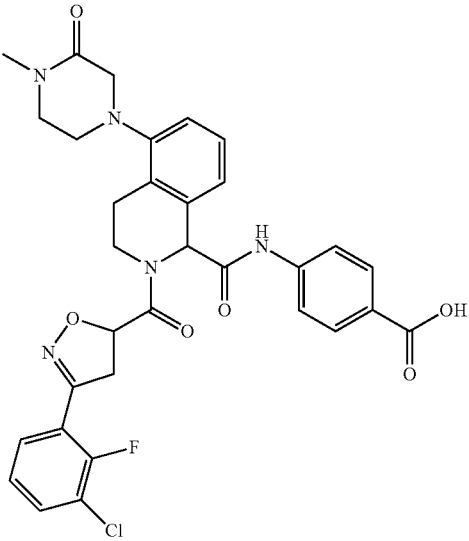 diastereomer A | 4-(2-(3-(3-chloro-2-fluorophenyl)-4,5-dihydroisoxazole-5-carbonyl)-5-(4-methyl-3-oxopiperazin-1-yl)-1,2,3,4-tetrahydroisoquinoline-1-carboxamido)benzoic acid, TFA salt | $^1$H NMR (500 MHz, methanol-d$_4$) δ 10.43 (s, 1H), 7.96-7.93 (m, 2H), 7.75 (ddd, J = 8.0, 6.5, 1.7 Hz, 1H), 7.67-7.64 (m, 2H), 7.53 (ddd, J = 8.2, 6.9, 1.7 Hz, 1H), 7.35-7.28 (m, 2H), 7.24 (td, J = 8.0, 1.1 Hz, 1H), 7.08 (dd, J = 7.7, 1.4 Hz, 1H), 5.80-5.74 (m, 2H), 4.36 (dt, J = 12.2, 5.1 Hz, 1H), 3.97-3.90 (m, 1H), 3.76 (ddd, J = 17.4, 11.5, 2.2 Hz, 1H), 3.72-3.64 (m, 2H), 3.63-3.55 (m, 2H), 3.52-3.46 (m, 1H), 3.29-3.25 (m, 1H), 3.24-3.15 (m, 2H), 3.06-3.03 (m, 2H) ppm. MS (ESI) m/z: 633.9 (M + H)$^+$. Analytical HPLC: RT = 7.99 min (Method A). (homochiral) |
| 281 | 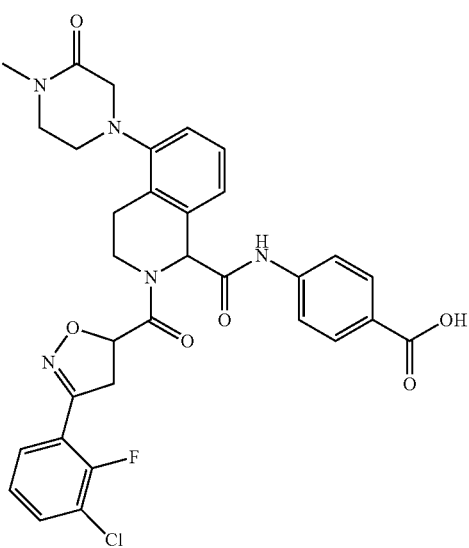 diastereomer B | 4-(2-(3-(3-chloro-2-fluorophenyl)-4,5-dihydroisoxazole-5-carbonyl)-5-(4-methyl-3-oxopiperazin-1-yl)-1,2,3,4-tetrahydroisoquinoline-1-carboxamido)benzoic acid, TFA | $^1$H NMR (500 MHz, methanol-d$_4$) δ 10.51 (s, 1H), 7.98-7.94 (m, 2H), 7.74 (ddd, J = 7.9, 6.4, 1.7 Hz, 1H), 7.68-7 64 (m, 2H), 7.62-7.57 (m, 1H), 7.36-7.28 (m, 2H), 7.25 (td, J = 8.0, 1.0 Hz, 1H), 7.10-7.37 (m, 1H), 5.83 (dd, J = 11.3, 6.9 Hz, 1H), 5.76 (s, 1H), 4.29 (dt, J = 12.5, 4.9 Hz, 1H), 4.05 (ddd, J = 17.4, 6.9, 1.8 Hz, 1H), 3.79-3.70 (m, 2H), 3.(8 (s, 1H), 3.64-3.48 (m, 3H), 3.26-3.19 (m, 3H), 3.06-3.03 (m, 4H) ppm. MS (ESI) m/z: 633.9 (M + H)$^+$. Analytical HPLC: RT = 8.13 min (Method A). (homochiral) |

TABLE 12-continued

| Example | Structure | Name | Analytical Data |
|---|---|---|---|
| 282 | 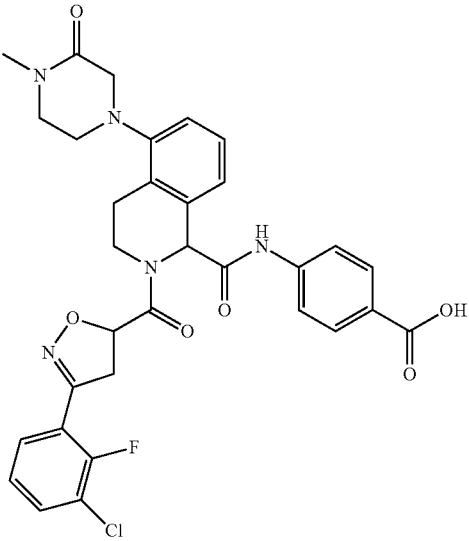 diastereomer C | 4-(2-(3-(3-chloro-2-fluorophenyl)-4,5-dihydroisoxazole-5-carbonyl)-5-(4-methyl-3-oxopiperazin-1-yl)-1,2,3,4-tetrahydroisoquinoline-1-carboxamido)benzoic acid, TFA salt | $^1$H NMR (500 MHz, methanol-$d_4$) δ 10.44 (s, 1H), 7.97-7.93 (m, 2H), 7.75 (ddd, J = 8.0, 6.3, 1.7 Hz, 1H), 7.67-7.64 (m, 2H), 7.59 (td, J = 7.6, 1.7 Hz, 1H), 7.35-7.28 (m, 2H), 7.24 (td, J = 8.0, 1.1 Hz, 1H), 7.08 (dd, J = 7.7, 1.4 Hz, 1H), 5.80-5.75 (m, 2H), 4.37 (dt, J = 12.0, 4.8 Hz, 1H), 3.94 (ddd, J = 17.3, 7.7, 1.9 Hz, 1H), 3.76 (ddd, J = 17.3, 11.4, 2.1 Hz, 1H), 3.72-3.64 (m, 2H), 3.63-3.55 (m, 2H), 3.52-3.45 (m, 1H), 3.30-3.25 (m, 1H), 3.24-3.15 (m, 2H), 3.06-3.03 (m, 3H) ppm. MS (ESI) m/z: 633.9 (M + H)$^+$. Analytical HPLC: RT = 8.00 min (Method A). (homochiral) |
| 283 | 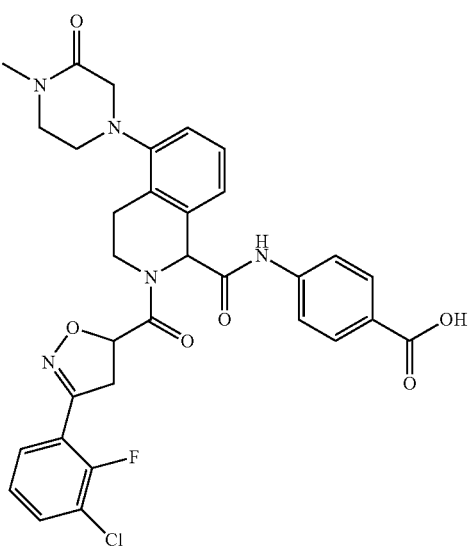 diastereomer D | 4-(2-(3-(3-chloro-2-fluorophenyl)-4,5-dihydroisoxazole-5-carbonyl)-5-(4-methyl-3-oxopiperazin-1-yl)-1,2,3,4-tetrahydroisoquinoline-1-carboxamido)benzoic acid, TFA salt | $^1$H NMR (500 MHz, methanol-$d_4$) δ 10.51 (s, 1H), 7.98-7.94 (m, 2H), 7.74 (ddd, J = 8.0, 6.5, 1.5 Hz, 1H), 7.68-7.64 (m, 2H), 7.62-7.57 (m, 1H), 7.36-7.29 (m, 2H), 7.27-7.23 (m, 1H), 7.09 (d, J = 6.9 Hz, 1H), 5.83 (dd, J = 11.4, 7.0 Hz, 1H), 5.76 (s, 1H), 4.29 (dt, J = 12.6, 5.0 Hz, 1H), 4.05 (ddd, J = 17.3, 6.9, 1.7 Hz, 1H), 3.79-3.71 (m, 2H), 3.68 (s, 1H), 3.64-3.48 (m, 4H), 3.26-3.17 (m, 3H), 3.05 (s, 3H) ppm. MS (ESI) m/z: 633.9 (M + H)$^+$. Analytical HPLC: RT = 8.13 min (Method A). (homochiral) |

TABLE 12-continued

| Example | Structure | Name | Analytical Data |
|---|---|---|---|
| 284 | 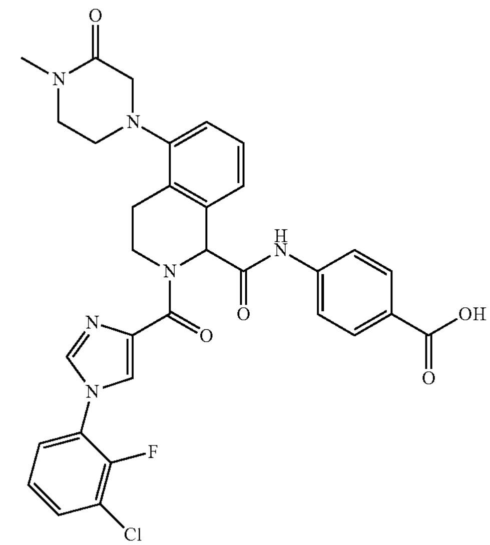 [SMILES: CN1CCN(c2cccc3c2CCN(C(=O)c2cn(-c4cccc(Cl)c4F)cn2)C3C(=O)Nc2ccc(C(=O)O)cc2)CC1=O] | 4-(2-(1-(3-chloro-2-fluorophenyl)-1H-imidazole-4-carbonyl)-5-(4-methyl-3-oxopiperazin-1-yl)-1,2,3,4-tetrahydroisoquinoline-1-carboxamido)benzoic acid, TFA salt | $^1$H NMR (500 MHz, methanol-$d_4$) δ 8.32 (s, 1H), 8.12 (br. s., 1H), 7.99 (d, J = 8.3 Hz, 2H), 7.74-7.63 (m, 3H), 7.44-7.37 (m, 2H), 7.33 (t, J = 8.0 Hz, 1H), 7.10 (d, J = 8.3 Hz, 2H), 5.86 (s, 1H), 4.64-4.56 (m, 1H), 4.09 (br. s., 1H), 3.74-3.48 (m, 6H), 3.24 (br. s., 1H), 3.06-3.03 (m, 3H) ppm. MS (ESI) m/z: 630.9 (M + H)$^+$. Analytical HPLC: RT = 7.45 min (Method A). (racemate) |
| 285 | 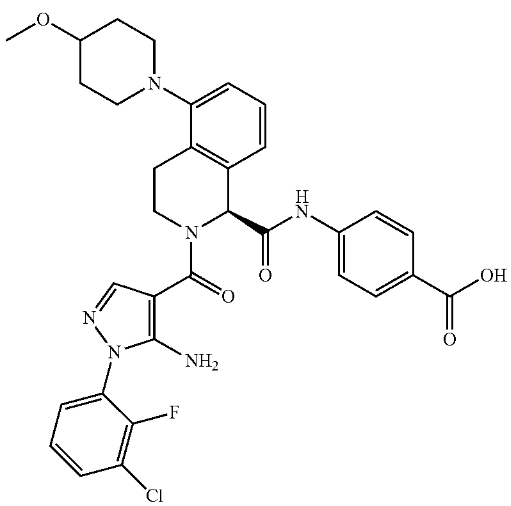 [SMILES: COC1CCN(c2cccc3c2CCN(C(=O)c2cnn(-c4cccc(Cl)c4F)c2N)[C@@H]3C(=O)Nc2ccc(C(=O)O)cc2)CC1] | (S)-4-(2-(5-amino-1-(3-chloro-2-fluorophenyl)-1H-pyrazole-4-carbonyl)-5-(4-methoxypiperidin-1-yl)-1,2,3,4-tetrahydroisoquinoline-1-carboxamido)benzoic acid, TFA salt | $^1$H NMR (500 MHz, methanol-$d_4$) δ 10.45-10.43 (m, 1H), 7.97-7.93 (m, 2H), 7.93 (s, 1H), 7.71-7.65 (m, 3H), 7.53 (d, J = 7.4 Hz, 1H), 7.49 (ddd, J = 8.1, 6.6, 1.5 Hz, 1H), 7.42-7.33 (m, 3H), 5.81 (s, 1H), 4.47 (dt, J = 11.1, 4.2 Hz, 1H), 3.82 (d, J = 3.9 Hz, 1H), 3.57-3.50 (m, 1H), 3.49-3.35 (m, 6H), 3.32-3.25 (m, 1H), 3.19 (td, J = 3.4, 1.7 Hz, 1H), 3.06 (br. s., 1H), 2.25-2.12 (m, 2H), 2.02-1.86 (m, 2H) ppm. MS (ESI) m/z: 647.0 (M + H). Analytical HPLC: RT = 4.70 min (Method A). (homochiral[b]) |
| 286 | 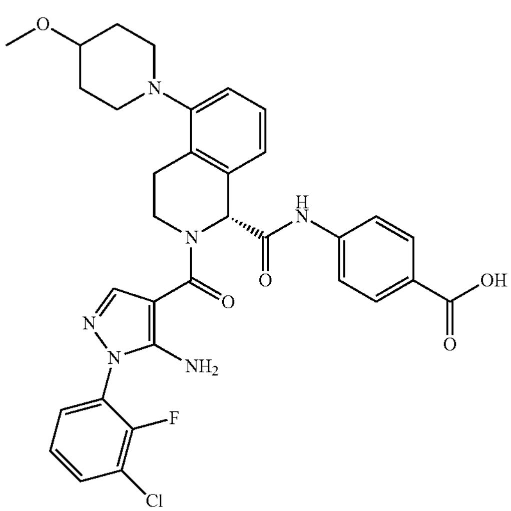 [SMILES: COC1CCN(c2cccc3c2CCN(C(=O)c2cnn(-c4cccc(Cl)c4F)c2N)[C@H]3C(=O)Nc2ccc(C(=O)O)cc2)CC1] | (R)-4-(2-(5-amino-1-(3-chloro-2-fluorophenyl)-1H-pyrazole-4-carbonyl)-5-(4-methoxypiperidin-1-yl)-1,2,3,4-tetrahydroisoquinoline-1-carboxamido)benzoic acid, TFA salt | $^1$H NMR (500 MHz, methanol-$d_4$) δ 10.43 (s, 1H), 7.98-7.94 (m, 2H), 7.93 (s, 1H), 7.72-7.66 (m, 3H), 7.50 (ddd, J = 8.1, 6.6, 1.5 Hz, 2H), 7.41-7.35 (m, 2H), 7.33 (d, J = 7.4 Hz, (H), 5.80 (s, 1H), 4.47 (dt, J = 11.0, 4.1 Hz, 1H), 3.82 (td, J = 10.9, 4.0 Hz, 6H), 3.56-3.49 (m, 1H), 3.45-3.35 (m, 4H), 3.32-3.26 (m, 1H), 3.20-3.10 (m, 1H), 3.08-2.97 (m, 1H), 2.24-2.12 (m, 2H), 1.93 (br. s., 2H) ppm. MS (ESI) m/z: 647.0 (M + H)$^+$. Analytical HPLC: RT = 4.61 min (Method A) (homochiral[b]) |

TABLE 12-continued

| Example | Structure | Name | Analytical Data |
|---|---|---|---|
| 287 | 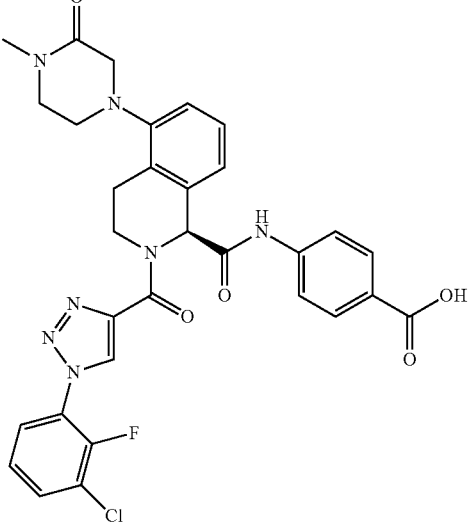 | (S)-4-(2-(1-(3-chloro-2-fluorophenyl)-1H-1,2,3-triazole-4-carbonyl)-5-(4-methyl-3-oxopiperizin-1-yl)-1,2,3,4-tetrahydroisoquinoline-1-carboxamido)benzoic acid, TFA salt | $^1$H NMR (500 MHz, methanol-$d_4$) δ 8.87 (d, J = 2.2 Hz, 1H), 7.97-7.93 (m, 2H), 7.85 (ddd, J = 8.2, 6.7, 1.4 Hz, 1H), 7.74-7.61 (m, 3H), 7.42 (td, J = 8.3, 1.4 Hz, 1H), 7.39-7.26 (m, 2H), 7.07 (d, J = 7.7 Hz, 1H), 6.57 (s, 1H), 5.88 (s, 1H), 4.66 (dt, J = 12.7, 4.9 Hz, 1H), 4.11 (ddd, J = 12.7, 8.9, 4.3 Hz, 1H), 3.71-3.43 (m, 4H), 3.27-3.15 (m, 3H), 3.02 (s, 3H) ppm. MS (ESI) m/z: 631.9 (M + H)$^+$. Analytical HPLC: RT = 5.28 min (Method A). (homochiral$^c$) |
| 288 | 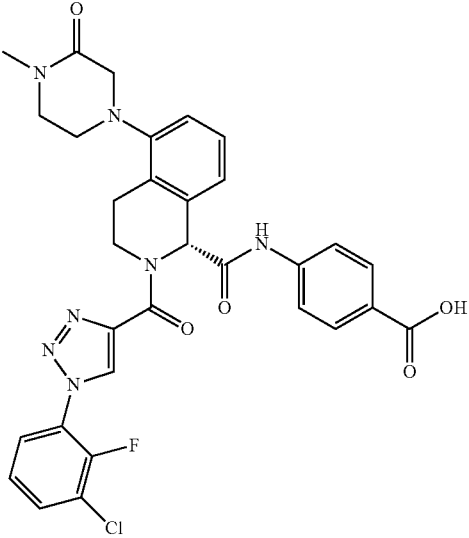 | (R)-4-(2-(1-(3-chloro-2-fluorophenyl)-1H-1,2,3-triazole-4-carbonyl)-5-(4-methyl-3-oxopiperazin-1-yl)-1,2,3,4-tetrahydroisoquinoline-1-carboxamido)benzoic acid, TFA salt | $^1$H NMR (500 MHz, methanol-$d_4$) δ 8.87 (d, J = 2.2 Hz, 1H), 7.98-7.91 (m, 3H), 7.85 (ddd, J = 8.1, 6.6, 1.5 Hz, 1H), 7.74-7.62 (m, 4H), 7.45-7.28 (m, 4H), 7.07 (d, J = 7.7 Hz, 1H), 5.88 (s, 1H), 4.66 (dt, J = 12.7, 4.8 Hz, 1H), 4.11 (ddd, J = 12.7, 8.7, 4.1 Hz, 1H), 3.71-3.44 (m, 4H), 3.27-3.15 (m, 3H), 3.02 (s, 3H) ppm. MS (ESI) m/z: 631.9 (M + H)$^+$. Analytical HPLC: RT = 5.28 min (Method A). (homochiral$^c$) |
| 289 | 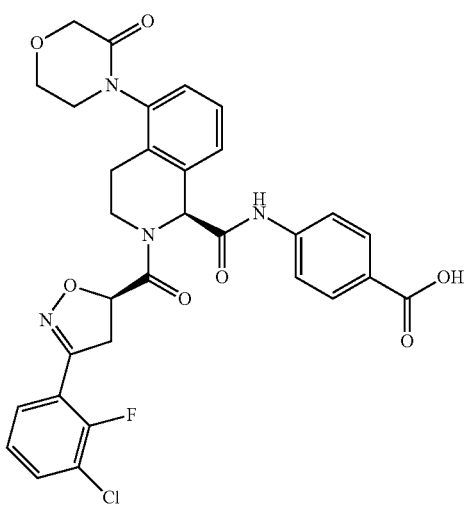 [SMILES: O=C(O)c1ccc(NC(=O)[C@@H]2c3cccc(N4CCOCC4=O)c3CCN2C(=O)[C@H]2CC(c3cccc(Cl)c3F)=NO2)cc1] | 4-((S)-2-((R)-3-(3-chloro-2-fluorophenyl)-4,5-dihydroisoxazole-5-carbonyl)-5-(3-oxomorpholino)-1,2,3,4-tetrahydroisoquinoline-1-carboxamido)benzoic acid, | $^1$H NMR (500 MHz, methanol-$d_4$) δ 10.52 (s, 1H), 7.99-7.94 (m, 2H), 7.78-7.72 (m, 1H), 7.72-7.66 (m, 2H), 7.64-7.56 (m, 2H), 7.45-7.40 (m, 1H), 7.32 (d, J = 8.0 Hz, 1H), 7.27-7.22 (m, 1H), 5.94 (s, 1H), 5.80-5.74 (m, 1H), 4.41-4.28 (m, 3H), 4.13-4.07 (m, 2H), 4.00-3.70 (m, 4H), 3.69-3.57 (m, 1H), 3.16-3.09 (m, 1H), 2.95-2.86 (m, 1H) ppm. MS (ESI) m/z: 620.8 (M + H)$^+$. Analytical HPLC: RT = 7.87 min (Method A). (homochiral) |

TABLE 12-continued

| Example | Structure | Name | Analytical Data |
|---|---|---|---|
| 290 | 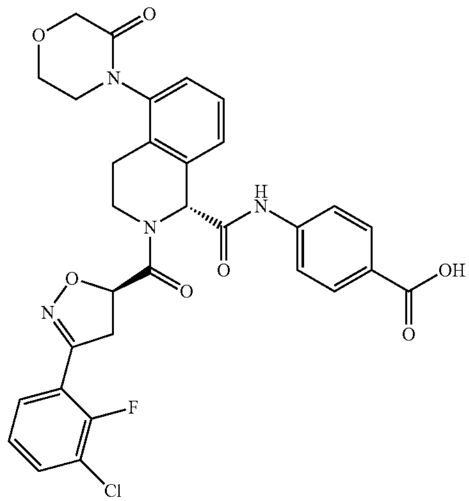 [SMILES: O=C(O)c1ccc(NC(=O)[C@H]2c3cccc(N4CCOCC4=O)c3CCN2C(=O)[C@H]2CC(c3cccc(Cl)c3F)=NO2)cc1] | 4-((S)-2-((R)-3-(3-chloro-2-fluorophenyl)-4,5-dihydroisoxazole-5-carbonyl)-5-(3-oxomorpholino)-1,2,3,4-tetrahydroisoquinoline-1-carboxamido)benzoic acid | $^1$H NMR (500 MHz, methanol-$d_4$) δ 10.59 (s, 1H), 7.99-7.94 (m, 2H), 7.76-7.56 (m, 5H), 7.42 (td, J = 7.8, 4.1 Hz, 1H), 7.35-7.30 (m, 1H), 7.24 (tdd, J = 8.0, 3.1, 1.0 Hz, 1H), 5.90 (d, J = 11.6 Hz, 1H), 5.83 (ddd, J = 11.4, 9.8, 6.9 Hz, 1H), 4.42-4.21 (m, 3H), 4.13-3.92 (m, 4H), 3.87-3.81 (m, 1H), 3.78-3.70 (m, 1H), 3.66-3.58 (m, 1H), 3.15-3.06 (m, 1H), 2.98-2.88 (m, 1H) ppm. MS (ESI, m/z: 620.9 (M + H)$^+$. Analytical HPLC: RT = 8.02 min (Method A). (homochiral) |
| 291 | 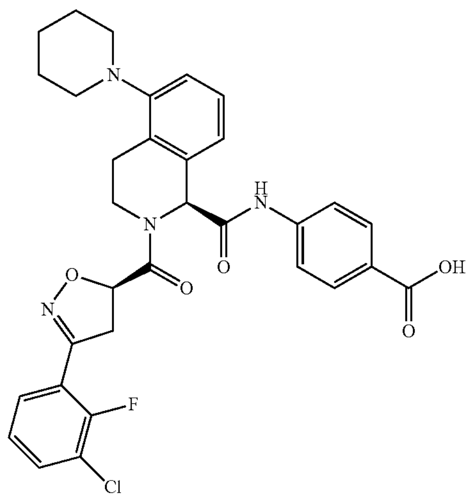 [SMILES: O=C(O)c1ccc(NC(=O)[C@@H]2c3cccc(N4CCCCC4)c3CCN2C(=O)[C@H]2CC(c3cccc(Cl)c3F)=NO2)cc1] | 4-((S)-2-((R)-3-(3-chloro-2-fluorophenyl)-4,5-dihydroisoxazole-5-carbonyl)-5-(piperidin-1-yl)-1,2,3,4-tetrahydroisoquinoline-1-carboxamido)benzoic acid, TFA salt | $^1$H NMR (500 MHz, methanol-$d_4$) δ 10.45 (s, 1H), 7.96-7.93 (m, 2H), 7.77-7.69 (m, 1H), 7.66-7.62 (m, 2H), 7.59 (ddd, J = 8.2, 6.9, 1.7 Hz, 1H), 7.50-7.43 (m, 1H), 7.37 (dt, J = 15.7, 7.9 Hz, 2H), 7.26-7.21 (m, 1H), 5.82 (s, 1H), 5.77 (dd, J = 11.4, .4, 7.6 Hz, 1H), 4.42 (dt, J = 12.1, 4.8 Hz, 1H), 3.95 (ddd, J = 17.3, 7.6, 1.8 Hz, 1H), 3.76 (ddd, J = 17.3, 11.4, 2.1 Hz, 1H), 3.73-3.67 (m, 1H), 3.24-3.18 (m, 3H), 1.93 (dt, J = 9.8, 5.0 Hz, 5H), 1.73 (br. s., 2H) ppm. MS (ESI) m/z: 604.9 (M + H)$^+$. Analytical HPLC: RT = 8.27 min (Method A). (homochiral) |
| 292 | 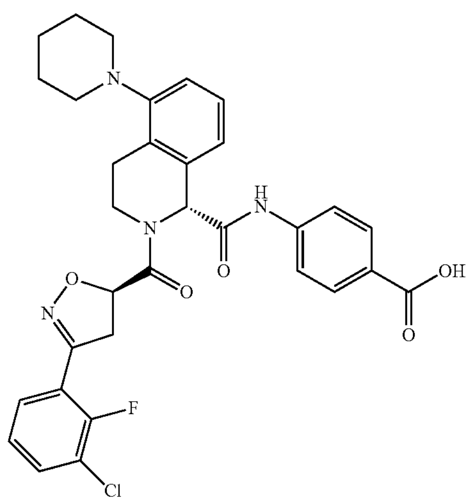 | 4-((R)-2-((R)-3-(3-chloro-2-fluorophenyl)-4,5-dihydroisoxazole-5-carbonyl)-5-(piperidin-1-yl)-1,2,3,4-tetrahydroisoquinoline-1-carboxamide)benzoic acid, TFA salt | $^1$H NMR (500 MHz, methanol-$d_4$) δ 7.97-7.94 (m, 2H), 7.73 (ddd, J = 8.0, 6.5, 1.5 Hz, 1H), 7.67-7.63 (m, 2H), 7.60 (ddd, J = 8.1, 6.9, 1.5 Hz, 1H), 7.48 (d, J = 7.2 Hz, 1H), 7.43-7.34 (m, 2H), 7.25 (td, J = 8.0, 0.8 Hz, 1H), 5.87-5.81 (m, 2H), 4.34 (dt, J = 12.5, 4.9 Hz, 1H), 4.08 (ddd, J = 17.4, 6.8. 1.9 Hz, 1H), 3.82 (ddd, J = 12.5, 8.9, 3.9 Hz, 1H), 3.75 (ddd, J = 17.4, 11.3, 1.8 Hz, 1H), 3.27-3.20 (m, 3H), 2.00-1.89 (m, 5H), 1.74 (br. s., 2H) ppm. MS (ESI) m/z: 604.9 (M + H)$^+$. Analytical HPLC: RT = 8.29 min (Method A). (homochiral) |

TABLE 12-continued

| Example | Structure | Name | Analytical Data |
|---|---|---|---|
| 293 | 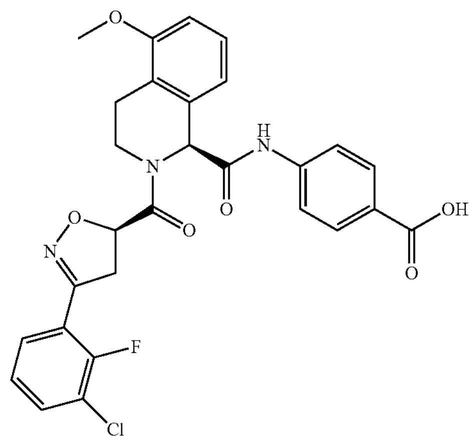 [SMILES: COc1cccc2c1CCN(C(=O)[C@H]1CC(c3cccc(Cl)c3F)=NO1)[C@@H]2C(=O)Nc1ccc(C(=O)O)cc1] | 4-((S)-2-((R)-3-(3-chloro-2-fluorophenyl)-4,5-dihydroisoxazole-5-carbonyl)-5-methoxy-1,2,3,4-tetrahydroisoquinoline-1-carboxamide)benzoic acid | $^1$H NMR (500 MHz, methanol-$d_4$) δ 10.43 (s, 1H), 7.98-7.94 (m, 2H), 7.74 (ddd, J = 7.9, 6.4, 1.7 Hz, 1H), 7.69-7.65 (m, 2H), 7.61-7.56 (m, 1H), 7.28-7.21 (m, 2H), 7.10 (d, J = 8.0 Hz, 1H), 6.93 (d, J = 8.0 Hz, 1H), 5.87 (s, 1H), 5.77 (dd, J = 11.4, 7.6 Hz, 1H), 4.29 (ddd, J = 12.7, 7.9, 4.7 Hz, 1H), 4.00-3.91 (m, 2H), 3.88 (s, 3H), 3.75 (ddd, J = 17.3, 11.4, 2.1 Hz, 1H), 3.15-3.08 (m, 1H), 3.06-2.99 (m, 1H) ppm. MS (ESI) m/z: 551.8 (M + H)$^+$. Analytical HPLC: RT = 9.90 min (Method A). (homochiral) |
| 294 | 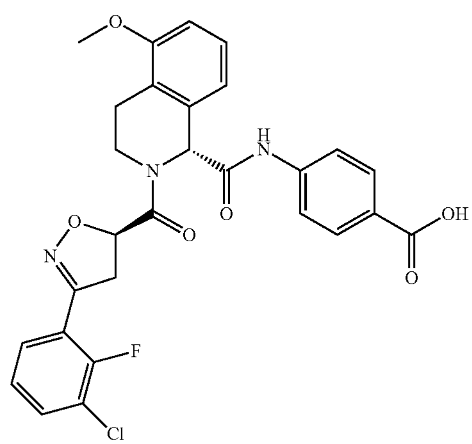 [SMILES: COc1cccc2c1CCN(C(=O)[C@H]1CC(c3cccc(Cl)c3F)=NO1)[C@H]2C(=O)Nc1ccc(C(=O)O)cc1] | 4-((R)-2-((R)-3-(3-chloro-2-fluorophenyl)-4,5-dihydroisoxazole-5-carbonyl)-5-methoxy-1,2,3,4-tetrahydroisoquinoline-1-carboxamido)benzoic acid | $^1$H NMR (500 MHz, methanol-$d_4$) δ 10.47 (s, 1H), 7.97-7.93 (m, 1H), 7.74-7.69 (m, 1H), 7.63-7.63 (m, 2H), 7.57 (ddd, J = 8.2, 6.9, 1.7 Hz, 1H), 7.26-7.20 (m, 2H), 7.11 (d, J = 8.0 Hz, 1H), 6.92 (d, J = 8.3 Hz, 1H), 5.84 (s, 1H), 5.81 (dd, J = 11.4, 7.0 Hz, 1H), 4.20 (ddd, J = 12.7, 7.6, 4.8 Hz, 1H), 4.06-3.95 (m, 2H), 3.88 (s, 3H), 3.73 (ddd, J = 17.4, 11.3, 1.8 Hz, 1H), 3.12-3.00 (m, 2H) ppm. MS (ESI) m/z: 551.9 (M + H)$^+$. Analytical HPLC: RT = 9.91 min (Method A). (homochiral) |
| 295 | 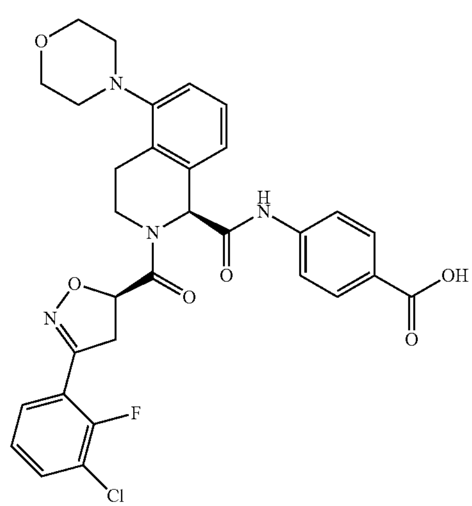 [SMILES: O=C(O)c1ccc(NC(=O)[C@@H]2c3cccc(N4CCOCC4)c3CCN2C(=O)[C@H]2CC(c3cccc(Cl)c3F)=NO2)cc1] | 4-((S)-2-((R)-3-(3-chloro-2-fluorophenyl)-4,5-dihydroisoxazole-5-carbonyl)-5-morpholino-1,2,3,4-tetrahydroisoquinoline-1-carboxamido)benzoic acid, TFA salt | $^1$H NMR (500 MHz, methanol-$d_4$) δ 10.41 (s, 1H), 7.96-7.92 (m, 2H), 7.74 (ddd, J = 7.9, 6.4, 1.7 Hz, 1H), 7.66-7.62 (m, 2H), 7.58 (ddd, J = 8.1, 6.9, 1.5 Hz, 1H), 7.31-7.25 (m, 2H), 7.23 (td, J = 3.0, 1.0 Hz, 1H), 7.09 (dd, J = 6.9, 2.2 Hz, 1H), 5.80-5.74 (m, 2H), 4.37 (dt, J = 12.0, 4.7 Hz, 1H), 3.96-3.82 (m, 5H), 3.76 (ddd, J = 17.4, 11.5, 1.9 Hz, 1H), 3.64 (ddd, J = 12.1, 9.2, 4.3 Hz, 1H), 3.28-3.21 (m, 1H), 3.03 (ddd, J = 11.7, 5.9, 2.8 Hz, 1H), 2.89 (ddd, J = 11.8, 6.3, 2.6 Hz, 1H) ppm. MS (ESI) m/z: 607.0 (M + H)$^+$. Analytical HPLC: RT = 9.48 min (Method A). (homochiral) |

TABLE 12-continued

| Example | Structure | Name | Analytical Data |
|---|---|---|---|
| 296 | 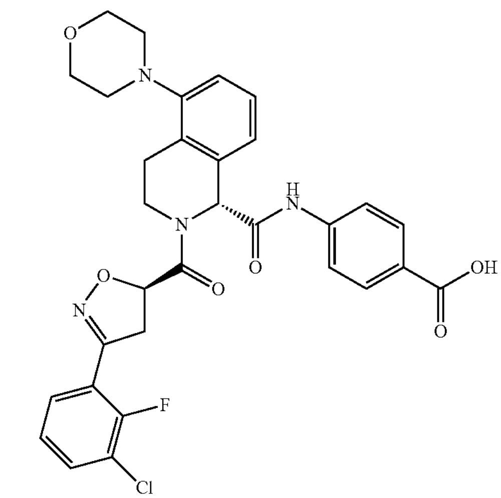 [SMILES: O=C(O)c1ccc(NC(=O)[C@H]2c3cccc(N4CCOCC4)c3CCN2C(=O)[C@H]2CC(c3cccc(Cl)c3F)=NO2)cc1] | 4-((S)-2-((R)-3-(3-chloro-2-fluorophenyl)-4,5-dihydroisoxazole-5-carbonyl)-5-morpholino-1,2,3,4-tetrahydroisoquinoline-1-carboxamido)benzoic acid, TFA salt | $^1$H NMR (500 MHz, methanol-$d_4$) δ 10.48 (s, 1H), 7.95-7.92 (m, 2H), 7.72 (ddd, J = 8.0, 6.3, 1.7 Hz, 1H), 7.66-7.62 (m, 2H), 7.58 (ddd, J = 8.0, 6.8, 1.7 Hz, 1H), 7.32-7.26 (m, 2H), 7.24 (td, J = 8.0, 1.0 Hz, 1H), 7.09 (dd, J = 7.7, 1.4 Hz, 1H), 5.83 (dd, J = 11.3, 6.9 Hz, 1H), 5.75 (s, 1H), 4.29 (dt, J = 12.5, 4.9 Hz, 1H), 4.04 (ddd, J = 17.3, 6.9, 1.9 Hz, 1H), 3.94-3.83 (m, 4H), 3.79-3.68 (m, 2H), 3.22 (t, J = 5.4 Hz, 23), 3.02 (ddd, J = 11.8, 6.1, 3.0 Hz, 2H), 2.90 (ddd, J = 11.6, 6.3, 2.8 Hz, 2H) ppm. MS (ESI) m/z: 607.0 (M + H)$^+$. Analytical HPLC: RT = 9.68 min (Method A). (homochiral) |
| 297 | 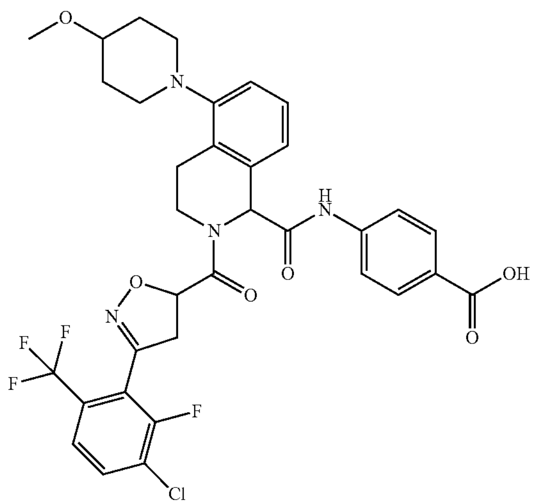 [SMILES: COC1CCN(c2cccc3c2CCN(C(=O)C2CC(c4c(C(F)(F)F)ccc(Cl)c4F)=NO2)C3C(=O)Nc2ccc(C(=O)O)cc2)CC1] | 4-(2-(3-(3-chloro-2-fluoro-6-(trifluoromethyl)phenyl)-4,5-dihydroisoxazole-5-carbonyl)-5-(4-methoxypiperidin-1-yl)-1,2,3,4-tetrahydroisoquinoline-1-carboxamido)benzoic acid, TFA salt | $^1$H NMR (500 MHz, methanol-$d_4$) δ 10.44 (s, 1H), 7.96-7.92 (m, 2H), 7.82 (t, J = 7.6 Hz, 1H), 7.71-7.62 (m, 3H), 7.45 (d, J = 7.4 Hz, 1H), 7.37-7.28 (m, 2H), 5.88-5.82 (m, 2H), 4.37 (dt, J = 12.0, 4.7 Hz, 1H), 3.83 (dd, J = 17.6, 8.0 Hz, 1H), 3.70-3.59 (m, 2H), 3.55-3.48 (m, 1H), 3.41 (s, 3H), 3.23-3.09 (m, 2H), 3.03 (br. s., 1H), 2.17 (ddd, J = 17.0, 13.4, 3.4 Hz, 2H), 1.99-1.84 (m, 2H) ppm. MS (ESI) m/z: 703.0 (M + H)$^+$. Analytical HPC: RT = 9.26 min (Method A). (diastereomeric mixture) |
| 298 | 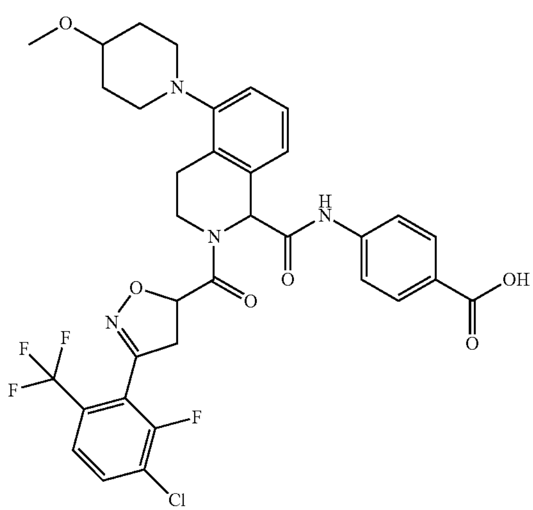 [SMILES: COC1CCN(c2cccc3c2CCN(C(=O)C2CC(c4c(C(F)(F)F)ccc(Cl)c4F)=NO2)C3C(=O)Nc2ccc(C(=O)O)cc2)CC1] | 4-(2-(3-(3-chloro-2-fluoro-6-(trifluoromethyl)phenyl)-4,5-dihydroisoxazole-5-carbonyl)-5-(4-methoxypiperidin-1-yl)-1,2,3,4-tetrahydroisoquinoline-1-carboxamido)benzoic acid, TFA salt | $^1$H NMR (500 MHz, methanol-$d_4$) δ 7.98-7.93 (m, 2H), 7.83 (t, J = 7.6 Hz, 1H), 7.70-7.64 (m, 3H), 7.48-7.28 (m, 3H), 5.92 (dd, J = 11.6, 7.2 Hz, 1H), 5.83 (s, 1H), 4.35-4.29 (m, 1H), 4.01 (dd, J = 17.5, 7.0 Hz, 1H), 3.79 (ddd, J = 12.7, 8.9, 4.0 Hz, 1H), 3.63-3.56 (m, 1H), 3.51 (br. s., 1H), 3.43-3.41 (m, 3H), 3.30-3.26 (m, 1H), 3.25-3.18 (m, 1H), 3.12 (br. s., 1H), 3.04 (br. s., 1H), 2.22-2.12 (m, 2H), 1.98-1.85 (m, 2H) ppm. MS (ESI) m/z: 703.1 (M + H)$^+$. Analytical HPLC: RT = 9.48 min (Method A). (diastereomeric mixture) |

TABLE 12-continued

| Example | Structure | Name | Analytical Data |
|---|---|---|---|
| 299 | 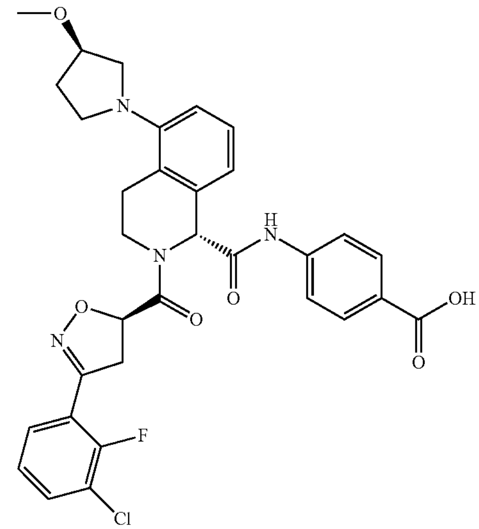 [SMILES: CO[C@@H]1CCN(c2cccc3c2CCN(C(=O)[C@H]2CC(c4cccc(Cl)c4F)=NO2)[C@H]3C(=O)Nc2ccc(C(=O)O)cc2)C1] | 4-((R)-2-((R)-3-(3-chloro-2-fluorophenyl)-4,5-dihydroisoxazole-5-carbonyl)-5-((R)-3-methoxypyrrolidin-1-yl)-1,2,3,4-tetrahydroisoquinoline-1-carboxamido)benzoic acid, TFA salt | $^1$H NMR (500 MHz, methanol-d$_4$) δ 10.47 (s, 1H), 7.97-7.94 (m, 3H), 7.76-7.72 (m, 2H), 7.66-7.63 (m, 3H), 7.62-7.57 (m, 2H), 7.28-7.22 (m, 4H), 7.07-7.02 (m, 1H), 5.84 (dd, J = 11.6, 6.9 Hz, 1H), 5.70 (s, 1H), 4.33 (dt, J = 12.6, 4.6 Hz, 1H), 4.19-4.14 (m, 1H), 4.06 (ddd, J = 17.4, 6.8, 1.7 Hz, 1H), 3.80-3.72 (m, 1H), 3.67-3.50 (m, 2H), 3.38 (s, 3H), 3.27-3.20 (m, 1H), 3.14-3.06 (m, 1H), 2.24-2.09 (m, 1H) ppm. MS (ESI) m/z: 621.0 (M + H)$^+$. Analytical HPLC: RT = 8.76 min (Method A). (homochiral$^d$) |
| 300 | 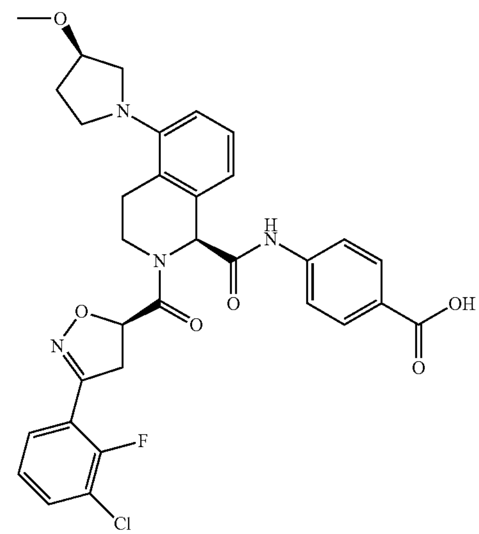 [SMILES: CO[C@@H]1CCN(c2cccc3c2CCN(C(=O)[C@H]2CC(c4cccc(Cl)c4F)=NO2)[C@@H]3C(=O)Nc2ccc(C(=O)O)cc2)C1] | 4-((S)-2-((R)-3-(3-chloro-2-fluorophenyl)-4,5-dihydroisoxazole-5-carbonyl)-5-((R)-3-methoxypyrrolidin-1-yl)-1,2,3,4-tetrahydroisoquinoline-1-carboxamido)benzoic acid, TFA salt | $^1$H NMR (500 MHz, methanol-d$_4$) δ 10.43 (s, 1H), 7.93 (d, J = 8.5 Hz, 2H), 7.75-7.71 (m 1H), 7.66-7.62 (m, 2H), 7.60-7.55 (m, 1H), 7.31-7.25 (m, 2H), 7.25-7.20 (m, 1H), 7.14 (dd, J = 7.0, 1.8 Hz, 1H), 5.79 (s, 1H), 5.77 (dd, J = 11.4, 7.6 Hz, 1H), 4.34 (dt, J = 12.4, 5.0 Hz, 1H), 4.21-4.14 (m, 1H), 3.94 (ddd, J = 17.3, 7.6, 1.8 Hz, 1H), 3.80-3.70 (m, 2H), 3.44 (d, J = 3.0 Hz, 2H), 3.41 (s, 3H), 3.29-3.22 (m, 1H), 3.15-3.07 (m, 1H), 2.34-2.26 (m, 1H), 2.10 (dtd, J = 13.1, 6.4, 3.6 Hz, 1H) ppm. MS (ESI) m/z: 621.0 (M + H)$^+$. Analytical HPLC: RT = 8.73 min (Method A). (homochiral$^d$) |
| 301 | 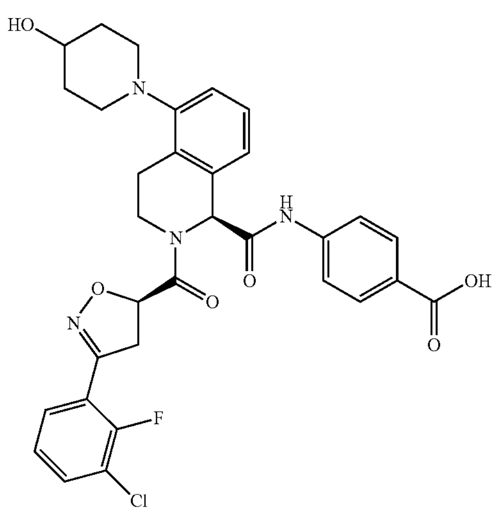 [SMILES: O=C(O)c1ccc(NC(=O)[C@@H]2c3cccc(N4CCC(O)CC4)c3CCN2C(=O)[C@H]2CC(c3cccc(Cl)c3F)=NO2)cc1] | 4-((S)-2-((R)-3-(3-chloro-2-fluorophenyl)-4,5-dihydroisoxazole-5-carbonyl)-5-(4-hydroxypiperidin-1-yl)-1,2,3,4-tetrahydroisoquinoline-1-carboxamido)benzoic acid, TFA salt | $^1$H NMR (500 MHz, methanol-d$_4$) δ 7.96-7.92 (m, 2H), 7.74 (ddd, J = 8.0, 6.3, 1.7 Hz, 1H), 7.66-7.62 (m, 2H), 7.61-7.56 (m, 1H), 7.47 (d, J = 5.5 Hz, 1H), 7.38 (d, J = 5.8 Hz, 1H), 7.24 (td, J = 8.0, 1.0 Hz, 1H), 5.83 (s, 1H), 5.77 (dd, J = 11.4, 7.6 Hz, 1H), 4.43 (dt, J = 12.0, 4.7 Hz, 1H), 4.00 (s, 2H), 3.99-3.92 (m, 2H), 3.80-3.68 (m, 2H), 3.54-3.43 (m, 2H), 3.26-3.17 (m, 2H), 3.13 (br. s., 1H), 2.22-2.11 (m, 2H), 1.91 (dd, J = 18.7, 9.4 Hz, 2H) ppm. MS (ESI) m/z: 621.0 (M + H)$^+$. Analytical HPLC: RT = 7.05 min (Method A). (homochiral) |

TABLE 12-continued

| Example | Structure | Name | Analytical Data |
|---|---|---|---|
| 302 | 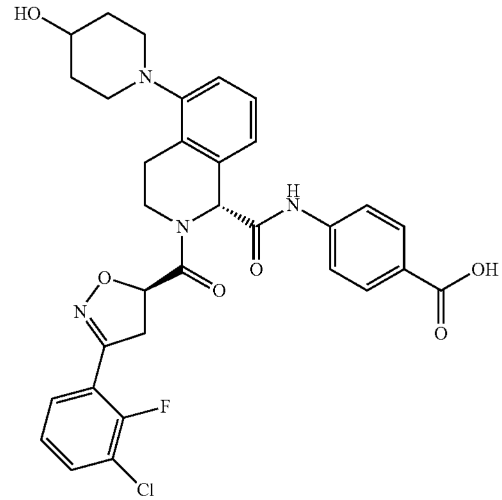 [SMILES: O=C(O)c1ccc(NC(=O)[C@H]2c3cccc(N4CCC(O)CC4)c3CCN2C(=O)[C@H]2CC(c3cccc(Cl)c3F)=NO2)cc1] | 4-((R)-2-((R)-3-(3-chloro-2-fluorophenyl)-4,5-dihydroisoxazole-5-carbonyl)-5-(4-hydroxypiperidin-1-yl)-1,2,3,4-tetrahydroisoquinoline-1-carboxamido)benzoic acid, TFA salt | $^1$H NMR (500 MHz, methanol-$d_4$) δ 7.97-7.93 (m, 2H), 7.75-7.70 (m, 1H), 7.67-7.63 (m, 2H), 7.62-7.57 (m, 1H), 7.51-7.46 (m, 1H), 7.41-7.37 (m, 1H), 7.28-7.21 (m, 1H), 5.87-5.81 (m, 2H), 4.37-4.31 (m, 1H), 4.08 (ddd, J = 17.3, 6.9, 1.7 Hz, 1H), 4.00 (s, 2H), 3.98-3.91 (m, 1H), 3.86-3.67 (m, 2H), 3.55-3.45 (m, 1H), 3.27-3.20 (m, 1H), 3.20-3.11 (m, 1H), 2.22-2.10 (m, 2H), 1.98-1.85 (m, 2H) ppm. MS (ESI) m/z: 621.0 (M + H)$^+$. Analytical HPLC: RT = 7.09 min (Method A). (homochiral) |
| 303 | diastereomer A | 4-(2-(3-(3-chloro-2-fluorophenyl)-4,5-dihydroisoxazole-5-carbonyl)-5-(4-methoxypiperidin-1-yl)-1,2,3,4-tetrahydroisoquinoline-1-carboxamido)benzoic acid, TFA salt | $^1$H NMR (500 MHz, methanol-$d_4$) δ 10.49 (s, 1H), 7.97-7.94 (m, 2H), 7.73 (ddd, J = 8.0, 6.5, 1.7 Hz, 1H), 7.67-7.64 (m, 2H), 7.62-7.58 (m, 1H), 7.39-7.33 (m, 1H), 7.32 (t, J = 7.7 Hz, 1H), 7.27-7.23 (m, 1H), 7.22 (d, J = 7.4 Hz, 1H), 5.84 (dd, J = 11.4, 7.0 Hz, 1H), 5.77 (s, 1H), 4.32 (dt, J = 12.4, 4.8 Hz, 1H), 4.06 (ddd, J = 17.5, 6.9, 1.8 Hz, 1H), 3.80-3.72 (m, 2H), 3.53-3.46 (m, 1H), 3.43 (s, 3H), 3.28-3.18 (m, 3H), 3.02 (br. s., 1H), 2.92 (d, J = 6.6 Hz, 1H), 2.15 (br. s., 2H), 1.86 (br. s., 2H) ppm. MS (ESI) m/z: 635 (M + H)$^+$. Analytical HPLC: RT = 9.31 min (Method A). (homochiral$^a$) |
| 304 | diastereomer B | 4-(2-(3-(3-chloro-2-fluorophenyl)-4,5-dihydroisoxazole-5-carbonyl)-5-(4-methoxypiperidin-1-yl)-1,2,3,4-tetrahydroisoquinoline-1-carboxamido)benzoic acid, TFA salt | $^1$H NMR (500 MHz, methanol-$d_4$) δ 10.49 (s, 1H), 7.97-7.94 (m, 2H), 7.73 (ddd, J = 8.0, 6.5, 1.5 Hz, 1H), 7.65 (dd, J = 8.7, 1.3 Hz, 2H), 7.62-7.57 (m, 1H), 7.43-7.38 (m, 1H), 7.34 (t, J = 7.7 Hz, 1H), 7.29-7.23 (m, 2H), 5.84 (dd, J = 11.3, 6.9 Hz, 1H), 5.75 (s, 1H), 4.32 (dt, J = 12.6, 4.8 Hz, 1H), 4.07 (ddd, J = 17.3, 6.9, 1.7 Hz, 1H), 3.82-3.72 (m, 2H), 3.51 (br. s., 1H), 3.43 (s, 3H), 3.29-3.18 (m, 2H), 3.08 (br. s., 1H), 2.98 (br. s., 1H), 2.17 (br. s., 2H), 1.89 (br. s., 2H) ppm. MS (ESI) m/z: 635 (M + H)$^+$. Analytical HPLC: RT = 9.26 min (Method A). (homochiral$^a$) |

TABLE 12-continued

| Example | Structure | Name | Analytical Data |
|---|---|---|---|
| 305 | 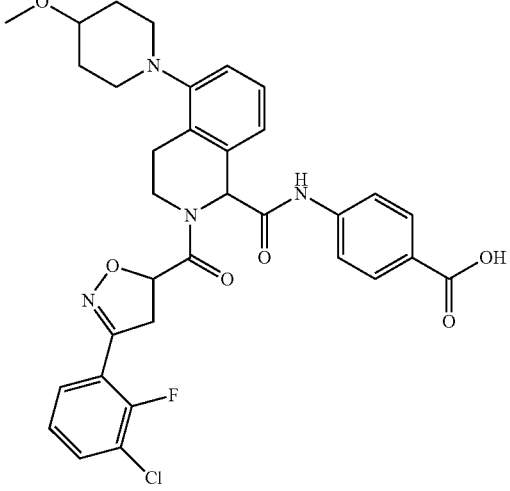<br>diastereomer C | 4-(2-(3-(3-chloro-2-fluorophenyl)-4,5-dihydroisoxazole-5-carbonyl)-5-(4-methoxypiperidin-1-yl)-1,2,3,4-tetrahydroisoquinoline-1-carboxamido)benzoic acid, TFA | $^1$H NMR (500 MHz, methanol-$d_4$) δ 10.43 (s, 1H), 7.94-7.91 (m, 2H), 7.72 (ddd, J = 7.9, 6.4, 1.7 Hz, 1H), 7.64-7.61 (m, 2H), 7.59-7.55 (m, 1H), 7.41 (d, J = 7.4 Hz, 1H), 7.33 (t, J = 7.8 Hz, 1H), 7.30-7.25 (m, 1H), 7.24-7.20 (m, 1H), 5.80 (s, 1H), 5.79-5.74 (m, 1H), 4.40 (dt, J = 12.0, 4.7 Hz, 1H), 3.94 (ddd, J = 17.3, 7.5, 1.7 Hz, 1H), 3.75 (ddd, J = 17.3, 11.6, 1.9 Hz, 1H), 3.71-3.65 (m, 1H), 3.51 (br. s., 1H), 3.42 (s, 3H), 3.20 (dt, J = 15.7, 4.3 Hz, 1H), 3.11 (d, J = 8.8 Hz, 1H), 3.00 (br. s., 1H), 2.22-2.10 (m, 2H), 1.90 (br. s., 2H) ppm. MS (ESI) m/z: 635 (M + H)$^+$. Analytical HPLC: RT = 9.21 min (Method A). (homochiral$^a$) |
| 306 | 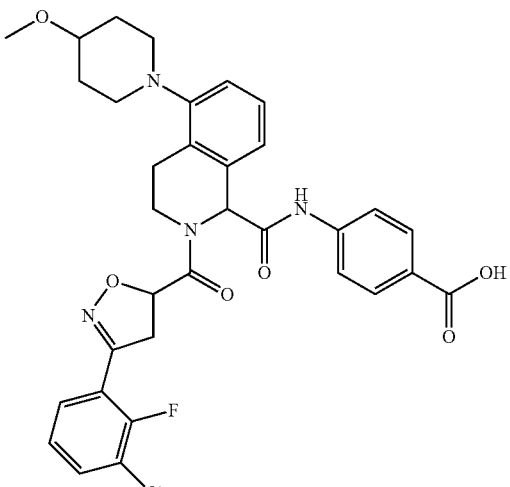<br>diastereomer D | 4-(2-(3-(3-chloro-2-fluorophenyl)-4,5-dihydroisoxazole-5-carbonyl)-5-(4-methoxypiperidin-1-yl)-1,2,3,4-tetrahydroisoquinoline-1-carboxamido)benzoic acid, TFA salt | $^1$H NMR (500 MHz, methanol-$d_4$) δ 10.43 (s, 1H), 7.94-7.91 (m, 2H), 7.73 (ddd, J = 8.0, 6.5, 1.5 Hz, 1H), 7.64-7.63 (m, 1H), 7.63-7.61 (m, 1H), 7.60-7.55 (m, 1H), 7.40 (d, J = 7.4 Hz, 1H), 7.33 (t, J = 7.8 Hz, 1H), 7.27 (d, J = 8.5 Hz, 1H), 7.23 (td, J = 8.0, 0.8 Hz, 1H), 5.80 (s, 1H), 5.77 (dd, J = 11.6, 7.7 Hz, 1H), 4.40 (dt, J = 12.0, 4.7 Hz, 1H), 3.94 (ddd, J = 17.4, 7.5, 1.8 Hz, 1H), 3.76 (ddd, J = 17.3, 11.6, 1.9 Hz, 1H), 3.71-3.65 (m, 1H), 3.51 (br. s., 1H), 3.42 (s, 3H), 3.23-3.16 (m, 1H), 3.10 (d, J = 8.3 Hz, 1H), 2.98 (br. s., 1H), 2.22-2.11 (m, 2H), 1.90 (br. s., 2H) ppm. MS (ESI) m/z: 635 (M + H)$^+$. Analytical HPLC: RT = 9.21 min (Method A). (homochiral$^a$) |

Chiral SFC methods:
$^a$CHIRALCEL ® OJ-H, 30 × 250 mm ID, 5mm, using 35% MeOH-DEA/65% CO$_2$ at 45.0 mL/min, 100 bar BP, 40° C.
$^b$CHIRALPAK ® AS-H, 21 × 250 mm ID, 5mm, using 30% IPA/70% CO$_2$ at 45.0 mL/min, 100 bar BP, 35° C.
$^c$CHIRALPAK ® AS-H, 21 × 250 mm ID, 5mm, using 30% IPA/70% CO$_2$ at 65.0 mL/min, 150 bar BP, 35° C.
$^d$CHTRALCEL ® OJ, 19 × 250 mm, 10 μ, using 30% Methanol/70% CO$_2$ at 45 mL/min, 100 Bar, 35° C.

EXAMPLE 307

4-(2-(1-(3-Chloro-2-fluorophenyl)pyrrolidine-3-carbonyl) 5-(4-methoxypiperidin-1-yl)-1,2,3,4-tetrahydroisoquinoline-1-carboxamido)benzoic acid, TFA salt

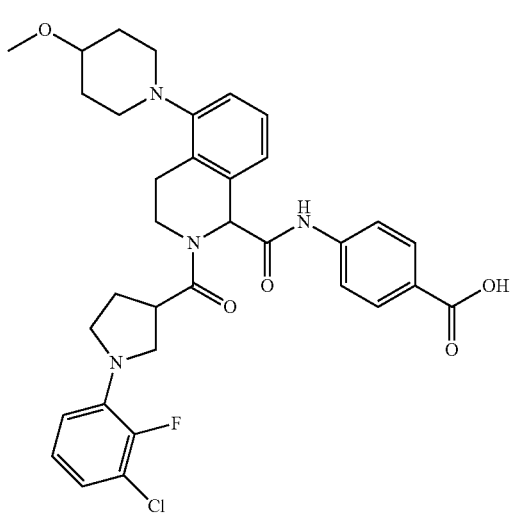 [SMILES: COC1CCN(c2cccc3c2CCN(C(=O)C2CCN(c4cccc(Cl)c4F)C2)C3C(=O)Nc2ccc(C(=O)O)cc2)CC1]

Example 307. 4-(2-(1-(3-Chloro-2-fluorophenyl)pyrrolidine-3-carbonyl)-5-(4-methoxypiperidin-1-yl)-1,2,3,4-tetrahydroisoquinoline-1-carboxamido)benzoic acid, TFA Salt: To a solution of 1-(3-chloro-2-fluorophenyl)pyrrolidine-3-carboxylic acid (12.19 mg, 0.050 mmol) in DCM (anhydrous) (1 mL) and under nitrogen was added 1-chloro-N,N,2-trimethylpropenylamine (0.024 mL, 0.175 mmol) and the reaction allowed to stir for 30 min. This mixture was added dropwise to a pre-cooled (0° C.) solution of Intermediate 28 (23.3 mg, 0.050 mmol) and TEA (0.035 mL, 0.250 mmol) in DCM (1 mL) and the mixture stirred at 0° C. for 30 min and then at ambient temperature overnight. Reaction mixture diluted with EtOAc and H$_2$O, phases separated and aqueous layer extracted 3× with EtOAc and combined extracts washed with brine, dried (Na$_2$SO$_4$), filtered and evaporated to a residue which was purified by normal phase column chromatography. The t-butyl ester was cleaved with 50% TFA/DCM, concentrated and purified by reverse phase prep. HPLC to give the title compound as the early eluting diastereomeric mixture. $^1$H NMR (500 MHz, methanol-d$_4$) δ 10.42 (s, 1H), 7.96-7.93 (m, 2H), 7.65-7.62 (m, 2H), 7.45 (d, J=7.7 Hz, 1H), 7.36 (t, J=7.8 Hz, 1H), 7.30 (d, J=7.4 Hz, 1H), 6.96 (td, J=8.1, 1.4 Hz, 1H), 6.78 (ddd, J=8.0, 6.4, 1.5 Hz, 1H), 6.72 (td, J=8.2, 1.5 Hz, 1H), 5.80 (s, 1H), 4.32 (dt, J=12.1, 4.7 Hz, 1H), 3.78-3.67 (m, 3H), 3.67-3.60 (m, 1H), 3.58-3.47 (m, 4H), 3.43 (s, 3H), 3.31-3.26 (m, 1H), 3.23-3.16 (m, 1H), 3.13 (br. s., 1H), 3.01 (br. s., 1H), 2.37-2.28 (m, 1H), 2.27-2.11 (m, 3H), 1.91 (br. s., 2H) ppm. MS (ESI) m/z: 635.1 (M+H)$^+$. Analytical HPLC: RT=9.84 min (Method A).

EXAMPLE 308

4-(2-(1-(3-Chloro-2-fluorophenyl)pyrrolidine-3-carbonyl)-5-(4-methoxypiperidin-1-yl)-1,2,3,4-tetrahydroisoquinoline-1-carboxamido)benzoic acid, TFA salt

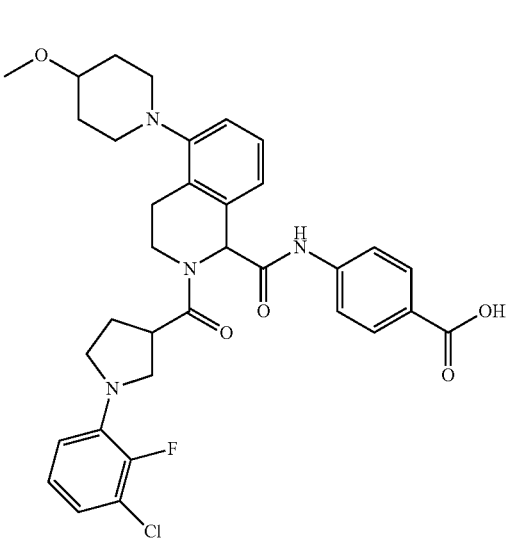 [SMILES: COC1CCN(c2cccc3c2CCN(C(=O)C2CCN(c4cccc(Cl)c4F)C2)C3C(=O)Nc2ccc(C(=O)O)cc2)CC1]

Example 308. 4-(2-(1-(3-Chloro-2-fluorophenyl)pyrrolidine-3-carbonyl)-5-(4-methoxypiperidin-1-yl)-1,2,3,4-tetrahydroisoquinoline-1-carboxamido)benzoic acid, TFA Salt: The title compound was isolated after purification of Example 307 by reverse phase prep. HPLC as the late eluting diastereomeric mixture. $^1$H NMR (500 MHz, methanol-d$_4$) δ 10.43 (s, 1H), 7.98-7.94 (m, 2H), 7.67-7.63 (m, 2H), 7.43 (d, J=7.2 Hz, 1H), 7.35 (t, J=7.7 Hz, 1H), 7.28 (d, J=7.4 Hz, 1H), 6.95 (td, J=8.3, 1.4 Hz, 1H), 6.76 (ddd, J=8.0, 6.3, 1.7 Hz, 1H), 6.70 (td, J=8.3, 1.4 Hz, 1H), 5.79 (s, 1H), 4.32 (dt, J=12.0, 4.7 Hz, 1H), 3.75-3.59 (m, 5H), 3.56-3.44 (m, 4H), 3.43 (s, 3H), 3.31-3.27 (m, 1H), 3.22-3.15 (m, 1H), 3.11 (br. s., 1H), 2.99 (br. s., 1H), 2.43-2.35 (m, 1H), 2.32-2.24 (m, 1H), 2.23-2.12 (m, 2H), 1.90 (br. s., 2H) ppm. MS (ESI) m/z: 635.1 (M+H)$^+$. Analytical HPLC RT=9.98 min (Method A)

The compounds in Table 13 were prepared in a similar manner Example 307 starting from Intermediate 28 utilizing the appropriate carboxylic acid and routine amide formation conditions. Final compounds were treated with 50% TFA/DCM and purified by reverse phase chromatography.

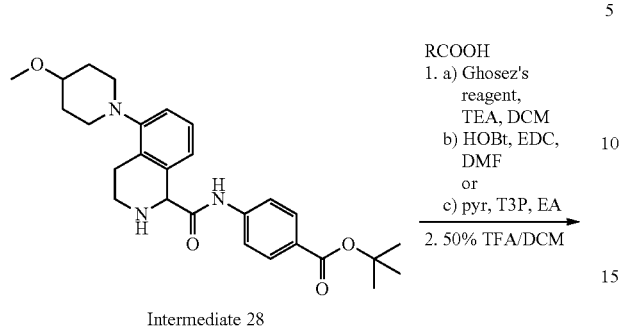

Intermediate 28

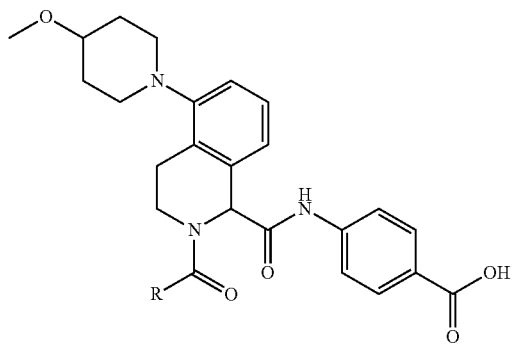

Examples 309-316

TABLE 13

| Example | Structure | Name | Analytical Data |
|---|---|---|---|
| 309 | ![structure] | 4-(2-(5-amino-1-(3-chloro-2-fluorophenyl)-1H-pyrazole-4-carbonyl)-5-(4-methoxypiperidin-1-yl)-1,2,3,4-tetrahydroisoquinoline-1-carboxamido)benzoic acid, 2 TFA salt | $^1$H NMR (500 MHz, methanol-$d_4$) δ 10.43 (s, 1H), 7.99-7.95 (m, 2H), 7.93 (s, 1H), 7.71-7.66 (m, 3H), 7.50 (ddd, J = 8.2, 6.7, 1.7 Hz, 2H), 7.42-7.31 (m, 3H), 5.80 (s, 1H), 4.51-4.44 (m, 1H), 3.82 (td, J = 11.0, 3.9 Hz, 1H), 3.54 (br. s., 1H), 3.43 (s, 3H), 3.41-3.36 (m, 2H), 3.32-3.26 (m, 1H), 3.21-3.13 (m, 1H), 3.05 (br. s., 1H), 2.24-2.12 (m, 2H), 1.94 (br. s., 2H) ppm. MS (ESI) m/z: 647.1 (M + H)$^+$. Analytical HPLC: RT = 8.05 min (Method A). (racemate) |
| 310 | ![structure] | 4-(2-(2-(3-chloro-2-fluorophenyl)oxazole-4-carbonyl)-5-(4-methoxypiperidin-1-yl)-1,2,3,4-tetrahydroisoquinoline-1-carboxamido)benzoic acid, TFA salt | $^1$H NMR (400 MHz, methanol-$d_4$) δ 8.58 (s, 1H), 7.99-7.94 (m, 2H), 7.71-7.64 (m, 3H), 7.43-7.37 (m, 1H), 7.32 (t, J = 8.0 Hz, 2H), 7.22 (d, J = 7.8 Hz, 1H), 5.87 (s, 1H), 4.64 (dt, J = 12.4, 4.6 Hz, 1H), 4.07 (ddd, J = 12.5, 8.8, 4.2 Hz, 1H), 3.45 (br. s., 1H), 3.40 (s, 3H), 3.25 (td, J = 9.0, 4.0 Hz, 2H), 3.01 (t, J = 9.2 Hz, 1H), 2.90 (br. s., 1H), 2.19-2.07 (m, 2H), 1.84 (br. s., 2H) ppm. MS (ESI) m/z: 633 (M + H)$^+$. Analytical HPLC: RT = 9.23 min (Method A). (racemate) |

TABLE 13-continued

| Example | Structure | Name | Analytical Data |
|---|---|---|---|
| 311 | 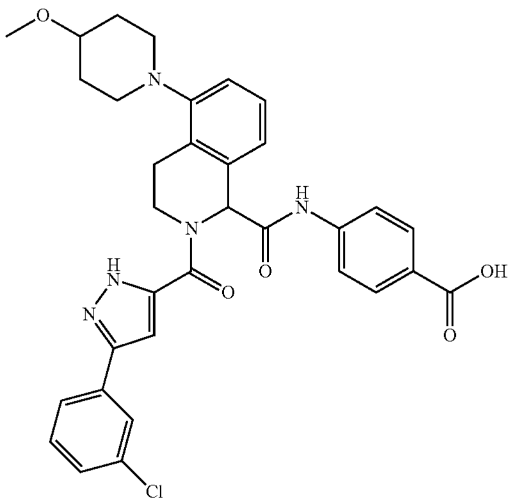 [SMILES: COC1CCN(c2cccc3c2CCN(C(=O)c2cc(-c4cccc(Cl)c4)n[nH]2)C3C(=O)Nc2ccc(C(=O)O)cc2)CC1] | 4-(2-(3-(3-chlorophenyl)-1H-pyrazole-5-carbonyl)-5-(4-methoxypiperidin-1-yl)-1,2,3,4-tetrahydroisoquinoline-1-carboxamido)benzoic acid, TFA salt | $^1$H NMR (400 MHz, methanol-d$_4$) δ 7.97 (d, J = 8.6 Hz, 2H), 7.83 (br. s., 1H), 7.74-7.67 (m, 3H), 7.50-7.33 (m, 4H), 7.12 (s, 1H), 5.90 (s, 1H), 4.61-4.52 (m, 1H), 4.04-3.93 (m, 1H), 3.56-3.46 (m, 1H), 3.41 (s, 3H), 3.25-3.16 (m, 1H), 3.10 (br. s., 1H), 3.00 (br. s., 1H), 2.16 (br. s., 2H), 1.89 (br. s., 2H) ppm. MS (ESI) m/z: 614.0 (M + H)$^+$. Analytical HPLC: RT = 8.70 min (Method A). (racemate) |
| 312 | 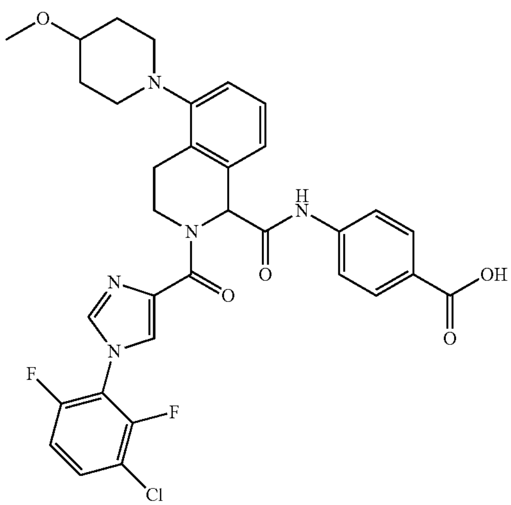 [SMILES: COC1CCN(c2cccc3c2CCN(C(=O)c2cn(-c4c(F)ccc(Cl)c4F)cn2)C3C(=O)Nc2ccc(C(=O)O)cc2)CC1] | 4-(2-(1-(3-chloro-2,6-difluorophenyl)-1H-imidazole-4-carbonyl)-5-(4-methoxypiperidin-1-yl)-1,2,3,4-tetrahydroisoquinoline-1-carboxamido)benzoic acid, TFA salt | $^1$H NMR (400 MHz, methanol-d$_4$) δ 8.12-8.01 (m, 1H), 7.96 (d, J = 8.3 Hz, 2H), 7.75-7.65 (m, 2H), 7.49 (d, J = 6.1 Hz, 1H), 7.41-7.28 (m, 2H), 5.89 (br. s., 1H), 4.63 (d, J = 12.1 Hz, 1H), 4.14 (br. s., 1H), 3.57-3.46 (m, 1H), 3.41 (s, 3H), 3.27-3.18 (m, 1H), 3.15 (dt, J = 3.3, 1.6 Hz, 1H), 3.06 (br. s., 1H), 2.18 (br. s., 2H), 2.03-1.81 (m, 2H) ppm. MS (ESI) m/z: 650.0 (M + H)$^+$. Analytical HPLC: RT = 8.03 min (Method A). (racemate) |
| 313 | 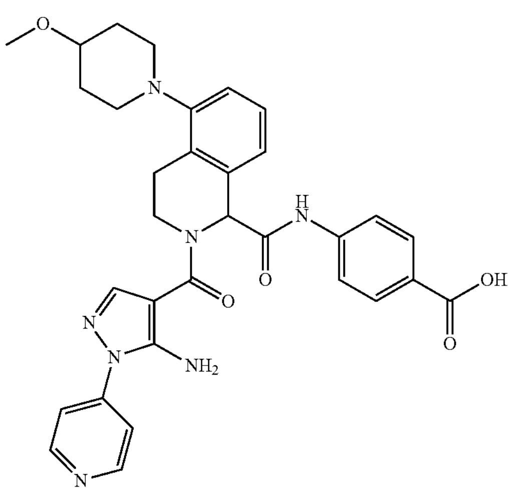 [SMILES: COC1CCN(c2cccc3c2CCN(C(=O)c2cnn(-c4ccncc4)c2N)C3C(=O)Nc2ccc(C(=O)O)cc2)CC1] | 4-(2-(5-amino-1-(pyridin-4-yl)-1H-pyrazole-4-carbonyl)-5-(4-methoxypiperidin-1-yl)-1,2,3,4-tetrahydroisoquinoline-1-carboxamido)benzoic acid, TFA salt | $^1$H NMR (500 MHz, methanol-d$_4$) δ 10.44 (br. s., 1H), 8.88-8.85 (m, 2H), 8.42-8.38 (m, 2H), 8.12 (s, 1H), 7.98 (d, J = 8.8 Hz, 2H), 7.69 (dd, J = 8.8, 1.9 Hz, 2H), 7.43-7.39 (m, 1H), 7.35-7.30 (m, 1H), 7.22-7.18 (m, 1H), 5.75 (s, 1H), 4.44-4.38 (m, 1H), 3.81-3.74 (m, 1H), 3.50-3.44 (m, 1H), 3.42 (s, 3H), 3.25-3.18 (m, 1H), 3.05-2.98 (m, 1H), 2.87-2.78 (m, 1H), 2.20-2.07 (m, 2H), 1.90-1.75 (m, 2H) ppm. MS (ESI) m/z: 596.0 (M + H)$^+$. Analytical HPLC: RT = 5.28 min (Method A). (racemate) |

TABLE 13-continued

| Example | Structure | Name | Analytical Data |
|---|---|---|---|
| 314 | 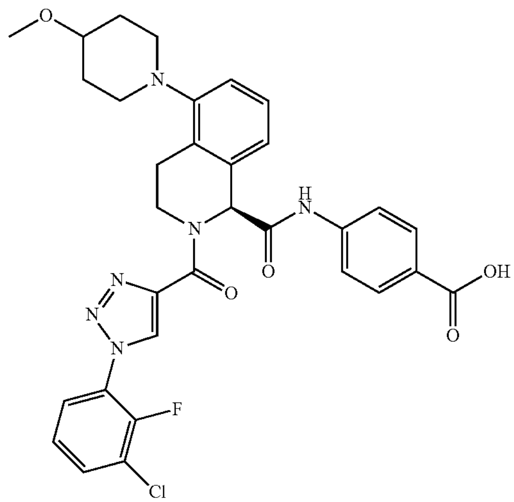 [SMILES: COC1CCN(c2cccc3c2CCN(C(=O)c2cn(-c4cccc(Cl)c4F)nn2)[C@@H]3C(=O)Nc2ccc(C(=O)O)cc2)CC1] | (S)-4-(2-(1-(3-chloro-2-fluorophenyl)-1H-1,2,3-triazole-4-carbonyl)-5-(4-methoxypiperidin-1-yl)-1,2,3,4-tetrahydroisoquinoline-1-carboxamido)benzoic acid, TFA salt | $^1$H NMR (500 MHz, methanol-d$_4$) δ 10.57 (s, 1H), 8.91 (d, J = 2.2 Hz, 1H), 8.00-7.94 (m, 2H), 7.90-7.85 (m, 1H), 7.77-7.72 (m, 1H), 7.72-7.64 (m, 2H), 7.53-7.29 (m, 4H), 5.94 (s, 1H), 4.73 (dt, J = 12.5, 4.9 Hz, 1H), 4.22-4.14 (m, 1H), 3.56-3.49 (m, 1H), 3.42 (s, 3H), 3.30-3.22 (m, 1H), 3.17-2.99 (m, 2H), 2.18 (br. s., 2H), 1.92 (br. s., 2H) ppm. MS (ESI) m/z: 633.0 (M + H)$^+$. Analytical HPLC: RT = 8.65 min (Method A). (homochiral$^a$) |
| 315 | 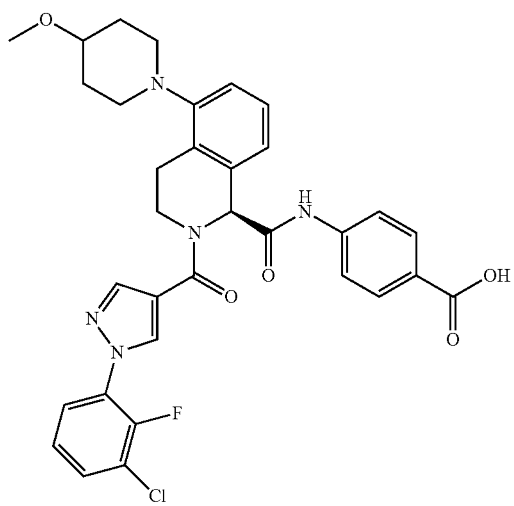 [SMILES: COC1CCN(c2cccc3c2CCN(C(=O)c2cnn(-c4cccc(Cl)c4F)c2)[C@@H]3C(=O)Nc2ccc(C(=O)O)cc2)CC1] | (S)-4-(2-(1-(3-chloro-2-fluorophenyl)-1H-pyrazole-4-carbonyl)-5-(4-methoxypiperidin-1-yl)-1,2,3,4-tetrahydroisoquinoline-1-carboxamido)benzoic acid, TFA salt | $^1$H NMR (500 MHz, methanol-d$_4$) δ 10.53 (br. s., 1H), 8.60 (br. s., 1H), 8.18 (s, 1H), 7.97 (d, J = 8.8 Hz, 2H), 7.82 (t, J = 7.2 Hz, 1H), 7.69 (d, J = 8.3 Hz, 2H), 7.60 (t, J = 7.0 Hz, 1H), 7.47 (d, J = 7.2 Hz, 1H), 7.37 (t, J = 7.7 Hz, 2H), 7.29 (d, J = 7.7 Hz, 1H), 5.85 (s, 1H), 4.47-4.39 (m, 1H), 3.86-3.78 (m, 1H), 3.54-3.48 (m, 1H), 3.43-3.41 (m, 3H), 3.28-3.21 (m, 1H), 3.14-3.05 (m, 1H), 2.96 (br. s., 1H), 2.22-2.09 (m, 2H), 1.89 (br. s., 2H). MS (ESI) m/z: 631.9 (M + H)$^+$. Analytical HPLC: RT = 8.66 min (Method A). (homochiral$^b$) |
| 316 | 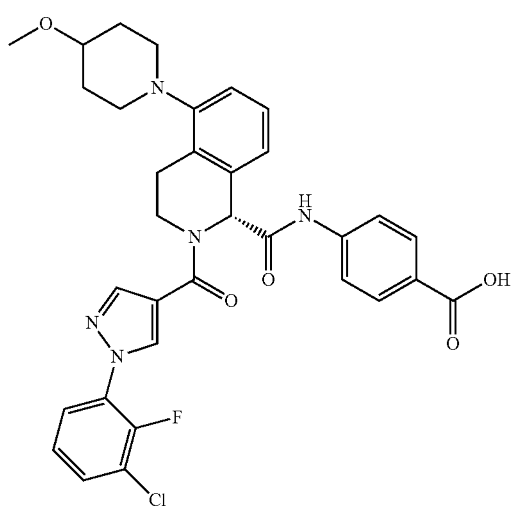 | (R)-4-(2-(1-(3-chloro-2-fluorophenyl)-1H-pyrazole-4-carbonyl)-5-(4-methoxypiperidin-1-yl)-1,2,3,4-tetrahydroisoquinoline-1-carboxamido)benzoic acid, TFA salt | $^1$H NMR (500 MHz, methanol-d$_4$) δ 10.54 (br. s., 1H), 8.59 (br. s., 1H), 8.17 (s, 1H), 7.96 (d, J = 8.8 Hz, 2H), 7.81 (t, J = 7.3 Hz, 1H), 7.68 (d, J = 8.3 Hz, 2H), 7.59 (t, J = 7.0 Hz, 1H), 7.50 (br. s., 1H), 7.41-7.28 (m, 3H), 5.86 (s, 1H), 4.46-4.39 (m, 1H), 3.82 (t, J = 9.4 Hz, 1H), 3.52 (br. s., 1H), 3.43-3.41 (m, 3H), 3.28-3.22 (m, 1H), 3.13 (br. s., 1H), 3.01 (br. s., 1H), 2.23-2.10 (m, 2H), 1.90 (br. s., 2H) ppm. MS (ESI) m/z: 631.9 (M + H)$^+$. Analytical HPLC: RT = 8.66 min (Method A). (homochiral$^b$) |

Chiral SFC methods:
$^a$CHIRALPAK ® AS-H, 21 × 250 mm ID, 5μ, using 20% IPA/80% CO$_2$ at 55.0 mL/min, 100 bar BP, 40° C.
$^b$CHIRALPAK ® AS-H, 21 × 250 mm ID, 5μ, using 30% IPA/70% CO$_2$ at 55.0 mL/min, 100 bar BP, 40° C.

EXAMPLE 317

4-(2-(5-Amino-1-(3-chloro-2-fluorophenyl)-1H-pyrazole-4-carbonyl)-5-(4-(dimethylcarbamoyl)piperidin-1-yl)-1,2,3,4-tetrahydroisoquinoline-1-carboxamido)benzoic acid, TFA salt

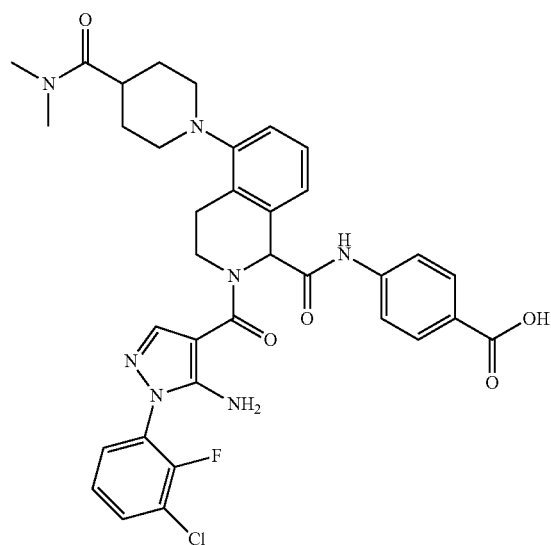 [SMILES: CN(C)C(=O)C1CCN(c2cccc3c2CCN(C(=O)c2cnn(-c4cccc(Cl)c4F)c2N)C3C(=O)Nc2ccc(C(=O)O)cc2)CC1]

EXAMPLE 318

4-(2-(5-Amino-1-(3-chloro-2-fluorophenyl)-1H-pyrazole-4-carbonyl)-5-(4-methyl-3-oxopiperazin-1-yl)-1,2,3,4-tetrahydroisoquinoline-1-carboxamido) benzoic acid, TFA salt

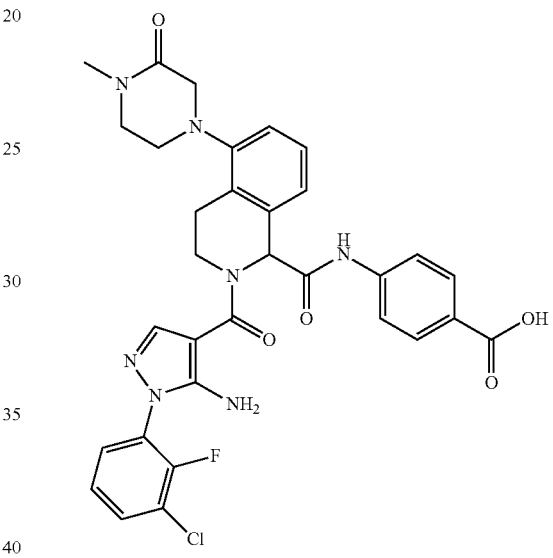

Example 317. 4-(2-(5-Amino-1-(3-chloro-2-fluorophenyl)-1H-pyrazole-4-carbonyl)-5-(4-(dimethylcarbamoyl)piperidin-1-yl)-1,2,3,4-tetrahydroisoquinoline-1-carboxamido)benzoic acid, TFA salt: The title compound was prepared in a similar manner as Example 309 starting from Intermediate 51. $^1$H NMR 500 MHz, methanol-$d_4$) δ 10.41 (s, 1H), 7.99-7.95 (m, 2H), 7.94 (s, 1H), 7.71-7.66 (m, 4H), 7.50 (td, J=7.4, 1.7 Hz, 1H), 7.46 (d, J=7.7 Hz, 1H), 7.41-7.34 (m, 2H), 7.26 (d, J=8.3 Hz, 1H), 5.78 (s, 1H), 4.50-4.44 (m, 1H), 3.84-3.76 (m, 1H), 3.43-3.36 (m, 2H), 3.18 (s, 3H), 3.17-3.12 (m, 1H), 2.99 (s, 3H), 2.95 (br. s., 2H), 2.14-1.88 (m, 4H) ppm. MS (ESI) m/z: 688.1 (M+H)$^+$. Analytical HPLC: RT=6.73 min (Method A).

Example 318. 4-(2-(5-Amino-1-(3-chloro-2-fluorophenyl)-1H-pyrazole-4-carbonyl)-5-(4-methyl-3-oxopiperazin-1-yl)-1,2,3,4-tetrahydroisoquinoline-1-carboxamido)benzoic acid, TFA salt: The title compound was prepared in a similar manner as Example 309 starting from Intermediate 52. $^1$H NMR (500 MHz, methanol-$d_4$) δ 7.99-7.95 (m, 2H), 7.93 (s, 1H), 7.71-7.67 (m, 3H), 7.50 (ddd, J=8.2, 6.7, 1.7 Hz, 1H), 7.42-7.35 (m, 2H), 7.32 (t, J=7.8 Hz, 1H), 7.09 (d, J=7.2 Hz, 1H), 5.76 (s, 1H), 4.47-4.41 (m, 1H), 3.82-3.71 (m, 2H), 3.62-3.55 (m, 2H), 3.52-3.45 (m, 1H), 3.31-3.27 (m, 2H), 3.22-3.16 (m, 1H), 3.05 (s, 3H) ppm. MS (ESI) m/z: 646.0 (M+H)$^+$. Analytical HPLC: RT=7.42 min (Method A).

EXAMPLE 319

4-(2-(3-Amino-1-(3-chloro-2-fluorophenyl)-1H-pyrazole-4-carbonyl)-5-(4-(2-(dimethylamino)ethoxy)piperidin-1-yl)-1,2,3,4-tetrahydroisoquinoline-1-carboxamido)benzoic acid, 2 TFA salt

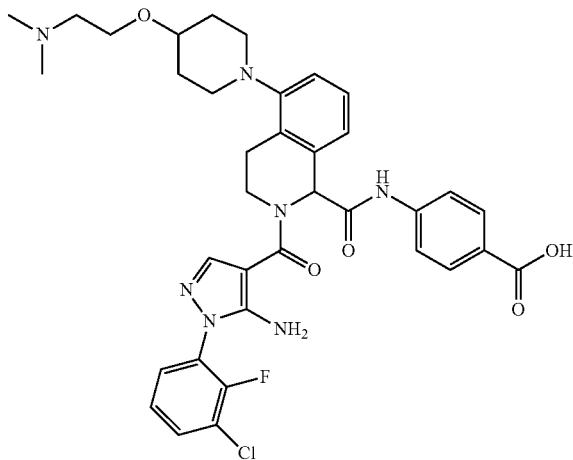 [SMILES: CN(C)CCOC1CCN(c2cccc3c2CCN(C(=O)c2cnn(-c4cccc(Cl)c4F)c2N)C3C(=O)Nc2ccc(C(=O)O)cc2)CC1]

Example 319. 4-(2-(5-Amino-1-(3-chloro-2-fluorophenyl)-1H-pyrazole-4-carbonyl)-5-(4-(2-(dimethylamino)ethoxy)piperidin-1-yl)-1,2,3,4-tetrahydroisoquinoline-1-carboxamido)benzoic acid, 2 TFA salt: The title compound was prepared in a similar manner as Example 309 starting from Intermediate 53. $^1$H NMR (500 MHz, methanol-$d_4$) δ 10.58-10.55 (m, 1H), 8.90 (d, J=1.9 Hz, 1H), 7.99 (d, J=8.8 Hz, 2H), 7.91-7.86 (m, 1H), 7.78-7.74 (m, 1H), 7.72-7.69 (m, 2H), 7.47 (td, J=8.2, 1.5 Hz, 1H), 7.36-7.27 (m, 2H), 7.11 (d, J=7.4 Hz, 1H), 5.88 (s, 1H), 4.77-4.71 (m, 1H), 4.11-4.04 (m, 1H), 3.89-3.85 (m, 2H), 3.68-3.61 (m, 1H), 2.96 (s, 6H), 2.80-2.73 (m, 1H), 2.13 (d, J=14.9 Hz, 2H), 1.96 (s, 2H), 1.91-1.79 (m, 2H) ppm. MS (ESI) m/z: 690.0 (M+H)$^+$. Analytical HPLC: RT=5.66 min (Method A).

EXAMPLE 320

4-(2-(5-(3-Chlorophenyl)nicotinoyl)-5-(4-methylpiperazin-1-yl)-1,2,3,4-tetrahydroisoquinoline-1-carboxamido)benzoic acid, 2 TFA salt

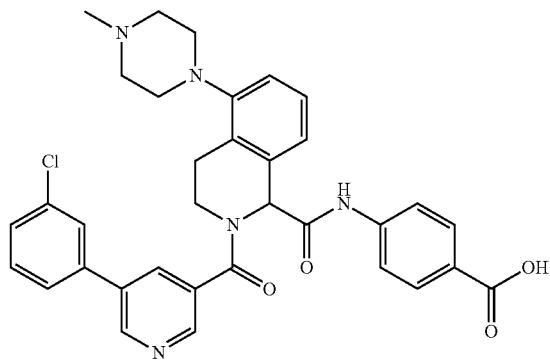 [SMILES: CN1CCN(c2cccc3c2CCN(C(=O)c2cncc(-c4cccc(Cl)c4)c2)C3C(=O)Nc2ccc(C(=O)O)cc2)CC1]

Example 320. 4-(2-(5-(3-Chlorophenyl)nicotinoyl)-5-(4-methylpiperazin-1-yl)-1,2,3,4-tetrahydroisoquinoline-1-carboxamido)benzoic acid, 2 TFA salt: The title compound was prepared in a similar manner as Example 309 starting from Intermediate 34 and utilizing commercially available 5-(3-chlorophenyl)nicotinic acid. $^1$H NMR (500 MHz, MeOD) δ 9.02 (1 H, d, J=1.93 Hz), 8.80 (1 H, d, J=1.65 Hz), 8.34-8.38 (1 H, m), 8.00 (2 H, d, J=8.80 Hz), 7.82 (1 H, s), 7.68-7.74 (2 H, m), 7.53 (2 H, ddd, J=15.61, 8.12, 7.91 Hz), 7.47 (1 H, d, J=7.70 Hz), 7.33-7.39 (1 H, m), 7.17 (1 H, d, J=8.25 Hz), 5.94 (1 H, s), 4.07 (1 H, dt, J=12.10, 4.68 Hz), 3.55-3.68 (3 H, m), 3.10-3.27 (3 H, m), 2.96-3.06 (4 H, m), 2.96-3.04 (5 H, m) ppm. MS (ESI) m/z: 610.0 (M+H)$^+$. Analytical HPLC: RT=5.40 min (Method A).

EXAMPLE 321

4-(5-(4-Methylpiperazin-1-yl)-2-(5-phenylnicotinoyl)-1,2,3,4-tetrahydroisoquinoline-1-carboxamido)benzoic acid

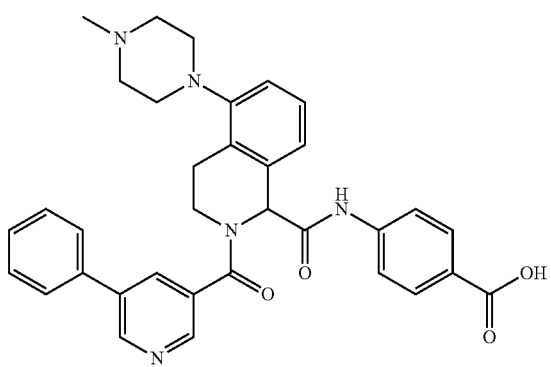 [SMILES: CN1CCN(c2cccc3c2CCN(C(=O)c2cncc(-c4ccccc4)c2)C3C(=O)Nc2ccc(C(=O)O)cc2)CC1]

Example 321. 4-(5-(4-Methylpiperazin-1-yl)-2-(5-phenylnicotinoyl)-1,2,3,4-tetrahydroisoquinoline-1-carboxamido)benzoic acid: The title compound was prepared in a similar manner as Example 309 starting from Intermediate 34 and utilizing commercially available 5-phenylnicotinic acid. $^1$H NMR (500 MHz, DMSO-$d_6$) δ 10.96 (s, 1H), 9.65 (br. s., 1H), 9.06 (d, J=2.2 Hz, 1H), 8.74 (d, J=1.9 Hz, 1H), 8.25 (t, J=2.1 Hz, 1H), 7.91 (d, J=8.8 Hz, 2H), 7.83 (d, J=7.2 Hz, 2H), 7.75 (d, J=8.8 Hz, 2H), 7.56-7.51 (m, 2H), 7.48 (d, J=7.4 Hz, 2H), 7.32 (t, J=7.8 Hz, 1H), 7.08 (d, J=8.0 Hz, 1H), 5.93 (s, 1H), 4.01-3.93 (m, 1H), 3.67 (ddd, J=12.2, 8.2, 4.1 Hz, 1H), 3.51 (d, J=8.3 Hz, 2H), 3.32-3.17 (m, 4H), 3.08-2.86 (m, 7H) ppm. MS (ESI) m/z: 576 (M+H)$^+$. Analytical HPLC: RT=4.43 min (Method A).

EXAMPLE 322

4-(2-(4-(3-Chloro-2-fluorophenyl)picolinoyl)-5-(4-methoxypiperidin-1-yl)-1,2,3,4-tetrahydroisoquinoline-1-carboxamido)benzoic acid, 2 TFA salt

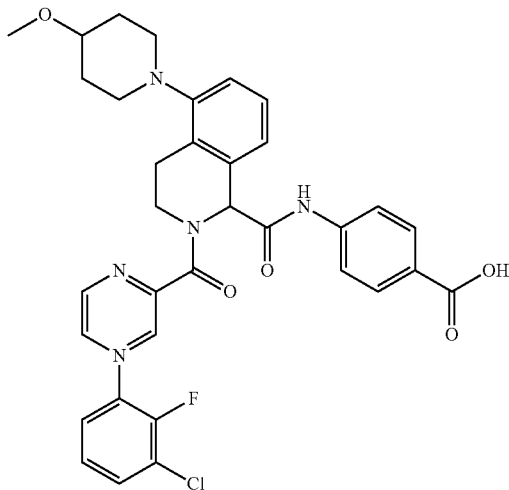

322A. tert-Butyl 4-(2-(4-bromopicolinoyl)-5-(4-methoxypiperidin-1-yl)-1,2,3,4-tetrahydroisoquinoline-1-carboxamido)benzoate: To a solution of 4-bromopicolinic acid (10.11 mg, 0.050 mmol) in DCM (1 mL) and under nitrogen was added 1-chloro-N,N,2-trimethylpropenylamine (0.024 mL, 0.175 mmol) and the reaction allowed to stir for 30 min. This mixture was added dropwise to a pre-cooled (0° C.) solution of Intermediate 28 (23.3 mg, 0.050 mmol) and TEA (0.035 mL, 0.250 mmol) in DCM (1 mL) and the mixture stirred at 0° C. for 30 min and then at ambient temperature overnight. The reaction mixture was diluted with EtOAc and H$_2$O, phases separated and aqueous layer extracted with EtOAc (3×) and the combined extracts washed with brine, dried (Na$_2$SO$_4$), filtered and evaporated to a residue which was purified by normal phase column chromatography to give the title compound (25.4 mg, 78% yield) as a solid. MS (ESI) m/z: 649 (M+H)$^+$.

322B. tert-Butyl 4-(2-(4-(3-chloro-2-fluoorophenyl)picolinoyl)-5-(4-methoxypiperidin-1-yl)-1,2,3,4-tetrahydroisoquinoline-1-carboxamido)benzoate: To a vial was charged with 322A (25.4 mg, 0.039 mmol), (3-chloro-2-fluorophenyl)boronic acid (6.82 mg, 0.039 mmol) and Pd(Ph$_3$P)$_4$ (4.52 mg, 3.91 μmol). The vial was purged with argon and dioxane (anhydrous-degassed) (2 mL) and Na$_2$CO$_3$ (2M aqueous-degassed) (0.059 mL, 0.117 mmol) were added and the reaction heated to 50° C. and stirred overnight. The reaction mixture was purified by normal phase column chromatography to give the title compound (9.8 mg, 0.014 mmol, 35.8% yield). MS (ESI) m/z: 699.1 (M+H)$^+$.

Example 322. 4-(2-(4-(3-Chloro-2-fluorophenyl)picolinoyl)-5-(4-methoxypiperidin-1-yl)-1,2,3,4-tetrahydroisoquinoline-1-carboxamido)benzoic acid, 2 TFA salt: To 322B (9.8 mg, 0.014 mmol) in DCM (1 mL) was added TFA (1 mL, 12.98 mmol) and the reaction was stirred at ambient temperature under nitrogen for 2 h. The reaction mixture was evaporated and purified by reverse phase prep. HPLC to give the desired product (5.09 mg, 39.6% yield) as a solid. $^1$H NMR (500 MHz, methanol-d$_4$) δ 8.81-8.75 (m, 1H), 8.02-7.91 (m, 4H), 7.81-7.77 (m, 1H), 7.74-7.70 (m, 2H), 7.66-7.59 (m, 3H), 7.50 (d, J=7.2 Hz, 1H), 7.46-7.29 (m, 4H), 5.96 (s, 1H), 4.19-4.01 (m, 2H), 3.82-3.74 (m, 1H), 3.51 (br. s., 1H), 3.42 (s, 3H), 3.28-3.22 (m, 1H), 3.20-2.99 (m, 3H), 2.25-2.10 (m, 2H), 2.03-1.81 (m, 2H) ppm. MS (ESI) m/z: 643.1 (M+H)$^+$. Analytical HPLC: RT=9.17 min (Method A).

EXAMPLE 323

4-(2-(5-(3-Chloro-2-fluorophenyl)nicotinoyl)-5-(4-methoxypiperidin-1-yl)-1,2,3,4-tetrahydroisoquinoline-1-carboxamido)benzoic acid, 2 TFA salt

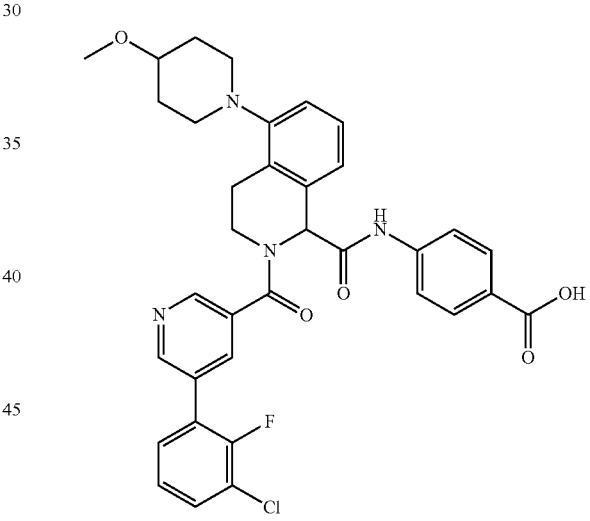

Example 323. 4-(2-(5-(3-Chloro-2-fluorophenyl)nicotinoyl)-5-(4-methoxypiperidin-1-yl)-1,2,3,4-tetrahydroisoquinoline-1-carboxamido)benzoic acid, 2 TFA salt: The title compound was prepared in a similar manner as Example 322 replacing 4-bromopicolinic acid with 5 bromonicotinic acid. $^1$H NMR (500 MHz, methanol-d$_4$) δ 10.67 (s, 1H), 8.95 (br. s., 1H), 8.86 (s, 1H), 8.33 (s, 1H), 7.99 (d, J=8.8 Hz, 2H), 7.71 (dd, J=8.8, 1.7 Hz, 2H), 7.65-7.56 (m, 2H), 7.48 (d, J=7.4 Hz, 1H), 7.37 (q, J=8.1 Hz, 2H), 7.32-7.25 (m, 1H), 5.93 (s, 1H), 4.09 (dt, J=12.2, 4.6 Hz, 1H), 3.70-3.62 (m, 1H), 3.53-3.45 (m, 1H), 3.41 (s, 3H), 3.30-3.23 (m, 1H), 3.18-3.10 (m, 1H), 3.07 (d, J=8.8 Hz, 1H), 2.96 (br. s., 1H), 2.13 (br. s., 2H), 1.86 (br. s., 2H) ppm. MS (ESI) m/z: 643.2 (M+H)$^+$. Analytical HPLC: RT=8.47 min (Method A).

EXAMPLE 324

4-(2-(2-(3-Chloro-2-fluorophenyl)isonicotinoyl)-5-(4-methoxypiperidin-1-yl)-1,2,3,4-tetrahydroisoquinoline-1-carboxamido)benzoic acid, 2 TFA salt

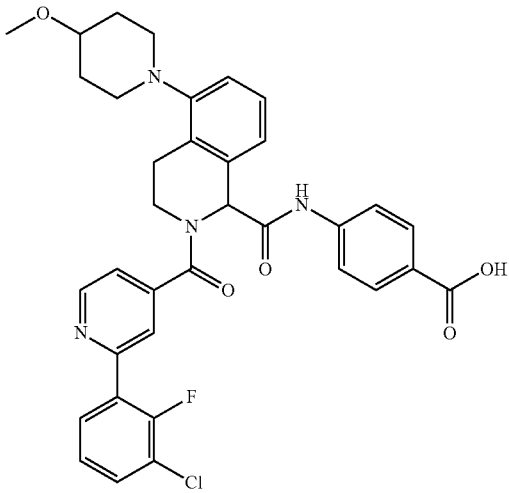 [SMILES: COC1CCN(c2cccc3c2CCN(C(=O)c2ccnc(-c4cccc(Cl)c4F)c2)C3C(=O)Nc2ccc(C(=O)O)cc2)CC1]

Example 324. 4 4-(2-(2-(3-Chloro-2-fluorophenyl)isonicotinoyl)-5-(4-methoxypiperidin-1-yl)-1,2,3,4-tetrahydroisoquinoline-1-carboxamido)benzoic acid, 2 TFA salt: The title compound was prepared in a similar manner as Example 322 replacing 4-bromopicolinic acid with 2-bromoisonicotinic acid. $^1$H NMR (500 MHz, methanol-$d_4$) δ 10.68 (s, 1H), 8.87 (dd, J=5.0, 0.5 Hz, 1H), 8.02-7.97 (m, 3H), 7.88-7.81 (m, 1H), 7.72 (dd, J=8.8, 1.9 Hz, 2H), 7.65-7.61 (m, 2H), 7.47 (d, J=7.4 Hz, 1H), 7.43-7.33 (m, 3H), 7.28 (d, J=6.9 Hz, 1H), 5.93 (s, 1H), 4.03 (dt, J=12.3, 4.8 Hz, 1H), 3.59 (ddd, J=12.5, 9.4, 3.7 Hz, 1H), 3.53-3.46 (m, 1H), 3.41 (s, 3H), 3.25 (dt, J=9.9, 5.0 Hz, 1H), 3.11 (dt, J=15.8, 4.5 Hz, 1H), 3.05 (br. s., 1H), 2.96 (br. s., 1H), 2.18-2.06 (m, 2H), 1.85 (br. s., 2H) ppm. MS (ESI) m/z: 643.2 (M+H)$^+$. Analytical HPLC: RT=8.90 min (Method A).

EXAMPLE 325

4-(2-(6-(3-Chloro-2-fluorophenyl)picolinoyl)-5-(4-methoxypiperidin-1-yl)-1,2,3,4-tetrahydroisoquinoline-1-carboxamido)benzoic acid, 2 TFA salt

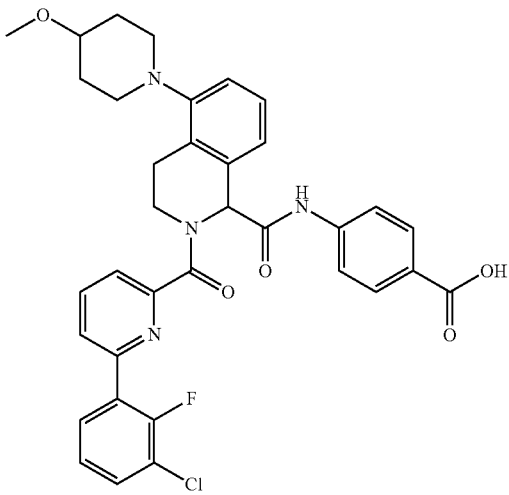 [SMILES: COC1CCN(c2cccc3c2CCN(C(=O)c2cccc(-c4cccc(Cl)c4F)n2)C3C(=O)Nc2ccc(C(=O)O)cc2)CC1]

4-(2-(6-(3-Chloro-2-fluorophenyl)picolinoyl)-5-(4-methoxypiperidin-1-yl)-1,2,3,4-tetrahydroisoquinoline-1-carboxamido)benzoic acid, 2 TFA salt: The title compound was prepared in a similar manner as Example 322 replacing 4-bromopicolinic acid with 6-bromopicolinic acid. $^1$H NMR (500 MHz, methanol-$d_4$) δ 8.11 (q, J=8.2 Hz, 2H), 8.02-7.99 (m, 2H), 7.98-7.95 (m, 2H), 7.91-7.87 (m, 1H), 7.82-7.78 (m, 2H), 7.75-7.71 (m, 2H), 7.63-7.58 (m, 2H), 7.46 (d, J=7.7 Hz, 1H), 7.39-7.24 (m, 5H), 5.94 (s, 1H), 4.24-4.12 (m, 2H), 3.99-3.83 (m, 2H), 3.28-3.21 (m, 1H), 3.20-3.12 (m, 1H), 3.12-2.94 (m, 2H), 2.15 (d, J=12.4 Hz, 2H), 1.86 (br. s., 2H) ppm. MS (ESI) m/z: 643.1 (M+H)$^+$. Analytical HPLC: RT=9.21 min (Method A).

EXAMPLE 326

4-(2-(3-(3-Chloro-2-fluorophenyl)piperidine-1-carbonyl)-5-(4-methoxypiperidin-1-yl)-1,2,3,4-tetrahydroisoquinoline-1-carboxamido)benzoic acid, TFA salt

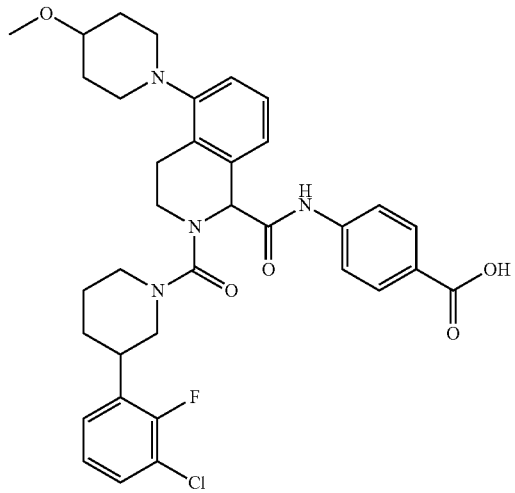 [SMILES: COC1CCN(c2cccc3c2CCN(C(=O)N2CCCC(c4cccc(Cl)c4F)C2)C3C(=O)Nc2ccc(C(=O)O)cc2)CC1]

326A. 3-(3-Chloro-2-fluorophenyl)pyridine, HCl: To a vial was charged 3-bromopyridine (500.1 mg, 3.17 mmol), (3-chloro-2-fluorophenyl)boronic acid (552 mg, 3.17 mmol) and Pd(Ph$_3$P)$_4$ (366 mg, 0.317 mmol). The vial was purged with argon and dioxane (12 mL) and Na$_2$CO$_3$ (2M aq.) (4.75 mL, 9.50 mmol) were added and the reaction heated to 50° C. and stirred overnight at this temperature. The reaction mixture was diluted with EtOAc/H$_2$O and the phases separated. The aqueous layer was further extracted with EtOAc (3×) and the combined organics washed with brine, dried (Na$_2$SO$_4$), filtered and evaporated to give a residue which was purified by normal phase column chromatography, evaporated, taken up in MeOH, and treated with 265 L (1 eq.) of HCl (conc. aq). The solvent was evaporated to give the desired product (681.1 mg, 88% yield) as a colorless solid. MS (ESI) m/z: 208.1 (M+H)$^+$.

326B. 3-(3-Chloro-2-fluorophenyl)piperidine, HCl: To a hydrogenation flask was charged 326A (110.6 mg, 0.453 mmol) and platinum(IV) oxide (72 mg, 0.317 mmol), the vial was purged with nitrogen and to the vial was added EtOH (absolute) (4 mL). The flask was again purged with nitrogen (3×), evacuated and an atmosphere of hydrogen (55 psi) was introduced and the reaction stirred for 1.5 h. The reaction was filtered through CELITE® with the aid of MeOH and evaporated to a dark residue for title compound (111.7 mg, 0.447 mmol, 99% yield). MS (ESI) m/z: 214.1 (M+H)+.

326C. (3-(3-Chloro-2-fluorophenyl)piperidin-1-yl)(1H-imidazol-1-yl)methanone: To a mixture of CDI (9.91 mg, 0.061 mmol) in DCM (1 mL) under nitrogen was added a solution of 326B (13.9 mg, 0.056 mmol) and TEA (7.75 µL, 0.056 mmol) in DCM (2 mL) dropwise and the mixture stirred at ambient temperature overnight. The reaction mixture was diluted with DCM and water, the phases separated and the aqueous extracted twice more with DCM. The combined extracts were dried (MgSO4), filtered and evaporated to give the desired product (14.7 mg, 85.3% yield) as a colorless glassine solid. MS (ESI) m/z: 308.0 (M+H)+.

326D. 1-(3-(3-Chloro-2-fluorophenyl)piperidine-1-carbonyl)-3-methyl-1H-imidazol-3-ium, iodide salt: To a solution of 326C (14.7 mg, 0.0478 mmol) in MeCN (3 mL) was added MeI (13.9 µL, 0.222 mmol) and the mixture stirred at ambient temperature. The reaction mixture was evaporated to give the desired product (18.5 mg, 74.0% yield) as a solid. MS (ESI) m/z: 322.0 (M+H)+.

326E. tert-Butyl 4-(2-(3-(3-chloro-2-fluorophenyl)piperidine-1-carbonyl)-5-(4-methoxypiperidin-1-yl)-1,2,3,4-tetrahydroisoquinoline-1-carboxamido)benzoate, TFA Salt: To a mixture of 327D (18.5 mg, 0.041 mmol) in DCM (1 mL) was added Intermediate 28 (15.32 mg, 0.033 mmol) and TEA (0.023 mL, 0.165 mmol) and the mixture stirred under nitrogen at ambient temperature overnight. The reaction mixture was purified by normal phase column chromatography to the desired product (1.78 mg, 6.6% yield) as a solid. MS (ESI) m/z: 705.2 (M+H)+.

Example 326. 4-(2-(3-(3-Chloro-2-fluorophenyl)piperidine-1-carbonyl)-5-(4-methoxypiperidin-1-yl)-1,2,3,4-tetrahydroisoquinoline-1-carboxamido)benzoic acid, TFA Salt: 326E (1.78 mg, 2.173 µmol) in DCM (0.75 mL) and MeCN (0.15 mL) was added TFA (0.75 mL, 9.73 mmol) and the reaction was stirred at ambient temperature under nitrogen for 1 h. The reaction mixture was evaporated to a residue which was purified by reverse phase prep. HPLC to give the desired product (0.90 mg, 51.6% yield) as a solid. 1H NMR (400 MHz, methanol-d4) δ 10.34 (br. s., 1H), 7.97 (dd, J=8.7, 1.6 Hz, 2H), 7.68 (ddd, J=8.9, 4.0, 1.5 Hz, 2H), 7.38-7.28 (m, 2H), 7.22-7.18 (m, 2H), 7.17-7.11 (m, 1H), 7.07-7.03 (m, 1H), 5.38 (d, J=13.9 Hz, 1H), 4.04-3.95 (m, 1H), 3.83 (t, J=14.7 Hz, 2H), 3.41 (s, 3H), 3.23 (q, J=7.3 Hz, 2H), 3.18-3.13 (m, 3H), 3.04-2.90 (m, 2H), 2.85-2.69 (m, 2H), 2.13-2.00 (m, 3H), 1.93-1.69 (m, 8H) ppm. MS (ESI) m/z: 649.1 (M+H)+. Analytical HPLC: RT=9.75 min (Method A).

EXAMPLE 327

4-(5-(4-Methoxypiperidin-1-yl)-2-(1-(2-methylpyridin-4-yl)-1H-pyrazole-4-carbonyl)-1,2,3,4-tetrahydroisoquinoline-1-carboxamido)benzoic acid, TFA salt

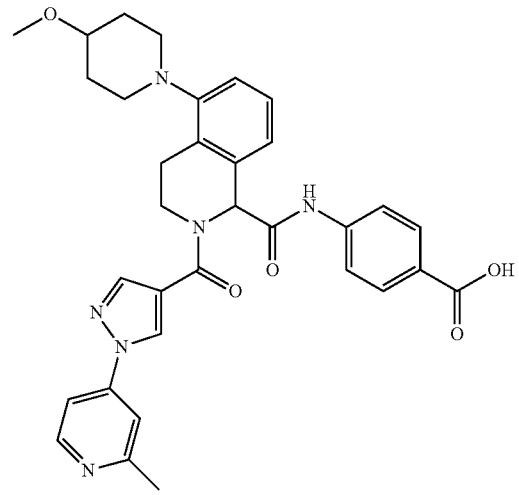 [SMILES: COC1CCN(c2cccc3c2CCN(C(=O)c2cnn(-c4ccnc(C)c4)c2)C3C(=O)Nc2ccc(C(=O)O)cc2)CC1]

327A tert-Butyl 4-(5-(4-methoxypiperidin-1-yl)-2-(1H-pyrazole-4-carbonyl)-1,2,3,4-tetrahydroisoquinoline-1-carboxamido)benzoate: To a septa capped pressure vial was charged 1H-pyrazole-4-carboxylic acid (148 mg, 1.320 mmol), Intermediate 4 (322.5 mg, 1.320 mmol) and tert-butyl 4-isocyanobenzoate (268 mg, 1.320 mmol) followed by MeOH (2.6 mL). The vial was sealed and the contents heated to 50° C. overnight. Reaction mixture was evaporated and purified by normal phase column chromatography to give the title compound (392.0 mg, 53.1% yield) as a straw colored solid. MS (ESI) m/z: 560.0 (M+H)+.

327B tert-Butyl 4-(5-(4-methoxypiperidin-1-yl)-2-(1-(2-methylpyridin-4-yl)-1H-pyrazole-4-carbonyl)-1,2,3,4-tetrahydroisoquinoline-1-carboxamido)benzoate, TFA: To 327A (26.4 mg, 0.047 mmol), (2-methylpyridin-4-yl)boronic acid (12.92 mg, 0.094 mmol) and Cu(OAc)2 (12.85 mg, 0.071 mmol) was added a mixture of pyridine (7.63 µl, 0.094 mmol) in DMF (500 µl) and the reaction stirred under air. The reaction mixture was filtered and purified by reverse phase prep HPLC to give the desired product (27.6 mg, 0.036 mmol, 77% yield) as a solid. MS (ESI) m/z: 651.1 (M+H)+.

Example 327. 4-(5-(4-Methoxypiperidin-1-yl)-2-(1-(2-methylpyridin-4-yl)-1H-pyrazole-4-carbonyl)-1,2,3,4-tetrahydroisoquinoline-1-carboxamido)benzoic acid, TFA Salt To 327B (27.6 mg, 0.036 mmol) in DCM (0.75 mL) and MeCN (0.15 mL) was added TFA (0.75 mL, 9.73 mmol) and the reaction was stirred at ambient temperature under nitrogen for 1 h. The reaction mixture was evaporated to a residue and purified by reverse phase prep HPLC to give desired product (1.62 mg, 2.286 µmol, 6.33% yield) as a solid. 1H NMR (400 MHz, methanol-d4) δ 10.54-10.49 (m, 1H), 9.08-9.03 (m, 1H), 8.75-8.65 (m, 1H), 8.33-8.27 (m, 2H), 8.26-8.20 (m, 1H), 8.01-7.94 (m, 2H), 7.73-7.65 (m, 2H), 7.36-7.24 (m, 2H), 7.10 (d, J=8.8 Hz, 1H), 5.83-5.79 (m, 1H), 4.41-4.32 (m, 1H), 3.84-3.73 (m, 1H), 3.41 (s, 3H), 3.47-3.29 (m, 2H), 3.29-3.21 (m, 2H), 3.21-3.05 (m, 2H), 2.95-2.84 (m, 1H), 2.83-2.76 (m, 3H), 2.73-2.64 (m, 1H), 2.16-2.02 (m, 2H), 1.82-1.65 (m, 2H) ppm. MS (ESI) m/z: 595.0 (M+H)+. Analytical HPLC: RT=0.69 min (Method E).

The Examples in Table 14 were prepared (library format) in a similar manner as Example 327 utilizing the appropriate boronic acid followed by TFA deprotection of t-butyl ester, and purification by reverse phase prep. HPLC.

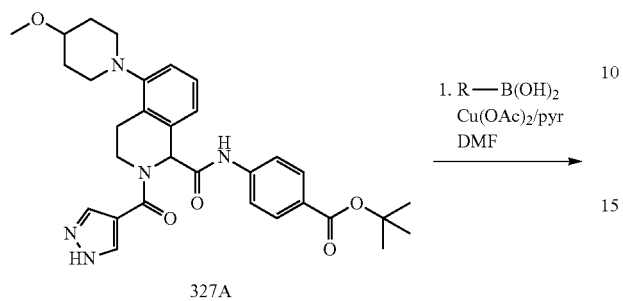

327A

1. R—B(OH)$_2$
Cu(OAc)$_2$/pyr
DMF

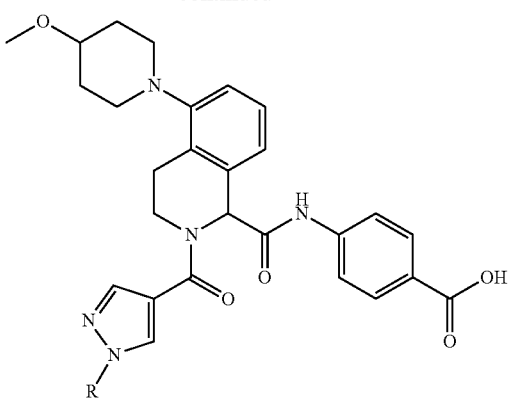

Examples 328-331

TABLE 14

| Example | Structure | Name | LCMS (M + H)$^+$ | HPLC RT (min) |
|---|---|---|---|---|
| 328 | 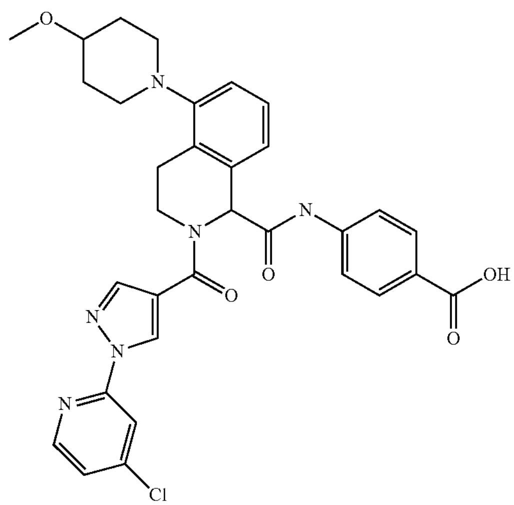 | 4-(2-(1-(5-chloropyridin-3-yl)-1H-pyrazole-4-carbonyl)-5-(4-methoxypiperidin-1-yl)-1,2,3,4-tetrahydroisoquinoline-1-carboxamido)benzoic acid, 2 TFA salt | 615.33 | 2.26 Method D |
| 329 | 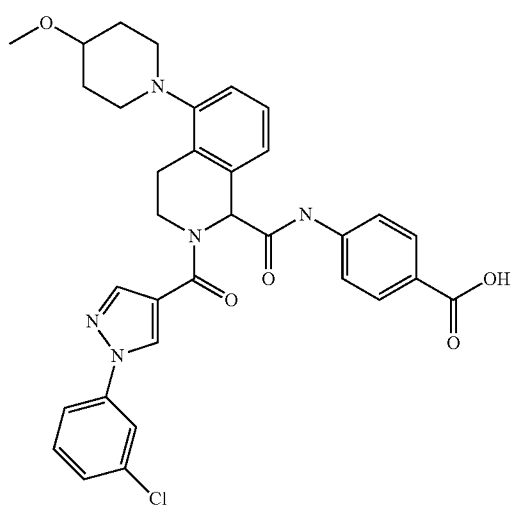 | 4-(2-(1-(3-chlorophenyl)-1H-pyrazole-4-carbonyl)-5-(4-methoxypiperidin-1-yl)-1,2,3,4-tetrahydroisoquinoline-1-carboxamido)benzoic acid, TFA salt | 614.25 | 2.57 Method D |

TABLE 14-continued
| Example | Structure | Name | LCMS (M + H)+ | HPLC RT (min) |
|---------|-----------|------|---------------|---------------|
| 330 | 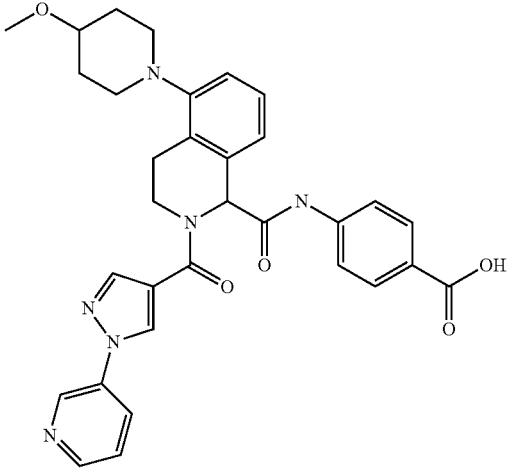 racemate | 4-(5-(4-methoxypiperidin-1-yl)-2-(1-(pyridin-3-yl)-1H-pyrazole-4-carbonyl)-1,2,3,4-tetrahydroisoquinoline-1-carboxamido)benzoic acid, 2 TFA salt | 581.24 | 1.97 Method D |
| 331 | 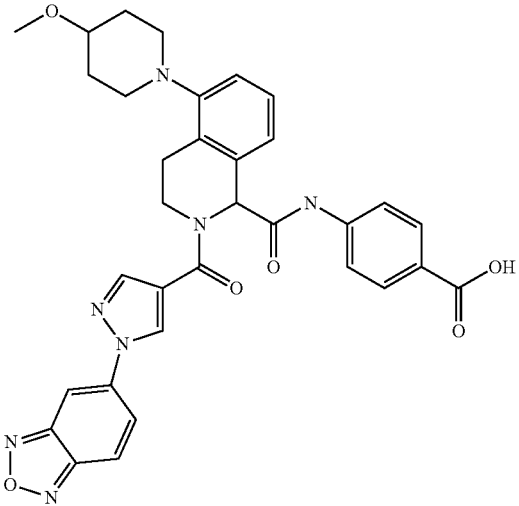 racemate | 4-(2-(1-(benzo[c][1,2,5]oxadiazol-5-yl)-1H-pyrazole-4-carbonyl)-5-(4-methoxypiperidin-1-yl)-1,2,3,4-tetrahydroisoquinoline-1-carboxamido)benzoic acid | 622.23 | 2.39 Method D |

EXAMPLE 332

4-(2-(1-(3-Chloro-2-fluorophenyl)-1H-1,2,3-triazole-4-carbonyl)-5-(2-oxopyridin-1(2H)-yl)-1,2,3,4-tetrahydroisoquinoline-1-carboxamido)benzoic acid

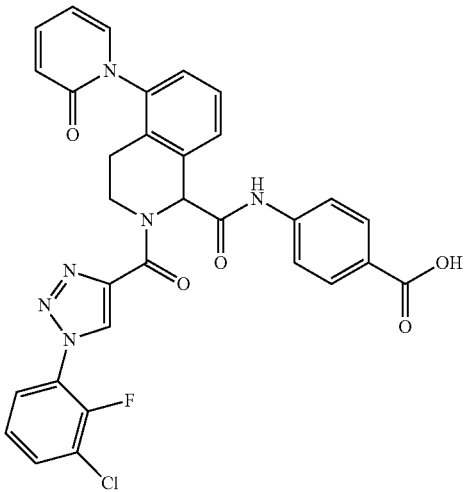 [SMILES: O=C(O)c1ccc(NC(=O)C2c3cccc(-n4ccccc4=O)c3CCN2C(=O)c2cn(-c3cccc(Cl)c3F)nn2)cc1]

332A. 1-((4-(tert-Butoxycarbonyl)phenyl)carbamoyl)-2-(1-(3-chloro-2-fluorophenyl)-1H-1,2,3-triazole-4-carbonyl)-1,2,3,4-tetrahydroisoquinolin-5-yl)boronic Acid: To a vial was charged Intermediate 24 (27.7 mg, 0.042 mmol), 4,4,4',4',5,5,5',5'-octamethyl-2,2'-bi(1,3,2-dioxaborolane) (12.89 mg, 0.051 mmol), potassium acetate (12.45 mg, 0.127 mmol), and PdCl$_2$(dppf) (3.09 mg, 4.23 µmol). The vial was capped with a septum, the vial purged with Ar and dioxane (1.5 mL) was added followed by heating under Ar to 85° C. The reaction was quenched with H$_2$O, EtOAc added and the phases separated. The aqueous layer was further extracted with EtOAc (3×) and the combined organics washed with brine, dried (Na$_2$SO$_4$), filtered and evaporated to a residue and purified by reverse phase prep HPLC to give the desired product ((2.5 mg, 4.0 mol). MS (ESI) m/z: 619.8 (M+H)$^+$.

332B. tert-Butyl 4-(2-(1-(3-chloro-2-fluorophenyl)-1H-1,2,3-triazole-4-carbonyl)-5-(2-oxopyridin-1(2H)-yl)-1,2,3,4-tetrahydroisoquinoline-1-carboxamido)benzoate: To 332A (2.5 mg, 4.0 µmol) in DMF-d7 (0.75 mL) was added pyridin-2(1H)-one (0.38 mg, 4.0 µmol) followed by a solution of pyridine (0.651, 8.1 µmol) in DCM (0.5 mL). The mixture was stirred for 5 min then Cu(OAc)$_2$ (1.1 mug, 6.1 µmol) was added and the reaction stirred under air overnight. The reaction mixture was diluted with MeOH and purified by reverse phase prep HPLC to give the desired product as a solid. MS (ESI) m/z: 668.9 (M+H)$^+$.

Example 332. 4-(2-(1-(3-Chloro-2-fluorophenyl)-1H-1,2,3-triazole-4-carbonyl)-5-(2-oxopyridin-1(2H)-yl)-1,2,3,4-tetrahydroisoquinoline-1-carboxamido)benzoic acid: To 332B in DCM (anhydrous) (0.75 mL) and MeCN (anhydrous) (0.15 mL) was added TFA (0.75 mL, 9.73 mmol) and the reaction was stirred at ambient temperature under nitrogen for 1 h. The solvent was removed under reduced pressure to yield a residue which was purified by prep HPLC to give the desire product (0.21 mg, 0.308 µmol) as a solid. $^1$H NMR (500 MHz, methanol-d$_4$) δ 8.89 (s, 1H), 8.13 (br. s., 1H), 7.99 (d, J=8.3 Hz, 2H), 7.87 (t, J=7.3 Hz, 2H), 7.72 (d, J=19.5 Hz, 3H), 7.52 (s, 1H), 7.47-7.36 (m, 3H), 7.16- 7.12 (m, 1H), 7.09 (d, J=7.7 Hz, 1H), 7.01 (d, J=8.5 Hz, 1H), 6.08 (s, 1H), 4.57 (s, 2H), 3.13-2.96 (m, 2H) ppm. MS (ESI) m/z: 612.8 (M+H)$^+$. Analytical HPLC: RT=9.75 min (Method A).

EXAMPLE 333

4-(2-(1-(3-Chloro-2-fluorophenyl)-1H-1,2,3-triazole-4-carbonyl)-5-(prop-1-en-2-yl)-1,2,3,4-tetrahydroisoquinoline-1-carboxamido)benzoic acid

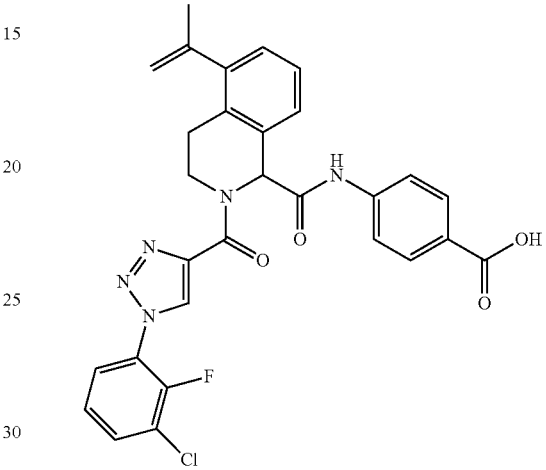

333A. 2-(Isoquinolin-5-yl)propan-2-ol: To a solution of 5-bromoisoquinoline (980.5 mg, 4.71 mmol) in THF (18 mL) under nitrogen and cooled to −78° C. was added dropwise n-BuLi (1.6 M in hexanes) (3.09 mL, 4.95 mmol). The mixture was stirred at this temperature for 20 minutes then a solution of acetone (0.381 mL, 5.18 mmol) in THF (2 mL) was added and the mixture allowed to warm to 0° C. The reaction was quenched with 5 mL saturated NH$_4$Cl and ethyl acetate was added. The phases were separated and the aqueous extracted twice more with ethyl acetate, the combined organic layers were washed with brine, dried (Na$_2$SO$_4$), filtered and evaporated to a residue which was purified by normal phase column chromatography give 333A (497.2 mg, 56.3% yield). MS (ESI) m/z: 188.2 (M+H)$^+$.

333B. 2-(1,2,3,4-Tetrahydroisoquinolin-5-yl)propan-2-ol: To a 50 mL hydrogenation flask was charged 333A (277.4 mg, 1.482 mmol) and platinum(IV) oxide (33.6 mg, 0.148 mmol), the flask was purged with nitrogen and to the flask was added EtOH (absolute) (15 mL). The flask was again purged with nitrogen (3×), evacuated and an atmosphere of hydrogen (55 psi) was introduced and the reaction stirred overnight. The reaction was filtered through CELITE® with the aid of MeOH and evaporated to give 333B (292.2 mg, 1.375 mmol, 93% yield) as a faint yellow colored solid. MS (ESI) m/z: 192.2 (M+H)$^+$.

333C. 2-(3,4-Dihydroisoquinolin-5-yl)propan-2-ol: To 338B (292.2 mg, 1.528 mmol) in DCM (15 mL) was added MnO$_2$ (2391 mg, 27.5 mmol) portionwise and the mixture stirred under nitrogen at ambient temperature overnight. The reaction mixture is filtered through a sintered glass funnel with 1.5 cm CELITE® pad with the aid of DCM and evaporated to give 333C (217.7 mg, 75% yield) as a solid. MS (ESI) m/z: 190.1 (M+H)$^+$.

333D. tert-Butyl 4-(2-(1-(3-chloro-2-fluorophenyl)-1H-1,2,3-triazole-4-carbonyl)-5-(2-hydroxypropan-2 yl) 1,2,3,4 tetrahydroisoquinoline-1-carboxamido)benzoate: To a septa capped pressure vial was charged 1-(3-chloro-2-fluorophenyl)-1H- 1,2,3-triazole-4-carboxylic acid (40.3 mg, 0.167 mmol), 334C (31.6 mg, 0.167 mmol) and tert-butyl 4-isocyanobenzoate (33.9 mg, 0.167 mmol) to which was added MeOH (334 µl). The vial was sealed and the contents heated to 50° C. overnight. The reaction mixture was purified by normal phase column chromatography to 333D (56.3 mg, 0.089 mmol, 53.2% yield) as a colorless solid. MS (ESI) m/z: 634.0 (M+H)$^+$.

Example 333. 4-(2-(1-(3-Chloro-2-fluorophenyl)-1H-1,2,3-triazole-4-carbonyl)-5-(prop-1-en-2-yl)-1,2,3,4-tetrahydroisoquinoline-1-carboxamido)benzoic acid: To 333D (3.5 mg, 5.52 µmol) in DCM (0.75 mL) and MeCN (0.15 mL) was added TFA (0.75 mL, 9.73 mmol) and the reaction was stirred at ambient temperature under nitrogen for 1 h. The solvent was removed under reduced pressure to yield a residue which was purified by reverse phase prep HPLC to give Example 333 (2.57 mg, 79% yield) as a solid. $^1$H NMR (500 MHz, methanol-$d_4$) δ 10.57 (s, 1H), 8.90 (d, J=2.2 Hz, 1H), 8.02-7.95 (m, 2H), 7.91-7.81 (m, 1H), 7.77-7.66 (m, 3H), 7.56-7.41 (m, 2H), 7.33-7.25 (m, 1H), 7.20 (d, J=6.9 Hz, 1H), 5.95 (s, 1H), 5.32 (s, 1H), 4.91 (s, 1H), 4.65 (dt, J=12.7, 5.1 Hz, 1H), 4.19 (ddd, J=12.8, 9.2, 3.9 Hz, 1H), 3.20-3.12 (m, 1H), 2.10 (s, 3H) ppm. MS (ESI) m/z: 559.9 (M+H)$^+$. Analytical HPLC: RT=13.12 min (Method A).

EXAMPLE 334

4-(5-Amino-2-(1-(3-chloro-2-fluorophenyl)-1H-1,2,3-triazole-4-carbonyl)-1,2,3,4-tetrahydroisoquinoline-1-carboxamido)benzoic acid, TFA salt

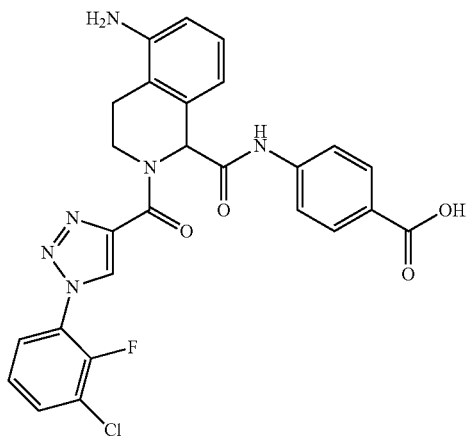 [SMILES: Nc1cccc2c1CCN(C(=O)c1cn(-c3cccc(Cl)c3F)nn1)C2C(=O)Nc1ccc(C(=O)O)cc1]

334A. 1,2,3,4-Tetrahydroisoquinolin-5-amine: Isoquinolin-5-amine (1.4 g, 9.71 mmol) was hydrogenated in the presence of PtO$_2$ in EtOH (100 mL). The reaction mixture was filtered and concentrated to give 335A. MS (ESI) m/z: 149.0 (M+H)$^+$.

334B. tert-Butyl 5-amino-3,4-dihydroisoquinoline-2(1H)-carboxylate: 334A was dissolved in dioxane (20 mL) and 1M NaOH (12.62 mL, 12.62 mmol) and Boc$_2$O was added (2.26 mL, 9.71 mmol). The organic solvent was evaporated and the remaining aqueous was diluted with water (20 mL) and ethyl acetate (50 mL). The aqueous layer was extracted with ethyl acetate (2×20 mL) and the combined organic layers were washed with brine (15 mL) and dried (MgSO$_4$), and evaporated to give 334B (2.4 g) as a light pink solid. $^1$H NMR (400 MHz, chloroform-d) δ 7.04 (t, J=7.7 Hz, 1H), 6.70-6.52 (m, 2H), 4.57 (s, 2H), 3.76-3.72 (m, 2H), 2.59 (t, J=5.9 Hz, 2H), 1.54-1.45 (m, 9H) ppm.

334C. tert-Butyl 5-(2,2,2-trifluoroacetamido)-3,4-dihydroisoquinoline-2(1H)-carboxylate: To a 0° C. solution of 334B (1 g, 4.03 mmol) in DCM (25 mL) was added TEA (0.842 mL, 6.04 mmol) and trifluoroacetic anhydride (0.569 mL, 4.03 mmol). The solvent was evaporated and the residue was purified by normal phase column chromatography to give 334C (1.27 g). $^1$H NMR (400 MHz, chloroform-d) δ 7.75 (br. s., 1H), 7.59 (d, J=6.8 Hz, 1H), 7.34-7.25 (m, 1H), 7.10 (d, J=7.6 Hz, 1H), 4.62 (s, 2H), 3.71 (t, J=5.9 Hz, 2H), 2.71 (t, J=5.8 Hz, 2H), 1.51 (s, 9H) ppm. MS (ESI) m/z: 244.9 (M+H-Boc)+.

334D. N-(3,4-Dihydroisoquinolin-5-yl)-2,2,2-trifluoroacetamide: 334C (1.27 g) was combined with water (10 mL) and 2,2,2-trifluoroethanol (1.5 mL) and heated in a microwave at 150° C. for 20 minutes. The solvent was evaporated and the residue was combined with dichloromethane and MnO$_2$ (6.30 g, 72.5 mmol) was added. The reaction mixture is filtered through CELITE® to give 334D (0.83 g) as a brown foam. MS (ESI) m/z: 243.0 (M+H)$^+$.

334E. tert-Butyl 4-(2-(1-(3-chloro-2-fluorophenyl)-1H-1,2,3-triazole-4-carbonyl)-5-(2,2,2-trifluoroacetamido)-1,2,3,4-tetrahydroisoquinoline-1-carboxamido) benzoate: In a vial was combined 1-(3-chloro-2-fluorophenyl)-1H-1,2,3-triazole-4-carboxylic acid (359 mg, 1.48 mmol), 334D (0.36 g, 1.486 mmol) and tert-butyl 4-isocyanobenzoate (0.302 g, 1.486 mmol) in MeOH (2.4 mL) and the mixture heated to 50° C. overnight. The reaction mixture was purified by reverse phase prep HPLC to give 334E (62.9 mg). MS (ESI) m/z: 686.9 (M+H)$^+$.

334F. tert-Butyl 4-(5-amino-2-(1-(3-chloro-2-fluorophenyl)-1H-1,2,3-triazole-4-carbonyl)-1,2,3,4-tetrahydroisoquinoline-1-carboxamido)benzoate: To a solution of 334E (62.9 mg, 0.092 mmol) in MeOH (3 mL) was added NaBH$_4$ (17.32 mg, 0.458 mmol) and the mixture stirred under nitrogen overnight. Additional NaBH$_4$ (17.32 mg, 0.458 mmol) was added and the mixture stirred under nitrogen for 2 h after which the reaction was quenched into NaHCO$_3$ and extracted with EtOAc (3×), the combined organics washed with brine, dried (Na$_2$SO$_4$), filtered and evaporated to a residue which was purified by normal phase column chromatography to give 334F (28.9 mg, 53.4% yield) as a solid. MS (ESI) m/z: 591.0 (M+H)$^+$.

Example 334. 4-(5-Amino-2-(1-(3-chloro-2-fluorophenyl)-1H-1,2,3-triazole-4-carbonyl)-1,2,3,4-tetrahydroisoquinoline-1-carboxamido)benzoic acid, TFA salt: To 334F (3.86 mg, 6.53 µmol) in DCM (0.75 mL) and MeCN (0.15 mL) was added TFA (0.75 mL, 9.73 mmol) and the reaction was stirred at ambient temperature under nitrogen for 1 h. The solvent was removed under reduced pressure to yield a residue which was purified by reverse phase prep HPLC to give Example 334 (2.28 mg, 51.1% yield) as a solid. $^1$H NMR (500 MHz, methanol-$d_4$) δ 10.60 (s, 1H), 8.93 (d, J=1.9 Hz, 1H), 8.00 (d, J=8.5 Hz, 2H), 7.91-7.85 (m, 1H), 7.78-7.69 (m, 3H), 7.50-7.29 (m, 3H), 7.19 (d, J=7.7 Hz, 1H), 6.04 (s, 1H), 4.61 (s, 2H), 3.23-2.97 (m, 3H) ppm. MS (ESI) m/z: 535.0 (M+H)$^+$. Analytical HPLC. RT—6.33 min (Method A).

EXAMPLE 335

N-(4-Carbamoylphenyl)-2-(1-(3-chloro-2-fluorophenyl)-1H-1,2,3-triazole-4-carbonyl)-5-(4-methoxypiperidin-1-yl)-1,2,3,4-tetrahydroisoquinoline-1-carboxamide, TFA salt

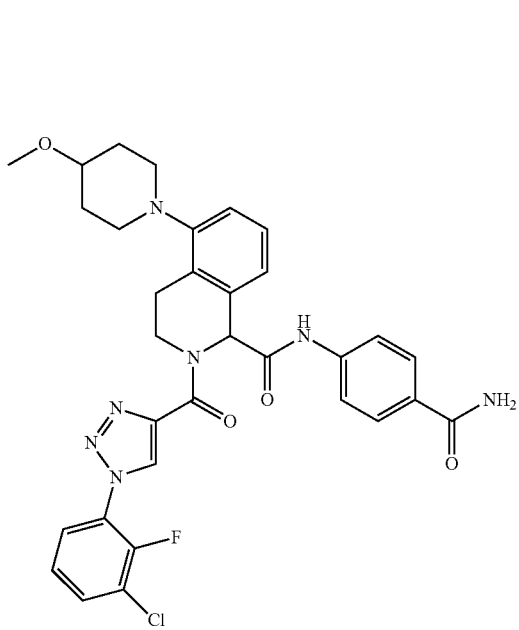 [SMILES: COC1CCN(c2cccc3c2CCN(C(=O)c2cn(-c4cccc(Cl)c4F)nn2)C3C(=O)Nc2ccc(C(N)=O)cc2)CC1]

Example 335. N-(4-Carbamoylphenyl)-2-(1-(3-chloro-2-fluorophenyl)-1H-1,2,3-triazole-4-carbonyl)-5-(4-methoxypiperidin-1-yl)-1,2,3,4-tetrahydroisoquinoline-1-carboxamide, TFA salt: To a solution of Example 215 (45.4 mg, 0.072 mmol) in DCM (2 mL) and under nitrogen was added 1-chloro-N,N,2-trimethylpropenylamine (9.88 μl, 0.072 mmol) and the reaction allowed to stir for 30 min. To this mixture was added dropwise to a solution of ammonia (7N in MeOH) (0.102 mL, 0.717 mmol) and the mixture stirred at ambient temperature overnight. The reaction mixture was evaporated to a residue which was purified by reverse phase prep HPLC to give Example 335 (3.48 mg, 6.18% yield) as a solid. $^1$H NMR (500 MHz, methanol-$d_4$) δ 8.91 (d, J=2.2 Hz, 1H), 7.91-7.80 (m, 3H), 7.78-7.64 (m, 3H), 7.54-7.31 (m, 4H), 5.94 (s, 1H), 4.74 (dt, J=12.8, 4.9 Hz, 1H), 4.20 (t, J=8.8 Hz, 1H), 3.59-3.49 (m, 1H), 3.43 (s, 3H), 3.21-2.99 (m, 2H), 2.24-2.12 (m, 4H), 1.94 (br. s., 4H) ppm. MS (ESI) m/z: 631.9 (M+H)$^+$. Analytical HPLC: RT=7.72 min (Method A).

EXAMPLE 336

4-((S)-2-((R)-3-(3-Chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid, TFA salt

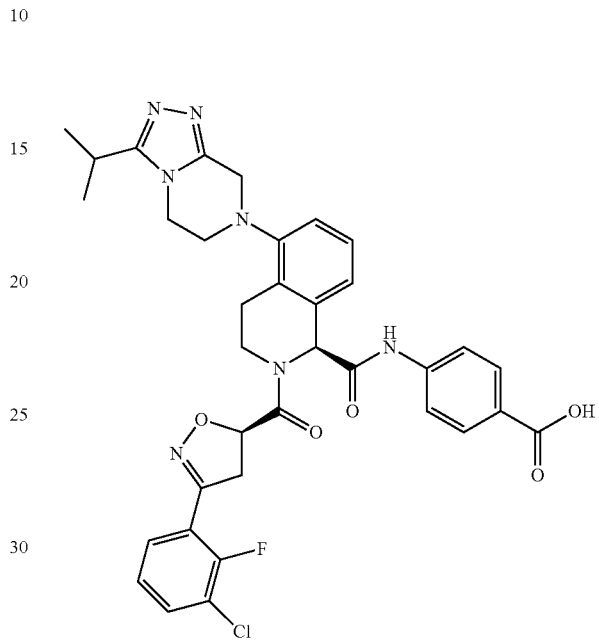

336A. 5-(3-Isopropyl-5,6-dihydro-[1,2,4]triazolo[4,3-a]pyrazin-7(8H)-yl)isoquinoline: 5-Bromoisoquinoline (5.2 g, 24.99 mmol) and 3-isopropyl-5,6,7,8-tetrahydro-[1,2,4]triazolo[4,3-a]pyrazine (4.99 g, 30.0 mmol) were added in equal portions to four separate large microwave vials containing Toluene(15 mL) and degassed with argon for 30 minutes. Sodium tert-butoxide (4.80 g, 50.0 mmol), BINAP (0.467 g, 0.750 mmol) and Pd$_2$(dba)$_3$ (0.229 g, 0.250 mmol) were added, the reactions sealed and heated to 90° C. for 3 days. After cooling to rt, the mixture was diluted with EtOAc (200 mL)/water (100 mL) and filtered. The aqueous layer was extracted with EtOAc (2×50 mL). The combined organic layer was washed with brine (50 mL), dried over MgSO4, filtered, concentrated, and purified by normal phase column chromatography to give 336A (4.65 g, 63.4% yield) as an olive foam. MS (ESI) m/z: 294 (M+H)$^+$.

336B. 5-(3-Isopropyl-5,6-dihydro-[1,2,4]triazolo[4,3-a]pyrazin-7(8H)-yl)-1,2,3,4-tetrahydroisoquinoline: 1A (5.92 g, 20.18 mmol) and platinum oxide (10% mmol catalyst load) were added to EtOH (200 mL) and subjected to a hydrogen atmosphere (55 psi) overnight. The suspension was filtered through a plug of CELITE® and filtrate concentrated. Yield assumed quantitative. Carried forward to next reaction as is. MS (ESI) m/z: 298 (M+H)$^+$.

336C. 5-(3-Isopropyl-5,6-dihydro-[1,2,4]triazolo[4,3-a]pyrazin-7(8H)-yl)-3,4-dihydroisoquinoline: Manganese dioxide (10.52 g, 121 mmol) was added to a stirring solution of 336B (2.0 g, 6.72 mmol) in DCM (75 mL) overnight. The reaction mixture was filtered through a plug of CELITE® and the filtrate concentrated to give 336C (1.54 g, 5.21 mmol, 78% yield) as a tan foam. Carried forward to next reaction as is. MS (ESI) m/z: 296 (M+H)$^+$.

336D. tert-Butyl 4-(2-((R)-3-(3-chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoate: 336C (1.90 g, 6.43 mmol), tert-butyl 4-isocyanobenzoate (1.31 g, 6.43 mmol), and (R)-3-(3-chloro-2-fluorophenyl)-4,5-dihydroisoxazole-5-carboxylic acid (1.57 g, 6.43 mmol) were added to MeOH (12.86 ml) and heated to 55° C. for 3 days. After evaporating excess MeOH, the crude material was purified by normal phase column chromatography to give 336D (3.33 g, 4.49 mmol, 69.7% yield) as diastereomeric mixture. MS (ESI) m/z: 742 (M+H)$^+$.

336E. tert-Butyl 4-((R)-2-((R)-3-(3-chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoate: The compound was isolated by chiral separation of 336D as the early eluting diastereomer using CHIRALPAK® IB, 30×250 mm ID, 5 μm eluting with 45% ethanol-isopropanol/55% CO$_2$ at 85 mL/min, 135 Bar, 40° C. MS (ESI) m/z: 742 (M+H)$^+$. Analytical HPLC: RT=7.52 min (Method B).

336F. tert-Butyl 4-((S)-2-((R)-3-(3-chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoate: The compound was isolated by chiral separation of 336D as the late eluting diastereomer using CHIRALPAK® IB, 30×250 mm ID, 5 μm eluting with 45% ethanol-isopropanol/55% CO$_2$ at 85 mL/min, 135 Bar, 40° C. This diastereomer elutes early by reverse phase analytical HPLC with respect to its opposite diastereomer. MS (ESI) m/z: 742 (M+H)$^+$. Analytical HPLC: RT=7.31 min (Method B).

Example 336. 4-((S)-2-((R)-3-(3-Chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid, TFA salt: 336F (1.0 g, 1.347 mmol) was treated with 50% TFA/DCM and stirred overnight. The reaction mixture was concentrated to dryness, purified by reverse phase chromatography, and product fractions lyophilized to give Example 336 (560 mg, 55%) as a white solid. $^1$H NMR (400 MHz, DMSO-d$_6$) δ 10.78 (s, 1H), 7.83-7.78 (m, 2H), 7.69-7.62 (m, 4H), 7.36 (d, J=7.3 Hz, 1H), 7.24 (q, J=7.5 Hz, 2H), 7.10 (d, J=7.9 Hz, 1H), 5.73 (s, 1H), 5.68 (dd, J=11.6, 7.6 Hz, 1H), 4.30 (br. s., 2H), 4.17 (dd, J=12.1, 5.5 Hz, 3H), 3.82 (dd, J=16.0, 7.6 Hz, 1H), 3.65-3.57 (m, 2H), 3.40-3.13 (m, 4H), 3.13-2.99 (m, 2H), 1.28 (s, 3H), 1.27 (s, 3H) ppm. MS (EST) m/z: 686.1 (M+H)$^+$. Analytical HPLC: RT=6.036 min (Method B).

EXAMPLE 337

4-((R)-2-((R)-3-(3-Chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid, TFA salt

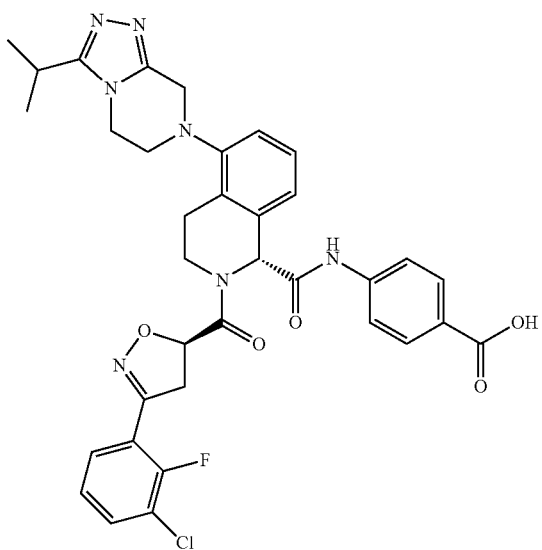 [SMILES: CC(C)c1nnc2n1CCN(c1cccc3c1CCN(C(=O)[C@H]1CC(c4cccc(Cl)c4F)=NO1)[C@H]3C(=O)Nc1ccc(C(=O)O)cc1)C2]

Example 337. 4-((R)-2-((R)-3-(3-Chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid, TFA salt: The title compound was prepared in a similar manner as Example 336 from 336E instead of 336F. $^1$H NMR (400 MHz, DMSO-d$_6$) δ 12.78 (br. s., 1H), 10.89 (br. s., 1H), 7.89 (d, J=8.8 Hz, 2H), 7.75-7.70 (m, 4H), 7.47 (d, J=7.5 Hz, 1H), 7.37-7.31 (m, 2H), 7.20 (d, J=7.9 Hz, 1H), 5.89 (dd, J=11.3, 7.2 Hz, 1H), 5.81 (s, 1H), 4.46 (br. s., 2H), 4.33-4.21 (m, 3H), 3.91 (dd, J=16.1, 7.0 Hz, 1H), 3.80-3.68 (m, 2H), 3.43-3.29 (m, 2H), 3.24-3.17 (m, 1H), 3.13-3.04 (m, 1H), 1.39 (s, 3H), 1.37 (s, 3H). MS (ESI) m/z: 686.1 (MI IT)$^+$. Analytical HPLC: RT=6.17 min (Method B).

EXAMPLE 338

4-((S)-2-((S)-3-(3-Chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid, TFA salt

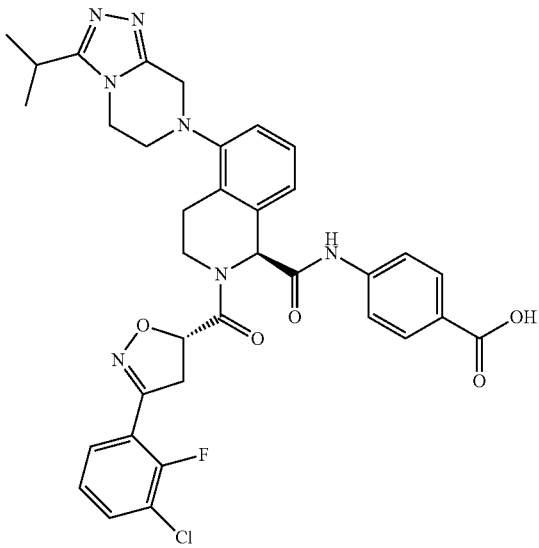 [SMILES: CC(C)c1nnc2n1CCN(c1cccc3c1CCN(C(=O)[C@@H]1CC(c4cccc(Cl)c4F)=NO1)[C@@H]3C(=O)Nc1ccc(C(=O)O)cc1)C2]

338A. tert-Butyl 4-(5-(3-isopropyl-5,6-dihydro-[1,2,4]triazolo[4,3-a]pyrazin-7(8H)-yl)-2-(2,2,2-trifluoroacetyl)-1,2,3,4-tetrahydroisoquinoline-1-carboxamido)benzoate: 337C (0.50 g, 1.69 mmol), tert-butyl 4-isocyanobenzoate (0.344 g, 1.69 mmol), TFA (0.193 g, 1.69 mmol), and MeOH (3.39 ml) were added to a small pressure vial. The vial was sealed and the mixture heated to 50° C. overnight. The reaction mixture was absorbed onto silica gel and purified by normal phase chromatography (0.511 g, 49.3% yield) to give 338A as a brown foam. MS (ESI) m/z: 613.4 (M+H)$^+$.

338B. tert-Butyl 4-(5-(3-isopropyl-5,6-dihydro-[1,2,4]triazolo[4,3-a]pyrazin-7(8H)-yl)-1,2,3,4-tetrahydroisoquinoline-1-carboxamido)benzoate, TFA salt: 338A. (0.500 g, 0.816 mmol) was dissolved in MeOH (10 mL)/DCM (3 mL), cooled to 0° C., and NaBH$_4$ (0.175 g, 4.90 mmol) added. After 2 hours, the reaction was concentrated to dryness. The residue was dissolved in EtOAc, washed in 1.5M K$_2$HPO$_4$ solution, brine and dried over sodium sulfate overnight. The solution was filtered, concentrated, and purified by reverse phase prep HPLC to give 338B as a clear, colorless oil (300 mg, 12.8%). MS (ESI) m/z: 517.3 (M+H)$^+$.

338C. tert-Butyl 4-((S)-2-((S)-3-(3-chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoate oate: T$_3$P (0.185 g, 0.290 mmol) was added to a solution of 338B (0.100 g, 0.194 mmol), (S)-3-(3-chloro-2-fluorophenyl)-4,5-dihydroisoxazole-5-carboxylic acid (0.052 g, 0.213 mmol), and DIPEA (0.101 ml, 0.581 mmol) in EtOAc (5 mL). After 4 hours, the reaction mixture was concentrated and purified by reverse phase prep. HPLC. The desired product was isolated as the early eluting diastereomer (11.4 mgs, 15.9%) after concentrating on a SPEEDVAC® overnight. MS (ESI) m/z: 742 (M+H)$^+$.

338D. tert-Butyl 4-((R)-2-((S)-3-(3-chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoate: The compound was isolated as the late eluting diastereomer (13.4 mgs, 18.7%) after 338C purification step. MS (ESI) m/z: 742 (M+H)$^+$.

Example 338. 4-((S)-2-((S)-3-(3-Chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid, TFA salt: 338C (0.0103 g, 10.62 µmol) was treated with 50% TFA/DCM. After 2 hours, the reaction mixture was concentrated, and purified by reverse phase prep. HPLC to give Example 338 (7.3 mg, 75%). $^1$H NMR (500 MHz, DMSO-d$_6$) δ 10.89 (s, 1H), 7.93-7.87 (m, 2H), 7.80-7.69 (m, 4H), 7.43 (d, J=7.7 Hz, 1H), 7.36-7.30 (m, 2H), 7.17 (d, J=8.0 Hz, 1H), 5.82-5.73 (m, 2H), 4.29-4.18 (m, 3H), 3.71 (d, J=11.3 Hz, 2H), 3.24-3.09 (m, 5H), 1.35 (dd, J=6.9, 1.7 Hz, 6H) ppm. MS (ESI) m/z: 686.1 (M+H)$^+$. Analytical HPLC: RT=1.37 min (Method C).

EXAMPLE 339

4-((R)-2-((S)-3-(3-Chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid, TFA salt

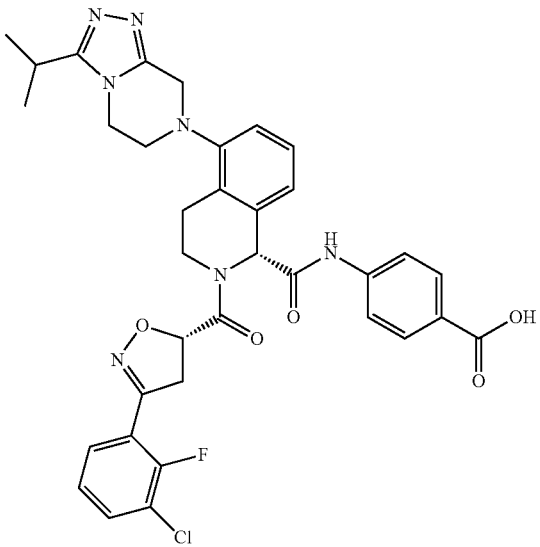 [SMILES: CC(C)c1nnc2n1CCN(c1cccc3c1CCN(C(=O)[C@@H]1CC(c4cccc(Cl)c4F)=NO1)[C@H]3C(=O)Nc1ccc(C(=O)O)cc1)C2]

Example 339. 4-((R)-2-((S)-3-(3-Chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid, TFA salt: The title compound was prepared in a similar manner as Example 338 from 338D instead of 338C. $^1$H NMR (500 MHz, DMSO-d$_6$) δ 10.89-10.85 (m, 1H), 7.91-7.83 (m, 2H), 7.77-7.63 (m, 5H), 7.42 (d, J=7.7 Hz, 1H), 7.36-7.29 (m, 2H), 7.17 (d, J=8.0 Hz, 1H), 5.89-5.85 (m, 1H), 5.76 (s, 1H), 4.27-4.14 (m, 4H), 3.95-3.84 (m, 3H), 3.79-3.70 (m, 2H), 3.20 (dd, J=13.8, 6.9 Hz, 2H), 3.11-3.03 (m, 2H), 1.36-1.26 (m, 6H) ppm. MS (ESI) m/z: 686.1 (M+H)$^+$. Analytical HPLC: RT=1.38 min (Method C).

EXAMPLE 340

4-((S)-2-((R)-3-(3-Chloro-2-fluorophenyl)-4,5-dihydroisoxazole-5-carbonyl)-5-(3-methyl-5,6-dihydro-[1,2,4]triazolo[4,3-a]pyrazin-7(8H)-yl)-1,2,3,4-tetrahydroisoquinoline-1-carboxamido)benzoic acid, TFA salt

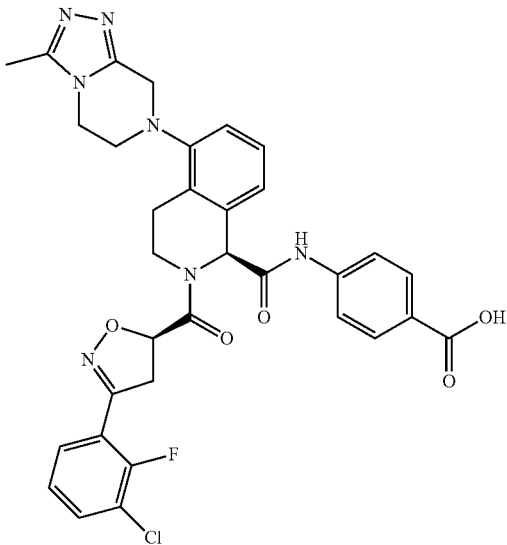 [SMILES: Cc1nnc2n1CCN(c1cccc3c1CCN(C(=O)[C@H]1CC(c4cccc(Cl)c4F)=NO1)[C@@H]3C(=O)Nc1ccc(C(=O)O)cc1)C2]

Example 340. 4-((S)-2-((R)-3-(3-Chloro-2-fluorophenyl)-4,5-dihydroisoxazole-5-carbonyl)-5-(3-methyl-5,6-dihydro-[1,2,4]triazolo[4,3-a]pyrazin-7(8H)-yl)-1,2,3,4-tetrahydroisoquinoline-1-carboxamido)benzoic acid, TFA salt: The title compound was prepared in a similar manner as Example 336 replacing 3-isopropyl-5,6,7,8-tetrahydro-[1,2,4]triazolo[4,3-a]pyrazine with 3-methyl-5,6,7,8-tetrahydro-[1,2,4]triazolo[4,3-a]pyrazine during the Buchwald reaction step. The compound was isolated as a the early eluting isomer during reverse phase prep. HPLC. MS (ESI) m/z: 659 (M+H)$^+$. Analytical HPLC: RT=5.69 min (Method B).

EXAMPLE 341

4-((R)-2-((R)-3-(3-Chloro-2-fluorophenyl)-4,5-dihydroisoxazole-5-carbonyl)-5-(3-methyl-5,6-dihydro-[1,2,4]triazolo[4,3-a]pyrazin-7(8H)-yl)-1,2,3,4-tetrahydroisoquinoline-1-carboxamido)benzoic acid, TFA salt

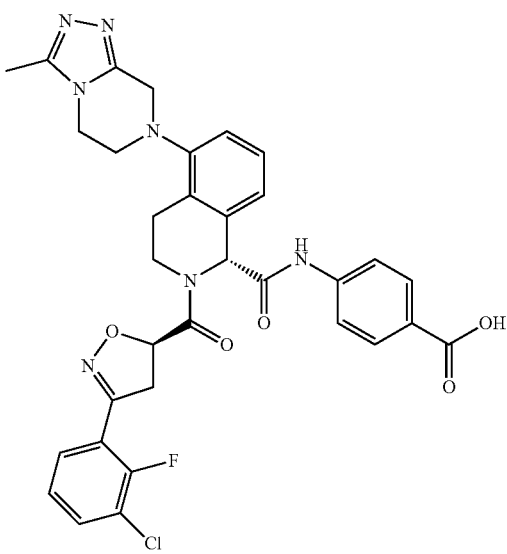 [SMILES: Cc1nnc2n1CCN(c1cccc3c1CCN(C(=O)[C@H]1CC(c4cccc(Cl)c4F)=NO1)[C@H]3C(=O)Nc1ccc(C(=O)O)cc1)C2]

Example 341. 4-((R)-2-((R)-3-(3-Chloro-2-fluorophenyl)-4,5-dihydroisoxazole-5-carbonyl)-5-(3-methyl-5,6-dihydro-[1,2,4]triazolo[4,3-a]pyrazin-7(8H)-yl)-1,2,3,4-tetrahydroisoquinoline-1-carboxamido)benzoic acid, TFA salt: The title compound was prepared in a similar manner as Example 336 replacing 3-isopropyl-5,6,7,8-tetrahydro-[1,2,4]triazolo[4,3-a]pyrazine with 3-methyl-5,6,7,8-tetrahydro-[1,2,4]triazolo[4,3-a]pyrazine during the Buchwald reaction step. The compound was isolated as a the late eluting isomer during reverse phase prep. HPLC. MS (ESI) m/z: 659 (M+H)$^+$. Analytical HPLC: RT=5.85 min (Method B).

EXAMPLE 342

(S)-2-((R)-3-(3-Chloro-2-fluorophenyl)-4,5-dihydroisoxazole-5-carbonyl)-N-(4-fluorophenyl)-5-(3-isopropyl-5,6-dihydro-[1,2,4]triazolo[4,3-a]pyrazin-7(8H)-yl)-1,2,3,4-tetrahydroisoquinoline-1-carboxamide, TFA salt

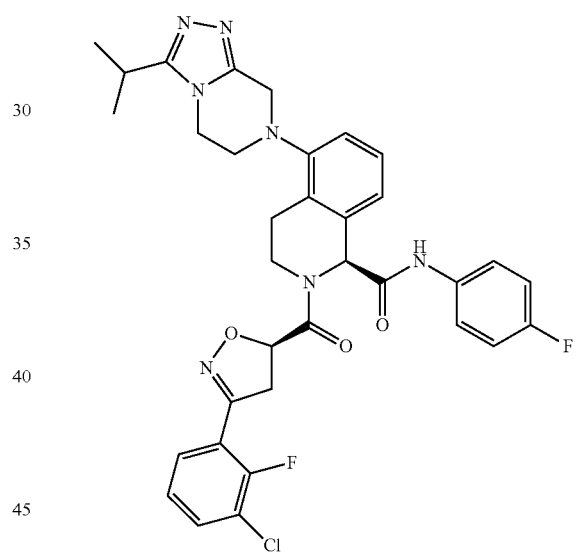

Example 342. (S)-2-((R)-3-(3-Chloro-2-fluorophenyl)-4,5-dihydroisoxazole-5-carbonyl)-N-(4-fluorophenyl)-5-(3-isopropyl-5,6-dihydro-[1,2,4]triazolo[4,3-a]pyrazin-7(8H)-yl)-1,2,3,4-tetrahydroisoquinoline-1-carboxamide, TFA: The title compound was prepared in a similar manner as Example 336 replacing tert-butyl 4-isocyanobenzoate with commercially available 1-fluoro-4-isocyanobenzene in the Ugi reaction step and isolated as the early eluting diastereomer by reverse phase prep. HPLC. $^1$H NMR (400 MHz, DMSO-$d_6$) δ 10.52 (s, 1H), 7.68-7.63 (m, 2H), 7.56-7.51 (m, 2H), 7.33 (d, J=7.7 Hz, 1H), 7.29-7.21 (m, 2H), 7.11-7.03 (m, 3H), 5.73-5.64 (m, 2H), 4.36-4.25 (m, 2H), 4.19-4.11 (m, 2H), 3.86-3.79 (m, 1H), 3.68-3.58 (m, 2H), 3.35-3.28 (m, 2H), 3.20-3.08 (m, 2H), 3.05-2.97 (m, 1H), 1.28-1.25 (m, J=6.9, 1.4 Hz, 6H) ppm. MS (ESI) m/z: 660 (M+H)$^+$. Analytical HPLC: RT=6.43 min (Method B).

391
EXAMPLE 343

(R)-2-((R)-3-(3-Chloro-2-fluorophenyl)-4,5-dihydroisoxazole-5-carbonyl)-N-(4-fluorophenyl)-5-(3-isopropyl-5,6-dihydro-[1,2,4]triazolo[4,3-a]pyrazin-7(8H)-yl)-1,2,3,4-tetrahydroisoquinoline-1-carboxamide, TFA salt

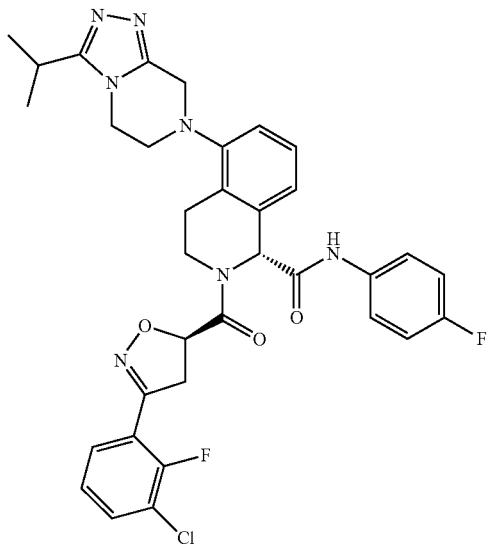 [SMILES: CC(C)c1nnc2n1CCN(c1cccc3c1CCN(C(=O)[C@H]1CC(c4cccc(Cl)c4F)=NO1)[C@H]3C(=O)Nc1ccc(F)cc1)C2]

Example 343 (R)-2-((R)-3-(3-Chloro-2-fluorophenyl)-4,5-dihydroisoxazole-5-carbonyl)-N-(4-fluorophenyl)-5-(3-isopropyl-5,6-dihydro-[1,2,4]triazolo[4,3-a]pyrazin-7(8H)-yl)-1,2,3,4-tetrahydroisoquinoline-1-carboxamide, TFA salt: The title compound was prepared in a similar manner as Example 336 replacing tert-butyl 4-isocyanobenzoate with commercially available 1-fluoro-4-isocyanobenzene in the Ugi reaction step and isolated as the late eluting diastereomer by reverse phase prep. HPLC. $^1$H NMR (400 MHz, DMSO-$d_6$) δ 10.57 (s, 1H), 7.74 (dd, J=7.8, 6.9 Hz, 2H), 7.62-7.58 (m, 2H), 7.41 (d, J=7.7 Hz, 1H), 7.33 (dt, J=10.1, 8.0 Hz, 2H), 7.18-7.12 (m, 3H), 5.88 (d, J=4.2 Hz, 1H), 5.76 (s, 1H), 4.40-4.33 (m, J=3.1 Hz, 2H), 4.26-4.16 (m, 3H), 3.91 (dd, J=16.1, 7.0 Hz, 1H), 3.80-3.71 (m, 2H), 3.41-3.35 (m, 2H), 3.25-3.14 (m, 2H), 3.09-3.02 (m, 1H), 1.36-1.33 (m, J=6.8 Hz, 6H) ppm. MS (ESI) m/z: 660 (M+H)$^+$. Analytical HPLC: RT—6.67 min (Method B).

What is claimed is:
1. A compound according to formula (II):

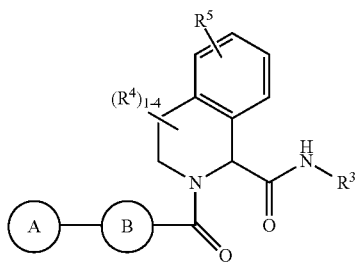

(II)

or a stereoisomer, tautomer, pharmaceutically acceptable salt thereof, wherein:
ring A is;

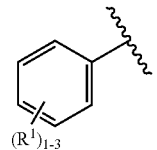

ring B is;

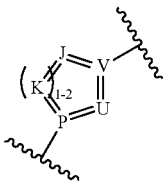

---- is an optional bond;
J, K, P, U, and V are each independently selected from the group consisting of: N, NH, O, S(O)$_p$, CR$^2$, and CR$^2$R$^2$;
R$^1$ is independently selected from the group consisting of: H, halo, CN, —CHF$_2$, and —CF$_3$;
R$^2$ is independently selected from the group consisting of: H, =O, OH, NH$_2$, CF$_3$, halo, C$_{1-4}$ alkyl (optionally substituted with OH), C$_{1-3}$ alkoxy, and C(O)C$_{1-3}$ alkyl;
R$^3$ is

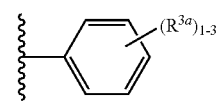

R$^{3a}$ is independently selected from the group consisting of: H, halogen, C$_{1-4}$ alkyl, —OH, =O, —CH$_2$OH, C$_{1-4}$ alkoxy, —CN, —CO$_2$H, —CH$_2$CO$_2$H, —CO$_2$(C$_{1-4}$ alkyl), —CH$_2$CO$_2$(C$_{1-4}$ alkyl) —CONH$_2$, —CONH (C$_{1-6}$ alkyl), —CON(C$_{1-4}$ alkyl)$_2$, R$^c$, and 5-membered heteroaryl substituted with 1-2 R$^d$;
R$^4$ is independently selected from the group consisting of: H, F, and C$_{1-4}$ alkyl;
R$^5$ is independently selected from the group consisting of: H, halo, C$_{1-4}$ alkyl substituted with 1-2 R$^b$, C$_{2-4}$ alkenyl substituted with 1-2 R$^b$, C$_{2-4}$alkynyl substituted with 1-2 R$^b$ OH, CN, NH$_2$, —NH(C$_{1-4}$ alkyl), N(C$_{1-4}$ alkyl)$_2$, C$_{1-4}$ alkoxy, —OCO(C$_{1-4}$ alkyl), —O—C$_{1-4}$ alkylene-O(C$_{1-4}$ alkyl), —O—C$_{1-4}$ alkylene-N(C$_{1-4}$ alkyl)$_2$, —CO$_2$H, —CO$_2$(C$_{1-4}$ alkyl), —CONH$_2$, —(CH$_2$)$_2$CONH$_2$, —CONR$^9$(C$_{1-4}$ alkyl), —CONR$^9$—C$_{1-4}$ alkylene-O(C$_{1-4}$ alkyl), —CON(C$_{1-4}$ alkyl)$_2$, —CONR$^9$—C$_{1-4}$ alkylene-N(C$_{1-4}$ alkyl)$_2$, —CON(C$_{1-4}$ alkyl)-C$_{1-4}$ alkylene-O(C$_{1-4}$ alkyl), —CONR$^9$—C$_{1-4}$ alkylene-CO$_2$(C$_{1-4}$ alkyl), —NR$^9$COC$_{1-4}$ alkyl, —NR$^9$CO$_2$C$_{1-4}$ alkyl, —NR$^9$CONH(C$_{1-4}$ alkyl), —NR$^9$CONR$^9$—C$_{1-4}$ alkylene-CO$_2$C$_{1-4}$ alkyl, —NR$^9$—C$_{1-4}$ alkylene-OH, —NR$^9$—C$_{1-4}$ alkylene-N (C$_{1-4}$ alkyl)$_2$, R$^8$, —OR$^8$, —O—C$_{1-4}$ alkylene-R$^8$, —COR$^8$, —CO$_2$R$^8$, —CONR$^9$R$^8$, —NR$^9$COR$^8$, —NR$^9$R$^8$, —NR$^9$CO$_2$R$^8$, and —NR$^9$CONR$^9$R$^8$;

$R^8$ is independently selected from the group consisting of: —(CH$_2$)$_n$—C$_{3-10}$ carbocycle and —(CH$_2$)$_n$-5- to 10-membered heterocycle containing carbon atoms and 1-4 heteroatoms selected from the group consisting of: N, NR$^a$, O, and S(O)$_p$; wherein said carbocycle or heterocycle is substituted with 1-3 R$^b$;

$R^9$ is independently selected from the group consisting of: H and C$_{1-4}$alkyl;

$R^a$ is independently selected from the group consisting of: H, C$_{1-4}$ alkyl substituted with 1-2 R$^d$, —(CH$_2$)$_n$OH, CO(C$_{1-4}$ alkyl), COCF$_3$, CH$_2$CF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$;

$R^b$ is independently selected from the group consisting of: H, =O, halo, CN, OH, NO$_2$, C$_{1-4}$ alkyl substituted with 1-2 R$^d$, C$_{1-4}$ alkoxy, OCF$_3$, —(CH$_2$)$_n$NH$_2$, —(CH$_2$)$_n$N(C$_{1-4}$ alkyl)$_2$, CO(C$_{1-4}$ alkyl), CO(C$_{1-4}$ haloalkyl), CO$_2$(C$_{1-4}$ alkyl), —(CH$_2$)$_n$—CONH$_2$, —(CH$_2$)$_n$—CONH(C$_{1-4}$ alkyl), —(CH$_2$)$_n$—CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —NHCO(C$_{1-4}$ alkyl), —NHCO$_2$(C$_{1-4}$ alkyl), —S(O)$_2$NH$_2$, —S(O)$_2$NH(C$_{1-4}$alkyl), S(O)$_2$N(C$_{1-4}$alkyl)$_2$, R$^c$, COR$^c$, CO$_2$R$^c$, —S(O)$_2$NH(C$_{1-4}$alkyl)R$^c$, NHCONHR$^c$, and CONHR$^c$;

optionally, R$^b$ and R$^b$ together with the carbon atom(s) to which they are both attached form a 5-6 membered heterocyclic ring containing carbon atoms and 1-4 heteroatoms selected from NR$^a$, O, and S(O)$_p$; wherein said heterocycle is optionally substituted with =O;

or R$^a$ and R$^b$ are combined to form a 5-6 membered heterocyclic ring containing carbon atoms and 1-4 heteroatoms selected from N, O, and S(O)$_p$, and optionally substituted with 1-3 R$^e$;

R$^c$ is independently selected from the group consisting of: —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 1-3 R$^d$;

R$^d$ is independently selected from the group consisting of: H, =O, halo, —OH, C$_{1-4}$ alkyl, NH$_2$, NH(C$_{1-4}$ alkyl), N(C$_{1-4}$ alkyl)$_2$, C$_{1-8}$ alkoxy optionally substituted with OH, and —NHCO(C$_{1-4}$ alkyl), and heterocycle containing carbon atoms and 1-4 heteroatoms selected from the group consisting of: N, NH, N(C$_{1-4}$ alkyl), O, and S(O)$_p$;

R$^e$ is independently selected from the group consisting of: H, halo, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —NHCO$_2$(C$_{1-4}$ alkyl), —(CH$_2$)$_n$—C$_{3-6}$ cycloalkyl, —(CH$_2$)$_n$-phenyl, and —(CH$_2$)$_n$-5- to 6-membered heterocycle;

n is independently selected from 0, 1, 2, 3, and 4; and
p is independently selected from 0, 1, and 2.

2. The compound of claim 1, having formula (III):

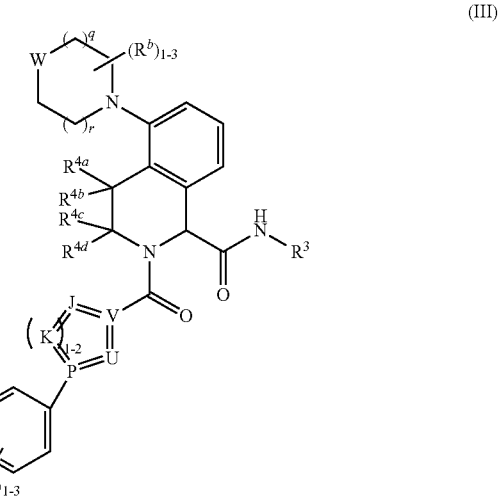

(III)

or a stereoisomer, tautomer, pharmaceutically acceptable salt thereof, wherein:
---- is an optional bond;
W is selected from the group consisting of CR$^b$R$^b$, N, NR$^a$, O, and S(O)$_p$;
J, K, P, U, and V are each independently selected from the group consisting of: N, NH, O, S(O)$_p$, CR$^2$, and CR$^2$R$^2$;
R$^2$ is selected from H, =O, OH, NH$_2$, CF$_3$, halo, and C$_{1-4}$ alkyl;
R$^{4a}$, R$^{4b}$, R$^{4c}$, and R$^{4d}$ are independently selected from the group consisting of: H, F, and C$_{1-4}$ alkyl;
R$^a$ is selected from the group consisting of: H, C$_{1-4}$ alkyl substituted with 1-2 R$^d$, —(CH$_2$)$_n$OH, CH$_2$CF$_3$, CO$_2$(C$_{1-4}$ alkyl), —CONH$_2$, and R$^c$;
R$^b$ is selected from the group consisting of: H, =O, halo, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —NHCO$_2$(C$_{1-4}$ alkyl), R$^c$, COR$^c$, CO$_2$R$^c$, and CONHR$^c$;
optionally, R$^b$ and R$^b$ together with the carbon atom to which they are both attached form a 5-6 membered heterocyclic ring containing carbon atoms and 1-4 heteroatoms selected from NR$^a$, O, and S(O)$_p$; wherein said heterocycle is optionally substituted with =O;
or R$^a$ and R$^b$ together form a 5-6 membered heterocyclic ring containing carbon atoms and 1-4 heteroatoms selected from N, O, and S(O)$_p$, and substituted with 1-3 R$^e$;
R$^c$ is selected from the group consisting of: —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 1-2 R$^d$;
R$^d$ is selected from the group consisting of: H, =O, halo, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and heterocycle containing carbon atoms and 1-4 heteroatoms selected from the group consisting of: N, NH, N(C$_{1-4}$ alkyl), O, and S(O)$_p$;

$R^e$ is selected from the group consisting of: H, halo, $C_{1-4}$ alkyl, $C_{1-4}$ alkoxy, $OCF_3$, $NH_2$, $N(C_{1-4}\ alkyl)_2$, $CO(C_{1-4}\ alkyl)$, $CO(C_{1-4}haloalkyl)$, $CO_2(C_{1-4}\ alkyl)$, $CONH_2$, —$CONH(C_{1-4}\ alkyl)$, —$CON(C_{1-4}\ alkyl)_2$, —$NHCO_2(C_{1-4}\ alkyl)$, —$(CH_2)_n$—$C_{3-6}$ cycloalkyl, —$(CH_2)_n$-phenyl, and —$(CH_2)_n$-5- to 6-membered heterocycle;

q, is selected from 0, 1, and 2; and r, is selected from 0, 1, and 2.

3. The compound of claim 2 having formula (IV):

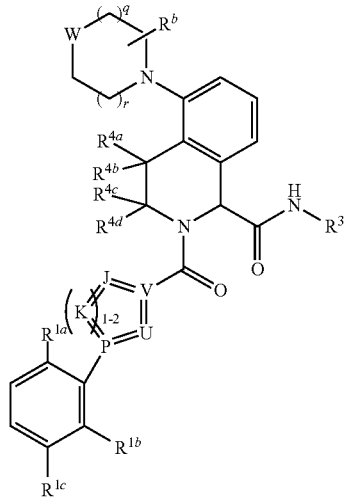

(IV)

or a stereoisomer, tautomer, pharmaceutically acceptable salt thereof, wherein:

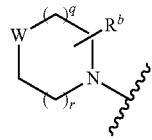

is selected from the group consisting of

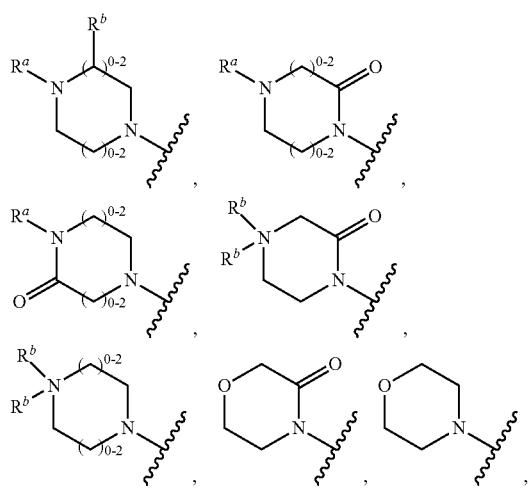

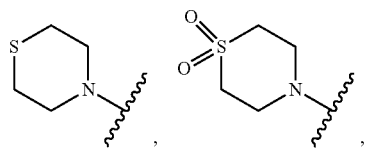

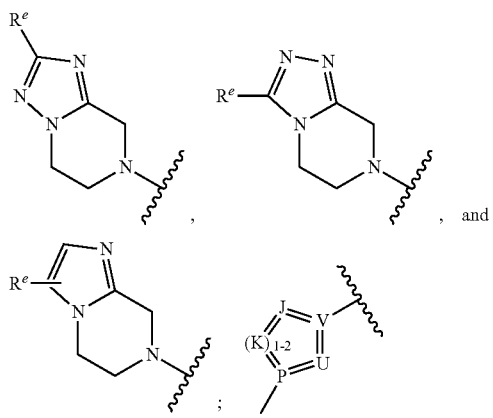

is selected from the group consisting of:

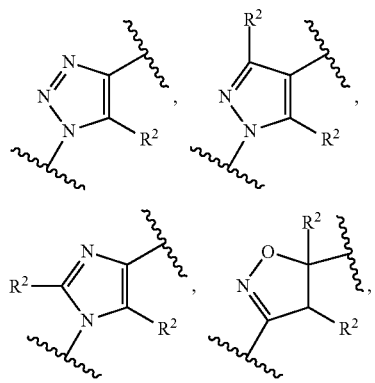

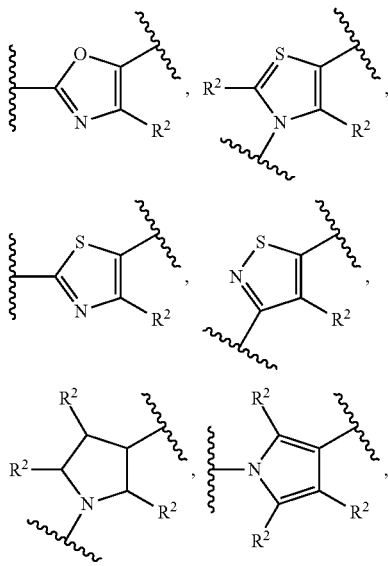

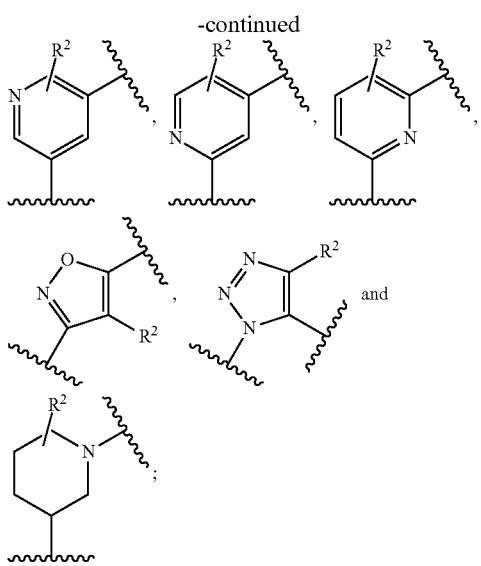

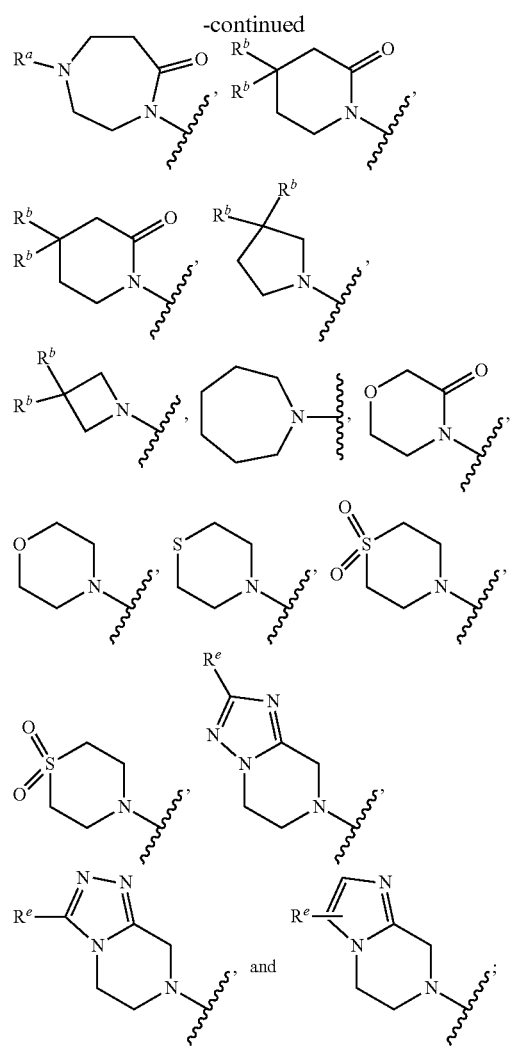

$R^{1a}$ is selected from the group consisting of: H, halo, CN, OH, $C_{1-4}$ alkoxy, —$CHF_2$, —$CF_3$, —$CH_2NH_2$, —$OCHF_2$, —$CO(C_{1-4}$ alkyl), —$CONH_2$, and —COOH;

$R^{1b}$ is selected from the group consisting of: H and halo;

$R^{1c}$ is selected from the group consisting of: H, halo, alkyl, and methoxy;

$R^3$ is

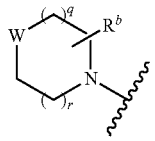

; and $R^{4c}$ and $R^d$ are independently selected from the group consisting of: H and Me.

4. The compound of claim 3, or a stereoisomer, tautomer, pharmaceutically acceptable salt thereof, wherein:

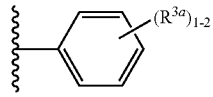

is selected from the group consisting of

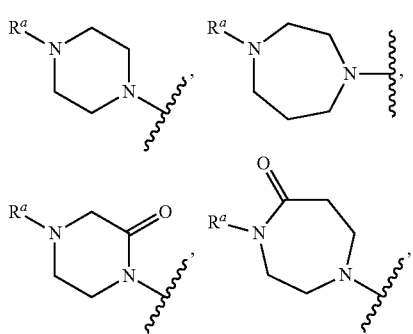

$R^b$ is selected from the group consisting of: H, $C_{1-4}$ alkyl, OH, CN, $NH_2$, —$N(C_{1-4}$ alkyl)$_2$, $C_{1-4}$ alkoxy, —OCO—$C_{1-4}$ alkyl, —$CO_2H$, —$CO_2(C_{1-4}$ alkyl), —$CONH_2$, —$CONR^9(C_{1-4}$ alkyl), —$CON(C_{1-4}$ alkyl)$_2$, $R^8$, —$OR^8$, —$COR^8$ and —$CO_2R^8$;

optionally, $R^b$ and $R^b$ together with the carbon atom to which they are both attached form a 5-6 membered heterocyclic ring containing carbon atoms and 1-4 heteroatoms selected from $NR^a$, O, and $S(O)_p$; wherein said heterocycle is unsubstituted or substituted with =O; and $R^e$ is selected from the group consisting of: H, halo, $C_{1-4}$alkyl, $C_{1-4}$ alkoxy, $OCF_3$, $NH_2$, $NO_2$, $N(C_{1-4}$ alkyl)$_2$, $CO(C_{1-4}$alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —$NHCO_2(C_{1-4}$ alkyl), —$(CH_2)_n$—$C_{3-6}$ cycloalkyl, —$(CH_2)_n$-phenyl, and —$(CH_2)_n$-5- to 6-membered heterocycle.

5. The compound of claim 4, or a stereoisomer, tautomer, pharmaceutically acceptable salt thereof, wherein:

$R^{1b}$ is selected from the group consisting of: H and F; and $R^{3a}$ is selected from the group consisting of: H, halo, CN, =O, $CH_2OH$, $CO_2H$, —$CO_2(C_{1-4}$ alkyl), —$CO_2(CH_2)_{1-2}CON(C_{1-4}$ alkyl)$_2$, —$CONH_2$, —$CONH(C_{1-4}$ alkyl), —$NHCO_2(C_{1-4}$ alkyl), imidazole, pyrazole, and triazole.

6. The compound of claim 4, or a stereoisomer, tautomer, pharmaceutically acceptable salt thereof, wherein:

$R^{1a}$ is selected from the group consisting of: H, F, Cl, CN, COMe, OH, OMe, $OCHF_2$, $CHF_2$, and $CF_3$;

$R^{1b}$ is selected from the group consisting of: H and F;

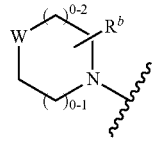

is selected from the group consisting of:

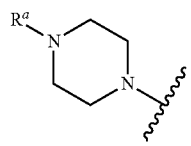, 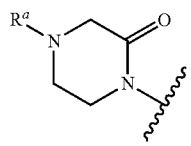,

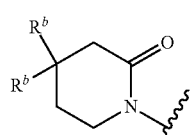, 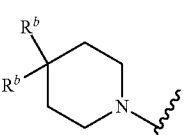,

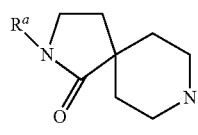, 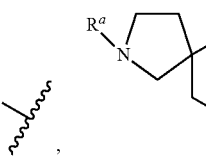,

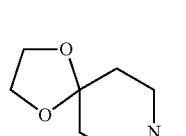, 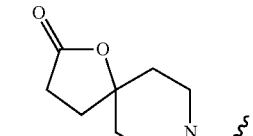,

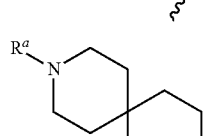, 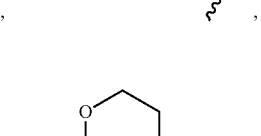,

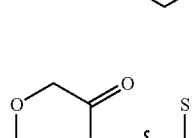, 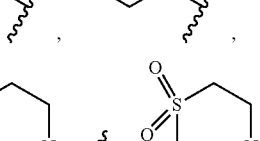,

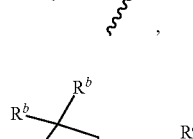, ,

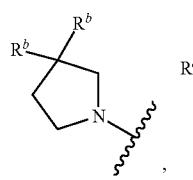, 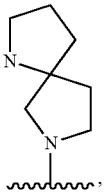,

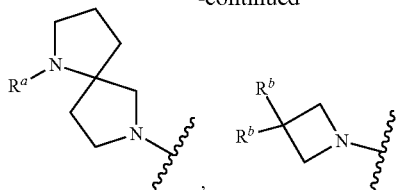,

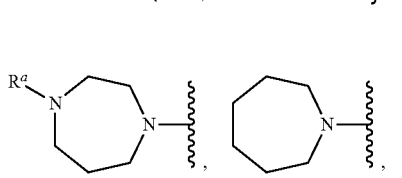,

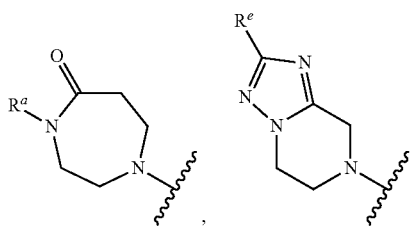,

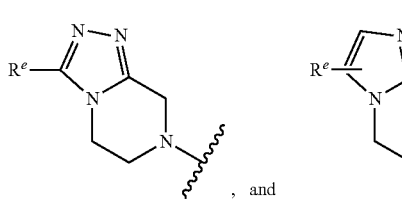

, and ;

$R^3$ is

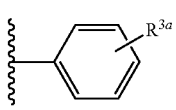

$R^{3a}$ is selected from the group consisting of: H, F, Cl, CN, $CO_2H$, —$CH_2CO_2H$, $CO_2Me$, —$CO_2Et$, —$CO_2$(i-Pr), —$CO_2$(t-Bu), —$CO_2$(n-Bu), and —$CO_2$(i-Bu);

$R^b$ is selected from the group consisting of: H, F, Me, Et, i-propyl, CN, OH, —OMe, —$CO_2Me$, —$CO_2Et$, —$CON(Me)_2$, $NH_2$, —$N(Me)_2$, —$O(CH_2)N(Me)_2$, —$O(CH_2)OMe$,

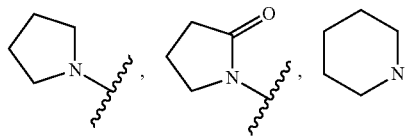

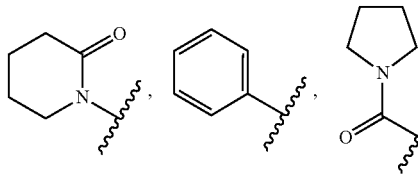

-continued

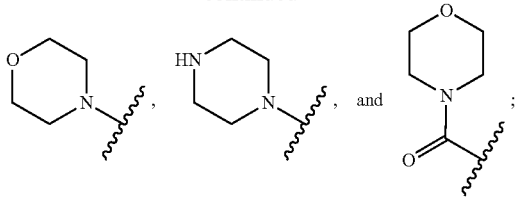

and

R$^e$ is selected from the group consisting of: H, halo, C$_{1-4}$ alkyl, C$_{1-4}$ alkoxy, OCF$_3$, NH$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —NHCO$_2$(C$_{1-4}$ alkyl), —(CH$_2$)$_n$—C$_{3-6}$ cycloalkyl, and —(CH$_2$)n-phenyl.

7. The compound of claim 2 having formula (V):

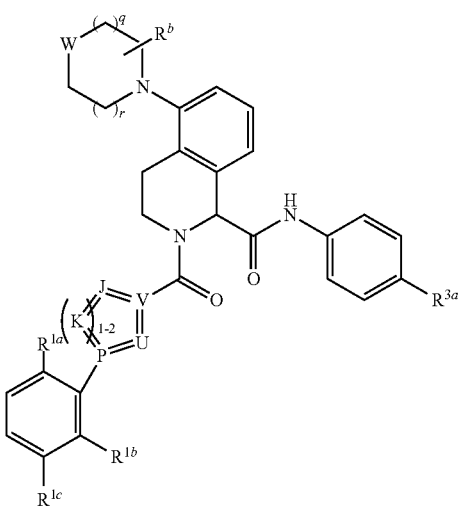

(V)

or a stereoisomer, tautomer, pharmaceutically acceptable salt thereof, wherein:

---- is an optional bond;

R$^{1a}$ is selected from the group consisting of: H, F, Cl, CHF$_2$, and CF$_3$;

R$^{1b}$ is selected from the group consisting of: H, F, and Cl;

R$^{1c}$ is selected from the group consisting of: H and Cl;

R$^{3a}$ is selected from the group consisting of: H, F, Cl, CN, CO$_2$H, —CH$_2$CO$_2$H, CO$_2$Me, —CO$_2$Et, —CO$_2$(i-Pr), —CO$_2$(t-Bu), —CO$_2$(n-Bu), and —CO$_2$(i-Bu);

q is 1 or 2; and
r is 1 or 2.

8. The compound of claim 1, or a stereoisomer, tautomer, pharmaceutically acceptable salt thereof, wherein:

R$^3$ is phenyl substituted with 1-2 R$^{3a}$;

R$^{3a}$ is selected from the group consisting of: H, halo, —OH, —O(C$_{1-4}$ alkyl), —CN, —CO$_2$H, —CONH$_2$, —CO$_2$(C$_{1-4}$ alkyl), and 5-membered heteroaryl substituted with 1-2 R$^d$; p1 R$^5$ is selected from the group consisting of: H, R$^8$, —OR$^8$, COR$^8$, —CONHR$^8$, and NHCONHR$^8$;

R$^8$ is selected from the group consisting of: —(CH$_2$)$_n$—C$_{3-6}$ cycloalkyl, —(CH$_2$)$_n$-phenyl and —(CH$_2$)$_n$-5- to 10-membered heterocycle containing carbon atoms and 1-4 heteroatoms selected from N, NR$^a$, O, and S(O)$_p$; wherein said cycloalkyl, phenyl and heterocycle are substituted with 1-3 R$^b$;

R$^a$ is selected from the group consisting of: H, C$_{1-4}$ alkyl, —(CH$_2$)$_n$OH, CO(C$_{1-4}$ alkyl), COCF$_3$, CH$_2$CF$_3$, CO$_2$(C$_{1-4}$ alkyl), —CONH—C$_{1-4}$ alkylene-CO$_2$(C$_{1-4}$ alkyl), C$_{1-4}$ alkylene-CO$_2$(C$_{1-4}$ alkyl), R$^c$, and CO$_2$R$^c$;

R$^b$ is selected from the group consisting of: H, =O, halo, CN, OH, NO$_2$, C$_{1-4}$ alkyl substituted with 1-2 R$^d$, C$_{1-4}$ alkoxy, OCF$_3$, —(CH$_2$)$_n$NH$_2$, —(CH$_2$)$_n$N(C$_{1-4}$ alkyl)$_2$, CO(C$_{1-4}$ alkyl), CO(C$_{1-4}$ haloalkyl), CO$_2$(C$_{1-4}$ alkyl), —(CH$_2$)$_n$—CONH$_2$, —(CH$_2$)$_n$—CONH(C$_{1-4}$ alkyl), —(CH$_2$)$_n$—CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —NHCO(C$_{1-4}$ alkyl), —NHCO$_2$(C$_{1-4}$ alkyl), —S(O)$_2$NH$_2$, —S(O)$_2$NH(C$_{1-4}$alkyl), R$^c$, COR$^c$, CO$_2$R$^c$, —S(O)$_2$NH(C$_{1-4}$alkyl)R$^c$, NHCONHR$^c$, and CONHR$^c$; and R$^c$ is selected from the group consisting of: —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, O, and S(O)$_p$; wherein each ring moiety is substituted with 1-2 R$^d$.

9. The compound of claim 8, having formula (VI):

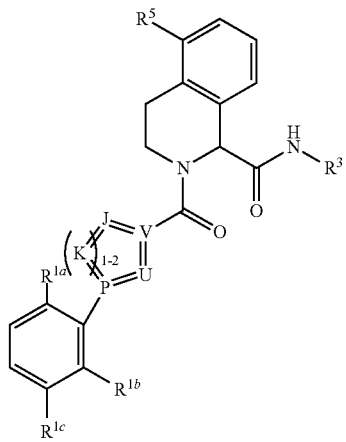

(VI)

or a stereoisomer, tautomer, pharmaceutically acceptable salt thereof, wherein:

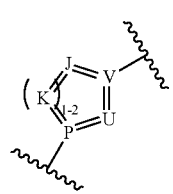

is selected from the group consisting of:

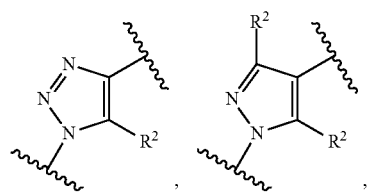

,

-continued

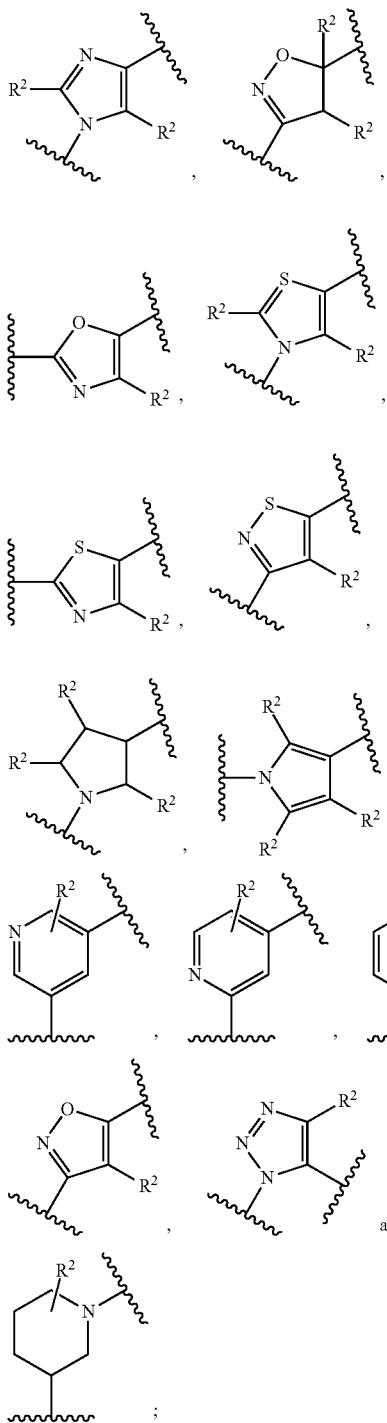

$R^{1a}$ is selected from the group consisting of: H, F, Cl, CN, OH, $C_{1-4}$ alkoxy, —$CHF_2$, —$CF_3$, —$CH_2NH_2$, —$OCHF_2$, —$CO(C_{1-4}$ alkyl), —$CONH_2$, and —COOH;

$R^{1b}$ is selected from the group consisting of: H and halo;

$R^{1c}$ is selected from the group consisting of: H, halo, $C_{1-2}$ alkyl, and methoxy;

$R^2$ is selected from the group consisting of: H, =O, OH, $NH_2$, $CF_3$, halo, and $C_{1-4}$ alkyl $R^3$ is

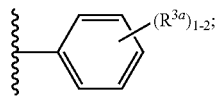

$R^{3a}$ is selected from the group consisting of: H, halo, —OH, —O($C_{1-4}$ alkyl), —CN, —$CO_2H$, —$CONH_2$, —$CO_2(C_{1-4}$ alkyl), and 5-membered heteroaryl substituted with 1-2 $R^d$.

10. The compound of claim 9, or a stereoisomer, tautomer, pharmaceutically acceptable salt thereof, wherein:

$R^{1a}$ is selected from the group consisting of: H, F, $CF_3$, and CO($C_{1-4}$ alkyl);

$R^{1b}$ is selected from the group consisting of: H and F;

$R^{1c}$ is Cl;

$R^3$ is

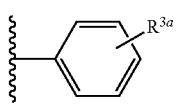

$R^{3a}$ is selected from the group consisting of: F, —OH, —OMe, —OEt, —CN, —$CO_2H$, —$CONH_2$, —$CO_2Me$, —$CO_2Et$, and —$CO_2$(t-butyl)

$R^5$ is selected from the group consisting of:

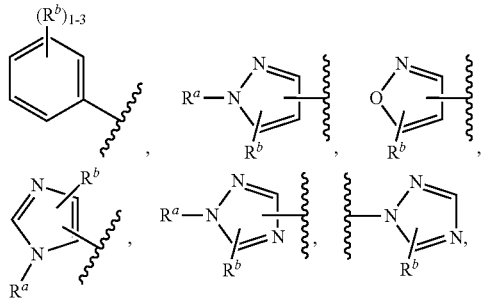

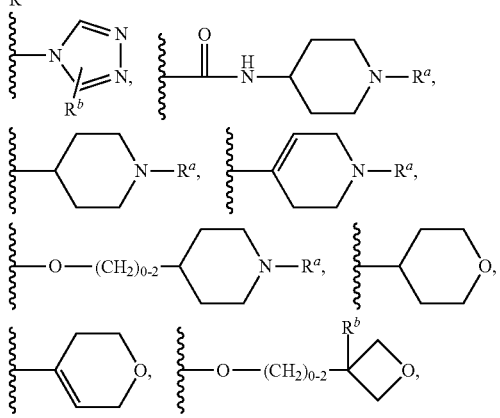

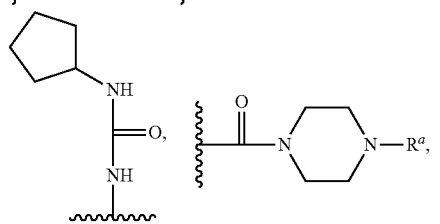

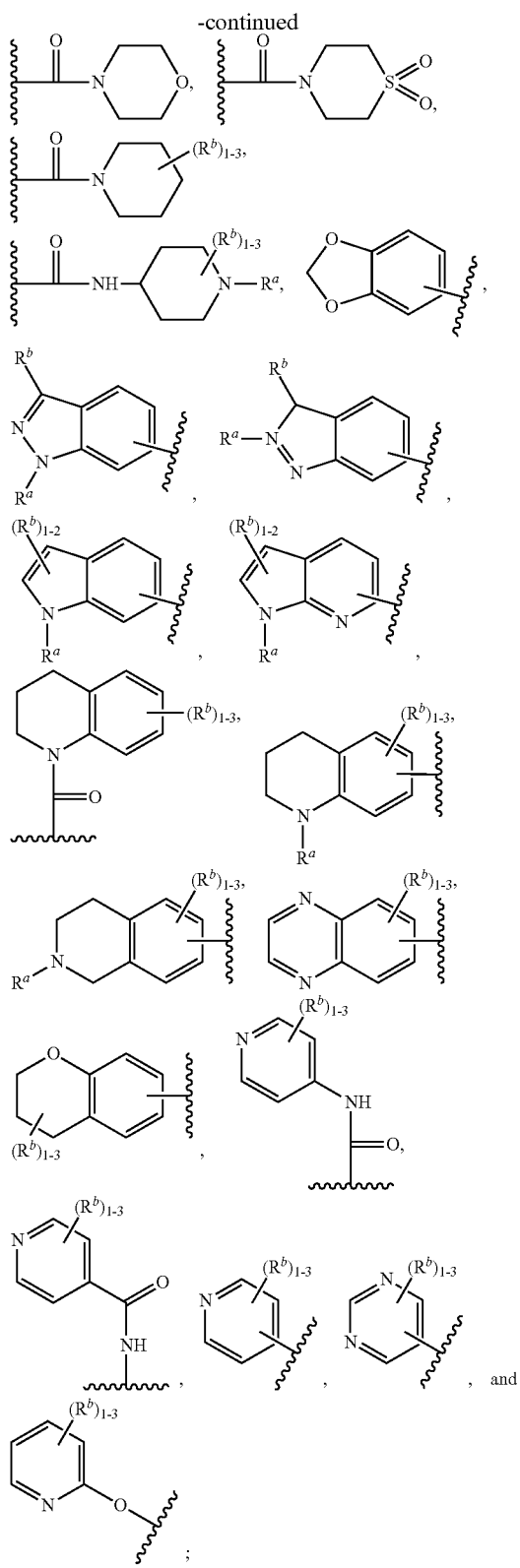

$R^a$ is selected from the group consisting of: H, Me, Et, —(CH$_2$)$_3$OH, COCF$_3$, COMe, CO$_2$Me, CO$_2$Et, CO$_2$(t-butyl), —CONH(CH$_2$)$_2$CO$_2$(C$_{1-4}$ alkyl), R$^c$, and CO$_2$R$^c$;

$R^b$ is selected from the group consisting of: H, Me, Et, Cl, OMe, OCF$_3$, NO$_2$, NH$_2$, N(Me)$_2$, CO$_2$Me, CO$_2$Et, CONH$_2$, —CONH(C$_{1-4}$ alkyl), —CON(C$_{1-4}$ alkyl)$_2$, —CONH(CH$_2$)$_{1-2}$O(C$_{1-4}$ alkyl), —CONH(CH$_2$)$_{1-2}$N (C$_{1-4}$ alkyl)$_2$, —NHCO$_2$(C$_{1-4}$ alkyl), R$^c$, COR$^c$, CONHR$^c$; and R$^c$ is selected from the group consisting of: —(CH$_2$)$_n$—C$_{3-6}$ cycloalkyl, —(CH$_2$)$_n$-phenyl, and —(CH$_2$)$_n$-5- to 6-membered heterocycle, wherein each ring moiety is substituted with 1-2 R$^d$.

11. The compound of claim 10, or a stereoisomer, tautomer, pharmaceutically acceptable salt thereof, wherein:
$R^{1a}$ is selected from the group consisting of: H, F, CF$_3$, and C(O)Me;
$R^{1b}$ is selected from the group consisting of: H and F;
$R^{1c}$ is Cl;
$R^{3a}$ is selected from the group consisting of: F and —CO$_2$H;
$R^b$ is selected from the group consisting of: Cl, OMe, OCF$_3$, NO$_2$, CONH$_2$, 13 CONHMe, —CONHEt, —CON(Me)$_2$, —CON(Et)$_2$, —CONH(CH$_2$)$_{1-2}$O(C$_{1-4}$ alkyl), —CONH(CH$_2$)$_{1-2}$N(C$_{1-4}$ alkyl)$_2$, NHCO$_2$Me, NHCO$_2$Et, and COR$^c$; and
$R^c$ is selected from the group consisting of: —(CH$_2$)$_n$—C$_{3-6}$ cycloalkyl, —(CH$_2$)$_n$-phenyl, and —(CH$_2$)$_n$-5- to 6-membered heterocycle, wherein each ring moiety is substituted with 1-2 R$^d$.

12. The compound of claim 1, or a stereoisomer, tautomer, pharmaceutically acceptable salt thereof, wherein:
$R^3$ is phenyl substituted with 1-2 R$^{3a}$
$R^5$ is selected from the group consisting of: H, halo, C$_{1-4}$ alkyl substituted with 1-2 R$^b$, C$_{2-4}$ alkenyl substituted with 1-2 R$^b$, —OH, CN, —NH$_2$, —N(C$_{1-4}$ alkyl)$_2$, —NH$_2$—C$_{1-4}$ alkylene-OH, —O—C$_{1-4}$ alkylene-O (C$_{1-4}$ alkyl), —O—C$_{1-4}$ alkylene-N(C$_{1-4}$ alkyl)$_2$, —NHCO(C$_{1-4}$ alkyl), —NHSO$_2$(C$_{1-4}$ alkyl);
$R^{3a}$ is selected from the group consisting of: CH$_2$OH and —CO$_2$H;
$R^b$ is selected from the group consisting of: NH$_2$, CONH$_2$, CO$_2$(C$_{1-4}$ alkyl), R$^c$, and COR$^c$; and
$R^c$ is selected from the group consisting of: —(CH$_2$)$_n$—C$_{3-6}$ cycloalkyl, —(CH$_2$)$_n$-phenyl, and —(CH$_2$)$_n$-5- to 6-membered heterocycle, wherein each ring moiety is substituted with 1-2 R$^d$.

13. The compound of claim 1, or a stereoisomer, tautomer, pharmaceutically acceptable salt thereof, wherein:
$R^5$ is selected from the group consisting of: H, C$_{1-4}$ alkyl substituted with 1-2 R$^b$, C$_{2-4}$ alkenyl substituted with 1-2 R$^b$, —N(Me)$_2$, —O(CH$_2$)$_2$N(Me)$_2$, O(CH$_2$)$_2$OMe, CONH(CH$_2$)$_2$N(Me)$_2$, —NHSO$_2$Me,

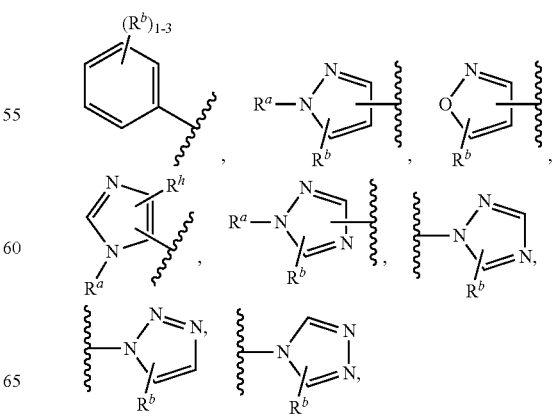

-continued

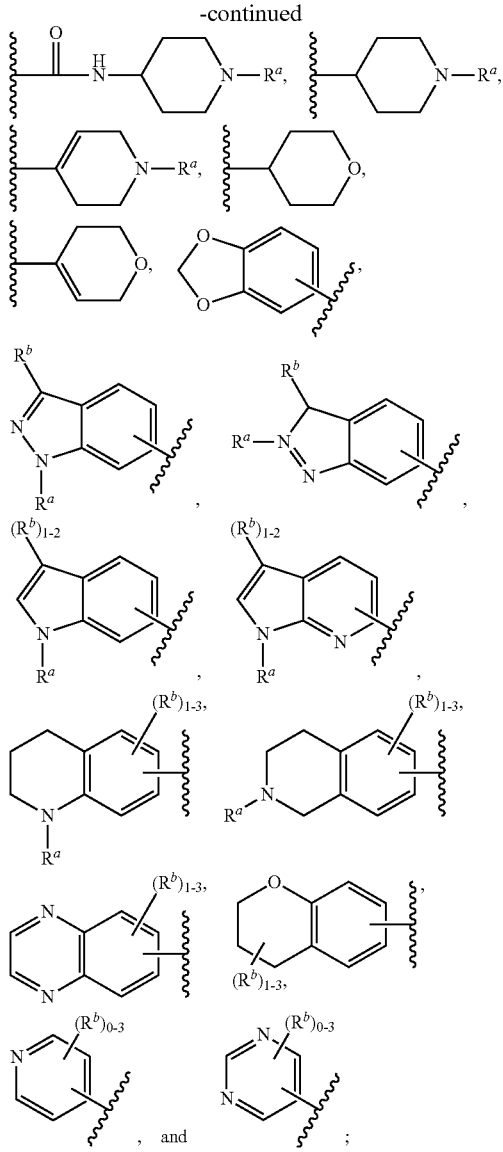

$R^{3a}$ is selected from the group consisting of: F, CN, CH₂OH, CO₂H, CO₂Me, CO₂Et, and CO₂(i-Bu);

$R^a$ is selected from the group consisting of: H, methyl, —(CH₂)₀₋₃OH, COMe, COCF₃, CO₂Me, $R^c$, and CO₂$R^c$;

$R^b$ is selected from the group consisting of: H, Cl, OMe, OCF₃, NO₂, NH₂, —N(Me)₂, —CO₂Me, —CO₂Et, CONH₂, —CONHMe, —CONHEt, —CON(Me)₂, —CONH(CH₂)₂OMe, —CONH(CH₂)₂N(Me)₂, —NHCO₂Et, —NHCO₂Me, $R^c$, COR$^c$ and CONHR$^c$;

$R^c$ is selected from the group consisting of: —(CH₂)₀₋₁phenyl, pyrrolidine, pyrazole, imidazole, triazole, —(CH₂)₀₋₂morpholine, piperidine, methylpiperidine, and methylpiperazine, wherein each ring moiety is substituted with 1-2 $R^d$; and $R^d$ is selected from the group consisting of: H, =O, pyrrolidine, and N(Me)₂.

14. A pharmaceutical composition, comprising: a pharmaceutically acceptable carrier and a therapeutically effective amount of a compound of claim 1.

15. The compound of claim 1 selected from:
4-(2-(1-(3-chloro-2-fluorophenyl)-1H-1,2,3-triazole-4-carbonyl)-1,2,3,4-tetrahydroisoquinoline-1-carboxamido)benzoic acid;
(R)-4-(2-(1-(3-chloro-2-fluorophenyl)-1H-1,2,3-triazole-4-carbonyl)-1,2,3,4-tetrahydroisoquinoline-1-carboxamido)benzoic acid;
(S)-4-(2-(1-(3-chloro-2-fluorophenyl)-1H-1,2,3-triazole-4-carbonyl)-1,2,3,4-tetrahydroisoquinoline-1-carboxamido)benzoic acid;
4-((S)-2-((R)-3-(3-chloro-2-fluorophenyl)-4,5-dihydroisoxazole-5-carbonyl)-1,2,3,4-tetrahydroisoquinoline-1-carboxamido)benzoic acid;
4-((R)-2-((R)-3-(3-chloro-2-fluorophenyl)-4,5-dihydroisoxazole-5-carbonyl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(4-((2-(dimethylamino)ethyl)carbamoyl)phenyl)-1,2,3,4-tetrahydroisoquinoline-1-carboxamido)benzoic acid;
4-(2-(1-(3-chloro-2-fluorophenyl)-5-methyl-1H-1,2,3-triazole-4-carbonyl)-5-(4-((2-(dimethylamino)ethyl)carbamoyl)phenyl)-1,2,3,4-tetrahydroisoquinoline-1-carboxamido)benzoic acid;
4-(2-(1-(3-chloro-2-fluorophenyl)-1H-pyrazole-4-carbonyl)-5-(4-((2-(dimethylamino)ethyl)carbamoyl)phenyl)-1,2,3,4-tetrahydroisoquinoline-1-carboxamido)benzoic acid;
4-(2-(1-(3-chloro-2-fluorophenyl)-5-methyl-1H-1,2,3-triazole-4-carbonyl)-5-(4-(dimethylcarbamoyl)phenyl)-1,2,3,4-tetrahydroisoquinoline-1-carboxamido)benzoic acid;
(S)-4-(2-(1-(3-chloro-2-fluorophenyl)-1H-1,2,3-triazole-4-carbonyl)-5-(4-((2-(dimethylamino)ethyl)carbamoyl)phenyl)-1,2,3,4-tetrahydroisoquinoline-1-carboxamido)benzoic acid;
(R)-4-(2-(1-(3-chloro-2-fluorophenyl)-1H-1,2,3-triazole-4-carbonyl)-5-(4-((2-(dimethylamino)ethyl)carbamoyl)phenyl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(pyrimidin-5-yl)-1,2,3,4-tetrahydroisoquinoline-1-carboxamido)benzoic acid;
(R)-4-(2-(1-(3-chloro-2-fluorophenyl)-1H-1,2,3-triazole-4-carbonyl)-5-(pyrimidin-5-yl)-1,2,3,4-tetrahydroisoquinoline-1-carboxamido)benzoic acid;
(S)-4-(2-(1-(3-chloro-2-fluorophenyl)-1H-1,2,3-triazole-4-carbonyl)-5-(pyrimidin-5-yl)-1,2,3,4-tetrahydroisoquinoline-1-carboxamido)benzoic acid;
(R)-4-(2-(1-(3-chloro-2-fluorophenyl)-1H-1,2,3-triazole-4-carbonyl)-5-(6-cyanopyridin-3-yl)-1,2,3,4-tetrahydroisoquinoline-1-carboxamido)benzoic acid;
(S)-4-(2-(1-(3-chloro-2-fluorophenyl)-1H-1,2,3-triazole-4-carbonyl)-5-(6-cyanopyridin-3-yl)-1,2,3,4-tetrahydroisoquinoline-1-carboxamido)benzoic acid;
4-((S)-2-((R)-3-(3-chloro-2-fluorophenyl)-4,5-dihydroisoxazole-5-carbonyl)-5-(pyrimidin-5-yl)-1,2,3,4-tetrahydroisoquinoline-1-carboxamido)benzoic acid;
4-((R)-2-((R)-3-(3-chloro-2-fluorophenyl)-4,5-dihydroisoxazole-5-carbonyl)-5-(pyrimidin-5-yl)-1,2,3,4-tetrahydroisoquinoline-1-carboxamido)benzoic acid;
4-((S)-2-((R)-3-(3-chloro-2-fluorophenyl)-4,5-dihydroisoxazole-5-carbonyl)-5-(6-(methylcarbamoyl)pyridin-3-yl)-1,2,3,4-tetrahydroisoquinoline-1-carboxamido)benzoic acid;

4-((R)-2-((R)-3-(3-chloro-2-fluorophenyl)-4,5-dihydroisoxazole-5-carbonyl)-5-(6-(methylcarbamoyl)pyridin-3-yl)-1,2,3,4-tetrahydroisoquinoline-1-carboxamido)benzoic acid;
4-((S)-2-((R)-3-(3-chloro-2-fluorophenyl)-4,5-dihydroisoxazole-5-carbonyl)-5-(5-fluoropyridin-3-yl)-1,2,3,4-tetrahydroisoquinoline-1-carboxamido)benzoic acid;
4-((R)-2-((R)-3-(3-chloro-2-fluorophenyl)-4,5-dihydroisoxazole-5-carbonyl)-5-(5-fluoropyridin-3-yl)-1,2,3,4-tetrahydroisoquinoline-1-carboxamido)benzoic acid;
4-((S)-2-((R)-3-(3-chloro-2-fluorophenyl)-4,5-dihydroisoxazole-5-carbonyl)-5-(5-methoxypyridin-3-yl)-1,2,3,4-tetrahydroisoquinoline-1-carboxamido)benzoic acid;
4-((R)-2-((R)-3-(3-chloro-2-fluorophenyl)-4,5-dihydroisoxazole-5-carbonyl)-5-(5-methoxypyridin-3-yl)-1,2,3,4-tetrahydroisoquinoline-1-carboxamindo)benzoic acid;
(R)-methyl 4-(2-(1-(3-chloro-2-fluorophenyl)-1H-1,2,3-triazole-4-carbonyl)-5-(pyrimidin-5-yl)-1,2,3,4-tetrahydroisoquinoline-1-carboxamido)benzoate;
(S)-methyl 4-(2-(1-(3-chloro-2-fluorophenyl)-1H-1,2,3-triazole-4-carbonyl)-5-(pyrimidin-5-yl)-1,2,3,4-tetrahydroisoquinoline-1-carboxamido)benzoate;
(S)-methyl 4-(2-(1-(3-chloro-2-fluorophenyl)-1H-1,2,3-triazole-4-carbonyl)-5-(6-(methylcarbamoyl)pyridin-3-yl)-1,2,3,4-tetrahydroisoquinoline-1-carboxamido)benzoate;
methyl 4-((S)-2-((R)-3-(3-chloro-2-fluorophenyl)-4,5-dihydroisoxazole-5-carbonyl)-5-(pyrimidin-5-yl)-1,2,3,4-tetrahydroisoquinoline-1-carboxamido)benzoate;
methyl 4-((R)-2-((R)-3-(3-chloro-2-fluorophenyl)-4,5-dihydroisoxazole-5-carbonyl)-5-(pyrimidin-5-yl)-1,2,3,4-tetrahydroisoquinoline-1-carboxamido)benzoate;
4-(5-(2-aminopyrimidin-5-yl)-2-(1-(3-chloro-2-fluorophenyl)-1H-1,2,3-triazole-4-carbonyl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(2-methoxypyrimidin-5-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(2-cyanopyrimidin-5-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(pyridin-3-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(2-hydroxypyrimidin-5-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(5-fluoropyridin-3-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(5-methoxypyridin-3-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(5-(methylcarbamoyl)pyridin-3-yl)-1,2,3,4-tetrahydroisoquinoline-1-carboxamido)benzoic acid;
4-(5-(2-aminopyridin-4-yl)-2-(1-(3-chloro-2-fluorophenyl)-1H-1,2,3-triazole-4-carbonyl)-1,2,3,4-tetrahydroisoquinoline-1-carboxamido)benzoic acid;
4-(5-(6-aminopyridin-3-yl)-2-(1-(3-chloro-2-fluorophenyl)-1H-1,2,3-triazole-4-carbonyl)-1,2,3,4-tetrahydroisoquinoline-1-carboxamido)benzoic acid;
4-(2-(1-(3-chloro-2-fluorophenyl)-1H-1,2,3-triazole-4-carbonyl)-1,1',2,2',3,3',4,4'-octahydro-[5,6'-biisoquinoline]-1-carboxamido)benzoic acid;
4-(2-(1-(3-chloro-2-fluorophenyl)-1H-1,2,3-triazole-4-carbonyl)-5-(1H-pyrazol-4-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(1-methyl-1H-pyrazol-5-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(1-methyl-1H-pyrazol-3-yl)-1,2,3,4-tetrahydroisoquinoline-1-carboxamido)benzoic acid;
(S)-4-(2-(1-(3-chloro-2-fluorophenyl)-1H-1,2,3-triazole-4-carbonyl)-5-(6-(methylcarbamoyl)pyridin-3-yl)-1,2,3,4-tetrahydroisoquinoline-1-carboxamido)benzoic acid;
(R)-4-(2-(1-(3-chloro-2-fluorophenyl)-1H-1,2,3-triazole-4-carbonyl)-5-(6-(methylcarbamoyl)pyridin-3-yl)-1,2,3,4-tetrahydroisoquinoline-1-carboxamido)benzoic acid;
4-(2-(5-amino-1-(3-chloro-2-fluorophenyl)-1H-pyrazole-4-carbonyl)-5-(pyrimidin-5-yl)-1,2,3,4-tetrahydroisoquinoline-1-carboxamido)benzoic acid;
4-(2-(5-amino-1-(3-chloro-2-fluorophenyl)-1H-pyrazole-4-carbonyl)-5-(6-(methylcarbamoyl)pyridin-3-yl)-1,2,3,4-tetrahydroisoquinoline-1-carboxamido)benzoic acid;
(R)-4-(2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamido)benzoic acid;
(S)-4-(2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamido)benzoic acid;
4-(2-(1-(3-chloro-2-fluorophenyl)-1H-pyrazole-4-carbonyl)-5-(4-(dimethylamino)piperidin-1-yl)-1,2,3,4-tetrahydroisoquinoline-1-carboxamido)benzoic acid;
(R)-4-(2-(1-(3-chloro-2-fluorophenyl)-1H-pyrazole-4-carbonyl)-5-(4-(dimethylamino)piperidin-1-yl)-1,2,3,4-tetrahydroisoquinoline-1-carboxamido)benzoic acid;
(S)-4-(2-(1-(3-chloro-2-fluorophenyl)-1H-pyrazole-4-carbonyl)-5-(4-(dimethylamino)piperidin-1-yl)-1,2,3,4-tetrahydroisoquinoline-1-carboxamido)benzoic acid;
4-(2-(1-(3-chloro-2-fluorophenyl)-1H-imidazole-4-carbonyl)-5-(4-(dimethylamino)piperidin-1-yl)-1,2,3,4-tetrahydroisoquinoline-1-carboxamido)benzoic acid;
(R)-4-(2-(1-(3-chloro-2-fluorophenyl)-1H-imidazole-4-carbonyl)-5-(4-(dimethylamino)piperidin-1-yl)-1,2,3,4-tetrahydroisoquinoline-1-carboxamido)benzoic acid;
(S)-4-(2-(1-(3-chloro-2-fluorophenyl)-1H-imidazole-4-carbonyl)-5-(4-(dimethylamino)piperidin-1-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(4-(dimethylcarbamoyl)piperidin-1-yl)-1,2,3,4-tetrahydroisoquinoline-1-carboxamido)benzoic acid;
(R)-4-(2-(1-(3-chloro-2-fluorophenyl)-1H-1,2,3-triazole-4-carbonyl)-5-(4-(dimethylcarbamoyl)piperidin-1-yl)-1,2,3,4-tetrahydroisoquinoline-1-carboxamido)benzoic acid;
(S)-4-(2-(1-(3-chloro-2-fluorophenyl)-1H-1,2,3-triazole-4-carbonyl)-5-(4-(dimethylcarbamoyl)piperidin-1-yl)-1,2,3,4-tetrahydroisoquinoline-1-carboxamido)benzoic acid;

4-(2-(1-(3-chloro-2-fluorophenyl)-1H-pyrazole-4-carbonyl)-5-(4-(dimethylcarbamoyl)piperidin-1-yl)-1,2,3,4-tetrahydroisoquinoline-1-carboxamido)benzoic acid;

(R)-4-(2-(1-(3-chloro-2-fluorophenyl)-1H-pyrazole-4-carbonyl)-5-(4-(dimethylcarbamoyl)piperidin-1-yl)-1,2,3,4-tetrahydroisoquinoline-1-carboxamido)benzoic acid;

(S)-4-(2-(1-(3-chloro-2-fluorophenyl)-1H-pyrazole-4-carbonyl)-5-(4-(dimethylcarbamoyl)piperidin-1-yl)-1,2,3,4-tetrahydroisoquinoline-1-carboxamido)benzoic acid;

(R)-4-(2-(1-(3-chloro-2-fluorophenyl)-1H-imidazole-4-carbonyl)-5-(4-(dimethylcarbamoyl)piperidin-1-yl)-1,2,3,4-tetrahydroisoquinoline-1-carboxamido)benzoic acid;

(S)-4-(2-(1-(3-chloro-2-fluorophenyl)-1H-imidazole-4-carbonyl)-5-(4-(dimethylcarbamoyl)piperidin-1-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid;

(R)-4-(2-(1-(3-chloro-2-fluorophenyl)-1H-1,2,3-triazole-4-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid;

(S)-4-(2-(1-(3-chloro-2-fluorophenyl)-1H-1,2,3-triazole-4-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(4-hydroxy-4-methylpiperidin-1-yl)-1,2,3,4-tetrahydroisoquinoline-1-carboxamido)benzoic acid;

4-(2-(1-(3-chloro-2-fluorophenyl)-1H-pyrazole-4-carbonyl)-5-(4-hydroxy-4-methylpiperidin-1-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(3-oxomorpholino)-1,2,3,4-tetrahydroisoquinoline-1-carboxamido)benzoic acid;

4-(2-(1-(3-chloro-2-fluorophenyl)-1H-pyrazole-4-carbonyl)-5-(4-methyl-7-oxo-1,4-diazepan-1-yl)-1,2,3,4-tetrahydroisoquinoline-1-carboxamido)benzoic acid;

4-(2-(1-(3-chloro-2,6-difluorophenyl)-5-oxopyrrolidine-3-carbonyl)-5-(4-methoxypiperidin-1-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(4-(2-oxopyrrolidin-1-yl)piperidin-1-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(1,1-dioxidothiomorpholino)-1,2,3,4-tetrahydroisoquinoline-1-carboxamido)benzoic acid;

4-(2-(1-(3-chloro-2-fluorophenyl)-1H-pyrazole-4-carbonyl)-5-(4-(2-oxopyrrolidin-1-yl)piperidin-1-yl)-1,2,3,4-tetrahydroisoquinoline-1-carboxamido)benzoic acid;

4-(2-(1-(3-chloro-2-fluorophenyl)-1H-pyrazole-4-carbonyl)-5-(2-oxo-1-oxa-8-azaspiro[4.5]-decan-8-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(2-oxo-1-oxa-8-azaspiro[4.5]decan-8-yl)-1,2,3,4-tetrahydroisoquinoline-1-carboxamido)benzoic acid;

4-(2-(1-(3-chloro-2-fluorophenyl)-1H-imidazole-4-carbonyl)-5-(2-oxo-1-oxa-8-azaspiro[4.5]decan-8-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(piperidin-1-yl)-1,2,3,4-tetrahydroisoquinoline-1-carboxamido)benzoic acid;

(R)-4-(2-(1-(3-chloro-2-fluorophenyl)-1H-1,2,3-triazole-4-carbonyl)-5-(4-methyl-2-oxopiperazin-1-yl)-1,2,3,4-tetrahydroisoquinoline-1-carboxamido)benzoic acid;

(S)-4-(2-(1-(3-chloro-2-fluorophenyl)-1H-1,2,3-triazole-4-carbonyl)-5-(4-methyl-2-oxopiperazin-1-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(2-oxopiperidin-1-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(3-ethoxyazetidin-1-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(3-methoxyazetidin-1-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-((R)-3-methoxypyrrolidin-1-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(4-hydroxypiperidin-1-yl)-1,2,3,4-tetrahydroisoquinoline-1-carboxamido)benzoic acid;

(S)-4-(2-(1-(3-chloro-2-fluorophenyl)-1H-1,2,3-triazole-4-carbonyl)-5-(4-hydroxypiperidin-1-yl)-1,2,3,4-tetrahydroisoquinoline-1-carboxamido)benzoic acid;

(R)-4-(2-(1-(3-chloro-2-fluorophenyl)-1H-1,2,3-triazole-4-carbonyl)-5-(4-hydroxypiperidin-1-yl)-1,2,3,4-tetrahydroisoquinoline-1-carboxamido)benzoic acid;

(R)-4-(2-(1-(3-chloro-2-fluorophenyl)-1H-pyrazole-4-carbonyl)-5-morpholino-1,2,3,4-tetrahydroisoquinoline-1-carboxamido)benzoic acid;

(S)-4-(2-(1-(3-chloro-2-fluorophenyl)-1H-pyrazole-4-carbonyl)-5-morpholino-1,2,3,4-tetrahydroisoquinoline-1-carboxamido)benzoic acid;

(S)-4-(2-(1-(3-chloro-2-fluorophenyl)-1H-1,2,3-triazole-4-carbonyl)-5-morpholino-1,2,3,4-tetrahydroisoquinoline-1-carboxamido)benzoic acid;

(S)-4-(2-(1-(3-chloro-2-fluorophenyl)-1H-imidazole-4-carbonyl)-5-morpholino-1,2,3,4-tetrahydroisoquinoline-1-carboxamido)benzoic acid;

4-(2-(1-(3-chloro-2-fluorophenyl)-1H-imidazole-4-carbonyl)-5-(4-(2-oxopyrrolidin-1-yl)piperidin-1-yl)-1,2,3,4-tetrahydroisoquinoline-1-carboxamido)benzoic acid;

2-(1-(3-chloro-2-fluorophenyl)-1H-pyrazole-4-carbonyl)-5-(4-(dimethylamino)piperidin-1-yl)-N-(4-(oxazol-2-yl)phenyl)-1,2,3,4-tetrahydroisoquinoline-1-carboxamide;

2-(1-(3-chloro-2-fluorophenyl)-1H-pyrazole-4-carbonyl)-5-(4-(dimethylamino)piperidin-1-yl)-N-(4-(2-ethyl-2H-tetrazol-5-yl)phenyl)-1,2,3,4-tetrahydroisoquinoline-1-carboxamide;

2-(1-(3-chloro-2-fluorophenyl)-1H-pyrazole-4-carbonyl)-5-(4-(dimethylamino)piperidin-1-yl)-N-(4-((tetrahydrofuran-2-yl)methoxy)phenyl)-1,2,3,4-tetrahydroisoquinoline-1-carboxamide;

2-(1-(3-chloro-2-fluorophenyl)-1H-pyrazole-4-carbonyl)-N-(4-(difluoromethoxy)phenyl)-5-(4-(dimethylamino)piperidin-1-yl)-1,2,3,4-tetrahydroisoquinoline-1-carboxamide;

2-(1-(3-chloro-2-fluorophenyl)-1H-pyrazole-4-carbonyl)-5-(4-(dimethylamino)piperidin-1-yl)-N-(4-methoxyphenyl)-1,2,3,4-tetrahydroisoquinoline-1-carboxamide;

2-(1-(3-chloro-2-fluorophenyl)-1H-1,2,3-triazole-4-carbonyl)-5-(4-(dimethylamino)piperidin-1-yl)-N-(4-(5-methyl-1,2,4-oxadiazol-3-yl)phenyl)-1,2,3,4-tetrahydroisoquinoline-1-carboxamide;

N-(4-carbamoylphenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide;

(R)-N-(4-carbamoylphenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide;

(S)-N-(4-carbamoylphenyl)-2-(1-(3-chloro-2-fluorophenyl)-1H-1,2, 3-triazole-4-carbonyl)-5-(4-(dimethylamino)piperidin-1-yl)-1,2,3,4-tetrahydroisoquinoline-1-carboxamide;

N-(4-(1H-pyrazol-4-yl)phenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide;

(R)-N-(4-(1H-pyrazol-4-yl)phenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide;

(S)-N-(4-(1H-pyrazol-4-yl)phenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide;

N-(4-(1H-tetrazol-5-yl)phenyl)-2-(1-(3-chloro-2-fluorophenyl)-1H-1,2,3-triazole-4-carbonyl)-5-(4-(dimethylamino)piperidin-1-yl)-1,2,3,4-tetrahydroisoquinoline-1-carboxamide;

4-(2-(1-(3-chloro-2-fluorophenyl)-1H-1,2,3-triazole-4-carbonyl)-5-(2-methyl-1-oxo-2,8-diazaspiro[4.5]decan-8-yl)-1,2,3,4-tetrahydroisoquinoline-1-carboxamido)benzoic acid;

4-(2-(1-(3-chloro-2-fluorophenyl)-1H-pyrazole-4-carbonyl)-5-(2-methyl-1-oxo-2,8-diazaspiro[4.5]decan-8-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-cyano-1,2,3,4-tetrahydroisoquinoline-1-carboxamido)benzoic acid;

4-(5-(aminomethyl)-2-(1-(3-chloro-2-fluorophenyl)-1H-1,2,3-triazole-4-carbonyl)-1,2,3,4-tetrahydroisoquinoline-1-carboxamido)benzoic acid;

4-(5-bromo-2-(1-(3-chloro-2-fluorophenyl)-1H-1,2,3-triazole-4-carbonyl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-((2-hydroxyethyl)amino)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(piperidin-4-yloxy)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(2-methoxyethoxy)-1,2,3,4-tetrahydroisoquinoline-1-carboxamido)benzoic acid;

4-((S)-2-((R)-3-(3-chloro-2-fluorophenyl)-4,5-dihydroisoxazole-5-carbonyl)-5-(2-methoxyethoxy)-1,2,3,4-tetrahydroisoquinoline-1-carboxamido)benzoic acid, 4-((R)-2-((R)-3-(3-chloro-2-fluorophenyl)-4,5-dihydroisoxazole-5-carbonyl)-5-(2-methoxyethoxy)-1,2,3,4-tetrahydroisoquinoline-1-carboxamido)benzoic acid;

ethyl 2-(4-(2-(1-(3-chloro-2-fluorophenyl)-1H-1,2,3-triazole-4-carbonyl)-5-(6-(methylcarbamoyl)pyridin-3-yl)-1,2,3,4-tetrahydroisoquinoline-1-carboxamido)phenyl)acetate;

2-(4-(2-(1-(3-chloro-2-fluorophenyl)-1H-1,2,3-triazole-4-carbonyl)-5-(6-(methylcarbamoyl)pyridin-3-yl)-1,2,3,4-tetrahydroisoquinoline-1-carboxamido)phenyl)acetic acid;

2-(1-(3-chloro-2-fluorophenyl)-1H-1,2,3-triazole-4-carbonyl)-5-(4-methoxypiperidin-1-yl)-N-phenyl-1,2,3,4-tetrahydroisoquinoline-1-carboxamide;

5-bromo-2-(1-(3-chloro-2-fluorophenyl)-1H-1,2,3-triazole-4-carbonyl)-N-phenyl-1,2,3,4-tetrahydroisoquinoline-1-carboxamide;

5-bromo-2-(1-(3-chloro-2-fluorophenyl)-1H-1,2,3-triazole-4-carbonyl)-N-(4-(hydroxymethyl)phenyl)-1,2,3,4-tetrahydroisoquinoline-1-carboxamide;

(R)-2-(1-(3-chloro-2-fluorophenyl)-1H-1,2,3-triazole-4-carbonyl)-N-(4-(hydroxymethyl)phenyl)-5-(4-methoxypiperidin-1-yl)-1,2,3,4-tetrahydroisoquinoline-1-carboxamide;

(S)-2-(1-(3-chloro-2-fluorophenyl)-1H-1,2,3-triazole-4-carbonyl)-N-(4-(hydroxymethyl)phenyl)-5-(4-methoxypiperidin-1-yl)-1,2,3,4-tetrahydroisoquinoline-1-carboxamide;

4-(2-(1-(3-chloro-2-fluorophenyl)-1H-1,2,3-triazole-4-carbonyl)-5-(oxetan-3-yloxy)-1,2,3,4-tetrahydroisoquinoline-1-carboxamido)benzoic acid;

4-(2-(1-(3-chloro-2-fluorophenyl)-1H-1,2,3-triazole-4-carbonyl)-5-((3-methyloxetan-3-yl)methoxy)-1,2,3,4-tetrahydroisoquinoline-1-carboxamido)benzoic acid;

N-(4-(1H-imidazol-2-yl)phenyl)-2-(1-(3-chloro-2-fluorophenyl)-1H-1,2,3-triazole-4-carbonyl)-5-(pyrimidin-5-yl)-1,2,3,4-tetrahydroisoquinoline-1-carboxamide;

N-(4-(1H-pyrazol-3-yl)phenyl)-2-(1-(3-chloro-2-fluorophenyl)-1H-1,2,3-triazole-4-carbonyl)-5-(pyrimidin-5-yl)-1,2,3,4-tetrahydroisoquinoline-1-carboxamide;

N-(4-(1H-1,2,4-triazol-5-yl)phenyl)-2-(1-(3-chloro-2-fluorophenyl)-1H-1,2,3-triazole-4-carbonyl)-5-(pyrimidin-5-yl)-1,2,3,4-tetrahydroisoquinoline-1-carboxamide;

(1R,4R)-methyl 4-(2-(1-(3-chloro-2-fluorophenyl)-1H-1,2,3-triazole-4-carbonyl)-5-(pyrimidin-5-yl)-1,2,3,4-tetrahydroisoquinoline-1-carboxamido)cyclohexanecarboxylate;

(1R,4R)-4-(2-(1-(3-chloro-2-fluorophenyl)-1H-1,2,3-triazole-4-carbonyl)-5-(pyrimidin-5-yl)-1,2,3,4-tetrahydroisoquinoline-1-carboxamido)cyclohexanecarboxylic acid;

(1S)-N-(4-(1H-imidazol-2-yl)phenyl)-2-(3-(3-chloro-2-fluorophenyl)-4,5-dihydroisoxazole-5-carbonyl)-5-(pyrimidin-5-yl)-1,2,3,4-tetrahydroisoquinoline-1-carboxamide;

(1R)-N-(4-(1H-imidazol-2-yl)phenyl)-2-(3-(3-chloro-2-fluorophenyl)-4,5-dihydroisoxazole-5-carbonyl)-5-(pyrimidin-5-yl)-1,2,3,4-tetrahydroisoquinoline-1-carboxamide;

N-(4-(1H-imidazol-2-yl)phenyl)-2-(1-(3-chloro-2-fluorophenyl)-5-methyl-1H-imidazole-4-carbonyl)-5-(pyrimidin-5-yl)-1,2,3,4-tetrahydroisoquinoline-1-carboxamide;

N-(4-(1H-imidazol-2-yl)phenyl)-2-(1-(3-chloro-2-fluorophenyl)-1H-imidazole-4-carbonyl)-5-(pyrimidin-5-yl)-1,2,3,4-tetrahydroisoquinoline-1-carboxamide;

(S)-N-(4-(1H-imidazol-2-yl)phenyl)-2-(1-(3-chloro-2-fluorophenyl)-1H-1,2,3-triazole-4-carbonyl)-5-(pyrimidin-5-yl)-1,2,3,4-tetrahydroisoquinoline-1-carboxamide;

(R)-N-(4-(1H-imidazol-2-yl)phenyl)-2-(1-(3-chloro-2-fluorophenyl)-1H-1,2,3-triazole-4-carbonyl)-5-(pyrimidin-5-yl)-1,2,3,4-tetrahydroisoquinoline-1-carboxamide;

N-(4-(1H-imidazol-2-yl)phenyl)-2-(1-(3-chloro-2-fluorophenyl)-5-methyl-1H-1,2,3-triazole-4-carbonyl)-5-(4-methoxypiperidin-1-yl)-1,2,3,4-tetrahydroisoquinoline-1-carboxamide;

N-(4-(1H-imidazol-2-yl)phenyl)-2-(1-(3-chloro-2-fluorophenyl)-1H-1,2,3-triazole-4-carbonyl)-5-(4-methoxypiperidin-1-yl)-1,2,3,4-tetrahydroisoquinoline-1-carboxamide;

methyl 4-(2-{[1-(3-chloro-2-fluorophenyl)-1H-1,2,3-triazol-4-yl]carbonyl}-5-(pyrimidin-5-yl)-1,2,3,4-tetrahydroisoquinoline-1-amido)bicyclo[2.2.2]octane-1-carboxylate;

4-(2-{[1-(3-chloro-2-fluorophenyl)-1H-1,2,3-triazol-4-yl]carbonyl}-5-(pyrimidin-5-yl)-1,2,3,4-tetrahydroisoquinoline-1-amido)bicyclo[2.2.2]octane-1-carboxylic acid;

4-(2-{[1-(3-chloro-2-fluorophenyl)-1H-1,2,3-triazol-4-yl]carbonyl}-5-(pyrimidin-5-yl)-1,2,3,4-tetrahydroisoquinoline-1-amido)bicyclo[2.2.2]octane-1-carboxylic acid;

4-(2-{[1-(3-chloro-2-fluorophenyl)-1H-1,2,3-triazol-4-yl]carbonyl}-5-(pyrimidin-5-yl)-1,2,3,4-tetrahydroisoquinoline-1-amido)bicyclo[2.2.2]octane-1-carboxylic acid;

4-(5-(4-methoxypiperidin-1-yl)-2-(4-methyl-2-(pyridin-3-yl)thiazole-5-carbonyl)-1,2,3,4-tetrahydroisoquinoline-1-carboxamido)benzoic acid;

4-(2-(1-(4-chlorophenyl)-2,5-dimethyl-1H-pyrrole-3-carbonyl)-5-(4-methoxypiperidin-1-yl)-1,2,3,4-tetrahydroisoquinoline-1-carboxamido)benzoic acid;

4-(2-(3-(2-chlorophenyl)isoxazole-5-carbonyl)-5-(4-methoxypiperidin-1-yl)-1,2,3,4-tetrahydroisoquinoline-1-carboxamido)benzoic acid;

4-(2-(1-(4-isopropoxyphenyl)-2-oxopyrrolidine-3-carbonyl)-5-(4-methoxypiperidin-1-yl)-1,2,3,4-tetrahydroisoquinoline-1-carboxamido)benzoic acid;

4-(2-(1-(3-chlorophenyl)-5-(trifluoromethyl)-1H-pyrazole-4-carbonyl)-5-(4-methoxypiperidin-1-yl)-1,2,3,4-tetrahydroisoquinoline-1-carboxamido)benzoic acid;

4-(2-(1-(3-chlorophenyl)-2-oxopyrrolidine-3-carbonyl)-5-(4-methoxypiperidin-1-yl)-1,2,3,4-tetrahydroisoquinoline-1-carboxamido)benzoic acid;

4-(2-(3-(3-fluorophenyl)isoxazole-5-carbonyl)-5-(4-methoxypiperidin-1-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(2-methoxypyridin-3-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(4-((dimethylamino)methyl)phenyl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(3-sulfamoylphenyl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(1-methyl-1H-indazol-5-yl)-1,2,3,4-tetrahydroisoquinoline-1-carboxamido)benzoic acid;

4-(5-(benzo[d][1,3]dioxol-5-yl)-2-(1-(3-chloro-2-fluorophenyl)-1H-1,2,3-triazole-4-carbonyl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(2,4-dimethoxypyrimidin-5-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(isoxazol-4-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(1H-indol-7-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(1H-indazol-6-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(2-methyl-2H-indazol-6-yl)-1,2,3,4-tetrahydroisoquinoline-1-carboxamido)benzoic acid;

4-(5-(4-(aminomethyl)phenyl)-2-(1-(3-chloro-2-fluorophenyl)-1H-1,2,3-triazole-4-carbonyl)-1,2,3,4-tetrahydroisoquinoline-1-carboxamido)benzoic acid;

4-(5-(3-(1H-pyrazol-5-yl)phenyl)-2-(1-(3-chloro-2-fluorophenyl)-1H-1,2,3-triazole-4-carbonyl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(3,6-dihydro-2H-pyran-4-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(6-(methylcarbamoyl)pyridin-3-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(1H-indazol-7-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(4-sulfamoylphenyl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(1-methyl-1H-indazol-4-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(1-methyl-1H-indazol-6-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(3-(5-methyl-1,3,4-oxadiazol-2-yl)phenyl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(6-(dimethylamino)pyridin-3-yl)-1,2,3,4-tetrahydroisoquinoline-1-carboxamido)benzoic acid;

4-(5-(3-(aminomethyl)phenyl)-2-(1-(3-chloro-2-fluorophenyl)-1H-1,2,3-triazole-4-carbonyl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(quinoxalin-6-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(4-oxo-4H-chromen-6-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(4-(N-cyclopropylsulfamoyl)phenyl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(3-(N,N-dimethylsulfamoyl)phenyl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(6-ethoxypyridin-3-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(2-(morpholinomethyl)phenyl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(2-fluoro-3-methoxyphenyl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(1H-pyrrolo[2,3-b]pyridin-5-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(6-cyanopyridin-3-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(2-(dimethylamino)pyrimidin-5-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(4-fluoro-3-(pyrrolidine-1-carbonyl)phenyl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(2-((dimethylamino)methyl)phenyl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(pyridin-4-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(1,2,3,6-tetrahydropyridin-4-yl)-1,2,3,4-tetrahydroisoquinoline-1-carboxamido)benzoic acid;
4-(5-(3-(2-amino-2-oxoethyl)phenyl)-2-(1-(3-chloro-2-fluorophenyl)-1H-1,2,3-triazole-4-carbonyl)-1,2,3,4-tetrahydroisoquinoline-1-carboxamido)benzoic acid;
4-(5-acetamido-2-(1-(3-chloro-2-fluorophenyl)-1H-1,2,3-triazole-4-carbonyl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-((1-methylpiperidin-4-yl)carbamoyl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(3-cyclopentylureido)-1,2,3,4-tetrahydroisoquinoline-1-carboxamido)benzoic acid;
4-(5-chloro-2-(1-(3-chloro-2-fluorophenyl)-1H-1,2,3-triazole-4-carbonyl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-fluoro-1,2,3,4-tetrahydroisoquinoline-1-carboxamido)benzoic acid;
4-(2-(1-(3-chloro-2-fluorophenyl)-1H-1,2,3-triazole-4-carbonyl)-5-((S)-3-hydroxy-2-oxopyrrolidin-1-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(2-oxo-4-(2,2,2-trifluoroethy)piperazin-1-yl)-1,2,3,4-tetrahydroisoquinoline-1-carboxamido)benzoic acid;
4-(2-(3-(3-chlorophenyisoxazole-5-carbonyl)-5-(4-methylpiperazin-1-yl)-1,2,3,4-tetrahydroisoquinoline-1-carboxamido)benzoic acid;
4-(2-(1-(3-chlorophenyl)-3-(trifluoromethyl)-1H-pyrazole-4-carbonyl)-5-(4-methylpiperazin-1-yl)-1,2,3,4-tetrahydroisoquinoline-1-carboxamido)benzoic acid;
4-(2-(1-(3-chlorophenyl)-1H-pyrazole-4-carbonyl)-5-(4-methylpiperazin-1-yl)-1,2,3,4-tetrahydroisoquinoline-1-carboxamido)benzoic acid;
4-(2-(1-(3-chlorophenyl)-1H-1,2,3-triazole-4-carbonyl)-5-(4-methylpiperazin-1-yl)-1,2,3,4-tetrahydroisoquinoline-1-carboxamido)benzoic acid;
4-(2-(3-(3-chloro-2-fluorophenyl)-4,5-dihydroisoxazole-5-carbonyl)-5-(4-methylpiperazin-1-yl)-1,2,3,4-tetrahydroisoquinoline-1-carboxamido)benzoic acid;
4-(2-(3-(3-chloro-2-fluorophenyl)-4,5-dihydroisoxazole-5-carbonyl)-5-(4-(pyrrolidin-1-yl)piperidin-1-yl)-1,2,3,4-tetrahydroisoquinoline-1-carboxamido)benzoic acid;
4-(2-(3-(3-chloro-2-fluorophenyl)-4,5-dihydroisoxazole-5-carbonyl)-5-(4-(pyrrolidin-1-yl)piperidin-1-yl)-1,2,3,4-tetrahydroisoquinoline-1-carboxamido)benzoic acid;
4-(2-(3-(3-chloro-2,6-difluorophenyl)-4,5-dihydroisoxazole-5-carbonyl)-5-(4-methylpiperazin-1-yl)-1,2,3,4-tetrahydroisoquinoline-1-carboxamido)benzoic acid;
4-(2-(1-(3-chlorophenyl)-1H-1,2,3-triazole-4-carbonyl)-5-(4-(2-oxopyrrolidin-1-yl)piperidin-1-yl)-1,2,3,4-tetrahydroisoquinoline-1-carboxamido)benzoic acid;
4-((S)-2-((R)-3-(3-chloro-2-fluorophenyl)-4,5-dihydroisoxazole-5-carbonyl)-5-(4-(2-oxopyrrolidin-1-yl)piperidin-1-yl)-1,2,3,4-tetrahydroisoquinoline-1-carboxamido)benzoic acid;
4-((R)-2-((R)-3-(3-chloro-2-fluorophenyl)-4,5-dihydroisoxazole-5-carbonyl)-5-(4-(2-oxopyrrolidin-1-yl)piperidin-1-yl)-1,2,3,4-tetrahydroisoquinoline-1-carboxamido)benzoic acid;
4-(2-(1-(3-chloro-2-fluorophenyl)-1H-1,2,3-triazole-5-carbonyl)-5-(4-methylpiperazin-1-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(4-(pyrrolidin-1-yl)piperidin-1-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(4-methylpiperazin-1-yl)-1,2,3,4-tetrahydroisoquinoline-1-carboxamido)benzoic acid;
4-(2-(5-amino-1-(3-chloro-2-fluorophenyl)-1H-pyrazole-4-carbonyl)-5-(4-methylpiperazin-1-yl)-1,2,3,4-tetrahydroisoquinoline-1-carboxamido)benzoic acid;
4-(2-(5-amino-1-(3-chloro-2-fluorophenyl)-1H-pyrazole-4-carbonyl)-5-(4-(pyrrolidin-1-yl)piperidin-1-yl)-1,2,3,4-tetrahydroisoquinoline-1-carboxamido)benzoic acid;
4-(2-(1-(3-chloro-2-fluorophenyl)-5-hydroxy-1H-pyrazole-4-carbonyl)-5-(4-methylpiperazin-1-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(4-methoxypiperidin-1-yl)-1,2,3,4-tetrahydroisoquinoline-1-carboxamido)benzoic acid;
4-(2-(3-(3-chlorophenyl)-4,5-dihydroisoxazole-5-carbonyl)-5-(4-methylpiperazin-1-yl)-1,2,3,4-tetrahydroisoquinoline-1-carboxamido)benzoic acid;
4-(2-(3-(3-chlorophenyl)-4,5-dihydroisoxazole-5-carbonyl)-5-(4-methylpiperazin-1-yl)-1,2,3,4-tetrahydroisoquinoline-1-carboxamido)benzoic acid;
N-(4-carbamoylphenyl)-2-(1-(3-chloro-2-fluorophenyl)-1H-1,2,3-triazole-4-carbonyl)-5-(4-(2-oxopyrrolidin-1-yl)piperidin-1-yl)-1,2,3,4-tetrahydroisoquinoline-1-carboxamide;
ethyl 4-(2-(1-(3-chloro-2-fluorophenyl)-1H-1,2,3-triazole-4-carbonyl)-5-(4-(pyrrolidin-1-yl)piperidin-1-yl)-1,2,3,4-tetrahydroisoquinoline-1-carboxamido)benzoate;
4-(5-(1-(3-chloro-2-fluorophenyl)-1H-1,2,3-triazole-4-carbonyl)-2-methyl-4,5,6,7-tetrahydro-2H-pyrazolo[4,3-c]pyridine-4-carboxamido)benzoic acid;

4-(5-(1-(3-chloro-2-fluorophenyl)-1H-1,2,3-triazole-4-carbonyl)-1,3-dimethyl-4,5,6,7-tetrahydro-1H-pyrazolo[4,3-c]pyridine-4-carboxamido)benzoic acid;

4-(5-(1-(3-chloro-2-fluorophenyl)-1H-1,2,3-triazole-4-carbonyl)-2,3-dimethyl-4,5,6,7-tetrahydro-2H-pyrazolo[4,3-c]pyridine-4-carboxamido)benzoic acid;

4-(7-(1-(3-chloro-2-fluorophenyl)-1H-1,2,3-triazole-4-carbonyl)-3-isopropyl-5,6,7,8-tetrahydro-[1,2,4]triazolo[4,3-a]pyrazine-8-carboxamido)benzoic acid;

4-(2-(1-(3-chloro-2-fluorophenyl)-1H-pyrazole-4-carbonyl)-5-(4-(2-methoxypropan-2-yl)piperidin-1-yl)-1,2,3,4-tetrahydroisoquinoline-1-carboxamido)benzoic acid;

4-(2-(1-(3-chloro-2-fluorophenyl)-1H-pyrazole-4-carbonyl)-5-(4-(2-(3-hydroxy-2-(hydroxymethyl)-2-methylpropoxy)propan-2-yl)piperidin-1-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(4-(oxetan-3-yl)piperazin-1-yl)-1,2,3,4-tetrahydroisoquinoline-1-carboxamido)benzoic acid;

4-((S)-2-((R)-3-(3-chloro-2-fluorophenyl)-4,5-dihydroisoxazole-5-carbonyl)-5-(4-(oxetan-3-yl)piperazin-1-yl)-1,2,3,4-tetrahydroisoquinoline-1-carboxamido)benzoic acid;

4-((R)-2-((R)-3-(3-chloro-2-fluorophenyl)-4,5-dihydroisoxazole-5-carbonyl)-5-(4-(oxetan-3-yl)piperazin-1-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(4-(2,2,2-trifluoroethyl)piperazin-1-yl)-1,2,3,4-tetrahydroisoquinoline-1-carboxamido)benzoic acid;

4-((S)-2-((R)-3-(3-chloro-2-fluorophenyl)-4,5-dihydroisoxazole-5-carbonyl)-5-(4-(2,2,2-trifluoroethyl)piperazin-1-yl)-1,2,3,4-tetrahydroisoquinoline-1-carboxamido)benzoic acid;

4-((R)-2-((R)-3-(3-chloro-2-fluorophenyl)-4,5-dihydroisoxazole-5-carbonyl)-5-(4-(2,2,2-trifluoroethyl)piperazin-1-yl)-1,2,3,4-tetrahydroisoquinoline-1-carboxamido)benzoic acid;

methyl 4-((S)-2-((R)-3-(3-chloro-2-fluorophenyl)-4,5-dihydroisoxazole-5-carbonyl)-5-(4-(oxetan-3-yl)piperazin-1-yl)-1,2,3,4-tetrahydroisoquinoline-1-carboxamido)benzoate;

methyl 4-((R)-2-((R)-3-(3-chloro-2-fluorophenyl)-4,5-dihydroisoxazole-5-carbonyl)-5-(4-(oxetan-3-yl)piperazin-1-yl)-1,2,3,4-tetrahydroisoquinoline-1-carboxamido)benzoate;

4-((1S)-2-(3-(3-chloro-2-fluorophenyl)-4,5-dihydroisoxazole-5-carbonyl)-5-(4-(oxetan-3-yl)piperidin-1-yl)-1,2,3,4-tetrahydroisoquinoline-1-carboxamido)benzoic acid;

(S)-2-((R)-3-(3-chloro-2-fluorophenyl)-4,5-dihydroisoxazole-5-carbonyl)-N-(2-fluorophenyl)-5-(4-methoxypiperidin-1-yl)-1,2,3,4-tetrahydroisoquinoline-1-carboxamide;

(R)-2-((R)-3-(3-chloro-2-fluorophenyl)-4,5-dihydroisoxazole-5-carbonyl)-N-(2-fluorophenyl)-5-(4-methoxypiperidin-1-yl)-1,2,3,4-tetrahydroisoquinoline-1-carboxamide;

(S)-2-((R)-3-(3-chloro-2-fluorophenyl)-4,5-dihydroisoxazole-5-carbonyl)-N-(3-fluorophenyl)-5-(4-methoxypiperidin-1-yl)-1,2,3,4-tetrahydroisoquinoline-1-carboxamide;

(R)-2-((R)-3-(3-chloro-2-fluorophenyl)-4,5-dihydroisoxazole-5-carbonyl)-N-(3-fluorophenyl)-5-(4-methoxypiperidin-1-yl)-1,2,3,4-tetrahydroisoquinoline-1-carboxamide;

(S)-2-((R)-3-(3-chloro-2-fluorophenyl)-4,5-dihydroisoxazole-5-carbonyl)-N-(4-fluorophenyl)-5-(4-methoxypiperidin-1-yl)-1,2,3,4-tetrahydroisoquinoline-1-carboxamide;

(R)-2-((R)-3-(3-chloro-2-fluorophenyl)-4,5-dihydroisoxazole-5-carbonyl)-N-(4-fluorophenyl)-5-(4-methoxypiperidin-1-yl)-1,2,3,4-tetrahydroisoquinoline-1-carboxamide;

4-((S)-2-((R)-3-(3-chloro-2-fluorophenyl)-4,5-dihydroisoxazole-5-carbonyl)-5-(4-methoxypiperidin-1-yl)-1,2,3,4-tetrahydroisoquinoline-1-carboxamido)-3-fluorobenzoic acid;

4-((R)-2-((R)-3-(3-chloro-2-fluorophenyl)-4,5-dihydroisoxazole-5-carbonyl)-5-(4-methoxypiperidin-1-yl)-1,2,3,4-tetrahydroisoquinoline-1-carboxamindo)-3-fluorobenzoic acid;

4-(2-(1-(3-chloro-2-fluorophenyl)-1H-1,2,3-triazole-4-carbonyl)-5-(1-methyl-1H-1,2,4-triazol-5-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(1-methyl-1H-imidazol-4-yl)-1,2,3,4-tetrahydroisoquinoline-1-carboxamido)benzoic acid;

4-((S)-2-((R)-3-(3-chloro-2-fluorophenyl)-4,5-dihydroisoxazole-5-carbonyl)-5-(4H-1,2,4-triazol-4-yl)-1,2,3,4-tetrahydroisoquinoline-1-carboxamido)benzoic acid;

4-((R)-2-((R)-3-(3-chloro-2-fluorophenyl)-4,5-dihydroisoxazole-5-carbonyl)-5-(4H-1,2,4-triazol-4-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(4H-1,2,4-triazol-4-yl)-1,2,3,4-tetrahydroisoquinoline-1-carboxamido)benzoic acid;

4-((S)-2-((R)-3-(3-chloro-2-fluorophenyl)-4,5-dihydroisoxazole-5-carbonyl)-5-(3-methyl-1H-1,2,4-triazol-1-yl)-1,2,3,4-tetrahydroisoquinoline-1-carboxamido)benzoic acid;

4-((R)-2-((R)-3-(3-chloro-2-fluorophenyl)-4,5-dihydroisoxazole-5-carbonyl)-5-(3-methyl-1H-1,2,4-triazol-1-yl)-1,2,3,4-tetrahydroisoquinoline-1-carboxamido)benzoic acid;

4-(2-(1-(3-chloro-2-fluorophenyl)-1H-pyrazole-4-carbonyl)-5-(4-methoxypiperidin-1-yl)-1,2,3,4-tetrahydroisoquinoline-1-carboxamido)benzoic acid;

4-(2-(1-(3-chloro-2-fluorophenyl)-5-methyl-1H-1,2,3-triazole-4-carbonyl)-5-(4-methoxypiperidin-1-yl)-1,2,3,4-tetrahydroisoquinoline-1-carboxamido)benzoic acid;

4-(2-(1-(3-chloro-2,6-difluorophenyl)-1H-1,2,3-triazole-4-carbonyl)-5-(4-methoxypiperidin-1-yl)-1,2,3,4-tetrahydroisoquinoline-1-carboxamido)benzoic acid;

4-(2-(1-(3-chloro-2-fluorophenyl)-5-oxopyrrolidine-3-carbonyl)-5-(4-methoxypiperidin-1-yl)-1,2,3,4-tetrahydroisoquinoline-1-carboxamido)benzoic acid;

4-(2-(3-(3-chloro-2,6-difluorophenyl)-4,5-dihydroisoxazole-5-carbonyl)-5-(4-methoxypiperidin-1-yl)-1,2,3,4-tetrahydroisoquinoline-1-carboxamido)benzoic acid;

4-(2-(3-(3-chloro-2,6-difluorophenyl)-4,5-dihydroisoxazole-5-carbonyl)-5-(4-methoxypiperidin-1-yl)-1,2,3,4-tetrahydroisoquinoline-1-carboxamido)benzoic acid;

4-(2-(1-(3-chlorophenyl)pyrrolidine-3-carbonyl)-5-(4-methoxypiperidin-1-yl)-1,2,3,4-tetrahydroisoquinoline-1-carboxamido)benzoic acid;

4-(2-(1-(3-chloro-2-fluorophenyl)-5-methyl-1H-pyrazole-4-carbonyl)-5-(4-methoxypiperidin-1-yl)-1,2,3,4-tetrahydroisoquinoline-1-carboxamido)benzoic acid;
4-(2-(1-(3-chloro-2-fluorophenyl)-5-oxopyrrolidine-3-carbonyl)-5-(4-methoxypiperidin-1-yl)-1,2,3,4-tetrahydroisoquinoline-1-carboxamido)benzoic acid;
4-(2-(1-(3-chlorophenyl)pyrrolidine-3-carbonyl)-5-(4-methoxypiperidin-1-yl)-1,2,3,4-tetrahydroisoquinoline-1-carboxamido)benzoic acid;
4-(2-(3-(3-chloro-2-fluorophenyl)-4,5-dihydroisoxazole-5-carbonyl)-5-(4-(2-hydroxypropan-2-yl)piperidin-1-yl)-1,2,3,4-tetrahydroisoquinoline-1-carboxamido)benzoic acid;
4-(2-(3-(3-chloro-2-fluorophenyl)-4,5-dihydroisoxazole-5-carbonyl)-5-(4-(2-hydroxypropan-2-yl)piperidin-1-yl)-1,2,3,4-tetrahydroisoquinoline-1-carboxamido)benzoic acid;
4-(2-(1-(3-chloro-2-fluorophenyl)-3-hydroxy-1H-pyrazole-4-carbonyl)-5-(4-methoxypiperidin-1-yl)-1,2,3,4-tetrahydroisoquinoline-1-carboxamido)benzoic acid;
4-(2-(3-(3-chloro-2,6-difluorophenypisoxazole-5-carbonyl)-5-(4-methoxypiperidin-1-yl)-1,2,3,4-tetrahydroisoquinoline-1-carboxamido)benzoic acid;
4-(2-(3-(3-chloro-2-fluorophenyl)-5-methyl-4,5-dihydroisoxazole-5-carbonyl)-5-(4-methoxypiperidin-1-yl)-1,2,3,4-tetrahydroisoquinoline-1-carboxamido)benzoic acid;
4-(2-(3-(3-chloro-2-fluorophenyl)-5-methyl-4,5-dihydroisoxazole-5-carbonyl)-5-(4-methoxypiperidin-1-yl)-1,2,3,4-tetrahydroisoquinoline-1-carboxamido)benzoic acid;
4-(2-(3-(3-chloro-2-fluorophenyl)isoxazole-5-carbonyl)-5-(4-methoxypiperidin-1-yl)-1,2,3,4-tetrahydroisoquinoline-1-carboxamido)benzoic acid;
4-(2-(3-(3-chloro-2-fluorophenypisothiazole-5-carbonyl)-5-(4-methoxypiperidin-1-yl)-1,2,3,4-tetrahydroisoquinoline-1-carboxamido)benzoic acid;
4-(2-(2-(3-chloro-2-fluorophenyl)thiazole-5-carbonyl)-5-(4-methoxypiperidin-1-yl)-1,2,3,4-tetrahydroisoquinoline-1-carboxamido)benzoic acid;
4-(2-(1-(3-chloro-2-fluorophenyl)-1H-imidazole-4-carbonyl)-5-(4-methoxypiperidin-1-yl)-1,2,3,4-tetrahydroisoquinoline-1-carboxamido)benzoic acid;
(R)-4-(2-(1-(3-chloro-2-fluorophenyl)-1H-imidazole-4-carbonyl)-5-(4-methoxypiperidin-1-yl)-1,2,3,4-tetrahydroisoquinoline-1-carboxamido)benzoic acid;
(S)-4-(2-(1-(3-chloro-2-fluorophenyl)-1H-imidazole-4-carbonyl)-5-(4-methoxypiperidin-1-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-(4-methyl-3-oxopiperazin-1-yl)-1,2,3,4-tetrahydroisoquinoline-1-carboxamido)benzoic acid;
4-(2-(1-(3-chloro-2-fluorophenyl)-1H-1,2,3-triazole-4-carbonyl)-5-methoxy-1,2,3,4-tetrahydroisoquinoline-1-carboxamido)benzoic acid;
4-(2-(3-(3-chloro-2-fluorophenyl)-4,5-dihydroisoxazole-5-carbonyl)-5-(4-(dimethylcarbamoyl)piperidin-1-yl)-1,2,3,4-tetrahydroisoquinoline-1-carboxamido)benzoic acid;
4-(2-(3-(3-chloro-2-fluorophenyl)-4,5-dihydroisoxazole-5-carbonyl)-5-(4-(dimethylcarbamoyl)piperidin-1-yl)-1,2,3,4-tetrahydroisoquinoline-1-carboxamido)benzoic acid;
4-(2-(3-(3-chloro-2-fluorophenyl)-4,5-dihydroisoxazole-5-carbonyl)-5-(4-(dimethylcarbamoyl)piperidin-1-yl)-1,2,3,4-tetrahydroisoquinoline-1-carboxamido)benzoic acid;
4-(2-(3-(3-chloro-2-fluorophenyl)-4,5-dihydroisoxazole-5-carbonyl)-5-(4-(dimethylcarbamoyl)piperidin-1-yl)-1,2,3,4-tetrahydroisoquinoline-1-carboxamido)benzoic acid;
4-(2-(3-(3-chloro-2-fluorophenyl)-4,5-dihydroisoxazole-5-carbonyl)-5-(4-methyl-3-oxopiperazin-1-yl)-1,2,3,4-tetrahydroisoquinoline-1-carboxamido)benzoic acid;
4-(2-(3-(3-chloro-2-fluorophenyl)-4,5-dihydroisoxazole-5-carbonyl)-5-(4-methyl-3-oxopiperazin-1-yl)-1,2,3,4-tetrahydroisoquinoline-1-carboxamido)benzoic acid;
4-(2-(3-(3-chloro-2-fluorophenyl)-4,5-dihydroisoxazole-5-carbonyl)-5-(4-methyl-3-oxopiperazin-1-yl)-1,2,3,4-tetrahydroisoquinoline-1-carboxamido)benzoic acid;
4-(2-(3-(3-chloro-2-fluorophenyl)-4,5-dihydroisoxazole-5-carbonyl)-5-(4-methyl-3-oxopiperazin-1-yl)-1,2,3,4-tetrahydroisoquinoline-1-carboxamido)benzoic acid;
4-(2-(1-(3-chloro-2-fluorophenyl)-1H-imidazole-4-carbonyl)-5-(4-methyl-3-oxopiperazin-1-yl)-1,2,3,4-tetrahydroisoquinoline-1-carboxamindo)benzoic acid;
(S)-4-(2-(5-amino-1-(3-chloro-2-fluorophenyl)-1H-pyrazole-4-carbonyl)-5-(4-methoxypiperidin-1-yl)-1,2,3,4-tetrahydroisoquinoline-1-carboxamido)benzoic acid;
(R)-4-(2-(5-amino-1-(3-chloro-2-fluorophenyl)-1H-pyrazole-4-carbonyl)-5-(4-methoxypiperidin-1-yl)-1,2,3,4-tetrahydroisoquinoline-1-carboxamido)benzoic acid;
(S)-4-(2-(1-(3-chloro-2-fluorophenyl)-1H-1,2,3-triazole-4-carbonyl)-5-(4-methyl-3-oxopiperazin-1-yl)-1,2,3,4-tetrahydroisoquinoline-1-carboxamido)benzoic acid;
(R)-4-(2-(1-(3-chloro-2-fluorophenyl)-1H-1,2,3-triazole-4-carbonyl)-5-(4-methyl-3-oxopiperazin-1-yl)-1,2,3,4-tetrahydroisoquinoline-1-carboxamido)benzoic acid;
4-((S)-2-((R)-3-(3-chloro-2-fluorophenyl)-4,5-dihydroisoxazole-5-carbonyl)-5-(3-oxomorpholino)-1,2,3,4-tetrahydroisoquinoline-1-carboxamido)benzoic acid;
4-((S)-2-((R)-3-(3-chloro-2-fluorophenyl)-4,5-dihydroisoxazole-5-carbonyl)-5-(3-oxomorpholino)-1,2,3,4-tetrahydroisoquinoline-1-carboxamido)benzoic acid;
4-((S)-2-((R)-3-(3-chloro-2-fluorophenyl)-4,5-dihydroisoxazole-5-carbonyl)-5-(piperidin-1-yl)-1,2,3,4-tetrahydroisoquinoline-1-carboxamido)benzoic acid;
4-((R)-2-((R)-3-(3-chloro-2-fluorophenyl)-4,5-dihydroisoxazole-5-carbonyl)-5-(piperidin-1-yl)-1,2,3,4-tetrahydroisoquinoline-1-carboxamido)benzoic acid;
4-((S)-2-((R)-3-(3-chloro-2-fluorophenyl)-4,5-dihydroisoxazole-5-carbonyl)-5-methoxy-1,2,3,4-tetrahydroisoquinoline-1-carboxamido)benzoic acid;
4-((R)-2-((R)-3-(3-chloro-2-fluorophenyl)-4,5-dihydroisoxazole-5-carbonyl)-5-methoxy-1,2,3,4-tetrahydroisoquinoline-1-carboxamido)benzoic acid;
4-((S)-2-((R)-3-(3-chloro-2-fluorophenyl)-4,5-dihydroisoxazole-5-carbonyl)-5-morpholino-1,2,3,4-tetrahydroisoquinoline-1-carboxamido)benzoic acid;
4-((S)-2-((R)-3-(3-chloro-2-fluorophenyl)-4,5-dihydroisoxazole-5-carbonyl)-5-morpholino-1,2,3,4-tetrahydroisoquinoline-1-carboxamido)benzoic acid;
4-(2-(3-(3-chloro-2-fluoro-6-(trifluoromethyl)phenyl)-4,5-dihydroisoxazole-5-carbonyl)-5-(4-methoxypiperidin-1-yl)-1,2,3,4-tetrahydroisoquinoline-1-carboxamido)benzoic acid;
4-(2-(3-(3-chloro-2-fluoro-6-(trifluoromethyl)phenyl)-4,5-dihydroisoxazole-5-carbonyl)-5-(4-methoxypiperidin-1-yl)-1,2,3,4-tetrahydroisoquinoline-1-carboxamido)benzoic acid;
4-((R)-2-((R)-3-(3-chloro-2-fluorophenyl)-4,5-dihydroisoxazole-5-carbonyl)-5-((R)-3-methoxypyrrolidin-1-yl)-1,2,3,4-tetrahydroisoquinoline-1-carboxamido)benzoic acid;

4-((S)-2-((R)-3-(3-chloro-2-fluorophenyl)-4,5-dihydroisoxazole-5-carbonyl)-5-((R)-3-methoxypyrrolidin-1-yl)-1,2,3,4-tetrahydroisoquinoline-1-carboxamido)benzoic acid;

4-((S)-2-((R)-3-(3-chloro-2-fluorophenyl)-4,5-dihydroisoxazole-5-carbonyl)-5-(4-hydroxypiperidin-1-yl)-1,2,3,4-tetrahydroisoquinoline-1-carboxamido)benzoic acid;

4-((R)-2-((R)-3-(3-chloro-2-fluorophenyl)-4,5-dihydroisoxazole-5-carbonyl)-5-(4-hydroxypiperidin-1-yl)-1,2,3,4-tetrahydroisoquinoline-1-carboxamido)benzoic acid;

4-(2-(3-(3-chloro-2-fluorophenyl)-4,5-dihydroisoxazole-5-carbonyl)-5-(4-methoxypiperidin-1-yl)-1,2,3,4-tetrahydroisoquinoline-1-carboxamido)benzoic acid;

4-(2-(3-(3-chloro-2-fluorophenyl)-4,5-dihydroisoxazole-5-carbonyl)-5-(4-methoxypiperidin-1-yl)-1,2,3,4-tetrahydroisoquinoline-1-carboxamido)benzoic acid;

4-(2-(3-(3-chloro-2-fluorophenyl)-4,5-dihydroisoxazole-5-carbonyl)-5-(4-methoxypiperidin-1-yl)-1,2,3,4-tetrahydroisoquinoline-1-carboxamido)benzoic acid;

4-(2-(3-(3-chloro-2-fluorophenyl)-4,5-dihydroisoxazole-5-carbonyl)-5-(4-methoxypiperidin-1-yl)-1,2,3,4-tetrahydroisoquinoline-1-carboxamido)benzoic acid;

4-(2-(1-(3-chloro-2-fluorophenyl)pyrrolidine-3-carbonyl)-5-(4-methoxypiperidin-1-yl)-1,2,3,4-tetrahydroisoquinoline-1-carboxamido)benzoic acid;

4-(2-(1-(3-chloro-2-fluorophenyl)pyrrolidine-3-carbonyl)-5-(4-methoxypiperidin-1-yl)-1,2,3,4-tetrahydroisoquinoline-1-carboxamido)benzoic acid;

4-(2-(5-amino-1-(3-chloro-2-fluorophenyl)-1H-pyrazole-4-carbonyl)-5-(4-methoxypiperidin-1-yl)-1,2,3,4-tetrahydroisoquinoline-1-carboxamido)benzoic acid;

4-(2-(2-(3-chloro-2-fluorophenyl)oxazole-4-carbonyl)-5-(4-methoxypiperidin-1-yl)-1,2,3,4-tetrahydroisoquinoline-1-carboxamido)benzoic acid;

4-(2-(3-(3-chlorophenyl)-1H-pyrazole-5-carbonyl)-5-(4-methoxypiperidin-1-yl)-1,2,3,4-tetrahydroisoquinoline-1-carboxamido)benzoic acid;

4-(2-(1-(3-chloro-2,6-difluorophenyl)-1H-imidazole-4-carbonyl)-5-(4-methoxypiperidin-1-yl)-1,2,3,4-tetrahydroisoquinoline-1-carboxamido)benzoic acid;

4-(2-(5-amino-1-(pyridin-4-yl)-1H-pyrazole-4-carbonyl)-5-(4-methoxypiperidin-1-yl)-1,2,3,4-tetrahydroisoquinoline-1-carboxamido)benzoic acid;

(S)-4-(2-(1-(3-chloro-2-fluorophenyl)-1H-1,2,3-triazole-4-carbonyl)-5-(4-methoxypiperidin-1-yl)-1,2,3,4-tetrahydroisoquinoline-1-carboxamido)benzoic acid;

(S)-4-(2-(1-(3-chloro-2-fluorophenyl)-1H-pyrazole-4-carbonyl)-5-(4-methoxypiperidin-1-yl)-1,2,3,4-tetrahydroisoquinoline-1-carboxamido)benzoic acid;

(R)-4-(2-(1-(3-chloro-2-fluorophenyl)-1H-pyrazole-4-carbonyl)-5-(4-methoxypiperidin-1-yl)-1,2,3,4-tetrahydroisoquinoline-1-carboxamido)benzoic acid;

4-(2-(5-amino-1-(3-chloro-2-fluorophenyl)-1H-pyrazole-4-carbonyl)-5-(4-(dimethylcarbamoyl)piperidin-1-yl)-1,2,3,4-tetrahydroisoquinoline-1-carboxamido)benzoic acid;

4-(2-(5-amino-1-(3-chloro-2-fluorophenyl)-1H-pyrazole-4-carbonyl)-5-(4-methyl-3-oxopiperazin-1-yl)-1,2,3,4-tetrahydroisoquinoline-1-carboxamido)benzoic acid;

4-(2-(5-amino-1-(3-chloro-2-fluorophenyl)-1H-pyrazole-4-carbonyl)-5-(4-(2-(dimethylamino)ethoxy)piperidin-1-yl)-1,2,3,4-tetrahydroisoquinoline-1-carboxamido)benzoic acid;

4-(2-(5-(3-chlorophenyl)nicotinoyl)-5-(4-methylpiperazin-1-yl)-1,2,3,4-tetrahydroisoquinoline-1-carboxamido)benzoic acid;

4-(5-(4-methylpiperazin-1-yl)-2-(5-phenylnicotinoyl)-1,2,3,4-tetrahydroisoquinoline-1-carboxamido)benzoic acid;

4-(2-(4-(3-chloro-2-fluorophenyl)picolinoyl)-5-(4-methoxypiperidin-1-yl)-1,2,3,4-tetrahydroisoquinoline-1-carboxamido)benzoic acid;

4-(2-(5-(3-chloro-2-fluorophenyl)nicotinoyl)-5-(4-methoxypiperidin-1-yl)-1,2,3,4-tetrahydroisoquinoline-1-carboxamido)benzoic acid;

4-(2-(2-(3-chloro-2-fluorophenyl)isonicotinoyl)-5-(4-methoxypiperidin-1-yl)-1,2,3,4-tetrahydroisoquinoline-1-carboxamido)benzoic acid;

4-(2-(6-(3-chloro-2-fluorophenyl)picolinoyl)-5-(4-methoxypiperidin-1-yl)-1,2,3,4-tetrahydroisoquinoline-1-carboxamido)benzoic acid;

4-(2-(3-(3-chloro-2-fluorophenyl)piperidine-1-carbonyl)-5-(4-methoxypiperidin-1-yl)-1,2,3,4-tetrahydroisoquinoline-1-carboxamido)benzoic acid;

4-(5-(4-methoxypiperidin-1-yl)-2-(1-(2-methylpyridin-4-yl)-1H-pyrazole-4-carbonyl)-1,2,3,4-tetrahydroisoquinoline-1-carboxamido)benzoic acid;

4-(2-(1-(5-chloropyridin-3-yl)-1H-pyrazole-4-carbonyl)-5-(4-methoxypiperidin-1-yl)-1,2,3,4-tetrahydroisoquinoline-1-carboxamido)benzoic acid;

4-(2-(1-(3-chlorophenyl)-1H-pyrazole-4-carbonyl)-5-(4-methoxypiperidin-1-yl)-1,2,3,4-tetrahydroisoquinoline-1-carboxamido)benzoic acid;

4-(5-(4-methoxypiperidin-1-yl)-2-(1-(pyridin-3-yl)-1H-pyrazole-4-carbonyl)-1,2,3,4-tetrahydroisoquinoline-1-carboxamido)benzoic acid;

4-(2-(1-(benzo[c][1,2,5]oxadiazol-5-yl)-1H-pyrazole-4-carbonyl)-5-(4-methoxypiperidin-1-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(2-oxopyridin-1(2H)-yl)-1,2,3,4-tetrahydroisoquinoline-1-carboxamido)benzoic acid;

4-(2-(1-(3-chloro-2-fluorophenyl)-1H-1,2,3-triazole-4-carbonyl)-5-(prop-1-en-2-yl)-1,2,3,4-tetrahydroisoquinoline-1-carboxamido)benzoic acid;

4-(5-amino-2-(1-(3-chloro-2-fluorophenyl)-1H-1,2,3-triazole-4-carbonyl)-1,2,3,4-tetrahydroisoquinoline-1-carboxamido)benzoic acid;

N-(4-carbamoylphenyl)-2-(1-(3-chloro-2-fluorophenyl)-1H-1,2,3-triazole-4-carbonyl)-5-(4-methoxypiperidin-1-yl)-1,2,3,4-tetrahydroisoquinoline-1-carboxamide;

4-((S)-2-((R)-3-(3-chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid;

4-((R)-2-((R)-3-(3-chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid;

4-((S)-2-((S)-3-(3-chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid;

4-((R)-2-((S)-3-(3-chloro-2-fluorophenyl)-4,5-dihydroisoxazole-5-carbonyl)-5-(3-isopropyl-5,6-dihydro-[1,2,4]triazolo[4,3-a]pyrazin-7(8H)-yl)-1,2,3,4-tetrahydroisoquinoline-1-carboxamido)benzoic acid;

4-((S)-2-((R)-3-(3-chloro-2-fluorophenyl)-4,5-dihydroisoxazole-5-carbonyl)-5-(3-methyl-5,6-dihydro-[1, 2,4]triazolo[4,3-a]pyrazin-7(8H)-yl)-1,2,3,4-tetrahydroisoquinoline-1-carboxamido)benzoic acid;

4-((R)-2-((R)-3-(3-chloro-2-fluorophenyl)-4,5-dihydroisoxazole-5-carbonyl)-5-(3-methyl-5,6-dihydro-[1,2,4]triazolo[4,3-a]pyrazin-7(8H)-yl)-1,2,3,4-tetrahydroisoquinoline-1-carboxamido)benzoic acid;

(S)-2-((R)-3-(3-chloro-2-fluorophenyl)-4,5-dihydroisoxazole-5-carbonyl)-N-(4-fluorophenyl)-5-(3-isopropyl-5,6-dihydro-[1,2,4]triazolo[4,3-a]pyrazin-7(8H)-yl)-1,2,3,4-tetrahydroisoquinoline-1-carboxamide; and (R)-2-((R)-3-(3-chloro-2-fluorophenyl)-4,5-dihydroisoxazole-5-carbonyl)-N-(4-fluorophenyl)-5-(3-isopropyl-5,6-dihydro-[1,2,4]triazolo[4,3-a]pyrazin-7(8H)-yl)-1,2,3,4-tetrahydroisoquinoline-1-carboxamide.

* * * * *